(12) United States Patent
Frincke

(10) Patent No.: US 7,947,846 B2
(45) Date of Patent: May 24, 2011

(54) 15-OXA-STEROID COMPOUNDS

(75) Inventor: James M. Frincke, San Diego, CA (US)

(73) Assignee: Harbor BioSciences, Inc., San Diego, CA (US)

( * ) Notice: Subject to any disclaimer, the term of this patent is extended or adjusted under 35 U.S.C. 154(b) by 0 days.

(21) Appl. No.: 12/633,721

(22) Filed: Dec. 8, 2009

(65) Prior Publication Data

US 2010/0222425 A1 Sep. 2, 2010

Related U.S. Application Data

(60) Continuation of application No. 11/234,675, filed on Sep. 23, 2005, now abandoned, which is a division of application No. 10/087,929, filed on Mar. 1, 2002, now abandoned, which is a continuation-in-part of application No. 09/675,470, filed on Sep. 28, 2000, now abandoned, and a continuation-in-part of application No. 09/535,675, filed on Mar. 23, 2000, now Pat. No. 6,667,299.

(60) Provisional application No. 60/272,624, filed on Mar. 1, 2001, provisional application No. 60/323,016, filed on Sep. 11, 2001, provisional application No. 60/340,054, filed on Nov. 1, 2001, provisional application No. 60/328,738, filed on Oct. 11, 2001, provisional application No. 60/338,015, filed on Nov. 8, 2001, provisional application No. 60/343,523, filed on Dec. 20, 2001, provisional application No. 60/190,140, filed on Mar. 16, 2000, provisional application No. 60/126,056, filed on Mar. 23, 1999, provisional application No. 60/164,048, filed on Nov. 8, 1999, provisional application No. 60/140,028, filed on Jun. 16, 1999.

(51) Int. Cl.
  *C07D 307/77* (2006.01)
  *A61K 31/34* (2006.01)
(52) U.S. Cl. ........................ 549/457; 514/468
(58) Field of Classification Search .......... 514/468; 549/457
  See application file for complete search history.

(56) References Cited

U.S. PATENT DOCUMENTS

| | | |
|---|---|---|
| 3,987,066 A | 10/1976 | Rosen |
| 4,066,666 A | 1/1978 | Rosen |
| 5,219,879 A | 6/1993 | Ko et al. |
| 7,696,189 B1 | 4/2010 | Frincke |
| 7,723,532 B2 | 5/2010 | Frincke et al. |
| 7,863,261 B2 | 1/2011 | Frincke |

FOREIGN PATENT DOCUMENTS

| | | |
|---|---|---|
| AU | 782736 B2 | 8/2005 |
| CA | 2388939 C | 6/2009 |
| EP | 1223941 B1 | 5/2008 |
| WO | WO 01/30802 A2 | 5/2001 |
| WO | WO 01/30802 A3 | 5/2001 |

*Primary Examiner* — Barbara P Badio
(74) *Attorney, Agent, or Firm* — Angelo Castellino; Daryl D Muenchau

(57) ABSTRACT

The invention relates to the use of compounds to treat a number of conditions, such as thrombocytopenia, neutropenia or the delayed effects of radiation therapy. Compounds that can be used in the invention include methyl-2,3,4-trihydroxy-1-O-(7,17-dioxoandrost-5-ene-3β-yl)-β-D-glucopyranosiduronate, 16α,3α-dihydroxy-5α-androstan-17-one or 3,7,16,17-tetrahydroxyandrost-5-ene, 3,7,16,17-tetrahydroxyandrost-4-ene, 3,7,16,17-tetrahydroxyandrost-1-ene or 3,7,16,17-tetrahydroxyandrostane that can be used in the treatment method.

15 Claims, No Drawings

US 7,947,846 B2

15-OXA-STEROID COMPOUNDS

CROSS-REFERENCE TO RELATED APPLICATIONS

This non-provisional application is a continuation of U.S. application Ser. No. 11/234,675, filed Sep. 23, 2005, which is a divisional application of U.S. application Ser. No. 10/087,929, filed Mar. 1, 2002, now abandoned, and which claims priority to and/or is a continuation-in-part of: (1) abandoned U.S. application Ser. No. 09/675,470, filed Sep. 28, 2000, which claims priority to abandoned U.S. provisional application Ser. No. 60/161,453, filed Oct. 25, 1999, and (2) abandoned U.S. provisional application Ser. No. 60/272,624, filed Mar. 1, 2001, and (3) abandoned U.S. provisional application Ser. No. 60/323,016, filed Sep. 10, 2001, and (4) abandoned U.S. provisional application Ser. No. 60/340,054, filed Nov. 1, 2001, and (5) abandoned U.S. provisional application Ser. No. 60/328,738, filed Oct. 11, 2001, and (6) abandoned U.S. provisional application Ser. No. 60/338,015, filed Nov. 8, 2001, and (7) abandoned U.S. provisional application Ser. No. 60/343,523, filed Dec. 20, 2001, and (8) abandoned U.S. application Ser. No. 09/820,483, filed Mar. 29, 2001, abandoned, which is claims priority from and/or is a continuation-in-part of (a) U.S. application Ser. No. 09/535,675, filed Mar. 23, 2000, now U.S. Pat. No. 6,667,299 B1, said 09/535,675 application claims priority to abandoned U.S. provisional application Ser. No. 60/190,140, filed Mar. 16, 2000, abandoned U.S. provisional application Ser. No. 60/126,056, filed Mar. 23, 1999, abandoned U.S. provisional application Ser. No. 60/164,048, filed Nov. 8, 1999, abandoned U.S. application Ser. No. 09/414,905, filed Oct. 8, 1999 and abandoned U.S. provisional application Ser. No. 60/140,028, filed Jun. 16, 1999, and (b) abandoned U.S. application Ser. No. 09/449,004, filed Nov. 24, 1999, which claims priority to abandoned U.S. provisional application Ser. No. 60/109,923, filed Nov. 24, 1998, abandoned U.S. provisional application Ser. No. 60/126,056, filed Mar. 23, 1999, and abandoned U.S. provisional application Ser. No. 60/124,087, filed Mar. 11, 1999 and (c) abandoned U.S. application Ser. No. 09/449,184, filed Nov. 24, 1999, which claims priority to abandoned U.S. provisional application Ser. No. 60/109,924, filed Nov. 24, 1998, abandoned U.S. provisional application Ser. No. 60/126,056, filed Mar. 23, 1999 and abandoned U.S. provisional application Ser. No. 60/124,087, filed Mar. 11, 1999 and (d) abandoned U.S. application Ser. No. 09/449,042, filed Nov. 24, 1999, which claims priority to abandoned U.S. provisional application Ser. No. 60/110,127, filed Nov. 27, 1998, abandoned U.S. provisional application Ser. No. 60/126,056, filed Mar. 23, 1999 and abandoned U.S. provisional application Ser. No. 60/124,087, filed Mar. 11, 1999 and (e) abandoned U.S. application Ser. No. 09/461,026, filed Dec. 15, 1999, which claims priority to abandoned U.S. provisional application Ser. No. 60/112,206, filed Dec. 15, 1998, and (f) abandoned U.S. application Ser. No. 09/586,673, filed Jun. 1, 2000, which claims priority to abandoned U.S. provisional application Ser. No. 60/145,823, filed Jul. 27, 1999, and (g) abandoned U.S. application Ser. No. 09/586,672, filed Jun. 1, 2000, which claims priority to abandoned U.S. provisional application Ser. No. 60/137,745, filed Jun. 3, 1999, and (h) abandoned U.S. application Ser. No. 09/414,905, filed Oct. 8, 1999, which claims priority to abandoned U.S. provisional application Ser. No. 60/140,028, filed Jun. 16, 1999, each of which is incorporated herein by reference in its entirety.

FIELD OF THE INVENTION

The invention relates to methods to make or use compounds, such as 16α-bromo-3β-hydroxy-5α-androstane-17-one (16α-bromoepiandrosterone or hereafter "BrEA") 3,7,16,17-tetrahydroxyandrost-5-ene, 3,7,16,17-tetrahydroxyandrostane, 3,17-dihydroxy-16-haloandrostane, methyl 2,3,4-trihydroxy-1-O-(7,17-dioxoandrost-5-ene-3β-yl)-β-D-glucopyranosiduronate and related compounds. The invention relates to the use of compounds to treat a number of conditions, such as thrombocytopenia and neutropenia.

DESCRIPTION OF THE INVENTION

Methods to prepare dehydroepiandrosterone ("DHEA") and other steroids and their biological properties have been described, see, e.g., U.S. Pat. Nos. 2,833,793, 2,911,418, 3,148,198, 3,471,480, 3,976,691, 4,268,441, 4,427,649, 4,542,129, 4,666,898, 4,956,355, 5,001,119, 5,043,165, 5,077,284, 5,028,631, 5,110,810, 5,157,031, 5,162,198, 5,175,154, 5,277,907, 5,292,730, 5,296,481, 5,372,996, 5,387,583, 5,407,684, 5,424,463, 5,461,042, 5,478,566, 5,506,223, 5,518,725, 5,527,788, 5,527,789, 5,532,230, 5,559,107, 5,562,910, 5,583,126, 5,585,371, 5,587,369, 5,591,736, 5,593,981, 5,610,150, 5,635,496, 5,641,766, 5,641,768, 5,656,621, 5,660,835, 5,686,438, 5,696,106, 5,700,793, 5,707,983, 5,709,878, 5,710,143, 5,714,481, 5,728,688, 5,736,537, 5,744,462, 5,753,237, 5,756,482, 5,776,921, 5,776,923, 5,780,460, 5,795,880, 5,798,347, 5,798,348, 5,804,576, 5,807,848, 5,807,849, 5,811,418, 5,824,313, 5,824,668, 5,824,671, 5,827,841, 5,837,269, 5,837,700, 5,843,932, 5,846,963, 5,859,000, 5,872,114 and 5,872,147; German patent numbers 2035738 and 2705917; PCT publication numbers WO 95/21617, WO 97/48367, WO 98/05338, WO 98/50040, WO 98/50041, WO 98/58650; European publication number 0020029; E. R. Glazier, *J. Org. Chem.* 1962 27:2937-2938, Ben-David, et al., *Proc. Soc. Expt. Biol. Med.* 1967 125:1136-1140, Coleman et al., *Diabetes* 1982 31:830, Oertel, et al., *J. Steroid Biochem.* 1972 3:493-496, Pashko, et al., *Carcinogenesis* 1981 2:717-721, Schwartz et al., *Nutr. Cancer* 1981 3:46-53; Dyner et al., *J. Acquired Immune Deficiency Syndromes* 1993 6:459-465; A. A. Afanasii and Y. A. Titov, *Total Steroid Synthesis*, Plenum Press, New York, 1970, see, e.g., p 1-304.

The use DHEA and other steroids in various applications have been described, e.g., U.S. Pat. Nos. 5,869,090, 5,863,910, 5,856,340, 5,824,668, 5,804,576, 5,753,237, 5,714,481, 5,709,878, 5,407,684, 5,206,008, 5,077,284, 4,978,532, 4,898,694, 4,542,129, 3,711,606 and 3,710,795. U.S. Pat. No. 4,956,355 and PCT publication number WO 97/48367, have described the use of certain steroid compounds to treat certain virus or bacterial infections, such as human immunodeficiency virus ("HIV") infection.

Various biological effects and/or metabolic conversions of steroid compounds have also been described, e.g., Batta et al., *J. Biol. Chem.* 1986 25:127-133, Belli et al., *Liver* 1991 11:162-169, Bhattacharjee et al., *Anal. Biochem.* 1992 201:233-236, Blake et al., *Int. J. Peptide Protein Res.* 1982 20:97-101, 1986 25:127-133, Bonaventura, *Am. J. Obstet. Gynecol.* 1978 131:403-409, Bucala et al., *J. Steroid Biochem.* 1986 25:127-133, Carey et al., *Biochem.* 1981 20:3637-3648, Chen et al., *Carcinogenesis* 1999 20:249-254, Chen et al., *Carcinogenesis* 1998 19:2187-2193, Chow et al., *Antisense Res. Dev.* 1994 4:81-86, Citro et al., *Dis. Colon Rectum* 1994 37(2 Suppl):5127-5132, Cleary, *Proc. Soc. Exp. Biol. Med.* 1991 196:8-16, Cleary, *Int. J. Biochem.* 1990 22:205-210, Crawford et al., *Lab. Invest.* 1994 71:42-51, Danenberg et al., *Antimicrob. Agents Chemother.* 1992 36:2275-2279, Dotzlaw et al., *Cancer Res.* 1999 59:529-532, Falany et al., *J. Steroid Biochem. Mol. Biol.* 1994 48:369-375, Faredin et al., *J. Investigative Dermatol.* 1969 52:357-361, Galigniana et al., *Mol.*

Pharmacol. 1999 55:317-323, Goto et al., *J. Chromatogr.* 1983 276:289-300, Grenot Biochem. 1992 31:7609-7621, Hofbauer et al., *Life Sci.* 1999 64:671-679, Huijghebaert et al., *J. Lipid Res.* 1986 27:742-752, Hurd et al., *Oncogene* 1999 18:1067-1072, Iida et al., *J. Lipid Res.* 1995 36:628-638, Jellinck et al., *Steroids* 1967 10:329-346, Jonsson et al., *J. Pediatr. Gastroenterol. Nutr.* 1995 20:394-402, Kalimi et al, *Mol. Cell. Biochem.* 1994 131:99-108, Kramer et al., *J. Biol. Chem.* 1994 269:10621-10627, LaRochelle et al., *Steroids* 1984 43: 209-217, Liao et al., *Carcinogenesis* 1998 19:2173-2180, Lillienau et al., *J. Clin. Invest.* 1992 89:420-431, Loria, *Psychoneuroendocrinology* 1997 22:S103-S108, Luscher et al *Mol. Immunol.* 1983 20:1099-1105, Manna et al., *J. Biol. Chem.* 1999 274:5909-5918, Marschall et al., *J. Biol. Chem.* 1989 264:12989-12993, Medh et al., *Cancer Res.* 1998 15:3684-3693, Mohan et al., *Steroids* 1992 57:244-247, Munoz de Toro et al., *J. Steroid Biochem. Mol. Biol.* 1998 67:333-339, Padgett et al., *J. Neuroimmunol.* 1998 84:61, Padgett et al., *Ann. N.Y. Acad. Sci.* 1995 774:323, Padgett et al., *J. Immunol.* 1994 153:1544-1552, Pashko et al., *Carcinogenesis* 1984 5:463-466, Pashko et al., *Carcinogenesis* 1981 2:717, Petrylak et al., *J. Clin. Oncology* 1999 17:958-967, Podesta et al., *Steroids* 1996 61:622-626, Regelson et al., *Ann. N.Y. Acad. Sci.* 1994 719:564, Schmassmann et al., *Gastroenterology* 1993 104:1171-1181, Schmassmann et al., *Hepatology* 1990 11:989-996, Schreiber et al., *Lancet* 353: 459-461, Schreiber, *Neth. J. Med.* 1998 53:S24-31, Schwartz et al., *Cancer Res.* 1988 48:4817, Shahidi et al., *Biochem. Biophys. Res. Commun.* 1999 254:559-565, Steer et al., *Ann. Rheum. Dis.* 1998 57:732-737, Suzuki et al., *Steroids* 1998 63:672-677, Suzuki et al., *Steroids* 1996 61:296-301, Swaan et al., *Bioconjugate Chem.* 1997 8:520-525, Tang et al, *Anti-cancer Drug Res.* 1998 13:815-824, Thomas et al., *J. Steroid Biochem.* 1986 25:103-108, Utsumi et al., *Cancer Res.* 1999 59:377-381, Vanden Heuvel, *J. Nutr.* 1999 129(2S Suppl.): 5755-5805, Wang et al., *Endocrinology* 1998 139:3903-3912, Wong et al., *J. Biol. Chem.* 1999 274:5443-5453, Xie et al., *Endocrinology* 1999 140:219-227, Yen et al., *Lipids* 1977 12:409-413, Zackheim et al., *Arch. Dermatology* 1998 134: 949-954, Zhang et al., *Biochim. Biophys. Acta* 1991 1096: 179-186, Zhu et al., *Carcinogenesis* 1988 19:2101-2106.

Mammalian immune responses to infections or other conditions are often characterized by responses mediated by different effector cell populations. In some situations, helper T cells designated Th1 in the murine system, facilitate immune effector functions that are typically dominated by cell-mediated responses. In other cases, helper T cells designated Th2 cells facilitate immune effector functions that are typically dominated by humoral responses. A vigorous Th1 response is usually desirable to help clear infections or to slow the progression of an infection. When a subject's immune response is biased to, or dominated by, a Th2-type response, the cytokines associated with the Th2 response tend to suppress the immune system's capacity to mount a vigorous Th1 response at the same time. The converse is also generally true. When mammalian immune responses begin to result in an increasing Th2 response, the Th1 response to the same condition tends to weaken. Insufficient Th1 responses may be associated with progression of some infections or other conditions, see, e.g., M. Clerici and G. M. Shearer, *Immunol. Today* 14:107-111, 1993; M. Clerici and G. M. Shearer, *Immunol. Today* 15:575-581, 1994. The invention provides compounds and compositions useful to enhance Th1 immune responses.

Hemopoiesis or hematopoiesis is the formation and development of the various types of blood cells and their progenitor cells. Mature cells are found in circulation or tissues such as the lymph nodes or the thymus. Many of the stem cells that give rise to mature forms reside in the bone marrow, although some may circulate in the blood for some time. Clinical blood cell deficiencies such as thrombocytopenia, neutropenia or erythropenia can arise from causes such as impaired hemopoiesis or abnormal loss or destruction of mature or immature blood cells.

Thrombocytopenia ("TP"), abnormally low platelet counts, can arise from impaired platelet production, sequestration of platelets in the spleen or abnormal loss of circulating platelets. Impaired production can result from causes such as chemotherapies or radiation therapies. Abnormal loss of circulating platelets is often associated with autoreactive antibodies that bind to platelets and reduce their life span. These underlying causes give rise to the various clinical forms of TP, such as autoimmune neonatal TP, immune thrombocytopenic purpra, radiation induced TP, chemotherapy induced TP and amegakaryocitic TP.

A number of treatment options are available and the selection of a treatment typically depends on the source of the disorder and its severity. Treatments include administering one or more of glucocorticoid steroids (e.g., prednisone, prednisolone), human IgG antibodies, anti-Rh(D)$^+$ antibodies for Rh (D)$^+$ patients, an androgen such as danazol, vinca alkaloids (e.g., vincristine, vinblastine), thrombopoietin and immunosuppresants (e.g., azathioprine, cyclophosphamide). Splenectomy is also indicated, for example when first line treatments fail. The goal of treatment is typically to increase platelet counts to 20,000 mm$^{-3}$ or more typically to at least about 50,000 mm$^{-3}$ and to maintain these levels.

Although the treatment options to increase platelet levels are generally known, they usually have a number of drawbacks. For example, infusion of IgG antibodies is not always effective and the treatment is relatively expensive. Other treatments, such as prednisone are also not always effective and they typically are discontinued or tapered off after several weeks due to toxicity or unwanted side effects. Splenectomy, which is relatively expensive and invasive, is also not always effective.

The sources of thrombocytopenia and treatment options have been described. See, e.g., *Hematology—Basic Principles and Practice*, 3$^{rd}$ edition, R. Hoffman, E. J. Benz Jr. et al., editors, Churchill Livingstone, New York, 2000 (see, e.g., Chapters 126-129 and 131 at pages 2096-2154 and 2172-2186), PCT publication WO 200035466.

Neutropenia ("NP"), is considered to exist clinically when neutrophils drop to below a level considered normal. NP can arise from impaired production of neutrophil precursors or mature neutrophils, movement of neutrophils from the circulation to tissue, abnormal circulating neutrophil loss or a combination of these causes. Impaired neutrophil production can be acquired from, e.g., treatment with a cytotoxic or cytostatic drug, chemotherapy, radiation therapy or an autoimmune response. The abnormal loss of circulating neutrophils in autoimmunity is associated with autoreactive antibodies that bind to the cells and reduce their life span. These underlying causes give rise to the various clinical forms of NP, such as postinfectious NP, drug-induced NP, autoimmune NP, or chronic idiopathic NP.

The sources of NP and treatment options have been described. See, e.g., *Hematology—Basic Principles and Practice*, 3$^{rd}$ edition, R. Hoffman, E. J. Benz Jr. et al., editors, Churchill Livingstone, New York, 2000 (see, e.g., Chapters 19, 41, 51, 79, 134 and 137 at pages 297-331, 720-762, 939-979, 1443-1500, 2220-2248 and 2257-2263).

The use of 3β-hydroxyandrost-5-ene-17-one, 3β,17β-dihydroxyandrost-5-ene and other steroids to modulate immune functions or to stimulate myelopoiesis has been described, see, e.g., M. H. Whitnall et al., *Int'l. J. Immunopharmacology* 2000 22:1-14. U.S. Pat. Nos. 5,162,198, 5,206,008, 5,292,730, 5,407,684, 5,461,042, 5,461,768, 5,478,566, 5,585,371, 5,635,496, 5,641,766, 5,753,237, 5,837,269, 5,885,977 and 5,919,465, PCT publication nos. WO93/20696 and WO99/25333.1. Porsova-Dutoit et al., *Physiological Res.* 2000 49 (Suppl. 1):543-556, R. L. Jesse et al., *Ann. N.Y. Acad. Sci.* 1995 774:281-290 and U.S. Pat. Nos. 5,532,230, 5,811,418 and 5,846,963 discuss the capacity of 3β-hydroxyandrost-5-ene-17-one, its 3-sulfate derivative and other steroids to affect platelet and neutrophil aggregation or their adhesion to endothelial cells.

U.S. Pat. Nos. 4,908,358 and 4,902,681 describe the capacity of compounds such as 5α-pregnan-3,20-dione, cortexolone, 17-hydroxyprogesterone and 16α-methylprogesterone to inhibit the clearance of antibody-coated cells from circulation in disorders such as immune thrombocytopenic purpura or immune hemolytic anemia.

U.S. Pat. Nos. 5,532,230, 5,686,438, 5,753,640 and 5,811,418 and J. Bratt and M. Heimburger, *Scand. J. Rheumatol.* 1999 28:308-313 describe the capacity of compounds such as 3β,7β-dihydroxyandrost-5-ene-17-one, prednisolone, and 3β-hydroxyandrost-5-ene-17-one to limit tissue damage in ischemic tissues by inhibiting adhesion of cells such as neutrophils to endothelial cells or to treat pulmonary hypertension.

U.S. Pat. No. 5,859,000 describes the capacity of compounds such as 3β,7β-dihydroxyandrost-5-ene-17-one and 3β-hydroxyandrost-5-ene-17-one to reduce mast cell mediated allergic reactions.

U.S. Pat. No. 5,763,433 and PCT publication WO 96/35428 describe the capacity of compounds related to dehydroepiandrosterone and 16α-halodehydroepiandrosterone to modulate immune responses and to treat conditions certain immune related conditions such as systemic lupus erythematosus.

U.S. Pat. Nos. 5,925,630, 5,939,545 and 5,962,443 describe the capacity of 19-nur-pregnane steroids, 3α-hydroxy-5α-pregnan-20-one and related steroids to modulate certain neurological activities such as hypothalamic function and GABA receptor activity.

Some proteins such as interleukin-6 ("IL-6"), erythropoietin ("EPO") and thrombopoietin ("TPO") have been examined for their capacity to enhance various aspects hemopoiesis, e.g., *Hematology—Basic Principles and Practice*, 3rd edition, R. Hoffman, E. J. Benz Jr. et al., editors, Churchill Livingstone, New York, 2000 (see, e.g., Chapter 14 at pages 154-202), O. J. Borge et al., *Blood* 1996 88:2859-2870, M. Cremer et al., *Ann. Hematol.* 1999 78:401-407, Y. Sasaki et al., *Blood* 1999 94:1952-1960, U.S. Pat. No. 5,879,673. Recombinant IL-6 was shown in model systems to affect platelet counts in peripheral circulation, e.g., Stahl et al., *Blood* 1991 78:1467-1475, although significant toxicities are associated with its administration to humans, e.g., Andus et al., *FEBS Lett.* 1987 221:18, J. Gauldie et al., *P.N.A.S. U.S.A.* 1987 84:7251-7255, T. Geiger et al., *Eur. J. Immunol.* 1988 18:717-721. The IL-6 molecule has been described in detail, e.g., publication no. WO 88/00206. Administration of proteins is typically expensive, given factors such as the complexity of producing pharmaceutical grade material.

The capacity of various compounds or agents such as deuterium oxide, lithium and butyrate to affect or to participate in biological functions of cells such as neutrophils has been described. See, e.g., M. F. Tsan and R. M. Turkall, *Inflammation* 1982 6:387-396, M. Nakamura et al., *Exp. Cell Res.* 1976 102:429-431, P. Blier et al., *Int. Clin. Psychopharmacol.* 1998 13:137-140, N. Turkozkan et al., *Int. J. Biochem.* 1993 25:1501-1504, L. V. Deriy et al., *Biochem. Biophys. Res. Commun.* 2000 275:241-246, M. T. Elghetany et al., *Leuk. Res.* 1997 21:801-806, E. Brandt et al., *J. Leukocyte Biol.* 2000 68:125-130, M. Boussac and J. Garin, Electrophoresis 2000 21:665-672, M. Niwa et al., *Life Sci.* 2000 18:1525-1534, D. A. Moulding et al., *J. Leukocyte Biol.* 1999 65:875-882 and D. Moulding et al., *Biologicals* 1996 24:301-306.

There is a current need for cost-effective pharmaceutical agents or treatment methods that are more effective in treating deficiencies of blood cells or reducing their symptoms. The present invention provides therapeutic agents and treatment methods to treat hemopoiesis deficiencies and disorders such as TP and NP. The agents and methods are thus useful to reduce one or more symptoms associated with any of these conditions. Also, the use of the invention agents and methods can be combined with one or more conventional treatments for these disorders.

Summary of invention embodiments. The invention provides a method to treat a blood cell deficiency in a subject in need thereof comprising administering to the subject, or delivering to the subject's tissues, an effective amount of a compound of formula 1

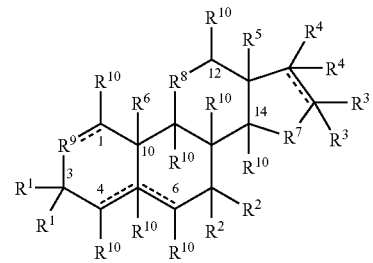

wherein, each $R^1$, $R^2$, $R^3$, $R^4$, $R^5$, $R^6$ and $R^{10}$ independently are —H, —$OR^{PR}$, —$SR^{PR}$, —$N(R^{PR})_2$, —O—Si—$(R^{13})_3$, —CHO, —CHS, —CH=NH, —CN, —SCN, —$NO_2$, —$OSO_3H$, —$OPO_3H$, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, a halogen, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, a nucleoside, a nucleotide, an oligonucleotide, a polymer, or, one or more of both $R^1$, $R^2$, $R^3$ or $R^4$ together comprise an independently selected spiro ring, or one more of $R^1$, $R^2$, $R^3$, $R^4$, $R^5$, $R^6$ and Fr are =O, =S, =N—OH, =$CH_2$, or a spiro ring and the hydrogen atom or the second variable group that is bonded to the same carbon atom is absent, or, one or more of two adjacent $R^1$-$R^6$ and $R^{10}$ comprise an independently selected an acetal, a thioacetal, ketal or thioketal, or all $R^3$ and $R^4$ together comprise a structure of formula 2

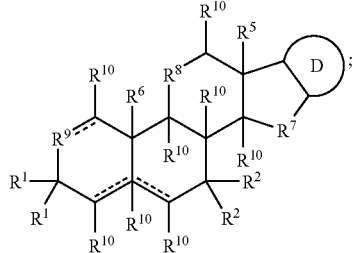

$R^7$ is —C($R^{10}$)$_2$—, —C($R^{10}$)$_2$—C($R^{10}$)$_2$—, —C($R^{10}$)$_2$—C($R^{10}$)$_2$—C($R^{10}$)$_2$—, —C($R^{10}$)$_2$—O—C($R^{10}$)$_2$—, —C($R^{10}$)$_2$—S—C($R^{10}$)$_2$—, —C($R^{10}$)$_2$—NR$^{PR}$—C($R^{10}$)$_2$—, —O—, —O—C($R^{10}$)$_2$—, —S—, —S—C($R^{10}$)$_2$—, —NR$^{PR}$— or —NR$^{PR}$—C($R^{10}$)$_2$—;

$R^8$ and $R^9$ independently are —C($R^{10}$)$_2$—, —C($R^{10}$)$_2$—C($R^{10}$)$_2$—, —O—, —O—C($R^{10}$)$_2$—, —S—, —S—C($R^{10}$)$_2$—, —NR$^{PR}$— or —NR$^{PR}$—C($R^{10}$)$_2$—, or one or both of $R^8$ or $R^9$ independently are absent, leaving a 5-membered ring;

$R^{13}$ independently is $C_{1-6}$ alkyl;

$R^{PR}$ independently is —H or a protecting group;

D is a heterocycle or a 4-, 5-, 6- or 7-membered ring that comprises saturated carbon atoms, wherein 1, 2 or 3 ring carbon atoms of the 4-, 5-, 6- or 7-membered ring are optionally independently substituted with —O—, —S— or —NR$^{PR}$— or where 1, 2 or 3 hydrogen atoms of the heterocycle or where 1, 2 or 3 hydrogen atoms of the 4-, 5-, 6- or 7-membered ring are substituted with —OR$^{PR}$, —SR$^{PR}$, —N(R$^{PR}$)$_2$, —O—Si—(R$^{13}$)$_3$, —CHO, —CHS, —CH=NH, —CN, —SCN, —NO$_2$, —OSO$_3$H, —OPO$_3$H, an ester, a thioester, a thionoester, a phosphoester, a phosphothioester, a phosphiniester, a sulfite ester, a sulfate ester, an amide, an amino acid, a peptide, an ether, a thioether, an acyl group, a thioacyl group, a carbonate, a carbamate, a halogen, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, a nucleoside, a nucleotide, an oligonucleotide or a polymer, or, one more of the ring carbons in D are substituted with =O, =S, =N—OH, =CH$_2$, or a spiro ring, or one or more of two adjacent ring carbons in D comprise an independently selected acetal, thioacetal, ketal or thioketal, or D comprises two 5- or 6-membered rings, wherein the rings are fused or are linked by 1 or 2 bonds, or a metabolic precursor or a biologically active metabolite thereof. In some embodiments, the compound is not 5-androstene-3β-ol-17-one, 5-androstene-3β,17β-diol, 5-androstene-3β,7β,17β-triol or a derivative of any of these three compounds that can convert to these compounds by hydrolysis.

Invention embodiments also provide a method to modulate an immune or cellular response in a subject in need thereof comprising administering to the subject, or delivering to the subject's tissues, an effective amount of a compound of formula 1

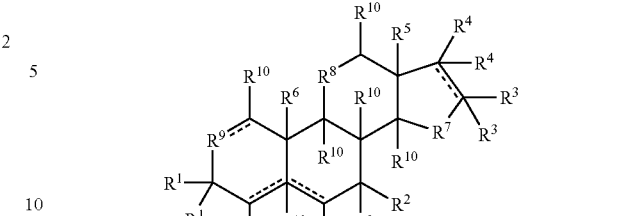

wherein,
each $R^1$, $R^2$, $R^3$, $R^4$, $R^5$, $R^6$ and $R^{10}$ independently are —H, —OR$^{PR}$, —SR$^{PR}$, —N(R$^{PR}$)$_2$, —O—Si—(R$^{13}$)$_3$, —CHO, —CHS, —CH=NH, —CN, —SCN, —NO$_2$, —OSO$_3$H, —OPO$_3$H, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, a halogen, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, a nucleoside, a nucleotide, an oligonucleotide, a polymer, or, one or more of both $R^1$, $R^2$, $R^3$ or $R^4$ together comprise an independently selected spiro ring, or one more of $R^1$, $R^2$, $R^3$, $R^4$, $R^5$, $R^6$ and $R^{10}$ independently are =O, =S, =N—OH, =CH$_2$, or a spiro ring, and the hydrogen atom or the second variable group that is bonded to the same carbon atom is absent, or, one or more of two adjacent $R^1$-$R^6$ and $R^{10}$ comprise an independently selected acetal, thioacetal, ketal or thioketal;

all $R^3$ and $R^4$ together comprise a structure of formula 2

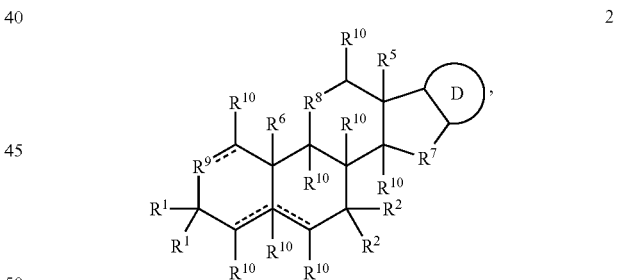

$R^7$ is —C($R^{10}$)$_2$—, —C($R^{10}$)$_2$—C($R^{10}$)$_2$—, —C($R^{10}$)$_2$—C($R^{10}$)$_2$—C($R^{10}$)$_2$—, —C($R^{10}$)$_2$—O—C($R^{10}$)$_2$—, —C($R^{10}$)$_2$—S—C($R^{10}$)$_2$—, —C($R^{10}$)$_2$—NR$^{PR}$—C($R^{10}$)$_2$—, —O—, —O—C($R^{10}$)$_2$—, —S—, —S—C($R^{10}$)$_2$—, —NR$^{PR}$— or —NR$^{PR}$—C($R^{10}$)$_2$—;

$R^8$ and $R^9$ independently are —C($R^{10}$)$_2$—, —C($R^{10}$)$_2$—C($R^{10}$)$_2$—, —O—, —O—C($R^{10}$)$_2$—, —S—, —S—C($R^{10}$)$_2$—, —NR$^{PR}$— or —NR$^{PR}$—C($R^{10}$)$_2$—, or one or both of $R^8$ or $R^9$ independently are absent, leaving a 5-membered ring;

$R^{13}$ independently is $C_{1-6}$ alkyl;

$R^{PR}$ independently is —H or a protecting group;

D is a heterocycle or a 4-, 5-, 6- or 7-membered ring that comprises saturated carbon atoms, wherein 1, 2 or 3 ring carbon atoms of the 4-, 5-, 6- or 7-membered ring are optionally independently substituted with —O—, —S— or —NR$^{PR}$— or where 1, 2 or 3 hydrogen atoms of the heterocycle or where 1, 2 or 3 hydrogen atoms of the 4-, 5-, 6- or 7-membered ring are independently substituted with —OR$^{PR}$, —SR$^{PR}$, —N(R$^{PR}$)$_2$, —O—Si—(R$^{13}$)$_3$, —CHO, —CHS, —CH=NH, —CN, —SCN, —NO$_2$, —OSO$_3$H, —OPO$_3$H, an ester, a thioester, a thionoester, a phosphoester, a phosphothioester, a phosphiniester, a sulfite ester, a sulfate ester, an amide, an amino acid, a peptide, an ether, a thioether, an acyl group, a thioacyl group, a carbonate, a carbamate, a halogen, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, a nucleoside, a nucleotide, an oligonucleotide or a polymer, or, one more of the D ring carbons are substituted with =O, =S, =N—OH, =CH$_2$, or a spiro ring, or two adjacent D ring carbons comprise an independently selected acetal, thioacetal, ketal or thioketal moiety, or D comprises two 5- or 6-membered rings, wherein the rings are fused or are linked by 1 or 2 bonds, or a metabolic precursor or a biologically active metabolite thereof, optionally provided that if the subject is in need of enhanced hemopoiesis, the compound is not 5-androstene-3β-ol-17-one, 5-androstene-3β,17β-diol, 5-androstene-3β,7β,17β-triol or a derivative of any of these three compounds that can convert to these compounds by hydrolysis. Immune and cellular response modulation includes enhancing Th1 immune responses, reducing Th2 immune responses, reducing inflammation and enhancing hemopoiesis.

In other embodiments, the invention provides a compound of formula 1, wherein two or three of R$^7$, R$^8$ and R$^9$ independently are not —CHR$^{10}$—, or —C(R$^{10}$)$_2$— and wherein the compound is optionally present in a composition that comprises one or more excipients.

Other embodiments include a method to enhance the expression of one or more cytokines or interleukins that facilitate Th1 or Tc1 immune responses in a subject or to reduce the expression of one or more cytokines or interleukins that facilitate Th2 or Tc2 immune response in a subject comprising administering to the subject an effective amount of a formula 1 compound, whereby the subject's Th1 or Tc1 immune response is enhanced to the subject's undesired Th2 or Tc2 immune response is reduced.

A further embodiment is a method to modulate a subject's innate immunity, Th1 immune responses, Tc1 immune responses, Th2 immune responses, Tc2 immune responses, or inflammation comprising administering an effective amount of a formula 1 compound to a subject or delivering the formula 1 compound to the subject's tissues.

Other embodiments are as described elsewhere in the specification including the numbered embodiments and the claims.

Definitions. As used herein and unless otherwise stated or implied by context, terms that are used herein have the meanings that are defined here. The descriptions of embodiments and examples that are described illustrate the invention and they are not intended to limit it in any way. Unless otherwise contraindicated or implied, e.g., by including mutually exclusive elements or options, in these definitions and throughout this specification, the terms "a" and "an" mean one or more and the term "or" means and/or.

An "invention formulation", "formulation" or the like means a composition that one can administer to a subject, e.g., human or animal, without further manipulations that change the ingredients or the ingredient proportions that are present. Formulations are suitable for human or veterinary applications and would typically have expected characteristics for the formulation, e.g., parenteral formulations for human use would usually be sterile.

An "invention composition", "composition" or the like means a composition, that is a formulation or that can be an intermediate one can use to make the formulations, i.e., a change(s) in an ingredient(s) or its amount(s) may be needed to make a formulation. Compositions may also comprise other types of materials, e.g., reagents for assays or cells that are optionally contacted with a formula 1 compound or mixtures of compounds. Thus, invention compositions include compositions where further processing may be required before it is a formulation, e.g., mixing or addition of a desired amount of an ingredient.

Phrases such as "administration of a compound of formula 1", "treatment with a formula 1 compound" or similar terms mean that the compound(s) is administered to, or delivered to, the subject or to the subject's tissues by one or more suitable methods, e.g., by an oral, topical, parenteral, buccal or sublingual route.

Expressions such as "a formula 1 compound(s)", "a formula 1 compound" and the like mean invention compositions or formulations where one or more than one formula 1 compound is present, e.g., in a composition, or is used in the disclosed method, typically 1, 2, 3 or 4, usually 1. Any reference to a "formula 1 compound", "one or more compounds of formula 1" or the like means that the formula 1 compound can have the formula 2 structure or any other structure disclosed herein that is within the definition of formula 1 compounds.

Reference to subject matter "as disclosed herein" such as a "therapeutic treatment or agent as disclosed herein", a "dosing protocol as disclosed herein" or a "clinical condition or symptom as disclosed herein" or the like means a treatment, agent, protocol, condition, symptom or the like that is described herein or in any reference that is cited herein.

An "excipient", "carrier", "pharmaceutically acceptable carrier" or similar terms mean one or more component(s) or ingredient(s) that is acceptable in the sense of being compatible with the other ingredients of invention compositions or formulations and not overly deleterious to the patient, animal, tissues or cells to which the formulation is to be administered.

As used here, "excipients" include liquids, such as benzyl benzoate, cottonseed oil, N,N-dimethylacetamide, a C$_{2-12}$ alcohol (e.g., ethanol), glycerol, peanut oil, a polyethylene glycol ("PEG"), vitamin E, poppyseed oil, propylene glycol, safflower oil, sesame oil, soybean oil and vegetable oil. Any solid excipient may be a fine powder or granulated. Excipients, as used herein may optionally exclude one or more excipient, e.g., chloroform, dioxane, vegetable oil, DMSO, other excipients or any combination of these. Excipients include one or more components typically used in the pharmaceutical formulation arts, e.g., one, two or more of fillers, binders, disintegrants, dispersants, preservatives, glidants and lubricants. Exemplary excipients include povidone, crospovidone, corn starch, carboxymethyl cellulose, hydroxypropyl methylcellulose, microcrystalline cellulose, gum arabic, polysorbate 80, butylparaben, propylparaben, methylparaben, BHA, EDTA, sodium lauryl sulfate, sodium chloride, potassium chloride, titanium dioxide, magnesium stearate, castor oil, olive oil, vegetable oil, buffering agents such as sodium hydroxide, monobasic sodium phosphate, dibasic sodium phosphate, potassium hydroxide, monobasic potassium phosphate, dibasic potassium phosphate, tribasic potassium phosphate, potassium carbonate, potassium bicarbonate, ammonium hydroxide, ammonium chloride, saccharides such as mannitol, glucose, fructose, sucrose or lactose any of which may be compressible or any of which may be spray dried.

A "subject" means a human or animal. Usually the animal is a mammal or vertebrate such as a primate, rodent, lagomorph, domestic animal or game animal. Primates include chimpanzees, cynomologous monkeys, spider monkeys, and macaques, e.g., Rhesus or Pan. Rodents and lagomorphs include mice, rats, woodchucks, ferrets, rabbits and hamsters. Domestic and game animals include cows, horses, pigs, sheep, deer, bison, buffalo, mink, felines, e.g., domestic cat, canines, e.g., dog, wolf and fox, avian species, e.g., chicken, turkey, emu and ostrich, and fish, e.g., trout, catfish and salmon. Subject includes any subset of the foregoing, e.g., all of the above, but excluding one or more groups or species such as humans, primates or rodents. Other subsets of subjects include subjects of a given species or group of species of varying ages, e.g., young humans, e.g., about 1 week of age to about 9 years of age, adolescent humans, e.g., about 10-19 years of age, adult humans, e.g., about 20-100 years of age, and mature adult or elderly humans, e.g., at least about 55 years of age, at least about 60 years of age, at least about 65 years of age or a range of ages such as about 60-100 years of age. Thus, as used herein, prevention or treatment of a disease, condition or symptom may include or exclude any subset of subjects that are grouped by age.

The terms "effective amount", "effective dose" or the like mean an amount of a formula 1 compound that is sufficient to elicit a desired response, e.g., restoration of normal immune responsiveness in an immunodeficient subject to which it is administered or to detectable modulation or amelioration of an immune or cellular parameter or a clinical condition or symptom. An effective amount may be a single dose or two or more subdoses of a formula 1 compound administered in one day, or it may be administered as multiple doses over a period of time, e.g., over 2 days to about 1 year.

References such as "a disease", "a disorder", "a condition", "a symptom" or "a complication" or the like mean that one or more disease, disorder, condition, symptom or complication may be treated.

Terms such as "use", "treat", "treatment", "address" or the like in the context of using the formula 1 compounds in the treatment methods or other methods disclosed herein mean that a formula 1 compound is administered to a subject, delivered to the subject's tissues or contacted with tissues, cells or cell free systems, e.g., as described herein or a reference cited herein. Typically such use or treatment results in detectable improvement in or amelioration of the condition or symptom being treated. Such amelioration may be transient, e.g., lasting for at least a few, e.g., about 1 to 24, hours or days, e.g., about 1-,7 days, or amelioration may be prolonged, e.g., lasting about 8 to about 60 days or more, or it may be permanent. A treatment may slow the progression or severity of a disease or symptom. A use or treatment may result in detectable modulation in a relevant immune parameter such as modulation of the level or activity of a target effector or suppressor immune cell population, interleukin, cytokine, chemokine, immunoglobulin or modulation of the level or activity of a relevant transcription factor, enzyme or cell biological activity. A treatment with the compounds may be used to prevent the onset of a disease, symptom or complication or to ameliorate a preexisting disease, condition, symptom or complication, or to facilitate elimination of a disease, condition, symptom or complication.

"Ameliorate", "amelioration", "improvement" or the like means a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with a formula 1 compound, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after a formula 1 compound is administered to a subject or is used in an assay or other method described herein or a cited reference, e.g., within about 1 hour of the administration or use of a formula 1 compound to about 3, 6, 9 months or more after a subject(s) has received a formula 1 compound.

The "modulation" of, e.g., a symptom, level or biological activity of a molecule, replication of a pathogen, cellular response, cellular activity or the like, means that the cell, level or activity, or the like is detectably increased or decreased. Such increase or decrease may be observed in treated subjects as compared to subjects not treated with a formula 1 compound, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after a formula 1 compound is administered to a subject or is used in an assay or other method described herein or a cited reference, e.g., within about 1 hour of the administration or use of a formula 1 compound to about 3, 6, 9 months or more after a subject(s) has received a formula 1 compound.

Terms such as "antigen", "immunogen" or the like mean a molecule that comprises one or more epitopes that are capable of stimulating a subject's immune system to make, e.g., a secretory, humoral or cellular antigen-specific response against the antigen or immunogen. These terms also include fragments or synthetic or natural derivatives of these molecules that retain at least a detectable capacity, e.g., at least about 10%, 20%, 30%, 40%, 50% or more of the native antigen's antigenic capacity, to stimulate a subject's immune system in a desired manner.

"Vaccine composition", "vaccine" or similar terms mean an agent suitable for stimulating a subject's immune system to ameliorate a current condition or to protect against or to reduce present or future harm or infection, e.g., reduced tumor cell proliferation or survival, reduced pathogen replication or spread in a subject or a detectably reduced unwanted symptom(s) associated with a condition. Vaccines may modulate, typically detectably enhance, humoral, cell mediated or innate immune responses.

"Immunization" means the process of inducing a detectable and continuing moderate or high level of antibody or cellular immune response that is directed against an antigen to which the subject has been exposed. Such responses are typically detectably maintained for at least about 3-48 months or more.

At various locations in the present disclosure, e.g., in any disclosed embodiments or in the claims, reference is made to compounds, compositions, formulations, or methods that comprise one or more specified components, elements or steps. Invention embodiments also specifically include those compounds, compositions, formulations or methods that consist of or that consist essentially of those specified components, elements or steps. The terms "comprising", "consist of" and "consist essentially of" have their normally accepted meanings under U.S. patent law. For example, disclosed compositions or methods that "comprise" a component or step are open and they include or read on those compositions or methods plus an additional component(s) or step(s). Similarly, disclosed compositions or methods that "consist of" a component or step are closed and they would not include or read on those compositions or methods having appreciable amounts of an additional component(s) or an additional step(s).

"Alkyl" as used here means linked normal, secondary, tertiary or cyclic carbon atoms, i.e., linear, branched, cyclic or any combination thereof. Alkyl moieties, as used herein, may be saturated, or unsaturated, i.e., the moiety may comprise one or more independently selected double bonds or triple bonds. Unsaturated alkyl moieties include moieties as described for alkenyl and alkynyl moieties described below. The number of carbon atoms in an alkyl group or moiety is 1 to about 50, e.g., about 1-30 or about 1-20, unless otherwise specified, e.g., $C_{1-8}$ alkyl means an alkyl moiety containing 1, 2, 3, 4, 5, 6, 7 or 8 carbon atoms. When an alkyl group is specified, species may include methyl, ethyl, 1-propyl (n-propyl), 2-propyl (i-propyl, —CH(CH$_3$)$_2$), 1-butyl (n-butyl), 2-methyl-1-propyl (i-butyl, —CH$_2$CH(CH$_3$)$_2$), 2-butyl (s-butyl, —CH(CH$_3$)CH$_2$CH$_3$), 2-methyl-2-propyl (t-butyl, —C(CH$_3$)$_3$), 1-pentyl (n-pentyl), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl, 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), cyclopropyl, cyclobutyl, cyclopentyl, cyclohexyl, cycloheptyl, cyclooctyl, —(CH$_2$)$_n$—(CHCH$_3$)$_m$—(CH$_2$)$_o$—CH$_3$ and —(CH$_2$)$_n$—(CHC$_2$H$_5$)$_m$—(CH$_2$)$_o$—CH$_3$ where n, m and o independently are 0, 1, 2, 3, 4, 5, 6, 7 or 8.

"Alkenyl" as used here means a moiety that comprises linked normal, secondary, tertiary or cyclic carbon atoms, i.e., linear, branched, cyclic or any combination thereof, that comprises one or more double bonds (e.g., —CH═CH—), e.g., 1, 2, 3, 4, 5, 6 or more, typically 1 or 2. The number of carbon atoms in an alkenyl group or moiety is 2 to about 50, e.g., about 2-30 or about 2-20, unless otherwise specified, e.g., $C_{2-8}$ alkenyl or C2-8 alkenyl means an alkenyl moiety containing 2, 3, 4, 5, 6, 7 or 8 carbon atoms. When an alkenyl group is specified, species may include vinyl, allyl, —(CH$_2$)$_n$—(CH═CH)—(CH$_2$)$_m$—CH$_3$, —(CH$_2$)$_n$—(CCH$_3$═CH)—(CH$_2$)$_m$—CH$_3$, —(CH$_2$)$_n$—(CH═CCH$_3$)—(CH$_2$)$_m$—CH$_3$ and —(CH$_2$)$_n$—(CH═CH)$_{0-1}$—(CH$_2$)$_m$—CH$_2$CH═CH$_2$, where n and m independently are 0, 1, 2, 3, 4, 5, 6, 7 or 8.

"Alkynyl" as used here means a moiety that comprises linked normal, secondary, tertiary or cyclic carbon atoms, i.e., linear, branched, cyclic or any combination thereof, that comprises one or more triple bonds (—C≡C—), e.g., 1, 2, 3, 4, 5, 6 or more, typically 1 or 2 triple bonds, optionally comprising 1, 2, 3, 4, 5, 6 or more double bonds, with the remaining bonds being single bonds. The number of carbon atoms in an alkenyl group or moiety is 2 to about 50, e.g., about 2-30 or about 2-20, unless otherwise specified, e.g., $C_{2-8}$ alkynyl or $C_{2-8}$ alkynyl means an alkynyl moiety containing 2, 3, 4, 5, 6, 7 or 8 carbon atoms. When an alkynyl group is specified, groups and species may include —C≡H, —CCCH$_3$, —CCCH$_2$CH$_3$, —CCC$_3$H$_7$, —CCCH$_2$C$_3$H$_7$, —(CH$_2$)$_n$—(C≡C)—(CH$_2$)$_m$—CH$_3$, and —(CH$_2$)$_n$—(C≡C)$_{0-1}$—(CH$_2$)$_m$—CH$_2$C≡CH, where n and m independently are 0, 1, 2, 3, 4, 5, 6, 7 or 8.

"Aryl" means phenyl or naphthyl.

"Substituted alkyl", "substituted alkenyl", "substituted heterocycle", "substituted aryl", "substituted monosaccharide" and the like mean an alkyl, alkenyl, heterocycle, aryl, monosaccharide or other group or moiety as defined herein that has a substituent(s) or that comprises a substituent(s) that replaces a hydrogen atom(s) and is bonded to a carbon atom(s) or a substituent(s) that interrupts a carbon atom chain. Substituted heterocycles may have a substituent bonded to a ring carbon or a ring heteroatom such as a nitrogen. Substituents include 1, 2, 3, 4, 5, 6 or more independently selected —O—, —S—, —NH—, —C(O)—, —C(O)OR$^{15}$, —C(O)OR$^{PR}$, —C(O)SR$^{15}$, —C(O)SR$^{PR}$, —CHO, —CH$_2$SH, —C═N—, —OH, —OR$^{15}$, —OR$^{PR}$, —C(O)OR$^{PR}$, —C(O)CH$_3$, —C(S)CH$_3$, —C(S)SH, —C(S)SR$^{15}$, —C(S)SR$^{PR}$, —C(O)CH$_2$OH, —C(O)CH$_2$F, —C(O)CH$_2$Cl, —C(O)CH$_2$Br, —C(O)CH$_2$I, —C(O)NHCH$_3$, —C(O)NHC$_2$H$_5$, —C(O)NHC(CH$_3$)$_3$, —O—CH$_2$—C(O)—C(CH$_3$)$_3$, —C(O)—C(CH$_3$)$_3$, —O—CH(CH$_3$)—O—C(CH$_3$)$_3$, —C(O)O—, —C(S)OR$^{PR}$, —C(S)O—, —OC(O)—, —C(O)H, —OCH$_2$—, —CH$_2$—O—CH$_2$—, —(CH$_2$)$_{1-2}$—O—(CH$_2$)$_2$—, —OCH$_2$CH$_2$—, —OCH$_2$O—, —OCH$_2$CH$_2$O—, —CH$_2$OH, —CH$_2$F, —CHF$_2$, —CF$_3$, —CH$_2$Cl, —CH$_2$Br, —CH$_2$I, —C$_2$H$_4$Cl, —C$_2$H$_4$Br, —C$_2$H$_4$I, —CH$_2$CH$_2$F, —CH$_2$CHF$_2$, —CH$_2$CF$_3$, —N(R$^{PR}$)$_2$, —NHR$^{PR}$, —NHC(O)—, —CH$_2$—NR$^{PR}$—, —CH$_2$—NHR$^{PR}$, —CH$_2$—NHC(O)—, —C(O)NH—, —C(O)NHR$^{PR}$, —OC(O)NR$^{PR}$—, —OC(O)NHR$^{PR}$, —C(═NH)—NH$_2$, —C(═NH)OH, —C(═N—NH$_2$)OH, —C(O)NHOH, —NH$_2$, —NHR$^{PR}$, ═NOH, —NHR$^{15}$, ═NR$^{15}$, ═N—, —NR$^{PR}$C(O)NR$^{PR}$—, —NR$^{PR}$C(O)NHR$^{PR}$, —NR$^{PR}$CH$_2$—, —NR$^{PR}$CH$_2$CH$_2$—, —NO$_2$, —S—, —SR$^{15}$, —SR$^{PR}$, —S(O)R$^{15}$, —S(O)OR$^{15}$, —S(O)—, —S(O)(O)—, —S(S)(O)—, —S(O)(O)—O—, —S(S)(O)—O—, —S(S)(S)—O—, —S(O)OR$^{PR}$, —S(O)(O)OH, —S(O)(O)OR$^{15}$, —S(O)(O)OR$^{PR}$, —S(O)OH, —S(O)OR$^{15}$, —S(O)OR$^{PR}$, —S(O)R$^{15}$, —S(O)R$^{PR}$, —S(S)OH, —S(O)SH, —S(O)SR$^{15}$, —CN, —SCN, —NO$_2$, —C(O)OH, —C(O)OR$^{15}$, —C(O)OR$^{PR}$, —C(O)SH, —C(O)SR$^{15}$, —C(O)SR$^{PR}$, —C(S)OH, —C(S)OR$^{15}$, —C(S)OR$^{PR}$, —O—P(O)(O)OH, —O—P(O)(O)OR$^{15}$, —O—P(O)(O)OR$^{PR}$, —O—P(S)(O)OH, —O—P(S)(O)OR$^{15}$, —O—P(S)(O)OR$^{PR}$, —O—P(O)(O)SH, —O—P(O)(O)SR$^{15}$, —O—P(O)(O)SR$^{PR}$, —F, —Cl, —Br, —I, -amino acid-, —O-monosaccharide, —O-disaccharide, —S-monosaccharide, —S-disaccharide, a polymer, e.g., a PEG, and combinations of these moieties and salts on any of these moieties that can form a salt, where R$^{PR}$ independently is hydrogen, a protecting group or both R$^{PR}$ are hydrogen or together are a protecting group and $R^{15}$ is —H, —CH$_3$, —C$_2$H$_5$, —C$_3$H$_7$, —C$_4$H$_9$, —C(CH$_3$)$_3$, —CH$_2$OH, —C$_2$H$_4$OH, —C$_3$H$_6$OH, —C$_4$H$_8$OH—C(CH$_2$OH)(CH$_3$)$_2$, —C$_3$H$_5$, —C$_4$H$_7$, optionally substituted C1-10 alkyl, C1-10 perfluoroalkyl, optionally substituted aryl, optionally substituted C1-12 alkylaryl, optionally substituted C1-12 arylalkyl, optionally substituted allyl, optionally substituted heterocycle, optionally substituted C1-4 alkyl-optionally substituted heterocycle or optionally substituted heterocycle-optionally substituted C1-4 alkyl. Substituents are independently chosen when more than one is present. Alkenyl and alkynyl groups that comprise a substituent(s), are optionally substituted at a carbon that is one or more methylene moiety removed from the double bond, e.g., separated by one, two, three or more independently selected —CH$_2$—, —CH(C$_{1-6}$ optionally substituted alkyl)-, —CH(C$_{1-6}$ optionally substituted alkenyl)-, —CH(C$_{1-6}$ optionally substituted alkynyl)-, —CH(optionally substituted heterocycle)-, —CH(optionally substituted aryl-optionally substituted alkyl)- or —CH(optionally substituted alkyl-optionally substituted aryl)-moieties.

"Heterocycle" or "heterocyclic" includes by way of example and not limitation the heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 1960, 82:5566. Heterocycles are typically bonded to moieties of which they are a part through a ring carbon atom, a ring nitrogen atom or a ring sulfur atom.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Typically, nitrogen bonded heterocycles include 1-aziridyl, 1-azetedyl, 1-pyrrolyl, 1-imidazolyl, 1-pyrazolyl, and 1-piperidinyl.

"Heteroaryl" means an aromatic ring or two or more fused rings that contain one or more aromatic rings where the ring or fused rings comprise 1, 2, 3 or more heteroatoms, usually oxygen (—O—), nitrogen (—NX—) or sulfur (—S—) where X is —H, a protecting group or C$_{1-6}$ alkyl, usually —H. Examples are as described for heterocycle.

"Alcohol" as used herein means an alcohol that comprises a C$_{1-12}$ alkyl moiety substituted at a hydrogen atom with one hydroxyl group. Alcohols include methanol, ethanol, n-propanol, i-propanol, n-butanol, i-butanol, s-butanol, t-butanol, n-pentanol, i-pentanol, n-hexanol, cyclohexanol, n-heptanol, n-octanol, n-nonanol and n-decanol. The carbon atoms in alcohols can be straight, branched or cyclic. Alcohol includes any subset of the foregoing, e.g., C$_{2-4}$ alcohols (alcohols having 2, 3 or 4 carbon atoms).

"Halogen" means fluorine, chlorine, bromine or iodine.

"Protecting group" means a moiety that prevents the atom to which it is linked from participating in unwanted reactions. For example, for —OR$^{PR}$, R$^{PR}$ may be hydrogen or a protecting group for the oxygen atom found in a hydroxyl, while for —C(O)—OR$^{PR}$, R$^{PR}$ may be hydrogen or a carboxyl protecting group, for —SR$^{PR}$, R$^{PR}$ may be hydrogen or a protecting group for sulfur in thiols for instance, and for —NHR$^{PR}$ or —N(R$^{PR}$)$_2$—, R$^{PR}$ may be hydrogen or a nitrogen atom protecting group for primary or secondary amines. Hydroxyl, amine and other reactive groups are found in formula 1 compounds at, e.g., R$^1$ or R$^2$. These groups may require protection against reactions taking place elsewhere in the molecule. The protecting groups for oxygen, sulfur or nitrogen atoms are usually used to prevent unwanted reactions with electrophilic compounds, such as acylating used, e.g., in steroid chemistry.

"Ester" means a moiety that comprises a —C(O)—O— structure. Typically, esters as used here comprise an organic moiety containing about 1-50 carbon atoms (e.g., about 2-20 carbon atoms) and 0 to about 10 independently selected heteroatoms (e.g., O, S, N, P, Si), where the organic moiety is bonded to a formula 1 steroid nucleus at, e.g., R$^1$ or R$^2$ through the —C(O)—O— structure, e.g., organic moiety-C(O)—O-steroid or organic moiety-O—C(O)-steroid. The organic moiety usually comprises one or more of any of the organic groups described above, e.g., C$_{1-20}$ alkyl moieties, C$_{2-20}$ alkenyl moieties, C$_{2-20}$ alkynyl moieties, aryl moieties, C$_{2-9}$ heterocycles or substituted derivatives of any of these, e.g., comprising 1, 2, 3, 4 or more substituents, where each substituent is independently chosen. Exemplary substitutions for hydrogen or carbon atoms in these organic groups are as described above for substituted alkyl moieties and include 1, 2, 3, 4, 5, 6 or more, usually 1, 2, or 3 —O—, —S—, —NR$^{PR}$— (including —NH—), —C(O)—, —CHO, —CHS, —C═NH, —C(S), ═O, ═S, —N(R$^{PR}$)$_2$ (including —NH$_2$), —C(O)OR$^{PR}$ (including —C(O)OH), —OC(O)R$^{PR}$ (including —O—C(O)—H), —OR$^{PR}$ (including —OH), —SR$^{PR}$ (including —SH), —NO$_2$, —CN, —SCN, —C$_6$H$_5$, —CH$_2$C$_6$H$_5$, —NHC(O)—, —C(O)NH—, —OC(O)—, —C(O)O—, —O-A8, —S-A8, —C(O)-A8, —OC(O)-A8, —C(O)O-A8, =N—, —N=, =N—OH, —OPO$_3$(R$^{PR}$)$_2$, —OSO$_3$H$_2$ or halogen moieties or atoms, where each R$^{PR}$ is —H, an independently selected protecting group or both R$^{PR}$ together comprise a protecting group, and A8 is C$_{1-8}$ alkyl, C$_{2-8}$ alkenyl, C$_{2-8}$ alkynyl, C$_{1-4}$ alkyl-aryl (e.g., benzyl), aryl (e.g. phenyl) or C$_{0-4}$ alkyl-C$_{2-9}$ heterocycle. Substitutions are independently chosen. The organic moiety includes compounds defined by the R$_4$ variable. The organic moieties exclude obviously unstable moieties, e.g., —O—O—, except where such unstable moieties are transient species that one can use to make a compound with sufficient chemical stability for one or more of the uses described herein, including for synthesis of the formula 1 or other compounds. The substitutions listed above are typically substituents that one can use to replace one or more carbon atoms, e.g., —O— or —C(O)—, or one or more hydrogen atom, e.g., halogen, —NH$_2$ or —OH. Exemplary esters include one or more independently selected acetate, enanthate, propionate, isopropionate, cyclopropionate, isobutyrate, butyrate, valerate, caproate, isocaproate, hexanoate, heptanoate, octanoate, nonanoate, decanoate, undecanoate, phenylacetate or benzoate, which are typically hydroxyl esters.

"Thioester" means a moiety that comprises a —C(O)—S— structure. Typically, thioesters as used here comprise an organic moiety containing about 1-50 carbon atoms (e.g., about 2-20 carbon atoms) and 0 to about 10 heteroatoms (e.g., O, S, N, P, Si), where the organic moiety is bonded to a formula 1 steroid nucleus at a variable group such as R$^1$, R$^2$, R$^3$, R$^4$ or R$^{10}$ through the —C(S)—O— structure, e.g., organic moiety-C(S)—O-steroid or organic moiety-O—C(S)-steroid. The organic moiety is as described above for esters.

"Thionoester" means a moiety that comprises a —C(S)—O— structure. Typically, thionoesters as used here comprise an organic moiety containing about 1-50 carbon atoms (e.g., about 2-20 carbon atoms) and 0 to about 10 heteroatoms (e.g., O, S, N, P, Si), where the organic moiety is bonded to a formula 1 steroid nucleus at a variable group such as R$^1$, R$^2$, R$^3$, R$^4$ or R$^{10}$ through the —C(S)—O— structure, e.g., organic moiety-C(S)—O-steroid or organic moiety-O—C(S)-steroid. The organic moiety is as described above for esters.

"Acetal" means a moiety that comprises (1) a —O—[C(CR$^{36}$)$_2$]$_{1-4}$—O— structure where the open valences are bonded to adjacent carbons on the steroid nucleus, e.g., the 16 and 17 positions or the 2 and 3 positions, or (2) a —O—[C(CR$^{36}$)$_2$]$_{1-4}$—O— structure where the open valences are bonded to the same carbon on the steroid nucleus, where each R$^{36}$ independently is —H, —F, —Cl, —Br, —I or an organic moiety such as C1-6 alkyl (e.g., methyl or ethyl), C2-6 alkenyl, aryl or a heterocycle, any of which are optionally substituted, e.g., —CF$_3$ or —CH$_2$OH. Typically, acetals as used here comprise an organic moiety containing about 1-50 carbon atoms (e.g., about 2-20 carbon atoms) and 0 to about 10 heteroatoms (e.g., O, S, N, P, Si), where the organic moiety is bonded to a formula 1 steroid nucleus at variable groups such as R$^1$, R$^2$, R$^3$, R$^4$ or R$^{10}$ through the —O—[C(CR$^{36}$)$_2$]$_{1-4}$—O— structure, e.g., 16-steroid-O—[C(CR$^{36}$)$_2$]$_{1-4}$—O-17-steroid or 17-steroid-O—[C(CR$^{36}$)$_2$]$_{1-4}$—O-17-steroid. The organic moiety is as described above for esters.

"Ketal" and "thioketal" mean an organic moiety that is bonded to two adjacent steroid ring atoms in the formula 1 compounds, e.g., ring atoms at the 1-2, 2-3, 3-4, 6-7, 14-15, 15-16 or 16-17 positions. The steroid ring atoms are carbon and the ketal is bonded to each adjacent carbon by an oxygen atom. Thioketals are bonded through one oxygen and one sulfur atom. One, two or more of two adjacent R$^1$-R$^6$ and R$^{10}$ may comprise an independently selected ketal or thioketal in any of the formula 1 compounds disclosed herein. The oxygen or sulfur atoms in ketals and thioketals are linked by an optionally substituted alkyl moiety. Typically the alkyl moiety is an optionally substituted C1-C6 alkylene such as —C(CH$_3$)$_2$—, —CH(CH$_3$)—, —CH$_2$—, —CH$_2$—CH$_2$—, —C(C$_2$-C$_4$ alkyl)$_2$- or —CH(C$_2$-C$_4$ alkyl)-. Exemplary ketal and thioketals include —O—C(CH$_3$)$_2$—O—, —O—C(CH$_3$)(heterocycle)-O—, —O—CH(heterocycle)-O—, —O—C(CH$_3$)(aryl)-O—, —O—CH(aryl)-O—, —S—C(CH$_3$)$_2$—O—, —O—CH$_2$—CH$_2$—O—, —O—C(CH$_3$)$_2$—CH$_2$—O—, —O—C(CH$_3$)$_2$—C(CH$_3$)$_2$—O—, —S—C(CH$_3$)$_2$—CH$_2$—O—, —O—C(CH$_3$)$_2$—CH$_2$—S— and the like.

"Thioacetal" means a moiety that comprises (1) a —S—[C(CR$^{36}$)$_2$]$_{1-4}$—O— or —S—[C(CR$^{36}$)$_2$]$_{1-4}$—S— structure where the open valences are bonded to adjacent carbons on the steroid nucleus, e.g., the 16 and 17 positions or the 2 and 3 positions, or (2) a —S—[C(CR$^{36}$)$_2$]$_{1-4}$—O— or —S—[C(CR$^{36}$)$_2$]$_{1-4}$—S— structure where the open valences are bonded to the same carbon on the steroid nucleus, where each R$^{36}$ independently is —H, —F, —Cl, —Br, —I or an organic moiety such as C1-6 alkyl (e.g., methyl or ethyl), C2-6 alkenyl, aryl or a heterocycle, any of which are optionally substituted, e.g., —CF$_3$ or —CH$_2$OH. Typically, thioacetals as used here comprise an organic moiety containing about 1-50 carbon atoms (e.g., about 2-20 carbon atoms) and 0 to about 10 heteroatoms (e.g., O, S, N, P, Si), where the organic moiety is bonded to a formula 1 steroid nucleus at variable groups such as R$^1$, R$^2$, R$^3$, R$^4$ or R$^{10}$ through the —S—[C(CR$^{36}$)$_2$]$_{1-4}$—O— or —S—[C(CR$^{36}$)$_2$]$_{1-4}$—S— structure, e.g., 16-steroid-S—[C(CR$^{36}$)$_2$]$_{1-4}$—O-17-steroid, 16-steroid-O—[C(CR$^{36}$)$_2$]$_{1-4}$—S-17-steroid, 16-steroid-S—[C(CR$^{36}$)$_2$]$_{1-4}$—S-17-steroid, 17-steroid-S—[C(CR$^{36}$)$_2$]$_{1-4}$—O-17-steroid, organic moiety-S—C(O)-steroid or steroid-S—C(O)-organic moiety. The organic moiety is as described above for esters.

"Phosphoester" or "phosphate ester" means a moiety that comprises a —O—P(OR$^{PR}$)(O)—O— structure where R$^{PR}$ is hydrogen (—H), a protecting group or an organic moiety as described for esters. Typically, phosphoesters as used here comprise a hydrogen atom, a protecting group or an organic moiety containing about 1-50 carbon atoms and 0 to about 10 heteroatoms (e.g., O, S, N, P, Si) linked to a formula 1 steroid nucleus at a variable group such as R$^1$-R$^6$, R$^{10}$, R$^{15}$, R$^{17}$ or R$^{18}$ through the —O—P(O)(O)—O— structure, e.g., organic moiety-O—P(O)(OH)—O-steroid. The organic moiety is as described above for esters.

"Phosphothioester" means a moiety that comprises a —O—P(SR$^{PR}$)(O)-structure where R$^{PR}$ is —H, a protecting group or an organic moiety as described for esters. Typically, phosphothioesters as used here comprise a hydrogen atom, a protecting group or an organic moiety containing about 1-50 carbon atoms and 0 to about 10 heteroatoms (e.g., O, S, N, P, Si) linked to a formula 1 steroid nucleus at a variable group such as R$^1$-R$^6$, R$^{10}$, R$^{15}$, R$^{17}$ or R$^{18}$ through the —O—P(O)(O)—O— structure, e.g., organic moiety-O—P(O)(SH)—O-steroid. The organic moiety is as described above for esters.

"Phosphonoester" means a moiety that comprises a —P(OR$^{PR}$)(O)— structure where R$^{PR}$ is —H, a protecting group or an organic moiety as described for esters. Typically, phosphonoesters as used here comprise a hydrogen atom, a protecting group or an organic moiety containing about 1-50 carbon atoms and 0 to about 10 heteroatoms (e.g., O, S, N, P, Si) linked to a formula 1 steroid nucleus at a variable group such as R$^1$-R$^6$, R$^{10}$, R$^{15}$, R$^{17}$ or R$^{18}$ through the —P(OR$^{PR}$)(O)—O— structure, i.e., organic moiety-P(OR$^{PR}$)(O)—O- steroid or steroid-P(OR$^{PR}$)(O)—O-organic moiety. The organic moiety is as described above for esters.

"Phosphiniester" means a moiety that comprises a —P(O) H— structure where R$^{PR}$ is —H, a protecting group or an organic moiety as described for esters. Typically, phosphiniesters as used here comprise a hydrogen atom, a protecting group or an organic moiety containing about 1-50 carbon atoms and 0 to about 10 heteroatoms (e.g., O, S, N, P, Si) linked to a formula 1 steroid nucleus at a variable group such as R$^1$-R$^6$, R$^{10}$, R$^{15}$, R$^{17}$ or R$^{18}$ through the —P(O)H— structure, i.e., organic moiety-P(O)H-steroid or steroid-P(O)H-organic moiety. The organic moiety is as described above for esters.

"Sulfate ester" means a moiety that comprises a —O—S(O)(O)—O— structure. Typically, sulfate esters as used here comprise a hydrogen atom, a protecting group or an organic moiety containing about 1-50 carbon atoms and 0 to about 10 heteroatoms (e.g., O, S, N, P, Si) linked to a formula 1 steroid nucleus at a variable group such as R$^1$-R$^6$, R$^{10}$, R$^{15}$, R$^{17}$ or R$^{18}$ through the —O—S(O)(O)—O— structure, e.g., organic moiety-O—S(O)(O)—O-steroid. The organic moiety is as described above for esters.

"Sulfite ester" means a moiety that comprises a —O—S(O)—O— structure. Typically, sulfite esters as used here comprise an organic moiety containing about 1-50 carbon atoms and 0 to about 10 heteroatoms (e.g., O, S, N, P, Si) linked to a formula 1 steroid nucleus at a variable group such as R$^1$-R$^6$, R$^{10}$, R$^{15}$, R$^{17}$ or R$^{18}$ through the —O—S(O)—O-structure, e.g., organic moiety-O—S(O)—O-steroid. The organic moiety is as described above for esters.

"Amide" means an organic moiety as described for ester that comprises 1, 2, 3, 4 or more —C(O)—NR$^{PR}$— moieties, usually 1 or 2, where R$^{PR}$ is —H or a protecting group, R$^{PR}$ is usually H. In some embodiments, the —C(O)NR$^{PR}$— group is linked to the steroid nucleus at a variable group such as R$^1$-R$^6$, R$^{10}$, R$^{15}$, R$^{17}$ or R$^{18}$, i.e., organic moiety-C(O)NR$^{PR}$-steroid or steroid-C(O)NR$^{PR}$-organic moiety. The organic moiety is as described above for esters.

"Ether" means an organic moiety as described for ester that comprises 1, 2, 3, 4 or more —O— moieties, usually 1 or 2. In some embodiments, the —O— group is linked to the steroid nucleus at a variable group such as R$^1$-R$^6$, R$^{10}$, R$^{15}$, R$^{17}$ or R$^{18}$, e.g., organic moiety-O-steroid. The organic moiety is as described above for esters.

"Thioether" means an organic moiety as described for ester that comprises 1, 2, 3, 4 or more —S— moieties, usually 1 or 2. In some embodiments, the —S— group is linked to the steroid nucleus at a variable group such as R$^1$-R$^6$, R$^{10}$, R$^{15}$, R$^{17}$ or R$^{18}$, e.g., organic moiety-S-steroid. The organic moiety is as described above for esters.

"Acyl group" means an organic moiety as described for ester that comprises 1, 2, 3, 4 or more —C(O)— groups. In some embodiments, the —C(O)— group is linked to the steroid nucleus at a variable group such as R$^1$-R$^6$, R$^{10}$, R$^{15}$, R$^{17}$ or R$^{18}$, e.g., organic moiety-C(O)-steroid. The organic moiety is as described above for esters.

"Thioacyl" means an organic moiety as described for ester that comprises 1, 2, 3, 4 or more —C(S)— groups. In some embodiments, the —C(S)— group is linked to the steroid nucleus at a variable group such as R$^1$-R$^6$, R$^{10}$, R$^{15}$, R$^{17}$ or R$^{18}$, e.g., organic moiety-C(S)-steroid. The organic moiety is as described above for esters.

"Carbonate" means an organic moiety as described for ester that comprises 1, 2, 3, 4 or more —O—C(O)—O— structures. Typically, carbonate groups as used here comprise an organic moiety containing about 1-50 carbon atoms and 0 to about 10 heteroatoms (e.g., O, S, N, P, Si) linked to a formula 1 steroid nucleus at a variable group such as R$^1$-R$^6$, R$^{10}$, R$^{15}$, R$^{17}$ or R$^{18}$ through the —O—C(O)—O— structure, e.g., organic moiety-O—C(O)—O-steroid. The organic moiety is as described above for esters.

"Carbamate" means an organic moiety as described for ester that comprises 1, 2, 3, 4 or more —O—C(O)NR$^{PR}$— structures where R$^{PR}$ is —H, a protecting group or an organic moiety as described for ester. Typically, carbamate groups as used here comprise an organic moiety containing about 1-50 carbon atoms and 0 to about 10 heteroatoms (e.g., O, S, N, P, Si) linked to a formula 1 steroid nucleus at a variable group such as R$^1$-R$^6$, R$^{10}$, R$^{15}$, R$^{17}$ or R$^{18}$ through the —O—C(O)—NR$^{PR}$— structure, e.g., organic moiety-O—C(O)—NR$^{PR}$-steroid or steroid-O—C(O)—NR$^{PR}$-organic moiety. The organic moiety is as described above for esters.

As used herein, "monosaccharide" means a polyhydroxy aldehyde or ketone having the empirical formula $(CH_2O)_n$ where n is 3, 4, 5, 6 or 7. Monosaccharide includes open chain and closed chain forms, but will usually be closed chain forms. Monosaccharide includes hexofuranose and pentofuranose sugars such as 2'-deoxyribose, ribose, arabinose, xylose, their 2'-deoxy and 3'-deoxy derivatives and their 2',3'-dideoxy derivatives. Monosaccharide also includes the 2',3' dideoxydidehydro derivative of ribose. Monosaccharides include the D-, L- and DL-isomers of glucose, fructose, mannose, idose, galactose, allose, gulose, altrose, talose, fucose, erythrose, threose, lyxose, erythrulose, ribulose, xylulose, ribose, arabinose, xylose, psicose, sorbose, tagatose, glyceraldehyde, dihydroxyacetone and their monodeoxy or other derivatives such as rhamnose and glucuronic acid or a salt of glucuronic acid. Monosaccharides are optionally protected or partially protected. Exemplary monosacharides include

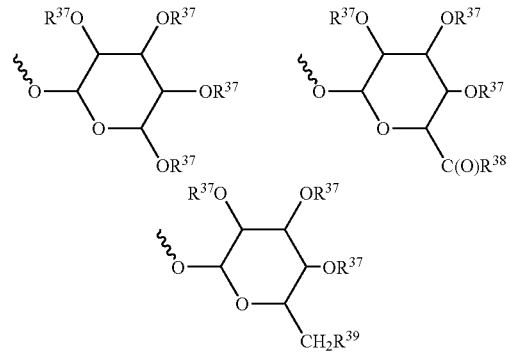

where R$^{37}$ independently is hydrogen, a protecting group, acetamido (—NH—Ac), optionally substituted alkyl such as methyl or ethyl, or an ester such as acetate or proprionate, R$^{38}$ is hydrogen, hydroxyl, —NH$_2$, —NHR$^{PR}$, optionally substituted alkyl such as methyl or ethyl, or a cation such as NH$_4^+$, Na$^+$ or K$^+$ and R$^{39}$ is hydrogen, hydroxyl, acetate, proprionate, optionally substituted alkyl such as methyl, ethyl, methoxy or ethoxy.

Optionally substituted alkyl group, optionally substituted alkenyl group, optionally substituted alkynyl group, optionally substituted aryl moiety and optionally substituted heterocycle mean an alkyl, alkenyl, alkynyl, aryl or heterocycle moiety that contains an optional substitution(s). Such moieties include C$_{1-20}$ alkyl moieties, C$_{2-20}$ alkenyl moieties, C$_{2-20}$ alkynyl moieties, aryl moieties, C$_{2-9}$ heterocycles or substituted derivatives of any of these. Typical substitutions for these organic groups are as described above for substituted alkyl moieties and include, e.g., 1, 2, 3, 4, 5, 6 or more, independently selected —O—, —S—, —NR$^{PR}$—, —C(O)—, —N(R$^{PR}$)$_2$, —C(O)OR$^{PR}$, —OC(O)R$^{PR}$, —OR$^{PR}$, —SR$^{PR}$, —NO$_2$, —CN, —NHC(O)—, —C(O)NH—, —OC(O)—, —C(O)O—, —O-A8, —S-A8, —C(O)-A8, —OC(O)-A8, —C(O)O-A8, =N—, —N=, —OPO$_2$R$^{PR}$, —OSO$_3$H or halogen moieties or atoms, where R$^{PR}$ independently is —H, a protecting group or both R$^{PR}$ together are a protecting group and A8 is C$_{1-8}$ alkyl, C$_{1-8}$ alkenyl, C$_{1-8}$ alkynyl, C$_{1-4}$ alkyl-aryl (e.g., benzyl), aryl (e.g. phenyl) or C$_{1-4}$ alkyl-C$_{1-5}$ heterocycle. Substitutions are independently chosen. The organic moieties as described here, and for other any other moieties described herein, exclude obviously unstable moieties, e.g., —O—O—, except where such unstable moieties are transient species that one can use to make a compound with sufficient chemical stability for the one or more of the uses described herein.

Optionally substituted "monosaccharide" comprise any C3-C7 sugar, D-, L- or DL-configurations, e.g., erythrose, glycerol, ribose, deoxyribose, arabinose, glucose, mannose, galactose, fucose, mannose, glucosamine, N-acetyl-neuraminic acid, N-acetylglucosamine, N-acetylgalactosamine that is optionally substituted at one or more hydroxyl groups. Suitable substitutions are as described above for substituted alkyl moieties and include independently selected hydrogen, hydroxyl, protected hydroxyl, carboxyl, azido, cyano, —O—C$_{1-6}$ alkyl, —S—C$_{1-6}$ alkyl, —O—C$_{2-6}$ alkenyl, —S—C$_{2-6}$ alkenyl, optionally protected amine, optionally protected carboxyl, halogen, thiol or protected thiol. The linkage between the monosaccharide and the steroid is α or β.

Optionally substituted "oligosaccharide" comprises two, three, four or more of any C3-C7 sugars that are covalently linked to each other. The linked sugars may have D-, L- or DL-configurations. Suitable sugars and substitutions are as described for monosaccharides. The linkage between the oligosaccharide and the steroid is α or β, as are the linkages between the monosaccharides that comprise the oligosaccharide.

Nucleoside includes 3TC, AZT, D4T, ddI, ddC, G, A, U, C, T, dG, dA, dT and dC.

Polymer includes biocompatible organic polymers, e.g., PEGs and polyhydroxyalkyl polymers.

PEG means an ethylene glycol polymer that contains about 20 to about 2000000 linked monomers, typically about 50-1000 linked monomers, usually about 100-300. Polyethylene glycols include PEGs containing various numbers of linked monomers or having differing average molecular weights, e.g., PEG20, PEG30, PEG40, PEG60, PEG80, PEG100, PEG115, PEG200, PEG300, PEG400, PEG500, PEG600, PEG1000, PEG1500, PEG2000, PEG 3350, PEG4000, PEG4600, PEG5000, PEG6000, PEG8000, PEG11000, PEG12000, PEG2000000 and any mixtures thereof.

As used herein, position numbers that are given for the formula 1 compounds use the numbering convention for cholesterol.

"Spiro ring" or "spiro structure" and similar terms mean cyclic structures that comprise 4, 5, 6, 7 or 8 ring members, i.e., they are 4-, 5-, 6-, 7- or 8-sided. In some embodiments, spiro structures share a carbon atom that is present in the steroid ring system, e.g., at the 2, 3, 7, 11, 15, 16 or 17 positions of the formula 1 compounds. Spiro structures include lactone rings or cyclic esters. Such spirolactones include 5 and 6 membered rings, e.g., a spiro compound with a spiro ring at the 17 position such as

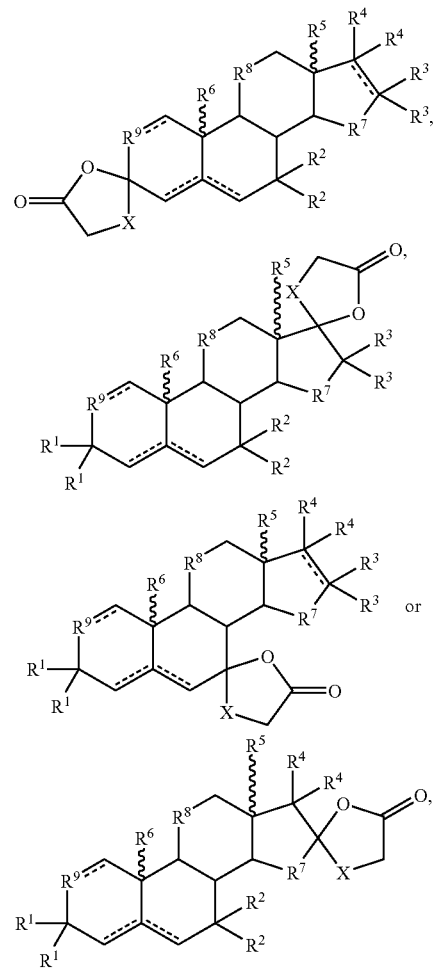

wherein X is —C(R$^{10}$)$_2$— or —CHR$^{10}$— and wherein independently selected R$^{10}$ groups are bonded to the 1-, 4-, 5-, 6-, 8-, 9-, 12-, and 14-positions. In some of these embodiments, the R$^{10}$ variable group independently is —H, —OH, —OCH$_3$, —CH$_3$ or an optionally substituted alkyl.

Unless otherwise stated or implied by context, expressions of a percentage of a liquid ingredient, e.g., an excipient, in an invention composition or formulation mean the ingredient's percent by volume (v/v). Thus, 20% propylene glycol means 20% v/v propylene glycol is present in an invention composition or formulation. The amount of excipient indicated in invention compositions is not affected by the form used, e.g., NF or USP grade solvent or excipient. Thus, an invention composition that comprises about 30% polyethylene glycol 300 NF can instead comprise a USP counterpart, provided that other limitations, such as the amount of water present, are not exceeded.

As used herein, "innate immunity" refers to one or more components typically associated with nonspecific immune defense mechanisms in a subject. These components include the alternate complement pathway, e.g., Factor B, Factor D and properdin; NK cells, phagocytes (monocytes, macrophages), neutrophils, eosinophils, dendritic cells, fibrocytes; anti-microbial chemicals, e.g., one or more of defensins; physical barriers—skin, mucosal epithelium; or certain interleukins, chemokines, cytokines, lung or alveolar macrophage respiratory burst activity or a lung surfactant protein such as surfactant protein A or surfactant protein D. Innate immunity plays a role in resistance to intracellular parasite infections, e.g., white blood cell infection, a liver infection, and other infections, e.g., lymph node infections. Detectable enhancement of innate immunity mechanism by formula 1 compounds or method described herein can also enhance phagolysosome fusion or movement, which some pathogens, e.g., intracellular bacteria such as mycobacteria, or *Listeria* inhibit.

Terms such as "immune disregulation", "immune disregulation condition", "unwanted immune response" and the like mean that a subject has or is subject to developing an immune response that is not desirable or is suboptimal for the subject's condition. Such disregulation or unwanted responses can arise from various clinical conditions or diseases or as a result of treatment of such conditions or diseases, e.g., inflammation, autoimmunity, organ or tissue transplant rejection (e.g., allograft, xenograft), infections, cancers, chemotherapy treatments, trauma, allergy conditions or in conditions where a subject mounts a Th1, Tc1, Th2 or Tc2 immune response that is considered to be pathogenic, ineffective, insufficient or suboptimal. Immune disregulation conditions are as described herein or in the cited references.

Terms such as "cellular response", "cellular activity", "biological response", "biological activity" and the like mean a response or activity that is detectably modulated in response to the presence of a formula 1 compound. Such responses or activities can be direct effects or indirect effects on one or more cellular activities or on the expression or level of one or more molecules that the affected cell(s) bind, sequester, synthesize or respond to. Such responses or activities include a detectable change in the synthesis or level of one or more cytokines, growth factors, transcription factors (including receptors and their cofactors), enzymes, Th1- or Th2-associated antibody subtype responses or the like. Typically, the cytokines, growth factors, transcription factors, enzymes or antibodies that are modulated are involved in the amelioration of a pathological condition or in the establishment, maintenance or progression of a pathological condition.

As used herein, references to CD molecules, specific immune cell subsets, immune responses and the like, generally use nomenclature that applies to molecules, cells or the like that are found in humans. Analogs or counterparts of such molecules, cells or the like in other species may have a differing nomenclature, but are included in this invention. A description of the nomenclature and function of various CD molecules and immune cell subsets are as found in the scientific literature. References to Th0, Th1 or Th2 cells and references to Th1 or Th2 immune responses in the context of human patients refers to the human counterparts of the murine Th0, Th1 or Th2 immune cells or responses. For reviews see, e.g., A. K. Abbas et al., editors, *Cellular and Molecular Immunology*, W.B. Saunders Company, third edition, 1997, ISBN 0-7216-4024-9, pages 4-469, and I. Kimber and M. K. Selgrade, editors, *T Lymphocyte Subpopulations in Immunotoxicology*, John Wiley & Sons Ltd., 1998, ISBN 0-471-97194-4, pages 1-53.

"Immunosuppressive molecule" means molecules such as cyclosporin, cyclohexamide, mitomycin C, adriamycin, taxol and amphotericin B. These molecules tend to have toxicities toward the immune system and are directly or indirectly immunosuppressive, e.g., they are toxic to dividing cells, they inhibit proliferation of immune cell precursors or they can downregulate an otherwise desired or improved immune response or condition.

"Steroid receptor" means a gene product, typically a protein monomer or dimer that can bind to a ligand, e.g., a natural steroid, a steroid analog, or another ligand such as a formula 1 compound or a metabolic precursor thereof or a metabolite thereof, a lipid, e.g., a prostaglandin, or the like. Steroid receptors include orphan steroid receptors. Orphan steroid receptors are proteins for which the natural ligand or biological function is at least partially unknown. As used here, steroid receptors include homodimers, e.g., SXR and $(CAR\beta)_2$, and heterodimers, e.g., PXR-CARβ or RXR-CARβ. Steroid receptors also include isoforms, e.g., PXR.1 and PXR.2 for the PXR receptor, and homologs of the steroid receptors, e.g., the homolog of CARβ known as MB67. Isoforms are typically generated by different splicing pathways for a nuclear RNA from one gene, while homologs are typically a distinct copy of a steroid receptor gene, where the gene copy encodes only relatively small differences compared to the reference steroid receptor gene product. Such differences are most often found in areas other than the dimerization region and the steroid binding region of the steroid receptor's structure. Typically isoforms and homologs bind the same or similar ligands as the reference gene product or steroid receptor. Steroid receptors may be of human or animal origin, e.g., obtained from cells, tissues or cDNA expression libraries derived from cells or tissues of any primate, rodent (including murine), avian, ovine, bovine, equine, canine or feline species or any of the species or any species within any group (e.g., Family or Genus) of species mentioned elsewhere herein or in any reference cited herein. Modulation of steroid receptors by formula 1 compounds can arise from (1) their direct interaction with a steroid receptor or a cofactor thereof or (2) indirect effects such as (A) detectably increased or decreased synthesis or level of the steroid receptor or (B) generation of a signal or stimulus that leads to detectable modulation of one or more biological activities of the receptor, e.g., detectable inhibition of steroid receptor mediated gene transcription or detectable enhancement of steroid receptor mediated gene transcription.

In the context of a combination of molecules that includes a steroid receptor and a formula 1 compound, "invention complexes" or "complexes" include a complex that comprises a steroid receptor and a formula 1 compound and optionally other molecules. These other molecules include (i) a DNA recognition sequence ("DNARS" hereafter), i.e., a sequence that the steroid receptor specifically recognizes and binds to and (ii) a transcription factor that can bind to the steroid receptor-formula 1 compound complex. As used herein, these complexes can arise in cells in vitro or in vivo, or in cell-free systems. Complexes include, for example, steroid receptor heterodimer-formula 1 compound combinations, steroid receptor homodimer-formula 1 compound combinations, steroid receptor monomer-formula 1 compound combinations, steroid receptor heterodimer-formula 1 compound-DNA (or DNARS) combinations, steroid receptor homodimer-formula 1 compound-DNA (or DNARS) combinations, steroid receptor heterodimer-formula 1 compound-transcription factor combinations, steroid receptor homodimer-formula 1 compound-transcription factor combinations, steroid receptor heterodimer-formula 1 compound-DNA (or DNARS)-transcription factor combinations and steroid receptor homodimer-formula 1 compound-DNA (or DNARS)-transcription factor combinations.

An "agonist" or an "antagonist" is a compound or composition that respectively, either detectably increases or decreases the activity of a receptor, an enzyme or another biological molecule, which can lead to increased or decreased transcription of a regulated gene or to another measurable effect. The increase or decrease in a receptor's or enzyme's activity will be an increase or a decrease of at least about 5%, 10%, 20%, 30%, 40%, 50%, 60%, 70%, 80%, 90%, 95% or a range about between any two of these values, for one or more measurable activities. Receptors, their accessory factors and associated transcription factors can modulate transcription of their target gene(s) by detectably enhancing transcription or decreasing it. Biological activities of receptors may also include modulating biological responses such as signal transduction within a cell or ion flux, e.g., sodium, potassium or calcium, across cell or organelle membranes.

Terms such as "biologically active metabolite" and the like mean derivatives of the formula 1 compounds that retain a detectable level, e.g., at least about 10%, at least about 20%, at least about 30% or at least about 50%, of at least one desired activity of the parent compound, e.g., antiinflammatory activity or stimulation of a desired immune response. Determination of a desired activity is accomplished essentially as described herein. Such metabolites can be generated in the gastrointestinal tract, in blood or in one or more subject tissues. Such metabolites are detected using standard analytical methods, e.g., GC-MS analysis of an optionally radiolabeled formula 1 compound and its metabolites, in blood, urine or other biological samples after it is administered to a subject by one or more routes as disclosed herein. Terms such as "metabolic precursor" of formula 1 compounds and the like can include compounds that generate a detectable level of the formula 1 compound or a detectable level, e.g., at least about 10%, at least about 20%, at least about 30% or at least about 50%, of at least one desired activity of the formula 1 compound. Determination of a desired activity is accomplished essentially as described herein. Conversion of metabolic precursors can occur in the gastrointestinal tract, in blood or in one or more subject tissues.

"Amino acid" means an amino acid moiety that comprises any naturally-occurring or synthetic amino acid residue, i.e., any moiety comprising at least one carboxyl and at least one amino residue directly linked by one, two three or more carbon atoms, typically one (α) carbon atom. The nature and identity of the intervening structure located between the carboxyl and amino groups can have a variety of structures including those described herein. Typically, amino acids linked to the steroid through the amine group have sufficient conformation and length to be capable of autocatalytic hydrolysis of the amino acid-steroid bond and release of the steroid. This can occur when the free carboxyl is generated in vivo by deesterification, deamidation or peptidolytic cleavage of the precursor containing a linkage between the amino acid's amine group and the steroid. Hydrolysis of the bond between an amino acid's carboxyl or amino group and the steroid can also occur by chemical or enzymatic activity, e.g., esterase cleavage or non-enzymatic hydrolysis.

In general, the amino acids corresponding to the residues employed in the formula 1 compounds are naturally occurring and have no significant pharmacological activity per se. However, optimal pharmacokinetic activity, (substantially complete hydrolysis upon hydrolysis of the distal amide or ester bond) may be achieved by using non-naturally occurring amino acid residues. The intervening structure may be as simple as methylene when the amino acid residue is glycyl, or substituted methylene for other α amino acids. The structure ordinarily contains up to about 5 carbon or heteroatoms in the direct linkage between the amino acid's carboxyl carbon and the amine nitrogen. Thus, amino acids can comprise intervening ethylene, propylene, butylene, or pentylene groups or their substituted analogs, such as for example, oxyesters or ethers in which oxygen replaces carbon and, as appropriate, hydrogen. An example of such an intervening structure would be —CH—O—C($R^{22}$)($R^{23}$)—, where $R^{22}$ and $R^{23}$ are independently selected hydrogen or organic moieties as described above for esters. In some embodiments one of $R^{22}$ and $R^{23}$ is hydrogen and the other is a C2-20 organic moiety. Typically the organic moieties contain about 1-20 carbon atoms and 0, 1, 2, 3, 4 or 5 independently selected heteroatoms, which are typically selected from oxygen, nitrogen, sulfur and phosphorus. In general, fewer intervening atoms are used when more rapid hydrolysis is desired, although larger structures are suitable if, e.g., they possess sufficient flexibility or have conformations to allow positioning of the carboxyl group in proximity to the amino acid-steroid bond.

Ordinarily, $R^{22}$ is —H, methyl or hydroxymethyl, usually —H, and $R^{23}$ is a side chain or group of a naturally occurring amino acid. Amino acid side chains include analogs where the side chain is a $C_{1-15}$ homolog of the corresponding natural compound, e.g., methylene, ethylene, propylene, butylene or a substituted derivative thereof, e.g., an alkyl, ether or alkoxy (e.g., methoxy, ethoxy, propoxy) substituted derivative. In general, for carboxyl-containing side chains, if the C atom of the side chain carboxyl is linked by 5 or less atoms to the N then the carboxyl optionally will be blocked, e.g. by esterification or amidation wherein the ester or amide bonds are hydrolyzable in vivo. $R^{22}$ also is taken together with $R^{30}$ to form a proline residue (—$CH_2$—)$_3$. Thus, $R^{23}$ is generally a side group such as —H, —$CH_3$, —$CH(CH_3)_2$, —$CH_2$—CH($CH_3$)$_2$, —$CHCH_3$—$CH_2$—$CH_3$, —$CH_2$—$C_6H_5$, —$CH_2CH_2$—S—$CH_3$, —$CH_2OH$, —$CH(OH)$—$CH_3$, —$CH_2$—SH, —$CH_2$—$C_6H_4OH$, —$CH_2$—CO—$NH_2$, —$CH_2$—$CH_2$—CO—$NH_2$, —$CH_2$—COOH, —$CH_2$—$CH_2$—COOH, —($CH_2$)$_4$—$NH_2$ and —($CH_2$)$_3$—NH—C($NH_2$)—$NH_2$. $R^{23}$ also includes 1-guanidinoprop-3-yl, benzyl, 4-hydroxybenzyl, imidazol-4-yl, indol-3-yl, methoxyphenyl and ethoxyphenyl. The optimal $R^{30}$ group is readily selected using routine assays.

In general, the amino acid residue has the structure shown in the formulas below. Ordinarily, n is 1 or 2, $R^{22}$ is —H and $R^{23}$ is a moiety containing one or more of the following groups: amino, carboxyl, amide, carboxyl ester, hydroxyl, $C_6$-$C_7$ aryl, ether (—O—), thioether (—S—), n-, s- or t-alkyl ($C_1$-$C_6$), guanidinyl, imidazolyl, indolyl, sulfhydryl, sulfoxide, and phosphoryl. The $R^{22}$ and $R^{23}$ substituents can have a wide variety of structures including those disclosed herein, e.g., esters, ethers or carbonates.

When the amino acid residues contain one or more chiral centers, any of the D, L, meso, threo or erythro (as appropriate) racemates or mixtures thereof, fall within the scope of this invention. In general, if it is desired to rely on non-enzymatic means of hydrolysis, D isomers should be used. On the other hand, L isomers may be more versatile since they can be susceptible to both non-enzymatic as well as potential targeted enzymatic hydrolysis, and are more efficiently transported by amino acid or dipeptidyl transport systems in the gastrointestinal tract.

Examples of suitable amino acid residues include the following: Glycyl; aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid residues; amino acid amides such as glutaminyl and asparaginyl; polyamino- or polybasic-monocarboxylic acids such as arginine, lysine, β-aminoalanine, γ-aminobutyrine, ornithine, citruline, homoarginine, homocitrulline, 5-hydroxy-2,6-diaminohexanoic acid (commonly, hydroxylysine, including allohydroxylysine) and diaminobutyric acid residues; other basic amino acid residues such as histidinyl; diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid residues; imino acids such as proline, 4- or 3-hydroxy-2-pyrrolidinecarboxylic acid (commonly, hydroxyproline, including allohydroxyproline), γ-methylproline, pipecolic acid, 5-hydroxypipecolic acid, —N([CH$_2$]$_n$COOR$^{PR}$)$_2$, wherein n is 1, 2, 3, 4, 5 or 6 and R$^{PR}$ is —H or a protecting group, and azetidine-2-carboxylic acid residues; a mono- or di-alkyl (typically C$_1$-C$_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid; isoleucine, alloisoleucine, tert-leucine, β-methyltryptophan and α-amino-β-ethyl-β-phenylpropionic acid residues; β-phenylserinyl; aliphatic α-amino-β-hydroxy acids such as serine, β-hydroxyleucine, β-hydroxynorleucine, β-hydroxynorvaline, and α-amino-β-hydroxystearic acid residues; α-Amino, α-, γ-, δ - or ε-hydroxy acids such as homoserine, γ-hydroxynorvaline, δ-hydroxynorvaline and epsilon-hydroxynorleucine residues; canavinyl and canalinyl; γ-hydroxyornithinyl; 2-Hexosaminic acids such as D-glucosaminic acid or D-galactosaminic acid residues; α-amino-β-thiols such as penicillamine, β-thiolnorvaline or β-thiolbutyrine residues; other sulfur containing amino acid residues including cysteine; homocystine; β-phenylmethionine; methionine; S-allyl-L-cysteine sulfoxide; 2-thiolhistidine; cystathionine; and thiol ethers of cysteine or homocysteine; phenylalanine, tryptophan and ring-substituted α amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro, 2-hydroxy-5-nitro and p-nitro-phenylalanine); furyl-, thienyl-, pyridyl-, pyrimidinyl-, purine or naphthylalanines; and tryptophan analogues and derivatives including kynurenine, 3-hydroxykynurenine, 2-hydroxytryptophan and 4-carboxytryptophan residues; α-amino substituted amino acid residues including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acid residues including serine, threonine, allothreonine, phosphoserine and phosphothreonine residues.

Any one of the foregoing or other known amino acids are suitably employed in this invention. Typically, amino acids are capable of autocatalytically hydrolyzing the amino acid-steroid bond. Thus, they typically contain, or upon being hydrolyzed in vivo, contain a free carboxyl group or amine group.

Also of interest are hydrophobic amino acids such as mono- or di-alkyl or aryl amino acids, cycloalkylamino acids and the like. These residues, together with R$^{29}$-R$^{34}$(R$^{31}$-R$^{34}$ are defined below) can contribute to cell permeability by modulating the lipophilicity of a formula 1 compound. Typically, the residue does not contain a sulfhydryl or guanidino substituent.

Peptide means one, 2, 3 or more of the two or more amino acids as defined above are bonded together, usually by an amide bond. Variable groups in the formula 1 compounds such as R$^1$-R$^{10}$ can comprise a peptide. Typically the amino acids are linked through normal peptide bonds, e.g., —CO—NH—, between adjacent amino acid residues. Peptides comprise dipeptides (dimers), tripeptides (trimers), short peptides of 4, 5, 6, 8, 10 or 15 residues, and longer peptides or proteins having about 100 or more residues. Formula 1 compounds that comprise a peptide can be used as immunogens, prodrugs or as synthetic precursors for other steroid derivatives. In one embodiment, the peptide will contain a peptidolytic enzyme cleavage site at the peptide bond linking the first residue and the next residue distal to the steroid residue. Such cleavage sites are optionally flanked by enzymatic recognition structures, e.g. particular residues recognized by a hydrolytic enzyme, e.g., a peptidase located in the serum or in cells.

Peptidolytic enzymes are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide having a given pair of residues and a free carboxyl terminus is covalently bonded through its α-amino group to the steroid nucleus. It is expected that the peptide will be cleaved by the appropriate dipeptidase, protease or by chemical hydrolysis, leaving the carboxyl of the proximal amino acid residue to autocatalytically cleave the amidate bond.

Examples of suitable dipeptidyl groups (designated by their single letter symbols) are shown in the tables below.

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

| Dipeptides |
|---|
| AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY, VV |

Such dipeptides include species where both amino acids are in the L configuration, the D configuration or mixtures of configurations.

Tripeptides, i.e., 3 linked amino acid residues, are also useful embodiments. Each amino acid in a tripeptide may be in an L, D or mixed configuration. Tripeptides include those where A, C, D, E, F, G, H, I, K, L, M, N, P, Q, R, S, T, V, W or Y is linked by a standard peptide bond to the amino or the carboxyl terminus of any of the dipeptides listed above. The sequence —X1-pro-X2-(where X1 is any amino acid and X2 is hydrogen, any amino acid residue or a carboxyl ester of proline) will be cleaved by luminal carboxypeptidase to yield X1 with a free carboxyl, which in turn autocatalytically cleaves the amidate bond. X2 usually will be a benzyl ester of the carboxy group of X2. Other embodiments include tetrapeptides such as ones where any two of the dipeptides listed above, which may be the same or different dipeptides (e.g., AA and AA linked together or, e.g., AA and GI linked together), are linked to each other by a peptide bond through the amino terminus or carboxyl terminus. One, 2 or more tetrapeptides may bonded to the formula 1 or formula 2 compound through the tetrapeptide's amino or carboxyl terminus.

In some embodiments, the formula 1 or formula 2 compound comprises one or more amino acids or peptides having the structure (A), (B) or (C):

(A) $R^{32}$—NH—$\{[C(R^{29})(R^{30})]_b$—C(O)—N(R$^{31}$)$\}_f$—[C(R$^{29}$)(R$^{30}$)]$_a$—C(O)—O-steroid, (B) $R^{33}$—O—$\{$C(O)—[C(R$^{29}$)(R$^{30}$)]$_d$—N(R$^{31}$)$\}_g$—C(O)—[C(R$^{29}$)(R$^{30}$)]$_c$—N(R$^{31}$)—O-steroid, or (C)$R^{33}$—O—$\{$C(O)—[C(R$^{29}$)(R$^{30}$)]$_d$—N(R$^{31}$)$\}_e$—C(O)—[C(R$^{29}$)(R$^{30}$)]$_c$—N(R$^{31}$)—C(O)—O-steroid, wherein (A), (B) or (C) are independently selected and they are bonded to 1, 2, 3 or more of $R^1$ through $R^4$, where each $R^{29}$-$R^{31}$ is independently selected; $R^{29}$ independently are —H or a C1-20 organic moiety (e.g., $C_{1-6}$ alkyl, e.g. —CH$_3$ or —C$_2$H$_5$); $R^{30}$ independently are the side chain of an amino acid, including the side chain of naturally occurring amino acids as described above, e.g., —H, —CH$_3$, —CH$_2$C$_6$H$_5$; $R^{31}$ is —H or a protecting group; $R^{32}$ and $R^{33}$ independently comprise —H, a protecting group, an ester or an amide where each atom or group is independently chosen; a, b, c and d independently are 1, 2, 3 or 5, usually 1; e, f and g independently are an integer from 0 to about 1000, typically they independently are 0, 1, 2, 3, 4, 5, 6, 7 or 8; a, b, c and d independently are 1 or 2; e, f and g independently are 0, 1, 2, 3, 4 or 5.

If the amino acid(s) or residue(s) has 2 or more amine groups, e.g., a lysinyl or arginyl, or ornithinyl residue, then $R^{29}$ is usually —H and $R^{30}$ may comprise —[C(R$^{34}$)$_2$]$_{n2}$N (R$^{PR}$)— where n2 is 0, 1, 2, 3, 4, 5 or 6, R$^{PR}$ is —H or a protecting group and each $R^{34}$ independently is —H, $C_1$-$C_{20}$ optionally substituted alkyl, $C_6$-$C_{20}$ optionally substituted aryl, $C_7$-$C_{20}$ optionally substituted alkylaryl, $C_7$-$C_{20}$ optionally substituted arylalkyl, $C_1$-$C_{20}$ optionally substituted alkoxy, $C_6$-$C_{20}$ optionally substituted aryloxy or hydroxyl. Such compounds will contain a plurality of steroid moieties. For example when both the epsilon (ε) or delta (δ) and alpha (α) amino groups of lysine or ornithine are substituted with steroid moieties the amidate is believed to be capable of releasing two molecules of active drug, each expected to emerge under different pharmacokinetics and therefore further sustaining the drug release.

Salts of formula 1 compounds. Invention embodiments include salts and complexes of formula 1 compounds, including pharmaceutically acceptable or salts that are relatively non-toxic. Some of the formula 1 compounds have one or more moieties that carry at least a partial positive or negative charge in aqueous solutions, typically at a pH of about 4-10, that can participate in forming a salt, a complex, a composition with partial salt and partial complex properties or other noncovalent interactions, all of which we refer to as a "salt(s)". Salts are usually biologically compatible or pharmaceutically acceptable or non-toxic, particularly for mammalian cells. Salts that are biologically toxic are optionally used with synthetic intermediates of formula 1 compounds. When a water-soluble composition is desired, monovalent salts are usually used.

Metal salts typically are prepared by reacting the metal hydroxide with a compound of this invention. Examples of metal salts that are optionally prepared in this way are salts containing Li$^+$, Na$^+$, and K$^+$. A less soluble metal salt can be precipitated from the solution of a more soluble salt by adding a suitable metal compound. Invention salts may be formed from acid addition of certain organic acids, such as organic carboxylic acids, and inorganic acids, such as alkylsulfonic acids or hydrogen halide acids, to acidic or basic centers on formula 1 compounds, such as basic centers on the invention pyrimidine base analogs. Metal salts include ones containing Na⁺, Li⁺, K⁺, Ca⁺⁺ or Mg⁺⁺. Other metal salts may contain aluminum, barium, strontium, cadmium, bismuth, arsenic or zinc ion.

Salt(s) of formula 1 compounds may comprise a combination of appropriate cations such as alkali and alkaline earth metal ions or ammonium and quaternary ammonium ions with the acid anion moiety of the phosphoric acid or phosphonic acid group, which may be present in invention polymers or monomers.

Salts are produced by standard methods, including dissolving free base in an aqueous, aqueous-alcohol or aqueous-organic solution containing the selected acid, optionally followed by evaporating the solution. The free base is reacted in an organic solution containing the acid, in which case the salt usually separates directly or one can concentrate the solution.

Suitable amine salts include amines having sufficient basicity to form a stable salt, usually amines of low toxicity including trialkyl amines (tripropylamine, triethylamine, trimethylamine), procaine, dibenzylamine, N-benzyl-betaphenethylamine, ephenamine, N,N'-dibenzylethylenediamine, N-ethylpiperidine, benzylamine and dicyclohexylamine.

Salts include organic sulfonic acid or organic carboxylic acid salts, made for example by addition of the acids to basic centers, typically amines. Exemplary sulfonic acids include $C_{6-16}$ aryl sulfonic acids, $C_{6-16}$ heteroaryl sulfonic acids and $C_{1-16}$ alkyl sulfonic acids such as phenyl sulfonic acid, a-naphthalene sulfonic acid, β-naphthalene sulfonic acid, (S)-camphorsulfonic acid, methyl ($CH_3SO_3H$), ethyl ($C_2H_5SO_3H$), n-propyl, i-propyl, n-butyl, s-butyl, i-butyl, t-butyl, pentyl and hexyl sulfonic acids. Exemplary organic carboxylic acids include $C_{1-16}$ alkyl, $C_{6-16}$ aryl carboxylic acids and $C_{4-16}$ heteroaryl carboxylic acids such as acetic, glycolic, lactic, pyruvic, malonic, glutaric, tartaric, citric, fumaric, succinic, malic, maleic, oxalic, hydroxymaleic, benzoic, hydroxybenzoic, phenylacetic, cinnamic, salicylic, nicotinic and 2-phenoxybenzoic.

Invention salts include those made from inorganic acids, e.g., HF, HCl, HBr, HI, $H_2SO_4$, $H_3PO_4$, $Na_2CO_3$, $K_2CO_3$, $CaCO_3$, $MgCO_3$ and $NaClO_3$. Suitable anions, which are optionally present with a cation such a $Ca^{++}$, $Mg^{++}$, $Li^{++}$, $Na^+$ or $K^+$, include arsenate, arsenite formate, sorbate, chlorate, perchlorate, periodate, dichromate, glycodeoxycholate, cholate, deoxycholate, desoxycholate, taurocholate, taurodeoxycholate, taurolithocholate, tetraborate, nitrate, nitrite, sulfite, sulfamate, hyposulfite, bisulfite, metabisulfite, thiosulfate, thiocyanate, silicate, metasilicate, $CN^-$, gluconate, gulcuronate, hippurate, picrate, hydrosulfite, hexafluorophosphate, hypochlorite, hypochlorate, borate, metaborate, tungstate and urate.

Salts also include the formula 1 compound salts with one or more amino acids. Many amino acids are suitable, especially the naturally-occurring amino acids found as protein components, although the amino acid typically is one bearing a side chain with a basic or acidic group, e.g., lysine, arginine, histidine or glutamic acid, or a neutral group such as glycine, serine, threonine, alanine, isoleucine, or leucine.

The invention compositions include formula 1 compounds, their hydrates and the compounds in their un-ionized, as well as zwitterionic form.

Stereoisomers. The formula 1 compounds include enriched or resolved optical isomers at any or all asymmetric atoms as are apparent from the depictions. Both racemic and diasteromeric mixtures, as well as the individual optical isomers can be isolated or synthesized so as to be substantially free of their enantiomeric or diastereomeric partners, and these are all within the scope of the invention. Chiral centers may be found in formula 1 compounds at, for example, one or more of $R^1$, $R^2$, $R^3$, $R^4$, or $R^{10}$.

One or more of the following methods are used to prepare the enantiomerically enriched or pure isomers herein. The methods are listed in approximately their order of preference, i.e., one ordinarily should employ stereospecific synthesis from chiral precursors before chromatographic resolution before spontaneous crystallization.

Stereospecific synthesis is described in the examples. Methods of this type conveniently are used when the appropriate chiral starting material is available and reaction steps are chosen do not result in undesired racemization at chiral sites. One advantage of stereospecific synthesis is that it does not produce undesired enantiomers that must be removed from the final product, thereby lowering overall synthetic yield. In general, those skilled in the art would understand what starting materials and reaction conditions should be used to obtain the desired enantiomerically enriched or pure isomers by stereospecific synthesis.

If a suitable stereospecific synthesis cannot be empirically designed or determined with routine experimentation then those skilled in the art would turn to other methods. One method of general utility is chromatographic resolution of enantiomers on chiral chromatography resins. These resins are packed in columns, commonly called Pirkle columns, and are commercially available. The columns contain a chiral stationary phase. The racemate is placed in solution and loaded onto the column, and thereafter separated by HPLC. See for example, Proceedings Chromatographic Society—International Symposium on Chiral Separations, Sep. 3-4, 1987. Examples of chiral columns that could be used to screen for the optimal separation technique would include Diacel Chriacel OD, Regis Pirkle Covalent D-phenylglycine, Regis Pirkle Type 1A, Astec Cyclobond II, Astec Cyclobond III, Serva Chiral D-DL=Daltosil 100, Bakerbond DNBLeu, Sumipax OA-1000, Merck Cellulose Triacetate column, Astec Cyclobond I-Beta, or Regis Pirkle Covalent D-Naphthylalanine. Not all of these columns are likely to be effective with every racemic mixture. However, those skilled in the art understand that a certain amount of routine screening may be required to identify the most effective stationary phase. When using such columns it is desirable to employ embodiments of the compounds of this invention in which the charges are not neutralized, e.g., where acidic functionalities such as carboxyl are not esterified or amidated.

Another method entails converting the enantiomers in the mixture to diasteriomers with chiral auxiliaries and then separating the conjugates by ordinary column chromatography. This is a very suitable method, particularly when the embodiment contains free carboxyl, amino or hydroxyl that will form a salt or covalent bond to a chiral auxiliary. Chirally pure amino acids, organic acids or organosulfonic acids are all worthwhile exploring as chiral auxiliaries, all of which are well known in the art. Salts with such auxiliaries can be formed, or they can be covalently (but reversibly) bonded to the functional group. For example, pure D or L amino acids can be used to amidate the carboxyl group of invention embodiments that comprise a carboxyl group and then separated by chromatography.

Enzymatic resolution is another method of potential value. In such methods one prepares covalent derivatives of the enantiomers in the racemic mixture, generally lower alkyl esters (for example of carboxyl), and then exposes the derivative to enzymatic cleavage, generally hydrolysis. For this method to be successful an enzyme must be chosen that is capable of stereospecific cleavage, so it is frequently necessary to routinely screen several enzymes. If esters are to be cleaved, then one selects a group of esterases, phosphatases, and lipases and determines their activity on the derivative. Typical esterases are from liver, pancreas or other animal organs, and include porcine liver esterase.

If the enantiomeric mixture separates from solution or a melt as a conglomerate, i.e., a mixture of enantiomerically pure crystals, then the crystals can be mechanically separated, thereby producing the enantiomerically enriched preparation. This method, however, is not practical for large-scale preparations and is of limited value for true racemic compounds.

Asymmetric synthesis is another technique for achieving enantiomeric enrichment. For example, a chiral protecting group is reacted with the group to be protected and the reaction mixture allowed to equilibrate. If the reaction is enantiomerically specific then the product will be enriched in that enantiomer.

Further guidance in the separation of enantiomeric mixtures can be found, by way of example and not limitation, in "Enantiomers, Racemates, and resolutions", Jean Jacques, Andre Collet, and Samuel H. Wilen (Krieger Publishing Company, Malabar, Fla., 1991, ISBN 0-89464-618-4): Part 2, Resolution of Enantiomer Mixture, pages 217-435; more particularly, section 4, Resolution by Direct Crystallization, pages 217-251, section 5, Formation and Separation of Diastereomers, pages 251-369, section 6, Crystallization-Induced Asymmetric Transformations, pages 369-378, and section 7, Experimental Aspects and Art of Resolutions, pages 378-435; still more particularly, section 5.1.4, Resolution of Alcohols, Transformation of Alcohols into Salt-Forming Derivatives, pages 263-266, section 5.2.3, Covalent Derivatives of Alcohols, Thiols, and Phenols, pages 332-335, section 5.1.1, Resolution of Acids, pages 257-259, section 5.1.2, Resolution of Bases, pages 259-260, section 5.1.3, Resolution of Amino Acids, page 261-263, section 5.2.1, Covalent Derivatives of Acids, page 329, section 5.2.2, Covalent derivatives of Amines, pages 330-331, section 5.2.4, Covalent Derivatives of Aldehydes, Ketones, and Sulfoxides, pages 335-339, and section 5.2.7, Chromatographic Behavior of Covalent Diastereomers, pages 348-354.

General methods. Methods have been described, for example Karl Fischer (KF) and loss on drying (LOD), to determine the content of water or solvents in various compositions. LOD measures all volatiles in a sample, while KF is typically used to measure all water. When water is the only volatile present, LOD values are equal to or less than KF values for a given composition. KF measures water in hydrates of a compound and LOD determines both water and the amount of other volatiles that may be present. Invention compositions and formulations are conveniently assayed for water content by KF titration (e.g., using a Metrohm 684 KF Coulometer or equivalent) according to a published procedure (*U.S. Pharmacopoeia*, vol. 23, 1995, chapter <921>, U.S. Pharmacopeial Convention, Inc., Rockville, Md.) and manufacturer's Coulometer instructions. The amount of material used in the assay, about 50-100 mg, is measured using a five-place analytical balance (Sartorius, Model RC210D, or a suitable equivalent). The amounts of water specified in invention compositions and formulations are the amount obtained by KF analysis.

Powder X-ray diffraction (XRD) methods have been used to characterize various crystalline compounds (see, e.g., *U.S. Pharmacopoeia*, volume 23, 1995, <941>, p. 1843-1845, U.S. Pharmacopeial Convention, Inc., Rockville, Md.; Stout et al., *X-Ray Structure Determination; A Practical Guide*, MacMillan Co., New York, N.Y., 1986). The diffraction pattern, or portions thereof, obtained from a crystalline compound is usually diagnostic for a given crystal form, although weak or very weak diffraction peaks may not always appear in replicate diffraction patterns obtained from successive batches of crystals. Also, the relative intensities of XRD bands, particularly at low angle X-ray incidence values (low Theta), may vary due to preferred orientation effects arising from differences in, e.g., crystal habit, particle size or other measurement conditions. Peaks on XRD spectra are typically defined at a given Theta value +/−about 0.1 to 0.2. XRD information from the 1, 2, 3, 4, 5 or more main intensity XRD peaks, optionally combined with one or more other diagnostic data (melting point, DSC, IR), is usually suitable to characterize or describe a crystalline material such as 16α-bromoepiandrosterone hemihydrate ("BrEA hemihydrate") from other crystal forms that contain the same compound.

Other techniques that are used to identify or describe a crystalline material such as BrEA hemihydrate include melting point (MP), differential scanning calorimetry (DSC) and infrared absorption spectroscopy (IR) data. DSC measures thermal transition temperatures at which a crystal absorbs or releases heat when its crystal structure changes or it melts. MP data and DSC thermal transition temperatures are typically reproducible within about 1 or 2° C. on successive analyses. IR measures absorption of infrared light that is associated with the presence of particular chemical bonds that are associated with groups, e.g., hydroxyl, that vibrate in response to particular light wavelengths.

BrEA hemihydrate. Formula 1 compounds include BrEA hemihydrate

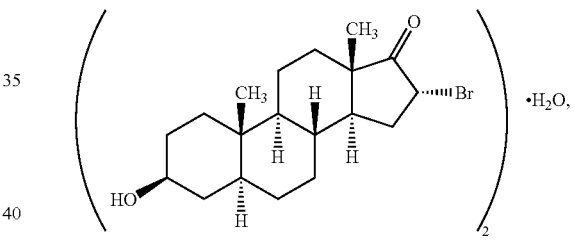

which is optionally characterized by reference to one or more physical properties such as its melting point, infrared absorption spectrum or its powder X-ray diffraction spectrum. Related embodiments include BrEA hemihydrate and one or more excipients, e.g., suitable for human pharmaceutical use or for veterinary use. Another related embodiment is a method to make BrEA hemihydrate comprising precipitating or crystallizing BrEA from a solution comprising ethanol and water.

BrEA hemihydrate is typically substantially free of other forms of BrEA, such as amorphous BrEA or anhydrous BrEA. As used herein, BrEA hemihydrate or crystalline BrEA hemihydrate refers to solid BrEA and water having an ordered arrangement of substantially all of the constituent molecules in a defined three-dimensional spatial pattern or lattice. Crystalline BrEA hemihydrate may comprise one or more crystal habits, e.g., tablets, rods, plates or needles. BrEA hemihydrate that is substantially free of other forms of BrEA means a dry or substantially dry (where a liquid(s) comprises less than about 10% w/w of the total weight) solid preparation where more than about 55% w/w of the BrEA in the preparation is present as BrEA hemihydrate. Such compositions typically comprise at least about 60% w/w, or at least about 70% w/w, or at least about 80% w/w, usually at least about 90% w/w or at least about 95% w/w, or at least about 98% w/w of BrEA hemihydrate, with the remaining BrEA being present as other forms of BrEA such as the amorphous or anhydrous BrEA. Solid BrEA hemihydrate will typically comprise at least about 90% w/w, usually at least about 97% or about 98% w/w of the compound and less than about 10% w/w, usually less than about 3% or 2% w/w of by-products, which may include the 16β isomer of BrEA or one or more by-products of BrEA synthesis. Often the amount of solid BrEA that is present in a solid or a liquid medium will not contain detectable amounts of other forms of BrEA (using standard analytical methods such as, e.g., FTIR, DSC or XRD) and the hemihydrate will may thus comprise about 99-100% w/w of the total amount of BrEA that is present.

Other invention embodiments include compositions that comprise a substantial amount of BrEA hemihydrate that is present in compositions that comprise one or more other forms of BrEA, e.g., amorphous BrEA or anhydrous BrEA, and optionally one or more additional components, such as any excipient described herein. As used herein, the "substantial amount" of BrEA hemihydrate in these compositions comprises at least about 15-20% w/w or at least about 20% w/w of BrEA hemihydrate of the total amount of BrEA that is present, typically at least about 25% w/w, more typically at least about 30% w/w, often at least about 35% w/w and usually at least about 45% w/w. These compositions are generally solids, e.g., formulations or unit dosages, but they also include suspensions, precipitates, gels and colloids that contain solid BrEA. Such suspensions or precipitates may arise from, e.g., precipitation of BrEA hemihydrate from a solution that contains water or from addition of solid BrEA to a liquid excipient(s). Obviously, compositions that comprise a substantial amount of BrEA may be substantially free of other forms of solid BrEA as discussed above.

BrEA hemihydrate may conveniently be identified by reference to BrEA hemihydrate characterized by one or more of (1) its melting or decomposition point or range (optionally expressed as +/−2° C.), (2) one or more BrEA hemihydrate DSC transition temperatures or ranges (any of which may be optionally expressed as +/−2° C.), (3) one or more characteristic BrEA hemihydrate IR absorption bands, (4) 1, 2, 3, 4, 5, 6 or more of the highest intensity XRD peaks (any one or more of which are optionally expressed as +/−0.1° Theta or +/−0.2° Theta) obtained from an XRD spectrum of BrEA hemihydrate using Cu—Kα radiation (e.g., obtained essentially according to the method described at *U.S. Pharmacopoeia*, volume 23, 1995, <941>, p. 1843-1845), (5) the presence of less than about 3% or less than about 2% w/w of other compounds, (6) a water content of dry BrEA hemihydrate of about 2.5% w/w (e.g., 2.3-2.7% w/w), where dry BrEA hemihydrate means compound dried by filtration, optionally washed once with an anhydrous solvent such as hexane, filtered again and dried in vacuo at about 60° C. until no further weight loss occurs over 24 hours at about 60° C. (e.g., where water content is determined essentially by the Karl Fisher or other method described at *U.S. Pharmacopoeia*, vol. 23, 1995, p 1801-1802 or 1840-1843 methods <731> or <921>), (7) cell constants and the orientation matrix obtained from single crystal X-ray crystallography of BrEA hemihydrate (obtained, e.g., essentially as described in WO 99/04774 at example 13), (8) a description of crystal shapes as observed at about 100× magnification to about 150× magnification by polarized light microscopy or (9) average BrEA hemihydrate crystal size and shape descriptions.

Thus, for example, BrEA hemihydrate may be characterized by or one or more of its IR absorption bands, e.g., the carbonyl peaks at 1741 $cm^{-1}$ and 1752 $cm^{-1}$, and either its melting or decomposition point or range and/or 1, 2, 3, 4, 5, 6 or more of the XRD peaks (usually the highest intensity peaks) at Theta (X-ray diffraction angle) values of 17.8, 23.8, 24.2, 26.9-27.2, 28.6, 30.1 and 32.2.

BrEA hemihydrate is suitable to prepare compositions comprising an excipient(s) suitable for human pharmaceutical use or for veterinary use. Such compositions are used to prepare formulations and unit dosages. Unit dosages typically comprise tablets, capsules, lozenges or sterile solutions, including sterile solutions for parenteral administration. Solid unit dosage forms typically comprise about 1-1000 mg of BrEA hemihydrate, typically about 20-400 mg, e.g., about 10 mg, about 25 mg, about 50 mg, about 100 mg, about 150 mg or about 250 mg per unit dose.

The invention provides a method to make BrEA hemihydrate comprising contacting water, 16α-bromo-3β-hydroxy-5α-androstan-17-one and a C1-C6 alcohol (e.g., methanol, ethanol, propanol, isopropanol, butanol) and water. Typically the only one C1-C6 alcohol is present, e.g., ethanol, which is anhydrous or which may comprise up to about 2% w/w water. In some embodiments, the method utilizes a solution that comprises about 5-25% w/w water, about 30-45% w/w ethanol and about 30-45% w/w of a BrEA preparation. Typical BrEA preparations are solid preparations that comprise at least about 80% w/w, usually at least about 90% w/w or at least about 95% w/w of BrEA. The solutions may comprise about 18-22% w/w water, about 37-43% w/w ethanol and about 37-43% w/w of a BrEA preparation. In conducting the precipitation or crystallization method, the solution will typically be at a temperature of about −20° C. to about 45° C., usually at about 0° C. to about 20° C. The solution is maintained at this temperature range for about 30 minutes to about 12 hours and the solution is optionally agitated using slow to moderate agitation during crystallization.

A related embodiment comprises a method to prepare BrEA hemihydrate comprising precipitating BrEA from a solution comprising at least about 15-25% w/w water, about 35-45% w/w of a BrEA preparation and at least about 35-45% w/w of one or more water-miscible solvents, typically $C_{1-6}$ alcohols (methanol, ethanol, propanol, isopropanol, butanol). The BrEA preparation may optionally comprise one or more by-products of BrEA synthesis. Typical BrEA hemihydrate preparations or batches comprise less than about 5% w/w, usually less than about 3% or about 2% w/w of other compounds, such as by-products of BrEA synthesis. Aspects of this method include contacting water with an organic solution that comprises BrEA and an organic solvent such as a C1-C6 alcohol (e.g., ethanol) or acetone. Addition of water to such solutions leads to precipitation of BrEA hemihydrate. Solutions that contain BrEA hemihydrate crystals or precipitate are invention embodiments that are used to prepare solid BrEA that is later dried and stored, typically at ambient temperatures and typically under conditions that limits or blocks light that reaches the compound.

Precipitation or crystallization of BrEA hemihydrate from water-containing solutions is accomplished by known methods, e.g., reducing the solution's temperature, using saturated or nearly saturated BrEA solutions, vacuum concentration of saturated or nearly saturated BrEA solutions (which is typically conducted at a relatively low temperature, usually about 15-25° C.), seeding with saturated or nearly saturated BrEA solutions with BrEA hemihydrate crystals (e.g., about 10-100 mg per 1-10 L of solution), by heating a saturated or nearly saturated BrEA solution (about 25-35° C. for a few minutes followed by allowing the temperature to fall or by actively cooling the solution) and optionally seeding the solution with BrEA hemihydrate crystals or by addition of a liquid, e.g., additional water or ethanol, to a saturated or nearly saturated BrEA ethanol-water solution, which causes the solution to become supersaturated. BrEA may also be precipitated from other solvents or solvent systems, including acetone and acetone-ethanol. Such solvents are typically water miscible. Two-stage precipitation of BrEA may also be used to recover solid BrEA hemihydrate, e.g., initial precipitation and recovery of the solid, followed by either cooling and seeding of the mother liquor or by allowing the mother liquor to stand, e.g., for about one, two or more days at ambient temperature, to obtain a second crop of crystals. Also, BrEA hemihydrate crystals may optionally be recrystallized, essentially as described herein, to further increase the purity of the final solid. Methods for crystallizing organic compounds have been described, e.g., A. S. Myerson, *Handbook of Industrial Crystallization,* 1993, Butterworth-Heinemann, Stoneham, Mass., p 1-101.

Other related embodiments comprise a product produced by the process of contacting a solution comprising BrEA and an organic solvent with water. Typically the solutions are as described above, e.g., a solution comprising about 3-5% v/v water and at least about 40% v/v of one or more water-miscible solvents, typically polar solvents such as $C_{1-6}$ alcohols or ketones (e.g., methanol, ethanol, propanol, isopropanol, butanol, typically ethanol or acetone). Such processes are accomplished by any one or more of the techniques described in the paragraph above, e.g., cooling of a saturated or nearly saturated BrEA water-ethanol solution and optionally seeding the cooled solution with BrEA hemihydrate. An embodiment related to this comprises solutions or solids that comprise wet BrEA hemihydrate crystals or wet filtered or centrifuged BrEA hemihydrate cakes, which may be obtained after crystallization. Examples of these embodiments include adding water to a BrEA-alcohol solution, e.g., slow addition of about 0.5-1.5 volumes or about 0.8-1.2 volumes of water to about 6 volumes of a BrEA-ethanol solution to obtain BrEA hemihydrate. Other examples of these embodiments include adding water to a BrEA-ketone solvent solution, e.g., slow addition of about 0.5-1.5 volumes or about 0.8-1.2 volumes of water to about 10 volumes of a BrEA-acetone solution to obtain BrEA hemihydrate.

Another related embodiment is BrEA hemihydrate that is milled to an average particle size of about 0.01-200 µM, or about 0.1-10 µM or about 0.5-5 µM. Average particle size or diameter for milled BrEA hemihydrate may thus be relatively small, e.g., about 0.03-2.0 µM or about 0.1-1.0 µM, or somewhat larger, e.g., about 0.5-5.0 µM or about 1-5.0 µM. Milled BrEA hemihydrate is suitable for preparing solid formulations and parenteral formulations for human or veterinary use. The milled material facilitates dissolution of BrEA hemihydrate in solvents or excipients and facilitates mixing with solids or solid excipients.

While it is possible to administer BrEA hemihydrate as a pure compound to a subject, it is usually presented as a solid formulation or used to prepare a liquid formulation. Formulations will typically be used to prepare unit dosages, e.g., tablets, capsules or lozenges for oral, buccal or sublingual administration, that comprise about 10-1000 mg or typically about 25-400 mg of BrEA hemihydrate. Alternatively, embodiments include a product for parenteral (e.g., subcutaneous, subdermal, intravenous, intramuscular, intraperitoneal) administration made by the process of contacting BrEA hemihydrate and a liquid excipient, e.g., any one, two, three or more of PEG 100, PEG 200, PEG 300, PEG 400, propylene glycol, benzyl benzoate, benzyl alcohol or ethanol, and optionally sterilizing the solution and optionally dispensing the solution into vials or ampules (typically amber glass), which may be single-use or multi-use and optionally storing the formulation at reduced temperature (about 0-12° C., or about 2-10° C.). Such products for parenteral administration typically comprise BrEA at a concentration of about 10-170 mg/mL, usually about 20-110 mg/mL or about 30-100 mg/mL, and optionally one or more of a salt, buffer or bacteriostat or preservative (e.g., NaCl, BHA, BHT or EDTA).

Other embodiments include a product produced by the process of contacting BrEA hemihydrate, which may be substantially free of other forms of BrEA, with an excipient suitable for human pharmaceutical use or for veterinary use. The product is useful to make formulations or unit dosage forms that contain the hemihydrate. Exemplary excipients include one or more of those disclosed herein, e.g., sucrose, mannitol, starch, carboxymethyl cellulose, magnesium stearate and the like.

Specific embodiments of formula 1 compounds. Other embodiments include compounds, compositions and formulations where one or more variable groups that are bonded to the formula 1 compounds, e.g., one or more of $R^1$-$R^6$, $R^{10}$, $R^{15}$, $R^{17}$ or $R^{18}$ comprise an amino acid or a peptide, e.g., $R^1$, $R^2$ or $R^4$ comprises an amino acid or a peptide, $R^3$ is a halogen and $R^5$ and $R^6$ are both —$CH_3$. The peptide at one or more of $R^1$-$R^6$ can comprise a cell surface binding peptide such as the entire protein or a sequence from fibronectin or retronectin.

In the formula 1 compounds, each $R^4$ is independently selected. In some embodiments one $R^4$ is hydrogen and the other is another moiety. In other embodiments, both $R^4$ are independently selected moieties other than hydrogen, e.g., a C1 to C20 organic moiety.

$R^1$-$R^6$, $R^{10}$, $R^{15}$, $R^{17}$ and $R^{18}$ include moieties, e.g., esters, thioesters, thionoesters, carbonates, amino acids, peptides and/or carbamates, that are chemically and/or enzymatically hydrolyzable, often under physiological conditions. Such moieties are independently chosen. Typically these moieties will give rise to —OH, —SH or —$NH_2$ at the $R^1$-$R^6$ positions of the steroid nucleus. Embodiments of formula 1 compounds include ones where (1) one of $R^1$, $R^2$ and $R^4$ is a hydrolyzable moiety (e.g., ester, thioester, thionoester, carbonate, amino acid, peptide or carbamate), the other two of $R^1$, $R^2$ and $R^4$ are —H, $R^3$ is not hydrogen and $R^5$ and $R^6$ are both —$CH_3$, (2) two of $R^1$, $R^2$ and $R^4$ are hydrolyzable moieties (e.g., independently chosen esters, thioesters, thionoesters, carbonates, amino acids, peptides and/or carbamates), the other of $R^1$, $R^2$ and $R^4$ is —H, $R^3$ is not hydrogen and $R^5$ and $R^6$ are both —$CH_3$, (3) $R^1$, $R^2$ and $R^4$ are hydrolyzable moieties, $R^3$ is not hydrogen and $R^5$ and $R^6$ are both —$CH_3$. In these embodiments, the $R^3$ group is typically in the β-configuration and the $R^1$, $R^2$ and $R^4$-$R^6$ groups are typically in the α-configuration.

In other embodiments, one or more of $R^1$-$R^6$, $R^{10}$, $R^{15}$, $R^{17}$ and $R^{18}$, usually one, comprises an amino acid or a peptide, while the remaining groups are independently selected from the moieties defined herein. In these embodiments, the peptides are typically dimers (dipeptides) or trimers (tripeptides). For example one of $R^1$, $R^2$ or $R^4$ comprises an amino acid, the remaining of $R^1$, $R^2$ or $R^4$ independently comprise —OH, =O, an ester, a carbonate or a carbamate, while $R^3$ is a halogen, hydroxyl or an ester and $R^5$ and $R^6$ independently are —H, —$(CH_2)_n$—$CH_3$, —$(CH_2)_n$—$CH_2OH$, or —$(CH_2)_n$—$CH_2F$, —$(CH_2)_{2-4}$—O—$(CH_2)_{2-4}$—$CH_3$, where n is 0, 1, 2, 3, 4, 5, 6, 7 or 8 often 0, 1, or 2, usually 0. Typically the ester, carbonate or carbamate are hydrolyzable under physiological conditions.

Hydrolyzable moieties typically comprise acyl groups, esters, ethers, thioethers, amides, amino acids, peptides, carbonates and/or carbamates. In general, the structure of hydrolyzable moieties is not critical and can vary. In some embodiments, these moieties contain a total of about 4 to about 10 carbon atoms. These hydrolyzable moieties in other embodiments comprise an organic moiety, as described above for ester, that contains 2, 3, 4, 5, 6, 7, 8, 9, 10, 11, 12 13, 14, 15 or 16 carbon atoms and 1, 2, 3, 4, 5, 6, 7 or 8 heteroatoms, e.g., oxygen, nitrogen or sulfur. These hydrolyzable moieties can comprise no groups that are charged in plasma, blood, intracellular cytoplasm or in the gut, or they can comprise 1, 2, 3 or more positive, negative or positive and negative charges under one or more of these conditions. The charges may be fractional depending on the group and the conditions it is under. These hydrolyzable moieties may comprise 1, 2, 3, 4 or more substitutions at a hydrogen atom(s) and/or a carbon atom(s), e.g., —OH, protected hydroxyl, —SH, protected thiol, carboxyl, protected carboxyl, amine, protected amine, —O—, —S—, —CO—, —CS—, alkoxy, alkylthio, alkenyloxy, aryl, —OP(O)(O)—O—, —OS(O)(O)—O— and/or heterocycle. Such substitutions are independently selected. Embodiments of formula 1 compounds include ones wherein one, two, three, four or more of the variable groups that are bonded to the steroid rings, e.g., $R^1$-$R^6$ or $R^{10}$, comprise a moiety that can hydrolyze or metabolize to, e.g., a —H, —OH, =O, —SH, =S, —COOH, —NH$_2$, —CH$_2$OH, —CH$_2$SH, —C(O)—C1-C6 alkyl-OH, —C(O)—C1-C6 alkyl-SH, —C(S)—C1-C6 alkyl-OH, —C(O)—C1-C6 alkyl or —C(O)—NH$_2$ atom or group.

Formula 1 compounds that comprise a hydrolyzable moiety(ies) may include one or more independently chosen —O—CHR$^{24}$C(O)OR$^{25}$, —S—CHR$^{24}$C(O)OR$^{25}$, —NH—CHR$^{24}$C(O)OR$^{25}$, —O—CHR$^{24}$C(S)OR$^{25}$, —S—CHR$^{24}$C(S)OR$^{25}$, —NH—CHR$^{24}$C(S)OR$^{25}$, —O—CHR$^{24}$OC(O)R$^{25}$, —S—CHR$^{24}$OC(O)R$^{25}$, —NH—CHR$^{24}$OC(O)R$^{25}$, —O—CHR$^{25}$, —O—CHR$^{24}$C(O)N(R$^{25}$)$_2$, —NH—CHR$^{24}$C(O)N(R$^{25}$)$_2$, —O—CHR$^{24}$OR$^{25}$, —S—CHR$^{24}$OR$^{25}$, —NH—CHR$^{24}$OR$^{25}$, —O—CHR$^{24}$C(R$^{25}$)$_2$CH$_2$OX, —S—CHR$^{24}$C(R$^{25}$)$_2$CH$_2$OX, —NH—CHR$^{24}$C(R$^{25}$)$_2$CH$_2$OX, —O—CHR$^{24}$C(R$^{25}$)$_2$OX, —S—CHR$^{24}$C(R$^{25}$)$_2$OX or —NH—CHR$^{24}$C(R$^{25}$)$_2$OX, groups that one or more of $R^1$-$R^6$, $R^{10}$, $R^{15}$, $R^{17}$ and $R^{18}$ comprise. For these hydrolyzable moieties, $R^{24}$ independently is —H, —CH$_2$—C$_6$H$_5$, —CH$_2$CH$_2$—C$_6$H$_5$, C$_{1-8}$ alkyl, C$_{2-8}$ alkenyl, aryl or heterocycle where each alkyl, alkenyl, aryl and heterocycle moiety is independently optionally substituted with 1, 2, or 3, usually 1, —O—, —S—, —NH—, halogen, aryl, —OX, —SX, —NHX, ketone (=O) or —CN moieties or the C$_{1-8}$ alkyl is optionally substituted with 3, 4, 5 or 6 halogens, and X is —H or a protecting group. Exemplary $R^{24}$ are —H, —CH$_3$, —C$_2$H$_5$, —CH$_2$—C$_{1-5}$ optionally substituted alkyl, —CH$_2$CH$_2$—C$_{1-4}$ optionally substituted alkyl and —CH$_2$CH$_2$—O—C$_{1-4}$ optionally substituted alkyl. $R^{25}$ independently is —H or a C$_{1-30}$ organic moiety such as —CH$_2$—C$_6$H$_5$, —CH$_2$CH$_2$—C$_6$H$_5$, C$_{1-12}$ alkyl, C$_{2-12}$ alkenyl, C$_{2-12}$ alkynyl, aryl, a heterocycle, —CH$_2$-heterocycle or —CH$_2$-aryl, where each alkyl, alkenyl, alkynyl, aryl, heterocycle, —CH$_2$-heterocycle or —CH$_2$-aryl moiety is independently optionally substituted with 1 or 2, usually 1, —O—, —S—, —NH—, halogen, aryl, —OX, —SX, —NHX, ketone (=O), —C(O)OX or —CN moieties or the C$_{1-12}$ alkyl, C$_{2-12}$ alkenyl or aryl, are optionally independently substituted with 3, 4, 5 or 6 halogens, where X is —H or a protecting group, or the aryl, heterocycle, —CH$_2$-heterocycle or —CH$_2$-aryl moieties are optionally independently substituted with 1, 2 or 3 C$_{1-4}$ alkyl moieties or with 1, 2 or 3 C$_{1-4}$ alkoxy moieties at the aryl moiety or at the heterocycle, usually at a ring carbon. Exemplary $R^{25}$ are —H, —CH$_3$, —C$_2$H$_5$, —C$_3$H$_7$, —C$_4$H$_9$, —C$_6$H$_{13}$, —C$_6$H$_5$, —C$_6$H$_4$OH, —C$_6$H$_4$OCH$_3$, —C$_6$H$_4$F, —CH$_2$—C$_{1-5}$ optionally substituted alkyl, —CH$_2$CH$_2$—(S)$_{0-1}$—C$_{1-4}$ optionally substituted alkyl and —CH$_2$CH$_2$—O—C$_{1-4}$ optionally substituted alkyl.

Invention embodiments include a composition comprising (1) a compound of formula 1 or 2 and one or more nonaqueous liquid excipients, wherein the composition comprises less than about 3% v/v water and (2) a compound of formula 1 or 2 and one or more solid excipients.

Invention embodiments include one or more compounds of formula 1 or formula 2 including formula 1 compounds having the structure

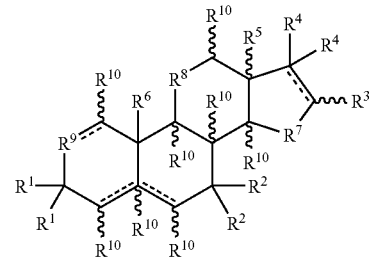

wherein,
$R^1$, $R^2$, $R^3$, $R^4$, $R^5$, $R^6$ and $R^{10}$ independently are —H, —OR$^{PR}$, —SR$^{PR}$, —N(R$^{PR}$)$_2$, —O—Si—(R$^{13}$)$_3$, —CHO, —CHS, —SCN, —CH=NH, —CN, —NO$_2$, —OSO$_3$H, —OPO$_3$H, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, an acetal, a thioacetal, a halogen, an optionally substituted alkyl group, an optionally substituted alkenyl group, an optionally substituted alkynyl group, an optionally substituted aryl moiety, an optionally substituted heteroaryl moiety, an optionally substituted monosaccharide, an optionally substituted oligosaccharide, a nucleoside, a nucleotide, an oligonucleotide, a polymer, or, one, two or more of $R^1$, $R^2$, $R^3$, $R^4$, $R^5$, $R^6$ and $R^{10}$ independently are =O, =S, =N—OH, =CH$_2$ or a spiro ring and the hydrogen atom that is bonded to the same carbon atom is absent, or, $R^3$ and $R^4$ together comprise a structure of formula 2

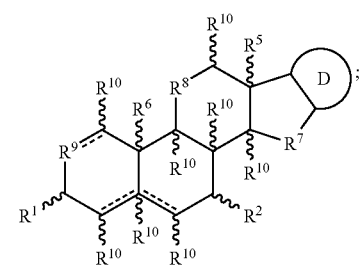

$R^7$ is —C(R$^{10}$)$_2$—, —C(R$^{10}$)$_2$—C(R$^{10}$)$_2$—, —C(R$^{10}$)$_2$—C(R$^{10}$)$_2$—C(R$^{10}$)$_2$—, —C(R$^{10}$)$_2$—O—C(R$^{10}$)$_2$—, —C(R$^{10}$)$_2$—S—C(R$^{10}$)$_2$—, —C(R$^{10}$)$_2$—NR$^{PR}$—C(R$^{10}$)$_2$—, —O—, —O—C(R$^{10}$)$_2$—, —S—, —S—C(R$^{10}$)$_2$—, —NR$^{PR}$—, —NR$^{PR}$—C(R$^{10}$)$_2$—, —CHR$^{10}$—, —CHR$^{10}$—CHR$^{10}$—, —CHR$^{10}$—CHR$^{10}$—, —CHR$^{10}$—O—CHR$^{10}$—, —CHR$^{10}$—S—CHR$^{10}$—, —CHR$^{10}$—NR$^{PR}$—CHR$^{10}$—, —O—, —O—CHR$^{10}$—, —S—, —S—CHR$^{10}$—, —NR$^{PR}$— or —NR$^{PR}$—CHR$^{10}$—;

R⁸ and R⁹ independently are —C(R¹⁰)₂—, —C(R¹⁰)₂—C(R¹⁰)₂—, —O—, —O—C(R¹⁰)₂—, —S—, —S—C(R¹⁰)₂—, —NR$^{PR}$—, —NR$^{PR}$—C(R¹⁰)₂—, —CHR¹⁰—, —CHR¹⁰—CHR¹⁰—, —O—, —O—CHR¹⁰—, —S—, —S—CHR¹⁰—, —NR$^{PR}$— or —NR$^{PR}$—CHR¹⁰—, or one or both of R⁸ or R⁹ independently are absent, leaving a 5-membered ring;

R⁸ and R⁹ independently are —CHR¹⁰—, —CHR¹⁰—CHR¹⁰—, —O—, —O—CHR¹⁰—, —S—, —S—CHR¹⁰—, —NR$^{PR}$— or —NR$^{PR}$—CHR¹⁰—, or R⁸ or R⁹ independently is absent, leaving a 5-membered ring;

R¹³ independently is C₁₋₆ alkyl;

R$^{PR}$ independently is —H or a protecting group for, e.g., an O, N or S atom;

D is a heterocycle or a 4-, 5-, 6- or 7-membered ring that comprises saturated carbon atoms, wherein 1, 2 or 3 ring carbon atoms of the 4-, 5-, 6- or 7-membered ring are optionally independently substituted with —O—, —S— or —NR$^{PR}$— or where 1, 2 or 3 hydrogen atoms of the heterocycle or where 1, 2 or 3 hydrogen atoms of the 4-, 5-, 6- or 7-membered ring are substituted with —OR$^{PR}$, —SR$^{PR}$, —N(R$^{PR}$)₂, —O—Si—(R¹³)₃, —CHO, —CHS, —CH=NH, —CN, —NO₂, —OSO₃H, —OPO₃H, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, an acetal, a thioacetal, a halogen, an optionally substituted alkyl group, an optionally substituted alkenyl group, an optionally substituted alkynyl group, an optionally substituted aryl moiety, an optionally substituted heteroaryl moiety, an optionally substituted monosaccharide, an optionally substituted oligosaccharide, a nucleoside, a nucleotide, an oligonucleotide or a polymer, or, one or more of the ring carbons are substituted with independently selected =O, =S, =N—OH, =CH₂ or a spiro ring, or D comprises two 5- or 6-membered rings, wherein the rings are fused or are linked by 1 or 2 bonds, wherein one, two or three of R⁷, R⁸ and R⁹ are not —CHR¹⁰— or —C(R¹⁰)₂—.

In the formula 1 or formula 2 compounds, whenever a variable moiety such as R⁷, R⁸ or R⁹ is defined to include moieties such as —O—CHR¹⁰— or —NR$^{PR}$—CHR¹⁰—, it is intended that such moieties can be present in either orientation relative to the other ring atoms that may be present, i.e., —O—CHR¹⁰—, —NR$^{PR}$—CHR¹⁰—, —CHR¹⁰—O— and —CHR¹⁰—NR$^{PR}$— are all included.

Embodiments of formula 1 compounds include or exclude any subset of compounds within the definition of formula 1, provided that at least one compound remains. For example, a subset of formula 1 compounds that are may be included, for example in the invention nonaqueous formulations and in the invention intermittent dosing protocols and immune modulation methods, are formula 1 compounds where R² is hydroxyl, or a group that can hydrolyze or metabolize to hydroxyl or thiol, in either configuration and R⁵ and R⁶ are methyl in the α-configuration. A subset compounds that are optionally excluded from formula 1 compounds comprises one or all compounds that are disclosed in one or more prior art references or publications, e.g., one or more compounds that are disclosed in one or more of the references cited herein, especially for those compounds that can render any claim or embodiment unpatentable for novelty, obviousness and/or inventive step reasons.

Exemplary embodiments of species and genera of formula 1 compounds are named as described below.

Group 1. Exemplary embodiments include the formula 1 compounds named according to the compound structure designations given in Tables A and B below. Each compound named in Table B is depicted as a compound having formula B

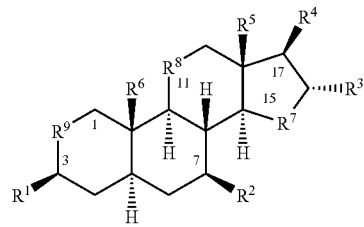

B where R⁵ and R⁶ are both —CH₃, there is no double bond at the 1-2-, 4-5- or 5-6-positions, one R⁴ is hydrogen, R⁷, R⁸ and R⁹ are all —CH₂— and R¹, R², R³ and R⁴ are the substituents designated in Table A. The compounds named according to Tables A and B are referred to as "group 1" compounds.

Compounds named in Table B are named by numbers assigned to R¹, R², R³ and R⁴ according to the following compound naming convention, R¹.R².R³.R⁴, based on the numbered chemical substituents depicted in Table A. Each Table A number specifies a different structure for each of R¹, R², R³ and R⁴. When R¹, R², R³ or R⁴ is a divalent moiety, e.g., =O, the hydrogen at the corresponding position is absent. Thus, the group 1 compound named 1.2.1.1 is a formula B structure with a β-hydroxyl bonded to carbons at the 3- and 7-positions (the variable groups R¹ and R² respectively), an α-bromine bonded to carbon 16 (the variable group R³) and double bonded oxygen (=O) at carbon 17 (the variable group R⁴), i.e., 1.2.1.1 has the structure shown below.

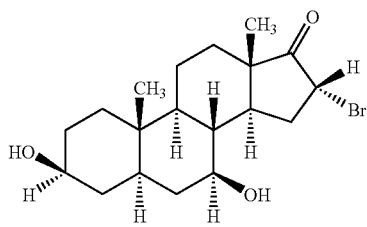

1.2.1.1

TABLE A

| | R¹ |
|---|---|
| 1 | —OH |
| 2 | =O |
| 3 | —SH |
| 4 | =S |
| 5 | —O—CH₃ |
| 6 | —O—S(O)(O)—O⁻Na⁺ |
| 7 | —O—S(O)(O)—OC₂H₅ |
| 8 | —CH₃ |
| 9 | —H |
| 10 | —OC(O)C(CH₃)₃ |
| | R² |
| 1 | —H |
| 2 | —OH |
| 3 | =O |

TABLE A-continued

| | |
|---|---|
| 4 | —CH₃ |
| 5 | —OCH₃ |
| 6 | —OC₂H₅ |
| 7 | —OCH₂CH₂CH₃ |
| 8 | —OCH₂CH₂CH₂CH₃ |
| 9 | —Cl |
| 10 | —Br |
| R³ | |
| 1 | —Br |
| 2 | —Cl |
| 3 | —I |
| 4 | —F |
| 5 | —H |
| 6 | —OH |
| 7 | =O |
| 8 | —O—C(O)—CH₃ |
| 9 | —O—C(O)—CH₂CH₃ |
| 10 | —O—C(O)—CH₂CH₂CH₃ |
| R⁴ | |
| 1 | =O |
| 2 | —OH |
| 3 | —H |
| 4 | —F |
| 5 | —Cl |
| 6 | —Br |
| 7 | —I |
| 8 | —O—C(O)—CH₃ |
| 9 | —O—C(O)—CH₂CH₃ |
| 10 | —O—C(O)—CH₂CH₂CH₃ |

TABLE B 1.1.1.1, 1.1.1.2, 1.1.1.3, 1.1.1.4, 1.1.1.5, 1.1.1.6, 1.1.1.7, 1.1.1.8, 1.1.1.9, 1.1.1.10,
1.1.2.1, 1.1.2.2, 1.1.2.3, 1.1.2.4, 1.1.2.5, 1.1.2.6, 1.1.2.7, 1.1.2.8, 1.1.2.9, 1.1.2.10,
1.1.3.1, 1.1.3.2, 1.1.3.3, 1.1.3.4, 1.1.3.5, 1.1.3.6, 1.1.3.7, 1.1.3.8, 1.1.3.9, 1.1.3.10,
1.1.4.1, 1.1.4.2, 1.1.4.3, 1.1.4.4, 1.1.4.5, 1.1.4.6, 1.1.4.7, 1.1.4.8, 1.1.4.9, 1.1.4.10,
1.1.5.1, 1.1.5.2, 1.1.5.3, 1.1.5.4, 1.1.5.5, 1.1.5.6, 1.1.5.7, 1.1.5.8, 1.1.5.9, 1.1.5.10,
1.1.6.1, 1.1.6.2, 1.1.6.3, 1.1.6.4, 1.1.6.5, 1.1.6.6, 1.1.6.7, 1.1.6.8, 1.1.6.9, 1.1.6.10,
1.1.7.1, 1.1.7.2, 1.1.7.3, 1.1.7.4, 1.1.7.5, 1.1.7.6, 1.1.7.7, 1.1.7.8, 1.1.7.9, 1.1.7.10,
1.1.8.1, 1.1.8.2, 1.1.8.3, 1.1.8.4, 1.1.8.5, 1.1.8.6, 1.1.8.7, 1.1.8.8, 1.1.8.9, 1.1.8.10,
1.1.9.1, 1.1.9.2, 1.1.9.3, 1.1.9.4, 1.1.9.5, 1.1.9.6, 1.1.9.7, 1.1.9.8, 1.1.9.9, 1.1.9.10,
1.1.10.1, 1.1.10.2, 1.1.10.3, 1.1.10.4, 1.1.10.5, 1.1.10.6, 1.1.10.7, 1.1.10.8, 1.1.10.9,
1.1.10.10, 1.2.1.1, 1.2.1.2, 1.2.1.3, 1.2.1.4, 1.2.1.5, 1.2.1.6, 1.2.1.7, 1.2.1.8, 1.2.1.9,
1.2.1.10, 1.2.2.1, 1.2.2.2, 1.2.2.3, 1.2.2.4, 1.2.2.5, 1.2.2.6, 1.2.2.7, 1.2.2.8, 1.2.2.9,
1.2.2.10, 1.2.3.1, 1.2.3.2, 1.2.3.3, 1.2.3.4, 1.2.3.5, 1.2.3.6, 1.2.3.7, 1.2.3.8, 1.2.3.9,
1.2.3.10, 1.2.4.1, 1.2.4.2, 1.2.4.3, 1.2.4.4, 1.2.4.5, 1.2.4.6, 1.2.4.7, 1.2.4.8, 1.2.4.9,
1.2.4.10, 1.2.5.1, 1.2.5.2, 1.2.5.3, 1.2.5.4, 1.2.5.5, 1.2.5.6, 1.2.5.7, 1.2.5.8, 1.2.5.9,
1.2.5.10, 1.2.6.1, 1.2.6.2, 1.2.6.3, 1.2.6.4, 1.2.6.5, 1.2.6.6, 1.2.6.7, 1.2.6.8, 1.2.6.9,
1.2.6.10, 1.2.7.1, 1.2.7.2, 1.2.7.3, 1.2.7.4, 1.2.7.5, 1.2.7.6, 1.2.7.7, 1.2.7.8, 1.2.7.9,
1.2.7.10, 1.2.8.1, 1.2.8.2, 1.2.8.3, 1.2.8.4, 1.2.8.5, 1.2.8.6, 1.2.8.7, 1.2.8.8, 1.2.8.9,
1.2.8.10, 1.2.9.1, 1.2.9.2, 1.2.9.3, 1.2.9.4, 1.2.9.5, 1.2.9.6, 1.2.9.7, 1.2.9.8, 1.2.9.9,
1.2.9.10, 1.2.10.1, 1.2.10.2, 1.2.10.3, 1.2.10.4, 1.2.10.5, 1.2.10.6, 1.2.10.7, 1.2.10.8,
1.2.10.9, 1.2.10.10, 1.3.1.1, 1.3.1.2, 1.3.1.3, 1.3.1.4, 1.3.1.5, 1.3.1.6, 1.3.1.7, 1.3.1.8,
1.3.1.9, 1.3.1.10, 1.3.2.1, 1.3.2.2, 1.3.2.3, 1.3.2.4, 1.3.2.5, 1.3.2.6, 1.3.2.7, 1.3.2.8,
1.3.2.9, 1.3.2.10, 1.3.3.1, 1.3.3.2, 1.3.3.3, 1.3.3.4, 1.3.3.5, 1.3.3.6, 1.3.3.7, 1.3.3.8,
1.3.3.9, 1.3.3.10, 1.3.4.1, 1.3.4.2, 1.3.4.3, 1.3.4.4, 1.3.4.5, 1.3.4.6, 1.3.4.7, 1.3.4.8,
1.3.4.9, 1.3.4.10, 1.3.5.1, 1.3.5.2, 1.3.5.3, 1.3.5.4, 1.3.5.5, 1.3.5.6, 1.3.5.7, 1.3.5.8,
1.3.5.9, 1.3.5.10, 1.3.6.1, 1.3.6.2, 1.3.6.3, 1.3.6.4, 1.3.6.5, 1.3.6.6, 1.3.6.7, 1.3.6.8,
1.3.6.9, 1.3.6.10, 1.3.7.1, 1.3.7.2, 1.3.7.3, 1.3.7.4, 1.3.7.5, 1.3.7.6, 1.3.7.7, 1.3.7.8,
1.3.7.9, 1.3.7.10, 1.3.8.1, 1.3.8.2, 1.3.8.3, 1.3.8.4, 1.3.8.5, 1.3.8.6, 1.3.8.7, 1.3.8.8,
1.3.8.9, 1.3.8.10, 1.3.9.1, 1.3.9.2, 1.3.9.3, 1.3.9.4, 1.3.9.5, 1.3.9.6, 1.3.9.7, 1.3.9.8,
1.3.9.9, 1.3.9.10, 1.3.10.1, 1.3.10.2, 1.3.10.3, 1.3.10.4, 1.3.10.5, 1.3.10.6, 1.3.10.7,
1.3.10.8, 1.3.10.9, 1.3.10.10, 1.4.1.1, 1.4.1.2, 1.4.1.3, 1.4.1.4, 1.4.1.5, 1.4.1.6, 1.4.1.7,
1.4.1.8, 1.4.1.9, 1.4.1.10, 1.4.2.1, 1.4.2.2, 1.4.2.3, 1.4.2.4, 1.4.2.5, 1.4.2.6, 1.4.2.7,
1.4.2.8, 1.4.2.9, 1.4.2.10, 1.4.3.1, 1.4.3.2, 1.4.3.3, 1.4.3.4, 1.4.3.5, 1.4.3.6, 1.4.3.7,
1.4.3.8, 1.4.3.9, 1.4.3.10, 1.4.4.1, 1.4.4.2, 1.4.4.3, 1.4.4.4, 1.4.4.5, 1.4.4.6, 1.4.4.7,
1.4.4.8, 1.4.4.9, 1.4.4.10, 1.4.5.1, 1.4.5.2, 1.4.5.3, 1.4.5.4, 1.4.5.5, 1.4.5.6, 1.4.5.7,
1.4.5.8, 1.4.5.9, 1.4.5.10, 1.4.6.1, 1.4.6.2, 1.4.6.3, 1.4.6.4, 1.4.6.5, 1.4.6.6, 1.4.6.7,
1.4.6.8, 1.4.6.9, 1.4.6.10, 1.4.7.1, 1.4.7.2, 1.4.7.3, 1.4.7.4, 1.4.7.5, 1.4.7.6, 1.4.7.7,
1.4.7.8, 1.4.7.9, 1.4.7.10, 1.4.8.1, 1.4.8.2, 1.4.8.3, 1.4.8.4, 1.4.8.5, 1.4.8.6, 1.4.8.7,
1.4.8.8, 1.4.8.9, 1.4.8.10, 1.4.9.1, 1.4.9.2, 1.4.9.3, 1.4.9.4, 1.4.9.5, 1.4.9.6, 1.4.9.7,
1.4.9.8, 1.4.9.9, 1.4.9.10, 1.4.10.1, 1.4.10.2, 1.4.10.3, 1.4.10.4, 1.4.10.5, 1.4.10.6,
1.4.10.7, 1.4.10.8, 1.4.10.9, 1.4.10.10, 1.5.1.1, 1.5.1.2, 1.5.1.3, 1.5.1.4, 1.5.1.5, 1.5.1.6,
1.5.1.7, 1.5.1.8, 1.5.1.9, 1.5.1.10, 1.5.2.1, 1.5.2.2, 1.5.2.3, 1.5.2.4, 1.5.2.5, 1.5.2.6,
1.5.2.7, 1.5.2.8, 1.5.2.9, 1.5.2.10, 1.5.3.1, 1.5.3.2, 1.5.3.3, 1.5.3.4, 1.5.3.5, 1.5.3.6,
1.5.3.7, 1.5.3.8, 1.5.3.9, 1.5.3.10, 1.5.4.1, 1.5.4.2, 1.5.4.3, 1.5.4.4, 1.5.4.5, 1.5.4.6,
1.5.4.7, 1.5.4.8, 1.5.4.9, 1.5.4.10, 1.5.5.1, 1.5.5.2, 1.5.5.3, 1.5.5.4, 1.5.5.5, 1.5.5.6,
1.5.5.7, 1.5.5.8, 1.5.5.9, 1.5.5.10, 1.5.6.1, 1.5.6.2, 1.5.6.3, 1.5.6.4, 1.5.6.5, 1.5.6.6,
1.5.6.7, 1.5.6.8, 1.5.6.9, 1.5.6.10, 1.5.7.1, 1.5.7.2, 1.5.7.3, 1.5.7.4, 1.5.7.5, 1.5.7.6,
1.5.7.7, 1.5.7.8, 1.5.7.9, 1.5.7.10, 1.5.8.1, 1.5.8.2, 1.5.8.3, 1.5.8.4, 1.5.8.5, 1.5.8.6,
1.5.8.7, 1.5.8.8, 1.5.8.9, 1.5.8.10, 1.5.9.1, 1.5.9.2, 1.5.9.3, 1.5.9.4, 1.5.9.5, 1.5.9.6,
1.5.9.7, 1.5.9.8, 1.5.9.9, 1.5.9.10, 1.5.10.1, 1.5.10.2, 1.5.10.3, 1.5.10.4, 1.5.10.5,
1.5.10.6, 1.5.10.7, 1.5.10.8, 1.5.10.9, 1.5.10.10, 1.6.1.1, 1.6.1.2, 1.6.1.3, 1.6.1.4, 1.6.1.5,
1.6.1.6, 1.6.1.7, 1.6.1.8, 1.6.1.9, 1.6.1.10, 1.6.2.1, 1.6.2.2, 1.6.2.3, 1.6.2.4, 1.6.2.5,
1.6.2.6, 1.6.2.7, 1.6.2.8, 1.6.2.9, 1.6.2.10, 1.6.3.1, 1.6.3.2, 1.6.3.3, 1.6.3.4, 1.6.3.5,
1.6.3.6, 1.6.3.7, 1.6.3.8, 1.6.3.9, 1.6.3.10, 1.6.4.1, 1.6.4.2, 1.6.4.3, 1.6.4.4, 1.6.4.5,
1.6.4.6, 1.6.4.7, 1.6.4.8, 1.6.4.9, 1.6.4.10, 1.6.5.1, 1.6.5.2, 1.6.5.3, 1.6.5.4, 1.6.5.5,
1.6.5.6, 1.6.5.7, 1.6.5.8, 1.6.5.9, 1.6.5.10, 1.6.6.1, 1.6.6.2, 1.6.6.3, 1.6.6.4, 1.6.6.5,
1.6.6.6, 1.6.6.7, 1.6.6.8, 1.6.6.9, 1.6.6.10, 1.6.7.1, 1.6.7.2, 1.6.7.3, 1.6.7.4, 1.6.7.5,
1.6.7.6, 1.6.7.7, 1.6.7.8, 1.6.7.9, 1.6.7.10, 1.6.8.1, 1.6.8.2, 1.6.8.3, 1.6.8.4, 1.6.8.5,
1.6.8.6, 1.6.8.7, 1.6.8.8, 1.6.8.9, 1.6.8.10, 1.6.9.1, 1.6.9.2, 1.6.9.3, 1.6.9.4, 1.6.9.5,

TABLE B-continued 1.6.9.6, 1.6.9.7, 1.6.9.8, 1.6.9.9, 1.6.9.10, 1.6.10.1, 1.6.10.2, 1.6.10.3, 1.6.10.4, 1.6.10.5,
1.6.10.6, 1.6.10.7, 1.6.10.8, 1.6.10.9, 1.6.10.10, 1.7.1.1, 1.7.1.2, 1.7.1.3, 1.7.1.4, 1.7.1.5,
1.7.1.6, 1.7.1.7, 1.7.1.8, 1.7.1.9, 1.7.1.10, 1.7.2.1, 1.7.2.2, 1.7.2.3, 1.7.2.4, 1.7.2.5,
1.7.2.6, 1.7.2.7, 1.7.2.8, 1.7.2.9, 1.7.2.10, 1.7.3.1, 1.7.3.2, 1.7.3.3, 1.7.3.4, 1.7.3.5,
1.7.3.6, 1.7.3.7, 1.7.3.8, 1.7.3.9, 1.7.3.10, 1.7.4.1, 1.7.4.2, 1.7.4.3, 1.7.4.4, 1.7.4.5,
1.7.4.6, 1.7.4.7, 1.7.4.8, 1.7.4.9, 1.7.4.10, 1.7.5.1, 1.7.5.2, 1.7.5.3, 1.7.5.4, 1.7.5.5,
1.7.5.6, 1.7.5.7, 1.7.5.8, 1.7.5.9, 1.7.5.10, 1.7.6.1, 1.7.6.2, 1.7.6.3, 1.7.6.4, 1.7.6.5,
1.7.6.6, 1.7.6.7, 1.7.6.8, 1.7.6.9, 1.7.6.10, 1.7.7.1, 1.7.7.2, 1.7.7.3, 1.7.7.4, 1.7.7.5,
1.7.7.6, 1.7.7.7, 1.7.7.8, 1.7.7.9, 1.7.7.10, 1.7.8.1, 1.7.8.2, 1.7.8.3, 1.7.8.4, 1.7.8.5,
1.7.8.6, 1.7.8.7, 1.7.8.8, 1.7.8.9, 1.7.8.10, 1.7.9.1, 1.7.9.2, 1.7.9.3, 1.7.9.4, 1.7.9.5,
1.7.9.6, 1.7.9.7, 1.7.9.8, 1.7.9.9, 1.7.9.10, 1.7.10.1, 1.7.10.2, 1.7.10.3, 1.7.10.4, 1.7.10.5,
1.7.10.6, 1.7.10.7, 1.7.10.8, 1.7.10.9, 1.7.10.10, 1.8.1.1, 1.8.1.2, 1.8.1.3, 1.8.1.4, 1.8.1.5,
1.8.1.6, 1.8.1.7, 1.8.1.8, 1.8.1.9, 1.8.1.10, 1.8.2.1, 1.8.2.2, 1.8.2.3, 1.8.2.4, 1.8.2.5,
1.8.2.6, 1.8.2.7, 1.8.2.8, 1.8.2.9, 1.8.2.10, 1.8.3.1, 1.8.3.2, 1.8.3.3, 1.8.3.4, 1.8.3.5,
1.8.3.6, 1.8.3.7, 1.8.3.8, 1.8.3.9, 1.8.3.10, 1.8.4.1, 1.8.4.2, 1.8.4.3, 1.8.4.4, 1.8.4.5,
1.8.4.6, 1.8.4.7, 1.8.4.8, 1.8.4.9, 1.8.4.10, 1.8.5.1, 1.8.5.2, 1.8.5.3, 1.8.5.4, 1.8.5.5,
1.8.5.6, 1.8.5.7, 1.8.5.8, 1.8.5.9, 1.8.5.10, 1.8.6.1, 1.8.6.2, 1.8.6.3, 1.8.6.4, 1.8.6.5,
1.8.6.6, 1.8.6.7, 1.8.6.8, 1.8.6.9, 1.8.6.10, 1.8.7.1, 1.8.7.2, 1.8.7.3, 1.8.7.4, 1.8.7.5,
1.8.7.6, 1.8.7.7, 1.8.7.8, 1.8.7.9, 1.8.7.10, 1.8.8.1, 1.8.8.2, 1.8.8.3, 1.8.8.4, 1.8.8.5,
1.8.8.6, 1.8.8.7, 1.8.8.8, 1.8.8.9, 1.8.8.10, 1.8.9.1, 1.8.9.2, 1.8.9.3, 1.8.9.4, 1.8.9.5,
1.8.9.6, 1.8.9.7, 1.8.9.8, 1.8.9.9, 1.8.9.10, 1.8.10.1, 1.8.10.2, 1.8.10.3, 1.8.10.4, 1.8.10.5,
1.8.10.6, 1.8.10.7, 1.8.10.8, 1.8.10.9, 1.8.10.10, 1.9.1.1, 1.9.1.2, 1.9.1.3, 1.9.1.4, 1.9.1.5,
1.9.1.6, 1.9.1.7, 1.9.1.8, 1.9.1.9, 1.9.1.10, 1.9.2.1, 1.9.2.2, 1.9.2.3, 1.9.2.4, 1.9.2.5,
1.9.2.6, 1.9.2.7, 1.9.2.8, 1.9.2.9, 1.9.2.10, 1.9.3.1, 1.9.3.2, 1.9.3.3, 1.9.3.4, 1.9.3.5,
1.9.3.6, 1.9.3.7, 1.9.3.8, 1.9.3.9, 1.9.3.10, 1.9.4.1, 1.9.4.2, 1.9.4.3, 1.9.4.4, 1.9.4.5,
1.9.4.6, 1.9.4.7, 1.9.4.8, 1.9.4.9, 1.9.4.10, 1.9.5.1, 1.9.5.2, 1.9.5.3, 1.9.5.4, 1.9.5.5,
1.9.5.6, 1.9.5.7, 1.9.5.8, 1.9.5.9, 1.9.5.10, 1.9.6.1, 1.9.6.2, 1.9.6.3, 1.9.6.4, 1.9.6.5,
1.9.6.6, 1.9.6.7, 1.9.6.8, 1.9.6.9, 1.9.6.10, 1.9.7.1, 1.9.7.2, 1.9.7.3, 1.9.7.4, 1.9.7.5,
1.9.7.6, 1.9.7.7, 1.9.7.8, 1.9.7.9, 1.9.7.10, 1.9.8.1, 1.9.8.2, 1.9.8.3, 1.9.8.4, 1.9.8.5,
1.9.8.6, 1.9.8.7, 1.9.8.8, 1.9.8.9, 1.9.8.10, 1.9.9.1, 1.9.9.2, 1.9.9.3, 1.9.9.4, 1.9.9.5,
1.9.9.6, 1.9.9.7, 1.9.9.8, 1.9.9.9, 1.9.9.10, 1.9.10.1, 1.9.10.2, 1.9.10.3, 1.9.10.4, 1.9.10.5,
1.9.10.6, 1.9.10.7, 1.9.10.8, 1.9.10.9, 1.9.10.10, 1.10.1.1, 1.10.1.2, 1.10.1.3, 1.10.1.4,
1.10.1.5, 1.10.1.6, 1.10.1.7, 1.10.1.8, 1.10.1.9, 1.10.1.10, 1.10.2.1, 1.10.2.2, 1.10.2.3,
1.10.2.4, 1.10.2.5, 1.10.2.6, 1.10.2.7, 1.10.2.8, 1.10.2.9, 1.10.2.10, 1.10.3.1, 1.10.3.2,
1.10.3.3, 1.10.3.4, 1.10.3.5, 1.10.3.6, 1.10.3.7, 1.10.3.8, 1.10.3.9, 1.10.3.10, 1.10.4.1,
1.10.4.2, 1.10.4.3, 1.10.4.4, 1.10.4.5, 1.10.4.6, 1.10.4.7, 1.10.4.8, 1.10.4.9, 1.10.4.10,
1.10.5.1, 1.10.5.2, 1.10.5.3, 1.10.5.4, 1.10.5.5, 1.10.5.6, 1.10.5.7, 1.10.5.8, 1.10.5.9,
1.10.5.10, 1.10.6.1, 1.10.6.2, 1.10.6.3, 1.10.6.4, 1.10.6.5, 1.10.6.6, 1.10.6.7, 1.10.6.8,
1.10.6.9, 1.10.6.10, 1.10.7.1, 1.10.7.2, 1.10.7.3, 1.10.7.4, 1.10.7.5, 1.10.7.6, 1.10.7.7,
1.10.7.8, 1.10.7.9, 1.10.7.10, 1.10.8.1, 1.10.8.2, 1.10.8.3, 1.10.8.4, 1.10.8.5, 1.10.8.6,
1.10.8.7, 1.10.8.8, 1.10.8.9, 1.10.8.10, 1.10.9.1, 1.10.9.2, 1.10.9.3, 1.10.9.4, 1.10.9.5,
1.10.9.6, 1.10.9.7, 1.10.9.8, 1.10.9.9, 1.10.9.10, 1.10.10.1, 1.10.10.2, 1.10.10.3,
1.10.10.4, 1.10.10.5, 1.10.10.6, 1.10.10.7, 1.10.10.8, 1.10.10.9, 1.10.10.10, 2.1.1.1,
2.1.1.2, 2.1.1.3, 2.1.1.4, 2.1.1.5, 2.1.1.6, 2.1.1.7, 2.1.1.8, 2.1.1.9, 2.1.1.10, 2.1.2.1,
2.1.2.2, 2.1.2.3, 2.1.2.4, 2.1.2.5, 2.1.2.6, 2.1.2.7, 2.1.2.8, 2.1.2.9, 2.1.2.10, 2.1.3.1,
2.1.3.2, 2.1.3.3, 2.1.3.4, 2.1.3.5, 2.1.3.6, 2.1.3.7, 2.1.3.8, 2.1.3.9, 2.1.3.10, 2.1.4.1,
2.1.4.2, 2.1.4.3, 2.1.4.4, 2.1.4.5, 2.1.4.6, 2.1.4.7, 2.1.4.8, 2.1.4.9, 2.1.4.10, 2.1.5.1,
2.1.5.2, 2.1.5.3, 2.1.5.4, 2.1.5.5, 2.1.5.6, 2.1.5.7, 2.1.5.8, 2.1.5.9, 2.1.5.10, 2.1.6.1,
2.1.6.2, 2.1.6.3, 2.1.6.4, 2.1.6.5, 2.1.6.6, 2.1.6.7, 2.1.6.8, 2.1.6.9, 2.1.6.10, 2.1.7.1,
2.1.7.2, 2.1.7.3, 2.1.7.4, 2.1.7.5, 2.1.7.6, 2.1.7.7, 2.1.7.8, 2.1.7.9, 2.1.7.10, 2.1.8.1,
2.1.8.2, 2.1.8.3, 2.1.8.4, 2.1.8.5, 2.1.8.6, 2.1.8.7, 2.1.8.8, 2.1.8.9, 2.1.8.10, 2.1.9.1,
2.1.9.2, 2.1.9.3, 2.1.9.4, 2.1.9.5, 2.1.9.6, 2.1.9.7, 2.1.9.8, 2.1.9.9, 2.1.9.10, 2.1.10.1,
2.1.10.2, 2.1.10.3, 2.1.10.4, 2.1.10.5, 2.1.10.6, 2.1.10.7, 2.1.10.8, 2.1.10.9, 2.1.10.10,
2.2.1.1, 2.2.1.2, 2.2.1.3, 2.2.1.4, 2.2.1.5, 2.2.1.6, 2.2.1.7, 2.2.1.8, 2.2.1.9, 2.2.1.10,
2.2.2.1, 2.2.2.2, 2.2.2.3, 2.2.2.4, 2.2.2.5, 2.2.2.6, 2.2.2.7, 2.2.2.8, 2.2.2.9, 2.2.2.10,
2.2.3.1, 2.2.3.2, 2.2.3.3, 2.2.3.4, 2.2.3.5, 2.2.3.6, 2.2.3.7, 2.2.3.8, 2.2.3.9, 2.2.3.10,
2.2.4.1, 2.2.4.2, 2.2.4.3, 2.2.4.4, 2.2.4.5, 2.2.4.6, 2.2.4.7, 2.2.4.8, 2.2.4.9, 2.2.4.10,
2.2.5.1, 2.2.5.2, 2.2.5.3, 2.2.5.4, 2.2.5.5, 2.2.5.6, 2.2.5.7, 2.2.5.8, 2.2.5.9, 2.2.5.10,
2.2.6.1, 2.2.6.2, 2.2.6.3, 2.2.6.4, 2.2.6.5, 2.2.6.6, 2.2.6.7, 2.2.6.8, 2.2.6.9, 2.2.6.10,
2.2.7.1, 2.2.7.2, 2.2.7.3, 2.2.7.4, 2.2.7.5, 2.2.7.6, 2.2.7.7, 2.2.7.8, 2.2.7.9, 2.2.7.10,
2.2.8.1, 2.2.8.2, 2.2.8.3, 2.2.8.4, 2.2.8.5, 2.2.8.6, 2.2.8.7, 2.2.8.8, 2.2.8.9, 2.2.8.10,
2.2.9.1, 2.2.9.2, 2.2.9.3, 2.2.9.4, 2.2.9.5, 2.2.9.6, 2.2.9.7, 2.2.9.8, 2.2.9.9, 2.2.9.10,
2.2.10.1, 2.2.10.2, 2.2.10.3, 2.2.10.4, 2.2.10.5, 2.2.10.6, 2.2.10.7, 2.2.10.8, 2.2.10.9,
2.2.10.10, 2.3.1.1, 2.3.1.2, 2.3.1.3, 2.3.1.4, 2.3.1.5, 2.3.1.6, 2.3.1.7, 2.3.1.8, 2.3.1.9,
2.3.1.10, 2.3.2.1, 2.3.2.2, 2.3.2.3, 2.3.2.4, 2.3.2.5, 2.3.2.6, 2.3.2.7, 2.3.2.8, 2.3.2.9,
2.3.2.10, 2.3.3.1, 2.3.3.2, 2.3.3.3, 2.3.3.4, 2.3.3.5, 2.3.3.6, 2.3.3.7, 2.3.3.8, 2.3.3.9,
2.3.3.10, 2.3.4.1, 2.3.4.2, 2.3.4.3, 2.3.4.4, 2.3.4.5, 2.3.4.6, 2.3.4.7, 2.3.4.8, 2.3.4.9,
2.3.4.10, 2.3.5.1, 2.3.5.2, 2.3.5.3, 2.3.5.4, 2.3.5.5, 2.3.5.6, 2.3.5.7, 2.3.5.8, 2.3.5.9,
2.3.5.10, 2.3.6.1, 2.3.6.2, 2.3.6.3, 2.3.6.4, 2.3.6.5, 2.3.6.6, 2.3.6.7, 2.3.6.8, 2.3.6.9,
2.3.6.10, 2.3.7.1, 2.3.7.2, 2.3.7.3, 2.3.7.4, 2.3.7.5, 2.3.7.6, 2.3.7.7, 2.3.7.8, 2.3.7.9,
2.3.7.10, 2.3.8.1, 2.3.8.2, 2.3.8.3, 2.3.8.4, 2.3.8.5, 2.3.8.6, 2.3.8.7, 2.3.8.8, 2.3.8.9,
2.3.8.10, 2.3.9.1, 2.3.9.2, 2.3.9.3, 2.3.9.4, 2.3.9.5, 2.3.9.6, 2.3.9.7, 2.3.9.8, 2.3.9.9,
2.3.9.10, 2.3.10.1, 2.3.10.2, 2.3.10.3, 2.3.10.4, 2.3.10.5, 2.3.10.6, 2.3.10.7, 2.3.10.8,
2.3.10.9, 2.3.10.10, 2.4.1.1, 2.4.1.2, 2.4.1.3, 2.4.1.4, 2.4.1.5, 2.4.1.6, 2.4.1.7, 2.4.1.8,
2.4.1.9, 2.4.1.10, 2.4.2.1, 2.4.2.2, 2.4.2.3, 2.4.2.4, 2.4.2.5, 2.4.2.6, 2.4.2.7, 2.4.2.8,
2.4.2.9, 2.4.2.10, 2.4.3.1, 2.4.3.2, 2.4.3.3, 2.4.3.4, 2.4.3.5, 2.4.3.6, 2.4.3.7, 2.4.3.8,
2.4.3.9, 2.4.3.10, 2.4.4.1, 2.4.4.2, 2.4.4.3, 2.4.4.4, 2.4.4.5, 2.4.4.6, 2.4.4.7, 2.4.4.8,
2.4.4.9, 2.4.4.10, 2.4.5.1, 2.4.5.2, 2.4.5.3, 2.4.5.4, 2.4.5.5, 2.4.5.6, 2.4.5.7, 2.4.5.8,
2.4.5.9, 2.4.5.10, 2.4.6.1, 2.4.6.2, 2.4.6.3, 2.4.6.4, 2.4.6.5, 2.4.6.6, 2.4.6.7, 2.4.6.8,
2.4.6.9, 2.4.6.10, 2.4.7.1, 2.4.7.2, 2.4.7.3, 2.4.7.4, 2.4.7.5, 2.4.7.6, 2.4.7.7, 2.4.7.8, TABLE B-continued 2.4.7.9, 2.4.7.10, 2.4.8.1, 2.4.8.2, 2.4.8.3, 2.4.8.4, 2.4.8.5, 2.4.8.6, 2.4.8.7, 2.4.8.8, 2.4.8.9, 2.4.8.10, 2.4.9.1, 2.4.9.2, 2.4.9.3, 2.4.9.4, 2.4.9.5, 2.4.9.6, 2.4.9.7, 2.4.9.8, 2.4.9.9, 2.4.9.10, 2.4.10.1, 2.4.10.2, 2.4.10.3, 2.4.10.4, 2.4.10.5, 2.4.10.6, 2.4.10.7, 2.4.10.8, 2.4.10.9, 2.4.10.10, 2.5.1.1, 2.5.1.2, 2.5.1.3, 2.5.1.4, 2.5.1.5, 2.5.1.6, 2.5.1.7, 2.5.1.8, 2.5.1.9, 2.5.1.10, 2.5.2.1, 2.5.2.2, 2.5.2.3, 2.5.2.4, 2.5.2.5, 2.5.2.6, 2.5.2.7, 2.5.2.8, 2.5.2.9, 2.5.2.10, 2.5.3.1, 2.5.3.2, 2.5.3.3, 2.5.3.4, 2.5.3.5, 2.5.3.6, 2.5.3.7, 2.5.3.8, 2.5.3.9, 2.5.3.10, 2.5.4.1, 2.5.4.2, 2.5.4.3, 2.5.4.4, 2.5.4.5, 2.5.4.6, 2.5.4.7, 2.5.4.8, 2.5.4.9, 2.5.4.10, 2.5.5.1, 2.5.5.2, 2.5.5.3, 2.5.5.4, 2.5.5.5, 2.5.5.6, 2.5.5.7, 2.5.5.8, 2.5.5.9, 2.5.5.10, 2.5.6.1, 2.5.6.2, 2.5.6.3, 2.5.6.4, 2.5.6.5, 2.5.6.6, 2.5.6.7, 2.5.6.8, 2.5.6.9, 2.5.6.10, 2.5.7.1, 2.5.7.2, 2.5.7.3, 2.5.7.4, 2.5.7.5, 2.5.7.6, 2.5.7.7, 2.5.7.8, 2.5.7.9, 2.5.7.10, 2.5.8.1, 2.5.8.2, 2.5.8.3, 2.5.8.4, 2.5.8.5, 2.5.8.6, 2.5.8.7, 2.5.8.8, 2.5.8.9, 2.5.8.10, 2.5.9.1, 2.5.9.2, 2.5.9.3, 2.5.9.4, 2.5.9.5, 2.5.9.6, 2.5.9.7, 2.5.9.8, 2.5.9.9, 2.5.9.10, 2.5.10.1, 2.5.10.2, 2.5.10.3, 2.5.10.4, 2.5.10.5, 2.5.10.6, 2.5.10.7, 2.5.10.8, 2.5.10.9, 2.5.10.10, 2.6.1.1, 2.6.1.2, 2.6.1.3, 2.6.1.4, 2.6.1.5, 2.6.1.6, 2.6.1.7, 2.6.1.8, 2.6.1.9, 2.6.1.10, 2.6.2.1, 2.6.2.2, 2.6.2.3, 2.6.2.4, 2.6.2.5, 2.6.2.6, 2.6.2.7, 2.6.2.8, 2.6.2.9, 2.6.2.10, 2.6.3.1, 2.6.3.2, 2.6.3.3, 2.6.3.4, 2.6.3.5, 2.6.3.6, 2.6.3.7, 2.6.3.8, 2.6.3.9, 2.6.3.10, 2.6.4.1, 2.6.4.2, 2.6.4.3, 2.6.4.4, 2.6.4.5, 2.6.4.6, 2.6.4.7, 2.6.4.8, 2.6.4.9, 2.6.4.10, 2.6.5.1, 2.6.5.2, 2.6.5.3, 2.6.5.4, 2.6.5.5, 2.6.5.6, 2.6.5.7, 2.6.5.8, 2.6.5.9, 2.6.5.10, 2.6.6.1, 2.6.6.2, 2.6.6.3, 2.6.6.4, 2.6.6.5, 2.6.6.6, 2.6.6.7, 2.6.6.8, 2.6.6.9, 2.6.6.10, 2.6.7.1, 2.6.7.2, 2.6.7.3, 2.6.7.4, 2.6.7.5, 2.6.7.6, 2.6.7.7, 2.6.7.8, 2.6.7.9, 2.6.7.10, 2.6.8.1, 2.6.8.2, 2.6.8.3, 2.6.8.4, 2.6.8.5, 2.6.8.6, 2.6.8.7, 2.6.8.8, 2.6.8.9, 2.6.8.10, 2.6.9.1, 2.6.9.2, 2.6.9.3, 2.6.9.4, 2.6.9.5, 2.6.9.6, 2.6.9.7, 2.6.9.8, 2.6.9.9, 2.6.9.10, 2.6.10.1, 2.6.10.2, 2.6.10.3, 2.6.10.4, 2.6.10.5, 2.6.10.6, 2.6.10.7, 2.6.10.8, 2.6.10.9, 2.6.10.10, 2.7.1.1, 2.7.1.2, 2.7.1.3, 2.7.1.4, 2.7.1.5, 2.7.1.6, 2.7.1.7, 2.7.1.8, 2.7.1.9, 2.7.1.10, 2.7.2.1, 2.7.2.2, 2.7.2.3, 2.7.2.4, 2.7.2.5, 2.7.2.6, 2.7.2.7, 2.7.2.8, 2.7.2.9, 2.7.2.10, 2.7.3.1, 2.7.3.2, 2.7.3.3, 2.7.3.4, 2.7.3.5, 2.7.3.6, 2.7.3.7, 2.7.3.8, 2.7.3.9, 2.7.3.10, 2.7.4.1, 2.7.4.2, 2.7.4.3, 2.7.4.4, 2.7.4.5, 2.7.4.6, 2.7.4.7, 2.7.4.8, 2.7.4.9, 2.7.4.10, 2.7.5.1, 2.7.5.2, 2.7.5.3, 2.7.5.4, 2.7.5.5, 2.7.5.6, 2.7.5.7, 2.7.5.8, 2.7.5.9, 2.7.5.10, 2.7.6.1, 2.7.6.2, 2.7.6.3, 2.7.6.4, 2.7.6.5, 2.7.6.6, 2.7.6.7, 2.7.6.8, 2.7.6.9, 2.7.6.10, 2.7.7.1, 2.7.7.2, 2.7.7.3, 2.7.7.4, 2.7.7.5, 2.7.7.6, 2.7.7.7, 2.7.7.8, 2.7.7.9, 2.7.7.10, 2.7.8.1, 2.7.8.2, 2.7.8.3, 2.7.8.4, 2.7.8.5, 2.7.8.6, 2.7.8.7, 2.7.8.8, 2.7.8.9, 2.7.8.10, 2.7.9.1, 2.7.9.2, 2.7.9.3, 2.7.9.4, 2.7.9.5, 2.7.9.6, 2.7.9.7, 2.7.9.8, 2.7.9.9, 2.7.9.10, 2.7.10.1, 2.7.10.2, 2.7.10.3, 2.7.10.4, 2.7.10.5, 2.7.10.6, 2.7.10.7, 2.7.10.8, 2.7.10.9, 2.7.10.10, 2.8.1.1, 2.8.1.2, 2.8.1.3, 2.8.1.4, 2.8.1.5, 2.8.1.6, 2.8.1.7, 2.8.1.8, 2.8.1.9, 2.8.1.10, 2.8.2.1, 2.8.2.2, 2.8.2.3, 2.8.2.4, 2.8.2.5, 2.8.2.6, 2.8.2.7, 2.8.2.8, 2.8.2.9, 2.8.2.10, 2.8.3.1, 2.8.3.2, 2.8.3.3, 2.8.3.4, 2.8.3.5, 2.8.3.6, 2.8.3.7, 2.8.3.8, 2.8.3.9, 2.8.3.10, 2.8.4.1, 2.8.4.2, 2.8.4.3, 2.8.4.4, 2.8.4.5, 2.8.4.6, 2.8.4.7, 2.8.4.8, 2.8.4.9, 2.8.4.10, 2.8.5.1, 2.8.5.2, 2.8.5.3, 2.8.5.4, 2.8.5.5, 2.8.5.6, 2.8.5.7, 2.8.5.8, 2.8.5.9, 2.8.5.10, 2.8.6.1, 2.8.6.2, 2.8.6.3, 2.8.6.4, 2.8.6.5, 2.8.6.6, 2.8.6.7, 2.8.6.8, 2.8.6.9, 2.8.6.10, 2.8.7.1, 2.8.7.2, 2.8.7.3, 2.8.7.4, 2.8.7.5, 2.8.7.6, 2.8.7.7, 2.8.7.8, 2.8.7.9, 2.8.7.10, 2.8.8.1, 2.8.8.2, 2.8.8.3, 2.8.8.4, 2.8.8.5, 2.8.8.6, 2.8.8.7, 2.8.8.8, 2.8.8.9, 2.8.8.10, 2.8.9.1, 2.8.9.2, 2.8.9.3, 2.8.9.4, 2.8.9.5, 2.8.9.6, 2.8.9.7, 2.8.9.8, 2.8.9.9, 2.8.9.10, 2.8.10.1, 2.8.10.2, 2.8.10.3, 2.8.10.4, 2.8.10.5, 2.8.10.6, 2.8.10.7, 2.8.10.8, 2.8.10.9, 2.8.10.10, 2.9.1.1, 2.9.1.2, 2.9.1.3, 2.9.1.4, 2.9.1.5, 2.9.1.6, 2.9.1.7, 2.9.1.8, 2.9.1.9, 2.9.1.10, 2.9.2.1, 2.9.2.2, 2.9.2.3, 2.9.2.4, 2.9.2.5, 2.9.2.6, 2.9.2.7, 2.9.2.8, 2.9.2.9, 2.9.2.10, 2.9.3.1, 2.9.3.2, 2.9.3.3, 2.9.3.4, 2.9.3.5, 2.9.3.6, 2.9.3.7, 2.9.3.8, 2.9.3.9, 2.9.3.10, 2.9.4.1, 2.9.4.2, 2.9.4.3, 2.9.4.4, 2.9.4.5, 2.9.4.6, 2.9.4.7, 2.9.4.8, 2.9.4.9, 2.9.4.10, 2.9.5.1, 2.9.5.2, 2.9.5.3, 2.9.5.4, 2.9.5.5, 2.9.5.6, 2.9.5.7, 2.9.5.8, 2.9.5.9, 2.9.5.10, 2.9.6.1, 2.9.6.2, 2.9.6.3, 2.9.6.4, 2.9.6.5, 2.9.6.6, 2.9.6.7, 2.9.6.8, 2.9.6.9, 2.9.6.10, 2.9.7.1, 2.9.7.2, 2.9.7.3, 2.9.7.4, 2.9.7.5, 2.9.7.6, 2.9.7.7, 2.9.7.8, 2.9.7.9, 2.9.7.10, 2.9.8.1, 2.9.8.2, 2.9.8.3, 2.9.8.4, 2.9.8.5, 2.9.8.6, 2.9.8.7, 2.9.8.8, 2.9.8.9, 2.9.8.10, 2.9.9.1, 2.9.9.2, 2.9.9.3, 2.9.9.4, 2.9.9.5, 2.9.9.6, 2.9.9.7, 2.9.9.8, 2.9.9.9, 2.9.9.10, 2.9.10.1, 2.9.10.2, 2.9.10.3, 2.9.10.4, 2.9.10.5, 2.9.10.6, 2.9.10.7, 2.9.10.8, 2.9.10.9, 2.9.10.10, 2.10.1.1, 2.10.1.2, 2.10.1.3, 2.10.1.4, 2.10.1.5, 2.10.1.6, 2.10.1.7, 2.10.1.8, 2.10.1.9, 2.10.1.10, 2.10.2.1, 2.10.2.2, 2.10.2.3, 2.10.2.4, 2.10.2.5, 2.10.2.6, 2.10.2.7, 2.10.2.8, 2.10.2.9, 2.10.2.10, 2.10.3.1, 2.10.3.2, 2.10.3.3, 2.10.3.4, 2.10.3.5, 2.10.3.6, 2.10.3.7, 2.10.3.8, 2.10.3.9, 2.10.3.10, 2.10.4.1, 2.10.4.2, 2.10.4.3, 2.10.4.4, 2.10.4.5, 2.10.4.6, 2.10.4.7, 2.10.4.8, 2.10.4.9, 2.10.4.10, 2.10.5.1, 2.10.5.2, 2.10.5.3, 2.10.5.4, 2.10.5.5, 2.10.5.6, 2.10.5.7, 2.10.5.8, 2.10.5.9, 2.10.5.10, 2.10.6.1, 2.10.6.2, 2.10.6.3, 2.10.6.4, 2.10.6.5, 2.10.6.6, 2.10.6.7, 2.10.6.8, 2.10.6.9, 2.10.6.10, 2.10.7.1, 2.10.7.2, 2.10.7.3, 2.10.7.4, 2.10.7.5, 2.10.7.6, 2.10.7.7, 2.10.7.8, 2.10.7.9, 2.10.7.10, 2.10.8.1, 2.10.8.2, 2.10.8.3, 2.10.8.4, 2.10.8.5, 2.10.8.6, 2.10.8.7, 2.10.8.8, 2.10.8.9, 2.10.8.10, 2.10.9.1, 2.10.9.2, 2.10.9.3, 2.10.9.4, 2.10.9.5, 2.10.9.6, 2.10.9.7, 2.10.9.8, 2.10.9.9, 2.10.9.10, 2.10.10.1, 2.10.10.2, 2.10.10.3, 2.10.10.4, 2.10.10.5, 2.10.10.6, 2.10.10.7, 2.10.10.8, 2.10.10.9, 2.10.10.10, 3.1.1.1, 3.1.1.2, 3.1.1.3, 3.1.1.4, 3.1.1.5, 3.1.1.6, 3.1.1.7, 3.1.1.8, 3.1.1.9, 3.1.1.10, 3.1.2.1, 3.1.2.2, 3.1.2.3, 3.1.2.4, 3.1.2.5, 3.1.2.6, 3.1.2.7, 3.1.2.8, 3.1.2.9, 3.1.2.10, 3.1.3.1, 3.1.3.2, 3.1.3.3, 3.1.3.4, 3.1.3.5, 3.1.3.6, 3.1.3.7, 3.1.3.8, 3.1.3.9, 3.1.3.10, 3.1.4.1, 3.1.4.2, 3.1.4.3, 3.1.4.4, 3.1.4.5, 3.1.4.6, 3.1.4.7, 3.1.4.8, 3.1.4.9, 3.1.4.10, 3.1.5.1, 3.1.5.2, 3.1.5.3, 3.1.5.4, 3.1.5.5, 3.1.5.6, 3.1.5.7, 3.1.5.8, 3.1.5.9, 3.1.5.10, 3.1.6.1, 3.1.6.2, 3.1.6.3, 3.1.6.4, 3.1.6.5, 3.1.6.6, 3.1.6.7, 3.1.6.8, 3.1.6.9, 3.1.6.10, 3.1.7.1, 3.1.7.2, 3.1.7.3, 3.1.7.4, 3.1.7.5, 3.1.7.6, 3.1.7.7, 3.1.7.8, 3.1.7.9, 3.1.7.10, 3.1.8.1, 3.1.8.2, 3.1.8.3, 3.1.8.4, 3.1.8.5, 3.1.8.6, 3.1.8.7, 3.1.8.8, 3.1.8.9, 3.1.8.10, 3.1.9.1, 3.1.9.2, 3.1.9.3, 3.1.9.4, 3.1.9.5, 3.1.9.6, 3.1.9.7, 3.1.9.8, 3.1.9.9, 3.1.9.10, 3.1.10.1, 3.1.10.2, 3.1.10.3, 3.1.10.4, 3.1.10.5, 3.1.10.6, 3.1.10.7, 3.1.10.8, 3.1.10.9, 3.1.10.10, 3.2.1.1, 3.2.1.2, 3.2.1.3, 3.2.1.4, 3.2.1.5, 3.2.1.6, 3.2.1.7, 3.2.1.8, 3.2.1.9, 3.2.1.10, 3.2.2.1, 3.2.2.2, 3.2.2.3, 3.2.2.4, 3.2.2.5, 3.2.2.6, 3.2.2.7, 3.2.2.8, 3.2.2.9, 3.2.2.10, 3.2.3.1, 3.2.3.2, 3.2.3.3, 3.2.3.4, 3.2.3.5, 3.2.3.6, 3.2.3.7, 3.2.3.8, 3.2.3.9, 3.2.3.10, 3.2.4.1, 3.2.4.2, 3.2.4.3, 3.2.4.4, 3.2.4.5, 3.2.4.6, 3.2.4.7, 3.2.4.8, 3.2.4.9, 3.2.4.10, 3.2.5.1, 3.2.5.2, 3.2.5.3, 3.2.5.4, 3.2.5.5, 3.2.5.6, 3.2.5.7, 3.2.5.8, 3.2.5.9, 3.2.5.10, TABLE B-continued 3.2.6.1, 3.2.6.2, 3.2.6.3, 3.2.6.4, 3.2.6.5, 3.2.6.6, 3.2.6.7, 3.2.6.8, 3.2.6.9, 3.2.6.10,
3.2.7.1, 3.2.7.2, 3.2.7.3, 3.2.7.4, 3.2.7.5, 3.2.7.6, 3.2.7.7, 3.2.7.8, 3.2.7.9, 3.2.7.10,
3.2.8.1, 3.2.8.2, 3.2.8.3, 3.2.8.4, 3.2.8.5, 3.2.8.6, 3.2.8.7, 3.2.8.8, 3.2.8.9, 3.2.8.10,
3.2.9.1, 3.2.9.2, 3.2.9.3, 3.2.9.4, 3.2.9.5, 3.2.9.6, 3.2.9.7, 3.2.9.8, 3.2.9.9, 3.2.9.10,
3.2.10.1, 3.2.10.2, 3.2.10.3, 3.2.10.4, 3.2.10.5, 3.2.10.6, 3.2.10.7, 3.2.10.8, 3.2.10.9,
3.2.10.10, 3.3.1.1, 3.3.1.2, 3.3.1.3, 3.3.1.4, 3.3.1.5, 3.3.1.6, 3.3.1.7, 3.3.1.8, 3.3.1.9,
3.3.1.10, 3.3.2.1, 3.3.2.2, 3.3.2.3, 3.3.2.4, 3.3.2.5, 3.3.2.6, 3.3.2.7, 3.3.2.8, 3.3.2.9,
3.3.2.10, 3.3.3.1, 3.3.3.2, 3.3.3.3, 3.3.3.4, 3.3.3.5, 3.3.3.6, 3.3.3.7, 3.3.3.8, 3.3.3.9,
3.3.3.10, 3.3.4.1, 3.3.4.2, 3.3.4.3, 3.3.4.4, 3.3.4.5, 3.3.4.6, 3.3.4.7, 3.3.4.8, 3.3.4.9,
3.3.4.10, 3.3.5.1, 3.3.5.2, 3.3.5.3, 3.3.5.4, 3.3.5.5, 3.3.5.6, 3.3.5.7, 3.3.5.8, 3.3.5.9,
3.3.5.10, 3.3.6.1, 3.3.6.2, 3.3.6.3, 3.3.6.4, 3.3.6.5, 3.3.6.6, 3.3.6.7, 3.3.6.8, 3.3.6.9,
3.3.6.10, 3.3.7.1, 3.3.7.2, 3.3.7.3, 3.3.7.4, 3.3.7.5, 3.3.7.6, 3.3.7.7, 3.3.7.8, 3.3.7.9,
3.3.7.10, 3.3.8.1, 3.3.8.2, 3.3.8.3, 3.3.8.4, 3.3.8.5, 3.3.8.6, 3.3.8.7, 3.3.8.8, 3.3.8.9,
3.3.8.10, 3.3.9.1, 3.3.9.2, 3.3.9.3, 3.3.9.4, 3.3.9.5, 3.3.9.6, 3.3.9.7, 3.3.9.8, 3.3.9.9,
3.3.9.10, 3.3.10.1, 3.3.10.2, 3.3.10.3, 3.3.10.4, 3.3.10.5, 3.3.10.6, 3.3.10.7, 3.3.10.8,
3.3.10.9, 3.3.10.10, 3.4.1.1, 3.4.1.2, 3.4.1.3, 3.4.1.4, 3.4.1.5, 3.4.1.6, 3.4.1.7, 3.4.1.8,
3.4.1.9, 3.4.1.10, 3.4.2.1, 3.4.2.2, 3.4.2.3, 3.4.2.4, 3.4.2.5, 3.4.2.6, 3.4.2.7, 3.4.2.8,
3.4.2.9, 3.4.2.10, 3.4.3.1, 3.4.3.2, 3.4.3.3, 3.4.3.4, 3.4.3.5, 3.4.3.6, 3.4.3.7, 3.4.3.8,
3.4.3.9, 3.4.3.10, 3.4.4.1, 3.4.4.2, 3.4.4.3, 3.4.4.4, 3.4.4.5, 3.4.4.6, 3.4.4.7, 3.4.4.8,
3.4.4.9, 3.4.4.10, 3.4.5.1, 3.4.5.2, 3.4.5.3, 3.4.5.4, 3.4.5.5, 3.4.5.6, 3.4.5.7, 3.4.5.8,
3.4.5.9, 3.4.5.10, 3.4.6.1, 3.4.6.2, 3.4.6.3, 3.4.6.4, 3.4.6.5, 3.4.6.6, 3.4.6.7, 3.4.6.8,
3.4.6.9, 3.4.6.10, 3.4.7.1, 3.4.7.2, 3.4.7.3, 3.4.7.4, 3.4.7.5, 3.4.7.6, 3.4.7.7, 3.4.7.8,
3.4.7.9, 3.4.7.10, 3.4.8.1, 3.4.8.2, 3.4.8.3, 3.4.8.4, 3.4.8.5, 3.4.8.6, 3.4.8.7, 3.4.8.8,
3.4.8.9, 3.4.8.10, 3.4.9.1, 3.4.9.2, 3.4.9.3, 3.4.9.4, 3.4.9.5, 3.4.9.6, 3.4.9.7, 3.4.9.8,
3.4.9.9, 3.4.9.10, 3.4.10.1, 3.4.10.2, 3.4.10.3, 3.4.10.4, 3.4.10.5, 3.4.10.6, 3.4.10.7,
3.4.10.8, 3.4.10.9, 3.4.10.10, 3.5.1.1, 3.5.1.2, 3.5.1.3, 3.5.1.4, 3.5.1.5, 3.5.1.6, 3.5.1.7,
3.5.1.8, 3.5.1.9, 3.5.1.10, 3.5.2.1, 3.5.2.2, 3.5.2.3, 3.5.2.4, 3.5.2.5, 3.5.2.6, 3.5.2.7,
3.5.2.8, 3.5.2.9, 3.5.2.10, 3.5.3.1, 3.5.3.2, 3.5.3.3, 3.5.3.4, 3.5.3.5, 3.5.3.6, 3.5.3.7,
3.5.3.8, 3.5.3.9, 3.5.3.10, 3.5.4.1, 3.5.4.2, 3.5.4.3, 3.5.4.4, 3.5.4.5, 3.5.4.6, 3.5.4.7,
3.5.4.8, 3.5.4.9, 3.5.4.10, 3.5.5.1, 3.5.5.2, 3.5.5.3, 3.5.5.4, 3.5.5.5, 3.5.5.6, 3.5.5.7,
3.5.5.8, 3.5.5.9, 3.5.5.10, 3.5.6.1, 3.5.6.2, 3.5.6.3, 3.5.6.4, 3.5.6.5, 3.5.6.6, 3.5.6.7,
3.5.6.8, 3.5.6.9, 3.5.6.10, 3.5.7.1, 3.5.7.2, 3.5.7.3, 3.5.7.4, 3.5.7.5, 3.5.7.6, 3.5.7.7,
3.5.7.8, 3.5.7.9, 3.5.7.10, 3.5.8.1, 3.5.8.2, 3.5.8.3, 3.5.8.4, 3.5.8.5, 3.5.8.6, 3.5.8.7,
3.5.8.8, 3.5.8.9, 3.5.8.10, 3.5.9.1, 3.5.9.2, 3.5.9.3, 3.5.9.4, 3.5.9.5, 3.5.9.6, 3.5.9.7,
3.5.9.8, 3.5.9.9, 3.5.9.10, 3.5.10.1, 3.5.10.2, 3.5.10.3, 3.5.10.4, 3.5.10.5, 3.5.10.6,
3.5.10.7, 3.5.10.8, 3.5.10.9, 3.5.10.10, 3.6.1.1, 3.6.1.2, 3.6.1.3, 3.6.1.4, 3.6.1.5, 3.6.1.6,
3.6.1.7, 3.6.1.8, 3.6.1.9, 3.6.1.10, 3.6.2.1, 3.6.2.2, 3.6.2.3, 3.6.2.4, 3.6.2.5, 3.6.2.6,
3.6.2.7, 3.6.2.8, 3.6.2.9, 3.6.2.10, 3.6.3.1, 3.6.3.2, 3.6.3.3, 3.6.3.4, 3.6.3.5, 3.6.3.6,
3.6.3.7, 3.6.3.8, 3.6.3.9, 3.6.3.10, 3.6.4.1, 3.6.4.2, 3.6.4.3, 3.6.4.4, 3.6.4.5, 3.6.4.6,
3.6.4.7, 3.6.4.8, 3.6.4.9, 3.6.4.10, 3.6.5.1, 3.6.5.2, 3.6.5.3, 3.6.5.4, 3.6.5.5, 3.6.5.6,
3.6.5.7, 3.6.5.8, 3.6.5.9, 3.6.5.10, 3.6.6.1, 3.6.6.2, 3.6.6.3, 3.6.6.4, 3.6.6.5, 3.6.6.6,
3.6.6.7, 3.6.6.8, 3.6.6.9, 3.6.6.10, 3.6.7.1, 3.6.7.2, 3.6.7.3, 3.6.7.4, 3.6.7.5, 3.6.7.6,
3.6.7.7, 3.6.7.8, 3.6.7.9, 3.6.7.10, 3.6.8.1, 3.6.8.2, 3.6.8.3, 3.6.8.4, 3.6.8.5, 3.6.8.6,
3.6.8.7, 3.6.8.8, 3.6.8.9, 3.6.8.10, 3.6.9.1, 3.6.9.2, 3.6.9.3, 3.6.9.4, 3.6.9.5, 3.6.9.6,
3.6.9.7, 3.6.9.8, 3.6.9.9, 3.6.9.10, 3.6.10.1, 3.6.10.2, 3.6.10.3, 3.6.10.4, 3.6.10.5,
3.6.10.6, 3.6.10.7, 3.6.10.8, 3.6.10.9, 3.6.10.10, 3.7.1.1, 3.7.1.2, 3.7.1.3, 3.7.1.4, 3.7.1.5,
3.7.1.6, 3.7.1.7, 3.7.1.8, 3.7.1.9, 3.7.1.10, 3.7.2.1, 3.7.2.2, 3.7.2.3, 3.7.2.4, 3.7.2.5,
3.7.2.6, 3.7.2.7, 3.7.2.8, 3.7.2.9, 3.7.2.10, 3.7.3.1, 3.7.3.2, 3.7.3.3, 3.7.3.4, 3.7.3.5,
3.7.3.6, 3.7.3.7, 3.7.3.8, 3.7.3.9, 3.7.3.10, 3.7.4.1, 3.7.4.2, 3.7.4.3, 3.7.4.4, 3.7.4.5,
3.7.4.6, 3.7.4.7, 3.7.4.8, 3.7.4.9, 3.7.4.10, 3.7.5.1, 3.7.5.2, 3.7.5.3, 3.7.5.4, 3.7.5.5,
3.7.5.6, 3.7.5.7, 3.7.5.8, 3.7.5.9, 3.7.5.10, 3.7.6.1, 3.7.6.2, 3.7.6.3, 3.7.6.4, 3.7.6.5,
3.7.6.6, 3.7.6.7, 3.7.6.8, 3.7.6.9, 3.7.6.10, 3.7.7.1, 3.7.7.2, 3.7.7.3, 3.7.7.4, 3.7.7.5,
3.7.7.6, 3.7.7.7, 3.7.7.8, 3.7.7.9, 3.7.7.10, 3.7.8.1, 3.7.8.2, 3.7.8.3, 3.7.8.4, 3.7.8.5,
3.7.8.6, 3.7.8.7, 3.7.8.8, 3.7.8.9, 3.7.8.10, 3.7.9.1, 3.7.9.2, 3.7.9.3, 3.7.9.4, 3.7.9.5,
3.7.9.6, 3.7.9.7, 3.7.9.8, 3.7.9.9, 3.7.9.10, 3.7.10.1, 3.7.10.2, 3.7.10.3, 3.7.10.4, 3.7.10.5,
3.7.10.6, 3.7.10.7, 3.7.10.8, 3.7.10.9, 3.7.10.10, 3.8.1.1, 3.8.1.2, 3.8.1.3, 3.8.1.4, 3.8.1.5,
3.8.1.6, 3.8.1.7, 3.8.1.8, 3.8.1.9, 3.8.1.10, 3.8.2.1, 3.8.2.2, 3.8.2.3, 3.8.2.4, 3.8.2.5,
3.8.2.6, 3.8.2.7, 3.8.2.8, 3.8.2.9, 3.8.2.10, 3.8.3.1, 3.8.3.2, 3.8.3.3, 3.8.3.4, 3.8.3.5,
3.8.3.6, 3.8.3.7, 3.8.3.8, 3.8.3.9, 3.8.3.10, 3.8.4.1, 3.8.4.2, 3.8.4.3, 3.8.4.4, 3.8.4.5,
3.8.4.6, 3.8.4.7, 3.8.4.8, 3.8.4.9, 3.8.4.10, 3.8.5.1, 3.8.5.2, 3.8.5.3, 3.8.5.4, 3.8.5.5,
3.8.5.6, 3.8.5.7, 3.8.5.8, 3.8.5.9, 3.8.5.10, 3.8.6.1, 3.8.6.2, 3.8.6.3, 3.8.6.4, 3.8.6.5,
3.8.6.6, 3.8.6.7, 3.8.6.8, 3.8.6.9, 3.8.6.10, 3.8.7.1, 3.8.7.2, 3.8.7.3, 3.8.7.4, 3.8.7.5,
3.8.7.6, 3.8.7.7, 3.8.7.8, 3.8.7.9, 3.8.7.10, 3.8.8.1, 3.8.8.2, 3.8.8.3, 3.8.8.4, 3.8.8.5,
3.8.8.6, 3.8.8.7, 3.8.8.8, 3.8.8.9, 3.8.8.10, 3.8.9.1, 3.8.9.2, 3.8.9.3, 3.8.9.4, 3.8.9.5,
3.8.9.6, 3.8.9.7, 3.8.9.8, 3.8.9.9, 3.8.9.10, 3.8.10.1, 3.8.10.2, 3.8.10.3, 3.8.10.4, 3.8.10.5,
3.8.10.6, 3.8.10.7, 3.8.10.8, 3.8.10.9, 3.8.10.10, 3.9.1.1, 3.9.1.2, 3.9.1.3, 3.9.1.4, 3.9.1.5,
3.9.1.6, 3.9.1.7, 3.9.1.8, 3.9.1.9, 3.9.1.10, 3.9.2.1, 3.9.2.2, 3.9.2.3, 3.9.2.4, 3.9.2.5,
3.9.2.6, 3.9.2.7, 3.9.2.8, 3.9.2.9, 3.9.2.10, 3.9.3.1, 3.9.3.2, 3.9.3.3, 3.9.3.4, 3.9.3.5,
3.9.3.6, 3.9.3.7, 3.9.3.8, 3.9.3.9, 3.9.3.10, 3.9.4.1, 3.9.4.2, 3.9.4.3, 3.9.4.4, 3.9.4.5,
3.9.4.6, 3.9.4.7, 3.9.4.8, 3.9.4.9, 3.9.4.10, 3.9.5.1, 3.9.5.2, 3.9.5.3, 3.9.5.4, 3.9.5.5,
3.9.5.6, 3.9.5.7, 3.9.5.8, 3.9.5.9, 3.9.5.10, 3.9.6.1, 3.9.6.2, 3.9.6.3, 3.9.6.4, 3.9.6.5,
3.9.6.6, 3.9.6.7, 3.9.6.8, 3.9.6.9, 3.9.6.10, 3.9.7.1, 3.9.7.2, 3.9.7.3, 3.9.7.4, 3.9.7.5,
3.9.7.6, 3.9.7.7, 3.9.7.8, 3.9.7.9, 3.9.7.10, 3.9.8.1, 3.9.8.2, 3.9.8.3, 3.9.8.4, 3.9.8.5,
3.9.8.6, 3.9.8.7, 3.9.8.8, 3.9.8.9, 3.9.8.10, 3.9.9.1, 3.9.9.2, 3.9.9.3, 3.9.9.4, 3.9.9.5,
3.9.9.6, 3.9.9.7, 3.9.9.8, 3.9.9.9, 3.9.9.10, 3.9.10.1, 3.9.10.2, 3.9.10.3, 3.9.10.4, 3.9.10.5,
3.9.10.6, 3.9.10.7, 3.9.10.8, 3.9.10.9, 3.9.10.10, 3.10.1.1, 3.10.1.2, 3.10.1.3, 3.10.1.4,
3.10.1.5, 3.10.1.6, 3.10.1.7, 3.10.1.8, 3.10.1.9, 3.10.1.10, 3.10.2.1, 3.10.2.2, 3.10.2.3,
3.10.2.4, 3.10.2.5, 3.10.2.6, 3.10.2.7, 3.10.2.8, 3.10.2.9, 3.10.2.10, 3.10.3.1, 3.10.3.2,
3.10.3.3, 3.10.3.4, 3.10.3.5, 3.10.3.6, 3.10.3.7, 3.10.3.8, 3.10.3.9, 3.10.3.10, 3.10.4.1,
3.10.4.2, 3.10.4.3, 3.10.4.4, 3.10.4.5, 3.10.4.6, 3.10.4.7, 3.10.4.8, 3.10.4.9, 3.10.4.10, TABLE B-continued 3.10.5.1, 3.10.5.2, 3.10.5.3, 3.10.5.4, 3.10.5.5, 3.10.5.6, 3.10.5.7, 3.10.5.8, 3.10.5.9, 3.10.5.10, 3.10.6.1, 3.10.6.2, 3.10.6.3, 3.10.6.4, 3.10.6.5, 3.10.6.6, 3.10.6.7, 3.10.6.8, 3.10.6.9, 3.10.6.10, 3.10.7.1, 3.10.7.2, 3.10.7.3, 3.10.7.4, 3.10.7.5, 3.10.7.6, 3.10.7.7, 3.10.7.8, 3.10.7.9, 3.10.7.10, 3.10.8.1, 3.10.8.2, 3.10.8.3, 3.10.8.4, 3.10.8.5, 3.10.8.6, 3.10.8.7, 3.10.8.8, 3.10.8.9, 3.10.8.10, 3.10.9.1, 3.10.9.2, 3.10.9.3, 3.10.9.4, 3.10.9.5, 3.10.9.6, 3.10.9.7, 3.10.9.8, 3.10.9.9, 3.10.9.10, 3.10.10.1, 3.10.10.2, 3.10.10.3, 3.10.10.4, 3.10.10.5, 3.10.10.6, 3.10.10.7, 3.10.10.8, 3.10.10.9, 3.10.10.10, 4.1.1.1, 4.1.1.2, 4.1.1.3, 4.1.1.4, 4.1.1.5, 4.1.1.6, 4.1.1.7, 4.1.1.8, 4.1.1.9, 4.1.1.10, 4.1.2.1, 4.1.2.2, 4.1.2.3, 4.1.2.4, 4.1.2.5, 4.1.2.6, 4.1.2.7, 4.1.2.8, 4.1.2.9, 4.1.2.10, 4.1.3.1, 4.1.3.2, 4.1.3.3, 4.1.3.4, 4.1.3.5, 4.1.3.6, 4.1.3.7, 4.1.3.8, 4.1.3.9, 4.1.3.10, 4.1.4.1, 4.1.4.2, 4.1.4.3, 4.1.4.4, 4.1.4.5, 4.1.4.6, 4.1.4.7, 4.1.4.8, 4.1.4.9, 4.1.4.10, 4.1.5.1, 4.1.5.2, 4.1.5.3, 4.1.5.4, 4.1.5.5, 4.1.5.6, 4.1.5.7, 4.1.5.8, 4.1.5.9, 4.1.5.10, 4.1.6.1, 4.1.6.2, 4.1.6.3, 4.1.6.4, 4.1.6.5, 4.1.6.6, 4.1.6.7, 4.1.6.8, 4.1.6.9, 4.1.6.10, 4.1.7.1, 4.1.7.2, 4.1.7.3, 4.1.7.4, 4.1.7.5, 4.1.7.6, 4.1.7.7, 4.1.7.8, 4.1.7.9, 4.1.7.10, 4.1.8.1, 4.1.8.2, 4.1.8.3, 4.1.8.4, 4.1.8.5, 4.1.8.6, 4.1.8.7, 4.1.8.8, 4.1.8.9, 4.1.8.10, 4.1.9.1, 4.1.9.2, 4.1.9.3, 4.1.9.4, 4.1.9.5, 4.1.9.6, 4.1.9.7, 4.1.9.8, 4.1.9.9, 4.1.9.10, 4.1.10.1, 4.1.10.2, 4.1.10.3, 4.1.10.4, 4.1.10.5, 4.1.10.6, 4.1.10.7, 4.1.10.8, 4.1.10.9, 4.1.10.10, 4.2.1.1, 4.2.1.2, 4.2.1.3, 4.2.1.4, 4.2.1.5, 4.2.1.6, 4.2.1.7, 4.2.1.8, 4.2.1.9, 4.2.1.10, 4.2.2.1, 4.2.2.2, 4.2.2.3, 4.2.2.4, 4.2.2.5, 4.2.2.6, 4.2.2.7, 4.2.2.8, 4.2.2.9, 4.2.2.10, 4.2.3.1, 4.2.3.2, 4.2.3.3, 4.2.3.4, 4.2.3.5, 4.2.3.6, 4.2.3.7, 4.2.3.8, 4.2.3.9, 4.2.3.10, 4.2.4.1, 4.2.4.2, 4.2.4.3, 4.2.4.4, 4.2.4.5, 4.2.4.6, 4.2.4.7, 4.2.4.8, 4.2.4.9, 4.2.4.10, 4.2.5.1, 4.2.5.2, 4.2.5.3, 4.2.5.4, 4.2.5.5, 4.2.5.6, 4.2.5.7, 4.2.5.8, 4.2.5.9, 4.2.5.10, 4.2.6.1, 4.2.6.2, 4.2.6.3, 4.2.6.4, 4.2.6.5, 4.2.6.6, 4.2.6.7, 4.2.6.8, 4.2.6.9, 4.2.6.10, 4.2.7.1, 4.2.7.2, 4.2.7.3, 4.2.7.4, 4.2.7.5, 4.2.7.6, 4.2.7.7, 4.2.7.8, 4.2.7.9, 4.2.7.10, 4.2.8.1, 4.2.8.2, 4.2.8.3, 4.2.8.4, 4.2.8.5, 4.2.8.6, 4.2.8.7, 4.2.8.8, 4.2.8.9, 4.2.8.10, 4.2.9.1, 4.2.9.2, 4.2.9.3, 4.2.9.4, 4.2.9.5, 4.2.9.6, 4.2.9.7, 4.2.9.8, 4.2.9.9, 4.2.9.10, 4.2.10.1, 4.2.10.2, 4.2.10.3, 4.2.10.4, 4.2.10.5, 4.2.10.6, 4.2.10.7, 4.2.10.8, 4.2.10.9, 4.2.10.10, 4.3.1.1, 4.3.1.2, 4.3.1.3, 4.3.1.4, 4.3.1.5, 4.3.1.6, 4.3.1.7, 4.3.1.8, 4.3.1.9, 4.3.1.10, 4.3.2.1, 4.3.2.2, 4.3.2.3, 4.3.2.4, 4.3.2.5, 4.3.2.6, 4.3.2.7, 4.3.2.8, 4.3.2.9, 4.3.2.10, 4.3.3.1, 4.3.3.2, 4.3.3.3, 4.3.3.4, 4.3.3.5, 4.3.3.6, 4.3.3.7, 4.3.3.8, 4.3.3.9, 4.3.3.10, 4.3.4.1, 4.3.4.2, 4.3.4.3, 4.3.4.4, 4.3.4.5, 4.3.4.6, 4.3.4.7, 4.3.4.8, 4.3.4.9, 4.3.4.10, 4.3.5.1, 4.3.5.2, 4.3.5.3, 4.3.5.4, 4.3.5.5, 4.3.5.6, 4.3.5.7, 4.3.5.8, 4.3.5.9, 4.3.5.10, 4.3.6.1, 4.3.6.2, 4.3.6.3, 4.3.6.4, 4.3.6.5, 4.3.6.6, 4.3.6.7, 4.3.6.8, 4.3.6.9, 4.3.6.10, 4.3.7.1, 4.3.7.2, 4.3.7.3, 4.3.7.4, 4.3.7.5, 4.3.7.6, 4.3.7.7, 4.3.7.8, 4.3.7.9, 4.3.7.10, 4.3.8.1, 4.3.8.2, 4.3.8.3, 4.3.8.4, 4.3.8.5, 4.3.8.6, 4.3.8.7, 4.3.8.8, 4.3.8.9, 4.3.8.10, 4.3.9.1, 4.3.9.2, 4.3.9.3, 4.3.9.4, 4.3.9.5, 4.3.9.6, 4.3.9.7, 4.3.9.8, 4.3.9.9, 4.3.9.10, 4.3.10.1, 4.3.10.2, 4.3.10.3, 4.3.10.4, 4.3.10.5, 4.3.10.6, 4.3.10.7, 4.3.10.8, 4.3.10.9, 4.3.10.10, 4.4.1.1, 4.4.1.2, 4.4.1.3, 4.4.1.4, 4.4.1.5, 4.4.1.6, 4.4.1.7, 4.4.1.8, 4.4.1.9, 4.4.1.10, 4.4.2.1, 4.4.2.2, 4.4.2.3, 4.4.2.4, 4.4.2.5, 4.4.2.6, 4.4.2.7, 4.4.2.8, 4.4.2.9, 4.4.2.10, 4.4.3.1, 4.4.3.2, 4.4.3.3, 4.4.3.4, 4.4.3.5, 4.4.3.6, 4.4.3.7, 4.4.3.8, 4.4.3.9, 4.4.3.10, 4.4.4.1, 4.4.4.2, 4.4.4.3, 4.4.4.4, 4.4.4.5, 4.4.4.6, 4.4.4.7, 4.4.4.8, 4.4.4.9, 4.4.4.10, 4.4.5.1, 4.4.5.2, 4.4.5.3, 4.4.5.4, 4.4.5.5, 4.4.5.6, 4.4.5.7, 4.4.5.8, 4.4.5.9, 4.4.5.10, 4.4.6.1, 4.4.6.2, 4.4.6.3, 4.4.6.4, 4.4.6.5, 4.4.6.6, 4.4.6.7, 4.4.6.8, 4.4.6.9, 4.4.6.10, 4.4.7.1, 4.4.7.2, 4.4.7.3, 4.4.7.4, 4.4.7.5, 4.4.7.6, 4.4.7.7, 4.4.7.8, 4.4.7.9, 4.4.7.10, 4.4.8.1, 4.4.8.2, 4.4.8.3, 4.4.8.4, 4.4.8.5, 4.4.8.6, 4.4.8.7, 4.4.8.8, 4.4.8.9, 4.4.8.10, 4.4.9.1, 4.4.9.2, 4.4.9.3, 4.4.9.4, 4.4.9.5, 4.4.9.6, 4.4.9.7, 4.4.9.8, 4.4.9.9, 4.4.9.10, 4.4.10.1, 4.4.10.2, 4.4.10.3, 4.4.10.4, 4.4.10.5, 4.4.10.6, 4.4.10.7, 4.4.10.8, 4.4.10.9, 4.4.10.10, 4.5.1.1, 4.5.1.2, 4.5.1.3, 4.5.1.4, 4.5.1.5, 4.5.1.6, 4.5.1.7, 4.5.1.8, 4.5.1.9, 4.5.1.10, 4.5.2.1, 4.5.2.2, 4.5.2.3, 4.5.2.4, 4.5.2.5, 4.5.2.6, 4.5.2.7, 4.5.2.8, 4.5.2.9, 4.5.2.10, 4.5.3.1, 4.5.3.2, 4.5.3.3, 4.5.3.4, 4.5.3.5, 4.5.3.6, 4.5.3.7, 4.5.3.8, 4.5.3.9, 4.5.3.10, 4.5.4.1, 4.5.4.2, 4.5.4.3, 4.5.4.4, 4.5.4.5, 4.5.4.6, 4.5.4.7, 4.5.4.8, 4.5.4.9, 4.5.4.10, 4.5.5.1, 4.5.5.2, 4.5.5.3, 4.5.5.4, 4.5.5.5, 4.5.5.6, 4.5.5.7, 4.5.5.8, 4.5.5.9, 4.5.5.10, 4.5.6.1, 4.5.6.2, 4.5.6.3, 4.5.6.4, 4.5.6.5, 4.5.6.6, 4.5.6.7, 4.5.6.8, 4.5.6.9, 4.5.6.10, 4.5.7.1, 4.5.7.2, 4.5.7.3, 4.5.7.4, 4.5.7.5, 4.5.7.6, 4.5.7.7, 4.5.7.8, 4.5.7.9, 4.5.7.10, 4.5.8.1, 4.5.8.2, 4.5.8.3, 4.5.8.4, 4.5.8.5, 4.5.8.6, 4.5.8.7, 4.5.8.8, 4.5.8.9, 4.5.8.10, 4.5.9.1, 4.5.9.2, 4.5.9.3, 4.5.9.4, 4.5.9.5, 4.5.9.6, 4.5.9.7, 4.5.9.8, 4.5.9.9, 4.5.9.10, 4.5.10.1, 4.5.10.2, 4.5.10.3, 4.5.10.4, 4.5.10.5, 4.5.10.6, 4.5.10.7, 4.5.10.8, 4.5.10.9, 4.5.10.10, 4.6.1.1, 4.6.1.2, 4.6.1.3, 4.6.1.4, 4.6.1.5, 4.6.1.6, 4.6.1.7, 4.6.1.8, 4.6.1.9, 4.6.1.10, 4.6.2.1, 4.6.2.2, 4.6.2.3, 4.6.2.4, 4.6.2.5, 4.6.2.6, 4.6.2.7, 4.6.2.8, 4.6.2.9, 4.6.2.10, 4.6.3.1, 4.6.3.2, 4.6.3.3, 4.6.3.4, 4.6.3.5, 4.6.3.6, 4.6.3.7, 4.6.3.8, 4.6.3.9, 4.6.3.10, 4.6.4.1, 4.6.4.2, 4.6.4.3, 4.6.4.4, 4.6.4.5, 4.6.4.6, 4.6.4.7, 4.6.4.8, 4.6.4.9, 4.6.4.10, 4.6.5.1, 4.6.5.2, 4.6.5.3, 4.6.5.4, 4.6.5.5, 4.6.5.6, 4.6.5.7, 4.6.5.8, 4.6.5.9, 4.6.5.10, 4.6.6.1, 4.6.6.2, 4.6.6.3, 4.6.6.4, 4.6.6.5, 4.6.6.6, 4.6.6.7, 4.6.6.8, 4.6.6.9, 4.6.6.10, 4.6.7.1, 4.6.7.2, 4.6.7.3, 4.6.7.4, 4.6.7.5, 4.6.7.6, 4.6.7.7, 4.6.7.8, 4.6.7.9, 4.6.7.10, 4.6.8.1, 4.6.8.2, 4.6.8.3, 4.6.8.4, 4.6.8.5, 4.6.8.6, 4.6.8.7, 4.6.8.8, 4.6.8.9, 4.6.8.10, 4.6.9.1, 4.6.9.2, 4.6.9.3, 4.6.9.4, 4.6.9.5, 4.6.9.6, 4.6.9.7, 4.6.9.8, 4.6.9.9, 4.6.9.10, 4.6.10.1, 4.6.10.2, 4.6.10.3, 4.6.10.4, 4.6.10.5, 4.6.10.6, 4.6.10.7, 4.6.10.8, 4.6.10.9, 4.6.10.10, 4.7.1.1, 4.7.1.2, 4.7.1.3, 4.7.1.4, 4.7.1.5, 4.7.1.6, 4.7.1.7, 4.7.1.8, 4.7.1.9, 4.7.1.10, 4.7.2.1, 4.7.2.2, 4.7.2.3, 4.7.2.4, 4.7.2.5, 4.7.2.6, 4.7.2.7, 4.7.2.8, 4.7.2.9, 4.7.2.10, 4.7.3.1, 4.7.3.2, 4.7.3.3, 4.7.3.4, 4.7.3.5, 4.7.3.6, 4.7.3.7, 4.7.3.8, 4.7.3.9, 4.7.3.10, 4.7.4.1, 4.7.4.2, 4.7.4.3, 4.7.4.4, 4.7.4.5, 4.7.4.6, 4.7.4.7, 4.7.4.8, 4.7.4.9, 4.7.4.10, 4.7.5.1, 4.7.5.2, 4.7.5.3, 4.7.5.4, 4.7.5.5, 4.7.5.6, 4.7.5.7, 4.7.5.8, 4.7.5.9, 4.7.5.10, 4.7.6.1, 4.7.6.2, 4.7.6.3, 4.7.6.4, 4.7.6.5, 4.7.6.6, 4.7.6.7, 4.7.6.8, 4.7.6.9, 4.7.6.10, 4.7.7.1, 4.7.7.2, 4.7.7.3, 4.7.7.4, 4.7.7.5, 4.7.7.6, 4.7.7.7, 4.7.7.8, 4.7.7.9, 4.7.7.10, 4.7.8.1, 4.7.8.2, 4.7.8.3, 4.7.8.4, 4.7.8.5, 4.7.8.6, 4.7.8.7, 4.7.8.8, 4.7.8.9, 4.7.8.10, 4.7.9.1, 4.7.9.2, 4.7.9.3, 4.7.9.4, 4.7.9.5, 4.7.9.6, 4.7.9.7, 4.7.9.8, 4.7.9.9, 4.7.9.10, 4.7.10.1, 4.7.10.2, 4.7.10.3, 4.7.10.4, 4.7.10.5, 4.7.10.6, 4.7.10.7, 4.7.10.8, 4.7.10.9, 4.7.10.10, 4.8.1.1, 4.8.1.2, 4.8.1.3, 4.8.1.4, 4.8.1.5, 4.8.1.6, 4.8.1.7, 4.8.1.8, 4.8.1.9, 4.8.1.10, 4.8.2.1, 4.8.2.2, 4.8.2.3, 4.8.2.4, 4.8.2.5, 4.8.2.6, 4.8.2.7, 4.8.2.8, 4.8.2.9, 4.8.2.10, 4.8.3.1, 4.8.3.2, 4.8.3.3, 4.8.3.4, 4.8.3.5, TABLE B-continued 4.8.3.6, 4.8.3.7, 4.8.3.8, 4.8.3.9, 4.8.3.10, 4.8.4.1, 4.8.4.2, 4.8.4.3, 4.8.4.4, 4.8.4.5,
4.8.4.6, 4.8.4.7, 4.8.4.8, 4.8.4.9, 4.8.4.10, 4.8.5.1, 4.8.5.2, 4.8.5.3, 4.8.5.4, 4.8.5.5,
4.8.5.6, 4.8.5.7, 4.8.5.8, 4.8.5.9, 4.8.5.10, 4.8.6.1, 4.8.6.2, 4.8.6.3, 4.8.6.4, 4.8.6.5,
4.8.6.6, 4.8.6.7, 4.8.6.8, 4.8.6.9, 4.8.6.10, 4.8.7.1, 4.8.7.2, 4.8.7.3, 4.8.7.4, 4.8.7.5,
4.8.7.6, 4.8.7.7, 4.8.7.8, 4.8.7.9, 4.8.7.10, 4.8.8.1, 4.8.8.2, 4.8.8.3, 4.8.8.4, 4.8.8.5,
4.8.8.6, 4.8.8.7, 4.8.8.8, 4.8.8.9, 4.8.8.10, 4.8.9.1, 4.8.9.2, 4.8.9.3, 4.8.9.4, 4.8.9.5,
4.8.9.6, 4.8.9.7, 4.8.9.8, 4.8.9.9, 4.8.9.10, 4.8.10.1, 4.8.10.2, 4.8.10.3, 4.8.10.4, 4.8.10.5,
4.8.10.6, 4.8.10.7, 4.8.10.8, 4.8.10.9, 4.8.10.10, 4.9.1.1, 4.9.1.2, 4.9.1.3, 4.9.1.4, 4.9.1.5,
4.9.1.6, 4.9.1.7, 4.9.1.8, 4.9.1.9, 4.9.1.10, 4.9.2.1, 4.9.2.2, 4.9.2.3, 4.9.2.4, 4.9.2.5,
4.9.2.6, 4.9.2.7, 4.9.2.8, 4.9.2.9, 4.9.2.10, 4.9.3.1, 4.9.3.2, 4.9.3.3, 4.9.3.4, 4.9.3.5,
4.9.3.6, 4.9.3.7, 4.9.3.8, 4.9.3.9, 4.9.3.10, 4.9.4.1, 4.9.4.2, 4.9.4.3, 4.9.4.4, 4.9.4.5,
4.9.4.6, 4.9.4.7, 4.9.4.8, 4.9.4.9, 4.9.4.10, 4.9.5.1, 4.9.5.2, 4.9.5.3, 4.9.5.4, 4.9.5.5,
4.9.5.6, 4.9.5.7, 4.9.5.8, 4.9.5.9, 4.9.5.10, 4.9.6.1, 4.9.6.2, 4.9.6.3, 4.9.6.4, 4.9.6.5,
4.9.6.6, 4.9.6.7, 4.9.6.8, 4.9.6.9, 4.9.6.10, 4.9.7.1, 4.9.7.2, 4.9.7.3, 4.9.7.4, 4.9.7.5,
4.9.7.6, 4.9.7.7, 4.9.7.8, 4.9.7.9, 4.9.7.10, 4.9.8.1, 4.9.8.2, 4.9.8.3, 4.9.8.4, 4.9.8.5,
4.9.8.6, 4.9.8.7, 4.9.8.8, 4.9.8.9, 4.9.8.10, 4.9.9.1, 4.9.9.2, 4.9.9.3, 4.9.9.4, 4.9.9.5,
4.9.9.6, 4.9.9.7, 4.9.9.8, 4.9.9.9, 4.9.9.10, 4.9.10.1, 4.9.10.2, 4.9.10.3, 4.9.10.4, 4.9.10.5,
4.9.10.6, 4.9.10.7, 4.9.10.8, 4.9.10.9, 4.9.10.10, 4.10.1.1, 4.10.1.2, 4.10.1.3, 4.10.1.4,
4.10.1.5, 4.10.1.6, 4.10.1.7, 4.10.1.8, 4.10.1.9, 4.10.1.10, 4.10.2.1, 4.10.2.2, 4.10.2.3,
4.10.2.4, 4.10.2.5, 4.10.2.6, 4.10.2.7, 4.10.2.8, 4.10.2.9, 4.10.2.10, 4.10.3.1, 4.10.3.2,
4.10.3.3, 4.10.3.4, 4.10.3.5, 4.10.3.6, 4.10.3.7, 4.10.3.8, 4.10.3.9, 4.10.3.10, 4.10.4.1,
4.10.4.2, 4.10.4.3, 4.10.4.4, 4.10.4.5, 4.10.4.6, 4.10.4.7, 4.10.4.8, 4.10.4.9, 4.10.4.10,
4.10.5.1, 4.10.5.2, 4.10.5.3, 4.10.5.4, 4.10.5.5, 4.10.5.6, 4.10.5.7, 4.10.5.8, 4.10.5.9,
4.10.5.10, 4.10.6.1, 4.10.6.2, 4.10.6.3, 4.10.6.4, 4.10.6.5, 4.10.6.6, 4.10.6.7, 4.10.6.8,
4.10.6.9, 4.10.6.10, 4.10.7.1, 4.10.7.2, 4.10.7.3, 4.10.7.4, 4.10.7.5, 4.10.7.6, 4.10.7.7,
4.10.7.8, 4.10.7.9, 4.10.7.10, 4.10.8.1, 4.10.8.2, 4.10.8.3, 4.10.8.4, 4.10.8.5, 4.10.8.6,
4.10.8.7, 4.10.8.8, 4.10.8.9, 4.10.8.10, 4.10.9.1, 4.10.9.2, 4.10.9.3, 4.10.9.4, 4.10.9.5,
4.10.9.6, 4.10.9.7, 4.10.9.8, 4.10.9.9, 4.10.9.10, 4.10.10.1, 4.10.10.2, 4.10.10.3,
4.10.10.4, 4.10.10.5, 4.10.10.6, 4.10.10.7, 4.10.10.8, 4.10.10.9, 4.10.10.10, 5.1.1.1,
5.1.1.2, 5.1.1.3, 5.1.1.4, 5.1.1.5, 5.1.1.6, 5.1.1.7, 5.1.1.8, 5.1.1.9, 5.1.1.10, 5.1.2.1,
5.1.2.2, 5.1.2.3, 5.1.2.4, 5.1.2.5, 5.1.2.6, 5.1.2.7, 5.1.2.8, 5.1.2.9, 5.1.2.10, 5.1.3.1,
5.1.3.2, 5.1.3.3, 5.1.3.4, 5.1.3.5, 5.1.3.6, 5.1.3.7, 5.1.3.8, 5.1.3.9, 5.1.3.10, 5.1.4.1,
5.1.4.2, 5.1.4.3, 5.1.4.4, 5.1.4.5, 5.1.4.6, 5.1.4.7, 5.1.4.8, 5.1.4.9, 5.1.4.10, 5.1.5.1,
5.1.5.2, 5.1.5.3, 5.1.5.4, 5.1.5.5, 5.1.5.6, 5.1.5.7, 5.1.5.8, 5.1.5.9, 5.1.5.10, 5.1.6.1,
5.1.6.2, 5.1.6.3, 5.1.6.4, 5.1.6.5, 5.1.6.6, 5.1.6.7, 5.1.6.8, 5.1.6.9, 5.1.6.10, 5.1.7.1,
5.1.7.2, 5.1.7.3, 5.1.7.4, 5.1.7.5, 5.1.7.6, 5.1.7.7, 5.1.7.8, 5.1.7.9, 5.1.7.10, 5.1.8.1,
5.1.8.2, 5.1.8.3, 5.1.8.4, 5.1.8.5, 5.1.8.6, 5.1.8.7, 5.1.8.8, 5.1.8.9, 5.1.8.10, 5.1.9.1,
5.1.9.2, 5.1.9.3, 5.1.9.4, 5.1.9.5, 5.1.9.6, 5.1.9.7, 5.1.9.8, 5.1.9.9, 5.1.9.10, 5.1.10.1,
5.1.10.2, 5.1.10.3, 5.1.10.4, 5.1.10.5, 5.1.10.6, 5.1.10.7, 5.1.10.8, 5.1.10.9, 5.1.10.10,
5.2.1.1, 5.2.1.2, 5.2.1.3, 5.2.1.4, 5.2.1.5, 5.2.1.6, 5.2.1.7, 5.2.1.8, 5.2.1.9, 5.2.1.10,
5.2.2.1, 5.2.2.2, 5.2.2.3, 5.2.2.4, 5.2.2.5, 5.2.2.6, 5.2.2.7, 5.2.2.8, 5.2.2.9, 5.2.2.10,
5.2.3.1, 5.2.3.2, 5.2.3.3, 5.2.3.4, 5.2.3.5, 5.2.3.6, 5.2.3.7, 5.2.3.8, 5.2.3.9, 5.2.3.10,
5.2.4.1, 5.2.4.2, 5.2.4.3, 5.2.4.4, 5.2.4.5, 5.2.4.6, 5.2.4.7, 5.2.4.8, 5.2.4.9, 5.2.4.10,
5.2.5.1, 5.2.5.2, 5.2.5.3, 5.2.5.4, 5.2.5.5, 5.2.5.6, 5.2.5.7, 5.2.5.8, 5.2.5.9, 5.2.5.10,
5.2.6.1, 5.2.6.2, 5.2.6.3, 5.2.6.4, 5.2.6.5, 5.2.6.6, 5.2.6.7, 5.2.6.8, 5.2.6.9, 5.2.6.10,
5.2.7.1, 5.2.7.2, 5.2.7.3, 5.2.7.4, 5.2.7.5, 5.2.7.6, 5.2.7.7, 5.2.7.8, 5.2.7.9, 5.2.7.10,
5.2.8.1, 5.2.8.2, 5.2.8.3, 5.2.8.4, 5.2.8.5, 5.2.8.6, 5.2.8.7, 5.2.8.8, 5.2.8.9, 5.2.8.10,
5.2.9.1, 5.2.9.2, 5.2.9.3, 5.2.9.4, 5.2.9.5, 5.2.9.6, 5.2.9.7, 5.2.9.8, 5.2.9.9, 5.2.9.10,
5.2.10.1, 5.2.10.2, 5.2.10.3, 5.2.10.4, 5.2.10.5, 5.2.10.6, 5.2.10.7, 5.2.10.8, 5.2.10.9,
5.2.10.10, 5.3.1.1, 5.3.1.2, 5.3.1.3, 5.3.1.4, 5.3.1.5, 5.3.1.6, 5.3.1.7, 5.3.1.8, 5.3.1.9,
5.3.1.10, 5.3.2.1, 5.3.2.2, 5.3.2.3, 5.3.2.4, 5.3.2.5, 5.3.2.6, 5.3.2.7, 5.3.2.8, 5.3.2.9,
5.3.2.10, 5.3.3.1, 5.3.3.2, 5.3.3.3, 5.3.3.4, 5.3.3.5, 5.3.3.6, 5.3.3.7, 5.3.3.8, 5.3.3.9,
5.3.3.10, 5.3.4.1, 5.3.4.2, 5.3.4.3, 5.3.4.4, 5.3.4.5, 5.3.4.6, 5.3.4.7, 5.3.4.8, 5.3.4.9,
5.3.4.10, 5.3.5.1, 5.3.5.2, 5.3.5.3, 5.3.5.4, 5.3.5.5, 5.3.5.6, 5.3.5.7, 5.3.5.8, 5.3.5.9,
5.3.5.10, 5.3.6.1, 5.3.6.2, 5.3.6.3, 5.3.6.4, 5.3.6.5, 5.3.6.6, 5.3.6.7, 5.3.6.8, 5.3.6.9,
5.3.6.10, 5.3.7.1, 5.3.7.2, 5.3.7.3, 5.3.7.4, 5.3.7.5, 5.3.7.6, 5.3.7.7, 5.3.7.8, 5.3.7.9,
5.3.7.10, 5.3.8.1, 5.3.8.2, 5.3.8.3, 5.3.8.4, 5.3.8.5, 5.3.8.6, 5.3.8.7, 5.3.8.8, 5.3.8.9,
5.3.8.10, 5.3.9.1, 5.3.9.2, 5.3.9.3, 5.3.9.4, 5.3.9.5, 5.3.9.6, 5.3.9.7, 5.3.9.8, 5.3.9.9,
5.3.9.10, 5.3.10.1, 5.3.10.2, 5.3.10.3, 5.3.10.4, 5.3.10.5, 5.3.10.6, 5.3.10.7, 5.3.10.8,
5.3.10.9, 5.3.10.10, 5.4.1.1, 5.4.1.2, 5.4.1.3, 5.4.1.4, 5.4.1.5, 5.4.1.6, 5.4.1.7, 5.4.1.8,
5.4.1.9, 5.4.1.10, 5.4.2.1, 5.4.2.2, 5.4.2.3, 5.4.2.4, 5.4.2.5, 5.4.2.6, 5.4.2.7, 5.4.2.8,
5.4.2.9, 5.4.2.10, 5.4.3.1, 5.4.3.2, 5.4.3.3, 5.4.3.4, 5.4.3.5, 5.4.3.6, 5.4.3.7, 5.4.3.8,
5.4.3.9, 5.4.3.10, 5.4.4.1, 5.4.4.2, 5.4.4.3, 5.4.4.4, 5.4.4.5, 5.4.4.6, 5.4.4.7, 5.4.4.8,
5.4.4.9, 5.4.4.10, 5.4.5.1, 5.4.5.2, 5.4.5.3, 5.4.5.4, 5.4.5.5, 5.4.5.6, 5.4.5.7, 5.4.5.8,
5.4.5.9, 5.4.5.10, 5.4.6.1, 5.4.6.2, 5.4.6.3, 5.4.6.4, 5.4.6.5, 5.4.6.6, 5.4.6.7, 5.4.6.8,
5.4.6.9, 5.4.6.10, 5.4.7.1, 5.4.7.2, 5.4.7.3, 5.4.7.4, 5.4.7.5, 5.4.7.6, 5.4.7.7, 5.4.7.8,
5.4.7.9, 5.4.7.10, 5.4.8.1, 5.4.8.2, 5.4.8.3, 5.4.8.4, 5.4.8.5, 5.4.8.6, 5.4.8.7, 5.4.8.8,
5.4.8.9, 5.4.8.10, 5.4.9.1, 5.4.9.2, 5.4.9.3, 5.4.9.4, 5.4.9.5, 5.4.9.6, 5.4.9.7, 5.4.9.8,
5.4.9.9, 5.4.9.10, 5.4.10.1, 5.4.10.2, 5.4.10.3, 5.4.10.4, 5.4.10.5, 5.4.10.6, 5.4.10.7,
5.4.10.8, 5.4.10.9, 5.4.10.10, 5.5.1.1, 5.5.1.2, 5.5.1.3, 5.5.1.4, 5.5.1.5, 5.5.1.6, 5.5.1.7,
5.5.1.8, 5.5.1.9, 5.5.1.10, 5.5.2.1, 5.5.2.2, 5.5.2.3, 5.5.2.4, 5.5.2.5, 5.5.2.6, 5.5.2.7,
5.5.2.8, 5.5.2.9, 5.5.2.10, 5.5.3.1, 5.5.3.2, 5.5.3.3, 5.5.3.4, 5.5.3.5, 5.5.3.6, 5.5.3.7,
5.5.3.8, 5.5.3.9, 5.5.3.10, 5.5.4.1, 5.5.4.2, 5.5.4.3, 5.5.4.4, 5.5.4.5, 5.5.4.6, 5.5.4.7,
5.5.4.8, 5.5.4.9, 5.5.4.10, 5.5.5.1, 5.5.5.2, 5.5.5.3, 5.5.5.4, 5.5.5.5, 5.5.5.6, 5.5.5.7,
5.5.5.8, 5.5.5.9, 5.5.5.10, 5.5.6.1, 5.5.6.2, 5.5.6.3, 5.5.6.4, 5.5.6.5, 5.5.6.6, 5.5.6.7,
5.5.6.8, 5.5.6.9, 5.5.6.10, 5.5.7.1, 5.5.7.2, 5.5.7.3, 5.5.7.4, 5.5.7.5, 5.5.7.6, 5.5.7.7,
5.5.7.8, 5.5.7.9, 5.5.7.10, 5.5.8.1, 5.5.8.2, 5.5.8.3, 5.5.8.4, 5.5.8.5, 5.5.8.6, 5.5.8.7,
5.5.8.8, 5.5.8.9, 5.5.8.10, 5.5.9.1, 5.5.9.2, 5.5.9.3, 5.5.9.4, 5.5.9.5, 5.5.9.6, 5.5.9.7,
5.5.9.8, 5.5.9.9, 5.5.9.10, 5.5.10.1, 5.5.10.2, 5.5.10.3, 5.5.10.4, 5.5.10.5, 5.5.10.6,
5.5.10.7, 5.5.10.8, 5.5.10.9, 5.5.10.10, 5.6.1.1, 5.6.1.2, 5.6.1.3, 5.6.1.4, 5.6.1.5, 5.6.1.6, TABLE B-continued 5.6.1.7, 5.6.1.8, 5.6.1.9, 5.6.1.10, 5.6.2.1, 5.6.2.2, 5.6.2.3, 5.6.2.4, 5.6.2.5, 5.6.2.6,
5.6.2.7, 5.6.2.8, 5.6.2.9, 5.6.2.10, 5.6.3.1, 5.6.3.2, 5.6.3.3, 5.6.3.4, 5.6.3.5, 5.6.3.6,
5.6.3.7, 5.6.3.8, 5.6.3.9, 5.6.3.10, 5.6.4.1, 5.6.4.2, 5.6.4.3, 5.6.4.4, 5.6.4.5, 5.6.4.6,
5.6.4.7, 5.6.4.8, 5.6.4.9, 5.6.4.10, 5.6.5.1, 5.6.5.2, 5.6.5.3, 5.6.5.4, 5.6.5.5, 5.6.5.6,
5.6.5.7, 5.6.5.8, 5.6.5.9, 5.6.5.10, 5.6.6.1, 5.6.6.2, 5.6.6.3, 5.6.6.4, 5.6.6.5, 5.6.6.6,
5.6.6.7, 5.6.6.8, 5.6.6.9, 5.6.6.10, 5.6.7.1, 5.6.7.2, 5.6.7.3, 5.6.7.4, 5.6.7.5, 5.6.7.6,
5.6.7.7, 5.6.7.8, 5.6.7.9, 5.6.7.10, 5.6.8.1, 5.6.8.2, 5.6.8.3, 5.6.8.4, 5.6.8.5, 5.6.8.6,
5.6.8.7, 5.6.8.8, 5.6.8.9, 5.6.8.10, 5.6.9.1, 5.6.9.2, 5.6.9.3, 5.6.9.4, 5.6.9.5, 5.6.9.6,
5.6.9.7, 5.6.9.8, 5.6.9.9, 5.6.9.10, 5.6.10.1, 5.6.10.2, 5.6.10.3, 5.6.10.4, 5.6.10.5,
5.6.10.6, 5.6.10.7, 5.6.10.8, 5.6.10.9, 5.6.10.10, 5.7.1.1, 5.7.1.2, 5.7.1.3, 5.7.1.4, 5.7.1.5,
5.7.1.6, 5.7.1.7, 5.7.1.8, 5.7.1.9, 5.7.1.10, 5.7.2.1, 5.7.2.2, 5.7.2.3, 5.7.2.4, 5.7.2.5,
5.7.2.6, 5.7.2.7, 5.7.2.8, 5.7.2.9, 5.7.2.10, 5.7.3.1, 5.7.3.2, 5.7.3.3, 5.7.3.4, 5.7.3.5,
5.7.3.6, 5.7.3.7, 5.7.3.8, 5.7.3.9, 5.7.3.10, 5.7.4.1, 5.7.4.2, 5.7.4.3, 5.7.4.4, 5.7.4.5,
5.7.4.6, 5.7.4.7, 5.7.4.8, 5.7.4.9, 5.7.4.10, 5.7.5.1, 5.7.5.2, 5.7.5.3, 5.7.5.4, 5.7.5.5,
5.7.5.6, 5.7.5.7, 5.7.5.8, 5.7.5.9, 5.7.5.10, 5.7.6.1, 5.7.6.2, 5.7.6.3, 5.7.6.4, 5.7.6.5,
5.7.6.6, 5.7.6.7, 5.7.6.8, 5.7.6.9, 5.7.6.10, 5.7.7.1, 5.7.7.2, 5.7.7.3, 5.7.7.4, 5.7.7.5,
5.7.7.6, 5.7.7.7, 5.7.7.8, 5.7.7.9, 5.7.7.10, 5.7.8.1, 5.7.8.2, 5.7.8.3, 5.7.8.4, 5.7.8.5,
5.7.8.6, 5.7.8.7, 5.7.8.8, 5.7.8.9, 5.7.8.10, 5.7.9.1, 5.7.9.2, 5.7.9.3, 5.7.9.4, 5.7.9.5,
5.7.9.6, 5.7.9.7, 5.7.9.8, 5.7.9.9, 5.7.9.10, 5.7.10.1, 5.7.10.2, 5.7.10.3, 5.7.10.4, 5.7.10.5,
5.7.10.6, 5.7.10.7, 5.7.10.8, 5.7.10.9, 5.7.10.10, 5.8.1.1, 5.8.1.2, 5.8.1.3, 5.8.1.4, 5.8.1.5,
5.8.1.6, 5.8.1.7, 5.8.1.8, 5.8.1.9, 5.8.1.10, 5.8.2.1, 5.8.2.2, 5.8.2.3, 5.8.2.4, 5.8.2.5,
5.8.2.6, 5.8.2.7, 5.8.2.8, 5.8.2.9, 5.8.2.10, 5.8.3.1, 5.8.3.2, 5.8.3.3, 5.8.3.4, 5.8.3.5,
5.8.3.6, 5.8.3.7, 5.8.3.8, 5.8.3.9, 5.8.3.10, 5.8.4.1, 5.8.4.2, 5.8.4.3, 5.8.4.4, 5.8.4.5,
5.8.4.6, 5.8.4.7, 5.8.4.8, 5.8.4.9, 5.8.4.10, 5.8.5.1, 5.8.5.2, 5.8.5.3, 5.8.5.4, 5.8.5.5,
5.8.5.6, 5.8.5.7, 5.8.5.8, 5.8.5.9, 5.8.5.10, 5.8.6.1, 5.8.6.2, 5.8.6.3, 5.8.6.4, 5.8.6.5,
5.8.6.6, 5.8.6.7, 5.8.6.8, 5.8.6.9, 5.8.6.10, 5.8.7.1, 5.8.7.2, 5.8.7.3, 5.8.7.4, 5.8.7.5,
5.8.7.6, 5.8.7.7, 5.8.7.8, 5.8.7.9, 5.8.7.10, 5.8.8.1, 5.8.8.2, 5.8.8.3, 5.8.8.4, 5.8.8.5,
5.8.8.6, 5.8.8.7, 5.8.8.8, 5.8.8.9, 5.8.8.10, 5.8.9.1, 5.8.9.2, 5.8.9.3, 5.8.9.4, 5.8.9.5,
5.8.9.6, 5.8.9.7, 5.8.9.8, 5.8.9.9, 5.8.9.10, 5.8.10.1, 5.8.10.2, 5.8.10.3, 5.8.10.4, 5.8.10.5,
5.8.10.6, 5.8.10.7, 5.8.10.8, 5.8.10.9, 5.8.10.10, 5.9.1.1, 5.9.1.2, 5.9.1.3, 5.9.1.4, 5.9.1.5,
5.9.1.6, 5.9.1.7, 5.9.1.8, 5.9.1.9, 5.9.1.10, 5.9.2.1, 5.9.2.2, 5.9.2.3, 5.9.2.4, 5.9.2.5,
5.9.2.6, 5.9.2.7, 5.9.2.8, 5.9.2.9, 5.9.2.10, 5.9.3.1, 5.9.3.2, 5.9.3.3, 5.9.3.4, 5.9.3.5,
5.9.3.6, 5.9.3.7, 5.9.3.8, 5.9.3.9, 5.9.3.10, 5.9.4.1, 5.9.4.2, 5.9.4.3, 5.9.4.4, 5.9.4.5,
5.9.4.6, 5.9.4.7, 5.9.4.8, 5.9.4.9, 5.9.4.10, 5.9.5.1, 5.9.5.2, 5.9.5.3, 5.9.5.4, 5.9.5.5,
5.9.5.6, 5.9.5.7, 5.9.5.8, 5.9.5.9, 5.9.5.10, 5.9.6.1, 5.9.6.2, 5.9.6.3, 5.9.6.4, 5.9.6.5,
5.9.6.6, 5.9.6.7, 5.9.6.8, 5.9.6.9, 5.9.6.10, 5.9.7.1, 5.9.7.2, 5.9.7.3, 5.9.7.4, 5.9.7.5,
5.9.7.6, 5.9.7.7, 5.9.7.8, 5.9.7.9, 5.9.7.10, 5.9.8.1, 5.9.8.2, 5.9.8.3, 5.9.8.4, 5.9.8.5,
5.9.8.6, 5.9.8.7, 5.9.8.8, 5.9.8.9, 5.9.8.10, 5.9.9.1, 5.9.9.2, 5.9.9.3, 5.9.9.4, 5.9.9.5,
5.9.9.6, 5.9.9.7, 5.9.9.8, 5.9.9.9, 5.9.9.10, 5.9.10.1, 5.9.10.2, 5.9.10.3, 5.9.10.4, 5.9.10.5,
5.9.10.6, 5.9.10.7, 5.9.10.8, 5.9.10.9, 5.9.10.10, 5.10.1.1, 5.10.1.2, 5.10.1.3, 5.10.1.4,
5.10.1.5, 5.10.1.6, 5.10.1.7, 5.10.1.8, 5.10.1.9, 5.10.1.10, 5.10.2.1, 5.10.2.2, 5.10.2.3,
5.10.2.4, 5.10.2.5, 5.10.2.6, 5.10.2.7, 5.10.2.8, 5.10.2.9, 5.10.2.10, 5.10.3.1, 5.10.3.2,
5.10.3.3, 5.10.3.4, 5.10.3.5, 5.10.3.6, 5.10.3.7, 5.10.3.8, 5.10.3.9, 5.10.3.10, 5.10.4.1,
5.10.4.2, 5.10.4.3, 5.10.4.4, 5.10.4.5, 5.10.4.6, 5.10.4.7, 5.10.4.8, 5.10.4.9, 5.10.4.10,
5.10.5.1, 5.10.5.2, 5.10.5.3, 5.10.5.4, 5.10.5.5, 5.10.5.6, 5.10.5.7, 5.10.5.8, 5.10.5.9,
5.10.5.10, 5.10.6.1, 5.10.6.2, 5.10.6.3, 5.10.6.4, 5.10.6.5, 5.10.6.6, 5.10.6.7, 5.10.6.8,
5.10.6.9, 5.10.6.10, 5.10.7.1, 5.10.7.2, 5.10.7.3, 5.10.7.4, 5.10.7.5, 5.10.7.6, 5.10.7.7,
5.10.7.8, 5.10.7.9, 5.10.7.10, 5.10.8.1, 5.10.8.2, 5.10.8.3, 5.10.8.4, 5.10.8.5, 5.10.8.6,
5.10.8.7, 5.10.8.8, 5.10.8.9, 5.10.8.10, 5.10.9.1, 5.10.9.2, 5.10.9.3, 5.10.9.4, 5.10.9.5,
5.10.9.6, 5.10.9.7, 5.10.9.8, 5.10.9.9, 5.10.9.10, 5.10.10.1, 5.10.10.2, 5.10.10.3,
5.10.10.4, 5.10.10.5, 5.10.10.6, 5.10.10.7, 5.10.10.8, 5.10.10.9, 5.10.10.10, 6.1.1.1,
6.1.1.2, 6.1.1.3, 6.1.1.4, 6.1.1.5, 6.1.1.6, 6.1.1.7, 6.1.1.8, 6.1.1.9, 6.1.1.10, 6.1.2.1,
6.1.2.2, 6.1.2.3, 6.1.2.4, 6.1.2.5, 6.1.2.6, 6.1.2.7, 6.1.2.8, 6.1.2.9, 6.1.2.10, 6.1.3.1,
6.1.3.2, 6.1.3.3, 6.1.3.4, 6.1.3.5, 6.1.3.6, 6.1.3.7, 6.1.3.8, 6.1.3.9, 6.1.3.10, 6.1.4.1,
6.1.4.2, 6.1.4.3, 6.1.4.4, 6.1.4.5, 6.1.4.6, 6.1.4.7, 6.1.4.8, 6.1.4.9, 6.1.4.10, 6.1.5.1,
6.1.5.2, 6.1.5.3, 6.1.5.4, 6.1.5.5, 6.1.5.6, 6.1.5.7, 6.1.5.8, 6.1.5.9, 6.1.5.10, 6.1.6.1,
6.1.6.2, 6.1.6.3, 6.1.6.4, 6.1.6.5, 6.1.6.6, 6.1.6.7, 6.1.6.8, 6.1.6.9, 6.1.6.10, 6.1.7.1,
6.1.7.2, 6.1.7.3, 6.1.7.4, 6.1.7.5, 6.1.7.6, 6.1.7.7, 6.1.7.8, 6.1.7.9, 6.1.7.10, 6.1.8.1,
6.1.8.2, 6.1.8.3, 6.1.8.4, 6.1.8.5, 6.1.8.6, 6.1.8.7, 6.1.8.8, 6.1.8.9, 6.1.8.10, 6.1.9.1,
6.1.9.2, 6.1.9.3, 6.1.9.4, 6.1.9.5, 6.1.9.6, 6.1.9.7, 6.1.9.8, 6.1.9.9, 6.1.9.10, 6.1.10.1,
6.1.10.2, 6.1.10.3, 6.1.10.4, 6.1.10.5, 6.1.10.6, 6.1.10.7, 6.1.10.8, 6.1.10.9, 6.1.10.10,
6.2.1.1, 6.2.1.2, 6.2.1.3, 6.2.1.4, 6.2.1.5, 6.2.1.6, 6.2.1.7, 6.2.1.8, 6.2.1.9, 6.2.1.10,
6.2.2.1, 6.2.2.2, 6.2.2.3, 6.2.2.4, 6.2.2.5, 6.2.2.6, 6.2.2.7, 6.2.2.8, 6.2.2.9, 6.2.2.10,
6.2.3.1, 6.2.3.2, 6.2.3.3, 6.2.3.4, 6.2.3.5, 6.2.3.6, 6.2.3.7, 6.2.3.8, 6.2.3.9, 6.2.3.10,
6.2.4.1, 6.2.4.2, 6.2.4.3, 6.2.4.4, 6.2.4.5, 6.2.4.6, 6.2.4.7, 6.2.4.8, 6.2.4.9, 6.2.4.10,
6.2.5.1, 6.2.5.2, 6.2.5.3, 6.2.5.4, 6.2.5.5, 6.2.5.6, 6.2.5.7, 6.2.5.8, 6.2.5.9, 6.2.5.10,
6.2.6.1, 6.2.6.2, 6.2.6.3, 6.2.6.4, 6.2.6.5, 6.2.6.6, 6.2.6.7, 6.2.6.8, 6.2.6.9, 6.2.6.10,
6.2.7.1, 6.2.7.2, 6.2.7.3, 6.2.7.4, 6.2.7.5, 6.2.7.6, 6.2.7.7, 6.2.7.8, 6.2.7.9, 6.2.7.10,
6.2.8.1, 6.2.8.2, 6.2.8.3, 6.2.8.4, 6.2.8.5, 6.2.8.6, 6.2.8.7, 6.2.8.8, 6.2.8.9, 6.2.8.10,
6.2.9.1, 6.2.9.2, 6.2.9.3, 6.2.9.4, 6.2.9.5, 6.2.9.6, 6.2.9.7, 6.2.9.8, 6.2.9.9, 6.2.9.10,
6.2.10.1, 6.2.10.2, 6.2.10.3, 6.2.10.4, 6.2.10.5, 6.2.10.6, 6.2.10.7, 6.2.10.8, 6.2.10.9,
6.2.10.10, 6.3.1.1, 6.3.1.2, 6.3.1.3, 6.3.1.4, 6.3.1.5, 6.3.1.6, 6.3.1.7, 6.3.1.8, 6.3.1.9,
6.3.1.10, 6.3.2.1, 6.3.2.2, 6.3.2.3, 6.3.2.4, 6.3.2.5, 6.3.2.6, 6.3.2.7, 6.3.2.8, 6.3.2.9,
6.3.2.10, 6.3.3.1, 6.3.3.2, 6.3.3.3, 6.3.3.4, 6.3.3.5, 6.3.3.6, 6.3.3.7, 6.3.3.8, 6.3.3.9,
6.3.3.10, 6.3.4.1, 6.3.4.2, 6.3.4.3, 6.3.4.4, 6.3.4.5, 6.3.4.6, 6.3.4.7, 6.3.4.8, 6.3.4.9,
6.3.4.10, 6.3.5.1, 6.3.5.2, 6.3.5.3, 6.3.5.4, 6.3.5.5, 6.3.5.6, 6.3.5.7, 6.3.5.8, 6.3.5.9,
6.3.5.10, 6.3.6.1, 6.3.6.2, 6.3.6.3, 6.3.6.4, 6.3.6.5, 6.3.6.6, 6.3.6.7, 6.3.6.8, 6.3.6.9,
6.3.6.10, 6.3.7.1, 6.3.7.2, 6.3.7.3, 6.3.7.4, 6.3.7.5, 6.3.7.6, 6.3.7.7, 6.3.7.8, 6.3.7.9,
6.3.7.10, 6.3.8.1, 6.3.8.2, 6.3.8.3, 6.3.8.4, 6.3.8.5, 6.3.8.6, 6.3.8.7, 6.3.8.8, 6.3.8.9,
6.3.8.10, 6.3.9.1, 6.3.9.2, 6.3.9.3, 6.3.9.4, 6.3.9.5, 6.3.9.6, 6.3.9.7, 6.3.9.8, 6.3.9.9, TABLE B-continued 6.3.9.10, 6.3.10.1, 6.3.10.2, 6.3.10.3, 6.3.10.4, 6.3.10.5, 6.3.10.6, 6.3.10.7, 6.3.10.8,
6.3.10.9, 6.3.10.10, 6.4.1.1, 6.4.1.2, 6.4.1.3, 6.4.1.4, 6.4.1.5, 6.4.1.6, 6.4.1.7, 6.4.1.8,
6.4.1.9, 6.4.1.10, 6.4.2.1, 6.4.2.2, 6.4.2.3, 6.4.2.4, 6.4.2.5, 6.4.2.6, 6.4.2.7, 6.4.2.8,
6.4.2.9, 6.4.2.10, 6.4.3.1, 6.4.3.2, 6.4.3.3, 6.4.3.4, 6.4.3.5, 6.4.3.6, 6.4.3.7, 6.4.3.8,
6.4.3.9, 6.4.3.10, 6.4.4.1, 6.4.4.2, 6.4.4.3, 6.4.4.4, 6.4.4.5, 6.4.4.6, 6.4.4.7, 6.4.4.8,
6.4.4.9, 6.4.4.10, 6.4.5.1, 6.4.5.2, 6.4.5.3, 6.4.5.4, 6.4.5.5, 6.4.5.6, 6.4.5.7, 6.4.5.8,
6.4.5.9, 6.4.5.10, 6.4.6.1, 6.4.6.2, 6.4.6.3, 6.4.6.4, 6.4.6.5, 6.4.6.6, 6.4.6.7, 6.4.6.8,
6.4.6.9, 6.4.6.10, 6.4.7.1, 6.4.7.2, 6.4.7.3, 6.4.7.4, 6.4.7.5, 6.4.7.6, 6.4.7.7, 6.4.7.8,
6.4.7.9, 6.4.7.10, 6.4.8.1, 6.4.8.2, 6.4.8.3, 6.4.8.4, 6.4.8.5, 6.4.8.6, 6.4.8.7, 6.4.8.8,
6.4.8.9, 6.4.8.10, 6.4.9.1, 6.4.9.2, 6.4.9.3, 6.4.9.4, 6.4.9.5, 6.4.9.6, 6.4.9.7, 6.4.9.8,
6.4.9.9, 6.4.9.10, 6.4.10.1, 6.4.10.2, 6.4.10.3, 6.4.10.4, 6.4.10.5, 6.4.10.6, 6.4.10.7,
6.4.10.8, 6.4.10.9, 6.4.10.10, 6.5.1.1, 6.5.1.2, 6.5.1.3, 6.5.1.4, 6.5.1.5, 6.5.1.6, 6.5.1.7,
6.5.1.8, 6.5.1.9, 6.5.1.10, 6.5.2.1, 6.5.2.2, 6.5.2.3, 6.5.2.4, 6.5.2.5, 6.5.2.6, 6.5.2.7,
6.5.2.8, 6.5.2.9, 6.5.2.10, 6.5.3.1, 6.5.3.2, 6.5.3.3, 6.5.3.4, 6.5.3.5, 6.5.3.6, 6.5.3.7,
6.5.3.8, 6.5.3.9, 6.5.3.10, 6.5.4.1, 6.5.4.2, 6.5.4.3, 6.5.4.4, 6.5.4.5, 6.5.4.6, 6.5.4.7,
6.5.4.8, 6.5.4.9, 6.5.4.10, 6.5.5.1, 6.5.5.2, 6.5.5.3, 6.5.5.4, 6.5.5.5, 6.5.5.6, 6.5.5.7,
6.5.5.8, 6.5.5.9, 6.5.5.10, 6.5.6.1, 6.5.6.2, 6.5.6.3, 6.5.6.4, 6.5.6.5, 6.5.6.6, 6.5.6.7,
6.5.6.8, 6.5.6.9, 6.5.6.10, 6.5.7.1, 6.5.7.2, 6.5.7.3, 6.5.7.4, 6.5.7.5, 6.5.7.6, 6.5.7.7,
6.5.7.8, 6.5.7.9, 6.5.7.10, 6.5.8.1, 6.5.8.2, 6.5.8.3, 6.5.8.4, 6.5.8.5, 6.5.8.6, 6.5.8.7,
6.5.8.8, 6.5.8.9, 6.5.8.10, 6.5.9.1, 6.5.9.2, 6.5.9.3, 6.5.9.4, 6.5.9.5, 6.5.9.6, 6.5.9.7,
6.5.9.8, 6.5.9.9, 6.5.9.10, 6.5.10.1, 6.5.10.2, 6.5.10.3, 6.5.10.4, 6.5.10.5, 6.5.10.6,
6.5.10.7, 6.5.10.8, 6.5.10.9, 6.5.10.10, 6.6.1.1, 6.6.1.2, 6.6.1.3, 6.6.1.4, 6.6.1.5, 6.6.1.6,
6.6.1.7, 6.6.1.8, 6.6.1.9, 6.6.1.10, 6.6.2.1, 6.6.2.2, 6.6.2.3, 6.6.2.4, 6.6.2.5, 6.6.2.6,
6.6.2.7, 6.6.2.8, 6.6.2.9, 6.6.2.10, 6.6.3.1, 6.6.3.2, 6.6.3.3, 6.6.3.4, 6.6.3.5, 6.6.3.6,
6.6.3.7, 6.6.3.8, 6.6.3.9, 6.6.3.10, 6.6.4.1, 6.6.4.2, 6.6.4.3, 6.6.4.4, 6.6.4.5, 6.6.4.6,
6.6.4.7, 6.6.4.8, 6.6.4.9, 6.6.4.10, 6.6.5.1, 6.6.5.2, 6.6.5.3, 6.6.5.4, 6.6.5.5, 6.6.5.6,
6.6.5.7, 6.6.5.8, 6.6.5.9, 6.6.5.10, 6.6.6.1, 6.6.6.2, 6.6.6.3, 6.6.6.4, 6.6.6.5, 6.6.6.6,
6.6.6.7, 6.6.6.8, 6.6.6.9, 6.6.6.10, 6.6.7.1, 6.6.7.2, 6.6.7.3, 6.6.7.4, 6.6.7.5, 6.6.7.6,
6.6.7.7, 6.6.7.8, 6.6.7.9, 6.6.7.10, 6.6.8.1, 6.6.8.2, 6.6.8.3, 6.6.8.4, 6.6.8.5, 6.6.8.6,
6.6.8.7, 6.6.8.8, 6.6.8.9, 6.6.8.10, 6.6.9.1, 6.6.9.2, 6.6.9.3, 6.6.9.4, 6.6.9.5, 6.6.9.6,
6.6.9.7, 6.6.9.8, 6.6.9.9, 6.6.9.10, 6.6.10.1, 6.6.10.2, 6.6.10.3, 6.6.10.4, 6.6.10.5,
6.6.10.6, 6.6.10.7, 6.6.10.8, 6.6.10.9, 6.6.10.10, 6.7.1.1, 6.7.1.2, 6.7.1.3, 6.7.1.4, 6.7.1.5,
6.7.1.6, 6.7.1.7, 6.7.1.8, 6.7.1.9, 6.7.1.10, 6.7.2.1, 6.7.2.2, 6.7.2.3, 6.7.2.4, 6.7.2.5,
6.7.2.6, 6.7.2.7, 6.7.2.8, 6.7.2.9, 6.7.2.10, 6.7.3.1, 6.7.3.2, 6.7.3.3, 6.7.3.4, 6.7.3.5,
6.7.3.6, 6.7.3.7, 6.7.3.8, 6.7.3.9, 6.7.3.10, 6.7.4.1, 6.7.4.2, 6.7.4.3, 6.7.4.4, 6.7.4.5,
6.7.4.6, 6.7.4.7, 6.7.4.8, 6.7.4.9, 6.7.4.10, 6.7.5.1, 6.7.5.2, 6.7.5.3, 6.7.5.4, 6.7.5.5,
6.7.5.6, 6.7.5.7, 6.7.5.8, 6.7.5.9, 6.7.5.10, 6.7.6.1, 6.7.6.2, 6.7.6.3, 6.7.6.4, 6.7.6.5,
6.7.6.6, 6.7.6.7, 6.7.6.8, 6.7.6.9, 6.7.6.10, 6.7.7.1, 6.7.7.2, 6.7.7.3, 6.7.7.4, 6.7.7.5,
6.7.7.6, 6.7.7.7, 6.7.7.8, 6.7.7.9, 6.7.7.10, 6.7.8.1, 6.7.8.2, 6.7.8.3, 6.7.8.4, 6.7.8.5,
6.7.8.6, 6.7.8.7, 6.7.8.8, 6.7.8.9, 6.7.8.10, 6.7.9.1, 6.7.9.2, 6.7.9.3, 6.7.9.4, 6.7.9.5,
6.7.9.6, 6.7.9.7, 6.7.9.8, 6.7.9.9, 6.7.9.10, 6.7.10.1, 6.7.10.2, 6.7.10.3, 6.7.10.4, 6.7.10.5,
6.7.10.6, 6.7.10.7, 6.7.10.8, 6.7.10.9, 6.7.10.10, 6.8.1.1, 6.8.1.2, 6.8.1.3, 6.8.1.4, 6.8.1.5,
6.8.1.6, 6.8.1.7, 6.8.1.8, 6.8.1.9, 6.8.1.10, 6.8.2.1, 6.8.2.2, 6.8.2.3, 6.8.2.4, 6.8.2.5,
6.8.2.6, 6.8.2.7, 6.8.2.8, 6.8.2.9, 6.8.2.10, 6.8.3.1, 6.8.3.2, 6.8.3.3, 6.8.3.4, 6.8.3.5,
6.8.3.6, 6.8.3.7, 6.8.3.8, 6.8.3.9, 6.8.3.10, 6.8.4.1, 6.8.4.2, 6.8.4.3, 6.8.4.4, 6.8.4.5,
6.8.4.6, 6.8.4.7, 6.8.4.8, 6.8.4.9, 6.8.4.10, 6.8.5.1, 6.8.5.2, 6.8.5.3, 6.8.5.4, 6.8.5.5,
6.8.5.6, 6.8.5.7, 6.8.5.8, 6.8.5.9, 6.8.5.10, 6.8.6.1, 6.8.6.2, 6.8.6.3, 6.8.6.4, 6.8.6.5,
6.8.6.6, 6.8.6.7, 6.8.6.8, 6.8.6.9, 6.8.6.10, 6.8.7.1, 6.8.7.2, 6.8.7.3, 6.8.7.4, 6.8.7.5,
6.8.7.6, 6.8.7.7, 6.8.7.8, 6.8.7.9, 6.8.7.10, 6.8.8.1, 6.8.8.2, 6.8.8.3, 6.8.8.4, 6.8.8.5,
6.8.8.6, 6.8.8.7, 6.8.8.8, 6.8.8.9, 6.8.8.10, 6.8.9.1, 6.8.9.2, 6.8.9.3, 6.8.9.4, 6.8.9.5,
6.8.9.6, 6.8.9.7, 6.8.9.8, 6.8.9.9, 6.8.9.10, 6.8.10.1, 6.8.10.2, 6.8.10.3, 6.8.10.4, 6.8.10.5,
6.8.10.6, 6.8.10.7, 6.8.10.8, 6.8.10.9, 6.8.10.10, 6.9.1.1, 6.9.1.2, 6.9.1.3, 6.9.1.4, 6.9.1.5,
6.9.1.6, 6.9.1.7, 6.9.1.8, 6.9.1.9, 6.9.1.10, 6.9.2.1, 6.9.2.2, 6.9.2.3, 6.9.2.4, 6.9.2.5,
6.9.2.6, 6.9.2.7, 6.9.2.8, 6.9.2.9, 6.9.2.10, 6.9.3.1, 6.9.3.2, 6.9.3.3, 6.9.3.4, 6.9.3.5,
6.9.3.6, 6.9.3.7, 6.9.3.8, 6.9.3.9, 6.9.3.10, 6.9.4.1, 6.9.4.2, 6.9.4.3, 6.9.4.4, 6.9.4.5,
6.9.4.6, 6.9.4.7, 6.9.4.8, 6.9.4.9, 6.9.4.10, 6.9.5.1, 6.9.5.2, 6.9.5.3, 6.9.5.4, 6.9.5.5,
6.9.5.6, 6.9.5.7, 6.9.5.8, 6.9.5.9, 6.9.5.10, 6.9.6.1, 6.9.6.2, 6.9.6.3, 6.9.6.4, 6.9.6.5,
6.9.6.6, 6.9.6.7, 6.9.6.8, 6.9.6.9, 6.9.6.10, 6.9.7.1, 6.9.7.2, 6.9.7.3, 6.9.7.4, 6.9.7.5,
6.9.7.6, 6.9.7.7, 6.9.7.8, 6.9.7.9, 6.9.7.10, 6.9.8.1, 6.9.8.2, 6.9.8.3, 6.9.8.4, 6.9.8.5,
6.9.8.6, 6.9.8.7, 6.9.8.8, 6.9.8.9, 6.9.8.10, 6.9.9.1, 6.9.9.2, 6.9.9.3, 6.9.9.4, 6.9.9.5,
6.9.9.6, 6.9.9.7, 6.9.9.8, 6.9.9.9, 6.9.9.10, 6.9.10.1, 6.9.10.2, 6.9.10.3, 6.9.10.4, 6.9.10.5,
6.9.10.6, 6.9.10.7, 6.9.10.8, 6.9.10.9, 6.9.10.10, 6.10.1.1, 6.10.1.2, 6.10.1.3, 6.10.1.4,
6.10.1.5, 6.10.1.6, 6.10.1.7, 6.10.1.8, 6.10.1.9, 6.10.1.10, 6.10.2.1, 6.10.2.2, 6.10.2.3,
6.10.2.4, 6.10.2.5, 6.10.2.6, 6.10.2.7, 6.10.2.8, 6.10.2.9, 6.10.2.10, 6.10.3.1, 6.10.3.2,
6.10.3.3, 6.10.3.4, 6.10.3.5, 6.10.3.6, 6.10.3.7, 6.10.3.8, 6.10.3.9, 6.10.3.10, 6.10.4.1,
6.10.4.2, 6.10.4.3, 6.10.4.4, 6.10.4.5, 6.10.4.6, 6.10.4.7, 6.10.4.8, 6.10.4.9, 6.10.4.10,
6.10.5.1, 6.10.5.2, 6.10.5.3, 6.10.5.4, 6.10.5.5, 6.10.5.6, 6.10.5.7, 6.10.5.8, 6.10.5.9,
6.10.5.10, 6.10.6.1, 6.10.6.2, 6.10.6.3, 6.10.6.4, 6.10.6.5, 6.10.6.6, 6.10.6.7, 6.10.6.8,
6.10.6.9, 6.10.6.10, 6.10.7.1, 6.10.7.2, 6.10.7.3, 6.10.7.4, 6.10.7.5, 6.10.7.6, 6.10.7.7,
6.10.7.8, 6.10.7.9, 6.10.7.10, 6.10.8.1, 6.10.8.2, 6.10.8.3, 6.10.8.4, 6.10.8.5, 6.10.8.6,
6.10.8.7, 6.10.8.8, 6.10.8.9, 6.10.8.10, 6.10.9.1, 6.10.9.2, 6.10.9.3, 6.10.9.4, 6.10.9.5,
6.10.9.6, 6.10.9.7, 6.10.9.8, 6.10.9.9, 6.10.9.10, 6.10.10.1, 6.10.10.2, 6.10.10.3,
6.10.10.4, 6.10.10.5, 6.10.10.6, 6.10.10.7, 6.10.10.8, 6.10.10.9, 6.10.10.10, 7.1.1.1,
7.1.1.2, 7.1.1.3, 7.1.1.4, 7.1.1.5, 7.1.1.6, 7.1.1.7, 7.1.1.8, 7.1.1.9, 7.1.1.10, 7.1.2.1,
7.1.2.2, 7.1.2.3, 7.1.2.4, 7.1.2.5, 7.1.2.6, 7.1.2.7, 7.1.2.8, 7.1.2.9, 7.1.2.10, 7.1.3.1,
7.1.3.2, 7.1.3.3, 7.1.3.4, 7.1.3.5, 7.1.3.6, 7.1.3.7, 7.1.3.8, 7.1.3.9, 7.1.3.10, 7.1.4.1,
7.1.4.2, 7.1.4.3, 7.1.4.4, 7.1.4.5, 7.1.4.6, 7.1.4.7, 7.1.4.8, 7.1.4.9, 7.1.4.10, 7.1.5.1,
7.1.5.2, 7.1.5.3, 7.1.5.4, 7.1.5.5, 7.1.5.6, 7.1.5.7, 7.1.5.8, 7.1.5.9, 7.1.5.10, 7.1.6.1,
7.1.6.2, 7.1.6.3, 7.1.6.4, 7.1.6.5, 7.1.6.6, 7.1.6.7, 7.1.6.8, 7.1.6.9, 7.1.6.10, 7.1.7.1,
7.1.7.2, 7.1.7.3, 7.1.7.4, 7.1.7.5, 7.1.7.6, 7.1.7.7, 7.1.7.8, 7.1.7.9, 7.1.7.10, 7.1.8.1, TABLE B-continued 7.1.8.2, 7.1.8.3, 7.1.8.4, 7.1.8.5, 7.1.8.6, 7.1.8.7, 7.1.8.8, 7.1.8.9, 7.1.8.10, 7.1.9.1,
7.1.9.2, 7.1.9.3, 7.1.9.4, 7.1.9.5, 7.1.9.6, 7.1.9.7, 7.1.9.8, 7.1.9.9, 7.1.9.10, 7.1.10.1,
7.1.10.2, 7.1.10.3, 7.1.10.4, 7.1.10.5, 7.1.10.6, 7.1.10.7, 7.1.10.8, 7.1.10.9, 7.1.10.10,
7.2.1.1, 7.2.1.2, 7.2.1.3, 7.2.1.4, 7.2.1.5, 7.2.1.6, 7.2.1.7, 7.2.1.8, 7.2.1.9, 7.2.1.10,
7.2.2.1, 7.2.2.2, 7.2.2.3, 7.2.2.4, 7.2.2.5, 7.2.2.6, 7.2.2.7, 7.2.2.8, 7.2.2.9, 7.2.2.10,
7.2.3.1, 7.2.3.2, 7.2.3.3, 7.2.3.4, 7.2.3.5, 7.2.3.6, 7.2.3.7, 7.2.3.8, 7.2.3.9, 7.2.3.10,
7.2.4.1, 7.2.4.2, 7.2.4.3, 7.2.4.4, 7.2.4.5, 7.2.4.6, 7.2.4.7, 7.2.4.8, 7.2.4.9, 7.2.4.10,
7.2.5.1, 7.2.5.2, 7.2.5.3, 7.2.5.4, 7.2.5.5, 7.2.5.6, 7.2.5.7, 7.2.5.8, 7.2.5.9, 7.2.5.10,
7.2.6.1, 7.2.6.2, 7.2.6.3, 7.2.6.4, 7.2.6.5, 7.2.6.6, 7.2.6.7, 7.2.6.8, 7.2.6.9, 7.2.6.10,
7.2.7.1, 7.2.7.2, 7.2.7.3, 7.2.7.4, 7.2.7.5, 7.2.7.6, 7.2.7.7, 7.2.7.8, 7.2.7.9, 7.2.7.10,
7.2.8.1, 7.2.8.2, 7.2.8.3, 7.2.8.4, 7.2.8.5, 7.2.8.6, 7.2.8.7, 7.2.8.8, 7.2.8.9, 7.2.8.10,
7.2.9.1, 7.2.9.2, 7.2.9.3, 7.2.9.4, 7.2.9.5, 7.2.9.6, 7.2.9.7, 7.2.9.8, 7.2.9.9, 7.2.9.10,
7.2.10.1, 7.2.10.2, 7.2.10.3, 7.2.10.4, 7.2.10.5, 7.2.10.6, 7.2.10.7, 7.2.10.8, 7.2.10.9,
7.2.10.10, 7.3.1.1, 7.3.1.2, 7.3.1.3, 7.3.1.4, 7.3.1.5, 7.3.1.6, 7.3.1.7, 7.3.1.8, 7.3.1.9,
7.3.1.10, 7.3.2.1, 7.3.2.2, 7.3.2.3, 7.3.2.4, 7.3.2.5, 7.3.2.6, 7.3.2.7, 7.3.2.8, 7.3.2.9,
7.3.2.10, 7.3.3.1, 7.3.3.2, 7.3.3.3, 7.3.3.4, 7.3.3.5, 7.3.3.6, 7.3.3.7, 7.3.3.8, 7.3.3.9,
7.3.3.10, 7.3.4.1, 7.3.4.2, 7.3.4.3, 7.3.4.4, 7.3.4.5, 7.3.4.6, 7.3.4.7, 7.3.4.8, 7.3.4.9,
7.3.4.10, 7.3.5.1, 7.3.5.2, 7.3.5.3, 7.3.5.4, 7.3.5.5, 7.3.5.6, 7.3.5.7, 7.3.5.8, 7.3.5.9,
7.3.5.10, 7.3.6.1, 7.3.6.2, 7.3.6.3, 7.3.6.4, 7.3.6.5, 7.3.6.6, 7.3.6.7, 7.3.6.8, 7.3.6.9,
7.3.6.10, 7.3.7.1, 7.3.7.2, 7.3.7.3, 7.3.7.4, 7.3.7.5, 7.3.7.6, 7.3.7.7, 7.3.7.8, 7.3.7.9,
7.3.7.10, 7.3.8.1, 7.3.8.2, 7.3.8.3, 7.3.8.4, 7.3.8.5, 7.3.8.6, 7.3.8.7, 7.3.8.8, 7.3.8.9,
7.3.8.10, 7.3.9.1, 7.3.9.2, 7.3.9.3, 7.3.9.4, 7.3.9.5, 7.3.9.6, 7.3.9.7, 7.3.9.8, 7.3.9.9,
7.3.9.10, 7.3.10.1, 7.3.10.2, 7.3.10.3, 7.3.10.4, 7.3.10.5, 7.3.10.6, 7.3.10.7, 7.3.10.8,
7.3.10.9, 7.3.10.10, 7.4.1.1, 7.4.1.2, 7.4.1.3, 7.4.1.4, 7.4.1.5, 7.4.1.6, 7.4.1.7, 7.4.1.8,
7.4.1.9, 7.4.1.10, 7.4.2.1, 7.4.2.2, 7.4.2.3, 7.4.2.4, 7.4.2.5, 7.4.2.6, 7.4.2.7, 7.4.2.8,
7.4.2.9, 7.4.2.10, 7.4.3.1, 7.4.3.2, 7.4.3.3, 7.4.3.4, 7.4.3.5, 7.4.3.6, 7.4.3.7, 7.4.3.8,
7.4.3.9, 7.4.3.10, 7.4.4.1, 7.4.4.2, 7.4.4.3, 7.4.4.4, 7.4.4.5, 7.4.4.6, 7.4.4.7, 7.4.4.8,
7.4.4.9, 7.4.4.10, 7.4.5.1, 7.4.5.2, 7.4.5.3, 7.4.5.4, 7.4.5.5, 7.4.5.6, 7.4.5.7, 7.4.5.8,
7.4.5.9, 7.4.5.10, 7.4.6.1, 7.4.6.2, 7.4.6.3, 7.4.6.4, 7.4.6.5, 7.4.6.6, 7.4.6.7, 7.4.6.8,
7.4.6.9, 7.4.6.10, 7.4.7.1, 7.4.7.2, 7.4.7.3, 7.4.7.4, 7.4.7.5, 7.4.7.6, 7.4.7.7, 7.4.7.8,
7.4.7.9, 7.4.7.10, 7.4.8.1, 7.4.8.2, 7.4.8.3, 7.4.8.4, 7.4.8.5, 7.4.8.6, 7.4.8.7, 7.4.8.8,
7.4.8.9, 7.4.8.10, 7.4.9.1, 7.4.9.2, 7.4.9.3, 7.4.9.4, 7.4.9.5, 7.4.9.6, 7.4.9.7, 7.4.9.8,
7.4.9.9, 7.4.9.10, 7.4.10.1, 7.4.10.2, 7.4.10.3, 7.4.10.4, 7.4.10.5, 7.4.10.6, 7.4.10.7,
7.4.10.8, 7.4.10.9, 7.4.10.10, 7.5.1.1, 7.5.1.2, 7.5.1.3, 7.5.1.4, 7.5.1.5, 7.5.1.6, 7.5.1.7,
7.5.1.8, 7.5.1.9, 7.5.1.10, 7.5.2.1, 7.5.2.2, 7.5.2.3, 7.5.2.4, 7.5.2.5, 7.5.2.6, 7.5.2.7,
7.5.2.8, 7.5.2.9, 7.5.2.10, 7.5.3.1, 7.5.3.2, 7.5.3.3, 7.5.3.4, 7.5.3.5, 7.5.3.6, 7.5.3.7,
7.5.3.8, 7.5.3.9, 7.5.3.10, 7.5.4.1, 7.5.4.2, 7.5.4.3, 7.5.4.4, 7.5.4.5, 7.5.4.6, 7.5.4.7,
7.5.4.8, 7.5.4.9, 7.5.4.10, 7.5.5.1, 7.5.5.2, 7.5.5.3, 7.5.5.4, 7.5.5.5, 7.5.5.6, 7.5.5.7,
7.5.5.8, 7.5.5.9, 7.5.5.10, 7.5.6.1, 7.5.6.2, 7.5.6.3, 7.5.6.4, 7.5.6.5, 7.5.6.6, 7.5.6.7,
7.5.6.8, 7.5.6.9, 7.5.6.10, 7.5.7.1, 7.5.7.2, 7.5.7.3, 7.5.7.4, 7.5.7.5, 7.5.7.6, 7.5.7.7,
7.5.7.8, 7.5.7.9, 7.5.7.10, 7.5.8.1, 7.5.8.2, 7.5.8.3, 7.5.8.4, 7.5.8.5, 7.5.8.6, 7.5.8.7,
7.5.8.8, 7.5.8.9, 7.5.8.10, 7.5.9.1, 7.5.9.2, 7.5.9.3, 7.5.9.4, 7.5.9.5, 7.5.9.6, 7.5.9.7,
7.5.9.8, 7.5.9.9, 7.5.9.10, 7.5.10.1, 7.5.10.2, 7.5.10.3, 7.5.10.4, 7.5.10.5, 7.5.10.6,
7.5.10.7, 7.5.10.8, 7.5.10.9, 7.5.10.10, 7.6.1.1, 7.6.1.2, 7.6.1.3, 7.6.1.4, 7.6.1.5, 7.6.1.6,
7.6.1.7, 7.6.1.8, 7.6.1.9, 7.6.1.10, 7.6.2.1, 7.6.2.2, 7.6.2.3, 7.6.2.4, 7.6.2.5, 7.6.2.6,
7.6.2.7, 7.6.2.8, 7.6.2.9, 7.6.2.10, 7.6.3.1, 7.6.3.2, 7.6.3.3, 7.6.3.4, 7.6.3.5, 7.6.3.6,
7.6.3.7, 7.6.3.8, 7.6.3.9, 7.6.3.10, 7.6.4.1, 7.6.4.2, 7.6.4.3, 7.6.4.4, 7.6.4.5, 7.6.4.6,
7.6.4.7, 7.6.4.8, 7.6.4.9, 7.6.4.10, 7.6.5.1, 7.6.5.2, 7.6.5.3, 7.6.5.4, 7.6.5.5, 7.6.5.6,
7.6.5.7, 7.6.5.8, 7.6.5.9, 7.6.5.10, 7.6.6.1, 7.6.6.2, 7.6.6.3, 7.6.6.4, 7.6.6.5, 7.6.6.6,
7.6.6.7, 7.6.6.8, 7.6.6.9, 7.6.6.10, 7.6.7.1, 7.6.7.2, 7.6.7.3, 7.6.7.4, 7.6.7.5, 7.6.7.6,
7.6.7.7, 7.6.7.8, 7.6.7.9, 7.6.7.10, 7.6.8.1, 7.6.8.2, 7.6.8.3, 7.6.8.4, 7.6.8.5, 7.6.8.6,
7.6.8.7, 7.6.8.8, 7.6.8.9, 7.6.8.10, 7.6.9.1, 7.6.9.2, 7.6.9.3, 7.6.9.4, 7.6.9.5, 7.6.9.6,
7.6.9.7, 7.6.9.8, 7.6.9.9, 7.6.9.10, 7.6.10.1, 7.6.10.2, 7.6.10.3, 7.6.10.4, 7.6.10.5,
7.6.10.6, 7.6.10.7, 7.6.10.8, 7.6.10.9, 7.6.10.10, 7.7.1.1, 7.7.1.2, 7.7.1.3, 7.7.1.4, 7.7.1.5,
7.7.1.6, 7.7.1.7, 7.7.1.8, 7.7.1.9, 7.7.1.10, 7.7.2.1, 7.7.2.2, 7.7.2.3, 7.7.2.4, 7.7.2.5,
7.7.2.6, 7.7.2.7, 7.7.2.8, 7.7.2.9, 7.7.2.10, 7.7.3.1, 7.7.3.2, 7.7.3.3, 7.7.3.4, 7.7.3.5,
7.7.3.6, 7.7.3.7, 7.7.3.8, 7.7.3.9, 7.7.3.10, 7.7.4.1, 7.7.4.2, 7.7.4.3, 7.7.4.4, 7.7.4.5,
7.7.4.6, 7.7.4.7, 7.7.4.8, 7.7.4.9, 7.7.4.10, 7.7.5.1, 7.7.5.2, 7.7.5.3, 7.7.5.4, 7.7.5.5,
7.7.5.6, 7.7.5.7, 7.7.5.8, 7.7.5.9, 7.7.5.10, 7.7.6.1, 7.7.6.2, 7.7.6.3, 7.7.6.4, 7.7.6.5,
7.7.6.6, 7.7.6.7, 7.7.6.8, 7.7.6.9, 7.7.6.10, 7.7.7.1, 7.7.7.2, 7.7.7.3, 7.7.7.4, 7.7.7.5,
7.7.7.6, 7.7.7.7, 7.7.7.8, 7.7.7.9, 7.7.7.10, 7.7.8.1, 7.7.8.2, 7.7.8.3, 7.7.8.4, 7.7.8.5,
7.7.8.6, 7.7.8.7, 7.7.8.8, 7.7.8.9, 7.7.8.10, 7.7.9.1, 7.7.9.2, 7.7.9.3, 7.7.9.4, 7.7.9.5,
7.7.9.6, 7.7.9.7, 7.7.9.8, 7.7.9.9, 7.7.9.10, 7.7.10.1, 7.7.10.2, 7.7.10.3, 7.7.10.4, 7.7.10.5,
7.7.10.6, 7.7.10.7, 7.7.10.8, 7.7.10.9, 7.7.10.10, 7.8.1.1, 7.8.1.2, 7.8.1.3, 7.8.1.4, 7.8.1.5,
7.8.1.6, 7.8.1.7, 7.8.1.8, 7.8.1.9, 7.8.1.10, 7.8.2.1, 7.8.2.2, 7.8.2.3, 7.8.2.4, 7.8.2.5,
7.8.2.6, 7.8.2.7, 7.8.2.8, 7.8.2.9, 7.8.2.10, 7.8.3.1, 7.8.3.2, 7.8.3.3, 7.8.3.4, 7.8.3.5,
7.8.3.6, 7.8.3.7, 7.8.3.8, 7.8.3.9, 7.8.3.10, 7.8.4.1, 7.8.4.2, 7.8.4.3, 7.8.4.4, 7.8.4.5,
7.8.4.6, 7.8.4.7, 7.8.4.8, 7.8.4.9, 7.8.4.10, 7.8.5.1, 7.8.5.2, 7.8.5.3, 7.8.5.4, 7.8.5.5,
7.8.5.6, 7.8.5.7, 7.8.5.8, 7.8.5.9, 7.8.5.10, 7.8.6.1, 7.8.6.2, 7.8.6.3, 7.8.6.4, 7.8.6.5,
7.8.6.6, 7.8.6.7, 7.8.6.8, 7.8.6.9, 7.8.6.10, 7.8.7.1, 7.8.7.2, 7.8.7.3, 7.8.7.4, 7.8.7.5,
7.8.7.6, 7.8.7.7, 7.8.7.8, 7.8.7.9, 7.8.7.10, 7.8.8.1, 7.8.8.2, 7.8.8.3, 7.8.8.4, 7.8.8.5,
7.8.8.6, 7.8.8.7, 7.8.8.8, 7.8.8.9, 7.8.8.10, 7.8.9.1, 7.8.9.2, 7.8.9.3, 7.8.9.4, 7.8.9.5,
7.8.9.6, 7.8.9.7, 7.8.9.8, 7.8.9.9, 7.8.9.10, 7.8.10.1, 7.8.10.2, 7.8.10.3, 7.8.10.4, 7.8.10.5,
7.8.10.6, 7.8.10.7, 7.8.10.8, 7.8.10.9, 7.8.10.10, 7.9.1.1, 7.9.1.2, 7.9.1.3, 7.9.1.4, 7.9.1.5,
7.9.1.6, 7.9.1.7, 7.9.1.8, 7.9.1.9, 7.9.1.10, 7.9.2.1, 7.9.2.2, 7.9.2.3, 7.9.2.4, 7.9.2.5,
7.9.2.6, 7.9.2.7, 7.9.2.8, 7.9.2.9, 7.9.2.10, 7.9.3.1, 7.9.3.2, 7.9.3.3, 7.9.3.4, 7.9.3.5,
7.9.3.6, 7.9.3.7, 7.9.3.8, 7.9.3.9, 7.9.3.10, 7.9.4.1, 7.9.4.2, 7.9.4.3, 7.9.4.4, 7.9.4.5,
7.9.4.6, 7.9.4.7, 7.9.4.8, 7.9.4.9, 7.9.4.10, 7.9.5.1, 7.9.5.2, 7.9.5.3, 7.9.5.4, 7.9.5.5,
7.9.5.6, 7.9.5.7, 7.9.5.8, 7.9.5.9, 7.9.5.10, 7.9.6.1, 7.9.6.2, 7.9.6.3, 7.9.6.4, 7.9.6.5,
7.9.6.6, 7.9.6.7, 7.9.6.8, 7.9.6.9, 7.9.6.10, 7.9.7.1, 7.9.7.2, 7.9.7.3, 7.9.7.4, 7.9.7.5, TABLE B-continued 7.9.7.6, 7.9.7.7, 7.9.7.8, 7.9.7.9, 7.9.7.10, 7.9.8.1, 7.9.8.2, 7.9.8.3, 7.9.8.4, 7.9.8.5,
7.9.8.6, 7.9.8.7, 7.9.8.8, 7.9.8.9, 7.9.8.10, 7.9.9.1, 7.9.9.2, 7.9.9.3, 7.9.9.4, 7.9.9.5,
7.9.9.6, 7.9.9.7, 7.9.9.8, 7.9.9.9, 7.9.9.10, 7.9.10.1, 7.9.10.2, 7.9.10.3, 7.9.10.4, 7.9.10.5,
7.9.10.6, 7.9.10.7, 7.9.10.8, 7.9.10.9, 7.9.10.10, 7.10.1.1, 7.10.1.2, 7.10.1.3, 7.10.1.4,
7.10.1.5, 7.10.1.6, 7.10.1.7, 7.10.1.8, 7.10.1.9, 7.10.1.10, 7.10.2.1, 7.10.2.2, 7.10.2.3,
7.10.2.4, 7.10.2.5, 7.10.2.6, 7.10.2.7, 7.10.2.8, 7.10.2.9, 7.10.2.10, 7.10.3.1, 7.10.3.2,
7.10.3.3, 7.10.3.4, 7.10.3.5, 7.10.3.6, 7.10.3.7, 7.10.3.8, 7.10.3.9, 7.10.3.10, 7.10.4.1,
7.10.4.2, 7.10.4.3, 7.10.4.4, 7.10.4.5, 7.10.4.6, 7.10.4.7, 7.10.4.8, 7.10.4.9, 7.10.4.10,
7.10.5.1, 7.10.5.2, 7.10.5.3, 7.10.5.4, 7.10.5.5, 7.10.5.6, 7.10.5.7, 7.10.5.8, 7.10.5.9,
7.10.5.10, 7.10.6.1, 7.10.6.2, 7.10.6.3, 7.10.6.4, 7.10.6.5, 7.10.6.6, 7.10.6.7, 7.10.6.8,
7.10.6.9, 7.10.6.10, 7.10.7.1, 7.10.7.2, 7.10.7.3, 7.10.7.4, 7.10.7.5, 7.10.7.6, 7.10.7.7,
7.10.7.8, 7.10.7.9, 7.10.7.10, 7.10.8.1, 7.10.8.2, 7.10.8.3, 7.10.8.4, 7.10.8.5, 7.10.8.6,
7.10.8.7, 7.10.8.8, 7.10.8.9, 7.10.8.10, 7.10.9.1, 7.10.9.2, 7.10.9.3, 7.10.9.4, 7.10.9.5,
7.10.9.6, 7.10.9.7, 7.10.9.8, 7.10.9.9, 7.10.9.10, 7.10.10.1, 7.10.10.2, 7.10.10.3,
7.10.10.4, 7.10.10.5, 7.10.10.6, 7.10.10.7, 7.10.10.8, 7.10.10.9, 7.10.10.10, 8.1.1.1,
8.1.1.2, 8.1.1.3, 8.1.1.4, 8.1.1.5, 8.1.1.6, 8.1.1.7, 8.1.1.8, 8.1.1.9, 8.1.1.10, 8.1.2.1,
8.1.2.2, 8.1.2.3, 8.1.2.4, 8.1.2.5, 8.1.2.6, 8.1.2.7, 8.1.2.8, 8.1.2.9, 8.1.2.10, 8.1.3.1,
8.1.3.2, 8.1.3.3, 8.1.3.4, 8.1.3.5, 8.1.3.6, 8.1.3.7, 8.1.3.8, 8.1.3.9, 8.1.3.10, 8.1.4.1,
8.1.4.2, 8.1.4.3, 8.1.4.4, 8.1.4.5, 8.1.4.6, 8.1.4.7, 8.1.4.8, 8.1.4.9, 8.1.4.10, 8.1.5.1,
8.1.5.2, 8.1.5.3, 8.1.5.4, 8.1.5.5, 8.1.5.6, 8.1.5.7, 8.1.5.8, 8.1.5.9, 8.1.5.10, 8.1.6.1,
8.1.6.2, 8.1.6.3, 8.1.6.4, 8.1.6.5, 8.1.6.6, 8.1.6.7, 8.1.6.8, 8.1.6.9, 8.1.6.10, 8.1.7.1,
8.1.7.2, 8.1.7.3, 8.1.7.4, 8.1.7.5, 8.1.7.6, 8.1.7.7, 8.1.7.8, 8.1.7.9, 8.1.7.10, 8.1.8.1,
8.1.8.2, 8.1.8.3, 8.1.8.4, 8.1.8.5, 8.1.8.6, 8.1.8.7, 8.1.8.8, 8.1.8.9, 8.1.8.10, 8.1.9.1,
8.1.9.2, 8.1.9.3, 8.1.9.4, 8.1.9.5, 8.1.9.6, 8.1.9.7, 8.1.9.8, 8.1.9.9, 8.1.9.10, 8.1.10.1,
8.1.10.2, 8.1.10.3, 8.1.10.4, 8.1.10.5, 8.1.10.6, 8.1.10.7, 8.1.10.8, 8.1.10.9, 8.1.10.10,
8.2.1.1, 8.2.1.2, 8.2.1.3, 8.2.1.4, 8.2.1.5, 8.2.1.6, 8.2.1.7, 8.2.1.8, 8.2.1.9, 8.2.1.10,
8.2.2.1, 8.2.2.2, 8.2.2.3, 8.2.2.4, 8.2.2.5, 8.2.2.6, 8.2.2.7, 8.2.2.8, 8.2.2.9, 8.2.2.10,
8.2.3.1, 8.2.3.2, 8.2.3.3, 8.2.3.4, 8.2.3.5, 8.2.3.6, 8.2.3.7, 8.2.3.8, 8.2.3.9, 8.2.3.10,
8.2.4.1, 8.2.4.2, 8.2.4.3, 8.2.4.4, 8.2.4.5, 8.2.4.6, 8.2.4.7, 8.2.4.8, 8.2.4.9, 8.2.4.10,
8.2.5.1, 8.2.5.2, 8.2.5.3, 8.2.5.4, 8.2.5.5, 8.2.5.6, 8.2.5.7, 8.2.5.8, 8.2.5.9, 8.2.5.10,
8.2.6.1, 8.2.6.2, 8.2.6.3, 8.2.6.4, 8.2.6.5, 8.2.6.6, 8.2.6.7, 8.2.6.8, 8.2.6.9, 8.2.6.10,
8.2.7.1, 8.2.7.2, 8.2.7.3, 8.2.7.4, 8.2.7.5, 8.2.7.6, 8.2.7.7, 8.2.7.8, 8.2.7.9, 8.2.7.10,
8.2.8.1, 8.2.8.2, 8.2.8.3, 8.2.8.4, 8.2.8.5, 8.2.8.6, 8.2.8.7, 8.2.8.8, 8.2.8.9, 8.2.8.10,
8.2.9.1, 8.2.9.2, 8.2.9.3, 8.2.9.4, 8.2.9.5, 8.2.9.6, 8.2.9.7, 8.2.9.8, 8.2.9.9, 8.2.9.10,
8.2.10.1, 8.2.10.2, 8.2.10.3, 8.2.10.4, 8.2.10.5, 8.2.10.6, 8.2.10.7, 8.2.10.8, 8.2.10.9,
8.2.10.10, 8.3.1.1, 8.3.1.2, 8.3.1.3, 8.3.1.4, 8.3.1.5, 8.3.1.6, 8.3.1.7, 8.3.1.8, 8.3.1.9,
8.3.1.10, 8.3.2.1, 8.3.2.2, 8.3.2.3, 8.3.2.4, 8.3.2.5, 8.3.2.6, 8.3.2.7, 8.3.2.8, 8.3.2.9,
8.3.2.10, 8.3.3.1, 8.3.3.2, 8.3.3.3, 8.3.3.4, 8.3.3.5, 8.3.3.6, 8.3.3.7, 8.3.3.8, 8.3.3.9,
8.3.3.10, 8.3.4.1, 8.3.4.2, 8.3.4.3, 8.3.4.4, 8.3.4.5, 8.3.4.6, 8.3.4.7, 8.3.4.8, 8.3.4.9,
8.3.4.10, 8.3.5.1, 8.3.5.2, 8.3.5.3, 8.3.5.4, 8.3.5.5, 8.3.5.6, 8.3.5.7, 8.3.5.8, 8.3.5.9,
8.3.5.10, 8.3.6.1, 8.3.6.2, 8.3.6.3, 8.3.6.4, 8.3.6.5, 8.3.6.6, 8.3.6.7, 8.3.6.8, 8.3.6.9,
8.3.6.10, 8.3.7.1, 8.3.7.2, 8.3.7.3, 8.3.7.4, 8.3.7.5, 8.3.7.6, 8.3.7.7, 8.3.7.8, 8.3.7.9,
8.3.7.10, 8.3.8.1, 8.3.8.2, 8.3.8.3, 8.3.8.4, 8.3.8.5, 8.3.8.6, 8.3.8.7, 8.3.8.8, 8.3.8.9,
8.3.8.10, 8.3.9.1, 8.3.9.2, 8.3.9.3, 8.3.9.4, 8.3.9.5, 8.3.9.6, 8.3.9.7, 8.3.9.8, 8.3.9.9,
8.3.9.10, 8.3.10.1, 8.3.10.2, 8.3.10.3, 8.3.10.4, 8.3.10.5, 8.3.10.6, 8.3.10.7, 8.3.10.8,
8.3.10.9, 8.3.10.10, 8.4.1.1, 8.4.1.2, 8.4.1.3, 8.4.1.4, 8.4.1.5, 8.4.1.6, 8.4.1.7, 8.4.1.8,
8.4.1.9, 8.4.1.10, 8.4.2.1, 8.4.2.2, 8.4.2.3, 8.4.2.4, 8.4.2.5, 8.4.2.6, 8.4.2.7, 8.4.2.8,
8.4.2.9, 8.4.2.10, 8.4.3.1, 8.4.3.2, 8.4.3.3, 8.4.3.4, 8.4.3.5, 8.4.3.6, 8.4.3.7, 8.4.3.8,
8.4.3.9, 8.4.3.10, 8.4.4.1, 8.4.4.2, 8.4.4.3, 8.4.4.4, 8.4.4.5, 8.4.4.6, 8.4.4.7, 8.4.4.8,
8.4.4.9, 8.4.4.10, 8.4.5.1, 8.4.5.2, 8.4.5.3, 8.4.5.4, 8.4.5.5, 8.4.5.6, 8.4.5.7, 8.4.5.8,
8.4.5.9, 8.4.5.10, 8.4.6.1, 8.4.6.2, 8.4.6.3, 8.4.6.4, 8.4.6.5, 8.4.6.6, 8.4.6.7, 8.4.6.8,
8.4.6.9, 8.4.6.10, 8.4.7.1, 8.4.7.2, 8.4.7.3, 8.4.7.4, 8.4.7.5, 8.4.7.6, 8.4.7.7, 8.4.7.8,
8.4.7.9, 8.4.7.10, 8.4.8.1, 8.4.8.2, 8.4.8.3, 8.4.8.4, 8.4.8.5, 8.4.8.6, 8.4.8.7, 8.4.8.8,
8.4.8.9, 8.4.8.10, 8.4.9.1, 8.4.9.2, 8.4.9.3, 8.4.9.4, 8.4.9.5, 8.4.9.6, 8.4.9.7, 8.4.9.8,
8.4.9.9, 8.4.9.10, 8.4.10.1, 8.4.10.2, 8.4.10.3, 8.4.10.4, 8.4.10.5, 8.4.10.6, 8.4.10.7,
8.4.10.8, 8.4.10.9, 8.4.10.10, 8.5.1.1, 8.5.1.2, 8.5.1.3, 8.5.1.4, 8.5.1.5, 8.5.1.6, 8.5.1.7,
8.5.1.8, 8.5.1.9, 8.5.1.10, 8.5.2.1, 8.5.2.2, 8.5.2.3, 8.5.2.4, 8.5.2.5, 8.5.2.6, 8.5.2.7,
8.5.2.8, 8.5.2.9, 8.5.2.10, 8.5.3.1, 8.5.3.2, 8.5.3.3, 8.5.3.4, 8.5.3.5, 8.5.3.6, 8.5.3.7,
8.5.3.8, 8.5.3.9, 8.5.3.10, 8.5.4.1, 8.5.4.2, 8.5.4.3, 8.5.4.4, 8.5.4.5, 8.5.4.6, 8.5.4.7,
8.5.4.8, 8.5.4.9, 8.5.4.10, 8.5.5.1, 8.5.5.2, 8.5.5.3, 8.5.5.4, 8.5.5.5, 8.5.5.6, 8.5.5.7,
8.5.5.8, 8.5.5.9, 8.5.5.10, 8.5.6.1, 8.5.6.2, 8.5.6.3, 8.5.6.4, 8.5.6.5, 8.5.6.6, 8.5.6.7,
8.5.6.8, 8.5.6.9, 8.5.6.10, 8.5.7.1, 8.5.7.2, 8.5.7.3, 8.5.7.4, 8.5.7.5, 8.5.7.6, 8.5.7.7,
8.5.7.8, 8.5.7.9, 8.5.7.10, 8.5.8.1, 8.5.8.2, 8.5.8.3, 8.5.8.4, 8.5.8.5, 8.5.8.6, 8.5.8.7,
8.5.8.8, 8.5.8.9, 8.5.8.10, 8.5.9.1, 8.5.9.2, 8.5.9.3, 8.5.9.4, 8.5.9.5, 8.5.9.6, 8.5.9.7,
8.5.9.8, 8.5.9.9, 8.5.9.10, 8.5.10.1, 8.5.10.2, 8.5.10.3, 8.5.10.4, 8.5.10.5, 8.5.10.6,
8.5.10.7, 8.5.10.8, 8.5.10.9, 8.5.10.10, 8.6.1.1, 8.6.1.2, 8.6.1.3, 8.6.1.4, 8.6.1.5, 8.6.1.6,
8.6.1.7, 8.6.1.8, 8.6.1.9, 8.6.1.10, 8.6.2.1, 8.6.2.2, 8.6.2.3, 8.6.2.4, 8.6.2.5, 8.6.2.6,
8.6.2.7, 8.6.2.8, 8.6.2.9, 8.6.2.10, 8.6.3.1, 8.6.3.2, 8.6.3.3, 8.6.3.4, 8.6.3.5, 8.6.3.6,
8.6.3.7, 8.6.3.8, 8.6.3.9, 8.6.3.10, 8.6.4.1, 8.6.4.2, 8.6.4.3, 8.6.4.4, 8.6.4.5, 8.6.4.6,
8.6.4.7, 8.6.4.8, 8.6.4.9, 8.6.4.10, 8.6.5.1, 8.6.5.2, 8.6.5.3, 8.6.5.4, 8.6.5.5, 8.6.5.6,
8.6.5.7, 8.6.5.8, 8.6.5.9, 8.6.5.10, 8.6.6.1, 8.6.6.2, 8.6.6.3, 8.6.6.4, 8.6.6.5, 8.6.6.6,
8.6.6.7, 8.6.6.8, 8.6.6.9, 8.6.6.10, 8.6.7.1, 8.6.7.2, 8.6.7.3, 8.6.7.4, 8.6.7.5, 8.6.7.6,
8.6.7.7, 8.6.7.8, 8.6.7.9, 8.6.7.10, 8.6.8.1, 8.6.8.2, 8.6.8.3, 8.6.8.4, 8.6.8.5, 8.6.8.6,
8.6.8.7, 8.6.8.8, 8.6.8.9, 8.6.8.10, 8.6.9.1, 8.6.9.2, 8.6.9.3, 8.6.9.4, 8.6.9.5, 8.6.9.6,
8.6.9.7, 8.6.9.8, 8.6.9.9, 8.6.9.10, 8.6.10.1, 8.6.10.2, 8.6.10.3, 8.6.10.4, 8.6.10.5,
8.6.10.6, 8.6.10.7, 8.6.10.8, 8.6.10.9, 8.6.10.10, 8.7.1.1, 8.7.1.2, 8.7.1.3, 8.7.1.4, 8.7.1.5,
8.7.1.6, 8.7.1.7, 8.7.1.8, 8.7.1.9, 8.7.1.10, 8.7.2.1, 8.7.2.2, 8.7.2.3, 8.7.2.4, 8.7.2.5,
8.7.2.6, 8.7.2.7, 8.7.2.8, 8.7.2.9, 8.7.2.10, 8.7.3.1, 8.7.3.2, 8.7.3.3, 8.7.3.4, 8.7.3.5,
8.7.3.6, 8.7.3.7, 8.7.3.8, 8.7.3.9, 8.7.3.10, 8.7.4.1, 8.7.4.2, 8.7.4.3, 8.7.4.4, 8.7.4.5,
8.7.4.6, 8.7.4.7, 8.7.4.8, 8.7.4.9, 8.7.4.10, 8.7.5.1, 8.7.5.2, 8.7.5.3, 8.7.5.4, 8.7.5.5, TABLE B-continued 8.7.5.6, 8.7.5.7, 8.7.5.8, 8.7.5.9, 8.7.5.10, 8.7.6.1, 8.7.6.2, 8.7.6.3, 8.7.6.4, 8.7.6.5, 8.7.6.6, 8.7.6.7, 8.7.6.8, 8.7.6.9, 8.7.6.10, 8.7.7.1, 8.7.7.2, 8.7.7.3, 8.7.7.4, 8.7.7.5, 8.7.7.6, 8.7.7.7, 8.7.7.8, 8.7.7.9, 8.7.7.10, 8.7.8.1, 8.7.8.2, 8.7.8.3, 8.7.8.4, 8.7.8.5, 8.7.8.6, 8.7.8.7, 8.7.8.8, 8.7.8.9, 8.7.8.10, 8.7.9.1, 8.7.9.2, 8.7.9.3, 8.7.9.4, 8.7.9.5, 8.7.9.6, 8.7.9.7, 8.7.9.8, 8.7.9.9, 8.7.9.10, 8.7.10.1, 8.7.10.2, 8.7.10.3, 8.7.10.4, 8.7.10.5, 8.7.10.6, 8.7.10.7, 8.7.10.8, 8.7.10.9, 8.7.10.10, 8.8.1.1, 8.8.1.2, 8.8.1.3, 8.8.1.4, 8.8.1.5, 8.8.1.6, 8.8.1.7, 8.8.1.8, 8.8.1.9, 8.8.1.10, 8.8.2.1, 8.8.2.2, 8.8.2.3, 8.8.2.4, 8.8.2.5, 8.8.2.6, 8.8.2.7, 8.8.2.8, 8.8.2.9, 8.8.2.10, 8.8.3.1, 8.8.3.2, 8.8.3.3, 8.8.3.4, 8.8.3.5, 8.8.3.6, 8.8.3.7, 8.8.3.8, 8.8.3.9, 8.8.3.10, 8.8.4.1, 8.8.4.2, 8.8.4.3, 8.8.4.4, 8.8.4.5, 8.8.4.6, 8.8.4.7, 8.8.4.8, 8.8.4.9, 8.8.4.10, 8.8.5.1, 8.8.5.2, 8.8.5.3, 8.8.5.4, 8.8.5.5, 8.8.5.6, 8.8.5.7, 8.8.5.8, 8.8.5.9, 8.8.5.10, 8.8.6.1, 8.8.6.2, 8.8.6.3, 8.8.6.4, 8.8.6.5, 8.8.6.6, 8.8.6.7, 8.8.6.8, 8.8.6.9, 8.8.6.10, 8.8.7.1, 8.8.7.2, 8.8.7.3, 8.8.7.4, 8.8.7.5, 8.8.7.6, 8.8.7.7, 8.8.7.8, 8.8.7.9, 8.8.7.10, 8.8.8.1, 8.8.8.2, 8.8.8.3, 8.8.8.4, 8.8.8.5, 8.8.8.6, 8.8.8.7, 8.8.8.8, 8.8.8.9, 8.8.8.10, 8.8.9.1, 8.8.9.2, 8.8.9.3, 8.8.9.4, 8.8.9.5, 8.8.9.6, 8.8.9.7, 8.8.9.8, 8.8.9.9, 8.8.9.10, 8.8.10.1, 8.8.10.2, 8.8.10.3, 8.8.10.4, 8.8.10.5, 8.8.10.6, 8.8.10.7, 8.8.10.8, 8.8.10.9, 8.8.10.10, 8.9.1.1, 8.9.1.2, 8.9.1.3, 8.9.1.4, 8.9.1.5, 8.9.1.6, 8.9.1.7, 8.9.1.8, 8.9.1.9, 8.9.1.10, 8.9.2.1, 8.9.2.2, 8.9.2.3, 8.9.2.4, 8.9.2.5, 8.9.2.6, 8.9.2.7, 8.9.2.8, 8.9.2.9, 8.9.2.10, 8.9.3.1, 8.9.3.2, 8.9.3.3, 8.9.3.4, 8.9.3.5, 8.9.3.6, 8.9.3.7, 8.9.3.8, 8.9.3.9, 8.9.3.10, 8.9.4.1, 8.9.4.2, 8.9.4.3, 8.9.4.4, 8.9.4.5, 8.9.4.6, 8.9.4.7, 8.9.4.8, 8.9.4.9, 8.9.4.10, 8.9.5.1, 8.9.5.2, 8.9.5.3, 8.9.5.4, 8.9.5.5, 8.9.5.6, 8.9.5.7, 8.9.5.8, 8.9.5.9, 8.9.5.10, 8.9.6.1, 8.9.6.2, 8.9.6.3, 8.9.6.4, 8.9.6.5, 8.9.6.6, 8.9.6.7, 8.9.6.8, 8.9.6.9, 8.9.6.10, 8.9.7.1, 8.9.7.2, 8.9.7.3, 8.9.7.4, 8.9.7.5, 8.9.7.6, 8.9.7.7, 8.9.7.8, 8.9.7.9, 8.9.7.10, 8.9.8.1, 8.9.8.2, 8.9.8.3, 8.9.8.4, 8.9.8.5, 8.9.8.6, 8.9.8.7, 8.9.8.8, 8.9.8.9, 8.9.8.10, 8.9.9.1, 8.9.9.2, 8.9.9.3, 8.9.9.4, 8.9.9.5, 8.9.9.6, 8.9.9.7, 8.9.9.8, 8.9.9.9, 8.9.9.10, 8.9.10.1, 8.9.10.2, 8.9.10.3, 8.9.10.4, 8.9.10.5, 8.9.10.6, 8.9.10.7, 8.9.10.8, 8.9.10.9, 8.9.10.10, 8.10.1.1, 8.10.1.2, 8.10.1.3, 8.10.1.4, 8.10.1.5, 8.10.1.6, 8.10.1.7, 8.10.1.8, 8.10.1.9, 8.10.1.10, 8.10.2.1, 8.10.2.2, 8.10.2.3, 8.10.2.4, 8.10.2.5, 8.10.2.6, 8.10.2.7, 8.10.2.8, 8.10.2.9, 8.10.2.10, 8.10.3.1, 8.10.3.2, 8.10.3.3, 8.10.3.4, 8.10.3.5, 8.10.3.6, 8.10.3.7, 8.10.3.8, 8.10.3.9, 8.10.3.10, 8.10.4.1, 8.10.4.2, 8.10.4.3, 8.10.4.4, 8.10.4.5, 8.10.4.6, 8.10.4.7, 8.10.4.8, 8.10.4.9, 8.10.4.10, 8.10.5.1, 8.10.5.2, 8.10.5.3, 8.10.5.4, 8.10.5.5, 8.10.5.6, 8.10.5.7, 8.10.5.8, 8.10.5.9, 8.10.5.10, 8.10.6.1, 8.10.6.2, 8.10.6.3, 8.10.6.4, 8.10.6.5, 8.10.6.6, 8.10.6.7, 8.10.6.8, 8.10.6.9, 8.10.6.10, 8.10.7.1, 8.10.7.2, 8.10.7.3, 8.10.7.4, 8.10.7.5, 8.10.7.6, 8.10.7.7, 8.10.7.8, 8.10.7.9, 8.10.7.10, 8.10.8.1, 8.10.8.2, 8.10.8.3, 8.10.8.4, 8.10.8.5, 8.10.8.6, 8.10.8.7, 8.10.8.8, 8.10.8.9, 8.10.8.10, 8.10.9.1, 8.10.9.2, 8.10.9.3, 8.10.9.4, 8.10.9.5, 8.10.9.6, 8.10.9.7, 8.10.9.8, 8.10.9.9, 8.10.9.10, 8.10.10.1, 8.10.10.2, 8.10.10.3, 8.10.10.4, 8.10.10.5, 8.10.10.6, 8.10.10.7, 8.10.10.8, 8.10.10.9, 8.10.10.10, 9.1.1.1, 9.1.1.2, 9.1.1.3, 9.1.1.4, 9.1.1.5, 9.1.1.6, 9.1.1.7, 9.1.1.8, 9.1.1.9, 9.1.1.10, 9.1.2.1, 9.1.2.2, 9.1.2.3, 9.1.2.4, 9.1.2.5, 9.1.2.6, 9.1.2.7, 9.1.2.8, 9.1.2.9, 9.1.2.10, 9.1.3.1, 9.1.3.2, 9.1.3.3, 9.1.3.4, 9.1.3.5, 9.1.3.6, 9.1.3.7, 9.1.3.8, 9.1.3.9, 9.1.3.10, 9.1.4.1, 9.1.4.2, 9.1.4.3, 9.1.4.4, 9.1.4.5, 9.1.4.6, 9.1.4.7, 9.1.4.8, 9.1.4.9, 9.1.4.10, 9.1.5.1, 9.1.5.2, 9.1.5.3, 9.1.5.4, 9.1.5.5, 9.1.5.6, 9.1.5.7, 9.1.5.8, 9.1.5.9, 9.1.5.10, 9.1.6.1, 9.1.6.2, 9.1.6.3, 9.1.6.4, 9.1.6.5, 9.1.6.6, 9.1.6.7, 9.1.6.8, 9.1.6.9, 9.1.6.10, 9.1.7.1, 9.1.7.2, 9.1.7.3, 9.1.7.4, 9.1.7.5, 9.1.7.6, 9.1.7.7, 9.1.7.8, 9.1.7.9, 9.1.7.10, 9.1.8.1, 9.1.8.2, 9.1.8.3, 9.1.8.4, 9.1.8.5, 9.1.8.6, 9.1.8.7, 9.1.8.8, 9.1.8.9, 9.1.8.10, 9.1.9.1, 9.1.9.2, 9.1.9.3, 9.1.9.4, 9.1.9.5, 9.1.9.6, 9.1.9.7, 9.1.9.8, 9.1.9.9, 9.1.9.10, 9.1.10.1, 9.1.10.2, 9.1.10.3, 9.1.10.4, 9.1.10.5, 9.1.10.6, 9.1.10.7, 9.1.10.8, 9.1.10.9, 9.1.10.10, 9.2.1.1, 9.2.1.2, 9.2.1.3, 9.2.1.4, 9.2.1.5, 9.2.1.6, 9.2.1.7, 9.2.1.8, 9.2.1.9, 9.2.1.10, 9.2.2.1, 9.2.2.2, 9.2.2.3, 9.2.2.4, 9.2.2.5, 9.2.2.6, 9.2.2.7, 9.2.2.8, 9.2.2.9, 9.2.2.10, 9.2.3.1, 9.2.3.2, 9.2.3.3, 9.2.3.4, 9.2.3.5, 9.2.3.6, 9.2.3.7, 9.2.3.8, 9.2.3.9, 9.2.3.10, 9.2.4.1, 9.2.4.2, 9.2.4.3, 9.2.4.4, 9.2.4.5, 9.2.4.6, 9.2.4.7, 9.2.4.8, 9.2.4.9, 9.2.4.10, 9.2.5.1, 9.2.5.2, 9.2.5.3, 9.2.5.4, 9.2.5.5, 9.2.5.6, 9.2.5.7, 9.2.5.8, 9.2.5.9, 9.2.5.10, 9.2.6.1, 9.2.6.2, 9.2.6.3, 9.2.6.4, 9.2.6.5, 9.2.6.6, 9.2.6.7, 9.2.6.8, 9.2.6.9, 9.2.6.10, 9.2.7.1, 9.2.7.2, 9.2.7.3, 9.2.7.4, 9.2.7.5, 9.2.7.6, 9.2.7.7, 9.2.7.8, 9.2.7.9, 9.2.7.10, 9.2.8.1, 9.2.8.2, 9.2.8.3, 9.2.8.4, 9.2.8.5, 9.2.8.6, 9.2.8.7, 9.2.8.8, 9.2.8.9, 9.2.8.10, 9.2.9.1, 9.2.9.2, 9.2.9.3, 9.2.9.4, 9.2.9.5, 9.2.9.6, 9.2.9.7, 9.2.9.8, 9.2.9.9, 9.2.9.10, 9.2.10.1, 9.2.10.2, 9.2.10.3, 9.2.10.4, 9.2.10.5, 9.2.10.6, 9.2.10.7, 9.2.10.8, 9.2.10.9, 9.2.10.10, 9.3.1.1, 9.3.1.2, 9.3.1.3, 9.3.1.4, 9.3.1.5, 9.3.1.6, 9.3.1.7, 9.3.1.8, 9.3.1.9, 9.3.1.10, 9.3.2.1, 9.3.2.2, 9.3.2.3, 9.3.2.4, 9.3.2.5, 9.3.2.6, 9.3.2.7, 9.3.2.8, 9.3.2.9, 9.3.2.10, 9.3.3.1, 9.3.3.2, 9.3.3.3, 9.3.3.4, 9.3.3.5, 9.3.3.6, 9.3.3.7, 9.3.3.8, 9.3.3.9, 9.3.3.10, 9.3.4.1, 9.3.4.2, 9.3.4.3, 9.3.4.4, 9.3.4.5, 9.3.4.6, 9.3.4.7, 9.3.4.8, 9.3.4.9, 9.3.4.10, 9.3.5.1, 9.3.5.2, 9.3.5.3, 9.3.5.4, 9.3.5.5, 9.3.5.6, 9.3.5.7, 9.3.5.8, 9.3.5.9, 9.3.5.10, 9.3.6.1, 9.3.6.2, 9.3.6.3, 9.3.6.4, 9.3.6.5, 9.3.6.6, 9.3.6.7, 9.3.6.8, 9.3.6.9, 9.3.6.10, 9.3.7.1, 9.3.7.2, 9.3.7.3, 9.3.7.4, 9.3.7.5, 9.3.7.6, 9.3.7.7, 9.3.7.8, 9.3.7.9, 9.3.7.10, 9.3.8.1, 9.3.8.2, 9.3.8.3, 9.3.8.4, 9.3.8.5, 9.3.8.6, 9.3.8.7, 9.3.8.8, 9.3.8.9, 9.3.8.10, 9.3.9.1, 9.3.9.2, 9.3.9.3, 9.3.9.4, 9.3.9.5, 9.3.9.6, 9.3.9.7, 9.3.9.8, 9.3.9.9, 9.3.9.10, 9.3.10.1, 9.3.10.2, 9.3.10.3, 9.3.10.4, 9.3.10.5, 9.3.10.6, 9.3.10.7, 9.3.10.8, 9.3.10.9, 9.3.10.10, 9.4.1.1, 9.4.1.2, 9.4.1.3, 9.4.1.4, 9.4.1.5, 9.4.1.6, 9.4.1.7, 9.4.1.8, 9.4.1.9, 9.4.1.10, 9.4.2.1, 9.4.2.2, 9.4.2.3, 9.4.2.4, 9.4.2.5, 9.4.2.6, 9.4.2.7, 9.4.2.8, 9.4.2.9, 9.4.2.10, 9.4.3.1, 9.4.3.2, 9.4.3.3, 9.4.3.4, 9.4.3.5, 9.4.3.6, 9.4.3.7, 9.4.3.8, 9.4.3.9, 9.4.3.10, 9.4.4.1, 9.4.4.2, 9.4.4.3, 9.4.4.4, 9.4.4.5, 9.4.4.6, 9.4.4.7, 9.4.4.8, 9.4.4.9, 9.4.4.10, 9.4.5.1, 9.4.5.2, 9.4.5.3, 9.4.5.4, 9.4.5.5, 9.4.5.6, 9.4.5.7, 9.4.5.8, 9.4.5.9, 9.4.5.10, 9.4.6.1, 9.4.6.2, 9.4.6.3, 9.4.6.4, 9.4.6.5, 9.4.6.6, 9.4.6.7, 9.4.6.8, 9.4.6.9, 9.4.6.10, 9.4.7.1, 9.4.7.2, 9.4.7.3, 9.4.7.4, 9.4.7.5, 9.4.7.6, 9.4.7.7, 9.4.7.8, 9.4.7.9, 9.4.7.10, 9.4.8.1, 9.4.8.2, 9.4.8.3, 9.4.8.4, 9.4.8.5, 9.4.8.6, 9.4.8.7, 9.4.8.8, 9.4.8.9, 9.4.8.10, 9.4.9.1, 9.4.9.2, 9.4.9.3, 9.4.9.4, 9.4.9.5, 9.4.9.6, 9.4.9.7, 9.4.9.8, 9.4.9.9, 9.4.9.10, 9.4.10.1, 9.4.10.2, 9.4.10.3, 9.4.10.4, 9.4.10.5, 9.4.10.6, 9.4.10.7, 9.4.10.8, 9.4.10.9, 9.4.10.10, 9.5.1.1, 9.5.1.2, 9.5.1.3, 9.5.1.4, 9.5.1.5, 9.5.1.6, 9.5.1.7, 9.5.1.8, 9.5.1.9, 9.5.1.10, 9.5.2.1, 9.5.2.2, 9.5.2.3, 9.5.2.4, 9.5.2.5, 9.5.2.6, 9.5.2.7, 9.5.2.8, 9.5.2.9, 9.5.2.10, 9.5.3.1, 9.5.3.2, 9.5.3.3, 9.5.3.4, 9.5.3.5, 9.5.3.6, 9.5.3.7, TABLE B-continued 9.5.3.8, 9.5.3.9, 9.5.3.10, 9.5.4.1, 9.5.4.2, 9.5.4.3, 9.5.4.4, 9.5.4.5, 9.5.4.6, 9.5.4.7,
9.5.4.8, 9.5.4.9, 9.5.4.10, 9.5.5.1, 9.5.5.2, 9.5.5.3, 9.5.5.4, 9.5.5.5, 9.5.5.6, 9.5.5.7,
9.5.5.8, 9.5.5.9, 9.5.5.10, 9.5.6.1, 9.5.6.2, 9.5.6.3, 9.5.6.4, 9.5.6.5, 9.5.6.6, 9.5.6.7,
9.5.6.8, 9.5.6.9, 9.5.6.10, 9.5.7.1, 9.5.7.2, 9.5.7.3, 9.5.7.4, 9.5.7.5, 9.5.7.6, 9.5.7.7,
9.5.7.8, 9.5.7.9, 9.5.7.10, 9.5.8.1, 9.5.8.2, 9.5.8.3, 9.5.8.4, 9.5.8.5, 9.5.8.6, 9.5.8.7,
9.5.8.8, 9.5.8.9, 9.5.8.10, 9.5.9.1, 9.5.9.2, 9.5.9.3, 9.5.9.4, 9.5.9.5, 9.5.9.6, 9.5.9.7,
9.5.9.8, 9.5.9.9, 9.5.9.10, 9.5.10.1, 9.5.10.2, 9.5.10.3, 9.5.10.4, 9.5.10.5, 9.5.10.6,
9.5.10.7, 9.5.10.8, 9.5.10.9, 9.5.10.10, 9.6.1.1, 9.6.1.2, 9.6.1.3, 9.6.1.4, 9.6.1.5, 9.6.1.6,
9.6.1.7, 9.6.1.8, 9.6.1.9, 9.6.1.10, 9.6.2.1, 9.6.2.2, 9.6.2.3, 9.6.2.4, 9.6.2.5, 9.6.2.6,
9.6.2.7, 9.6.2.8, 9.6.2.9, 9.6.2.10, 9.6.3.1, 9.6.3.2, 9.6.3.3, 9.6.3.4, 9.6.3.5, 9.6.3.6,
9.6.3.7, 9.6.3.8, 9.6.3.9, 9.6.3.10, 9.6.4.1, 9.6.4.2, 9.6.4.3, 9.6.4.4, 9.6.4.5, 9.6.4.6,
9.6.4.7, 9.6.4.8, 9.6.4.9, 9.6.4.10, 9.6.5.1, 9.6.5.2, 9.6.5.3, 9.6.5.4, 9.6.5.5, 9.6.5.6,
9.6.5.7, 9.6.5.8, 9.6.5.9, 9.6.5.10, 9.6.6.1, 9.6.6.2, 9.6.6.3, 9.6.6.4, 9.6.6.5, 9.6.6.6,
9.6.6.7, 9.6.6.8, 9.6.6.9, 9.6.6.10, 9.6.7.1, 9.6.7.2, 9.6.7.3, 9.6.7.4, 9.6.7.5, 9.6.7.6,
9.6.7.7, 9.6.7.8, 9.6.7.9, 9.6.7.10, 9.6.8.1, 9.6.8.2, 9.6.8.3, 9.6.8.4, 9.6.8.5, 9.6.8.6,
9.6.8.7, 9.6.8.8, 9.6.8.9, 9.6.8.10, 9.6.9.1, 9.6.9.2, 9.6.9.3, 9.6.9.4, 9.6.9.5, 9.6.9.6,
9.6.9.7, 9.6.9.8, 9.6.9.9, 9.6.9.10, 9.6.10.1, 9.6.10.2, 9.6.10.3, 9.6.10.4, 9.6.10.5,
9.6.10.6, 9.6.10.7, 9.6.10.8, 9.6.10.9, 9.6.10.10, 9.7.1.1, 9.7.1.2, 9.7.1.3, 9.7.1.4, 9.7.1.5,
9.7.1.6, 9.7.1.7, 9.7.1.8, 9.7.1.9, 9.7.1.10, 9.7.2.1, 9.7.2.2, 9.7.2.3, 9.7.2.4, 9.7.2.5,
9.7.2.6, 9.7.2.7, 9.7.2.8, 9.7.2.9, 9.7.2.10, 9.7.3.1, 9.7.3.2, 9.7.3.3, 9.7.3.4, 9.7.3.5,
9.7.3.6, 9.7.3.7, 9.7.3.8, 9.7.3.9, 9.7.3.10, 9.7.4.1, 9.7.4.2, 9.7.4.3, 9.7.4.4, 9.7.4.5,
9.7.4.6, 9.7.4.7, 9.7.4.8, 9.7.4.9, 9.7.4.10, 9.7.5.1, 9.7.5.2, 9.7.5.3, 9.7.5.4, 9.7.5.5,
9.7.5.6, 9.7.5.7, 9.7.5.8, 9.7.5.9, 9.7.5.10, 9.7.6.1, 9.7.6.2, 9.7.6.3, 9.7.6.4, 9.7.6.5,
9.7.6.6, 9.7.6.7, 9.7.6.8, 9.7.6.9, 9.7.6.10, 9.7.7.1, 9.7.7.2, 9.7.7.3, 9.7.7.4, 9.7.7.5,
9.7.7.6, 9.7.7.7, 9.7.7.8, 9.7.7.9, 9.7.7.10, 9.7.8.1, 9.7.8.2, 9.7.8.3, 9.7.8.4, 9.7.8.5,
9.7.8.6, 9.7.8.7, 9.7.8.8, 9.7.8.9, 9.7.8.10, 9.7.9.1, 9.7.9.2, 9.7.9.3, 9.7.9.4, 9.7.9.5,
9.7.9.6, 9.7.9.7, 9.7.9.8, 9.7.9.9, 9.7.9.10, 9.7.10.1, 9.7.10.2, 9.7.10.3, 9.7.10.4, 9.7.10.5,
9.7.10.6, 9.7.10.7, 9.7.10.8, 9.7.10.9, 9.7.10.10, 9.8.1.1, 9.8.1.2, 9.8.1.3, 9.8.1.4, 9.8.1.5,
9.8.1.6, 9.8.1.7, 9.8.1.8, 9.8.1.9, 9.8.1.10, 9.8.2.1, 9.8.2.2, 9.8.2.3, 9.8.2.4, 9.8.2.5,
9.8.2.6, 9.8.2.7, 9.8.2.8, 9.8.2.9, 9.8.2.10, 9.8.3.1, 9.8.3.2, 9.8.3.3, 9.8.3.4, 9.8.3.5,
9.8.3.6, 9.8.3.7, 9.8.3.8, 9.8.3.9, 9.8.3.10, 9.8.4.1, 9.8.4.2, 9.8.4.3, 9.8.4.4, 9.8.4.5,
9.8.4.6, 9.8.4.7, 9.8.4.8, 9.8.4.9, 9.8.4.10, 9.8.5.1, 9.8.5.2, 9.8.5.3, 9.8.5.4, 9.8.5.5,
9.8.5.6, 9.8.5.7, 9.8.5.8, 9.8.5.9, 9.8.5.10, 9.8.6.1, 9.8.6.2, 9.8.6.3, 9.8.6.4, 9.8.6.5,
9.8.6.6, 9.8.6.7, 9.8.6.8, 9.8.6.9, 9.8.6.10, 9.8.7.1, 9.8.7.2, 9.8.7.3, 9.8.7.4, 9.8.7.5,
9.8.7.6, 9.8.7.7, 9.8.7.8, 9.8.7.9, 9.8.7.10, 9.8.8.1, 9.8.8.2, 9.8.8.3, 9.8.8.4, 9.8.8.5,
9.8.8.6, 9.8.8.7, 9.8.8.8, 9.8.8.9, 9.8.8.10, 9.8.9.1, 9.8.9.2, 9.8.9.3, 9.8.9.4, 9.8.9.5,
9.8.9.6, 9.8.9.7, 9.8.9.8, 9.8.9.9, 9.8.9.10, 9.8.10.1, 9.8.10.2, 9.8.10.3, 9.8.10.4, 9.8.10.5,
9.8.10.6, 9.8.10.7, 9.8.10.8, 9.8.10.9, 9.8.10.10, 9.9.1.1, 9.9.1.2, 9.9.1.3, 9.9.1.4, 9.9.1.5,
9.9.1.6, 9.9.1.7, 9.9.1.8, 9.9.1.9, 9.9.1.10, 9.9.2.1, 9.9.2.2, 9.9.2.3, 9.9.2.4, 9.9.2.5,
9.9.2.6, 9.9.2.7, 9.9.2.8, 9.9.2.9, 9.9.2.10, 9.9.3.1, 9.9.3.2, 9.9.3.3, 9.9.3.4, 9.9.3.5,
9.9.3.6, 9.9.3.7, 9.9.3.8, 9.9.3.9, 9.9.3.10, 9.9.4.1, 9.9.4.2, 9.9.4.3, 9.9.4.4, 9.9.4.5,
9.9.4.6, 9.9.4.7, 9.9.4.8, 9.9.4.9, 9.9.4.10, 9.9.5.1, 9.9.5.2, 9.9.5.3, 9.9.5.4, 9.9.5.5,
9.9.5.6, 9.9.5.7, 9.9.5.8, 9.9.5.9, 9.9.5.10, 9.9.6.1, 9.9.6.2, 9.9.6.3, 9.9.6.4, 9.9.6.5,
9.9.6.6, 9.9.6.7, 9.9.6.8, 9.9.6.9, 9.9.6.10, 9.9.7.1, 9.9.7.2, 9.9.7.3, 9.9.7.4, 9.9.7.5,
9.9.7.6, 9.9.7.7, 9.9.7.8, 9.9.7.9, 9.9.7.10, 9.9.8.1, 9.9.8.2, 9.9.8.3, 9.9.8.4, 9.9.8.5,
9.9.8.6, 9.9.8.7, 9.9.8.8, 9.9.8.9, 9.9.8.10, 9.9.9.1, 9.9.9.2, 9.9.9.3, 9.9.9.4, 9.9.9.5,
9.9.9.6, 9.9.9.7, 9.9.9.8, 9.9.9.9, 9.9.9.10, 9.9.10.1, 9.9.10.2, 9.9.10.3, 9.9.10.4, 9.9.10.5,
9.9.10.6, 9.9.10.7, 9.9.10.8, 9.9.10.9, 9.9.10.10, 9.10.1.1, 9.10.1.2, 9.10.1.3, 9.10.1.4,
9.10.1.5, 9.10.1.6, 9.10.1.7, 9.10.1.8, 9.10.1.9, 9.10.1.10, 9.10.2.1, 9.10.2.2, 9.10.2.3,
9.10.2.4, 9.10.2.5, 9.10.2.6, 9.10.2.7, 9.10.2.8, 9.10.2.9, 9.10.2.10, 9.10.3.1, 9.10.3.2,
9.10.3.3, 9.10.3.4, 9.10.3.5, 9.10.3.6, 9.10.3.7, 9.10.3.8, 9.10.3.9, 9.10.3.10, 9.10.4.1,
9.10.4.2, 9.10.4.3, 9.10.4.4, 9.10.4.5, 9.10.4.6, 9.10.4.7, 9.10.4.8, 9.10.4.9, 9.10.4.10,
9.10.5.1, 9.10.5.2, 9.10.5.3, 9.10.5.4, 9.10.5.5, 9.10.5.6, 9.10.5.7, 9.10.5.8, 9.10.5.9,
9.10.5.10, 9.10.6.1, 9.10.6.2, 9.10.6.3, 9.10.6.4, 9.10.6.5, 9.10.6.6, 9.10.6.7, 9.10.6.8,
9.10.6.9, 9.10.6.10, 9.10.7.1, 9.10.7.2, 9.10.7.3, 9.10.7.4, 9.10.7.5, 9.10.7.6, 9.10.7.7,
9.10.7.8, 9.10.7.9, 9.10.7.10, 9.10.8.1, 9.10.8.2, 9.10.8.3, 9.10.8.4, 9.10.8.5, 9.10.8.6,
9.10.8.7, 9.10.8.8, 9.10.8.9, 9.10.8.10, 9.10.9.1, 9.10.9.2, 9.10.9.3, 9.10.9.4, 9.10.9.5,
9.10.9.6, 9.10.9.7, 9.10.9.8, 9.10.9.9, 9.10.9.10, 9.10.10.1, 9.10.10.2, 9.10.10.3,
9.10.10.4, 9.10.10.5, 9.10.10.6, 9.10.10.7, 9.10.10.8, 9.10.10.9, 9.10.10.10, 10.1.1.1,
10.1.1.2, 10.1.1.3, 10.1.1.4, 10.1.1.5, 10.1.1.6, 10.1.1.7, 10.1.1.8, 10.1.1.9, 10.1.1.10,
10.1.2.1, 10.1.2.2, 10.1.2.3, 10.1.2.4, 10.1.2.5, 10.1.2.6, 10.1.2.7, 10.1.2.8, 10.1.2.9,
10.1.2.10, 10.1.3.1, 10.1.3.2, 10.1.3.3, 10.1.3.4, 10.1.3.5, 10.1.3.6, 10.1.3.7, 10.1.3.8,
10.1.3.9, 10.1.3.10, 10.1.4.1, 10.1.4.2, 10.1.4.3, 10.1.4.4, 10.1.4.5, 10.1.4.6, 10.1.4.7,
10.1.4.8, 10.1.4.9, 10.1.4.10, 10.1.5.1, 10.1.5.2, 10.1.5.3, 10.1.5.4, 10.1.5.5, 10.1.5.6,
10.1.5.7, 10.1.5.8, 10.1.5.9, 10.1.5.10, 10.1.6.1, 10.1.6.2, 10.1.6.3, 10.1.6.4, 10.1.6.5,
10.1.6.6, 10.1.6.7, 10.1.6.8, 10.1.6.9, 10.1.6.10, 10.1.7.1, 10.1.7.2, 10.1.7.3, 10.1.7.4,
10.1.7.5, 10.1.7.6, 10.1.7.7, 10.1.7.8, 10.1.7.9, 10.1.7.10, 10.1.8.1, 10.1.8.2, 10.1.8.3,
10.1.8.4, 10.1.8.5, 10.1.8.6, 10.1.8.7, 10.1.8.8, 10.1.8.9, 10.1.8.10, 10.1.9.1, 10.1.9.2,
10.1.9.3, 10.1.9.4, 10.1.9.5, 10.1.9.6, 10.1.9.7, 10.1.9.8, 10.1.9.9, 10.1.9.10, 10.1.10.1,
10.1.10.2, 10.1.10.3, 10.1.10.4, 10.1.10.5, 10.1.10.6, 10.1.10.7, 10.1.10.8, 10.1.10.9,
10.1.10.10, 10.2.1.1, 10.2.1.2, 10.2.1.3, 10.2.1.4, 10.2.1.5, 10.2.1.6, 10.2.1.7, 10.2.1.8,
10.2.1.9, 10.2.1.10, 10.2.2.1, 10.2.2.2, 10.2.2.3, 10.2.2.4, 10.2.2.5, 10.2.2.6, 10.2.2.7,
10.2.2.8, 10.2.2.9, 10.2.2.10, 10.2.3.1, 10.2.3.2, 10.2.3.3, 10.2.3.4, 10.2.3.5, 10.2.3.6,
10.2.3.7, 10.2.3.8, 10.2.3.9, 10.2.3.10, 10.2.4.1, 10.2.4.2, 10.2.4.3, 10.2.4.4, 10.2.4.5,
10.2.4.6, 10.2.4.7, 10.2.4.8, 10.2.4.9, 10.2.4.10, 10.2.5.1, 10.2.5.2, 10.2.5.3, 10.2.5.4,
10.2.5.5, 10.2.5.6, 10.2.5.7, 10.2.5.8, 10.2.5.9, 10.2.5.10, 10.2.6.1, 10.2.6.2, 10.2.6.3,
10.2.6.4, 10.2.6.5, 10.2.6.6, 10.2.6.7, 10.2.6.8, 10.2.6.9, 10.2.6.10, 10.2.7.1, 10.2.7.2,
10.2.7.3, 10.2.7.4, 10.2.7.5, 10.2.7.6, 10.2.7.7, 10.2.7.8, 10.2.7.9, 10.2.7.10, 10.2.8.1,
10.2.8.2, 10.2.8.3, 10.2.8.4, 10.2.8.5, 10.2.8.6, 10.2.8.7, 10.2.8.8, 10.2.8.9, 10.2.8.10,
10.2.9.1, 10.2.9.2, 10.2.9.3, 10.2.9.4, 10.2.9.5, 10.2.9.6, 10.2.9.7, 10.2.9.8, 10.2.9.9,

TABLE B-continued 10.2.9.10, 10.2.10.1, 10.2.10.2, 10.2.10.3, 10.2.10.4, 10.2.10.5, 10.2.10.6, 10.2.10.7, 10.2.10.8, 10.2.10.9, 10.2.10.10, 10.3.1.1, 10.3.1.2, 10.3.1.3, 10.3.1.4, 10.3.1.5, 10.3.1.6, 10.3.1.7, 10.3.1.8, 10.3.1.9, 10.3.1.10, 10.3.2.1, 10.3.2.2, 10.3.2.3, 10.3.2.4, 10.3.2.5, 10.3.2.6, 10.3.2.7, 10.3.2.8, 10.3.2.9, 10.3.2.10, 10.3.3.1, 10.3.3.2, 10.3.3.3, 10.3.3.4, 10.3.3.5, 10.3.3.6, 10.3.3.7, 10.3.3.8, 10.3.3.9, 10.3.3.10, 10.3.4.1, 10.3.4.2, 10.3.4.3, 10.3.4.4, 10.3.4.5, 10.3.4.6, 10.3.4.7, 10.3.4.8, 10.3.4.9, 10.3.4.10, 10.3.5.1, 10.3.5.2, 10.3.5.3, 10.3.5.4, 10.3.5.5, 10.3.5.6, 10.3.5.7, 10.3.5.8, 10.3.5.9, 10.3.5.10, 10.3.6.1, 10.3.6.2, 10.3.6.3, 10.3.6.4, 10.3.6.5, 10.3.6.6, 10.3.6.7, 10.3.6.8, 10.3.6.9, 10.3.6.10, 10.3.7.1, 10.3.7.2, 10.3.7.3, 10.3.7.4, 10.3.7.5, 10.3.7.6, 10.3.7.7, 10.3.7.8, 10.3.7.9, 10.3.7.10, 10.3.8.1, 10.3.8.2, 10.3.8.3, 10.3.8.4, 10.3.8.5, 10.3.8.6, 10.3.8.7, 10.3.8.8, 10.3.8.9, 10.3.8.10, 10.3.9.1, 10.3.9.2, 10.3.9.3, 10.3.9.4, 10.3.9.5, 10.3.9.6, 10.3.9.7, 10.3.9.8, 10.3.9.9, 10.3.9.10, 10.3.10.1, 10.3.10.2, 10.3.10.3, 10.3.10.4, 10.3.10.5, 10.3.10.6, 10.3.10.7, 10.3.10.8, 10.3.10.9, 10.3.10.10, 10.4.1.1, 10.4.1.2, 10.4.1.3, 10.4.1.4, 10.4.1.5, 10.4.1.6, 10.4.1.7, 10.4.1.8, 10.4.1.9, 10.4.1.10, 10.4.2.1, 10.4.2.2, 10.4.2.3, 10.4.2.4, 10.4.2.5, 10.4.2.6, 10.4.2.7, 10.4.2.8, 10.4.2.9, 10.4.2.10, 10.4.3.1, 10.4.3.2, 10.4.3.3, 10.4.3.4, 10.4.3.5, 10.4.3.6, 10.4.3.7, 10.4.3.8, 10.4.3.9, 10.4.3.10, 10.4.4.1, 10.4.4.2, 10.4.4.3, 10.4.4.4, 10.4.4.5, 10.4.4.6, 10.4.4.7, 10.4.4.8, 10.4.4.9, 10.4.4.10, 10.4.5.1, 10.4.5.2, 10.4.5.3, 10.4.5.4, 10.4.5.5, 10.4.5.6, 10.4.5.7, 10.4.5.8, 10.4.5.9, 10.4.5.10, 10.4.6.1, 10.4.6.2, 10.4.6.3, 10.4.6.4, 10.4.6.5, 10.4.6.6, 10.4.6.7, 10.4.6.8, 10.4.6.9, 10.4.6.10, 10.4.7.1, 10.4.7.2, 10.4.7.3, 10.4.7.4, 10.4.7.5, 10.4.7.6, 10.4.7.7, 10.4.7.8, 10.4.7.9, 10.4.7.10, 10.4.8.1, 10.4.8.2, 10.4.8.3, 10.4.8.4, 10.4.8.5, 10.4.8.6, 10.4.8.7, 10.4.8.8, 10.4.8.9, 10.4.8.10, 10.4.9.1, 10.4.9.2, 10.4.9.3, 10.4.9.4, 10.4.9.5, 10.4.9.6, 10.4.9.7, 10.4.9.8, 10.4.9.9, 10.4.9.10, 10.4.10.1, 10.4.10.2, 10.4.10.3, 10.4.10.4, 10.4.10.5, 10.4.10.6, 10.4.10.7, 10.4.10.8, 10.4.10.9, 10.4.10.10, 10.5.1.1, 10.5.1.2, 10.5.1.3, 10.5.1.4, 10.5.1.5, 10.5.1.6, 10.5.1.7, 10.5.1.8, 10.5.1.9, 10.5.1.10, 10.5.2.1, 10.5.2.2, 10.5.2.3, 10.5.2.4, 10.5.2.5, 10.5.2.6, 10.5.2.7, 10.5.2.8, 10.5.2.9, 10.5.2.10, 10.5.3.1, 10.5.3.2, 10.5.3.3, 10.5.3.4, 10.5.3.5, 10.5.3.6, 10.5.3.7, 10.5.3.8, 10.5.3.9, 10.5.3.10, 10.5.4.1, 10.5.4.2, 10.5.4.3, 10.5.4.4, 10.5.4.5, 10.5.4.6, 10.5.4.7, 10.5.4.8, 10.5.4.9, 10.5.4.10, 10.5.5.1, 10.5.5.2, 10.5.5.3, 10.5.5.4, 10.5.5.5, 10.5.5.6, 10.5.5.7, 10.5.5.8, 10.5.5.9, 10.5.5.10, 10.5.6.1, 10.5.6.2, 10.5.6.3, 10.5.6.4, 10.5.6.5, 10.5.6.6, 10.5.6.7, 10.5.6.8, 10.5.6.9, 10.5.6.10, 10.5.7.1, 10.5.7.2, 10.5.7.3, 10.5.7.4, 10.5.7.5, 10.5.7.6, 10.5.7.7, 10.5.7.8, 10.5.7.9, 10.5.7.10, 10.5.8.1, 10.5.8.2, 10.5.8.3, 10.5.8.4, 10.5.8.5, 10.5.8.6, 10.5.8.7, 10.5.8.8, 10.5.8.9, 10.5.8.10, 10.5.9.1, 10.5.9.2, 10.5.9.3, 10.5.9.4, 10.5.9.5, 10.5.9.6, 10.5.9.7, 10.5.9.8, 10.5.9.9, 10.5.9.10, 10.5.10.1, 10.5.10.2, 10.5.10.3, 10.5.10.4, 10.5.10.5, 10.5.10.6, 10.5.10.7, 10.5.10.8, 10.5.10.9, 10.5.10.10, 10.6.1.1, 10.6.1.2, 10.6.1.3, 10.6.1.4, 10.6.1.5, 10.6.1.6, 10.6.1.7, 10.6.1.8, 10.6.1.9, 10.6.1.10, 10.6.2.1, 10.6.2.2, 10.6.2.3, 10.6.2.4, 10.6.2.5, 10.6.2.6, 10.6.2.7, 10.6.2.8, 10.6.2.9, 10.6.2.10, 10.6.3.1, 10.6.3.2, 10.6.3.3, 10.6.3.4, 10.6.3.5, 10.6.3.6, 10.6.3.7, 10.6.3.8, 10.6.3.9, 10.6.3.10, 10.6.4.1, 10.6.4.2, 10.6.4.3, 10.6.4.4, 10.6.4.5, 10.6.4.6, 10.6.4.7, 10.6.4.8, 10.6.4.9, 10.6.4.10, 10.6.5.1, 10.6.5.2, 10.6.5.3, 10.6.5.4, 10.6.5.5, 10.6.5.6, 10.6.5.7, 10.6.5.8, 10.6.5.9, 10.6.5.10, 10.6.6.1, 10.6.6.2, 10.6.6.3, 10.6.6.4, 10.6.6.5, 10.6.6.6, 10.6.6.7, 10.6.6.8, 10.6.6.9, 10.6.6.10, 10.6.7.1, 10.6.7.2, 10.6.7.3, 10.6.7.4, 10.6.7.5, 10.6.7.6, 10.6.7.7, 10.6.7.8, 10.6.7.9, 10.6.7.10, 10.6.8.1, 10.6.8.2, 10.6.8.3, 10.6.8.4, 10.6.8.5, 10.6.8.6, 10.6.8.7, 10.6.8.8, 10.6.8.9, 10.6.8.10, 10.6.9.1, 10.6.9.2, 10.6.9.3, 10.6.9.4, 10.6.9.5, 10.6.9.6, 10.6.9.7, 10.6.9.8, 10.6.9.9, 10.6.9.10, 10.6.10.1, 10.6.10.2, 10.6.10.3, 10.6.10.4, 10.6.10.5, 10.6.10.6, 10.6.10.7, 10.6.10.8, 10.6.10.9, 10.6.10.10, 10.7.1.1, 10.7.1.2, 10.7.1.3, 10.7.1.4, 10.7.1.5, 10.7.1.6, 10.7.1.7, 10.7.1.8, 10.7.1.9, 10.7.1.10, 10.7.2.1, 10.7.2.2, 10.7.2.3, 10.7.2.4, 10.7.2.5, 10.7.2.6, 10.7.2.7, 10.7.2.8, 10.7.2.9, 10.7.2.10, 10.7.3.1, 10.7.3.2, 10.7.3.3, 10.7.3.4, 10.7.3.5, 10.7.3.6, 10.7.3.7, 10.7.3.8, 10.7.3.9, 10.7.3.10, 10.7.4.1, 10.7.4.2, 10.7.4.3, 10.7.4.4, 10.7.4.5, 10.7.4.6, 10.7.4.7, 10.7.4.8, 10.7.4.9, 10.7.4.10, 10.7.5.1, 10.7.5.2, 10.7.5.3, 10.7.5.4, 10.7.5.5, 10.7.5.6, 10.7.5.7, 10.7.5.8, 10.7.5.9, 10.7.5.10, 10.7.6.1, 10.7.6.2, 10.7.6.3, 10.7.6.4, 10.7.6.5, 10.7.6.6, 10.7.6.7, 10.7.6.8, 10.7.6.9, 10.7.6.10, 10.7.7.1, 10.7.7.2, 10.7.7.3, 10.7.7.4, 10.7.7.5, 10.7.7.6, 10.7.7.7, 10.7.7.8, 10.7.7.9, 10.7.7.10, 10.7.8.1, 10.7.8.2, 10.7.8.3, 10.7.8.4, 10.7.8.5, 10.7.8.6, 10.7.8.7, 10.7.8.8, 10.7.8.9, 10.7.8.10, 10.7.9.1, 10.7.9.2, 10.7.9.3, 10.7.9.4, 10.7.9.5, 10.7.9.6, 10.7.9.7, 10.7.9.8, 10.7.9.9, 10.7.9.10, 10.7.10.1, 10.7.10.2, 10.7.10.3, 10.7.10.4, 10.7.10.5, 10.7.10.6, 10.7.10.7, 10.7.10.8, 10.7.10.9, 10.7.10.10, 10.8.1.1, 10.8.1.2, 10.8.1.3, 10.8.1.4, 10.8.1.5, 10.8.1.6, 10.8.1.7, 10.8.1.8, 10.8.1.9, 10.8.1.10, 10.8.2.1, 10.8.2.2, 10.8.2.3, 10.8.2.4, 10.8.2.5, 10.8.2.6, 10.8.2.7, 10.8.2.8, 10.8.2.9, 10.8.2.10, 10.8.3.1, 10.8.3.2, 10.8.3.3, 10.8.3.4, 10.8.3.5, 10.8.3.6, 10.8.3.7, 10.8.3.8, 10.8.3.9, 10.8.3.10, 10.8.4.1, 10.8.4.2, 10.8.4.3, 10.8.4.4, 10.8.4.5, 10.8.4.6, 10.8.4.7, 10.8.4.8, 10.8.4.9, 10.8.4.10, 10.8.5.1, 10.8.5.2, 10.8.5.3, 10.8.5.4, 10.8.5.5, 10.8.5.6, 10.8.5.7, 10.8.5.8, 10.8.5.9, 10.8.5.10, 10.8.6.1, 10.8.6.2, 10.8.6.3, 10.8.6.4, 10.8.6.5, 10.8.6.6, 10.8.6.7, 10.8.6.8, 10.8.6.9, 10.8.6.10, 10.8.7.1, 10.8.7.2, 10.8.7.3, 10.8.7.4, 10.8.7.5, 10.8.7.6, 10.8.7.7, 10.8.7.8, 10.8.7.9, 10.8.7.10, 10.8.8.1, 10.8.8.2, 10.8.8.3, 10.8.8.4, 10.8.8.5, 10.8.8.6, 10.8.8.7, 10.8.8.8, 10.8.8.9, 10.8.8.10, 10.8.9.1, 10.8.9.2, 10.8.9.3, 10.8.9.4, 10.8.9.5, 10.8.9.6, 10.8.9.7, 10.8.9.8, 10.8.9.9, 10.8.9.10, 10.8.10.1, 10.8.10.2, 10.8.10.3, 10.8.10.4, 10.8.10.5, 10.8.10.6, 10.8.10.7, 10.8.10.8, 10.8.10.9, 10.8.10.10, 10.9.1.1, 10.9.1.2, 10.9.1.3, 10.9.1.4, 10.9.1.5, 10.9.1.6, 10.9.1.7, 10.9.1.8, 10.9.1.9, 10.9.1.10, 10.9.2.1, 10.9.2.2, 10.9.2.3, 10.9.2.4, 10.9.2.5, 10.9.2.6, 10.9.2.7, 10.9.2.8, 10.9.2.9, 10.9.2.10, 10.9.3.1, 10.9.3.2, 10.9.3.3, 10.9.3.4, 10.9.3.5, 10.9.3.6, 10.9.3.7, 10.9.3.8, 10.9.3.9, 10.9.3.10, 10.9.4.1, 10.9.4.2, 10.9.4.3, 10.9.4.4, 10.9.4.5, 10.9.4.6, 10.9.4.7, 10.9.4.8, 10.9.4.9, 10.9.4.10, 10.9.5.1, 10.9.5.2, 10.9.5.3, 10.9.5.4, 10.9.5.5, 10.9.5.6, 10.9.5.7, 10.9.5.8, 10.9.5.9, 10.9.5.10, 10.9.6.1, 10.9.6.2, 10.9.6.3, 10.9.6.4, 10.9.6.5, 10.9.6.6, 10.9.6.7, 10.9.6.8, 10.9.6.9, 10.9.6.10, 10.9.7.1, 10.9.7.2, 10.9.7.3, 10.9.7.4, 10.9.7.5, 10.9.7.6, 10.9.7.7, 10.9.7.8, 10.9.7.9, 10.9.7.10, 10.9.8.1, 10.9.8.2, 10.9.8.3, 10.9.8.4, 10.9.8.5, 10.9.8.6, 10.9.8.7, 10.9.8.8, 10.9.8.9, 10.9.8.10, 10.9.9.1, 10.9.9.2, 10.9.9.3, 10.9.9.4, 10.9.9.5, 10.9.9.6, 10.9.9.7, 10.9.9.8, 10.9.9.9, 10.9.9.10, 10.9.10.1, 10.9.10.2, 10.9.10.3, 10.9.10.4, 10.9.10.5, 10.9.10.6, 10.9.10.7, TABLE B-continued 10.9.10.8, 10.9.10.9, 10.9.10.10, 10.10.1.1, 10.10.1.2, 10.10.1.3, 10.10.1.4, 10.10.1.5,
10.10.1.6, 10.10.1.7, 10.10.1.8, 10.10.1.9, 10.10.1.10, 10.10.2.1, 10.10.2.2, 10.10.2.3,
10.10.2.4, 10.10.2.5, 10.10.2.6, 10.10.2.7, 10.10.2.8, 10.10.2.9, 10.10.2.10, 10.10.3.1,
10.10.3.2, 10.10.3.3, 10.10.3.4, 10.10.3.5, 10.10.3.6, 10.10.3.7, 10.10.3.8, 10.10.3.9,
10.10.3.10, 10.10.4.1, 10.10.4.2, 10.10.4.3, 10.10.4.4, 10.10.4.5, 10.10.4.6, 10.10.4.7,
10.10.4.8, 10.10.4.9, 10.10.4.10, 10.10.5.1, 10.10.5.2, 10.10.5.3, 10.10.5.4, 10.10.5.5,
10.10.5.6, 10.10.5.7, 10.10.5.8, 10.10.5.9, 10.10.5.10, 10.10.6.1, 10.10.6.2, 10.10.6.3,
10.10.6.4, 10.10.6.5, 10.10.6.6, 10.10.6.7, 10.10.6.8, 10.10.6.9, 10.10.6.10, 10.10.7.1,
10.10.7.2, 10.10.7.3, 10.10.7.4, 10.10.7.5, 10.10.7.6, 10.10.7.7, 10.10.7.8, 10.10.7.9,
10.10.7.10, 10.10.8.1, 10.10.8.2, 10.10.8.3, 10.10.8.4, 10.10.8.5, 10.10.8.6, 10.10.8.7,
10.10.8.8, 10.10.8.9, 10.10.8.10, 10.10.9.1, 10.10.9.2, 10.10.9.3, 10.10.9.4, 10.10.9.5,
10.10.9.6, 10.10.9.7, 10.10.9.8, 10.10.9.9, 10.10.9.10, 10.10.10.1, 10.10.10.2,
10.10.10.3, 10.10.10.4, 10.10.10.5, 10.10.10.6, 10.10.10.7, 10.10.10.8, 10.10.10.9,
10.10.10.10

Additional exemplary formula B compound groups include the following compound groups disclosed below. Unless otherwise specified, the configurations of all hydrogen atoms and R groups for the following compound groups are as defined for the group 1 compounds of formula B above.

Group 2. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 5-6 position is present. Thus, group 2 compound 1.3.1.1 has the structure

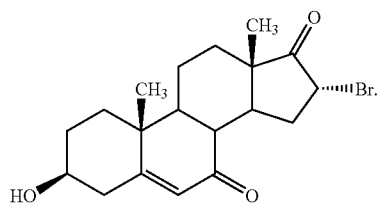

1.3.1.1

Group 3. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus as described for group 1 compounds, except that double bonds at the 1-2- and 5-6 positions are present. Thus, group 3 compound 2.2.5.1 has the structure

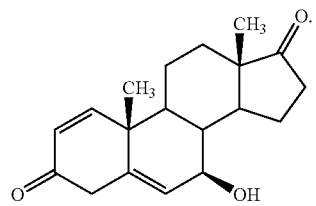

2.2.5.1

Group 4. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 1-2 position is present. Thus, group 4 compound 5.2.7.8 has the structure

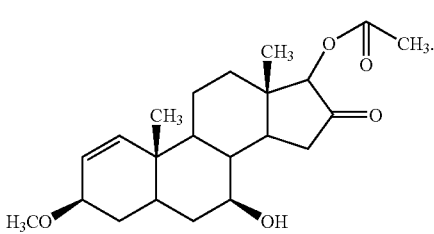

5.2.7.8

Group 5. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 4-5 position is present. Thus, the group 5 compound named 3.5.2.9 has the structure

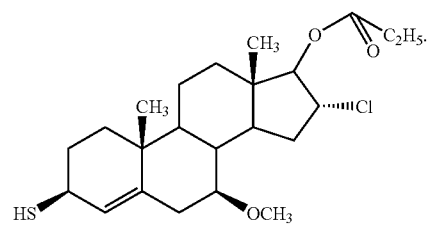

3.5.2.9

Group 6. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at both the 1-2 and 4-5 positions are present. Thus, the group 6 compound named 10.2.7.8 has the structure

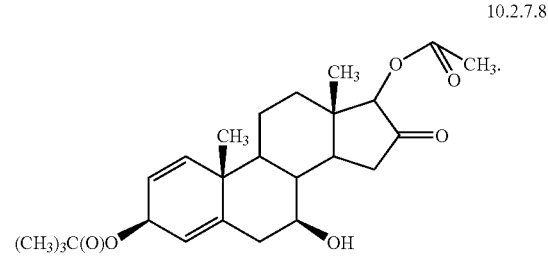

10.2.7.8

Group 7. Group 7 comprises the 6 compound groups described above, except that $R^5$ is hydrogen instead of methyl, i.e., it comprises 6 subgroups, 7-1, 7-2, 7-3, 7-4, 7-5 and 7-6. Thus, subgroup 7-1 has the same steroid nucleus as group 1 above, i.e., no double bond is present, but $R^5$ is —H. Subgroup 7-2 comprises the same steroid nucleus as group 2 above, i.e., a double bond is present at the 5-6-position, but $R^5$ is —H, Compound subgroups 7-3 through 7-6 are assigned a steroid nucleus in the same manner. Thus, the subgroup 7-1 through subgroup 7-6 compounds named 1.2.1.9 have the structures subgroup 7-1 compound 1.2.1.9

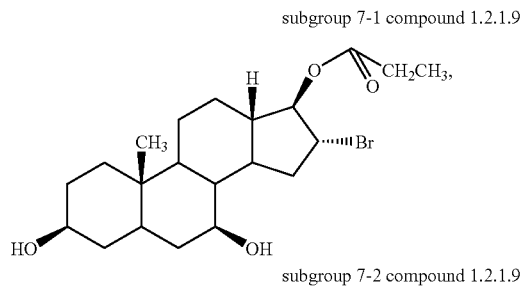

subgroup 7-2 compound 1.2.1.9

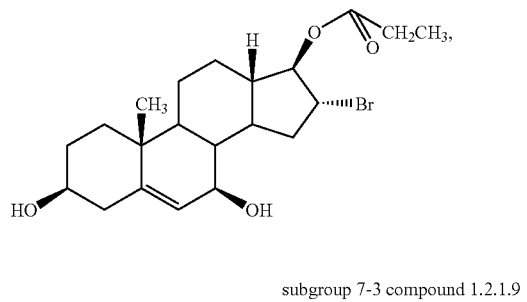

subgroup 7-3 compound 1.2.1.9

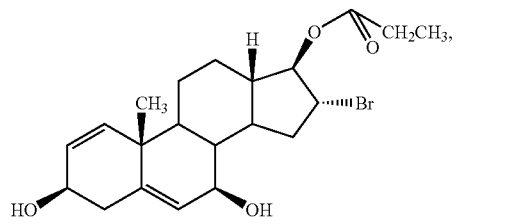

subgroup 7-4 compound 1.2.1.9

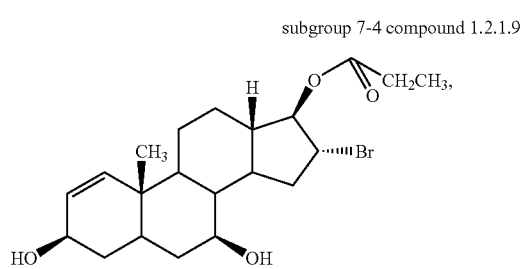

subgroup 7-5 compound 1.2.1.9

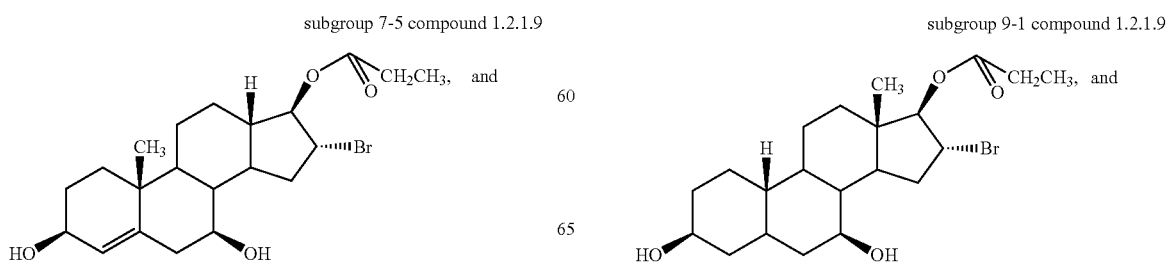

subgroup 7-6 compound 1.2.1.9

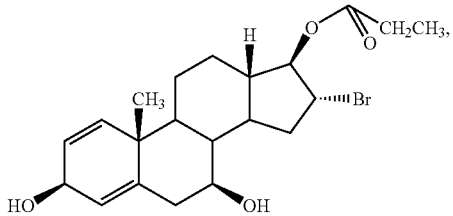

Group 8. Group 8 comprises 6 subgroups of compounds, i.e., each compound named in groups 1-6, except that $R^5$ of formula B is —$CH_2OH$ instead of methyl. The subgroups 8-1 through subgroup 8-6 compounds have structures that are named in the same manner as group 1-6 compounds, except that —$CH_2OH$ instead of methyl is present at $R^5$. These groups are named in essentially the same manner as subgroups 7-1 through 7-6. Thus, subgroup 8-1 and subgroup 8-2 compounds named 1.2.1.9 have the structures

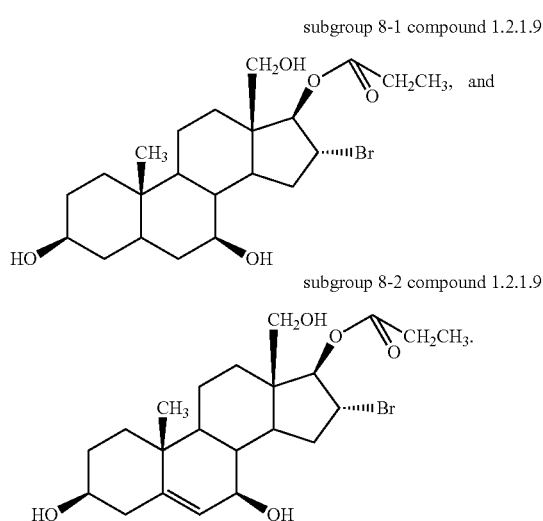

Group 9. Group 9 comprises each compound named in compound groups 1-8, except that $R^6$ of formula B is hydrogen instead of methyl. Thus group 9 comprises subgroups 9-1 through 9-8-6, i.e., 9-1, 9-2, 9-3, 9-4, 9-5, 9-6, 9-7-1, 9-7-2, 9-7-3, 9-7-4, 9-7-5, 9-7-6, 9-8-1, 9-8-2, 9-8-3, 9-8-4, 9-8-5 and 9-8-6. Subgroups 9-1 through 9-8-6 compounds have structures that are named in essentially the same manner as subgroup 7-1 through 7-6 compounds, except that —H instead of methyl is present at $R^6$. Thus, subgroup 9-1 and subgroup 9-2 compounds named 1.2.1.9 have the structures subgroup 9-2 compound 1.2.1.9

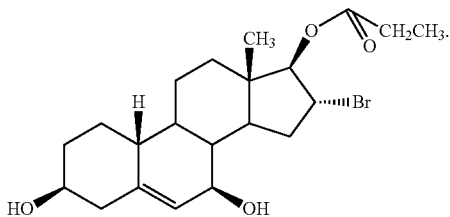

Subgroup 9-7-1 compound 1.2.1.9 has the same structure as group 9-1 compound 1.2.1.9, except that $R^5$ is hydrogen in the β configuration, instead of a methyl group in the β configuration. Similarly, the group 9-8-1 compound 1.2.1.9 has the same structure as group 9-1 compound 1.2.1.9, except that $R^5$ is hydroxymethyl (—CH$_2$OH) in the β configuration, instead of a methyl group in the β configuration. Group 9-7-2 compound 1.2.1.9 has the same structure as the group 9-7-1 compound, except that a double bond is present at the 5-6 position.

Thus, subgroups 9-1 through 9-6 have hydrogen at $R^6$, but each has a different double bond structure, e.g., no double bond in subgroup 9-1 and double bonds at 1-2 and 4-5 in subgroup 9-6. Subgroups 9-7-1 through 9-7-6 also comprises six subgroups, but they have hydrogen at $R^5$ and $R^6$, but each has a different double bond structure for each of the six subgroups, e.g., no double bond in subgroup 9-7-1 and double bonds at positions 1-2 and 4-5 in subgroup 9-7-6. Subgroups 9-8-1 through 9-8-6 all have hydrogen at $R^6$ and —CH$_2$OH at $R^5$, but each has a different double bond structure in each, e.g., no double bond in subgroup 9-8-1 and double bonds at positions 1-2 and 4-5 in group 9-8-6.

Groups 10. Group 10 comprises each compound named in groups 1 through 8, but where $R^6$ of formula B is —CH$_2$OH instead of methyl. The subgroups 10-1 through group 10-6 compounds have structures that are named in essentially the same manner as compounds in group 9, except that —CH$_2$OH instead of methyl is present at $R^6$. Thus, subgroup 10-1 and subgroup 10-2 compounds named 1.2.1.9 have the structures subgroup 10-1 compound 1.2.1.9

subgroup 10-2 compound 1.2.1.9

Subgroup 10-7-1 compound 1.2.1.9 has the same structure as subgroup 10-1 compound 1.2.1.9, except that $R^5$ is hydrogen in the β configuration, instead of a methyl group in the β configuration. Similarly, the subgroup 10-8-1 compound 1.2.1.9 has the same structure as group 10-1 compound 1.2.1.9, except that $R^5$ is hydroxymethyl (—CH$_2$OH) in the β configuration, instead of a methyl group in the β configuration. Subgroup 10-7-2 compound 1.2.1.9 has the same structure as the subgroup 10-7-1 compound, except that a double bond is present at the 5-6 position.

Thus, subgroups 10-1 through 10-8-6 comprise 18 separate groups, each of which has —CH$_2$OH at $R^6$. Subgroups 10-1 through 10-6 comprise different six subgroups where each has a different double bond structure, e.g., no double bond in subgroup 10-1 and double bonds at 1-2 and 4-5 in subgroup 10-6. Subgroups 10-7-1 through 10-7-6 all have —CH$_2$OH at $R^6$ and hydrogen at $R^5$, but each has a different double bond structure for each of the six groups, e.g., no double bond in subgroup 10-7-1 and double bonds at positions 1-2 and 4-5 in subgroup 10-7-6. Similarly, subgroups 10-8-1 through 10-8-6 all six have —CH$_2$OH at $R^6$ and at $R^5$, but each has a different double bond structure in each of the six subgroups, e.g., no double bond in subgroup 10-8-1 and double bonds at positions 1-2 and 4-5 in subgroup 10-8-6. The 18 groups are 10-1, 10-2, 10-3, 10-4, 10-5, 10-6, 10-7-1, 10-7-2, 10-7-3, 10-7-4, 10-7-5, 10-7-6, 10-8-1, 10-8-2, 10-8-3, 10-8-4, 10-8-5 and 10-8-6.

Group 11. Group 11 comprises each compound named in compound groups 1-10, but where $R^1$ moieties (or substituents) 1-10 listed in Table A are replaced with the following moieties:

1  —O—C(O)—CH$_2$CH$_2$CH$_2$CH$_3$   (—O—C(O)—CH$_2$CH$_2$CH$_2$CH$_3$ replaces —OH, which is $R^1$ moiety 1 in Table A)
2  —O—C(O)—CH$_2$CH$_2$CH$_2$CH$_2$CH$_2$CH$_3$
3  —O—C(O)—CH$_2$CH$_2$OCH$_2$CH$_3$
4  —O—C(O)—CH$_2$CH$_2$OCH$_2$CH$_2$OCH$_2$CH$_3$
5  —O—C(O)—CH$_2$CH$_2$CH$_2$CH$_2$OCH$_2$CH$_3$
6  —O—C(O)—CH$_2$CH$_2$OCH$_2$CH$_2$CH$_2$CH$_3$
7  —O—C$_6$H$_4$C$_{1-8}$
8  —O—C$_6$H$_3$F$_2$
9  —O—C$_6$H$_4$—O(CH$_2$)$_2$—O—CH$_2$CH$_3$
10 —O—C$_6$H$_4$—C(O)O(CH$_2$)$_{0-9}$CH$_3$ The subgroup 11-1 through subgroup 11-6 compounds have structures that are named in essentially the same manner as described for the groups above, except that moieties 1-10 of table A are replaced by the moieties 1-10 at $R^1$. Thus subgroup 11-1 and 11-2 compounds named 1.2.1.9 have the structures subgroup 11-1 compound 1.2.1.9 subgroup 11-2 compound 1.2.1.9

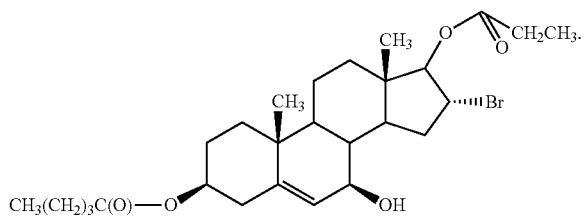

Subgroup 11-7-1 and 11-7-2 compounds named 1.2.1.9 have the structures subgroup 11-7-1 compound 1.2.1.9

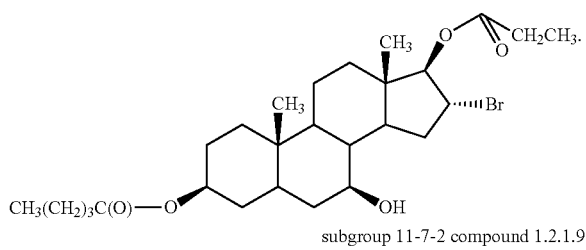

subgroup 11-7-2 compound 1.2.1.9

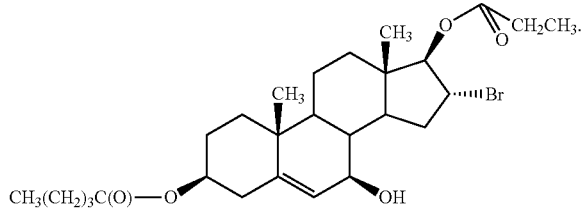

Subgroup 11-8-1 and 11-8-2 compounds named 1.2.1.9 have the structures subgroup 11-8-1 compound 1.2.1.9

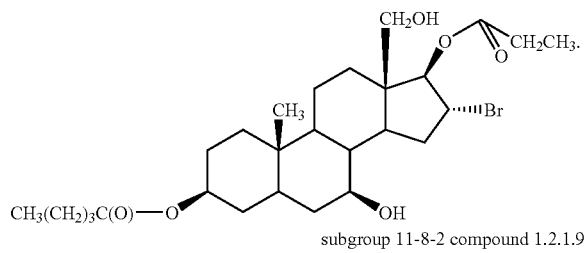

subgroup 11-8-2 compound 1.2.1.9

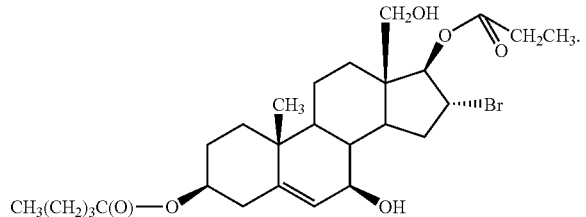

Group 11 comprises 54 separate subgroups, subgroups 11-1 through 11-10-8-6, where each of which has the $R^1$ moieties shown in this group and the remaining moieties as shown in the other groups described above. Subgroups 11-1 through 11-6 each have a different double bond structure, e.g., no double bond in subgroup 11-1 and double bonds at 1-2 and 4-5 in subgroup 11-6. Subgroups 11-7-1 through 11-7-6 all have —CH$_2$OH at $R^6$ and hydrogen at $R^5$, but each has a different double bond structure, e.g., no double bond in subgroup 11-7-1 and double bonds at positions 1-2 and 4-5 in subgroup 11-7-6. Subgroups 11-8-1 through 11-8-6 comprise all have —CH$_2$OH at $R^6$ and at $R^5$, but each has a different double bond structure in each of the six groups, e.g., no double bond in group 11-8-1 and double bonds at positions 1-2 and 4-5 in group 11-8-6. The compounds in the remaining groups are named in essentially the same manner.

The 54 groups are 11-1, 11-2, 11-3, 11-4, 11-5, 11-6, 11-7-1, 11-7-2, 11-7-3, 11-7-4, 11-7-5, 11-7-6, 11-8-1, 11-8-2, 11-8-3, 11-8-4, 11-8-5, 11-8-6, 11-9-1, 11-9-2, 11-9-3, 11-9-4, 11-9-5, 11-9-6, 11-10-1, 11-10-2, 11-10-3, 11-10-4, 11-10-5, 11-10-6, 11-9-7-1, 11-9-7-2, 11-9-7-3, 11-9-7-4, 11-9-7-5, 11-9-7-6, 11-10-7-1, 11-10-7-2, 11-10-7-3, 11-10-7-4, 11-10-7-5, 11-10-7-6, 11-9-8-1, 11-9-8-2, 11-9-8-3, 11-9-8-4, 11-9-8-5, 11-9-8-6, 11-10-8-1, 11-10-8-2, 11-10-8-3, 11-10-8-4, 11-10-8-5 and 11-10-8-6.

Group 12. Group 12 comprises each compound named in groups 1 through 10, but where $R^1$ moieties 1-10 listed in Table A are replaced with the following moieties:

1 —O—P(O)(O)—OCH$_2$CH(CH$_3$)CH$_3$ (—O—P(O)(O)—OCH$_2$CH(CH$_3$)CH$_3$ replaces —OH, which is $R^1$ moiety 1 in Table A)
2 —O—P(O)(O)—OCH$_2$CH$_2$CH$_2$CH$_2$CH$_3$
3 —O—P(O)(O)—OCH$_2$CH$_2$CH$_2$CH$_2$CH$_2$CH$_3$
4 —O—P(O)(O)—OCH$_2$CH$_2$CH(CH$_2$CH$_2$)CH$_3$
5 —O—CH$_2$CH$_2$CH$_2$CH$_2$CH$_2$CH$_3$
6 —O—C1-C6 alkyl(OH)$_{0-2}$
7 —C1-C6 alkyl(OH)$_{0-2}$
8 —C(O)—C1-C6 alkyl(OH)$_{0-2}$
9 —O-monosaccharide
10 —O-disaccharide Group 12 comprises 54 separate subgroups, subgroups 12-1 through 12-10-8-6, where each of which has the $R^1$ moieties shown in this group and the remaining moieties as shown in the other groups described above. The subgroups are defined essentially as described for group 11 above. The 54 subgroups are 12-1, 12-2, 12-3, 12-4, 12-5, 12-6, 12-7-1, 12-7-2, 12-7-3, 12-7-4, 12-7-5, 12-7-6, 12-8-1, 12-8-2, 12-8-3, 12-8-4, 12-8-5, 12-8-6, 12-9-1, 12-9-2, 12-9-3, 12-9-4, 12-9-5, 12-9-6, 12-10-1, 12-10-2, 12-10-3, 12-10-4, 12-10-5, 12-10-6, 12-9-7-1, 12-9-7-2, 12-9-7-3, 12-9-7-4, 12-9-7-5, 12-9-7-6, 12-10-7-1, 12-10-7-2, 12-10-7-3, 12-10-7-4, 12-10-7-5, 12-10-7-6, 12-9-8-1, 12-9-8-2, 12-9-8-3, 12-9-8-4, 12-9-8-5, 12-9-8-6, 12-10-8-1, 12-10-8-2, 12-10-8-3, 12-10-8-4, 12-10-8-5 and 12-10-8-6.

Group 13. Group 13 comprises each compound named in groups 1 through 10, but where $R^1$ moieties 1-10 listed in Table A are replaced with the following moieties:

1 —O—(CH$_2$)$_4$—CH$_3$(—O—(CH$_2$)$_4$—CH$_3$ replaces —OH, which is $R^1$ moiety 1 in Table A)
2 —O-oligosaccharide
3 —O-polyethylene glycol (e.g., PEG20, PEG100, PEG200 or PEG400)
4 —O—C(O)—NH$_{0-2}$(C1-C6 alkyl)$_{0-2}$
5 —C(O)—NH$_{0-2}$(C1-C6 alkyl)$_{0-2}$
6 —O—C(O)—NH(CH$_2$)$_{2-4}$—O—C1-C4 alkyl(OH)$_{0-2}$
7 —O—C(O)—CH$_3$
8 —O—C(O)—C2-C5 alkyl(OH)$_{0-2}$
9 —O—C(O)—CH$_2$CH$_2$CH$_3$
10 —O—C(O)—CH(NH$_2$)—R$^{42}$ (R$^{42}$ is —H, C$_2$-C$_6$ alkyl or an amino acid side chain)

Group 13 comprises 54 separate subgroups, subgroups 13-1 through 13-10-8-6, where each of which has the $R^1$ moieties shown in this group and the remaining moieties as shown in the other groups described above. The subgroups are defined essentially as described for group 11 above. The 54 subgroups are 13-1, 13-2, 13-3, 13-4, 13-5, 13-6, 13-7-1, 13-7-2, 13-7-3, 13-7-4, 13-7-5, 13-7-6, 13-8-1, 13-8-2, 13-8-3, 13-8-4, 13-8-5, 13-8-6, 13-9-1, 13-9-2, 13-9-3, 13-9-4, 13-9-5, 13-9-6, 13-10-1, 13-10-2, 13-10-3, 13-10-4, 13-10-5, 13-10-6, 13-9-7-1, 13-9-7-2, 13-9-7-3, 13-9-7-4, 13-9-7-5, 13-9-7-6, 13-10-7-1, 13-10-7-2, 13-10-7-3, 13-10-7-4, 13-10-7-5, 13-10-7-6, 13-9-8-1, 13-9-8-2, 13-9-8-3, 13-9-8-4, 13-9-8-5, 13-9-8-6, 13-10-8-1, 13-10-8-2, 13-10-8-3, 13-10-8-4, 13-10-8-5 and 13-10-8-6.

Group 14. Group 14 comprises each compound named in groups 1 through 10, but where $R^1$ moieties 1-10 listed in Table A are replaced with the following moieties:
1 —C(O)—$CH_3$
2 —O—$CH_2C_6H_5$
3 —C(S)—$CH_3$
4 —O—C0-C6 alkyl-heterocycle
5 —C0-C6 alkyl-heterocycle
6 —O—$CH_2C_6H_4F$
7 —O—$CH_2C_6H_3(OCH_3)_2$
8 —C(O)—C2-C4 alkyl-O—C1-C3 alkyl
9 —C(O)—C0-C4 alkyl-NH—(C1-C3 alkyl)$_{0-1}$-H
10 —O—$CH_2C_6H_4OCH_2CH_3$ Group 14 comprises 54 separate subgroups, subgroups 14-1 through 14-10-8-6, where each of which has the $R^1$ moieties shown in this group and the remaining moieties as shown in the other groups described above. These subgroups are defined essentially as described for group 11 above. The 54 subgroups are 14-1, 14-2, 14-3, 14-4, 14-5, 14-6, 14-7-1, 14-7-2, 14-7-3, 14-7-4, 14-7-5, 14-7-6, 14-8-1, 14-8-2, 14-8-3, 14-8-4, 14-8-5, 14-8-6, 14-9-1, 14-9-2, 14-9-3, 14-9-4, 14-9-5, 14-9-6, 14-10-1, 14-10-2, 14-10-3, 14-10-4, 14-10-5, 14-10-6, 14-9-7-1, 14-9-7-2, 14-9-7-3, 14-9-7-4, 14-9-7-5, 14-9-7-6, 14-10-7-1, 14-10-7-2, 14-10-7-3, 14-10-7-4, 14-10-7-5, 14-10-7-6, 14-9-8-1, 14-9-8-2, 14-9-8-3, 14-9-8-4, 14-9-8-5, 14-9-8-6, 14-10-8-1, 14-10-8-2, 14-10-8-3, 14-10-8-4, 14-10-8-5 and 14-10-8-6.

Group 15. Group 15 comprises each compound named in groups 1 through 10, but where $R^1$ moieties 1-10 listed in Table A are replaced with the following groups:
1 —O—C(O)—$CH_2CH_2NH_2$ (—O—C(O)—$CH_2CH_2NH_2$ replaces —OH, which is $R^1$ moiety 1 in Table A)
2 —O—C(O)—C1-C6 alkyl-$NH_2$
3 —C(O)—C1-C6 alkyl-$NH_2$
4 —O—C(O)—C1-C6 alkyl-$(OH)_{0-2}$
5 —C(O)—C1-C6 alkyl-$(OH)_{0-2}$
6 —O—C(O)—C1-C6 alkyl-$(SH)_{0-2}$
7 —C(O)—C1-C6 alkyl-$(SH)_{0-2}$
8 —O—C(O)—$CH_2CH_2CH_2SH$
9 —S—C(O)—C1-C6 alkyl-$(OH)_{0-2}$
10 —C(S)—C1-C6 alkyl-$(OH)_{0-2}$ Group 15 comprises 54 separate subgroups, subgroups 15-1 through 15-10-8-6, where each of which has the $R^1$ moieties shown in this group and the remaining moieties as shown in the other groups described above. These subgroups are defined essentially as described for group 11 above. The 54 subgroups are 15-1, 15-2, 15-3, 15-4, 15-5, 15-6, 15-7-1, 15-7-2, 15-7-3, 15-7-4, 15-7-5, 15-7-6, 15-8-1, 15-8-2, 15-8-3, 15-8-4, 15-8-5, 15-8-6, 15-9-1, 15-9-2, 15-9-3, 15-9-4, 15-9-5, 15-9-6, 15-10-1, 15-10-2, 15-10-3, 15-10-4, 15-10-5, 15-10-6, 15-9-7-1, 15-9-7-2, 15-9-7-3, 15-9-7-4, 15-9-7-5, 15-9-7-6, 15-10-7-1, 15-10-7-2, 15-10-7-3, 15-10-7-4, 15-10-7-5, 15-10-7-6, 15-9-8-1, 15-9-8-2, 15-9-8-3, 15-9-8-4, 15-9-8-5, 15-9-8-6, 15-10-8-1, 15-10-8-2, 15-10-8-3, 15-10-8-4, 15-10-8-5 and 15-10-8-6.

Group 16. Groups 16 comprises each compound named in groups 1 through 10, but where $R^1$ moieties 1-10 listed in Table A are replaced with the following groups:
1 —O—C(O)-A4-$NH_2$, where A4-$NH_2$ is a 4 carbon alkyl group substituted with —$NH_2$ (—O—C(O)-A4-$NH_2$ replaces —OH, which is $R^1$ moiety 1 in Table A)
2 —O—C(O)-A6-$NH_2$, where A6-$NH_2$ is a 6 carbon alkyl group substituted with —$NH_2$
3 —O—C(O)-A8-$NH_2$, where A8-$NH_2$ is a 8 carbon alkyl group substituted with —$NH_2$
4 —O—C(O)-A4-OH, where A4-OH is a 4 carbon alkyl group substituted with —OH or —O—
5 —O—C(O)-A6-OH, where A6-OH is a 6 carbon alkyl group substituted with —OH or —O—
6-O—C(O)-A8-OH, where A8-OH is a 8 carbon alkyl group substituted with —OH or —O—
7 —F
8 —$C_{1-9}$
9 —Br
10 —I Group 16 comprises 54 separate subgroups, subgroups 16-1 through 16-10-8-6, where each of which has the $R^1$ moieties shown in this group and the remaining moieties as shown in the other groups described above. These groups are defined essentially as described for group 11 above. The 54 subgroups are 16-1, 16-2, 16-3, 16-4, 16-5, 16-6, 16-7-1, 16-7-2, 16-7-3, 16-7-4, 16-7-5, 16-7-6, 16-8-1, 16-8-2, 16-8-3, 16-8-4, 16-8-5, 16-8-6, 16-9-1, 16-9-2, 16-9-3, 16-9-4, 16-9-5, 16-9-6, 16-10-1, 16-10-2, 16-10-3, 16-10-4, 16-10-5, 16-10-6, 16-9-7-1, 16-9-7-2, 16-9-7-3, 16-9-7-4, 16-9-7-5, 16-9-7-6, 16-10-7-1, 16-10-7-2, 16-10-7-3, 16-10-7-4, 16-10-7-5, 16-10-7-6, 16-9-8-1, 16-9-8-2, 16-9-8-3, 16-9-8-4, 16-9-8-5, 16-9-8-6, 16-10-8-1, 16-10-8-2, 16-10-8-3, 16-10-8-4, 16-10-8-5 and 16-10-8-6.

Group 17. Group 17 comprises each compound named in compound groups 1 through 10, but where $R^1$ moieties 1-10 listed in Table A are replaced with the following groups:
1 —O—S(O)(O)—O—C1-C8 optionally substituted alkyl
2 —O—P(O)(OH)—O—C1-C8 optionally substituted alkyl
3 —O—P(S)(OH)—O—C1-C8 optionally substituted alkyl
4 —O—P(O)(OH)—S—C1-C8 optionally substituted alkyl
5 —O—S(O)(O)—$OR^{44}$ ($R^{44}$ is H, $NH_4^+$, $Na^+$, $K^+$, $HN^+(CH_3)_4$, $N^+(CH_3)_4$, $HN^+(C2H_5)_3$ C1-C8 alkyl (e.g., —$CH_3$, —$C2H_5$ or —$C3H_7$), or pyridinium$^+$)
6 —O—P(O)(OH)—$OR^{44}$
7 —O—P(O)(OH)—$SR^{44}$
8 —O—S(O)(O)—O-2',3'-dipalmitoyl-1'-glyceryl
9 —O-(3β-O-1β)-D-glucuronic acid-$R^{44}$
10 —O-(3β-O-1β)-tri-o-acetyl-D-glucuronic acid-$R^{44}$ Group 17 comprises 54 separate subgroups, subgroups 17-1 through 17-10-8-6, where each of which has the $R^1$ moieties shown in this group and the remaining moieties as shown in the other groups described above. These subgroups are defined essentially as described for group 11 above. The 54 subgroups are 17-1, 17-2, 17-3, 17-4, 17-5, 17-6, 17-7-1, 17-7-2, 17-7-3, 17-7-4, 17-7-5, 17-7-6, 17-8-1, 17-8-2, 17-8-3, 17-8-4, 17-8-5, 17-8-6, 17-9-1, 17-9-2, 17-9-3, 17-9-4, 17-9-5, 17-9-6, 17-10-1, 17-10-2, 17-10-3, 17-10-4, 17-10-5, 17-10-6, 17-9-7-1, 17-9-7-2, 17-9-7-3, 17-9-7-4, 17-9-7-5, 17-9-7-6, 17-10-7-1, 17-10-7-2, 17-10-7-3, 17-10-7-4, 17-10-7-5, 17-10-7-6, 17-9-8-1, 17-9-8-2, 17-9-8-3, 17-9-8-4, 17-9-8-5, 17-9-8-6, 17-10-8-1, 17-10-8-2, 17-10-8-3, 17-10-8-4, 17-10-8-5 and 17-10-8-6.

Group 18. Group 18 comprises each compound named in groups 1 through 17, but where $R^4$ moieties 1-10 listed in Table A are replaced with the following moieties:

1 —O—C(O)CH$_2$NH$_2$
2 —O—C(O)C(CH$_3$)H—NH$_2$
3 —O—C(O)C(CH$_2$C$_6$H$_5$)H—NH$_2$
4 —O—C(O)—O—NHC(CH$_3$)H—CO$_2$H
5 —O—C(O)—O—NHCH$_2$—CO$_2$H
6 —O—C(O)—O—NH(CH$_2$C$_6$H$_5$)H—CO$_2$H
7 —O—C(O)—CF$_3$
8 —O—C(O)—CH$_2$CF$_3$
9 —O—C(O)—(CH$_2$)$_3$CF$_3$
10 —O—C(O)—(CH$_2$)$_5$CH$_3$

Group 18 comprises 432 separate subgroups, 18-1 through 18-17-10-8-6, where each of which has the $R^4$ moieties shown in this group and the remaining moieties as shown in the other groups described above. These groups are defined essentially as described for the groups described above. The groups are 18-1 through 18-6, 18-7-1 through 18-7-6, 18-8-1 through 18-8-6, 18-9-1 through 18-9-6, 18-10-1 through 18-10-6, 18-9-7-1 through 18-9-7-6, 18-9-8-1 through 18-9-8-6, 18-10-7-1 through 18-10-7-6, 18-10-8-1 through 18-10-8-6, 18-11-1 through 18-11-6, 18-11-7-1 through 18-11-7-6, 18-11-8-1 through 18-11-8-6, 18-11-9-1 through 18-11-9-6, 18-11-10-1 through 18-11-10-6, 18-11-9-7-1 through 18-11-9-7-6, 18-11-9-8-1 through 18-11-9-8-6, 18-11-10-7-1 through 18-11-10-7-6, 18-11-10-8-1 through 18-11-10-8-6, 18-12-1 through 18-12-6, 18-12-7-1 through 18-12-7-6, 18-12-8-1 through 18-12-8-6, 18-12-9-1 through 18-12-9-6, 18-12-10-1 through 18-12-10-6, 18-12-9-7-1 through 18-12-9-7-6, 18-12-9-8-1 through 18-12-9-8-6, 18-12-10-7-1 through 18-12-10-7-6, 18-12-10-8-1 through 18-12-10-8-6, 18-13-1 through 18-13-6, 18-13-7-1 through 18-13-7-6, 18-13-8-1 through 18-13-8-6, 18-13-9-1 through 18-13-9-6, 18-13-10-1 through 18-13-10-6, 18-13-9-7-1 through 18-13-9-7-6, 18-13-9-8-1 through 18-13-9-8-6, 18-13-10-7-1 through 18-13-10-7-6, 18-13-10-8-1 through 18-13-10-8-6, 18-14-1 through 18-14-6, 18-14-7-1 through 18-14-7-6, 18-14-8-1 through 18-14-8-6, 18-14-9-1 through 18-14-9-6, 18-14-10-1 through 18-14-10-6, 18-14-9-7-1 through 18-14-9-7-6, 18-14-9-8-1 through 18-14-9-8-6, 18-14-10-7-1 through 18-14-10-7-6, 18-14-10-8-1 through 18-14-10-8-6, 18-15-1 through 18-15-6, 18-15-7-1 through 18-15-7-6, 18-15-8-1 through 18-15-8-6, 18-15-9-1 through 18-15-9-6, 18-15-10-1 through 18-15-10-6, 18-15-9-7-1 through 18-15-9-7-6, 18-15-9-8-1 through 18-15-9-8-6, 18-15-10-7-1 through 18-15-10-7-6, 18-15-10-8-1 through 18-15-10-8-6, 18-16-1 through 18-16-6, 18-16-7-1 through 18-16-7-6, 18-16-8-1 through 18-16-8-6, 18-16-9-1 through 18-16-9-6, 18-16-10-1 through 18-16-10-6, 18-16-9-7-1 through 18-16-9-7-6, 18-16-9-8-1 through 18-16-9-8-6, 18-16-10-7-1 through 18-16-10-7-6, 18-16-10-8-1 through 18-16-10-8-6, 18-17-1 through 18-17-6, 18-17-7-1 through 18-17-7-6, 18-17-8-1 through 18-17-8-6, 18-17-9-1 through 18-17-9-6, 18-17-10-1 through 18-17-10-6, 18-17-9-7-1 through 18-17-9-7-6, 18-17-9-8-1 through 18-17-9-8-6, 18-17-10-7-1 through 18-17-10-7-6 and 18-17-10-8-1 through 18-17-10-8-6.

Group 19. Group 19 comprises each compound named in compound groups 1 through 17, but where $R^4$ moieties 1-10 listed in Table A are replaced with the following moieties:

1 —O—C(O)—O—CH$_3$
2 —O—C(O)—O—CH$_2$CH$_3$
3 —O—C(O)—O—C$_3$H$_7$
4 —O—C(O)—O—C$_4$H$_9$
5 —O—C(O)—O—C$_6$H$_{13}$
6 —O—C(O)—O—C$_6$H$_5$
7 —O—C(O)—O—C$_6$H$_4$OH
8 —O—C(O)—O—C$_6$H$_4$OCH$_3$
9 —O—C(O)—O—C$_6$H$_4$OCH$_2$CH$_3$
10 —O—C(O)—O—C$_6$H$_4$F

Group 19 comprises 432 separate subgroups, 19-1 through 19-17-10-8-6, where each of which has the $R^4$ moieties shown in this group and the remaining moieties as shown in the other groups described above. These subgroups are defined essentially as described for group 18 above. The subgroups are 19-1 through 19-6, 19-7-1 through 19-7-6, 19-8-1 through 19-8-6, 19-9-1 through 19-9-6 and so on essentially as described for group 18 compounds.

Group 20. Group 20 comprises each compound named in groups 1 through 17, but where $R^4$ moieties 1-10 listed in Table A are replaced with the following moieties:

1 —O—S(O)(O)—OR$^{44}$ (R$^{44}$ is H, NH$_4^+$, Na$^+$, K$^+$, HN$^+$(CH$_3$)$_3$, N$^+$(CH$_3$)$_4$, HN$^+$(C$_2$H$_5$)$_3$ C1-C8 optionally substituted alkyl (e.g., —CH$_3$, —C$_2$H$_5$ or —C$_3$H$_7$), or pyridinium$^+$)
2 —O—P(O)(OH)—SR$^{44}$
3 —C(O)—C$_1$-C$_8$ optionally substituted alkyl
4 —CH(OH)—C$_1$-C$_8$ optionally substituted alkyl
5 —C≡CH
6 —C≡C—(CH$_2$)$_{1-4}$—H
7 —C(O)—CH$_2$—OH
8 —C(S)—CH$_2$—OH
9 —O—S(O)(O)—O-2',3'-dipalmitoyl-1'-glyceryl
10 —O-(3-O-1β)-tri-O-acetyl-D-glucuronic acid-R$^{44}$ Group 20 comprises 432 separate subgroups, 20-1 through 20-17-10-8-6 comprise 432 separate groups, each of which has the $R^4$ moieties defined for this group and the remaining moieties as shown in the other groups described above. These subgroups are defined essentially as described for group 18 above. The subgroups are 20-1 through 20-6, 20-7-1 through 20-7-6, 20-8-1 through 20-8-6, 20-9-1 through 20-9-6 and so on essentially as described for group 18 compounds.

Group 21. Group 21 comprises each compound named in compound groups 1 through 17, but where $R^4$ moieties 1-10 listed in Table A are replaced with the following moieties:

1 —O—C(S)—O—C1-C4 alkyl
2 —S—C(S)—O—C1-C4 alkyl
3 —SH
4 =S
5 —O—C1-C6 optionally substituted alkyl
6 —O—C1-C6-optionally substituted alkyl-optionally substituted aryl
7 —S—C1-C6 optionally substituted alkyl
8 —O—C(O)—CH(NH$_2$)—R$^{42}$ (R$^{42}$ is —H, C2-C6 alkyl or an amino acid side chain)
9 —C0-C4 alkyl-heterocycle
10 —O-polyethylene glycol (e.g., PEG20, PEG100, PEG200 or PEG400)

Group 21 comprises 432 separate subgroups, 21-1 through 21-17-10-8-6 comprise 432 separate groups, each of which has the $R^4$ moieties defined for this group and the remaining moieties as shown in the other groups described above. These subgroups are defined essentially as described for group 18 above. The subgroups are 21-1 through 21-6, 21-7-1 through 21-7-6, 21-8-1 through 21-8-6, 21-9-1 through 21-9-6 and so on essentially as described for group 18 compounds.

Group 22. Group 22 comprises each compound named in compound groups 1 through 21, but where $R^2$ moieties 1-10 listed in Table A are replaced with the following moieties:

1 —O—C(S)—O—C1-C8 alkyl-(OH)$_{0-2}$
2 —O—C(S)—O—C1-C8 alkyl-(OH)$_{0-2}$
3 —C(O)—C1-C6 alkyl-O—C1-C2 alkyl
4 —C(O)—C1-C6 alkyl-(S)$_{0-1}$—C1-C2 alkyl-(OH)$_{0-1}$ 5 —C(O)—C1-C6 alkyl-NH$_{0-2}$(C1-C4 alkyl)$_{0-2}$
6 —O—C(O)—C0-C4 alkyl-heterocycle
7 —C(O)—O—C1-C4 alkyl-C6H$_{3-5}$—(OH)$_{0-2}$
8 —O—C(O)—O—C1-C4 alkyl-C6H$_{3-5}$—(OH)$_{0-2}$
9 —O—C(O)—C1-C4 alkyl-C6H$_{3-5}$—(O—C1-C4 alkyl)$_{0-2}$
10 —O—C(O)—C1-C4 alkyl-C6H$_{3-5}$-(halogen)$_{0-2}$ Group 22 comprises subgroups 22-1 through 22-21-17-10-8-6, which name compounds or genera of compounds essentially as described for the other compound groups above. The 1728 subgroups in group 22 are 22-1 through 22-6, 22-7-1 through 22-7-6, 22-8-1 through 22-8-6, 22-9-1 through 22-9-6 and so on essentially as described for the groups above.

Group 23. Group 23 comprises each compound named in compound groups 1 through 21, but where $R^2$ moieties 1-10 listed in Table A are replaced with the following moieties:
1 —O—C$_{0-4}$ alkyl-heterocycle
2 —O—C(O)—C$_{0-4}$ alkyl-heterocycle
3 —SH
4 =S
5 —C2-C6 alkyl-(OH)$_{1-2}$
6 —O—CHR$^{24}$—C(O)—R$^{25}$
7 —O—CHR$^{24}$—C(O)—N(R$^{25}$)$_2$
8 —O—CHR$^{24}$—C(O)—NHR$^{25}$
9 —O—CHR$^{24}$—C(O)—NH$_2$
10 —O—CHR$^{24}$—C(O)—OC$_6$H$_5$ Group 23 comprises subgroups 24-1 through 24-23-21-17-10-8-6, which name compounds or genera of compounds essentially as described for the other compound groups above. The subgroups in group 24 are 24-1 through 24-6, 24-7-1 through 24-7-6, 24-8-1 through 24-8-6, 24-9-1 through 24-9-6 and so on essentially as described for the groups above.

Group 24. Group 24 comprises each compound named in compound groups 1 through 23 where $R^3$ moieties 1-10 listed in Table A are replaced with the following moieties:
1 —O—C(S)—O—C1-C8 alkyl-(OH)$_{0-2}$
2 —O—C(O)—O—C1-C8 alkyl-(OH)$_{0-2}$
3 —C(O)—C1-C6 alkyl-O—C1-C2 alkyl
4 —C(O)—C1-C6 alkyl-(S)$_{0-1}$—C1-C2 alkyl-(OH)$_{0-1}$
5 —C(O)—C1-06 alkyl-NH$_{0-2}$(C1-C4 alkyl)$_{0-2}$
6 —O—C(O)—C0-C4 alkyl-heterocycle
7 —C(O)—O—C1-C4 alkyl-C6H$_{3-5}$—(OH)$_{0-2}$
8 —O—C(O)—O—C1-C4 alkyl-C6H$_{3-5}$—(OH)$_{0-2}$
9 —O—C(O)—C1-C4 alkyl-C6H$_{3-5}$—(O—C1-C4 alkyl)$_{0-2}$
10 —O—C(O)—C1-C4 alkyl-C6H$_{3-5}$-(halogen)$_{0-2}$ Group 24 comprises subgroups 23-1 through 23-21-17-10-8-6, which name compounds or genera of compounds essentially as described for the other compound groups above. The 1728 subgroups in group 23 are 23-1 through 23-6, 23-7-1 through 23-7-6, 23-8-1 through 23-8-6, 23-9-1 through 23-9-6 and so on essentially as described for the groups above.

Group 25. Group 25 comprises each compound named in compound groups 1 through 23, but where $R^3$ moieties 1-10 listed in Table A are replaced with the following moieties:
1 —O—C$_{0-4}$ alkyl-heterocycle
2 —O—C(O)—C$_{0-4}$ alkyl-heterocycle
3 —SH
4 =S
5 —C$_2$-C$_6$ alkyl-(OH)$_{1-2}$
6 —O—CHR$^{24}$—C(O)—R$^{25}$
7 —O—CHR$^{24}$—C(O)—N(R$^{25}$)$_2$
8 —O—CHR$^{24}$—C(O)—NHR$^{25}$
9 —O—CHR$^{24}$—C(O)—NH$_2$
10 —O—CHR$^{24}$—C(O)—OC$_6$H$_5$ Group 25 comprises subgroups 25-1 through 25-23-21-17-10-8-6, which name compounds or genera of compounds essentially as described for the other compound groups above. The subgroups in group 25 are 25-1 through 25-6, 25-7-1 through 25-7-6, 25-8-1 through 25-8-6, 25-9-1 through 25-9-6 and so on essentially as described for the groups above.

Group 26. Group 26 comprises each compound or genus named in compound groups 1 through 25, but wherein $R^1$ is not divalent, i.e., it is not bonded to the carbon atom at the 3 position by a double bond (e.g., $R^1$ is not =O) and it is in the α-configuration, instead of the β-configuration as shown in formula B.

Group 26 comprises subgroups 26-1 through 26-25-23-21-17-10-8-6, which name compounds or genera of compounds essentially as described for the other compound groups above. The subgroups in group 26 are 26-1 through 26-6, 26-7-1 through 26-7-6, 26-8-1 through 26-8-6, 26-9-1 through 26-9-6 and so on essentially as described for the groups above.

Group 27. Group 27 comprises each compound or genus named in compound groups 1 through 26, but wherein $R^2$ is not divalent, i.e., it is not bonded to the carbon atom at the 3 position by a double bond (e.g., $R^2$ is not =O) and it is in the α-configuration, instead of the β-configuration as shown in formula B.

Group 27 comprises subgroups 27-1 through 27-26-25-23-21-17-10-8-6, which name compounds or genera of compounds essentially as described for the other compound groups above. The subgroups in group 27 are 27-1 through 27-6, 27-7-1 through 27-7-6, 27-8-1 through 27-8-6, 27-9-1 through 27-9-6 and so on essentially as described for the groups above.

Group 28. Group 28 comprises each compound or genus named in compound groups 1 through 27, but wherein $R^3$ is not divalent, i.e., it is not bonded to the carbon atom at the 3 position by a double bond (e.g., $R^3$ is not =O) and it is in the β-configuration, instead of the α-configuration as shown in formula B.

Group 28 comprises subgroups 28-1 through 28-27-26-25-23-21-17-10-8-6, which name compounds or genera of compounds essentially as described for the other compound groups above. The subgroups in group 28 are 28-1 through 28-6, 28-7-1 through 28-7-6, 28-8-1 through 28-8-6, 28-9-1 through 28-9-6 and so on essentially as described for the groups above.

Group 29. Group 29 comprises each compound or genus named in compound groups 1 through 28, but wherein $R^4$ is not divalent, i.e., it is not bonded to the carbon atom at the 3 position by a double bond (e.g., $R^4$ is not =O) and it is in the α-configuration, instead of the β-configuration as shown in formula B.

Group 29 comprises subgroups 29-1 through 29-28-27-26-25-23-21-17-10-8-6, which name compounds or genera of compounds essentially as described for the other compound groups above. The subgroups in group 29 are 29-1 through 29-6, 29-7-1 through 29-7-6, 29-8-1 through 29-8-6, 29-9-1 through 29-9-6 and so on essentially as described for the groups above.

Group 30. Group 30 comprises each compound or genus named in compound groups 1 through 29, but wherein $R^5$ is in the α-configuration, instead of the 3-configuration as shown in formula B.

Group 30 comprises subgroups 30-1 through 30-29-28-27-26-25-23-21-17-10-8-6, which name compounds or genera of compounds essentially as described for the other compound groups above. The subgroups in group 30 are 30-1 through 30-6, 30-7-1 through 30-7-6, 30-8-1 through 30-8-6, 30-9-1 through 30-9-6 and so on essentially as described for the groups above.

Group 31. Group 31 comprises each compound or genus named in compound groups 1 through 30, but wherein $R^5$ is in the α-configuration, instead of the β-configuration as shown in formula B.

Group 31 comprises subgroups 31-1 through 31-30-29-28-27-26-25-23-21-17-10-8-6, which name compounds or genera of compounds essentially as described for the other compound groups above. The subgroups in group 31 are 31-1 through 31-6, 31-7-1 through 31-7-6, 31-8-1 through 31-8-6, 31-9-1 through 31-9-6 and so on essentially as described for the groups above.

Group 32. Group 32 comprises each compound or genus named in compound groups 1 through 31, but wherein the hydrogen atom at the 5 position is in the β-configuration, instead of the α-configuration as shown in formula B.

Group 32 comprises subgroups 32-1 through 32-31-30-29-28-27-26-25-23-21-17-10-8-6, which name compounds or genera of compounds essentially as described for the other compound groups above. The subgroups in group 32 are 32-1 through 32-6, 32-7-1 through 32-7-6, 32-8-1 through 32-8-6, 32-9-1 through 32-9-6 and so on essentially as described for the groups above.

Group 33. Group 33 comprises each compound or genus named in compound groups 1 through 32, but wherein the hydrogen atom at the 8 position is in the α-configuration, instead of the β-configuration as shown in formula B.

Group 33 comprises subgroups 33-1 through 33-32-31-30-29-28-27-26-25-23-21-17-10-8-6, which name compounds or genera of compounds essentially as described for the other compound groups above. The subgroups in group 33 are 33-1 through 33-6, 33-7-1 through 33-7-6, 33-8-1 through 33-8-6, 33-9-1 through 33-9-6 and so on essentially as described for the groups above.

Group 34. Group 34 comprises each compound or genus named in compound groups 1 through 33, but wherein the hydrogen atom at the 9 position is in the β-configuration, instead of the α-configuration as shown in formula B.

Group 34 comprises subgroups 34-1 through 34-33-32-31-30-29-28-27-26-25-23-21-17-10-8-6, which name compounds or genera of compounds essentially as described for the other compound groups above. The subgroups in group 34 are 34-1 through 34-6, 34-7-1 through 34-7-6, 34-8-1 through 34-8-6, 34-9-1 through 34-9-6 and so on essentially as described for the groups above.

Group 35. Group 35 comprises each compound or genus named in compound groups 1 through 34, but wherein the hydrogen atom at the 14 position is in the β-configuration, instead of the α-configuration as shown in formula B.

Group 35 comprises subgroups 35-1 through 35-34-33-32-31-30-29-28-27-26-25-23-21-17-10-8-6, which name compounds or genera of compounds essentially as described for the other compound groups above. The subgroups in group 35 are 35-1 through 35-6, 35-7-1 through 35-7-6, 35-8-1 through 35-8-6, 35-9-1 through 35-9-6 and so on essentially as described for the groups above.

Group 36. Group 36 comprises each compound or genus named in compound groups 1 through 35, but wherein $R^4$ in formula B is not divalent, and a second monovalent $R^4$ is present at the 17 position, and the second $R^4$ is a moiety other than hydrogen. As used here, monovalent $R^4$ means that the second $R^4$ moiety is bonded to the carbon atom at the 17 position by a single bond.

The second $R^4$ optionally comprises —OH, —OR$^{PR}$, —SH, —SR$^{PR}$, —NH$_2$, —NHR$^{PR}$, a halogen, optionally substituted alkyl, optionally substituted alkenyl, optionally substituted alkynyl, optionally substituted aryl, optionally substituted alkylaryl, an optionally substituted heterocycle, an ester, an ether, a thioester, a thionoester, a thioether, an optionally substituted monosaccharide, an optionally substituted oligosaccharide, a carbonate, a carbamate, an amide or an amino acid. Any of these moieties, may comprise any $R^4$ structure disclosed herein.

Exemplary second $R^4$ moieties include —C≡C—(CH$_2$)$_n$H (e.g., —C≡CH and —C≡C—CH$_3$), —C═C—(CH$_2$)$_n$H, —(CH$_2$)$_n$H (e.g., —CH$_3$, —C$_2$H$_5$, —C$_3$H$_7$), —(CH$_2$)$_n$C$_6$H$_5$, wherein n is 0, 1, 2, 3, 4, 5, 6, 7 or 8 and any of these exemplary second $R^4$ moieties optionally comprise 1, 2, 3, 4 or more independently selected —O—, —OH, ═O, —S—, —SH, ═S, —NH—, —NH$_2$, —COOH, —COOR$^{PR}$, —F, —Cl, —Br, —I, —SCN, —CN, —NO$_2$, ═NHO, —CH$_3$, —CF$_3$, —C$_2$H$_5$ or —C$_6$H$_5$ moieties that replace (or substitute) one or more hydrogen or carbon atoms, wherein such moieties may be adjacent to one another, e.g., they can comprise —C(O)—NH— or —NH—C(O)—NH—. Typically moieties that replace a hydrogen or carbon atom will not replace a divalent or trivalent carbon atom, e.g., in —CH═CH— or in —C≡C— and specific embodiments include one or more substitutions at carbons that are separated from a —CH═CH— or —C≡C— moiety by one, two, three or more —CH$_2$-moieties. In some embodiments, one or two hydrogen atoms that are bonded to the distal carbon atom is substituted by one or two —OH, ═O—SH, ═S, —NH$_2$, —COOH, —COOR$^{PR}$, —F, —Cl, —Br, —I, —SCN, —CN, —NO$_2$ or ═NHO moieties.

Group 36 comprises subgroups 36-1 through 36-35-34-33-32-31-30-29-28-27-26-25-23-21-17-10-8-6, which name compounds or genera of compounds essentially as described for the other compound groups above. The subgroups in group 36 are 36-1 through 36-6, 36-7-1 through 36-7-6, 36-8-1 through 36-8-6, 36-9-1 through 36-9-6 and so on essentially as described for the groups above.

Group 37. Group 37 comprises each compound or genus named in compound groups 1 through 36, but wherein $R^7$ in formula B is not —CH$_2$— or a heteroatom, i.e., $R^{10}$ is bonded to $R^7$ in formula B and it is not a hydrogen atom.

The $R^{10}$ optionally comprises —OH, ═O, —OR$^{PR}$, —SH, ═S, —SR$^{PR}$, —NH$_2$, —NHR$^{PR}$, a halogen, optionally substituted alkyl, optionally substituted alkenyl, optionally substituted alkynyl, optionally substituted aryl, optionally substituted alkylaryl, an optionally substituted heterocycle, an ester, an ether, a thioester, a thionoester, a thioether, an optionally substituted monosaccharide, an optionally substituted oligosaccharide, a carbonate, a carbamate, an amide or an amino acid. Any of these moieties, may comprise any $R^{10}$ structure disclosed herein.

Exemplary second $R^4$ moieties include —C≡C—(CH$_2$)$_n$H (e.g., —C≡CH and —C≡C—CH$_3$), —C═C—(CH$_2$)$_n$H, —(CH$_2$)$_n$H (e.g., —CH$_3$, —C$_2$H$_5$, —C$_3$H$_7$), —(CH$_2$)$_n$C$_6$H$_5$, wherein n is 0, 1, 2, 3, 4, 5, 6, 7 or 8 and any of these exemplary second $R^4$ moieties optionally comprise 1, 2, 3, 4 or more independently selected —O—, —OH, ═O, —S—, —SH, ═S, —NH—, —NH$_2$, —COOH, —COOR$^{PR}$, —F, —Cl, —Br, —I, —SCN, —CN, —NO$_2$, ═NHO, —CH$_3$, —CF$_3$, —C$_2$H$_5$ or —C$_6$H$_5$ moieties that replace (or substitute) one or more hydrogen or carbon atoms, wherein such moieties may be adjacent to one another, e.g., they can comprise —C(O)—NH— or —NH—C(O)—NH—. In some embodiments, the moieties that replace a hydrogen or carbon atom will not replace a divalent or trivalent carbon atom, or a hydrogen that is bonded to such a carbon atom, e.g., in —CH═CH— or in —C≡C— and specific embodiments include one or more substitutions at carbons that are separated from a —CH=CH— or —C≡C— moiety by one, two, three or more —CH$_2$— moieties. In some embodiments, one or two hydrogen atoms that are bonded to the distal carbon atom is substituted by one, two or three —OH, =O—SH, =S, —NH$_2$, —COOH, —COOR$^{PR}$, —F, —Cl, —Br, —I, —SCN, —CN, —NO$_2$ or =NHO moieties.

Group 37 comprises subgroups 37-1 through 37-36-35-34-33-32-31-30-29-28-27-26-25-23-21-17-10-8-6, which name compounds or genera of compounds essentially as described for the other compound groups above. The subgroups in group 37 are 37-1 through 37-6, 37-7-1 through 37-7-6, 37-8-1 through 37-8-6, 37-9-1 through 37-9-6 and so on essentially as described for the groups above.

Group 38. Group 38 comprises each compound or genus named in compound groups 1 through 37, but wherein R$^8$ in formula B is not —CH$_2$— or a heteroatom, i.e., R$^{10}$ is bonded to R$^8$ in formula B and it is not a hydrogen atom.

This R$^{10}$ optionally comprises —OH, =O, —OR$^{PR}$, —SH, =S, —SR$^{PR}$, —NH$_2$, —NHR$^{PR}$, a halogen, optionally substituted alkyl, optionally substituted alkenyl, optionally substituted alkynyl, optionally substituted aryl, optionally substituted alkylaryl, an optionally substituted heterocycle, an ester, an ether, a thioester, a thionoester, a thioether, an optionally substituted monosaccharide, an optionally substituted oligosaccharide, a carbonate, a carbamate, an amide or an amino acid. Any of these moieties, may comprise any R$^{10}$ structure disclosed herein.

Other exemplary R$^{10}$ moieties include —C≡C—(CH$_2$)$_n$H (e.g., —C≡CH and —C≡C—CH$_3$), —C=C—(CH$_2$)$_n$H, —(CH$_2$)$_n$H (e.g., —CH$_3$, —C$_2$H$_5$, —C$_3$H$_7$), —(CH$_2$)$_n$C$_6$H$_5$, wherein n is 0, 1, 2, 3, 4, 5, 6, 7 or 8 and any of these exemplary second R$^4$ moieties optionally comprise 1, 2, 3, 4 or more independently selected —O—, —OH, =O, —S—, —SH, =S, —NH—, —NH$_2$, —COOH, —COOR$^{PR}$, —F, —Cl, —Br, —I, —SCN, —CN, —NO$_2$, =NHO, —CH$_3$, —CF$_3$, —C$_2$H$_5$ or —C$_6$H$_5$ moieties that replace (or substitute) one or more hydrogen or carbon atoms, wherein such moieties may be adjacent to one another, e.g., they can comprise —C(O)—NH— or —NH—C(O)—NH—. In some embodiments, moieties that replace a hydrogen or carbon atom will not replace a divalent or trivalent carbon atom, or a hydrogen that is bonded to such a carbon atom, e.g., in —CH=CH— or in —C=C— and specific embodiments include one or more substitutions at carbons that are separated from a —CH=CH— or —C≡C— moiety by one, two, three or more —CH$_2$— moieties. In some embodiments, one or two hydrogen atoms that are bonded to the distal carbon atom is substituted by one, two or three —OH, =O—SH, =S, —NH$_2$, —COOH, —COOR$^{PR}$, —F, —Cl, —Br, —I, —SCN, —CN, —NO$_2$ or =NHO moieties.

Group 38 comprises subgroups 38-1 through 38-37-36-35-34-33-32-31-30-29-28-27-26-25-23-21-17-10-8-6, which name compounds or genera of compounds essentially as described for the other compound groups above. The subgroups in group 38 are 38-1 through 38-6, 38-7-1 through 38-7-6, 38-8-1 through 38-8-6, 38-9-1 through 38-9-6 and so on essentially as described for the groups above.

Group 39. Group 39 comprises each compound or genus named in compound groups 1 through 38, but wherein R$^9$ in formula B is not —CH$_2$— or a heteroatom, i.e., R$^{10}$ is bonded to R$^9$ in formula B and it is not a hydrogen atom and wherein when a double bond is present at the 1-2 position, this R$^{10}$ is not bonded to R$^9$ by a double bond. Thus, the carbon atom at the 2 position is not pentavalent or charged.

This R$^{10}$ optionally comprises —OH, =O, —OR$^{PR}$, —SH, =S, —SR$^{PR}$, —NH$_2$, —NHR$^{PR}$, a halogen, optionally substituted alkyl, optionally substituted alkenyl, optionally substituted alkynyl, optionally substituted aryl, optionally substituted alkylaryl, an optionally substituted heterocycle, an ester, an ether, a thioester, a thionoester, a thioether, an optionally substituted monosaccharide, an optionally substituted oligosaccharide, a carbonate, a carbamate, an amide or an amino acid. Any of these moieties, may comprise any R$^{10}$ structure disclosed herein.

Other exemplary R$^{10}$ moieties include —C≡C—(CH$_2$)$_n$H (e.g., —C≡H and —C≡C—CH$_3$), —C=C—(CH$_2$)$_n$H, —(CH$_2$)$_n$H (e.g., —CH$_3$, —C$_2$H$_5$, —(CH$_2$)$_n$C$_6$H$_5$, wherein n is 0, 1, 2, 3, 4, 5, 6, 7 or 8 and any of these exemplary second R$^4$ moieties optionally comprise 1, 2, 3, 4 or more independently selected —O—, —OH, =O, —S—, —SH, =S, —NH—, —NH$_2$, —COOH, —COOR$^{PR}$, —F, —Cl, —Br, —I, —SCN, —CN, —NO$_2$, =NHO, —CH$_3$, —CF$_3$, —C$_2$H$_5$ or —C$_6$H$_5$ moieties that replace (or substitute) one or more hydrogen or carbon atoms, wherein such moieties may be adjacent to one another, e.g., they can comprise —C(O)—NH— or —NH—C(O)—NH—. In some embodiments the moieties that replace a hydrogen or carbon atom will not replace a divalent or trivalent carbon atom, or a hydrogen that is bonded to such a carbon atom, e.g., in —CH=CH— or in —C=C— and specific embodiments include one or more substitutions at carbons that are separated from a —CH=CH— or —C≡C— moiety by one, two, three or more —CH$_2$— moieties. In some embodiments, one or two hydrogen atoms that are bonded to the distal carbon atom is substituted by one, two or three —OH, =O—SH, =S, —NH$_2$, —COOH, —COOR$^{PR}$, —F, —Cl, —Br, —I, —SCN, —CN, —NO$_2$ or =NHO moieties.

Group 39 comprises subgroups 39-1 through 39-38-37-36-35-34-33-32-31-30-29-28-27-26-25-23-21-17-10-8-6, which name compounds or genera of compounds essentially as described for the other compound groups above. The subgroups in group 39 are 39-1 through 39-6, 39-7-1 through 39-7-6, 39-8-1 through 39-8-6, 39-9-1 through 39-9-6 and so on essentially as described for the groups above.

Group 40. Group 40 comprises each compound or genus named in compound groups 1 through 39, wherein R$^7$ in formula B is —O—, instead of a —CH$_2$— or —CHR$^{10}$— moiety, where R$^{10}$ is not hydrogen. Group 40 comprises subgroups 40-1 through 40-39-38-37-36-35-34-33-32-31-30-29-28-27-26-25-23-21-17-10-8-6, which name compounds or genera of compounds essentially as described for the other compound groups. The subgroups in group 40 are 40-1 through 40-6, 40-7-1 through 40-7-6, 40-8-1 through 40-8-6, 40-9-1 through 40-9-6 and so on essentially as described for the groups above. The subgroup 40-1, 40-2 40-8-1, 40-8-2, 40-11-1 and 40-11-2 compounds named 1.2.5.9 have the structures

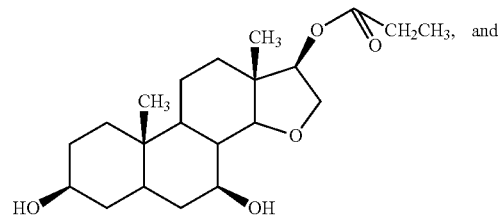

subgroup 40-1 compound 1.2.5.9

-continued subgroup 40-2 compound 1.2.5.9

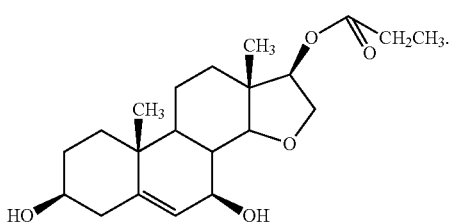

Subgroup 40-8-1 and 40-8-2 compounds named 1.2.5.9 have the structures subgroup 40-8-1 compound 1.2.5.9

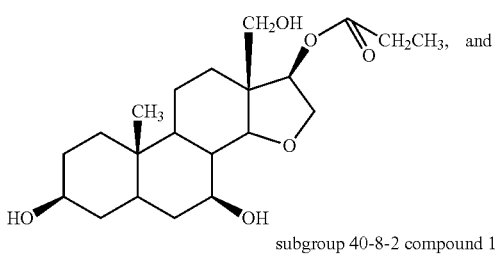

subgroup 40-8-2 compound 1.2.5.9

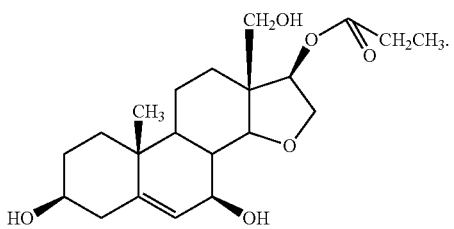

The subgroup 40-11-1 and 40-11-2 compounds named 1.2.5.9 have the structures subgroup 40-11-1 compound 1.2.5.9

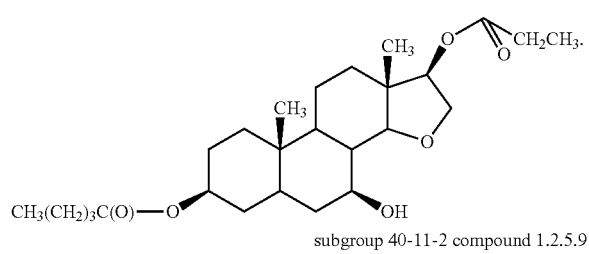

subgroup 40-11-2 compound 1.2.5.9

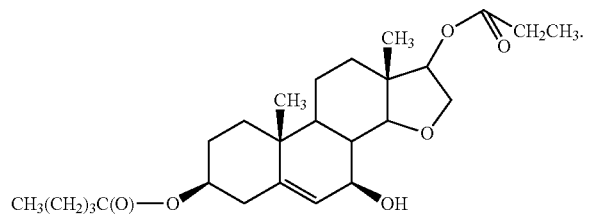

Group 41. Group 41 comprises each compound or genus named in compound groups 1 through 39, wherein $R^8$ in formula B is —O—, instead of a —CH$_2$— or —CHR$^{10}$— moiety, where $R^{10}$ is not hydrogen. Group 41 comprises subgroups 41-1 through 41-39-38-37-36-35-34-33-32-31-30-29-28-27-26-25-23-21-17-10-8-6, which name compounds or genera of compounds essentially as described for the other compound groups. The subgroups in group 41 are 41-1 through 41-6, 41-7-1 through 41-7-6, 41-8-1 through 41-8-6, 41-9-1 through 41-9-6 and so on essentially as described for the groups above. Group 41 compounds are named in essentially the same manner as described for group 40 and other compound groups. Thus, for example, subgroup 41-1, 41-2, 41-8-1, 41-8-2, 41-11-1 and 41-11-2 compounds named 1.2.5.9 have the structures shown for these compounds in group 40, except that an oxygen atom is present at the 11 position and no oxygen is present at the position.

Group 42. Group 42 comprises each compound or genus named in compound groups 1 through 39, wherein $R^8$ in formula B is —O—, instead of a —CH$_2$— or —CHR$^{10}$— moiety, where $R^{10}$ is not hydrogen. Group 42 comprises subgroups 42-1 through 42-39-38-37-36-35-34-33-32-31-30-29-28-27-26-25-23-21-17-10-8-6, which name compounds or genera of compounds essentially as described for the other compound groups. The subgroups in group 42 are 42-1 through 42-6, 42-7-1 through 42-7-6, 42-8-1 through 42-8-6, 42-9-1 through 42-9-6 and so on essentially as described for the groups above. Group 42 compounds are named in essentially the same manner as described for group 40 and other compound groups. Thus, for example, subgroup 42-1, 42-2, 42-8-1, 42-8-2, 42-11-1 and 42-11-2 compounds named 1.2.5.9 have the structures shown for these compounds in group 40, except that an oxygen atom is present at the 2 position and no oxygen is present at the position.

This group does not include species or genera of compounds wherein a double bond is present at the 1-2 position, since this would make the oxygen atom charged. Therefore, there is, e.g., no group 42-3, 42-4, 42-6, 42-7-3, 42-7-4 or 42-7-6, since the 3, 4 and 6 groups and their variants all have a double bond at the 1-2 position.

Group 43. Group 43 comprises each compound or genus named in compound groups 1 through 39, wherein $R^7$ in formula B is —NH—, instead of a —CH$_2$— or —CHR$^{10}$— moiety, where $R^{10}$ is not hydrogen. Group 43 comprises subgroups 43-1 through 43-39-38-37-36-35-34-33-32-31-30-29-28-27-26-25-23-21-17-10-8-6, which name compounds or genera of compounds essentially as described for the other compound groups. The subgroups in group 43 are 43-1 through 43-6, 43-7-1 through 43-7-6, 43-8-1 through 43-8-6, 43-9-1 through 43-9-6 and so on essentially as described for the groups above. The subgroup 43-1, 43-2 43-8-1, 43-8-2, 43-11-1 and 43-11-2 compounds named 1.2.5.9 have the structures shown for these compounds in group 40, except that —NH— is present at the 15 position instead of oxygen.

Group 44. Group 44 comprises each compound or genus named in compound groups 1 through 39, wherein $R^8$ in formula B is —NH—, instead of a —CH$_2$— or —CHR$^{10}$— moiety, where $R^{10}$ is not hydrogen. Group 44 comprises subgroups 44-1 through 44-39-38-37-36-35-34-33-32-31-30-29-28-27-26-25-23-21-17-10-8-6, which name compounds or genera of compounds essentially as described for the other compound groups. The subgroups in group 44 are 44-1 through 44-6, 44-7-1 through 44-7-6, 44-8-1 through 44-8-6, 44-9-1 through 44-9-6 and so on essentially as described for the groups above. Group 44 compounds are named in essentially the same manner as described for group 40 and other compound groups. Thus, for example, subgroup 44-1, 44-2, 44-8-1, 44-8-2, 44-11-1 and 44-11-2 compounds named 1.2.5.9 have the structures shown for these compounds in group 40, except that —NH— is present at the 11 position and no oxygen is present at the 15 position.

Group 45. Group 45 comprises each compound or genus named in compound groups 1 through 39, wherein $R^9$ in formula B is —NH— or —N=, instead of a —CH$_2$— or —CHR$^{10}$— moiety, where $R^{10}$ is not hydrogen. Group 45 comprises subgroups 45-1 through 45-39-38-37-36-35-34-33-32-31-30-29-28-27-26-25-23-21-17-10-8-6, which name compounds or genera of compounds essentially as described for the other compound groups. The subgroups in group 45 are 45-1 through 45-6, 45-7-1 through 45-7-6, 45-8-1 through 45-8-6, 45-9-1 through 45-9-6 and so on essentially as described for the groups above. Group 45 compounds are named in essentially the same manner as described for group 40 and other compound groups. Thus, for example, subgroup 45-1, 45-2, 45-8-1, 45-8-2, 45-11-1 and 45-11-2 compounds named 1.2.5.9 have the structures shown for these compounds in group 40, except that —NH— is present at the 2 position and no oxygen is present at the 15 position.

Group 46. Group 46 comprises each compound or genus named in compound groups 1 through 39, wherein $R^7$ in formula B is —S—, instead of a —CH$_2$— or —CHR$^{10}$— moiety, where $R^{10}$ is not hydrogen. Group 46 comprises subgroups 46-1 through 46-39-38-37-36-35-34-33-32-31-30-29-28-27-26-25-23-21-17-10-8-6, which name compounds or genera of compounds essentially as described for the other compound groups. The subgroups in group 46 are 46-1 through 46-6, 46-7-1 through 46-7-6, 46-8-1 through 46-8-6, 46-9-1 through 46-9-6 and so on essentially as described for the groups above. The subgroup 46-1, 46-2 46-8-1, 46-8-2, 46-11-1 and 46-11-2 compounds named 1.2.5.9 have the structures shown for these compounds in group 40, except that —S— is present at the 15 position instead of oxygen.

Group 47. Group 47 comprises each compound or genus named in compound groups 1 through 39, wherein $R^8$ in formula B is —S—, instead of a —CH$_2$— or —CHR$^{10}$— moiety, where $R^{10}$ is not hydrogen. Group 47 comprises subgroups 47-1 through 47-39-38-37-36-35-34-33-32-31-30-29-28-27-26-25-23-21-17-10-8-6, which name compounds or genera of compounds essentially as described for the other compound groups. The subgroups in group 47 are 47-1 through 47-6, 47-7-1 through 47-7-6, 47-8-1 through 47-8-6, 47-9-1 through 47-9-6 and so on essentially as described for the groups above. Group 47 compounds are named in essentially the same manner as described for group 40 and other compound groups. Thus, for example, subgroup 47-1, 47-2, 47-8-1, 47-8-2, 47-11-1 and 47-11-2 compounds named 1.2.5.9 have the structures shown for these compounds in group 40, except that —S— is present at the 11 position and no oxygen is present at the 15 position.

Group 48. Group 48 comprises each compound or genus named in compound groups 1 through 39, wherein $R^9$ in formula B is —S—, instead of a —CH$_2$— or —CHR$^{10}$— moiety, where $R^{10}$ is not hydrogen. Group 48 comprises subgroups 48-1 through 48-39-38-37-36-35-34-33-32-31-30-29-28-27-26-25-23-21-17-10-8-6, which name compounds or genera of compounds essentially as described for the other compound groups. The subgroups in group 48 are 48-1 through 48-6, 48-7-1 through 48-7-6, 48-8-1 through 48-8-6, 48-9-1 through 48-9-6 and so on essentially as described for the groups above. Group 48 compounds are named in essentially the same manner as described for group 40 and other compound groups. Thus, for example, subgroup 48-1, 48-2, 48-8-1, 48-8-2, 48-11-1 and 48-11-2 compounds named 1.2.5.9 have the structures shown for these compounds in group 40, except that —S— is present at the 2 position and no oxygen is present at the 15 position.

This group does not include species or genera of compounds wherein a double bond is present at the 1-2 position. Therefore, there is, e.g., no group 48-3, 48-4, 48-6, 48-7-3, 48-7-4 or 48-7-6, since the 3, 4 and 6 groups and their variants all have a double bond at the 1-2 position.

Group 49. Group 49 comprises each compound or genus named in compound groups 1 through 39, but wherein two of $R^7$, $R^8$ and $R^9$ in formula B independently are —O—, —NH—, =NH— or —S—, instead of —CH$_2$— or —CHR$^{10}$—, where $R^{10}$ is not hydrogen. This group includes 27 combinations of two heteroatoms (O, N or S) that are at any two of $R^7$, $R^8$ and $R^9$. These are (49c1, i.e., combination number 1) O2-O11 (i.e., oxygen at the 2 and 11 positions), (49c2) O2-O15, (49c3) O11-O15, (49c4) O2-N11 (i.e., oxygen at the 2-position and nitrogen at the 11 position), (49c5) O2-N15, (49c6) O11-N15, (49c7) O2-S11 (i.e., oxygen at the 2-position and sulfur at the 11 position), (49c8) O2-S15, (49c9) O11-S15, (49c10) N2-N11, (49c11) N2-N15, (49c12) N11-N15, (49c13) N2-O11, (49c14) N2-O15, (49c15) N11-O15, (49c16) N2-S11, (49c17) N2-S15, (49c18) N11-S15, (49c19) S2-S11, (49c20) S2-S15, (49c21) S11-S15, (49c22) S2-O11, (49c23) S2-O15, (49c24) S11-O15, (49c25) S2-N11, (49c26) S2-N15 and (49c27) S11-N15.

Group 49 comprises subgroups 49c1-1 through 49c27-39-38-37-36-35-34-33-32-31-30-29-28-27-26-25-23-21-17-10-8-6, which name compounds or genera of compounds essentially as described for the other compound groups. The subgroups in group 49 are 49c1-1 through 49c1-6, 49c1-7-1 through 49c1-7-6, 49c1-8-1 through 49c1-8-6, 49c1-9-1 through 49c1-9-6 and so on essentially as described for the groups above. Group 49 compounds are named in essentially the same manner as described for group 40 and other compound groups. Thus, for example, subgroup 49c1-1, 49c1-2, 49c1-8-1, 49c1-8-2, 49c1-11-1 and 49c1-11-2 compounds named 1.2.5.9 have the structures shown for these compounds in group 40, except that —O— is present at the 2 and 11 positions and no oxygen is present at the 15 position. Similarly, subgroup 49c10-1, 49c10-2, 49c10-8-1, 49c10-8-2, 49c10-11-1 and 49c10-11-2 compounds named 1.2.5.9 have the structures shown for these compounds in group 40, except that —NH— or =N— is present at the 2 and 11 positions and no oxygen is present at the 15 position. This group does not include species or genera of compounds wherein a double bond and either —O— or —S— is present at the 2-position.

Group 50. Group 50 comprises each compound or genus named in compound groups 1 through 39, but wherein all three of $R^7$, $R^8$ and $R^9$ in formula B independently are —O—, —NH—, =NH— or —S—, instead of —CH$_2$— or —CHR$^{10}$—, where $R^{10}$ is not hydrogen. This group includes all combinations of 3 heteroatoms (O, N or S) that are at $R^7$, $R^8$ and $R^9$. The combinations are defined essentially as described for the combinations in group 49. They are (50c1) O2-O11-O15, (50c2) O2-O11-N15, (50c3) O2-N11-O15, (50c4) O2-N11-N15, (50c5) O2-O11-S15, (50c6) O2-S11-O15, (50c7) O2-S11-S15, (50c8) N2-N11-N15, (50c9) N2-N11-O15, (50c10) N2-O11-N15, (50c11) N2-O11-O15, (50c12) N2-N11-S15, (50c13) N2-S11-N15, (50c14) N2-S11-S15, (50c15) S2-S11-S15, (50c16) S2-S11-O15, (50c17) S2-O11-S15, (50c18) S2-S11-O15, (50c19) S2-S11-N15, (50c20) S2-N11-S15, (50c21) S2-N11-N15, (50c22) S2-N11-S15, (50c23) O2-S11-N15, (50c24) N2-O11-S15, (50c25) N2-S11-O15, (50c26) S2-O11-N15 and (50c27) S2-N11-O15.

Group 50 comprises subgroups 50c1-1 through 50c27-39-38-37-36-35-34-33-32-31-30-29-28-27-26-25-23-21-17-10-8-6, which name compounds or genera of compounds essentially as described for the other compound groups. The subgroups in group 50 are 50c1-1 through 50c1-6, 50c1-7-1 through 50c1-7-6, 50c1-8-1 through 50c1-8-6, 50c1-9-1 through 50c1-9-6 and so on essentially as described for the groups above. Group 50 compounds are named in essentially the same manner as described for group 40 and other compound groups. Thus, for example, subgroup 50c1-1, 50c1-2, 50c1-8-1, 50c1-8-2, 50c1-11-1 and 50c1-11-2 compounds named 1.2.5.9 have the structures shown for these compounds in group 40, except that —O— is also present at the 2 and 11 positions. Similarly, subgroup 50c10-1, 50c10-2, 50c10-8-1, 50c10-8-2, 50c10-11-1 and 50c10-11-2 compounds named 1.2.5.9 have the structures shown for these compounds in group 40, except that —NH— or =N— is present at the 2 and 15 positions and oxygen is present at the 11 position. This group does not include species or genera of compounds wherein a double bond and either —O— or —S— is present at the 2-position.

Group 51. Group 51 comprises each compound or genus named in compound groups 1 through 50, but wherein $R^7$ comprises a —X—$CHR^{10}$— moiety, where X is —O—, —$NR^{PR}$— or —S—. This group includes all $R^7$ moieties, i.e., (51a1) —O—$CHR^{10}$—, (51a2) —$NR^{PR}$—$CHR^{10}$—, (51a3) —S—$CHR^{10}$—, (51a4) —$CHR^{10}$—O—, (51a5) —$CHR^{10}$—$NR^{PR}$— and (51a6) —$CHR^{10}$—S—. Group 51 comprises subgroups 51a1-1 through 51a6-50c27-49c27-48-47-46-45-44-43-42-41-40-39-38-37-36-35-34-33-32-31-30-29-28-27-39-38-37-36-35-34-33-32-31-30-29-28-27-26-25-23-21-17-10-8-6, which name compounds or genera of compounds essentially as described for the other compound groups. The subgroups in group 51 are 51a1-1 through 51a1-6, 51a1-7-1 through 51a1-7-6, 51a1-8-1 through 51a1-8-6, 5a1-9-1 through 51a1-9-6 and so on essentially as described for the groups above.

In some embodiments, the $R^{10}$ included in $R^7$ is hydrogen. In others, the $R^{10}$ included in $R^7$ is optionally comprises —OH, =O, —$OR^{PR}$, —SH, =S, —$SR^{PR}$, —$NH_2$, —$NHR^{PR}$, a halogen, optionally substituted alkyl, optionally substituted alkenyl, optionally substituted alkynyl, optionally substituted aryl, optionally substituted alkylaryl, an optionally substituted heterocycle, an ester, an ether, a thioester, a thionoester, a thioether, an optionally substituted monosaccharide, an optionally substituted oligosaccharide, a carbonate, a carbamate, an amide or an amino acid. The $R^{10}$ may comprise any $R^{10}$ structure disclosed herein.

Other exemplary $R^{10}$ moieties include —C≡C—$(CH_2)_n$H (e.g., —C≡H and —C≡C—$CH_3$), —C≡C—$(CH_2)_n$H, —$(CH_2)_n$H (e.g., —$CH_3$, —$C_2H_5$, —$(CH_2)_nC_6H_5$, wherein n is 0, 1, 2, 3, 4, 5, 6, 7 or 8 and any of these exemplary $R^{10}$ moieties optionally comprise 1, 2, 3, 4 or more independently selected —O—, —OH, =O, —S—, —SH, =S, —NH—, —$NH_2$, —COOH, —$COOR^{PR}$, —F, —Cl, —Br, —I, —SCN, —CN, —$NO_2$, =NHO, —$CH_3$, —$CF_3$, —$C_2H_5$ or —$C_6H_5$ moieties that replace (or substitute) one or more hydrogen or carbon atoms, wherein such moieties may be adjacent to one another, e.g., they can comprise —C(O)—NH— or —NH—C(O)—NH—. In some embodiments the moieties that replace a hydrogen or carbon atom will not replace a divalent or trivalent carbon atom, or a hydrogen that is bonded to such a carbon atom, e.g., in —CH=CH— or in —C≡C— and specific embodiments include one or more substitutions at carbons that are separated from a —CH=CH— or —C≡C— moiety by one, two, three or more —$CH_2$— moieties. In some embodiments, one or two hydrogen atoms that are bonded to the distal carbon atom is substituted by one, two or three —OH, =O —SH, =S, —$NH_2$, —COOH, —$COOR^{PR}$, —F, —Cl, —Br, —I, —SCN, —CN, —$NO_2$ or =NHO moieties.

Group 52. Group 52 comprises each compound or genus named in compound groups 1 through 49, but wherein $R^7$ is absent and the ring in formula B that contains $R^7$ comprises a cyclobutyl moiety with $R^3$ and one or two $R^4$ bonded to it. Group 52 comprises subgroups 52-1 through 52-51a6-50c27-49c27-48-47-46-45-44-43-42-41-40-39-38-37-36-35-34-33-32-31-30-29-28-27-39-38-37-36-35-34-33-32-31-30-29-28-27-26-25-23-21-17-10-8-6, which name compounds or genera of compounds essentially as described for the other compound groups. The subgroups in group 52 are 52-1 through 52-6, 52-7-1 through 52-7-6, 52-8-1 through 52-8-6, 52-9-1 through 52-9-6 and so on essentially as described for the groups above.

Group 53. Group 53 comprises each compound or genus named in compound groups 1 through 52, but wherein $R^8$ is absent and the ring in formula B that contains $R^8$ comprises a 5 membered ring moiety. Group 53 comprises subgroups 53-1 through 53-52-51a6-50c27-49c27-48-47-46-45-44-43-42-41-40-39-38-37-36-35-34-33-32-31-30-29-28-27-39-38-37-36-35-34-33-32-31-30-29-28-27-26-25-23-21-17-10-8-6, which name compounds or genera of compounds essentially as described for the other compound groups. The subgroups in group 53 are 53-1 through 53-6, 53-7-1 through 53-7-6, 53-8-1 through 53-8-6, 53-9-1 through 53-9-6 and so on essentially as described for the groups above.

The subgroups here do not include compounds or genera where two ring heteroatoms are present as described in group 49 and where both $R^7$ and $R^8$ are absent ("group 53-52-49-..."), since such groups are mutually incompatible. This holds for all of the compound groups described herein, i.e., whenever the structures that a first group or subgroup specifies is incompatible with the structure that a second group or subgroup specifies, then the structure that the first group or subgroup specifies is not included. However, all other possible compounds and genera are included in such compound groups.

Group 54. Group 54 comprises each compound or genus named in compound groups 1 through 53, but wherein $R^9$ is absent and the ring in formula B that contains $R^9$ comprises a 5 membered ring moiety. Group 54 comprises subgroups 54-1 through 54-53-52-51a6-50c27-49c27-48-47-46-45-44-43-42-41-40-39-38-37-36-35-34-33-32-31-30-29-28-27-39-38-37-36-35-34-33-32-31-30-29-28-27-26-25-23-21-17-10-8-6, which name compounds or genera of compounds essentially as described for the other compound groups. The subgroups in group 54 are 54-1 through 54-6, 54-7-1 through 54-7-6, 54-8-1 through 54-8-6, 54-9-1 through 54-9-6 and so on essentially as described for the groups above. The subgroups here do not include, e.g., compounds or genera where two or three ring heteroatoms are present as described in group 49 or 50 and where two or three of $R^7$, $R^8$ and $R^9$ are absent (e.g., "group 54-52-49-...").

The individual compounds and genera named in groups 1-54 above may also be named using any suitable formal or informal chemical nomenclature. Thus, as will be apparent, individual compounds in these groups include 16α-bromoepiandrosterone, 16α-hydroxyepiandrosterone, 3α,16α-dihydroxy-5α-androstane-17-one, 3α,16α,17β-trihydroxy-5α-androstane, 3α,16α,17α-trihydroxy-5α-androstane, 3β,17β-dihydroxyandrost-5-ene or 3β,7β,17β-trihydroxyandrost-5-ene, 7-oxodehydroepiandrosterone, 16α-fluoroandrost-5-ene-17-one, 7α-hydroxy-16α-fluoroandrost-5-ene-17-one, 7β-hydroxy-16α-fluoroandrost-5-ene-17-one, 17α-hydroxy-16α-fluoroandrost-5-ene, 17β-hydroxy-16α-fluoroandrost-5-ene and the like.

Any of the species of compounds or genera of compounds that are disclosed herein, e.g., as named in compound groups 1 through 54-53-52-51a6-50c27-49c27-48-47-46-45-44-43-42-41-40-39-38-37-36-35-34-33-32-31-30-29-28-27-39-38-

37-36-35-34-33-32-31-30-29-28-27-26-25-23-21-17-10-8-6 or elsewhere in this disclosure, are suitable for use in the methods as described herein or in the cited references.

Additional embodiments of the formula 1 compounds include any compound or genus of compounds that are disclosed herein, e.g., any of the compounds or genera of compounds in groups 1 through 54 wherein one or both of $R^5$ or $R^6$ independently comprises —$CH_2SH$, —CHO, —$CH_2NRPR$, —$CH_2NH_2$, —$C_2H_5$, —$C_2H_4OH$, —$C_2H_4SH$, —$C_2H_4NH_2$, —$CH_2CHO$, —$CH_2CH_2NR^{PR}$, —$CH_2CH_2OH$, —$CH_2CH_2SH$, —$CH_2CH_2C_6H_5$, —$CH_2C_6H_5$ or —$C_6H_5$ wherein any phenyl ($C_6H_5$) moiety in the foregoing groups is optionally substituted at the phenyl ring with 1, 2, 3, 4 or 5 moieties independently selected from those described for esters herein and including $C_{1-6}$ alkyl (optionally substituted with 1 or 2 independently selected —OH, —SH, —O—, —S— or —NH—) C1-6 alkoxy, —F, —Cl, —Br, —I, —CN, —$NO_2$, —OH, —SH, —$COOR^{PR}$, —$NHR^{PR}$ and —C(O)—C1-6 alkyl.

In some embodiments, one or more of the variable groups that are bonded to the formula 1 compound, e.g., $R^1$-$R^6$, $R^{10}$, $R^{15}$, $R^{17}$ and $R^{18}$, independently have the structure(s) and/or independently comprise the named compounds, —H, —OH, =O, —SH, =S, —$NH_2$, —CN, —$N_3$, halogen, —CHO, —CHS, =$CH_2$, =NOH, =NOC(O)$CH_3$, —C(O)—$CH_3$, —C(O)—$(CH_2)_{14}$—$CH_3$, —C≡H, —C≡$CH_3$, —CH=$CH_2$, —CH=$CH_2CH_3$, —O—C(O)—$(CH_2)_m$—$(CF_2)_n$—$CH_3$, —O—C(O)—$(CH_2)_m$—$(CF_2)_n$—$CF_3$, —O—C(O)—$(CH_2)_m$—$(CF_2)_n$—$CH_2F$, —O—C(O)—O—$(CH_2)_m$—$(CF_2)_n$—$CH_3$, —O—C(O)—O—$(CH_2)_m$—$(CF_2)_n$—$CF_3$, —O—C(O)—O—$(CH_2)_m$—$(CF_2)_n$—$CH_2F$, —O—C(O)—NH—$(CH_2)_m$—$(CF_2)_n$—$CH_3$, C(O)—NH—$(CH_2)_m$—$(CF_2)_n$—$CF_3$, —O—C(O)—NH—$(CH_2)_m$—$(CF_2)_n$—$CH_2F$ (where m is 1, 2, 3, 4, 5, 6, 7, 8, 9 or 10, n is 0, 1, 2, 3, 4, 5, 6, 7, 8, 9 or 10, usually n is 0), —CH($CH_3$)—$(CH_2)_2$—C(O)NH—$CH_2COOH$, —CH($CH_3$)—$(CH_2)_2$—C(O)NH—$CH_2SO_3H$, —OSi($CH_3$)$_2$C($CH_3$)$_3$, —C(OH)=$CHCH_3$, =CH$(CH_2)_{0-15}CH_3$, —$(CH_2)_{0-14}CH_2F$, —$(CH_2)_{0-14}CH_2Cl$, —$(CH_2)_{0-14}CH_2Br$, —$(CH_2)_{0-14}CH_2I$, —$(CH_2)_{2-10}$—O—$(CH_2)_{0-4}$—$CH_3$, —$(CH_2)_{2-10}$—S—$(CH_2)_{0-4}$—$CH_3$, —$(CH_2)_{2-10}$—NH—$(CH_2)_{0-4}$—$CH_3$, —O—$(CH_2)_{0-14}CH_2F$, —O—$(CH_2)_{0-14}CH_2Cl$, —O—$(CH_2)_{0-14}CH_2Br$, —O—$(CH_2)_{0-14}CH_2I$, —O—$(CH_2)_{2-10}$—$(CH_2)_{0-4}$—$CH_3$, —O—$(CH_2)_{2-10}$—S—$(CH_2)_{0-4}CH_3$, —O—$(CH_2)_{2-10}$—NH—$(CH_2)_{0-4}CH_3$, —O—C(O)—$(CH_2)_{0-14}CH_2F$, —O—C(O)—$(CH_2)_{0-14}CH_2Cl$, —O—C(O)—$(CH_2)_{0-14}CH_2Br$, —O—C(O)—$(CH_2)_{0-14}CH_2I$, —O—C(O)—$(CH_2)_{2-10}$—O—$(CH_2)_{0-4}$O—$H_3$, —O—C(O)—$(CH_2)_{2-10}$—S—$(CH_2)_{3-4}$—$CH_3$, —O—C(O)—$(CH_2)_{2-10}$—NH—$(CH_2)_{3-4}CH_3$, —O—C(S)—$(CH_2)_{0-14}CH_2F$, —O—C(S)—$(CH_2)_{0-14}CH_2Cl$, —O—C(S)—$(CH_2)_{0-14}CH_2Br$, —O—C(S)—$(CH_2)_{0-14}CH_2I$, —O—C(S)—$(CH_2)_{2-10}$—O—$(CH_2)_{0-4}CH_3$, —O—C(S)—$(CH_2)_{2-10}$—S—$(CH_2)_{0-4}$—$CH_3$, —O—C(S)—$(CH_2)_{2-10}$—NH—$(CH_2)_{0-4}$—$CH_3$, —$(CH_2)_{0-16}NH_2$, —$(CH_2)_{0-15}CH_3$, —$(CH_2)_{0-15}CN$, —$(CH_2)_{0-15}CH$=$CH_2$, —$(CH_2)_{0-15}NHCH(O)$, —$(CH_2)_{0-16}NH$—$(CH_2)_{0-15}CH_3$, —$(CH_2)_{0-15}CCH$, —$(CH_2)_{0-15}OC(O)CH_3$, —$(CH_2)_{0-15}OCH(OH)CH_3$, —$(CH_2)_{0-15}C(O)OCH_3$, —$(CH_2)_{0-15}C(O)OCH_2CH_3$, —$(CH_2)_{0-15}C(O)(CH_2)_{0-15}CH_3$, —$(CH_2)_{0-15}C(O)(CH_2)_{0-15}CH_2OH$, —$O(CH_2)_{1-16}NH_2$, —$O(CH_2)_{1-15}CH_3$, —$O(CH_2)_{1-15}CN$, —$O(CH_2)_{1-15}CH$=$CH_2$, —$O(CH_2)_{1-15}NHCH(O)$, —$O(CH_2)_{1-16}NH$—$(CH_2)_{1-15}CH_3$, —$O(CH_2)_{1-15}CCH$, —$O(CH_2)_{1-15}C(O)CH_3$, —$O(CH_2)_{1-15}OCH(OH)CH_3$, —$O(CH_2)_{1-15}C(O)OCH_3$, —$O(CH_2)_{1-15}C(O)OCH_2CH_3$, —$O(CH_2)_{1-15}C(O)(CH_2)_{0-15}CH_3$, —$O(CH_2)_{1-15}C(O)(CH_2)_{0-15}CH_2OH$, —OC(O)$(CH_2)_{1-16}NH_2$, —OC(O)$(CH_2)_{1-15}CH_3$, —C(O)O$(CH_2)_{1-15}CN$, —C(O)O$(CH_2)_{1-15}CH$=$CH_2$, —OC(O)$(CH_2)_{1-15}NHCH(O)$, —OC(O)$(CH_2)_{1-16}NH$—$(CH_2)_{1-15}CH_3$, —OC(O)$(CH_2)_{1-15}CCH$, —OC(O)$(CH_2)_{1-15}OC(O)CH_3$, —OC(O)$(CH_2)_{1-15}OCH(OH)CH_3$, —OC(O)$(CH_2)_{1-15}C(O)OCH_3$, —OC(O)$(CH_2)_{1-15}C(O)OCH_2CH_3$, —OC(O)$(CH_2)_{1-15}C(O)(CH_2)_{0-15}CH_3$, —OC(O)$(CH_2)_{1-15}C(O)(CH_2)_{0-15}CH_2OH$, phosphoenolpyruvate, D-glucosamine, glucholic acid, glucuronic acid, pantothenic acid, pyruvic acid, glucose, fructose, mannose, sucrose, lactose, fucose, rhamnose, galactose, ribose, (O-1)-D-galactopyranosyl-(1-O-4)-D-glucopyranoside, (O-1)-tetra-O-acetyl-D-glucopyranosyl-(1-O-4)-tri-O-acetyl-D-glucopyranoside, 2'-deoxyribose, 3'-deoxyribose, glycerol, 3-phosphoglycerate, a PEG (PEG 20, PEG 100, PEG 200, PEG 10000), a polyoxyalkylene polymer, glycine, alanine, phenylalanine, threonine, proline, 4-hydroxyproline or an oligonucleotide or analog that comprises about 4 to about 21 monomers.

In some embodiments, an $R^3$ and an $R^4$ of the formula 1 compounds comprises a ring(s) structure. Exemplary compounds of formula 2 include the following structures,

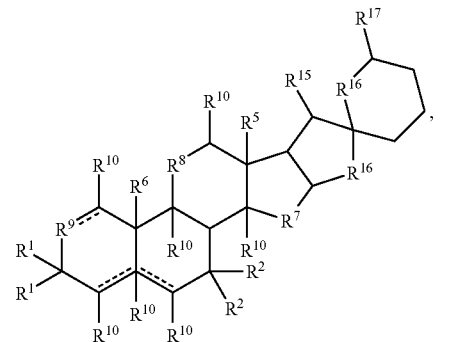

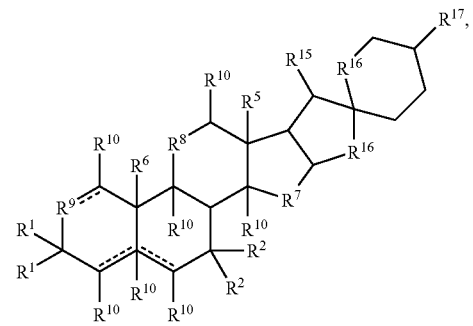

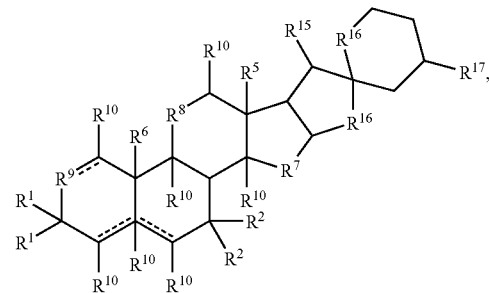

-continued

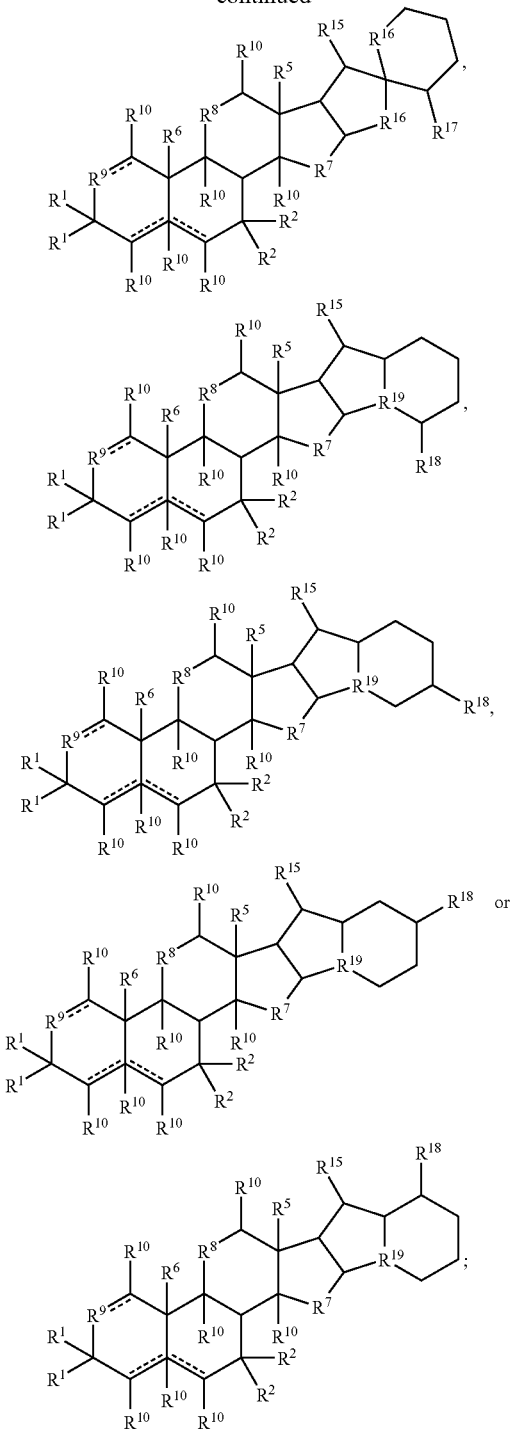

wherein, $R^{16}$ independently are —$CH_2$—, —O—, —S— or —NH—; $R^{15}$, $R^{17}$ and $R^{18}$ independently are —H, —$OR^{PR}$, —$SR^{PR}$, —$N(R^{PR})_2$, —O—Si—$(R^{13})_3$, —CHO, —CHS, —CH=NH, —CN, —SCN, —$NO_2$, —$OSO_3H$, —$OPO_3H$, an ester, a thioester, a thionoester, a phosphoester, a phosphothioester, a phosphonoester, a sulfite ester, a sulfate ester, an amide, an amino acid, a peptide, an ether, a thioether, an acyl group, a thioacyl group, a carbonate, a carbamate, an acetal, a thioacetal, a halogen, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, a nucleoside, a nucleotide, an oligonucleotide, a polymer, or, one or more of $R^{15}$, $R^{17}$ and $R^{18}$ independently are =O, =S, =NOH or =$CH_2$ and the hydrogen atom that is bonded to the same carbon atom is absent; and $R^{19}$ is nitrogen or CH.

Such compounds include any of these structures wherein one, two or three of $R^7$, $R^8$ and $R^9$ are independently —O—, —S—, or —NH— or wherein one or both of $R^5$ and $R^6$ independently are —H, —$CH_3$, —$CH_2OR^{PR}$, —$CH_2OH$, —$CH_2SH$, —$CH_2SR^{PR}$, —$CH_2O$—C(O)—$C_{1-10}$ alkyl, —$CH_2S$—C(O)—$C_{1-10}$ alkyl, —$CH_2O$—C(O)—$C_{1-10}$ alkenyl, —$CH_2S$—C(O)—$C_{1-10}$ alkenyl, —$CH_2O$—C(O)—$C_{0-4}$ alkyl-heterocycle, —$CH_2S$—C(O)—$C_{0-4}$ alkyl-heterocycle, —$CH_2O$—C(O)—$C_{0-4}$ alkyl-phenyl, —$CH_2S$—C(O)—$C_{0-4}$ alkyl-phenyl, wherein any $C_{1-10}$ alkyl, heterocycle or phenyl moiety is optionally substituted with one or more substituents, wherein the one or more substituents are one, two, three or more independently selected —O—, =O, —$OR^{PR}$, —S—, =S, —$SR^{PR}$, —NH—, —$N(R^{PR})_2$ or —C(O)—NH—, wherein each $R^{PR}$ independently is —H or a protecting group.

Exemplary formula 1 compounds will comprise compounds where the steroid has the structure

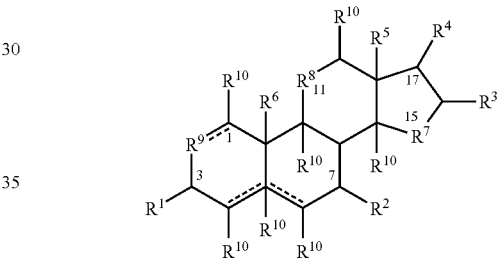

and (1) one of the atoms or groups described immediately above at the 1, 2, 3, 4, 5, 6, 7, 8, 9, 11, 12, 15, 16 or 17 positions, with independently selected groups at the remaining variable group positions, e.g., —H, —OH, =O, —SH, —CHO, —$CH_2$—, —O—, —S—, —NH—, halogen, optionally substituted alkyl, acyl, ester or any other moiety described herein, (2) two of these groups, which are the same or are independently selected and are at, e.g., the 2,3, 2,7, 2,11, 2,15, 2,16, 2,17, 3,7, 3,11, 3,15, 3,16, 3,17, 7,11, 7,15, 7,16, 7,17, 11,15, 11,16, 11,17 or 16,17 positions, with independently selected groups at the remaining variable group positions, e.g., —H, —OH, =O, —SH, —CHO, —$CH_2$—, —O—, —S—, —NH—, halogen, optionally substituted alkyl, acyl, ester or any other moiety described herein, (3) three of these groups, which are the same or are independently selected and are at, e.g., the 2,3,7, 2,3,11, 2,3,15, 2,3,16, 2,3,17, 3,7,11, 3,7,15, 3,7,16, 3,7,17, 7,11,15, 7,11, 16, 7,11,17, 11,15,16, 11,15,17, or 15,16,17 positions, with independently selected groups at the remaining variable group positions, e.g., —H, —OH, =O, —SH, —CHO, —$CH_2$—, —O—, —S—, —NH—, halogen, optionally substituted alkyl, acyl, ester or any other moiety described herein, (4) four of these groups, which are the same or are independently selected and are at, e.g., the 2,3,7,11, 2,3,7,15, 2,3,7, 16, 2,3,7,17, 3,7,11,15, 3,7,11,16, 3,7,11,17, 7,11,15,16, 7,11,15,17 or 11,15,16,17 positions, with independently selected groups at the remaining variable group positions, e.g., —H, —OH, =O, —SH, —CHO, —$CH_2$—, —O—, —S—, —NH—, halogen, optionally substituted alkyl, acyl, ester or any other moiety described herein or (5) any of the foregoing compounds in (1) through (4) wherein 1, 2 or 3 $R^{10}$ at the 1, 4, 5, 6, 9, 12 and 14 positions are —OH, —SH, halogen, an ester, a thioester, a thionoester, optionally substituted alkyl (e.g., C1-C8), optionally substituted alkoxy (e.g., C1-C8), optionally substituted alkenyl (e.g., C2-C8), or an optionally substituted heterocycle or any other moiety described herein and the remaining $R^{10}$ are —H.

When a substituent is an oligonucleotide or a polymer usually only a one of these is bonded to the formula 1 compound. Typically, when $R^1$-$R^2$ and $R^4$-$R^6$ comprise one or more of these substituents (or others described herein), the substituent is present in the β-configuration, while $R^3$ typically comprises a substituent in the β-configuration. In some embodiments, $R^2$ is in the α-configuration.

In some embodiments, one or more of the variable groups that are bonded to the formula 1 compounds, e.g., $R^1$-$R^6$, $R^{10}$, $R^{15}$, $R^{17}$ and $R^{18}$, independently comprise a nucleoside, a nucleotide, an oligonucleotide or an analog of any of these moieties. Typically such moieties are linked to the steroid nucleus through a terminal hydroxyl, thiol, acyl moiety or amine at the 5', 3' or 2' positions, when a hydroxyl, thiol, acyl moiety or amine is present at that position. For oligonucleotides and oligonucleotide analogs, the linkage to the steroid occasionally is through a sugar hydroxyl at an internal 2' position.

Analogs of phosphodiester linkages include phosphorothioate linkages and others as described in the cited references. Oligonucleotide coupling groups means any moiety suitable for generating a phosphodiester linkage or phosphodiester analog linkage between adjacent nucleotides or their analogs. Suitable oligonucleotide coupling groups include —OH, H-phosphonate, alkylphosphonamidites or phosphoramidites such as β-cyanoethyl-phosphoramidite, N,N-diisopropylamino-β-cyanoethoxyphosphine and others as described in the cited references. Suitable purine and pyrimidine bases include adenine, guanine, cytosine, thymine, uracil and others as described in the cited references. Suitable nucleosides, nucleotides, oligonucleotides and their analogs have been described, see e.g., U.S. Pat. Nos. 4,725,677, 4,973,679, 4,997,927, 4,415,732, 4,458,066, 5,047,524, 4,959,463, 5,212,295, 5,386,023, 5,489,677, 5,594,121, 5,614,622, 5624621; and PCT publication Nos. WO 92/07864, WO 96/29337, WO 97/14706, WO 97/14709, WO 97/31009, WO 98/04585 and WO 98/04575 all of which are incorporated herein by reference. The formula 1 compounds, e.g., species or genera named in any of the compound groups 1 through 54-53-52-51a6-50c27-49c27-48-47-46-45-44-43-42-41-40-39-38-37-36-35-34-33-32-31-30-29-28-27-39-38-37-36-35-34-33-32-31-30-29-28-27-26-25-23-21-17-10-8-6, are suitable for linkage to oligonucleotides modulate the lipophilicity of oligonucleotides or the transport or permeation of an oligonucleotide into cells. Such linkages may be biologically labile to facilitate release of the steroid from the oligonucleotide once the conjugate has entered the cell.

Individual formula 1 compounds, e.g., those named in any of the compound groups 1 through 54 are suitable for use as standards for various analytical methods, e.g., for use in HPLC, MS, NMR, IR or other analytical methods. Thus, to aid in the determination of, e.g., the structure of a metabolite of a formula 1 compound or a structurally related compound, another structurally related formula 1 compound could be used. Metabolism of formula 1 compounds will include one or more of hydroxylation or conjugation, usually to a —OH moiety, with a moiety such as sulfate, phosphate or a monosaccharide such as glucuronic acid at, e.g., the 2, 3, 7, 11, 15, 16 or 17 positions. In these embodiments, the appropriate use of a formula 1 compound of known structure as a standard can aid in or verify the identification of metabolites that are projected to have closely related structures. Information regarding the identification can be useful or sometimes is necessary for, e.g., obtaining regulatory approval to market a therapeutic agent such as a formula 1 compound or understanding the potential biological role that a formula 1 compound or its metabolite can play in one of the applications disclosed herein or in a cited reference. To facilitate such uses, the formula 1 compound may be labeled as appropriate, e.g., using a formula 1 compound with, e.g., a $^{13}C$ atom at 1, 2 or more of the 1, 2, 3, 4, 6, 7, 11, 12, 15, 16, 17, 18 or 19 positions in the steroid.

Table 2 shows these and other exemplary moieties that one or more of $R^1$-$R^6$, $R^{10}$, $R^{15}$, $R^{17}$ and $R^{18}$ independently can comprise. Pr means a protecting group. These moieties are often bonded to one or more of the $R^1$, $R^2$ and $R^4$ positions, usually to one or two of those positions. For structures with more than one of a given variable, e.g., X in structure A3 or A5, each is independently selected.

TABLE 2

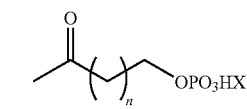

n = 0, 1, 2, 3, 4, 5
X = H, Pr

A

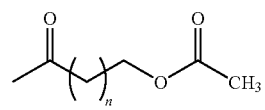

n = 1, 2, 3, 4, 5

B

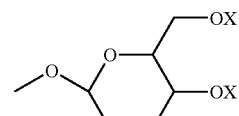

X = —H, —C(O)CH$_3$

C

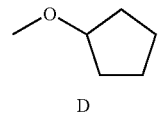

D

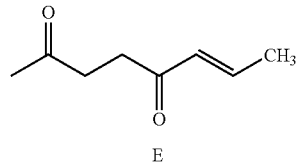

E

TABLE 2-continued
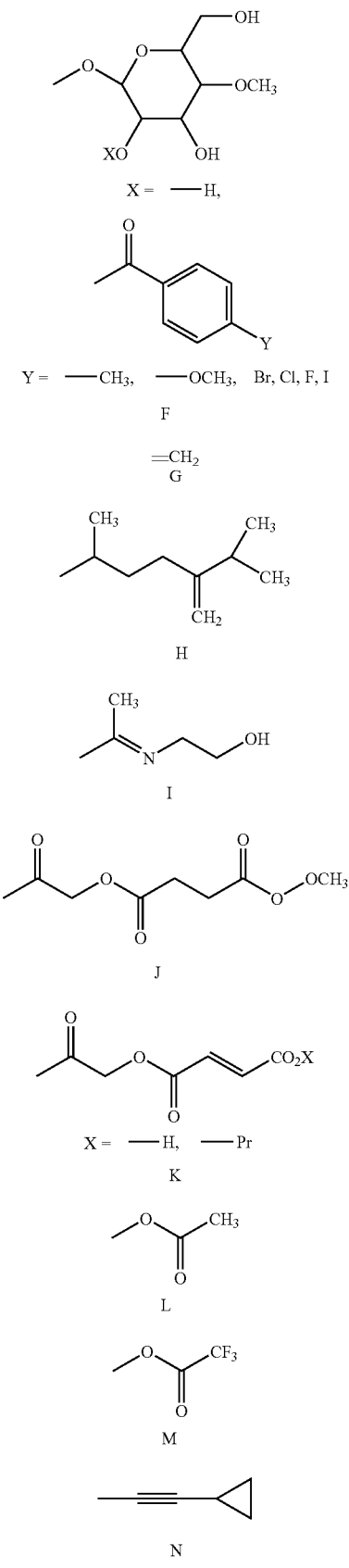
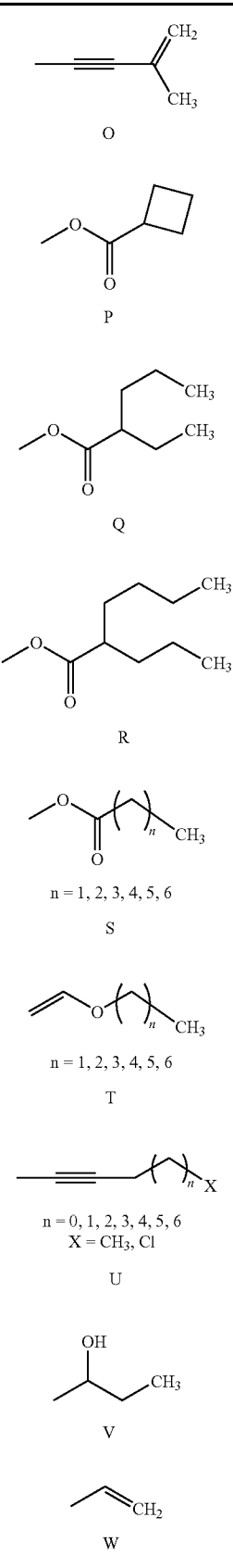

TABLE 2-continued

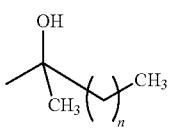

n = 0, 1, 2, 3, 4, 5, 6,

X

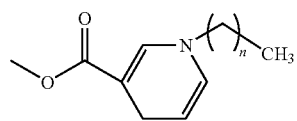

n = 0, 1, 2, 3, 4, 5, 6

Y

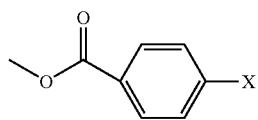

X = F, Cl, Br, NO$_2$,
OCH$_3$, OC$_2$H$_5$, CN

Z

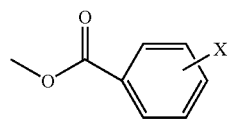

X = H, F, Cl, Br, NO$_2$,
OCH$_3$, OC$_2$H$_5$, CN

A1

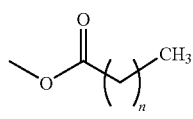

n = 1, 2, 3, 4, 5, 6

A2

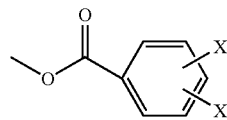

X = H, F, Cl, Br, NO$_2$,
OCH$_3$, OC$_2$H$_5$, CN

A3

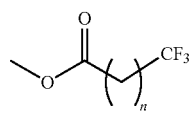

n = 0, 1, 2, 3, 4, 5, 6

A4

TABLE 2-continued

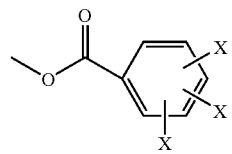

X = H, F, Cl, Br, NO$_2$,
OCH$_3$, OC$_2$H$_5$, CN

A5

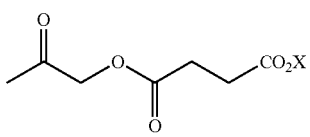

X = H, Pr

A6

Typical containers for storage of compositions and formulations that comprise a formula 1 compound will limit the amount of water that reaches the materials contained therein. Typically, formulations are packaged in hermetically or induction sealed containers. The containers are usually induction sealed. Water permeation characteristics of containers have been described, e.g., Containers—Permeation, chapter, USP 23 <671>, United States Pharmacopeial Convention, Inc., 12601 Twinbrook Parkway, Rockville, Md. 20852, pp.: 1787 et seq. (1995).

The use of formula A compounds for treatment of certain diseases, e.g., infections such as malaria, HCV or *Cryptosporidium*, has been described. Formula A compounds have the structure

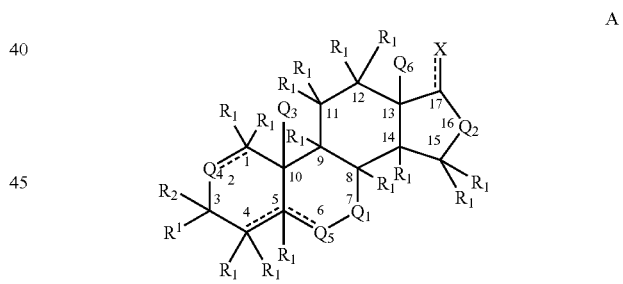

A where $Q_1$ is —C(R$_1$)$_2$— or —C(O)—; $Q_2$ is —C(R$_1$)$_2$—, —C(R$_1$)(Y)—, —C(Y)— or —CH$_2$—CH$_2$—; $Q_3$ is —H or —C(R$_1$)$_3$—; $Q_4$ is —C(R$_1$)$_2$—, —C(O)—, hydroxyvinylidine (—CH(CH=CHOH)—) or methyl methylene (—CH(CH)$_3$—); $Q_5$ is —C(R$_1$)$_2$— or —C(O)—; X and Y independently are —OH, —H, lower alkyl (e.g., C$_{1-6}$ alkyl), —O—C(O)—R$_5$, —C(O)—OR$_5$, halogen (i.e., —F, —Cl, —Br or —I) or =O; each R$_1$ independently is —H, —F, —Cl, —Br, —I, —OH, C$_{1-6}$ alkoxy, or C$_{1-6}$ alkyl; R$_2$ is —H, —OH, —F, —Cl, —Br, —I, C$_{1-6}$ alkyl, C$_{1-6}$ alkoxy, —OR$_3$, an ester (e.g., —O—C(O)—R$_4$ or —C(O)—O—R$_4$), a thionoester (e.g., —O—C(S)—R$_4$ or —C(S)—O—R$_4$), a thioacetal (e.g., —S—C(O)—R$_4$, or —C(O)—S—R$_4$), a sulfate ester (e.g., —O—S(O)(O)—O—R$_4$), a sulfonate ester (e.g., —O—S(O)—O—R$_4$) or a carbamate (e.g., —O—C(O)—NH—R$_4$ or —NH—C(O)—O—R$_4$) or R$_2$, together with the R$_1$ that is bonded to the same carbon atom is =O; R$_3$ is —S(O)(O)—

OM, —S(O)(O)—O—CH$_2$—CH(O—C(O)—R$_6$)—CH$_2$—C(O)—R$_6$, —P(O)(O)—O—CH$_2$—CH(O—C(O)—R$_7$)—CH$_2$—O—C(O)—R$_7$, a glucuronide group of structure (B)

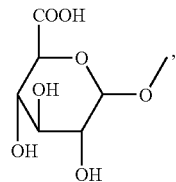

(B)

or R$_3$ is C$_{1-18}$ alkyl, C$_{2-18}$ alkenyl, C$_{2-18}$ alkynyl, a C$_{1-18}$ ester or a C$_{1-18}$ thioester, a C$_{1-18}$ thionoester, where any of the foregoing C$_{1-18}$ or C$_{2-18}$ moieties are optionally substituted at one or more hydrogen atoms with one or more independently selected —OR$^{PR}$, (including —OH), —NHR$^{PR}$, (including —NH$_2$) or —SR$^{PR}$, (including —SH) groups, or R$_3$ is a C$_{1-18}$ fatty acid, C$_{2-10}$ alkynyl, (J)$_n$-phenyl-C$_{1-6}$-alkyl, (J)$_n$-phenyl-C$_{2-6}$-alkenyl; R$_4$ is —H, a protecting group, optionally substituted C$_{1-18}$ alkyl, optionally substituted C$_{1-18}$ alkenyl, optionally substituted C$_{1-18}$ alkynyl, optionally substituted aryl, optionally substituted aryl-C$_{1-6}$ alkyl, optionally substituted aryl-C$_{2-6}$ alkenyl, optionally substituted aryl-C$_{2-6}$ alkynyl, optionally substituted heterocycle-C$_{1-6}$ alkyl, optionally substituted C$_{2-6}$ alkenyl-heterocycle, optionally substituted C$_{2-6}$ alkynyl-heterocycle or an optionally substituted heterocycle, where any of the foregoing moieties are optionally substituted at one, two, three, four, five or more carbon or hydrogen atoms with one or more independently selected —O—, —S—, —NR$^{PR}$— (including —NH—), —NH—C(O)—, —OR$^{PR}$ (including —OH), —NHR$^{PR}$ (including —NH$_2$), —SR$^{PR}$ (including —SH), =O, =S, =N—OH, =CH$_2$, —CN, —SCN, —NO$_2$, —F, —Cl, —Br or —I groups or atoms; each R$_5$ independently is straight or branched C$_{1-14}$ alkyl; each R$_6$ independently is straight or branched C$_{1-14}$ alkyl; each R$_7$ independently is straight or branched C$_{1-14}$ alkyl or a glucuronide group of structure (B); each R$^{PR}$ independently is —H or an independently selected protecting group; n is 0, 1, 2 or 3; each J independently is —F, —Cl, —Br, —I, C$_{1-4}$ alkyl, C$_{1-4}$ alkenyl, C$_{1-4}$ alkoxy, carboxy, nitro, sulfate, sulfonyl, a C$_{1-6}$ carboxyl ester or a C$_{1-6}$ sulfate ester; M is hydrogen, sodium, —S(O)(O)—O—CH$_2$—CH(O—C(O)—R$_6$)—CH$_2$—O—C(O)—R$_6$, —P(O)(O)—O—CH$_2$—CH(O—C(O)—R$_7$)—CH$_2$—O—C(O)—R$_7$ or a glucuronide group of structure (A); the dotted lines in formula 1 represent an optional double bond, provided that there are not double bonds at both the 4-5 and 5-6 positions and provided that when a double bond is present, zero or 1 R$_1$ group is bonded to carbon atoms at the 1-, 2-, 4-, 5-, 6- or 17 positions so that these carbon atoms are tetravalent; and the salts, stereoisomers, positional isomers, metabolites, analogs or precursors.

The formula A compounds, including compounds where both R$_1$ at the 11-position are not hydroxyl, alkoxy or a moiety that can hydrolyze to a hydroxyl, are generally suitable for use in the methods and compositions that are disclosed herein, e.g., their use to enhance a subject's Th1 immune responses or to treat inflammation. Methods of administration and dosages for these compounds are essentially as described herein.

The invention provides compounds having the formula V

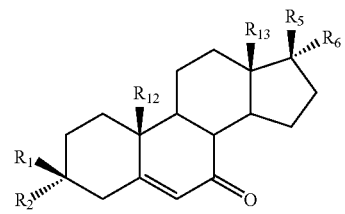

or a pharmaceutically acceptable salt, ester, amide, or prodrug thereof,
wherein (a) R$_1$ and R$_2$ are each independently selected from the group consisting of a hydrogen atom and a glucuronide group having the formula

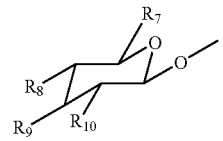

wherein (i) R$_7$ is an alkyl ester wherein the alkyl is optionally substituted, and (ii) R$_9$, R$_9$ and R$_{10}$ are each —OR$_{14}$, wherein R$_{14}$ is a hydrogen atom or a protected hydroxy; and (iii) at least one of R$_1$ or R$_2$ is not hydrogen; (b) R$_5$ and R$_6$ are each independently selected from the group consisting of a hydrogen atom, optionally substituted alkyl, hydroxy, and a protected hydroxy; or R$_5$ and R$_6$ taken together form an oxygen atom, which, together with the carbon atom to which R$_5$ and R$_6$ are joined, forms a ketone group; and (c) R$_{12}$ and R$_{13}$ are each independently selected from the group consisting of a hydrogen atom, optionally substituted alkyl (e.g., methyl, ethyl or —CHO), hydroxy, and a protected hydroxy. Such compounds include ones wherein (1) the protected hydroxy is an ester such as an acetate or proprionate, (2) one of R$_1$ and R$_2$ is a hydrogen atom and the other one of R$_1$ and R$_2$ is said glucuronide, (3) R$_5$ and R$_6$ are each independently selected from the group consisting of a hydrogen atom, hydroxy, and acetate, e.g., one of R$_5$ and R$_6$ is a hydrogen atom and the other is acetate, (4) R$_{12}$ and R$_{13}$ are methyl, and/or (5) R$_7$ is a methyl ester. These compounds include ones where R$_1$ is a glucuronide group, R$_2$ is a hydrogen atom, and R$_5$ and R$_6$ together are =O and methyl 2,3,4-trihydroxy-1-O-(7,17-dioxoandrost-5-ene-3β-yl)-β-D-glucopyranosiduronate and methyl 2,3,4-tri-O-acetyl-1-O-(7,17-dioxoandrost-5-ene-3β-yl)-β-D-glucopyranosid-uronate, or a pharmaceutically acceptable salt, ester, ether, amide, or prodrug thereof.

Other compounds have the formula VI

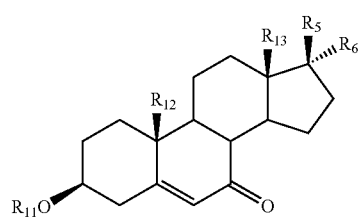

or a pharmaceutically acceptable salt, ester, amide, or prodrug thereof,
wherein (a) R$_5$ and R$_6$ are each independently selected from the group consisting of a hydrogen atom and a glucuronide group having the formula

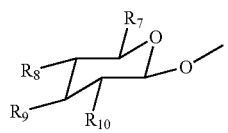

wherein (i) $R_7$ is an alkyl ester wherein the alkyl is optionally substituted, and (ii) $R_8$, $R_9$ and $R_{10}$ are each —$OR_{14}$, wherein $R_{14}$ is a hydrogen atom or a protected hydroxy; and (iii) at least one of $R_5$ and $R_6$ is not hydrogen; (b) $R_{11}$ is a hydrogen atom or a protected hydroxy; and (c) $R_{12}$ and $R_{13}$ are each independently selected from the group consisting of a hydrogen atom, optionally substituted alkyl, hydroxy, and a protected hydroxy. Such compounds include ones wherein (1) the protected hydroxy may be an ester, e.g., acetate or proprionate, (2) one of $R_5$ and $R_6$ is a hydrogen atom and the other one of $R_5$ and $R_6$ is a glucuronide, (3) $R_5$ is a glucuronide group and $R_6$ is a hydrogen atom, (4) $R_{12}$ and $R_{13}$ are methyl, and/or (5) $R_7$ is methyl ester. These compounds include methyl-2,3,4-trihydroxy-1-O-(3β-αcetoxyandrost-5-ene-7-oxo-17β-yl)-β-D-gluco-pyranosiduronate and methyl-2,3,4-tri-β-acetyl-1-O-(3β-αcetoxyandrost-5-ene-7-oxo-17β-yl)-β-D-glucopyranosiduronate, or a pharmaceutically acceptable salt, ester, ether, amide, or prodrug thereof.

Additional compounds include VII

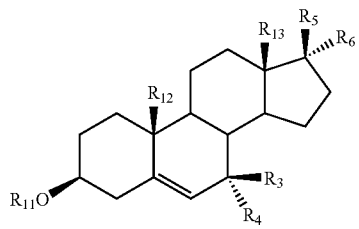

or a pharmaceutically acceptable salt, ester, amide, or prodrug thereof, wherein (a) $R_3$ and $R_4$ are each independently selected from the group consisting of a hydrogen atom and a glucuronide group having the formula

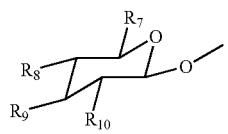

wherein (i) $R_7$ is an alkyl ester wherein the alkyl is optionally substituted, and (ii) $R_8$, $R_9$ and $R_{10}$ are each —$OR_{14}$, wherein $R_{14}$ is a hydrogen atom, optionally substituted alkyl, cycloalkyl, e.g., C3, 4, 5, 6, 7, or 8 cycloalkyl, or a protected hydroxy; and (iii) at least one of $R_3$ and $R_4$ is not hydrogen; (b) $R_5$ and $R_6$ are each independently selected from the group consisting of a hydrogen atom, optionally substituted alkyl, hydroxy, and a protected hydroxy; or $R_5$ and $R_6$ taken together form an oxygen atom, which, together with the carbon atom to which $R_5$ and $R_6$ are joined, forms a ketone group; (c) $R_{11}$ is a hydrogen atom or a protected hydroxy; and (d) $R_{12}$ and $R_{13}$ are each independently selected from the group consisting of a hydrogen atom, optionally substituted alkyl, hydroxy, and a protected hydroxy. Such compounds include ones wherein (1) the protected hydroxy may be an ester, e.g., acetate or proprionate, (2) $R_3$ and $R_4$ are —H and a glucuronide, (3) $R_5$ and $R_6$ are each independently selected from the group consisting of —H, hydroxy, and acetoxy, e.g., they are —H and acetoxy, (4) $R_{12}$ and $R_{13}$ are methyl and/or $R_7$ is methyl ester. Such compounds include ones wherein $R_3$ is a glucuronide group, $R_4$ is —H, $R_5$ is acetate, or wherein $R_6$ is —H and wherein $R_3$ is —H, $R_4$ is a glucuronide group, and $R_5$ and $R_6$ together form =O, and methyl-2,3,4-tri-O-acetyl-1-O-(3β,17β-diacetoxyandrost-5-ene-7β-yl)-β-D-gluco-pyranosiduronate, methyl 1-O-(3β,17β-diacetoxyandrost-5-ene-7β-yl)-β-D-gluco-pyranosiduronate, and methyl-2,3,4-tri-O-acetyl-1-O-(3β-acetoxy-17-oxoandrost-5-ene-7α-yl)-β-D-glucopyranosiduronate, or a pharmaceutically acceptable salt, ester, ether, amide, or prodrug thereof.

The compounds also include compounds having the formula VIII

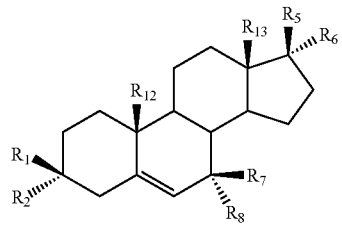

or a pharmaceutically acceptable salt, ester, amide, or prodrug thereof, wherein (a) $R_1$ and $R_2$ are each independently selected from the group consisting of a hydrogen atom and —$OR_{14}$, wherein (i) $R_{14}$ is selected from the group consisting of a hydrogen atom, optionally substituted alkyl, and a protected hydroxy; and (ii) at least one of $R_1$ or $R_2$ is not hydrogen; (b) $R_5$, $R_6$, $R_7$, and $R_8$ are each independently selected from the group consisting of a hydrogen atom, optionally substituted alkyl, hydroxy, and a protected hydroxy; or $R_5$ and $R_6$ taken together form an oxygen atom, which, together with the carbon atom to which $R_5$ and $R_6$ are joined, forms a ketone group; or $R_7$ and $R_8$ taken together form an oxygen atom, which, together with the carbon atom to which $R_7$ and $R_8$ are joined, forms a ketone group; and (c) $R_{12}$ and $R_{13}$ are each independently selected from the group consisting of a hydrogen atom, alkyl, hydroxy, and a protected hydroxy. Such compounds include ones wherein (1) the protected hydroxy is an ester, e.g., acetate or proprionate, or a trialkylsilyl, e.g., t-butyldimethylsilyl, and wherein $R_1$ and $R_2$ are —H and —$OR_{14}$ where $R_{14}$ is optionally selected from methyl, ethyl, n-propyl, i-propyl, n-butyl, sec-butyl, t-butyl, pentyl, hexyl, n-octyl, n-dodecyl, 1-ethoxyethyl, t-butyldimethylsilyl, tetrahydropyran-2-yl, and —C(O)CH₃, (2) $R_5$ and $R_6$ are each independently selected from the group consisting of —H, —OH, and trialkylsilyl, e.g., $R_5$ and $R_6$ are —H and a trialkylsilyl or $R_5$ and $R_6$ are —H and —OH or $R_5$ and $R_6$ together are =O, (3) $R_{12}$ and $R_{13}$ are methyl, and/or (4) $R_7$ and $R_8$ are independently —H, —OH or trialkylsilyl, e.g., $R_7$ and $R_8$ are —H and a trialkylsilyl or $R_7$ and $R_8$ are —H and —OH or $R_7$ and $R_8$ together are =O. These compounds include 3β-tosyloxyandrost-5-ene-17-one, 3β-methoxyandrost-5-ene-17-one, 3β-methoxyandrost-5-ene-7,17-dione, 3β-methoxy-17,17-ethylenedioxyandrost-5-ene-7-one, 3β-methoxy-17,17-ethylenedioxyandrost-5-ene-7β-ol, 3β-methoxy-17,17-ethylenedioxyandrost-5-ene-7α-ol, 3β-methoxyandrost-5-ene-7β,17β-diol, 3β-acetoxy-7α-bromoandrost-5-ene-17-one, 3β-acetoxy-7-methoxyandrost-5-ene-17-one, 3β-methoxyandrost-5-ene-17β-ol, 3β-methoxy-17β-hydroxyandrost-5-ene-7-one, 3β-methoxy-17β-acetoxyandrost-5-ene-7-one, 3β-t-butoxyandrost-5-ene-17-one, 3β-t-butoxyandrost-5-ene-7,17-dione, 3β-t-butyldimethylsilyloxyandrost-5-ene-7,17-dione, 3β,17β-di(t-butyldimethylsilyloxy)androst-5-ene-7-one, 3β-acetoxyandrost-5-ene-7β,17β-diol, 3β-acetoxyandrost-5-ene-7β,17β-di(t-butyldimethylsilyl) ether, 3β-acetoxy-17β-t-butyldimethylsilyloxyandrost-5-ene-7-one, 3β-(2-tetrahydropyranoxy)androst-5-ene-7,17-dione, 3β-dodecanoxyandrost-5-ene-17-one, 3β-dodecanoxyandrost-5-ene-7,17-dione, 3β-(1'-ethoxy)ethoxyandrost-5-ene-17-one, and 3β-(1'-ethoxy)ethoxyandrost-5-ene-7,17-dione, or the pharmaceutically acceptable salt, ester, ether, amide, or prodrug thereof.

Other compounds have the formula IX

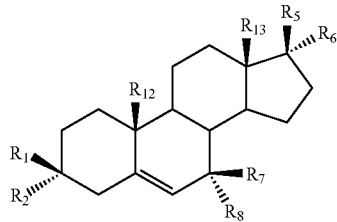

or a pharmaceutically acceptable salt, ester, amide, or prodrug thereof, wherein (a) $R_1$ and $R_2$ are each independently selected from the group consisting of a hydrogen atom and —O—C(O)—$OR_{14}$, wherein (i) $R_{14}$ is selected from the group consisting of a hydrogen atom, optionally substituted alkyl, and a carbocyclic ring; and (ii) at least one of $R_1$ or $R_2$ is not hydrogen; (b) $R_5$, $R_6$, $R_7$, and $R_8$ are each independently selected from the group consisting of a hydrogen atom, optionally substituted alkyl, hydroxy, —O—C(O)—$OR_{14}$, and a protected hydroxy; or $R_5$ and $R_6$ taken together form an oxygen atom, which, together with the carbon atom to which $R_5$ and $R_6$ are joined is =O (a ketone); or $R_7$ and $R_8$ taken together form an oxygen atom, which, together with the carbon atom to which $R_7$ and $R_8$ are joined is =O; and (c) $R_{12}$ and $R_{13}$ are each independently selected from the group consisting of a hydrogen atom, alkyl, hydroxy, and a protected hydroxy. Such compounds include ones wherein (1) the protected hydroxy is an ester, e.g., acetate or proprionate, (2) $R_1$ and $R_2$ are —H and —O—C(O)—$OR_{14}$ and $R_{14}$ optionally is methyl, ethyl, propyl, n-butyl, sec-butyl, t-butyl, n-octyl, n-dodecyl, 1-ethoxyethyl, 9-fluorenylmethyl or —C(O)CH$_3$, (3) $R_5$ and $R_6$ independently are —H, —OH, —O—C(O)—OCH$_3$, —O—C(O)—OC$_2$H$_5$, —O—C(O)—OC$_3$H$_7$, —O—C(O)—OC$_4$H$_9$, —O—C(O)—OCH$_2$C$_2$H$_3$, —O—C(O)—OCH$_2$C$_3$H$_5$ or —O—C(O)—O—(CH$_2$)$_2$—O—C$_2$H$_5$, (3) $R_5$ and $R_6$ are —H and —OH, e.g., $R_5$ and $R_6$ are —H and —OH or together are =O, (4) $R_{12}$ and $R_{13}$ are methyl, (4) $R_7$ and $R_8$ are each independently selected from the group consisting of a hydrogen atom, hydroxy, and trialkylsilyl, e.g., $R_7$ and $R_8$ are —H and —OH or together are =O. These compounds include 3β-carbomethoxyandrost-5-ene-7,17-dione, 3β-carboallyloxyandrost-5-ene-7,17-dione, 3β-carboethoxyandrost-5-ene-7,17-dione, 3β-carboisobutoxyandrost-5-ene-7,17-dione, 3β,17β-dicaromethoxyandrost-5-ene-7-one, 3β-carbooctyloxyandrost-5-ene-7,17-dione, 3β-carbo(9-fluorenyl)methoxyandrost-5-ene-7,17-dione, 3β-carbomethoxyandrost-5-ene-7β,17β-diol, 3β-carboethoxyandrost-5-ene-7β,17β-diol, and 3β-carbooctyloxyandrost-5-ene-7β,17β-diol, or an pharmaceutically acceptable salt, ester, ether, amide, or prodrug thereof.

The compounds of formulas V, VI, VII, VIII and IX can be incorporated into a composition comprising the compound and an excipient, e.g., an excipient disclosed herein. Such compositions are useful to treat subjects having or subject to developing the diseases, conditions or symptoms disclosed herein, e.g., obesity, diabetes, hyperlipidemia, infection, cancer, immune suppression conditions, inflammation or autoimmune conditions. The compounds can thus be used in a method of treatment comprising administering an amount effective of one of these compounds to a subject (e.g., a mammal or human) to treat the disease, condition or symptom or to modulate the subject's immune system, e.g., to enhance a Th1 immune response or to modulate a subject's weight or to slow the progression of a disease or condition.

Dosing protocols or methods. In treating any of the conditions or symptoms disclosed herein, one can continuously (daily) or intermittently administer the formula 1 compound(s) to a subject suffering from or susceptible to the condition or symptom. In treating a condition such as an infection, a hyperproliferation condition, an inflammation condition or another condition disclosed herein with a formula 1 compound intermittent dosing can avoid or ameliorate some of the undesired aspects normally associated with discontinuous dosing. Such undesired aspects include development of resistance of a pathogen such as a pathogen disclosed herein, e.g., a virus or bacterium such as HIV or *Staphylococcus aureus* or a parasite such as a *Plasmodium* parasite, to the therapeutic agent, failure of the patient or subject to adhere to a daily dosing regimen or reduction of the dosages of other therapeutic agents and/or their associated unwanted side effects or toxicities.

In any of the continuous (daily) or intermittent dosing protocols described herein, or in treating any of the diseases, conditions or symptoms described herein, the formula 1 compound(s) can be administered by one or more suitable routes, e.g., oral, buccal, sublingual, intramuscular (i.m.), subcutaneous (s.c.), intravenous (i.v.), intradermal, another parenteral route or by an aerosol. The daily dose in such methods will typically comprise about 0.05 mg/kg/day to about 200 mg/kg/day, or about 0.1 to about 100 mg/kg/day, including about 0.2 mg/kg/day, 0.5 mg/kg/day, about 1 mg/kg/day, about 2 mg/kg/day, about 4 mg/kg/day, about 6 mg/kg/day, about 10 mg/kg/day, about 20 mg/kg/day, about 40 mg/kg/day or about 100 mg/kg/day. Higher dosages, e.g., about 250 mg/kg/day, about 300 mg/kg/day or about 350 mg/kg/day can also be utilized, e.g., in some veterinary applications. One can administer the formula 1 compound(s) orally using about 4 to about 60 mg/kg/day, usually about 6-30 mg/kg/day. In some embodiments, the intermittent dosing methods exclude dosing protocols that are commonly used to deliver contraceptive steroids to, e.g., human females, such as daily dosing for 21 days, followed by no dosing for 7 days. In some embodiments, the non-aqueous formulations described herein that comprise a formula 1 compound(s) are administered i.m. or s.c., while aqueous formulations that contain formula 1 compound(s) is administered by i.v., i.m., s.c. or other parenteral routes.

Intermittent dosing embodiments include administration of a formula 1 compound, e.g., orally, topically or parenterally as follows: (1) daily dosing for about 3 to about 190 days (e.g., about 3 to about 20 days), (2) no dosing of the formula 1 compound for about 4 to about 190 consecutive days (e.g., about 4 to about 20 days), (3) daily dosing for about 3 to about 190 days (e.g., about 3 to about 20 days), and (4) optionally repeating the dosing protocol 1, 2, 3, 4, 5, 6, 10, 15, 20, 30 or more times. Often, the dosing of steps (1) and (3) will be maintained for about 3-15 consecutive days, usually about 3, 4, 5 or 6 consecutive days. In general, steps (1)-(3) of the dosing protocol recited above, will be repeated at least one time, typically at least 2, 3, 4, 5 or 6 times. For infections that tend to remain chronic, e.g., HIV, HCV or other chronic virus or parasite infection, the intermittent dosing protocol is typically maintained over a relatively long time period, e.g., for at least about 6 months to about 5 or more years.

In some embodiments, the number of days of continuous dosing in steps (1) and (3) is the same in each round of treatment, i.e., each time period in step (1) and (3) is the same in the initial and subsequent rounds of the method. In other embodiments they differ. Thus, in some embodiments, step (1) may comprise daily dosing of about 20 mg/day to about 1500 mg/day (e.g., about 50, 75, 100, 125, 150, 175, 200, 225, 250, 275, 300, 325, 350 or 400 mg/day) of a formula 1 compound for 2, 3, 4, 5, 6, 7 or more consecutive days.

Then, step (2) may comprise not administering any formula 1 compound for at least about 4, 5, 6, 7, 14, 21, 28, 42, 56, 84, 98, 112 or more consecutive days. Step (3) could comprise daily administration of about 20 mg/day to about 1500 mg/day (e.g., about 50, 75, 100, 125, 150, 175, 200, 225, 250, 275, 300, 325, 350 or 400 mg/day) of a formula 1 compound for 2, 3, 4, 5, 6, 7 or more consecutive days. Steps (1) through (3) is optionally repeated for about 1-30 or more times. On days when the formula 1 compound is administered to the subject, it may be delivered in a single dose or in two, three or more subdoses at, e.g., about 12 hour or about 8 hour time intervals. Administration of the formula 1 compound would be by one or more of the routes described herein.

Exemplary embodiments comprise (a) administering a formula 1 compound(s), e.g., BrEA or an ester or carbonate of BrEA, once every other day for about 3, 5, 7, 9, 11, 13, 20 or more days, followed by (b) no dosing for about 1, 2, 3, 4, 5, 6, 10, 15, 20, 25, 30, 35, 40, 45, 50, 55, 70, 84, 98, 112 or more days and then (c) administering the formula 1 compound(s) at least once more on one day, e.g., administering the formula 1 compound(s) once every other day for about 3, 5, 7, 11, 13, 20 or more days and (d) optionally repeating (a), (b) and (c) 1, 2, 3, 4, 5 or 6 times or more. A subset of these embodiments comprise (a) administering a formula 1 compound(s), e.g., BrEA or an ester or carbonate of BrEA, once every other day for about 3, 5, 7, 9, 11, 13, 20 or more days, followed by (b) no dosing for at least about 7-190 consecutive days, e.g., about 10-40 days, and then (c) administering the formula 1 compound(s) at least once more on one day, e.g., administering the formula 1 compound(s) once every other day for about 3, 5, 7, 9, 11, 13, or more days and (d) optionally repeating (a), (b) and (c) 1, 2, 3, 4, 5 or 6 times or more. In any of these embodiments, one can administer the formula 1 compound(s) in 2 or 3 subdoses per day.

Other embodiments comprise (a) administering a formula 1 compound(s), e.g., BrEA or an ester or carbonate of BrEA, once every day (or in 2 or 3 daily subdoses) for 3-15 or about 8-12 days, followed by (b) no dosing for 1, 2, 3, 4, 5, 6, 10, 15, 20, 25, 30, 35, 40, 45, 50, 56, 70, 84, 98, 112 or more days and then (c) administering the formula 1 compound(s) at least once more on one day, e.g., administering the formula 1 compound(s) once per day for about 3-15 or about 8-12 consecutive days essentially as described in step (a) and (d) optionally repeating (a), (b) and (c) 1, 2, 3, 4, 5 or 6 times or more. A subset of these embodiments are (a) administering a formula 1 compound(s), e.g., BrEA or an ester or carbonate of BrEA, once every day for about 10 days, followed by (b) no dosing for about 10-40 days and then (c) administering the formula 1 compound(s) at least once more on one day, e.g., administering the formula 1 compound(s) once per day for about 10 days and (d) optionally repeating (a), (b) and (c) 1, 2, 3, 4, 5 or 6 times or more. In any of these embodiments, one can administer the formula 1 compound(s) in 2 or 3 subdoses per day.

One aspect of invention intermittent dosing is monitoring the subject's response to a particular dosing regimen or schedule, e.g., to any intermittent administration method disclosed herein. For example, while dosing a subject who has a viral infection (e.g., HCV, HIV, SIV, SHIV), one can measure the subject's or pathogen's response, e.g., amelioration of one or more symptoms or a change in infectious particles or viral DNA or RNA in the serum or a change in an immune parameter of interest. Once a response is observed dosing can be continued for one, two or three additional days, followed by discontinuing the dosing for at least one day (at least 24 hours), usually for at least about 2, 3, 4, 5, 6, 7, 14, 21, 28, 42, 56, 70, 84, 98, 112 or more days. Once the subject's response shows signs of remission (e.g., a symptom begins to intensify, viral serum DNA or RNA begins to increase or an immune parameter, e.g., as described herein, begins to deteriorate), dosing can be resumed for another course. An aspect of the subject's response to formula 1 compound(s) is that the subject may show a measurable response within a short time, usually about 5-10 days, which allows straightforward tracking of the subject's response, e.g., by monitoring viral titer in peripheral white blood cells ("PBMC"), by measuring viral nucleic acid levels in the blood or by measuring a white blood cell population(s) or expression of a cytokine or interleukin by e.g., white blood cells or a subset(s) thereof. One may monitor one or more immune cell subsets, e.g., NK, LAK, dendritic cells or cells that mediate ADCC immune responses, during and after intermittent dosing to monitor the subject's response and to determine when further administration of the formula 1 compound is indicated. These cell subsets are monitored as described herein, e.g., by flow cytometry.

For any of the treatments or methods described herein, prolonged beneficial effects or a sustained immune response by a subject may result from a single administration or a few daily administrations of the formula 1 compound for from intermittent treatment with the formula 1 compound. A single administration means that a formula 1 compound is administered to the subject in one, two, three or more doses within a 24 hour period and no further administration of any formula 1 compound to the subject occurs for at least about 7-90 days, e.g., about for at least about 30 days to about 2 months, or for about 1.5, 2, 3, 4, 5, 6 or more months. Prolonged beneficial effects or immune responses may also persist after a short course of treatment has been completed (e.g., daily dosing for 2, 3, 4, 5 or 6 days) and the subject is no longer receiving any formula 1 compound, or, in some cases, any other therapeutic treatment to treat the primary cause of the subject's pathological condition. Such beneficial effects can persist for more than about 5-30 days, e.g., for at least about 21, 28, 42, 56, 70, 84, 98, 112 or more days.

Other intermittent dosing embodiments comprise administering to a subject having or susceptible to a condition as described herein an effective amount of a formula 1 compound using an initial induction or high dosing regimen. The high dosing regimen may comprise, e.g., 1, 2, 3, 4, 5, 6, 7 or more daily doses of about 4 to about 40 mg/kg that are administered daily, every other day, every $3^{rd}$ day, every $4^{th}$ day or every $5^{th}$ day. Then, the subject is not dosed with a formula 1 compound for a period, e.g., of about 7, 14, 21, 28, 42, 56, 70, 84, 98, 112 or more consecutive days. Then a lower daily dosing regimen is administered to the subject, e.g., about 0.2 mg/kg to about 4 or about 6 mg/kg, essentially as described for the high dosing regimen. Alternatively, this low dosing regimen may comprise 1, 2, 3, 6 or more rounds of a low to moderate initial level, e.g., about 2 to about 10 mg/kg/day, optionally followed by subsequent rounds of daily dosing that decrease the initial low to moderate level by about 10%, 20%, 30%, 40% or more in each subsequent round of treatment, which is continued until administration is discontinued.

In some cases, beneficial effects from treatment have been observed for more than 3 months (4 or 5 or more months) after a short course of treatment of a subject with a formula 1 compound. Thus, administration of a formula 1 compound provides a method to help protect a subject against progression of an infection or against adverse consequences of unwanted immune reactions (e.g., inflammation) or against immunosuppression (from infection, chemotherapy, or as disclosed herein), without any dosing of the compound for at least 3 months after an initial dosing protocol, which could be an intermittent or a continuous dosing protocol over, e.g., 1 day to about 4 months (1-15 days, about 1 month, about 2 months, etc).

Dosages of the formula 1 compound, routes of administration and the use of combination therapies with other standard therapeutic agents or treatments could be applied essentially as described above for any of the diseases or conditions that are disclosed herein. Thus, the formula 1 compounds may be administered prophylactically or therapeutically in chronic conditions or they may be administered at the time of or relatively soon after an acute event such as the onset of surgery, a migraine or the occurrence of trauma, e.g., accidental central nervous system injury or a cerebral stroke or infarction. For acute events, the formula 1 compounds may thus be administered concurrently, e.g., within about 15 minutes or about 30 minutes of the onset or occurrence of the acute event, or at a later time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours after the onset or occurrence of the acute event. The formula 1 compounds may thus be administered at about 6-120 hours, or about 8-48 hours, about 10-24 hours or about 12-16 hours after an acute event starts or occurs.

Alternatively, the formula 1 compounds may thus be administered before, e.g., within about 15 minutes or about 30 minutes before the onset or occurrence of a planned or anticipated acute event, or at an earlier time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours before the onset or occurrence of the acute event. The formula 1 compounds may thus be administered at about 6-120 hours, or about 8-48 hours, about 10-24 hours or about 12-16 hours before the planned or anticipated acute event starts or occurs.

Invention embodiments include a method to modulate an immune or cellular response in a subject in need thereof comprising administering to the subject, or delivering to the subject's tissues, an effective amount of a compound of formula 1. Immune and cellular response modulation includes enhancing Th1 immune responses, reducing Th2 immune responses, reducing Th1 immune responses, enhancing Th2 immune responses, reducing unwanted or pathological inflammation, enhancing hemopoiesis or modulating the synthesis, level or a biological activity of a biomolecule such as (1) a transcription factor such as a steroid receptor or other associated steroid receptor factor, (2) a purine such as adenosine, (3) a nucleotide cofactor such as NADPH, (4) a cytokine or interleukin or a receptor for a cytokine or interleukin, or (5) another biomolecule as disclosed herein. Such enhancements, reductions, levels or activities are usually in an easily detectable range, e.g., a change compared to a suitable control of at least about 5%, 10%, 20%, 30%, 40%, 50%, 60%, 70%, 80%, 90%, 95% or a range that is between about any two of these values. Typically the subject is in need of such treatment, e.g., by having a clinical condition disclosed herein or being subject to developing such a condition, e.g., having been exposed or potentially exposed to a pathogen or having a predisposing condition such as precancer.

In some embodiments one or more formula 1 compounds or groups of formula 1 compounds may excluded from one or more of the uses disclosed herein. For example, if the subject is in need of enhanced hemopoiesis, the formula 1 compound optionally excludes 5-androstene-3β-ol-17-one, 5-androstene-3β,17β-diol, 5-androstene-3β,7β,17β-triol or a derivative of any of these three compounds that can convert to these compounds by hydrolysis, or if the subject has or is susceptible to developing a memory impairing neurological disorder or memory impairment condition, the compound is not 5-androstene-3β-ol-7,17-dione or 5-androstene-3β,7-diol-17-one or a derivative of these compounds that can has a group at the 7-position that can convert to —OH or =O by hydrolysis. In other embodiments, formula 1 compound is not 4-pregnene-11β,17α,21-triol-3,20-dione, 17α,21-dihydroxypregn-4-ene-3,11,20-trione, 11β,21-dihydroxy-3,20-dioxopregn-4-en-18-al, 11β,17α,21-trihydroxypregna-1,4-diene-3,20-dione, 17α,21-dihydroxypregna-1,4-diene-3,11,20-trione, 3β-hydroxypregn-5-ene-20-one, 3β-hydroxyandrost-5-ene-17-one, pregn-4-ene-3,20-dione, 21-hydroxypregn-4-ene-3,20-dione, 9-fluoro-11β,16α,21-trihydroxy-16-methylpregna-1,4-diene-3,20-dione, 9-fluoro-11β,16α,17β,21-tetrahydroxypregna-1,4-diene-3,20-dione, 9-fluoro-11β,17α,21-trihydroxy-16-methylpregna-1,4-diene-3,20-dione, dehydroepiandrosterone-3-sulfate, 1,4-pregnadiene-17α,21-diol-3,11,20-trione, androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone, 4-dihydrotestosterone, 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol, testosterone, methyl testosterone, testolactone, oxymetholone, fluoxymesterone, acetoxypregnenolone, allylestrenol, anagestone acetate, chlormadinone acetate, cyproterone, cyproterone acetate, desogestrel, dihydrogesterone, dimethisterone, ethisterone (17α-ethynyltestosterone), ethynodiol diacetate, fluorogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone, progesterone, cyproterone acetate, norethindrone, norethindrone acetate, levonorgestrel, an ester of any of the foregoing compounds (e.g., acetate, enanthate, propionate, isopropionate, cyclopropionate, isobutyrate, butyrate, valerate, caproate, isocaproate, hexanoate, heptanoate, octanoate, nonanoate, decanoate, undecanoate, phenylacetate or benzoate esters, e.g., hydroxyl esters), a naturally occurring glucorcorticoid, a species disclosed herein or a derivative of any of these that can convert to these molecules by hydrolysis or metabolism, e.g., a metabolizable or hydrolyzable ester or ether such as a cyclic ketal, an acetate, a diacetete, a proprionate, a diproprionate, or an O-alkyl, an acyl, e.g., —C(O)—C1-C6 alkyl or another moiety that is bonded at, e.g., a variable group such as for $R^1$-$R^6$ as disclosed herein.

Synthesis methods. Reagents and reaction conditions that one can use to make the formula 1 compounds have been described, see e.g., the citations above, U.S. Pat. Nos. 5,874,598, 5,874,597, 5,874,594, 5,840,900; PCT publication number WO 9901579. General chemical synthetic methods to link a variety of organic moieties to various reactive groups have been described. For example, in G. T. Hermanson, *Bioconjugate Techniques*, Academic Press, 1996, functional targets such as amino acids, peptides and carbohydrates are described at pages 3-136, while the chemistries of reactive groups in the functional targets, e.g., amine, thiol, carboxyl, hydroxyl, aldehyde, ketone and reactive hydrogen atoms (e.g., —H linked to an electron-donating moiety such as a heteroaryl moiety) are described at pages 137-166. This reference also describes reagents useful to make the derivatives, e.g., zero-length cross-linkers, heterobifunctional cross-linkers, homobifunctional cross-linkers, tags, probes and polymers are described at pages 169-416 and 605-638. This reference also describes synthetic methods to modify oligonucleotides at pages 639-671.

In one aspect, amino acids or peptides are linked to the steroid through the amine group using a coupling reagent such as phosgene (Cl—CO—Cl) or Cl—CS—Cl and suitably protected amino acids or peptides and steroids, which are protected as needed. Such linkage generates an intervening —CO—O— or a —CS—O— moiety between the amino acid or peptide and the steroid nucleus.

By way of exemplification and not limitation, the following methods are used to prepare the one or more of the compounds disclosed herein. Starting materials and straightforward variations of the schemes are found, e.g., in the following references, which are incorporated herein by reference: A. P. Davis, et al., Tetrahedron Lett., 33: 5111-5112, 1992; I. Takashi, et al., Chem. Pharm. Bull., 34: 1929-1933, 1986; I. Weisz, et al., Arch. Pharm., 319: 952-953, 1986; T. Watabe, et al., J. Med. Chem., 13: 311-312, 1970; M. Davis, et al., J. Chem. Soc. C., (11): 1045-1052, 1967; R. C. Cambie, et al., J. Chem. Soc., Perkin Trans. 1, (20): 2250-2257, 1977; L. Minale, et al., J. Chem. Soc., Perkin Trans. 1, (20): 2380-2384, 1974; C. K. Lai, et al., Steroids, 42: 707-711, 1983; S. Irie, et al., Synthesis, (9): 1135-1138, 1996; E. J. Corey, J. Am. Chem. Soc., 118: 8765-8766, 1996; M. E. Annunziato, et al., Bioconjugate Chem., 4: 212-218, 1993; N. J. Cussans, et al., J. Chem. Soc., Perkin Trans. 1, (8): 1650-1653, 1980; D. H. R. Barton, et al., J. Chem. Soc., Chem. Commun., (9): 393-394, 1978; H. Loibner, et al., Helv. Chim. Acta, 59: 2100-2113, 1976; T. R. Kasturi, et al., Proc. Indian Acad. Sci., [Ser.]: Chem. Sci., 90: 281-290, 1981; T. Back, J. Org. Chem., 46: 1442-1446, 1981; A. Canovas, et al., Helv. Chim. Acta, 63: 486-487, 1980; R. J. Chorvat, et al., J. Org. Chem., 43: 966-972, 1978; M. Gumulka, et al., Can. J. Chem., 63: 766-772, 1985; H. Suginome, et al., J. Org. Chem., 55: 2170-2176, 1990; C. R. Engel, et al., Can. Heterocycles, 28: 905-922, 1989; H. Sugimone, et al., Bull. Chem. Soc. Jpn., 62: 193-197, 1989; V. S. Salvi, et al., Can. Steroids, 48: 47-53, 1986; C. R. Engel, et al., Can. Steroids, 47: 381-399, 1986; H. Suginome, et al., Chem. Lett., (5): 783-786, 1987; T. Iwadare, et al., J. Chem. Soc., Chem. Commun., (11): 705-706, 1985; H. Nagano, et al., J. Chem. Soc., Chem. Commun., (10): 656-657, 1985; V. S. Salvi, et al., Steroids, 27: 717-725, 1976; C. H. Engel, et al, Steroids, 25: 781-790, 1975; M. Gobbini, et al., Steroids, 61: 572-582, 1996; A. G. Gonzalez, et al., Tetrahedron, 46: 1923-1930, 1990; S. C. Bobzin, et al., J. Org. Chem., 54: 3902-3907, 1989; B. Solaja, et al., Croat. Chem. Acta, 59: 1-17, 1986; Y. Kashman, et al., Tetrahedron, 27: 3437-3445, 1971; K. Yoshida, et al., Chem. Pharm. Bull. (Tokyo), 15: 1966-1978, 1967; P. B. Sollman, et al., Chem. Commun. (11): 552-554, 1967; H. Suginome, et al., J. Org. Chem., 55: 2170-2176, 1990; H. Suginome, et al., Journal Chem. Lett., (5): 783-786, 1987; G. A. Tolstikov, et al., Zh. Org. Khim., 22: 121-132, 1986; T. Terasawa, et al., J. Chem. Soc., Perkin Trans. 1, (4): 990-1003, 1979; Z. Zhuang, et al., Yougi Huaxue, (4): 281-285, 1986; W. T. Smith, et al., Trans. Ky. Acad. Sci., 45: 76-77, 1984; A. K. Batta, et al., Steroids, 64: 780-784, 1999; B. Ruan, et al., Steroids, 65: 29-39, 2000; L. Gamido, et al., Steroids, 65: 85-88, 2000; P. Ramesh, et al., Steroids, 64: 785-789, 1999; M. Numazawa, et al., Steroids, 64: 187-196, 1999; P. N. Rao, et al., Steroids, 64: 205-212, 1999; M. Numazawa, et al., Steroids, 64: 320-327, 1999; U.S. Pat. Nos. 3,281,431, 3,301,872, 3,325,535, 3,325,536, 3,952,018, 4,602,008, 5,571,795, 5,627,270, 5,681,964, 5,744,453; international publication numbers WO 9408588, WO 9508558, WO 9508559, WO 9638466, WO 9809450; United Kingdom patent numbers GB 1168227, GB 813529, GB 802618; French patent number 824529; Japan patent number JP 45010134; European patent applications EP 232788, EP 430078; and German patent number DE 19631189.

Exemplary synthesis methods are shown below.

Scheme 1. For the structures shown in scheme 1, $R^5$-$R^9$ are as defined for formula 1 compounds. Thus, when $R^5$ and $R^6$ are both —$CH_3$ in the β-configuration, $R^7$, $R^8$ and $R^9$ are all —$CH_2$—, H at the 9 and 14 positions are in the α-configuration, acetate at the 3-position is in the β-configuration, and H at the 8 position is in the β-configuration, the first compound in scheme 1 is DHEA acetate. The acetate groups at the 3, 7, 16, 17 or other positions in this scheme and in other schemes disclosed herein may independently be other ester moieties as described herein, e.g., $C_{2-50}$ esters including —C(O)—$(CH_2)_{0-4}$—$(CF_2)_{0-4}$—$CF_3$, including —C(O)—$CF_3$, —C(O)—$C_{2-29}$ optionally substituted alkyl, —C(O)—$CH_2$—$C_{2-28}$ optionally substituted alkenyl, —C(O)—$CH_2$—$C_{2-28}$ optionally substituted alkynyl, —C(O)—$(CH_2)_{0-6}$-optionally substituted phenyl, or —C(O)—$(CH_2)_{0-6}$-optionally substituted heterocycle or other organic moieties as disclosed herein or in the cited references.

Typical substituents for these organic moieties are as described herein, including one, two, three or more independently selected —O—, =O, optionally protected hydroxyl, —S—, optionally protected thiol, —NH—, optionally protected —$NH_2$, optionally protected —C(O)OH, —C(O)—NH—, —C(O)—$NH_2$, —$NH_2$—C(O)—H, —$NH_2$—C(O)—$C_{0-4}H_{1-9}$, —$NH_2$—C(O)—O—$C_{0-4}H_{1-9}$, —CN, —$NO_2$, —$N_3$ or halogen. Reactive groups are protected as needed, e.g., =O would usually be protected in the LiCR reaction that is used to generate compound 1 in scheme 1 below.

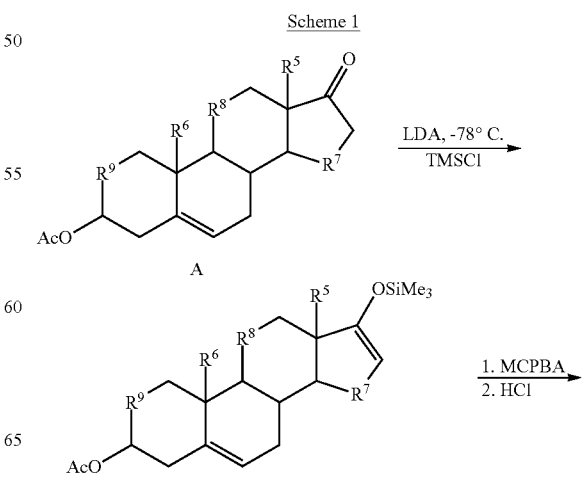

Scheme 1

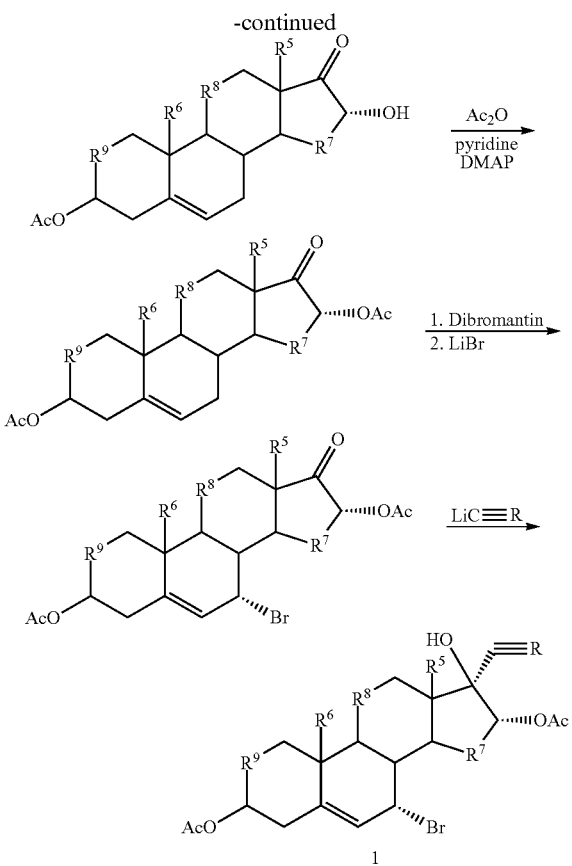

Abbreviations:
LDA = lithium diisopropyl amide; MCPBA = m-chloroperbenzoic acid; TMSCl = trimethylchlorosilane; DMAP = 4-dimethylaminopyridine; Dibromantin = 1,3-dibromo-4,4-dimethylhydantoin.
R = CR$^A$; R$^A$ = —H or a C1-C50 organic moiety as described herein, e.g., —H, —C$_{1-20}$ optionally substituted alkyl, —C$_{1-20}$ optionally substituted alkenyl, —C$_{1-20}$ optionally substituted alkynyl, —(CH$_2$)$_{0-6}$-optionally substituted phenyl or —(CH$_2$)$_{0-6}$-optionally substituted heterocycle.

Scheme 2. Compounds of formula 2 are prepared from structure A compounds shown in scheme 1 using the last two steps of Scheme 1: (1a) dibromantin, (1b) LiBr, (2) Li—C≡R, where R is CR$^A$ and R$^A$ is as defined above, e.g., —H, —CH$_3$, —CH$_2$N$_3$, —CH$_2$NH$_2$, —CH$_2$—O-organic moiety, —CH$_2$—S-organic moiety, —C$_{1-12}$ optionally substituted alkyl. When R$^7$, R$^8$ and R$^9$ are all —CH$_2$—, H at the 9 and 14 positions are in the α-configuration and H at the 8 position is in the β-configuration the first compound in scheme 1 is DHEA acetate. Typical substituents for the R$^A$ alkyl moiety includes one, two or more independently selected —O—, optionally protected =O, optionally protected hydroxyl, —S—, optionally protected thiol, —NH—, optionally protected —NH$_2$, optionally protected —C(O)OH, —C(O)—NH—, —C(O)—NH$_2$, —NH$_2$—C(O)—H, —NH$_2$—C(O)—C$_{0-4}$H$_{1-9}$, —NH$_2$—C(O)—O—C$_{0-4}$H$_{1-9}$, —CN, —NO$_2$, —N$_3$ or halogen.

Scheme 2

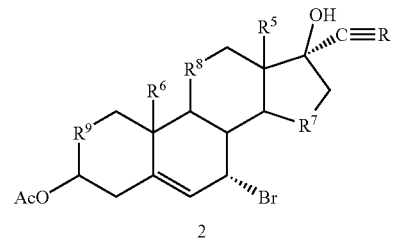

Scheme 3. The allylic bromination at C-7 is done as in Scheme 1. R and R$^A$ are as defined in Schemes 1 and 2.

Scheme 3

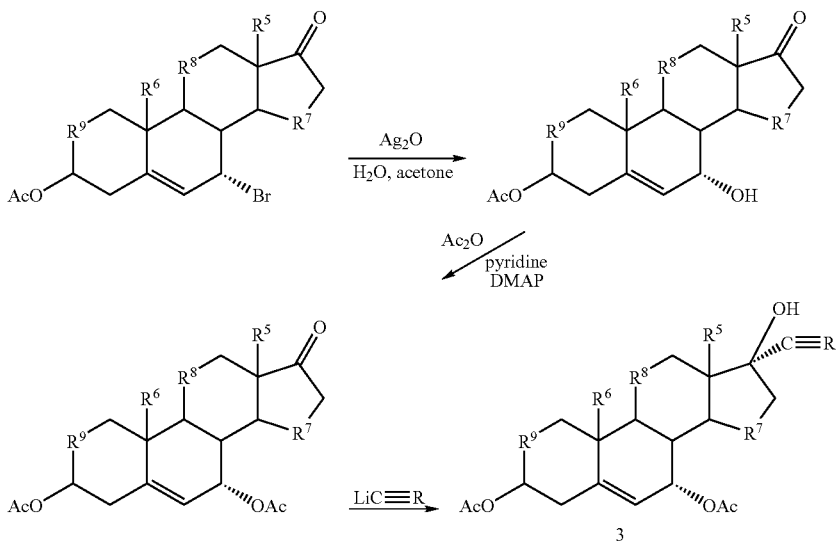

Scheme 4. The addition of lithium reagent (lithium acetylide when R is —CH) to the 17-position >O=O in the presence of the bromide at C-16 results in epoxide formation or in a pinacol rearrangement (not shown). Alternatively, compounds without the C-7 acetate of structure 3 can be dehydrated by mild acid catalysis to form compounds of formula 4 by treatment of the alkene with $Br_2$, $H_2O$. R and $R^A$ are as defined in Schemes 1 and 2.

Scheme 4

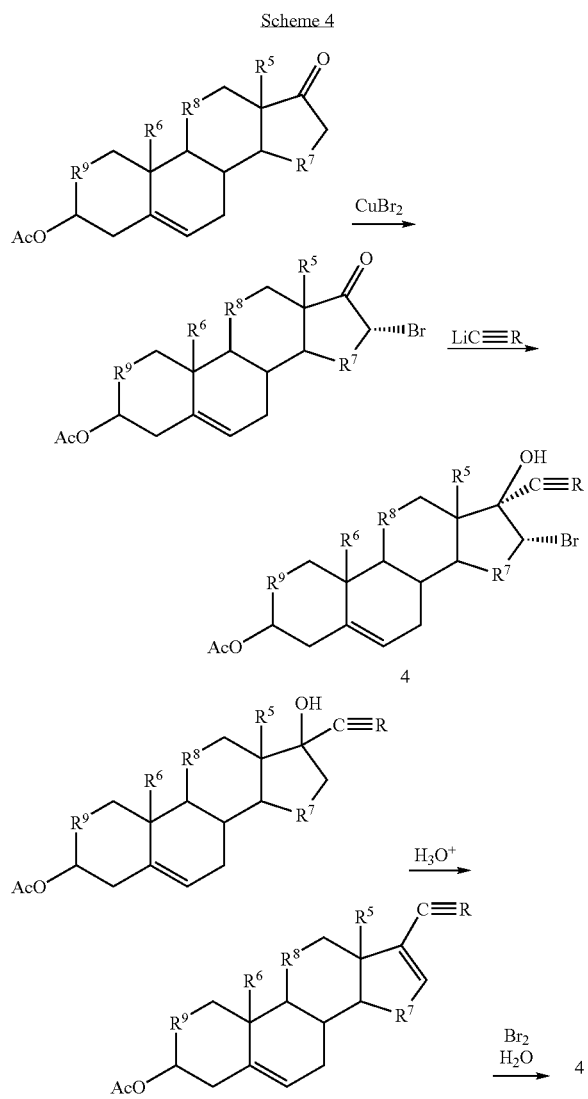

Scheme 5. Sodium borohydride gives a mixture of epimers at C-7, which may be separated by standard methods, e.g., HPLC, TLC or column chromatography. To obtain the pure 7α-OH compound, allylic bromination followed by hydrolysis is accomplished as described in Schemes 1 and 3.

Scheme 5

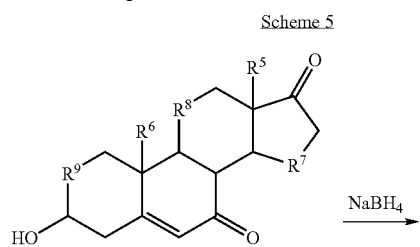

-continued

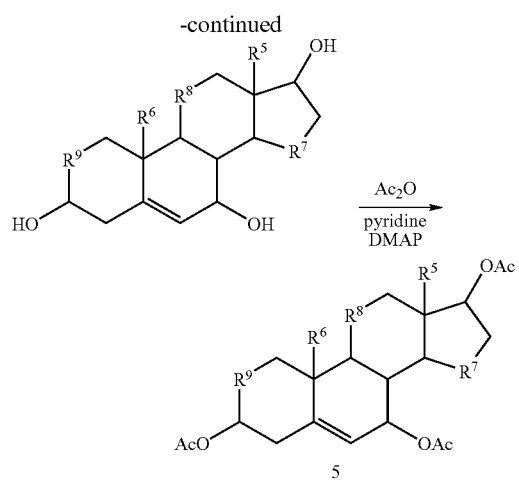

Scheme 6

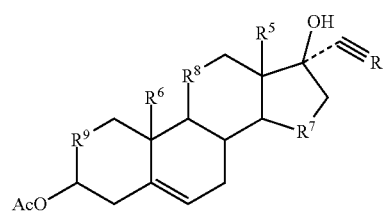

Scheme 6. Formula 6 compounds are prepared by treatment of the acetate A with lithium acetylide as in Schemes 1, 2, 3 or 4. R and $R^A$ are as defined in Schemes 1 and 2.

Scheme 7. Formula 7 compounds are prepared from the 3-acetate A with reagents described in Schemes 1 and 4. R and $R^A$ are as defined in Schemes 1 and 2.

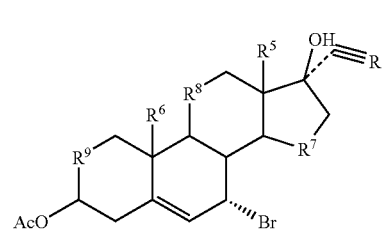

Scheme 8. Formula 8 compounds are prepared from the formula A compounds by sodium borohydride reduction at C-17 followed by acetylation.

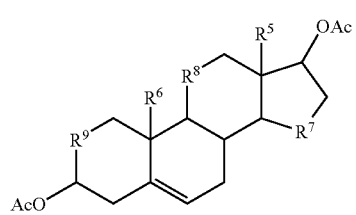

Scheme 9. The starting material is made using reactions described in Schemes 1 and 3. Rearrangement of the C-17 carbonyl to the C-16 position followed by reduction with $NaBH_4$ selectively gives the C-16 β hydroxy function.

Scheme 9

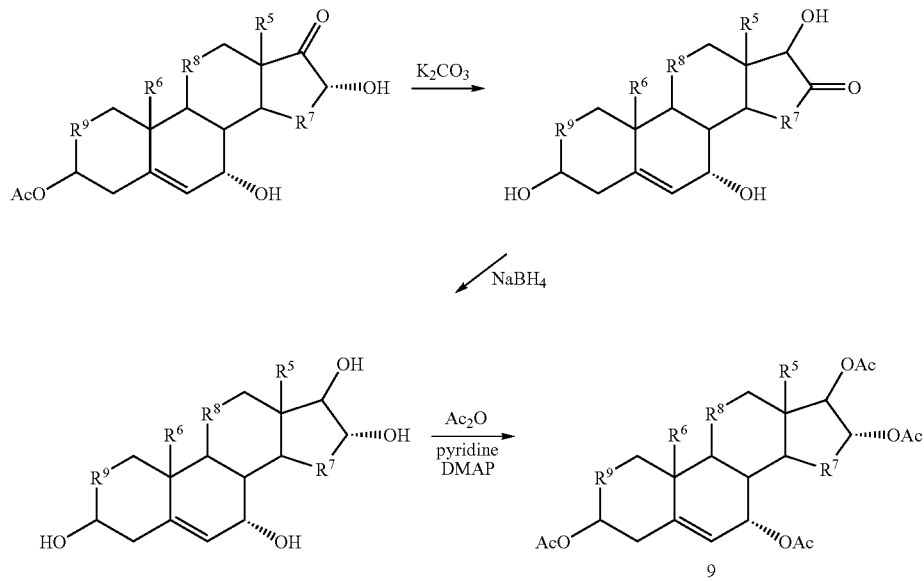

Scheme 10. Reduction and acetylation at C-3 and hydrolysis and oxidation at C-17 will allow formula 10a and 10b compounds to undergo functionalization as shown in Schemes 1-9 at C-3, C-16 and C-17. The 7-oxo acetate can be substituted for the formula A compound 3-acetate and functionalization at C-3, C-16 and C-17 is achieved similarly for T-oxo compounds using the reactions shown in schemes 1-9.

Treatment of 10a with LDA, followed by alkylation of the enolate allows introduction of side chains such as $R^{10}$, which may be, e.g., C1-C20 alkyl (methyl, ethyl), C1-C20 alkenyl $(CH_2=CH-(CH_2)_{0-6}-)$, benzyl, $-(CH_2)_{1-4}-O-(CH_2)_{0-4}-CH_3$.

Schemes 1-9 show the introduction of the hydroxyl function at the positions shown. Methods to convert hydroxyl to other functional groups are accomplished essentially as described, e.g., in the references cited herein. For example, esters, of formula 1-10c compounds, such as $-O-C(O)-R^B$ where $R^B$ is a $C_{1-50}$ organic moiety, are prepared from the steroid alcohol by treatment with the appropriate acid anhydride or acid chloride ($R^B-C(O)-Cl$) to form any desired ester. Ethers, such as $-O-R^B$, are prepared from alcohols by formation of the alkaline metal alkoxide ($N^+$ or $K^+$) followed by treatment with a primary or secondary iodide ($R^B-I$). Thionoesters, $R^B-C(S)-O-$, are prepared by treating the $R^B-C(O)-O-$ ester with Lawesson's reagent.

Scheme 10

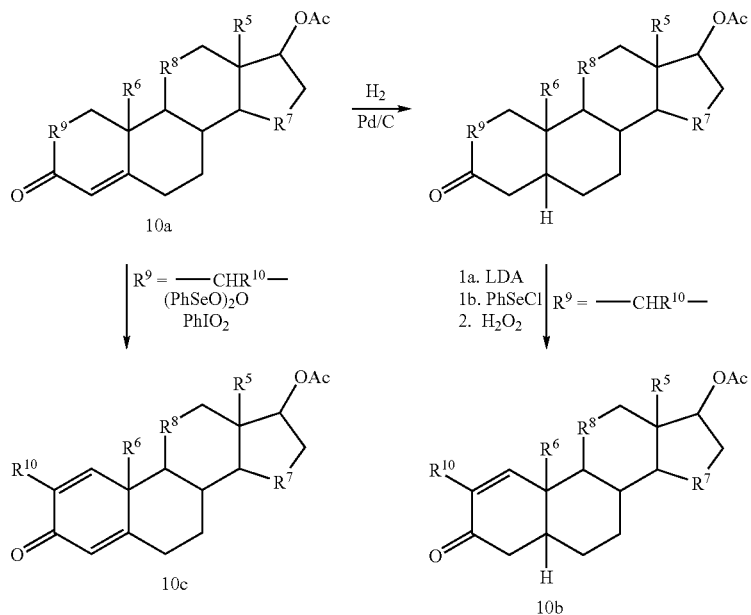

Sulfates, NaO—S(O)(O)—O—, $R^B$—O—S(O)(O)—O—, e.g., $CH_3(CH_2)_{0-18}$—S(O)(O)—O—, are prepared by treatment of alcohols with chlorosulfonic acid followed by NaOH or alternatively by oxidation of sulfites using $KMnO_4$. If the alkyl (e.g., methyl) ester is desired alkylchloro-sulfonate (methylchloro-sulfonate) can be used. Sulfites HO—S(O)—O— and ammonium salts $NH_4O$—S(O)—O, or $R^BO$—S(O)—O— esters (e.g., $CH_3O$—S(O)—O—) are prepared by standard methods. The ammonium salts are prepared by treatment of alcohols with ammonia and sulfur dioxide. The esters such as alkyl, alkenyl and alkynyl esters (e.g., methyl ester) are obtained when alcohols are treated with alkylchlorosulfite (e.g., methycholorosulfite), alkenylchlorosulfite or alkynylchlorosulfite in the presence of a suitable base such as triethylamine. Phosphoesters, $R^BO$—P($OR^{PR}$)(O)—O— are prepared by treating the alcohol with diethylchlorophosphate in the presence of $Na_2CO_3$. Alternatively, if the alcohol is treated with phosphoric acid diesters in the presence of triphenylphospine ($PPh_3$) and diethylazodicarboxylate (DEAD) the corresponding triesters are formed with inversion (Mitsunobu reaction).

Phosphothioesters, $R^BO$—P($SR^{PR}$)(O)—O— are generated by treatment of alcohols with the monothio analog of diethylchlorophosphate as described for phosphoesters yielding the phosphothioesters. Carbonates, $R^BO$—C(O)—O— are generated from the corresponding steroid alcohol using the chloroformate ($R^B$—C(O)—Cl), e.g., $C_{1-20}$ alkyl, alkenyl or alkynyl chloroformates (e.g. $CH_3(CH_2)_{0-5}$—C(O)Cl). Carbamates, $R^B$—NH—C(O)—O— are made from steroid alcohols by treatment with isocyanates ($R^BN$=C=O) or NaOCN in the presence of trifluororoacetic acid. Aminoacid esters, ZNX—CHY—C(O)—O— are generated by coupling the steroid alcohol with the acid chloride of the N-protected amino acid.

Oxidation of hydroxyl groups that are linked to the steroid nucleus is used to obtain ketones and related functionalities. For example, conversion of alcohols to ketones can be achieved using a variety of oxidizing agents such as $CrO_3$ in AcOH, or pyridinium cholorchromate, pyridinium dichromate or oxalyl chloride with triethylamine (Swern oxidation). Thioketones (=S) are prepared by treating ketones with Lawesson's reagent (2,4-bis(4-methoxyphenyl)-1,3,2,4-dithiadiphosphetane-2,4-disulfide; commercially available from Aldrich). Thioacetals, —C($SR^B$)($SR^B$)—, are prepared from ketones (—C(O)—) by treatment with $R^B$—SH thiols under acid catalysis conditions (e.g., HCl). Phosphonoesters, RO—P($OR^{PR}$)(O)—, are generated by addition of the phosphorus acid diester to ketones in the presence of KF to yield hydroxy phosphonoesters. One may optionally remove the hydroxy group using a dehydration and hydrogenation sequence.

Substitution of hydroxyl groups is used to generate a number of functionalities. For example, thiols, —SH, are prepared from alcohols by conversion of the alcohol with inversion to the bromide using $PBr_3$. Treatment of the bromide with thiourea followed by NaOH gives the thiol. Thioethers, $R^B$—S—, are prepared from thiols by treatment with NaOH and the required halide, e.g., alkyl halide. Alternatively, alcohol derivatives like tosylates or mesylates can be displaced by thiolate anions, $R^B$—S⁻, to yield the thioether. Thioesters, R—C(O)—S—, are prepared by treating the tosylate (mesylate) of the alcohol with the sodium salt of the thioacid.

Substitution of hydroxyl groups can be used to generate both esters, $R^BO$—C(O)—, and amides, $NHR^B$—C(O)—, linked to the steroid at carbon atoms. For amides and amines, $R^B$ is —H, a protecting group or a $C_{1-50}$ organic moiety. These are synthesized from the steroid bromide with inversion by displacement with NaCN. The cyanide group can be hydrolyzed to the amide or the acid. The acid is esterified or treated by standard peptide coupling reactions with an acid-protected amino acid in the presence of a suitable carboxyl activating agents such as dicyclohexylcarbodiimide (DCC) to form steroid —C(O)—NH—CHY—C(O)—OR, where Y is the side chain of an amino acid or a C1-C10 organic moiety and R is a protecting group (or hydrogen when deprotected).

Amines and derivatives of amines, e.g., $R^BNH$—, $R^B$—C(O)NH—, $R^BOC(O)$—NH— or $R^BO$—C(O)—$CHR^B$—NH— linked to steroid carbon atoms, are typically prepared by standard methods. For example, amines ($NH_2$-steroid) are generally prepared using the Hoffmann rearrangement ($Br_2$, NaOH) from the amide ($NH_2$—C(O)-steroid) or the Curtius rearrangement ($NaN_3$) from the acid chloride of the steroid. The $R^B$ substituent can subsequently be introduced by alkylation. Steroid alcohols can be used as starting materials under standard Mitsunobu conditions ($PPh_3$, DEAD) to yield N-Boc sulfonamides using N-(t-butoxycarbonyl)-p-toluenesulfonamide. One can selectively remove either protecting group. Treatment with trifluoroacetic acid affords the sulfonamide ($R^B$—S(O)(O)—NH-steroid). Alternatively, sodium napthalenide deprotects to give the N-Boc compound. Amines ($NH_2$-steroid) can be converted to amides ($R^B$—C(O)—NH-steroid) using acyl chlorides ($R^B$—C(O)—Cl). Treatment with ethyl chloroformate gives the N-carbamate ($R^BO$—C(O)—NH-steroid). The amine ($NH_2$-steroid) can be alkylated with an α-bromoester to yield the amino acid substituted steroid ($R^B$—O—C(O)—CHY—NH-steroid).

Where reactions such as substitutions give a product mixture, the desired intermediate is optionally separated from other products or at least partially enriched (e.g., enriched at least about 10-fold, usually at least about 50-100-fold) from other products before subsequent reactions are conducted. Substitution at steroid carbon atoms will generally proceed with greatest efficiency at the 3-position, which is relatively sterically unhindered and C-17 is generally somewhat less accessible than the C-3 position. The relative reactivities of the C-3, C-7, C-17 and C-16 positions allows one to use their reactivities to control the sequential introduction of different functional groups into the same steroid molecule. Also, groups, such as hydroxyl at more reactive positions, C-3 or C-17, may be sequentially protected or deprotected to allow introduction of functional groups at other positions, such as C-7 or C-16.

Polymers such as PEG are linked to the compounds essentially as described above. For example, PEG200 or PEG300 is linked to the steroid at the 3, 7, 16, 17 or other positions by an ether linkage (PEG-O-steroid) using a PEG alkoxide (PEG-ONa), to displace the steroid bromide. Alternatively, PEG-Br can be treated with the steroid alkoxide. Polyethylene glycol esters such as those described in U.S. Pat. No. 5,681,964 can also be prepared using a suitable formula 1 compound and the methods described therein. Monosaccharides or polysaccharides and oligonucleotides are linked to steroid hydroxyl groups using known methods, see e.g., U.S. Pat. No. 5,627,270.

Formula 1 steroid analogs that comprise one or more ring heteroatoms are synthesized according to the following methods.

Scheme 11. Formula 1 compounds that comprise two or three ring heteroatoms are prepared as shown in the following schemes. In the scheme, X is —$CH_2$—, —NH—, —O—, or —S—; $R^{40}$ is —H or —Br; $R^{41}$ is an organic moiety having about 12 carbon atoms or less, typically C1-C8 optionally substituted alkyl (e.g., methyl, hydroxymethyl, ethyl, propyl, —CH(O), —CH(S)) or C2-C8 optionally substituted alkenyl having a single double bond (e.g., vinyl) with 1, 2, 3 or more independently selected substituents (e.g., —OH, —COOH, —O—) and with any substituents that comprise a functional group generally being protected. Preparation of compound 20 from 19 is accomplished using a glycol such as HOC(CH$_3$)$_2$C(CH$_3$)$_2$OH in acid (H$^+$) (B. H. Lipshutz et al., *Synth. Commun.* 12: 267, 1982). The use of a bulky protecting group facilitates generation of a double bond at the 5-6 position over the 4-5 position.

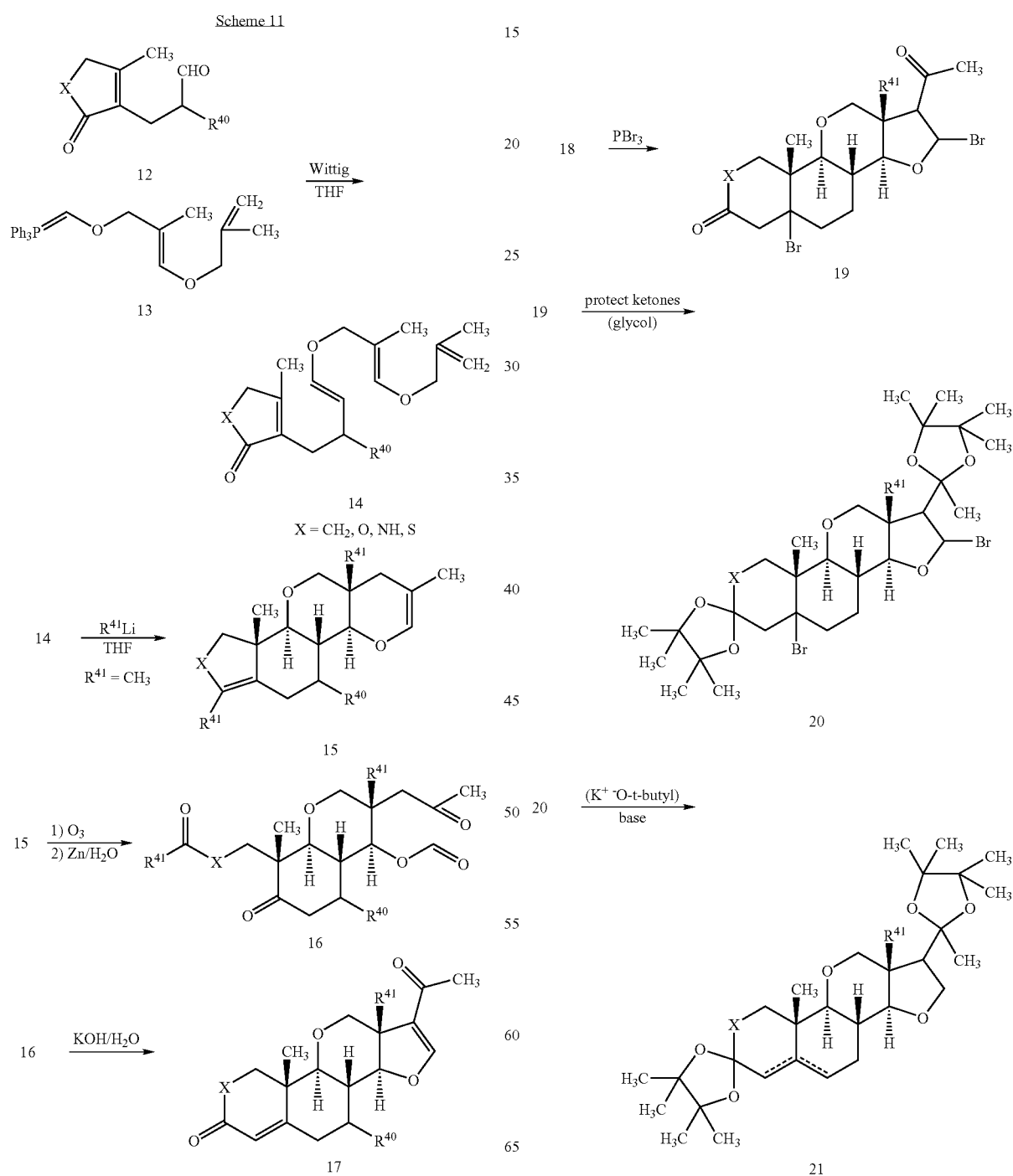

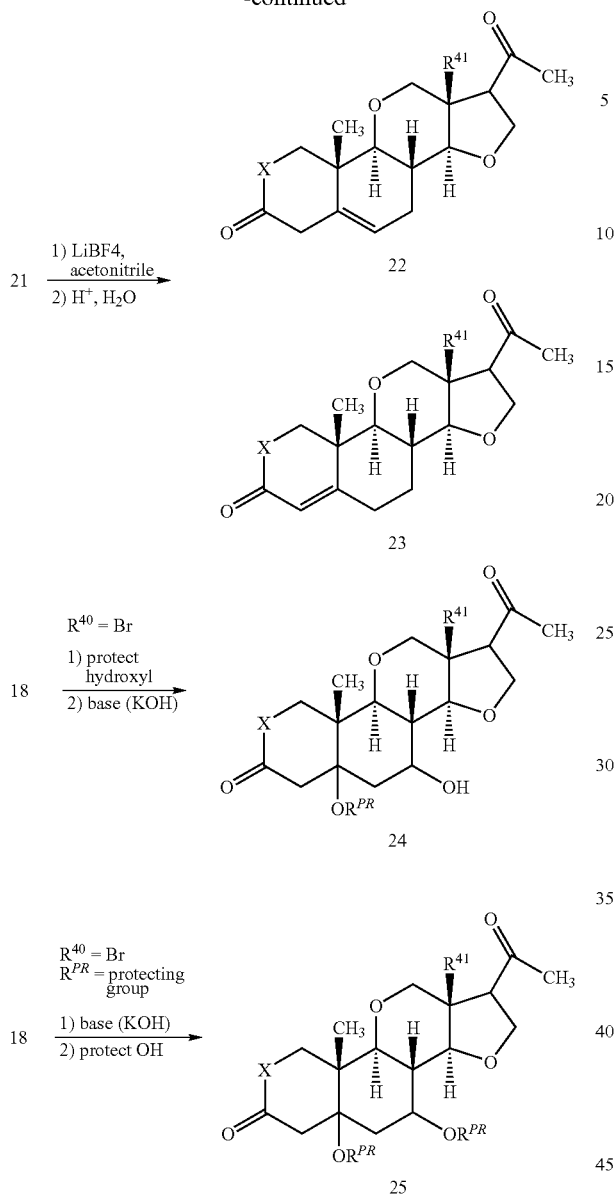

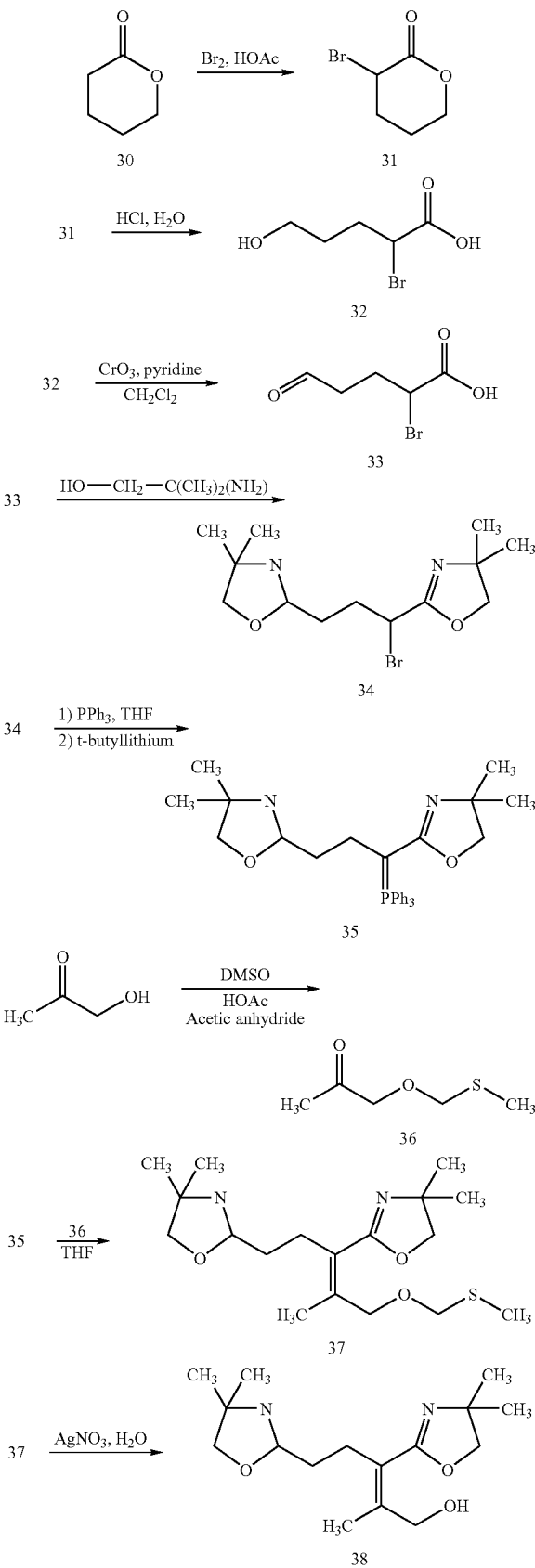

Schemes 12A-12D. Compounds of structure 12 are generated as shown in the schemes below. Most of the reactions are conducted essentially as described. See e.g., W. D. Langley, *Org. Syn. I*, 122, 1932 (compound 30); R. Ratcliffe et al., *J. Org. Chem.* 35: 4000, 1970 (compound 32); A. I. Meyers et al., *J. Org. Chem.* 39: 2787, 1974 (compound 33, 41); J. L. Isidor et al., *J. Org. Chem.* 38: 544, 1973 (compound 35); G. Wittig et al., *Chem. Ber.* 87: 1318, 1954 (compound 36); P. M. Pojer et al., *Tet. Lett.* 3067, 1976 (compound 38); A. Maercker, *Org. React.* 14: 270, 1965 (compound 37); E. J. Corey et al., *Tet. Lett.* 3269 1975 (compound 37); R. S. Tipson, *J. Org. Chem.* 9: 235, 1944 (compound 39); G. W. Kabalka, *J. Org. Chem.* 51: 2386, 1986; B. B. Carson et al., *Org. Synth.* 1: 179, 1941 (compound 43); H. J. Bestman et al., *Justus Liebigs Ann. Chem.* 693: 132 1966 (compound 39); M. Miyano et al., *J. Org. Chem.* 37: 268, 1972 (compound 51); W. H. Glaze et al., *J. Org. Chem.* 33: 1987, 1968 (compound 52).

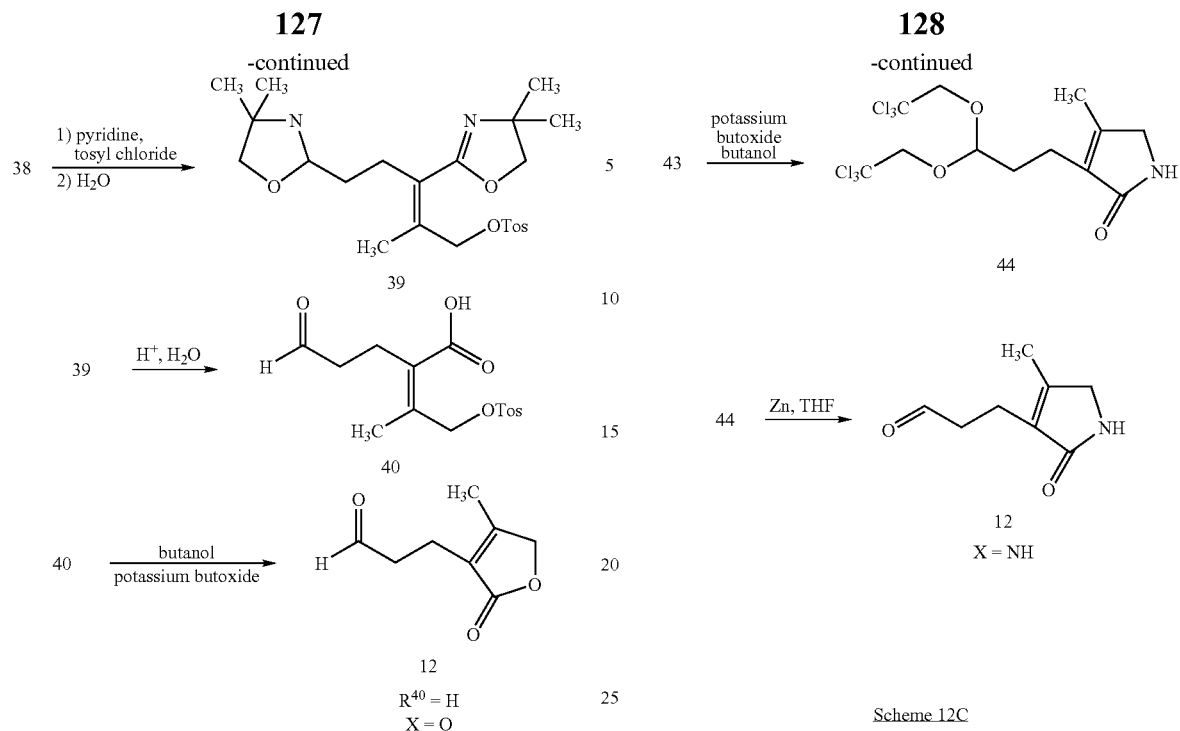
Compounds of structure 12 where X is NH, S and CH$_2$ are prepared as shown in schemes 12B, 12C and 12D respectively.
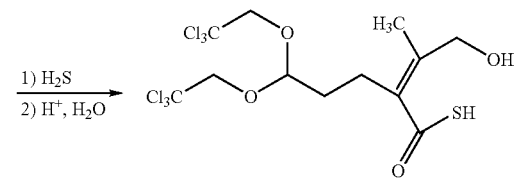
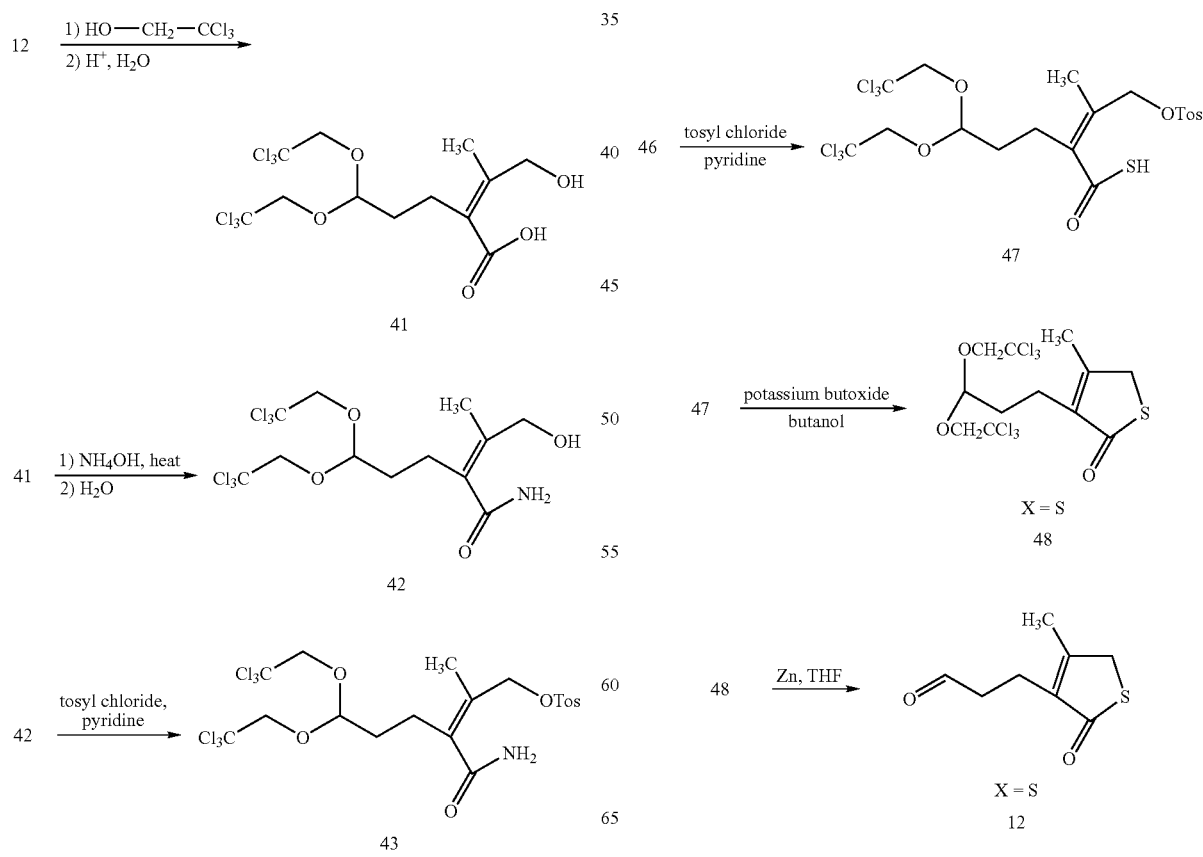

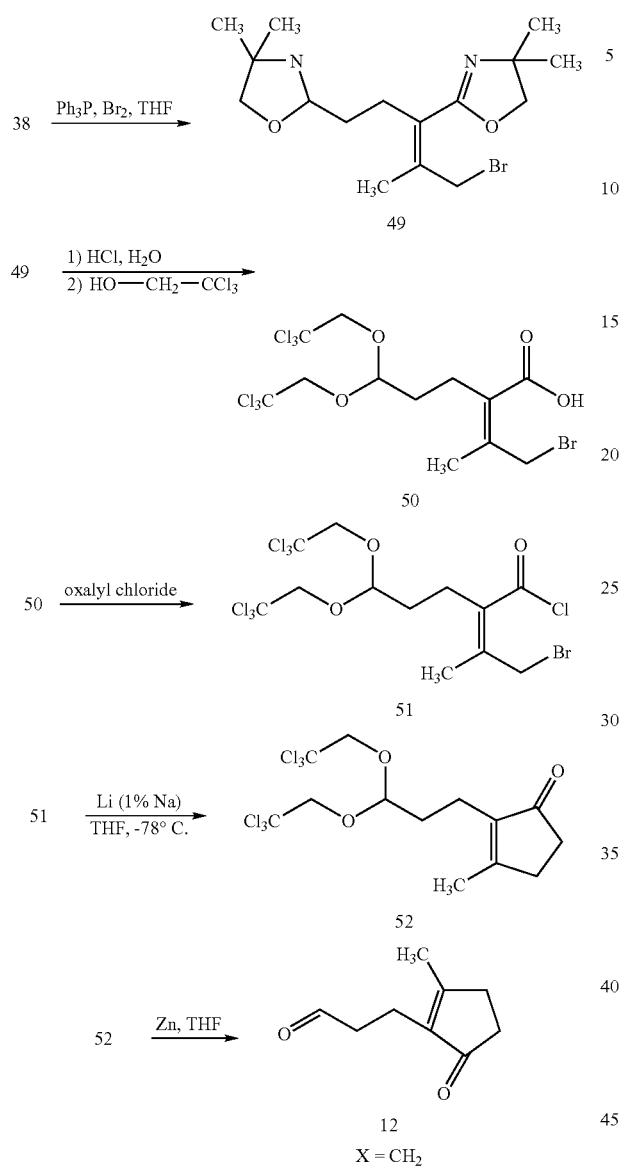

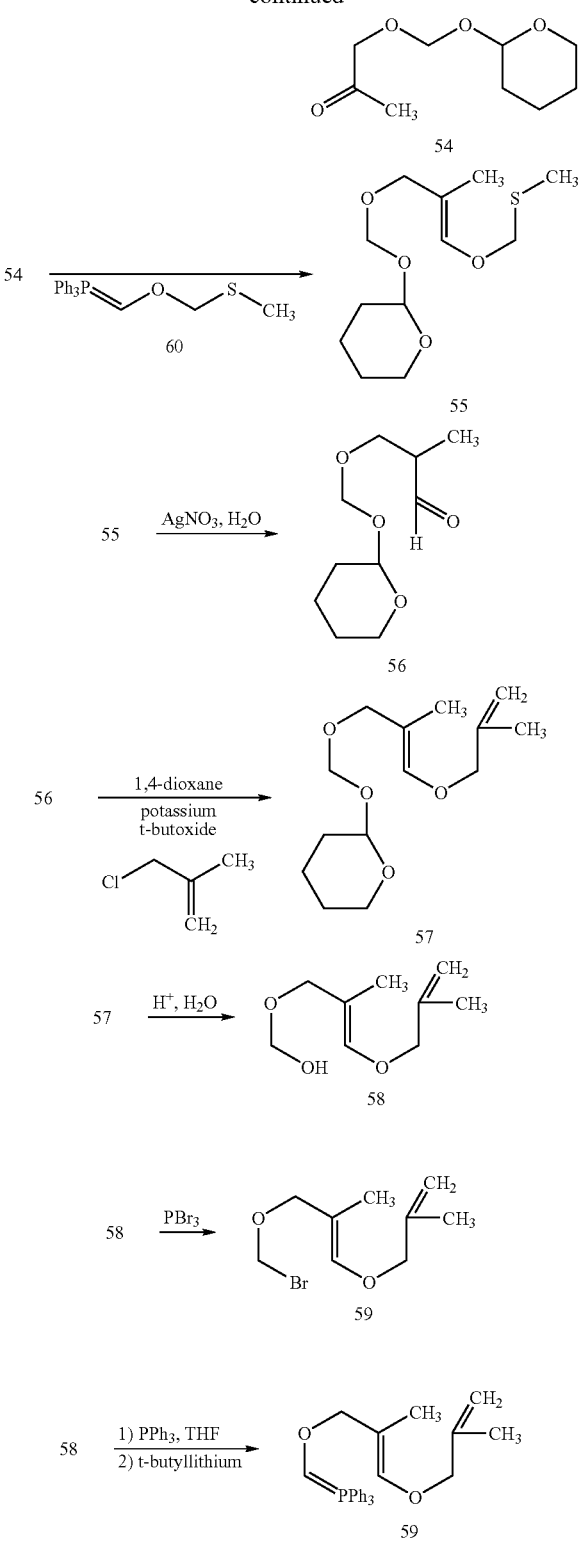

Scheme 13. The scheme and reactions shown below are used to prepare the compound of structure 13 and related compounds that are used to introduce oxygen, carbon, nitrogen or sulfur into the $R^7$ and $R^8$ positions of formula 1 compounds. The reactant in the preparation of compound 63, 3-chloro-2-methylpropene (reg. No. 563-47-3), is available commercially (e.g., Aldrich, Fluka).

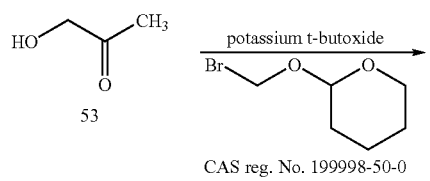

Compound 13 and analogs of compound 13 where $CH_2$, S or NH $CH_2$ replaces oxygen are prepared as shown in the following reactions. Conditions suitable for conversion of compound 106 to 107 have been described (T. Hamada et al., *Heterocycles* 12: 647, 1979; T. Hamada et al., *J. Am. Chem. Soc.* 108: 140, 1986).

Scheme 13
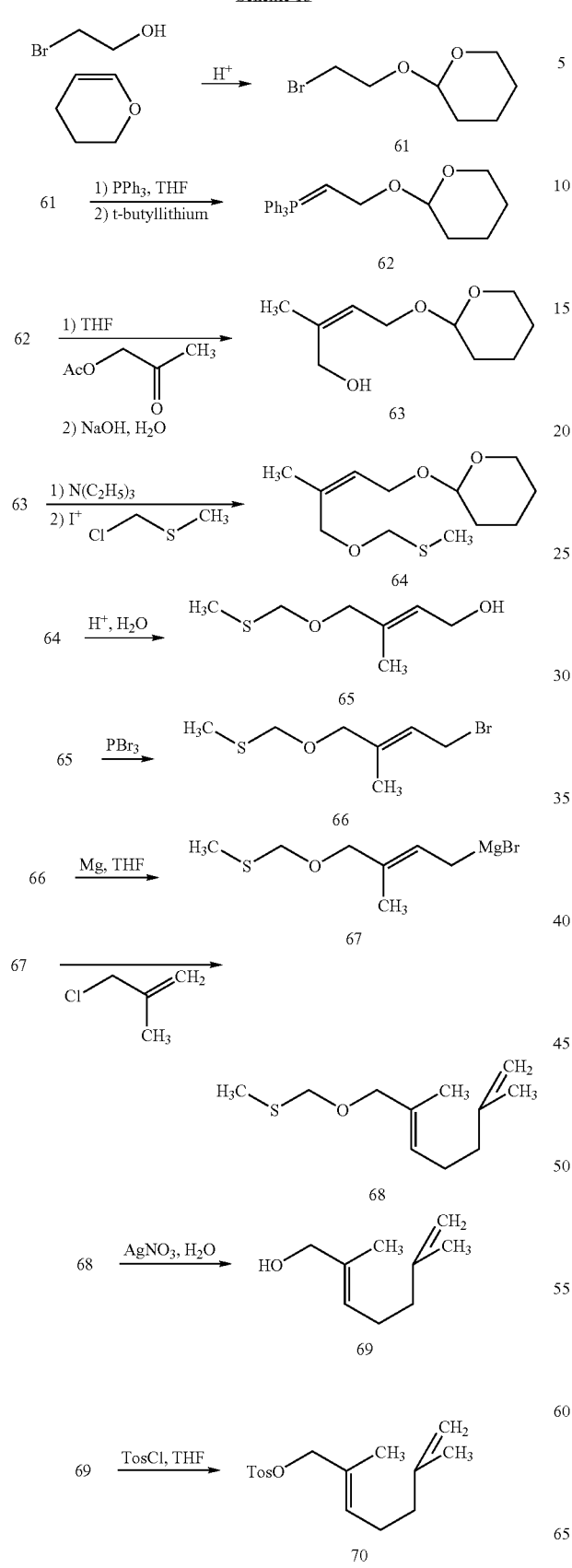
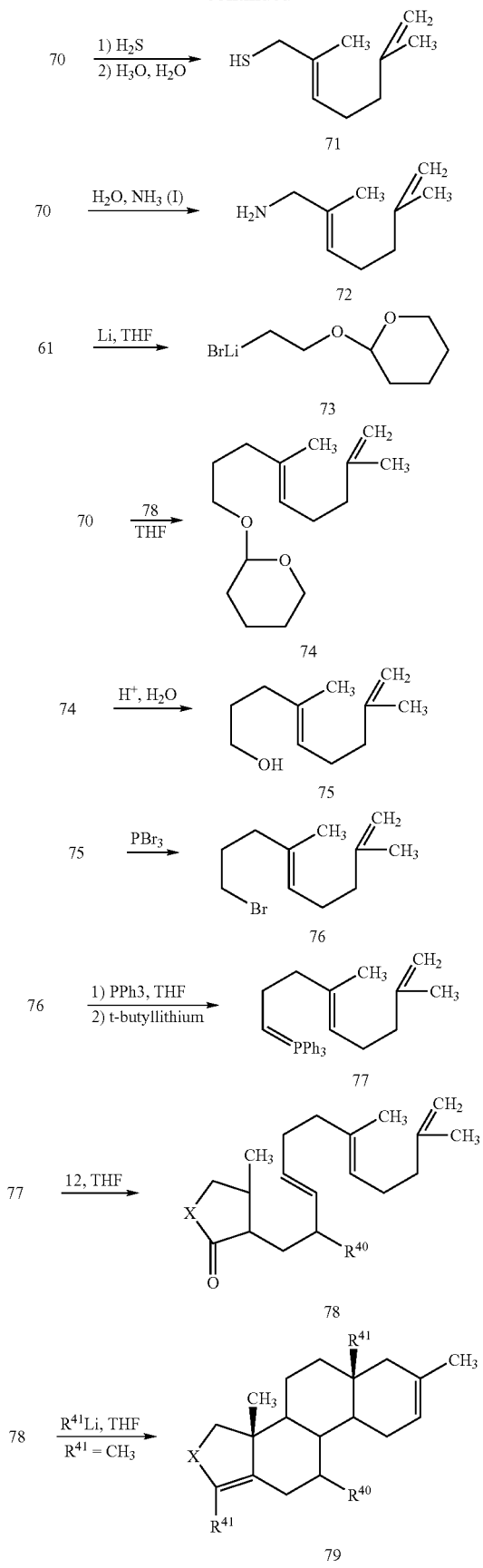

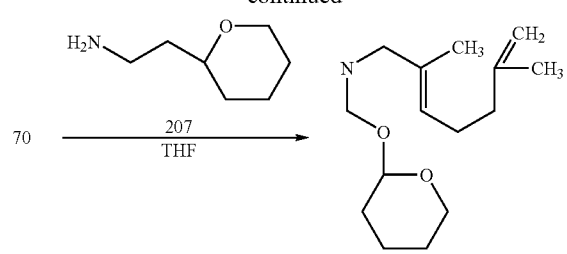
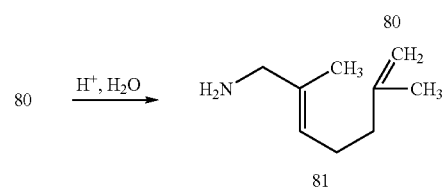
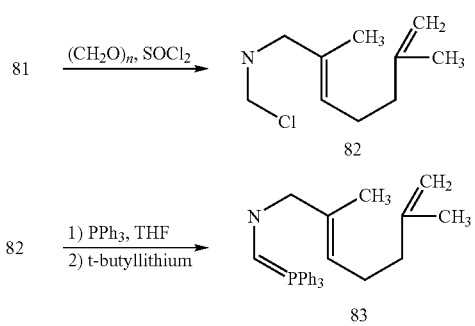
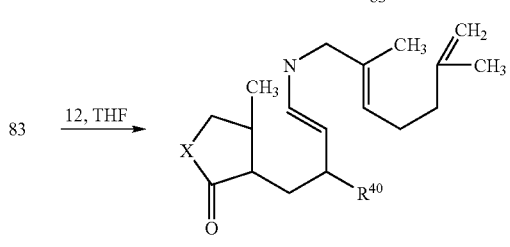
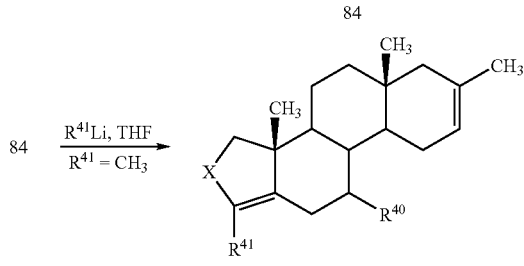
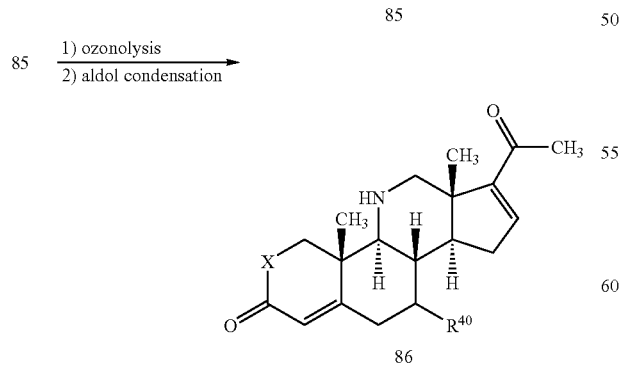
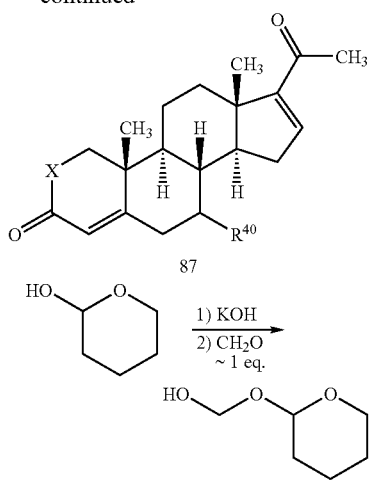
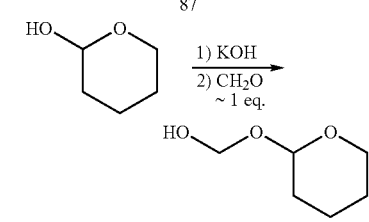
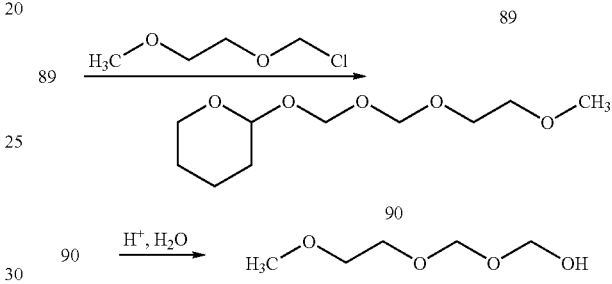
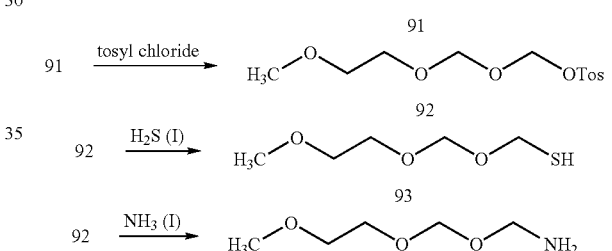
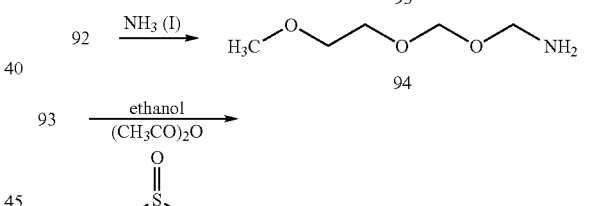
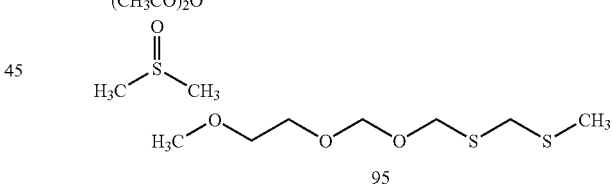
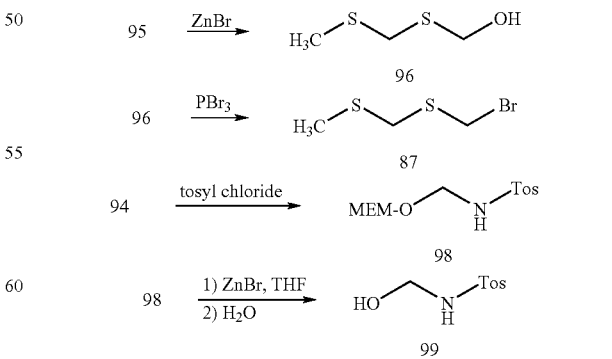

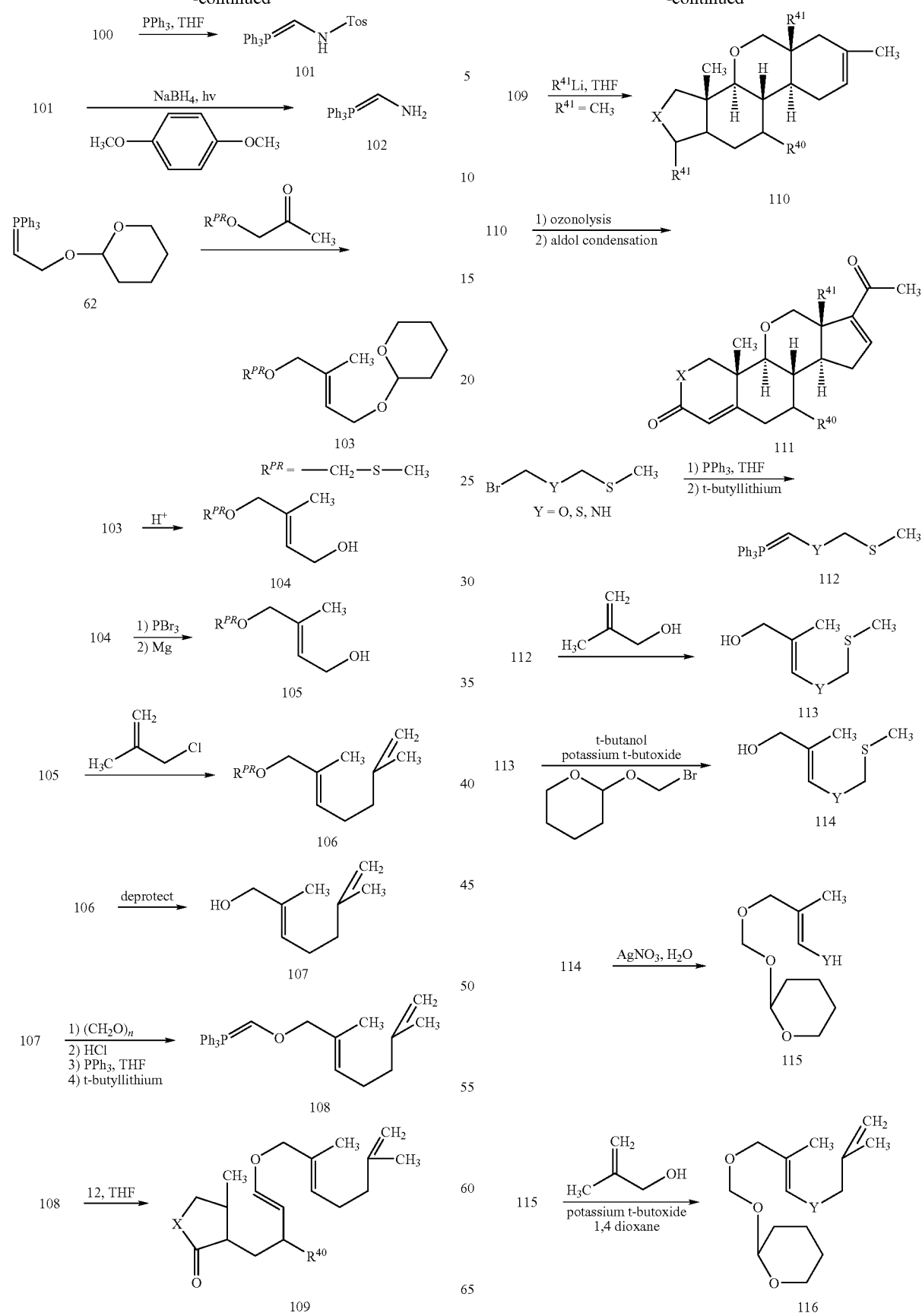

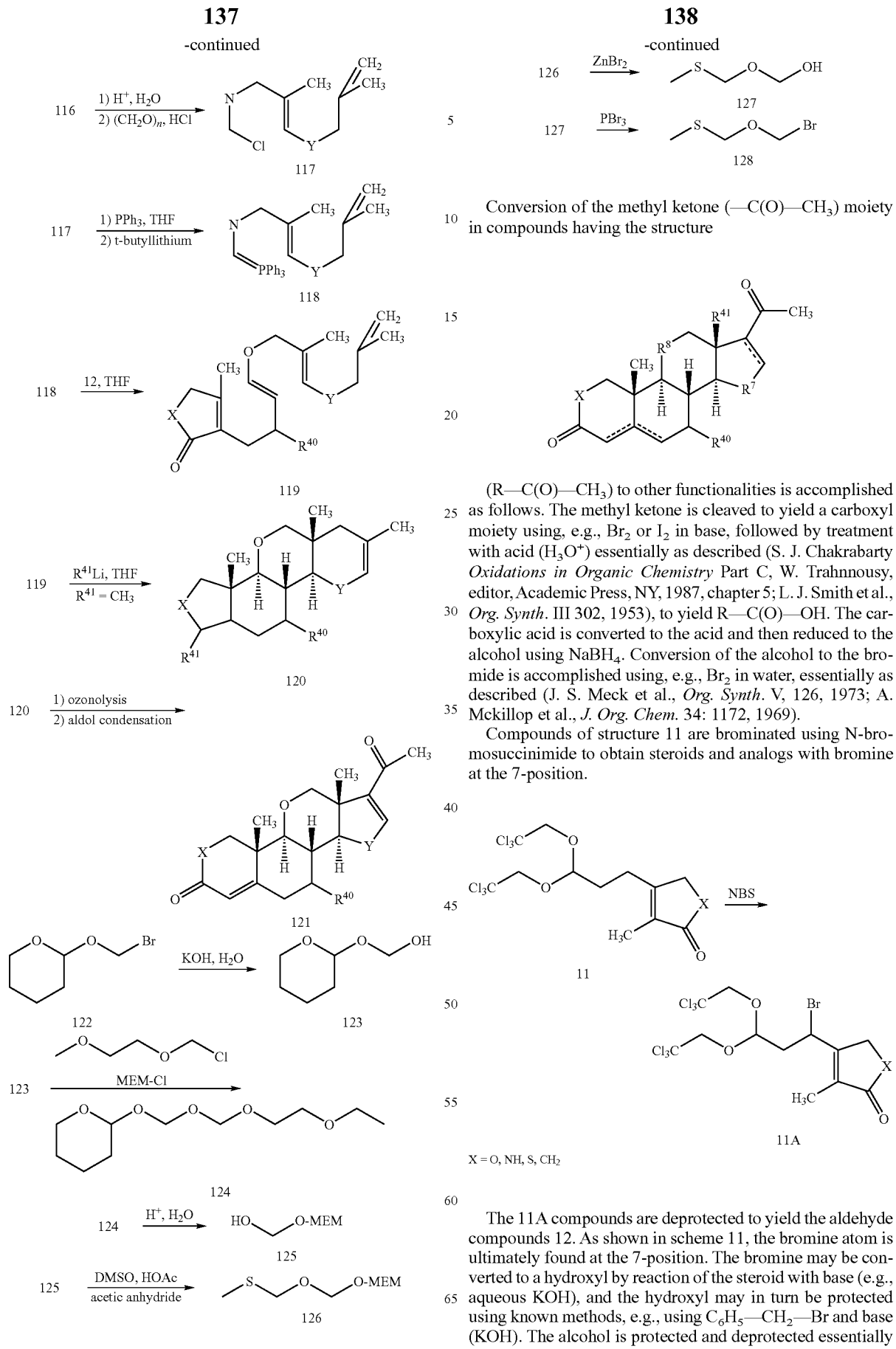

Conversion of the methyl ketone (—C(O)—CH$_3$) moiety in compounds having the structure (R—C(O)—CH$_3$) to other functionalities is accomplished as follows. The methyl ketone is cleaved to yield a carboxyl moiety using, e.g., Br$_2$ or I$_2$ in base, followed by treatment with acid (H$_3$O$^+$) essentially as described (S. J. Chakrabarty *Oxidations in Organic Chemistry* Part C, W. Trahnnousy, editor, Academic Press, NY, 1987, chapter 5; L. J. Smith et al., *Org. Synth*. III 302, 1953), to yield R—C(O)—OH. The carboxylic acid is converted to the acid and then reduced to the alcohol using NaBH$_4$. Conversion of the alcohol to the bromide is accomplished using, e.g., Br$_2$ in water, essentially as described (J. S. Meck et al., *Org. Synth*. V, 126, 1973; A. Mckillop et al., *J. Org. Chem*. 34: 1172, 1969).

Compounds of structure 11 are brominated using N-bromosuccinimide to obtain steroids and analogs with bromine at the 7-position.

The 11A compounds are deprotected to yield the aldehyde compounds 12. As shown in scheme 11, the bromine atom is ultimately found at the 7-position. The bromine may be converted to a hydroxyl by reaction of the steroid with base (e.g., aqueous KOH), and the hydroxyl may in turn be protected using known methods, e.g., using C$_6$H$_5$—CH$_2$—Br and base (KOH). The alcohol is protected and deprotected essentially using described methods, see, e.g., W. H. Hartung et al., *Org. React.* 7: 263, 1953; E. J. Rerst et al., *J. Org. Chem.* 29: 3725, 1968; A. M. Felix et al., *J. Org. Chem.* 43: 4194, 1978; D. A. Evans et al., *J. Am. Chem. Soc.* 101: 6789, 1979; international publication number WO 98/02450. Similar reactions are used to convert a bromine at other positions to a hydroxyl. Other substituents are linked to the steroids essentially as described in schemes 1-10.

Alternative routes to introduce a functional group into the 7-position are also suitable. For example, formula 1 compounds that have a double bond at the 5-6 position and are unsubstituted at the 7-position are optionally protected, e.g., hydroxyl groups are protected with acetate, and a ketone is introduced into the 7-position by oxidation with chromic acid essentially as described (U.S. Pat. No. 2,170,124). The carbonyl (=O) at 7 is reduced to a hydroxyl using mild conditions, e.g., Al(Oi-Pr)$_3$, to avoid reducing the 5-6 double bond.

Selective hydrogenation of a double bond at the 16-17 position without reduction of a double bond at 5-6 is accomplished using H$_2$ and Pd. In general, ketones (=O) can be protected using a glycol, e.g., reaction with ethylene glycol in p-toluenesulfonic acid and benzene, before subsequent oxidation or reduction reactions are conducted.

Various groups that may comprise the formula 1 compounds described herein, e.g., hydroxyl groups or ketones bonded to the steroid nucleus, or substituted alkyl groups, substituted heterocycles, amino acids and peptides, can contain one or more reactive moieties such as hydroxyl, carboxyl, amino or thiol. Intermediates used to make formula 1 compounds may be protected as is apparent in the art. Noncyclic and cyclic protecting groups and corresponding cleavage reactions are described in "Protective Groups in Organic Chemistry", Theodora W. Greene (John Wiley & Sons, Inc., New York, 1991, ISBN 0-471-62301-6) (hereafter "Greene") and will not be detailed here. In the context of the present invention, these protecting groups are groups that can be removed from a formula 1 compound without irreversibly changing the covalent bond structure or oxidation/reduction state of the remainder of the molecule. For example, the protecting group, —R$^{PR}$, that is bonded to an —O— or —NH— group can be removed to form —OH or —NH$_2$, respectively, without affecting other covalent bonds in the molecule. At times, when desired, more than one protecting group can be removed at a time, or they can be removed sequentially. In formula 1 compounds containing more than one protecting group, the protecting groups are the same or different.

Protecting groups are removed by known procedures, although it will be understood that the protected intermediates fall within the scope of this invention. The removal of the protecting group may be arduous or straight-forward, depending upon the economics and nature of the conversions involved. In general, one will use a protecting group with exocyclic amines or with carboxyl groups during synthesis of a formula 1 compound. For most therapeutic applications amine groups should be deprotected. Protecting groups commonly are employed to protect against covalent modification of a sensitive group in reactions such as alkylation or acylation. Ordinarily, protecting groups are removed by, e.g. hydrolysis, elimination or aminolysis. Thus, simple functional considerations will suffice to guide the selection of a reversible or an irreversible protecting group at a given locus on the formula 1 compounds. Suitable protecting groups and criteria for their selection are described in T. W. Greene and P. G. M. Wuts, Eds. "Protective Groups in Organic Synthesis" 2nd edition, Wiley Press, at pps. 10-142, 143-174, 175-223, 224-276, 277-308, 309-405 and 406-454.

Determination of whether a group is a protecting group is made in the conventional manner, e.g., as described by Kocienski, Philip J.; "*Protecting Groups*" (Georg Thieme Verlag Stuttgart, New York, 1994) (hereafter "Kocienski"), Section 1.1, page 2, and Greene Chapter 1, pages 1-9. In particular, a group is a protecting group if when, based on mole ratio, 90% of that protecting group has been removed by a deprotection reaction, no more than 50%, typically 25%, more typically 10%, of the deprotected product molecules have undergone changes to their covalent bond structure or oxidation/reduction state other than those occasioned by the removal of the protecting group. When multiple protecting groups of the same type are present in the molecule, the mole ratios are determined when all of the groups of that type are removed. When multiple protecting groups of different types are present in the molecule, each type of protecting group is treated (and the mole ratios are determined) independently or together with others depending on whether the deprotection reaction conditions pertinent to one type are also pertinent to the other types present. In one embodiment, a group is a protecting group if when, based on mole ratio determined by conventional techniques, 90% of that protecting group has been removed by a conventional deprotection reaction, no more than 50%, typically 25%, more typically 10%, of the deprotected product molecules have undergone irreversible changes to their covalent bond structure or oxidation/reduction state other than those occasioned by the removal of the protecting group. Irreversible changes require chemical reactions (beyond those resulting from aqueous hydrolysis, acid/base neutralization or conventional separation, isolation or purification) to restore the covalent bond structure or oxidation/reduction state of the deprotected formula 1 compound.

Protecting groups are also described in detail together with general concepts and specific strategies for their use in Kocienski, Philip J.; "Protecting Groups" (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184, Chapter 6, Amino Protecting Groups, pages 185-243, Chapter 7, Epilog, pages 244-252, and Index, pages 253-260, are incorporated with specificity in the context of their contents. More particularly, Sections 2.3 Silyl Ethers, 2.4 Alkyl Ethers, 2.5 Alkoxyalkyl Ethers (Acetals), 2.6 Reviews (hydroxy and thiol protecting groups), 3.2 Acetals, 3.3 Silylene Derivatives, 3.4 1,1,3,3-Tetraisopropyldisiloxanylidene Derivatives, 3.5 Reviews (diol protecting groups), 4.2 Esters, 4.3 2,6,7-Trioxabicyclo[2.2.2]octanes [OBO] and Other Ortho Esters, 4.4 Oxazolines, 4.5 Reviews (carboxyl protecting groups), 5.2 O,O-Acetals, 5.3 S,S-Acetals, 5.4 O,S-Acetals, 5.5 Reviews (carbonyl protecting groups), 6.2 N-Acyl Derivatives, 6.3 N-Sulfonyl Derivatives, 6.4 N-Sulfenyl Derivatives, 6.5 N-Alkyl Derivatives, 6.6 N-Silyl Derivatives, 6.7 Imine Derivatives, and 6.8 Reviews (amino protecting groups), are each incorporated with specificity where protection/deprotection of the requisite functionalities is discussed. Further still, the tables "Index to the Principal Protecting Groups" appearing on the inside front cover and facing page, "Abbreviations" at page xiv, and "reagents and Solvents" at page xv are each incorporated in their entirety herein at this location.

Typical hydroxy protecting groups are described in Greene at pages 14-118 and include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy) methyl, 2-(Trimethylsilyl)ethoxymethyl, Tetrahydropyranyl, 3-Bromotetrahydropyranyl, Tetrahydropthiopyranyl, 1-Methoxycyclohexyl, 4-methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl); Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p, p'-Dinitrobenzhydryl, 5-Dibenzosuberyl, Triphenylmethyl, alpha-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4',4''-Tris(4,5-dichlorophthalimidophenyl) methyl, 4,4',4''-Tris(levulinoyloxyphenyl)methyl, 4,4',4''-Tris(benzoyloxyphenyl)methyl, 3-(Imidazol-1-ylmethyl)bis(4', 4''-dimethoxyphenyl)methyl, 1,1-Bis (4-methoxyphenyl)-1'-pyrenylmethyl, 9-Anthryl, 9-(9-Phenyl)xanthenyl, 9-(9-Phenyl-10-oxo) anthryl, 1,3-Benzodithiolan-2-yl, Benzisothiazolyl, S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Choroacetate, Dichloroacetate, Trichloroacetate, Trifluoroacetate, Methoxyacetate, Triphenyl-methoxyacetate, Phenoxyacetate, p-Chlorophenoxyacetate, p-poly-Phenylacetate, 3-Phenylpropionate, 4-Oxopentanoate (Levulinate), 4,4-(Ethylenedithio) pentanoate, Pivaloate, Adamantoate, Crotonate, 4-Methoxycrotonate, Benzoate, p-Phenylbenzoate, 2,4, 6-Trimethylbenzoate (Mesitoate); Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio) ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate); Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy) butyrate, 2-(Methylthiomethoxymethyl)benzoate); Miscellaneous Esters (2,6-Dichloro-4-methylphenoxyacetate, 2,6-Dichloro-4-(1,1,3,3-tetramethyl-butyl)phenoxyacetate, 2,4-Bis(1,1-dimethylpropyl)phenoxyacetate, Chorodiphenylacetate, Isobutyrate, Monosuccinoate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitro-phenylsulfenate); and Sulfonates (Sulfate, Methanesulfonate (Mesylate), Benzylsulfonate, Tosylate (Tos)).

More typically hydroxy protecting groups include substituted methyl ethers, substituted benzyl ethers, silyl ethers, and esters including sulfonic acid esters, still more typically, trialkylsilyl ethers, tosylates and acetates.

Typical 1,2- and 1,3-diol protecting groups are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidene, 1,2-Dimethoxyethylidene, alpha-Methoxybenzylidene, 1-(N,N-Dimethylamino)ethylidene Derivative, alpha-(N,N-Dimethylamino)benzylidene Derivative, 2-Oxacyclopentylidene); and Silyl Derivatives (Di-t-butylsilylene Group, 1,3-(1,1,3,3-Tetraiso-propyldisiloxanylidene) Derivative, Tetra-t-butoxydisiloxane-1,3-diylidene Derivative, Cyclic Carbonates, Cyclic Boronates, Ethyl Boronate, Phenyl Boronate).

More typically, 1,2- and 1,3-diol protecting groups include epoxides and acetonides.

Typical amino protecting groups are described in Greene at pages 315-385 and include Carbamates (Methyl and Ethyl, 9-Fluorenylmethyl, 9(2-Sulfo)fluoroenylmethyl, 9-(2,7-Dibromo) fluorenylmethyl, 2,7-Di-t-buthyl-[9-(10,10-dioxo-10,10,10,10-tetrahydrothioxanthyl)]-methyl, 4-Methoxyphenacyl); Substituted Ethyl (2,2,2-Trichoroethyl, 2-Trimethylsilylethyl, 2-Phenylethyl, 1-(1-Adamantyl)-1-methylethyl, 1,1-Dimethyl-2-haloethyl, 1,1-Dimethyl-2,2-dibromoethyl, 1,1-Dimethyl-2,2,2-trichloroethyl, 1-Methyl-1-(4-biphenylyl)ethyl, 1-(3,5-Di-t-butylphenyl)-1-methylethyl, 2-(2'- and 4'-Pyridyl)ethyl, 2-(N,N-Dicyclohexylcarboxamido)ethyl, t-Butyl, 1-Adamantyl, Vinyl, Allyl, 1-Isopropylallyl, Cinnamyl, 4-Nitrocinnamyl, 8-Quinolyl, N-Hydroxypiperidinyl, Alkyldithio, Benzyl, p-Methoxybenzyl, p-Nitrobenzyl, p-Bromobenzyl, p-Chorobenzyl, 2,4-Dichlorobenzyl, 4-Methylsulfinylbenzyl, 9-Anthrylmethyl, Diphenylmethyl); Groups With Assisted Cleavage (2-Methylthioethyl, 2-Methylsulfonylethyl, 2-(p-Toluenesulfonyl)ethyl, [2-(1,3-Dithianyl)]methyl, 4-Methylthiophenyl, 2,4-Dimethylthiophenyl, 2-Phosphonioethyl, 2-Triphenylphosphonioisopropyl, 1,1-Dimethyl-2-cyanoethyl, m-Choro-p-acyloxybenzyl, p-(Dihydroxyboryl)benzyl, 5-Benzisoxazolylmethyl, 2-(Trifluoromethyl)-6-chromonylmethyl); Groups Capable of Photolytic Cleavage (m-Nitrophenyl, 3,5-Dimethoxybenzyl, o-Nitrobenzyl, 3,4-Dimethoxy-6-nitrobenzyl, Phenyl(o-nitrophenyl)methyl); Urea-Type Derivatives (Phenothiazinyl-(10)-carbonyl Derivative, N'-p-Toluenesulfonylaminocarbonyl, N'-Phenylaminothiocarbonyl); Miscellaneous Carbamates (t-Amyl, S-Benzyl Thiocarbamate, p-Cyanobenzyl, Cyclobutyl, Cyclohexyl, Cyclopentyl, Cyclopropylmethyl, p-Decyloxybenzyl, Diisopropylmethyl, 2,2-Dimethoxycarbonylvinyl, o-(N,N-Dimethyl-carboxamido) benzyl, 1,1-Dimethyl-3-(N,N-dimethylcarboxamido)propyl, 1,1-Dimethylpropynyl, Di(2-pyridyl)methyl, 2-Furanylmethyl, 2-Iodoethyl, Isobornyl, Isobutyl, Isonicotinyl, p-(p'-Methoxyphenylazo)benzyl, 1-Methylcyclobutyl, 1-Methylcyclohexyl, 1-Methyl-1-cyclopropylmethyl, 1-Methyl-1-(3, 5-dimethoxyphenyl)ethyl, 1-Methyl-1-(p-phenylazophenyl) ethyl, 1-Methyl-1-phenylethyl, 1-Methyl-1-(4-pyridyl)ethyl, Phenyl, p-(Phenylazo)-benzyl, 2,4,6-Tri-t-butylphenyl, 4-(Trimethylammonium)benzyl, 2,4,6-Trimethylbenzyl); Amides (N-Formyl, N-Acetyl, N-Choroacetyl, N-Trichoroacetyl, N-Trifluoroacetyl, N-Phenylacetyl, N-3-Phenylpropionyl, N-Picolinoyl, N-3-Pyridylcarboxamide, N-Benzoylphenylalanyl Derivative, N-Benzoyl, N-p-Phenylbenzoyl); Amides With Assisted Cleavage (N-o-Nitrophenylacetyl, N-o-Nitrophenoxyacetyl, N-Acetoacetyl, (N'-Dithiobenzyloxycarbonylamino)acetyl, N-3-(p-Hydroxyphenyl)propionyl, N-3-(o-Nitrophenyl)propionyl, N-2-Methyl-2-(o-nitrophenoxy)propionyl, N-2-Methyl-2-(o-phenylazophenoxy)propionyl, N-4-Chlorobutyryl, N-3-Methyl-3-nitrobutyryl, N-o-Nitrocinnamoyl, N-Acetylmethionine Derivative, N-o-Nitrobenzoyl, N-o-(Benzoyloxymethyl)benzoyl, 4,5-Diphenyl-3-oxazolin-2-one); Cyclic Imide Derivatives (N-Phthalimide, N-Dithiasuccinoyl, N-2,3-Diphenylmaleoyl, N-2,5-Dimethylpyrrolyl, N-1,1,4,4-Tetramethyl-disilylazacyclopentane Adduct, 5-Substituted 1,3-Dimethyl-1,3,5-triazacyclo-hexan-2-one, 5-Substituted 1,3-Dibenzyl-1,3,5-triazacyclohexan-2-one, 1-Substituted 3,5-Dinitro-4-pyridonyl); N-Alkyl and N-Aryl Amines (N-Methyl, N-Allyl, N-[2-(Trimethylsilyl)ethoxy]methyl, N-3-Acetoxypropyl, N-(1-Isopropyl-4-nitro-2-oxo-3-pyrrolin-3-yl), Quaternary Ammonium Salts, N-Benzyl, N-Di(4-methoxyphenyl)methyl, N-5-Dibenzosuberyl, N-Triphenylmethyl, N-(4-Methoxyphenyl)diphenylmethyl, N-9-Phenylfluorenyl, N-2,7-Dichloro-9-fluorenylmethylene, N-Ferrocenylmethyl, N-2-Picolylamine N'-Oxide); Imine Derivatives (N-1,1-Dimethylthiomethylene, N-Benzylidene, N-p-methoxybenzylidene, N-Diphenylmethylene, N-[(2-Pyridyl)mesityl]methylene, N,(N',N'-Dimethylaminomethylene, N,N'-Isopropylidene, N-p-Nitrobenzylidene, N-Salicylidene, N-5-Chlorosalicylidene, N-(5-Chloro-2-hydroxyphenyl)phenylmethylene, N-Cyclohexylidene); Enamine Derivative (N-(5,5-Dimethyl-3-oxo-1-cyclohexenyl)); N-Metal Derivatives (N-Borane Derivatives, N-Diphenylborinic Acid Derivative, N-[Phenyl(pentacarbonylchromium- or -tungsten)]carbenzyl, N-Copper or N-Zinc Chelate); N—N Derivatives (N-Nitro, N-Nitroso, N-Oxide); N—P Derivatives (N-Diphenylphosphinyl, N-Dimethylthiophosphinyl, N-Diphenylthiophosphinyl, N-Dialkyl Phosphoryl, N-Dibenzyl Phosphoryl, N-Diphenyl Phosphoryl); N—Si Derivatives; N—S Derivatives; N-Sulfenyl Derivatives (N-Benzenesulfenyl, N-o-Nitrobenzenesulfenyl, N-2,4-Dinitrobenzenesulfenyl, N-Pentachlorobenzenesulfenyl, N-2-nitro-4-methoxybenzenesulfenyl, N-Triphenylmethylsulfenyl, N-3-Nitropyridinesulfenyl); and N-Sulfonyl Derivatives (N-p-Toluenesulfonyl, N-Benzenesulfonyl, N-2,3,6-Trimethyl-4-methoxybenzenesulfonyl, N-2,4,6-Trimethoxybenzenesulfonyl, N-2,6-Dimethyl-4-methoxybenzenesulfonyl, N-Pentamethylbenzenesulfonyl, N-2,3,5,6,-Tetramethyl-4-methoxybenzenesulfonyl, N-4-methoxybenzenesulfonyl, N-2,4,6-Trimethylbenzenesulfonyl, N-2,6-Dimethoxy-4-methylbenzenesulfonyl, N-2,2,5,7,8-Pentamethylchroman-6-sulfonyl, N-methanesulfonyl, N-β-trimethylsilyethanesulfonyl, N-9-anthracenesulfonyl, N-4-(4',8'-Dimethoxynaphthylmethyl)benzenesulfonyl, N-benzylsulfonyl, N-trifluoromethylsulfonyl, N-phenacylsulfonyl).

More typically, amino protecting groups include carbamates and amides, still more typically, N-acetyl groups.

Groups capable of biological cleavage typically include prodrugs. A large number of such groups are described in "Design of Prodrugs", Hans Bundgaard (Elsevier, N.Y., 1985, ISBN 0-444-80675-X) (Bundgaard) and will not be detailed here. In particular, Bundgaard, at pages 1-92, describes prodrugs and their biological cleavage reactions for a number of functional group types. Prodrugs for carboxyl and hydroxyl groups are detailed in Bundgaard at pages 3 to 10, for amides, imides and other NH-acidic compounds at pages 10 to 27, amines at pages 27 to 43, and cyclic prodrugs at pages 62 to 70. These moieties are optionally bonded to the steroid at one, two or more of the variable groups that are bonded to the rings in the formula 1 compounds, e.g., one or more $R^1$-$R^6$, $R^{10}$, $R^{15}$, $R^{17}$ and $R^{18}$.

Metabolites. Also falling within the scope of this invention are the in vivo metabolites of the compounds described herein and the use of the metabolites for use in the therapeutic treatments or other methods described herein or in the cited references. This includes metabolites or products that are novel and unobvious over the prior art as new compounds as such and their uses. Metabolites may result for example from the oxidation, reduction, hydrolysis, amidation, esterification, glycosidation and the like of the administered formula 1 compound, due to enzymatic or chemical processes. Metabolites may be generated in vivo in a subject or they may arise ex vivo from cells or tissues, e.g., from a mammal such as a human, rodent or a primate. Accordingly, the invention includes novel and unobvious compounds produced by a process comprising contacting a compound of this invention with a subject or a subject's cells or tissue for a period of time sufficient to yield detectable amounts of a metabolic product thereof. Such products typically are identified by preparing a radiolabeled or mass labeled formula 1 compound that comprises, e.g., 1, 2, 3 or more $^{13}C$, $^{14}C$, $^3H$, $^2H$, $^{131}I$, $^{32}P$, $^{35}S$ or $^{99}Tc$ atoms bonded to the compound, and administering it as a trace labeled compound along with the unlabeled compound. The labeled and unlabeled compound is administered by any suitable route (by, e.g., a buccal, sublingual, parenteral, topical or oral route) in a detectable dose (e.g. greater than about 0.1 µg/kg, or at least about 10 µg/kg or at least about 0.5 mg/kg of the labeled compound) to a subject, e.g., an animal or mammal such as rat, mouse, guinea pig, primate, or to a human. After administration sufficient time is allowed for metabolism to occur (typically about 30 seconds to 30 hours) and conversion products are isolated from one or more of the urine, blood, plasma, feces or other suitable biological sources. The amount of labeled formula 1 compound that is administered to a subject will vary with the specific activity of the labeled compound. Exemplary metabolic conversions of formula 1 compounds include modification of hydrogen atoms or other moieties that are bonded to, e.g., one or more of the 1, 2, 3, 4, 6, 7, 11, 15, 16 or 17 positions. Exemplary conversions at these one or more of positions include hydroxylation of ring atoms, e.g., ring carbon atoms, conjugation of hydroxyl groups that are bonded to one or more of those positions with moieties such as sulfate, phosphate or a monosaccharide or disaccharide such as glucuronic acid and hydrolysis of moieties such as esters or alkoxy groups.

Exemplary radiolabeled and heavy atom labeled formula 1 compounds include ones that comprise 1, 2, 3 or more $^{13}C$, $^{14}C$, $^2H$, $^3H$, $^{131}I$, $^{32}P$ or $^{35}S$ atoms that are at (or bonded to), e.g., one, two, three or more of the 1, 2, 3, 4, 5, 6, 7, 8, 9, 10, 11, 12, 15, 16, 17, 18 or 19 positions. In some embodiments, the molecule comprises only one or two types, e.g., $^{13}C$ or $^3H$, of labeled atoms. Suitably labeled compounds include any of the compounds disclosed herein, e.g., any formula 1 compound in compound groups 1 through 54. Such labeled compounds may comprise, e.g., a $^{13}C$ at the 18 or 19 positions and one two or three $^3H$ may be bonded to the $^{13}C$ atom(s) or to a ring carbon(s). Other formula 1 compounds may comprise one or two $^2H$ or $^3H$ atoms bonded to one or more of the 1, 2, 4, 5, 6, 11 or 12 positions and optionally a $^{13}C$ at the 18 or 19 position(s).

These products or metabolites are easily isolated since they are labeled (others are isolated, e.g., by the use of antibodies capable of binding epitopes surviving in the metabolite). The metabolite structures are determined in conventional fashion, e.g. by MS, GC-MS, HPLC including reverse phase HPLC, or NMR analysis. See, e.g., H. L. J. Makin et al., eds. *Steroid Analysis* 1995, Chapman & Hall, ISBN 0751401285. In general, analysis of metabolites is accomplished in the same way as conventional drug metabolism studies, which are known to those skilled in the art. The conversion products, especially when they are not otherwise found in vivo, are useful in diagnostic assays for therapeutic dosing of the formula 1 compounds even if they possess only limited therapeutic activity of their own.

Formulations and compositions for preparing formulations. Invention embodiments include formulations described here and elsewhere in this disclosure. While it is possible for the formula 1 compound(s) to be administered alone it is usual to present them as formulations. The formulations, both for veterinary and for human use, comprise at least one formula 1 compound, together with one or more excipients and optionally one or more additional therapeutic ingredients.

This aspect of the invention includes compositions comprising one or more pharmaceutically acceptable excipients or carriers. The compositions are used to prepare formulations suitable for human or animal use. Suitable administration routes for formulations include oral, rectal, nasal, topical (including buccal and sublingual), vaginal, rectal and parenteral (including subcutaneous, intramuscular, intravenous, intradermal, intrathecal, intraocular and epidural). In general, aqueous and non-aqueous liquid or cream formulations are delivered by a parenteral, oral or topical route. In other embodiments, such as the invention intermittent dosing methods, the formula 1 compound(s) may be present as an aqueous or a non-aqueous liquid formulation or a solid formulation suitable for administration by any of the routes disclosed herein, e.g., oral, topical, buccal, sublingual, parenteral, inhaled aerosol or a depot such as a subcutaneous depot or an intraperitoneal or intramuscular depot. It will be appreciated that the preferred route may vary with, for example, the subject's pathological condition or weight or the subject's response to therapy with a formula 1 compound or other therapy that is used or that is appropriate to the circumstances.

The formulations include those suitable for the foregoing administration routes. The formulations may conveniently be presented in unit dosage form and may be prepared by any of the methods known in the art of pharmacy. Techniques, excipients and formulations generally are found in, e.g., *Remington's Pharmaceutical Sciences*, Mack Publishing Co., Easton, Pa. 1985, 17$^{th}$ edition, Nema et al., *PDA J. Pharm. Sci. Tech.* 1997 51:166-171, G. Cole, et al., editors, Pharmaceutical Coating Technology, 1995, Taylor & Francis, ISBN 0 136628915, H. A. Lieberman, et al., editors, Pharmaceutical Dosage Forms, 1992 2$^{nd}$ revised edition, volumes 1 and 2, Marcel Dekker, ISBN 0824793870, J. T. Carstensen. *Pharmaceutical Preformulation*, 1998, pages 1-306, Technomic Publishing Co. ISBN 1566766907. Exemplary excipients for formulations include emulsifying wax, propyl gallate, citric acid, lactic acid, polysorbate 80, sodium chloride, isopropyl palmitate, glycerin, white petrolatum and other excipients disclosed herein.

Methods to make invention formulations include the step of bringing into association or contacting a formula 1 compound(s) with one or more excipient, such as one described herein or in the cited references. In general the formulations are prepared by uniformly and intimately bringing into association the formula 1 compound(s) with liquid excipients or finely divided solid excipients or both, and then, if appropriate, shaping the product.

Formulations suitable for oral administration are prepared as discrete units such as capsules, cachets or tablets each containing a predetermined amount of the formula 1 compound(s); as a powder or granules; as solution or a suspension in an aqueous liquid or a non-aqueous liquid; or as an oil-in-water liquid emulsion or a water-in-oil liquid emulsion. The formula 1 compound(s) may also be presented as a bolus, electuary or paste.

A tablet is made by compression or molding, optionally with one or more accessory ingredients. Compressed tablets may be prepared by compressing in a suitable machine the formula 1 compound(s) in a free-flowing form such as a powder or granules, optionally mixed with a binder, lubricant, inert diluent, preservative, surface active or dispersing agent. Molded tablets may be made by molding in a suitable machine a mixture of the powdered or granulated formula 1 compound and one or more excipients, which are optionally moistened, with an inert liquid diluent or excipient. The tablets may optionally be coated or scored and optionally are formulated so as to provide slow or controlled release of the formula 1 compound(s) therefrom. An exemplary tablet or caplet (a capsule shaped tablet) formulation suitable for buccal or sublingual delivery of a formula 1 compound to a subject's tissues comprises about 25 or 50 mg of a formula 1 compound such as BrEA hemihydrate comprising per 25 mg of the formula 1 compound about 6.2 mg povidone, about 0.62 mg magnesium stearate, about 45 mg mannitol and about 48 mg of compressible sucrose.

For infections of the eye or other external tissues e.g., the mouth or skin, the formulations are typically applied as a topical ointment or cream containing the formula 1 compound(s) in an amount of, for example, about 0.075 to about 20% w/w (including formula 1 compound(s) in a range between about 0.1% and 20% in increments of 0.1% w/w such as about 0.6% w/w, about 0.7% w/w, about 1% w/w, about 1.5% w/w, about 2% w/w, about 2.5% w/w, about 3% w/w, about 5% w/w, about 7% w/w, about 10% w/w etc.), including about 0.2 to 15% w/w and about 0.5 to 10% w/w. When formulated in an ointment, the formula 1 compound(s) may be employed with either a paraffinic or a water-miscible ointment base. Alternatively, they may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, butane 1,4-diol, mannitol, sorbitol, glycerol and a polyethylene glycol (including, e.g., PEG 300 and PEG 400) and mixtures thereof. The topical formulations may include a compound that enhances absorption or penetration of the formula 1 compound(s) through the skin or other affected areas. Examples of such dermal penetration enhancers include dimethyl sulphoxide and related analogs.

The oily phase of the emulsions of this invention may be constituted from known excipients in a known manner. While the phase may comprise an emulsifier (otherwise known as an emulgent), it desirably comprises a mixture of at least one emulsifier with a fat or an oil or with both a fat and an oil. A hydrophilic emulsifier may be included together with a lipophilic emulsifier, which acts as a stabilizer. Some embodiments include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulations include Tween60™, Span80™, cetostearyl alcohol, benzyl alcohol, myristyl alcohol, glyceryl monostearate and sodium lauryl sulfate.

The choice of suitable oils or fats for the formulation is based on achieving the desired cosmetic properties. Creams are generally a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils are used.

Formulations suitable for topical administration to the eye include eye drops wherein the formula 1 compound(s) is dissolved or suspended in a suitable excipient(s), including an aqueous solvent for a formula 1 compound(s) that comprise at least about 0.5, one, two or more charges at pH values near neutrality, e.g., about pH 6-8. The formula 1 compound(s) is typically present in such formulations in a concentration of about 0.5-20% w/w, about 1-10% w/w or about 2-5% w/w.

Formulations suitable for topical administration to oral mucosa include lozenges or tablets comprising the formula 1 compound(s) in a flavored basis or a monosaccharide or disaccharide such as sucrose, lactose or glucose and acacia or tragacanth; pastilles comprising the formula 1 compound(s) in an inert basis such as gelatin and glycerin, or sucrose and acacia; and mouthwashes comprising the formula 1 compound(s) in a suitable liquid excipient(s). In some embodiments, the lozenges or tablets optionally comprise the property of rapid dissolution or disintegration, e.g., disintegration within about 15 seconds to about 2 minutes, while in others, the lozenges or tablets comprise the property of slower dissolution or disintegration, e.g., disintegration within about 2 minutes to about 10 minutes or more.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the formula 1 compound(s) such excipients as are known in the art to be appropriate.

Formulations suitable for parenteral administration include aqueous and non-aqueous sterile injection solutions which may contain anti-oxidants, buffers, bacteriostats, salts (e.g., NaCl, potassium or sodium carbonate or bicarbonate or potassium or sodium phosphates) and solutes which render the formulation isotonic with the blood of the intended subject; and aqueous and non-aqueous sterile suspensions which may include suspending agents or thickening agents. In general, the formula 1 compound that is present in liquid compositions or formulations is completely dissolved in aqueous or non-aqueous excipients. However, in some embodiments, e.g., transient compositions or some formulations, the formula 1 compound is partially dissolved while the remaining portion is present as a solid, which can be a suspension or a colloid.

Exemplary formulations suitable for parenteral delivery of formula 1 compounds to subjects such as humans or animals typically comprise one, two, three or more excipients. Exemplary embodiments include (1) any two, three or four of propylene glycol, PEG200, PEG300, ethanol and benzyl benzoate and (2) any two, three or four of propylene glycol, PEG100, PEG200, PEG300, PEG400 and benzyl benzoate. Another exemplary formulation suitable for parenteral use include an aqueous BrEA hemihydrate suspension comprising about 50-120 mg/mL of BrEA hemihydrate that has an average particle size of 20 µm or less, about 0.05-0.2% w/v carboxymethylcellulose sodium, about 1-3% w/v polysorbate 80, about 0.75-0.85% w/v NaCl, about 0.023% w/v dibasic sodium phosphate, about 0.101% w/v monobasic sodium phosphate, about 0-0.5% ethanol v/v, pH 6.5+/−0.4 and optionally about 0.1-0.3% w/v of a preservative such as methylparaben.

Exemplary compositions and formulations generally comprise about 0.01-10% of a formula 1 compound, usually about 1-5%, and about 0.01-3% water, typically about 0.05-3%, usually about 0.1-1%. The formulations include unit or multiunit dosages suitable for parenteral administration once or twice per day or once per 2-3 days. Unit dosages comprise about 3-1000 mg of formula 1 compound per unit dose, typically about 5-500 mg, usually about 10-200 mg. For treating retroviruses such as HIV in humans, a unit dose usually comprises about 10-250 mg of BrEA hemihydrate, usually about 100-200 mg, in a volume of about 1-6 mL, usually about 2-4 mL.

Formulations, or compositions disclosed herein for use to make formulations suitable for administration by the routes disclosed herein optionally comprise an average particle size in the range of about 0.01 to about 500 microns, about 0.1 to about 100 microns or about 0.5 to about 75 microns. Average particle sizes include a range between 0.01 and 500 microns in 0.05 micron or in 0.1 micron or other increments, e.g., an average particle size of about 0.05, 0.1, 0.5, 1, 1.5, 2.0, 2.5, 3.0, 3.5, 4.0, 4.5, 5.0, 5.5, 6, 7, 8, 9, 10, 15, 20, 25, 30, 35, 40, 50, 60, 75, 85, 100, 120, etc. microns). When formula 1 compounds or compositions that comprise a formula 1 compound are used as intermediates to make a formulation, they may comprise one, two, three or more of these average particle sizes, or size ranges. In preparing any of the compositions or formulations that are disclosed herein and that comprise a formula 1 compound (and optionally one or more excipients), one may optionally mill, sieve or otherwise granulate the compound or composition to obtain a desired particle size, e.g., as described above.

Milling may occur before or after the formula 1 compound is contacted with one or more excipients. For example, one may mill a formula 1 compound such as 16α-bromoepiandrosterone hemihydrate, to obtain an average particle size (or diameter) of about 0.05-50 µM or about 0.5-10 µM (e.g., about 0.04, 0.1, 0.5, 1, 1.5, 2, 2.5, 5, 10, 15, 20, 40, 60, 80, 100 or 120 µM average particle size or diameter) before contacting the milled formula 1 compound with a liquid or solid excipient. In some cases the formula 1 compound is milled or sieved to obtain an average particle size of about 5 µm or about 10 µm before it is contacted with a solid or liquid excipient(s) to obtain a solution or suspension or a powder suitable for making a tablet, capsule or other dosage form as described herein or in the cited references.

As used herein, reference to an average particle size or an average particle diameter means that the material, e.g., a formula 1 compound(s), an excipient(s) or a composition that comprises both, is ground, milled, sieved or otherwise treated so as to comprise the specified average size. It is to be understood that some particles may be larger or smaller, but the composition or the formula 1 compound(s) will comprise a significant proportion of the material with the specified size or within an acceptable range of the specified size. Micronization methods include milling by ball mills, pin mills, jet mills (e.g., fluid energy jet mills) and grinding, sieving and precipitation of a compound(s) from a solution, see, e.g., U.S. Pat. Nos. 4,919,341, 5,202,129, 5,271,944, 5,424,077 and 5,455,049. Average particle size is determined by, e.g., transmission electron microscopy, scanning electron microscopy, light microscopy, X-ray diffractometry and light scattering methods or Coulter counter analysis.

Thus, the formula 1 compounds may comprise a powder that consists of one, two or more of these average particle sizes and the powder may be contacted with a solid excipient(s), suitably mixed and optionally compressed or formed into a desired shape. Alternatively, such a formula 1 compound(s) is contacted with a liquid excipient(s) to prepare a liquid formulation or a liquid composition that is incorporated into a solid formulation. Suitable micronized formulations thus include aqueous or oily solutions or suspensions of the formula 1 compound(s).

Formulations suitable for aerosol administration typically will comprise a fine powder, e.g., having an average particle size of about 0.1 to about 20 microns or any one, two or more of the average particle sizes within this range that are described above. The powder is typically delivered by rapid inhalation through the nasal passage or by inhalation through the mouth so as to reach the bronchioles or alveolar sacs of the lungs.

Formulations suitable for aerosol, dry powder or tablet administration may be prepared according to conventional methods and may be delivered with other therapeutic agents such as compounds heretofore used in the treatment or prophylaxis of viral or other infections as described herein. Such formulations may be administered, e.g., orally, parenterally (e.g., intravenous, intramuscular, subcutaneous, intradermal, intrathecal), topically, sublingually or by a buccal or sublingual route.

Micronized formula 1 compound is useful, e.g., to facilitate mixing, dissolution or uniform suspension of the formula 1 compound in one or more liquid or solid excipients, e.g., a PEG such as PEG 300 or PEG 400, or propylene glycol or benzyl benzoate, a complexing agent, such as a cyclodextrin (e.g., an $\alpha$-, $\beta$- or $\gamma$-cyclodextrin such as hydroxypropyl-$\beta$-cyclodextrin). Micronized formula 1 compound is also useful to facilitate uniformly distributing drug substance when the micronized compound is contacted with one or more solid excipients (e.g., a filler, a binder, a disintegrant, complexing agent (e.g., a cyclodextrin such as hydroxypropyl-$\beta$-cyclodextrin), a preservative, a buffer or a lubricant).

In related embodiments, suitable compositions or formulations comprise a formula 1 compound that is present in two or more physical forms. For example, a liquid composition or formulation may comprise a formula 1 compound that is present in solution and as undissolved particles, which may be milled as described herein. Alternatively, a solid composition or formulation may comprise a formula 1 compound that is present as an amorphous form and as a crystal or in an encapsulated granule. Such encapsulated granules may comprise a slow release type formulation and the formula 1 compound that is present may be in one or more physical forms, e.g., liquids or solids as described herein, but usually as a solid in tablets or other solid formulations.

The formulations are presented in unit-dose or multi-dose containers, for example sealed ampules and vials, and may be stored in a freeze-dried (lyophilized) condition requiring only the addition of the sterile liquid excipient, for example water for injection, immediately prior to use. Extemporaneous injection solutions and suspensions are prepared from sterile powders, granules and tablets as described above. Unit dosage formulations are those containing a daily dose or unit daily sub-dose, as recited herein, or an appropriate fraction thereof, of the formula 1 compound(s).

It should be understood that in addition to the ingredients particularly mentioned above the formulations of this invention may include other agents or excipients conventional in the art having regard to the type of formulation in question, for example those suitable for oral administration may include flavoring agents.

Formulations made from or comprising a formula 1 compound such as BrEA hemihydrate are optionally stored under conditions that limit the amount of light or water that reaches the formulation, e.g., in a sealed container that holds a formulation or unit dosage form and optionally contains silica gel or activated carbon. Water permeation characteristics of containers have been described, e.g., Containers—Permeation, Chapter, USP 23, 1995, U.S. Pharmacopeial Convention, Inc., Rockville, Md., p. 1787. Storage of BrEA hemihydrate or formulations that contain it is typically at about 4-30° C.

The invention further provides veterinary compositions comprising at least one formula 1 compound together with a veterinary excipient(s) therefor. Veterinary excipients are materials useful for the purpose of administering the composition and may be solid, liquid or gaseous materials that are otherwise inert or acceptable in the veterinary art and are compatible with the formula 1 compound(s). These veterinary compositions may be administered orally, parenterally or by any other desired route.

Invention formulations include controlled release pharmaceutical formulations containing a formula 1 compound(s) ("controlled release formulations", "slow release formulations" or the like) in which the release of the formula 1 compound(s) is controlled or regulated to allow less frequency dosing or to improve the pharmacokinetic or toxicity profile of a given formula 1 compound(s). Polymers and other materials that are suitable to prepare controlled release formulations that comprise a formula 1 compound have been described, e.g., U.S. Pat. Nos. 4,652,443, 4,800,085, 4,808, 416, 5,013,727, 5,188,840.

Thus, microcapsules, granules or other shaped forms may comprise a formula 1 compound and a slow release polymer or polymer matrix that comprises or consists of one or more of ethylene dimethacrylate, diethylene glycol dimethacrylate, diethylene glycol diacrylate, triethylene glycol dimethacrylate, triethylene glycol diacrylate, tetrathylene glycol dimethacrylate, tetraethylene glycol diacrylate, polyethylene glycol dimethacrylate, polyethylene glycol diacrylate, diethylaminoethyl dimethacrylate, glycidyl methacrylate, epoxy acrylate, glycidyl acrylate, hydroxyethyl methacrylate, hydroxyethyl acrylate, hydroxypropyl methacrylate, hydroxypropyl acrylate, hydroxybutyl methacrylate, hydroxybutyl acrylate, hydroxyhexyl methacrylate, hydroxyhexyl acrylate, butanediol dimethacrylate, butanediol diacrylate, propanediol dimethacrylate, propanediol diacrylate, pentanediol dimethacrylate, pentanediol diacrylate, hexanediol dimethacrylate, hexanediol diacrylate, neopentyl glycol dimethacrylate, neopentyl glycol diacrylate, trimethylopropane triacrylate, trimethylolpropane trimethacrylate, trimethyloethane triacrylate, trimethylolethane trimethacrylate, polypropyleneglycol diacrylate, and polypropylene glycol dimethacrylate.

An effective dose of formula 1 compound(s) depends in part on one or more of the nature of the condition being treated, toxicity, whether the formula 1 compound(s) is being used prophylactically (generally lower doses) or against an active infection or condition, the method of delivery, and the formulation. For use in humans, the effective dosage will typically be determined by the clinician using conventional dose escalation studies. In other subjects, the dose is obtained by similar dose escalation analyses. For humans, an effective dose can be expected to be from about 0.05 to about 50 mg/kg body weight per day, e.g., about 2 mg/kg/day, about 4 mg/kg/day, about 6 mg/kg/day, or about 8 mg/kg/day. For example, for topical delivery the daily candidate dose for an adult human of approximately 70 kg body weight will range from about 1 mg to about 500 mg, generally between about 5 mg and about 40 mg, and may take the form of single or multiple doses or administration sites. For non-human subjects, e.g., mammals such as rodents or primates, the effective daily dosage may comprise about 0.05 mg/kg/day to about 300 mg/kg/day, including about 1 mg/kg/day to about 100 mg/kg/day. As used herein, an "effective dosage" or an "effective amount" of a formula 1 compound(s) is one that is sufficient to result in, e.g., a detectable change in a symptom or an immune parameter such as one described herein.

An effective dosage (or daily dosage) may be administered to a subject over a period of time, e.g., at least about 1-14 days before a symptom change or an immune parameter detectably changes. Effective dosages may include any of the dosages as described herein.

Embodiments include formulations that comprise a liposome or lipid complex that comprises a formula 1 compound(s), e.g., BrEA or an ester, carbamate, carbonate, amino acid or peptide thereof. Such formulations are prepared according to known methods, e.g., U.S. Pat. Nos. 4,427,649, 5,043,165, 5,714,163, 5,744,158, 5,783,211, 5,795,589, 5,795,987, 5,798,348, 5,811,118, 5,820,848, 5,834,016 and 5,882,678. The liposomes optionally contain an additional therapeutic agent(s), e.g., amphotericin B, cis-platin, adriamycin, a protease inhibitor, a nucleoside or a nucleotide analog, such as one of those mentioned herein. Formulations that comprise liposomes can be delivered to a subject by any standard route, e.g., oral, aerosol or parenteral (e.g., s.c., i.v. or i.m.).

Liposome formulations can be used to enhance delivery of the formula 1 compound(s) to certain cell types such as tumor cells (see e.g., U.S. Pat. No. 5,714,163) or to cells of the reticuloendothelial system ("RES"). The RES includes macrophages, mononuclear phagocytic cells, Kupfer cells, cells lining the sinusoids of the spleen, lymph nodes, and bone marrow, and the fibroblastic reticular cells of hematopoietic tissues. In general, RES cells are phagocytic and they are targets for targeted delivery of a formula 1 compound(s) in vitro or in vivo using liposomes, or other compositions or formulations. Thus, one can deliver formula 1 compound to a neoplasm that is derived from reticuloendothelial tissue (reticuloendothelioma). The liposomes may optionally comprise a peptide from an infectious agent such as a malaria parasite, a virus or a tumor associated antigen. The peptides may facilitate the generation of a MHC class II and B cell response.

Invention embodiments include the product made by a process of combining, mixing or otherwise contacting a formula 1 compound such as BrEA hemihydrate and one, two or more excipients. Such products are produced by routine methods of contacting the ingredients. Such products optionally contain a diluent, a disintegrant, a lubricant, a binder, or other excipients described herein or in references cited herein.

Other embodiments include compositions that transiently occur when a method step or operation is performed. For example, when a formula 1 compound such as BrEA, containing less than about 3% water is contacted with an excipient, e.g., a PEG, an alcohol, propylene glycol or benzyl benzoate, the composition before addition of one ingredient with another is a non-homogenous mixture. As the ingredients are contacted, the mixture's homogeneity increases and the proportion of ingredients relative to each other approaches a desired value. Thus, invention compositions, which contain less than about 3% water can comprise about 0.0001-99% of a formula 1 compound such as BrEA and one or more excipients. These transient compositions are intermediates that necessarily arise when one makes an invention composition or formulation and they are included in invention embodiments to the extent that they are useful in the disclosed methods or that they are patentable.

When a formula 1 compound and an excipient(s) is contacted or mixed, the final composition may comprise a homogenous mixture or it may comprise a mixture that is not homogenous for one or more of the compounds that are present in the composition. Compositions and formulations that are either homogenous or non-homogenous are included in the scope of the invention. Non-homogenous compositions can be used to make controlled release formulations.

Invention embodiments include compositions and formulations that comprise less than about 3% water, a formula 1 compound and a compound that is not generally considered suitable for human use but is useful to make an invention formulation for veterinary use. Veterinary formulations are compositions useful for the purpose of administering invention compositions to primates, cats, dogs, horses, cows, rabbits and other subjects and may contain excipients acceptable in the veterinary art and are compatible with formula 1 compounds such as BrEA. These veterinary compositions may not always be suitable for human use because they contain an excipient that is not suitable for human use, e.g., an alcohol other than ethanol such as methanol, propanol or butanol. Typically such excipients will be present at relatively low levels, e.g., about 1-30%, usually about 1-5%.

Invention embodiments include compositions and formulations, e.g., unit dosage forms and sterile solutions, that comprise (1) about 1-100 mg/mL of a formula 1 compound(s), about 57.5% propylene glycol, about 25% PEG300, about 12.5% ethanol and about 5% benzyl benzoate; (2) about 1-60 mg/mL of a formula 1 compound(s), about 70% propylene glycol, about 25% PEG300 and about 5% benzyl benzoate; (3) about 1-60 mg/mL of a formula 1 compound(s), about 25% PEG300, about 35% propylene glycol, about 35% mannitol and about 5% benzyl benzoate; (4) about 1-60 mg/mL of a formula 1 compound(s), about 57.5% propylene glycol, a mixture comprising about 25% PEG300 and PEG200 (e.g., PEG300:PEG200 in a ratio of about 1:10 to about 10:1), about 12.5% ethanol and about 5% benzyl benzoate; (5) about 1-60 mg/mL of a formula 1 compound(s), about 75% propylene glycol, a mixture comprising about 25% PEG300 and PEG200 (e.g., a PEG300:PEG200 in a ratio of about 1:10 to about 10:1) and about 5% benzyl benzoate; (6) about 1-60 mg/mL of a formula 1 compound(s), about 25% PEG300 and PEG200 (e.g., PEG300:PEG200 in a ratio of about 1:10 to about 10:1), about 35% propylene glycol, about 35% mannitol and about 5% benzyl benzoate; (7) any of formulations (1) through (6) where the formula 1 compound(s) is about 40-55 mg/mL; (8) any of formulations (1) through (6) where the formula 1 compound(s) is about 30-100 mg/mL; (9) any of formulations (1) through (8) where 1, 2, 3 or 4 formula 1 compounds are present; (10) any of formulations (1) through (8) where 1 or 2 formula 1 compounds are present; (11) any of formulations (1) through (8) where 1 formula 1 compound is present; (12) any of formulations (1)

through (11) where the formula 1 compound comprises independently at 1, 2 or 3 of any of the variable groups that are bonded to the formula 1 compounds, e.g., $R^1$-$R^6$, $R^{10}$, $R^{15}$, $R^{17}$ or $R^{18}$, an independently selected ester, thioester, carbonate, carbamate, amino acid or peptide of 1 or 2 independently selected formula 1 compounds; (13) any of formulations (1) through (12) where the formula 1 compound comprises or is BrEA or BrEA hemihydrate; (14) any of formulations (1) through (13) where the formula 1 compound comprises or is an ester, a sulfate ester, a monosaccharide conjugate or phosphoester of BrEA.

Exemplary embodiments include liquid formulations that comprise a formula 1 compound, one, two, three, four or more excipients and less than about 3% v/v water, wherein the formulation is optionally disposed in containers that exclude water. These excipients are optionally selected from those disclosed herein. Such formulations optionally comprise less than about 2% v/v water, less than about 1% v/v water, less than about 0.5% v/v water, less than about 0.2% v/v water or less than about 0.1% v/v water. Such formulations are suitable for use in methods to modulate an immune response or cellular response in a subject in need thereof comprising administering to the subject, or delivering to the subject's tissues, an effective amount of a compound of formula 1. The subject in need thereof would have, or be subject to, a condition such as one disclosed herein as amenable to treatment, prevention, amelioration using a formula 1 compound, which is optionally combined with the use of another therapeutic treatment or agent as disclosed herein or in the cited references. These formulations are suitable for use in any of the dosing methods or protocols disclosed herein, including the intermittent dosing protocols disclosed herein.

Buccal formulations. Formula 1 compounds may be administered to subjects by buccal or sublingual dosing. The buccal area generally refers to the subject's mouth and pharynx, and the buccal mucosa includes the mucosa of the mouth and pharynx. The sublingual area refers generally to the mucosa below and adjacent to the tongue. Formulations suitable for buccal or sublingual administration typically comprise about 1-100 mg of formula 1 compound per unit dose, often about 2-60 mg. Buccal or sublingual formulations may comprise a tablet that contains about 1, 5, 10, 15, 20, 25, 30, 35, 40, 50 or 60 mg of a formula 1 compound. Solid and liquid buccal or sublingual formulations optionally include one, two, three or more excipients such as fillers, binders, lubricants, antioxidants, preservatives, flavoring agents or disintegrants, e.g., lactose, sucrose, mannitol, Tween-80, magnesium stearate, butylated hydroxyanisole, butylated hydroxytoluene, cyclodextrins (e.g., α-cyclodextrins, β-cyclodextrins, γ-cyclodextrins, hydroxypropyl-β-cyclodextrin), carbomers, hydrolyzed polyvinylalcohol, polyethylene oxide, polyacrylates, hydroxypropylmethylcellulose, hydroxypropylcellulose, and combinations thereof. Such formulations may be a unit solid such as a tablet, or a powder or liquid. Buccal tablets may comprise a concave surface for contacting the buccal mucosa and adhering to it. A buccal or sublingual dosage may comprise a compressed tablet of a substantially uniform mixture of a bioerodible polymeric carrier, which on sustained contact with the oral mucosa, substantially or completely erodes within a predetermined period in the range of about 10 minutes to about 24 hours. In some embodiments, the formula 1 compound is administered by a method for administering the compound to the subject, e.g., to a mammal or a human, comprising affixing a unit dosage or tablet to the subject's buccal mucosa in a region at or near the upper gum between the first bicuspid on the left and the first bicuspid on the right (or an alternative location for the dosage unit is the inner lip area opposing the this upper gum area) and optionally allowing the tablet to remain in place until erosion thereof is complete or nearly complete. Exemplary excipients may comprise a combination of polyethylene oxide and a carbomer, e.g., wherein the polyethylene oxide and the carbomer are in an approximately 1:5 to 5:1 ratio by weight.

Tablets or unit dosages for buccal or sublingual delivery may be about 5 mm in diameter and 2 mm in height, so that the unit dosage occupies about 40 mm³. Such dosages will typically weigh less than about 100 mg (e.g., about 5 to 60 mg), with a contact surface area of about 10-30 mm², e.g., about 15-20 mm². Such dosages will generally be about 4-10 mm in diameter and about 1-3 mm in height. When a polymer excipient is used, it optionally comprises a polymer having sufficient tack to ensure that the dosage unit adheres to the buccal mucosa for a sufficient time period, e.g., the time period during which drug is to be delivered to the buccal mucosa. The polymeric excipient is gradually "bioerodible," and it hydrolyzes, dissolves, erodes or disintegrates (collectively "erodes") at a predetermined rate upon contact with water or saliva. The polymeric carrier is generally sticky when moist, but not when dry, for convenience in handling. The average molecular weight of the polymer may be about 400 to 1,000,000, or about 1,000 to 100,000. Higher the molecular weight polymers generally erode more slowly.

For these buccal and sublingual dosages, a pharmaceutically acceptable polymer(s) can be used. Such polymers will provide a suitable degree of adhesion and the desired drug release profile, and are generally compatible with the drug to be administered and any other components that may be present in the buccal dosage unit. The polymeric carriers optionally comprise hydrophilic (water-soluble and water-swellable) polymers that adhere to the wet surface of the buccal mucosa. Examples of polymeric carriers that are useful herein include acrylic acid polymers and co, e.g., those known as "carbomers" (Carbopol™, which may be obtained from B.F. Goodrich, is one such polymer). Other suitable polymers include hydrolyzed polyvinylalcohol; polyethylene oxides (e.g., Sentry Polyox™ water soluble resins, available from Union Carbide); polyacrylates (e.g., Gantrez™, which may be obtained from GAF); vinyl polymers and copolymers; polyvinylpyrrolidone; dextran; guar gum; pectins; starches; and cellulosic polymers such as hydroxypropyl methylcellulose, (e.g., Methocel™, which may be obtained from the Dow Chemical Company), hydroxypropyl cellulose (e.g., Klucel™, which may be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like. The carrier may also comprise two or more suitable polymers in combination, for example, a carbomer combined in an approximately 1:5 to 5:1 ratio, by weight, with a polyethylene oxide.

Buccal dosages may contain only the formula 1 compound and the polymer(s). However, it may be desirable in some cases to include one or more additional excipients. For example, a lubricant may be included to facilitate the process of manufacturing the dosage units; lubricants may also optimize erosion rate and drug flux. If a lubricant is present, it may optionally represent about 0.01 wt. % to about 2 wt. %, or about 0.01 wt. % to 0.5 wt. %, of the dosage unit. Suitable lubricants include, but are not limited to, magnesium stearate, calcium stearate, stearic acid, sodium stearylfumarate, talc, hydrogenated vegetable oils and polyethylene glycol. However, modulating the particle size of the components in the dosage unit and/or the density of the unit can provide a similar effect, e.g., improved manufacturability, and optimization of erosion rate and drug flux without addition of a lubricant.

Other excipients are also optionally incorporated into buccal unit dosages. Such additional optional excipients include, one or more disintegrants, diluents, binders, enhancers, or the like. Examples of disintegrants that may be used include, but are not limited to, cross-linked polyvinylpyrrolidones, such as crospovidone (e.g., Polyplasdone™ XL, which may be obtained from GAF), cross-linked carboxylic methylcelluloses, such as croscarmelose (e.g., Ac-di-sol™, which may be obtained from FMC), alginic acid, and sodium carboxymethyl starches (e.g., Explotab™, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., Di-Tab™, which may be obtained from Stauffer), sugars that have been processed by cocrystallization with dextrin (e.g., co-crystallized sucrose and dextrin such as Di-Pak™, which may be obtained from Amstar), lactone, calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Permeation enhancers may also be present in the novel dosage units in order to increase the rate at which the active agent passes through the buccal mucosa. Examples of permeation enhancers include, but are not limited to, polyethylene glycol monolaurate ("PEGML"), glycerol monolaurate, lecithin, the 1-substituted azacycloheptan-2-ones, particularly 1-n-dodecylcyclaza-cycloheptan-2-one (available under the trademark Azone™ from Nelson Research & Development Co., Irvine, Calif.), lower alkanols (e.g., ethanol), SEPA™ (available from Macrochem Co., Lexington, Mass.), cholic acid, taurocholic acid, bile salt type enhancers, and surfactants such as Tergitol™, Nonoxynol-9™ and TWEEN-80™.

Flavorings are optionally included in buccal or sublingual formulations. Any suitable flavoring may be used, e.g., one or more of mannitol, sucrose, glucose, lactose, lemon, lemon lime, orange, menthol or artificial sweeteners such as aspartame, saccharin sodium, dipotassium glycyrrhizinate, stevia and thaumatin. Some sweeteners such as sucrose may also aid in dissolution or erosion of solid formulations. Coloring agents may also be added, e.g., any of the water soluble FD&C dyes or mixtures thereof, e.g., one or more of FD&C Yellow No. 5, FD&C RED No. 2, FD&C Blue No. 2, etc., food lakes or red iron oxide. In addition such formulations dosages may be formulated with one or more preservatives or bacteriostatic agents, e.g., methyl hydroxybenzoate, propyl hydroxybenzoate, chlorocresol, benzalkonium chloride, or the like.

Other embodiments include solid buccal or sublingual formulations comprising (i) a formula 1 compound and (ii) erythritol, (iii) crystalline cellulose and (iv) a disintegrant, e.g., crospovidone. These formulations are capable of buccal disintegration or dissolution and may further comprise mannitol. These formulations may dissolve completely in solely saliva within about 1-10 minutes of administration to a subject. The erythritol is optionally contained in a proportion of about 5-90 parts by weight, based on 100 parts by weight of the solid buccal formulation. The crystalline cellulose is optionally contained in a proportion of about 3-50 parts by weight, based on 100 parts by weight of the formulation. The disintegrant is optionally contained in a proportion of 1-10 parts by weight. In any of the solid buccal or sublingual formulations the ingredients are generally uniformly mixed, although non-uniform mixtures may be used. An exemplary formulation comprises a solid capable of buccal disintegration or dissolution, which comprises (i) about 0.3-50 parts by weight of a formula 1 compound, (ii) about 50-80 parts by weight of erythritol, (iii) about 5-20 parts by weight of crystalline cellulose and (iv) about 3-7 parts by weight of a disintegrant, which optionally is one or more of crospovidone, croscarmellose, croscarmellose sodium, carmellose calcium, carboxymethylstarch sodium, low substituted hydroxypropyl cellulose or corn starch. Examples of the crystalline cellulose include products of various grade such as CEOLUS KG801, avicel PH101, avicel PH102, avicel PH301, avicel PH302, avicel RC-591 (crystalline cellulose carmellose sodium) and so on. One crystalline cellulose may be used or two or more species may be used in combination. The disintegrant, e.g., crospovidone, may be used singly or in combination with other disintegrants. Crospovidone includes any cross-linked 1-ethenyl-2-pyrrolidinone homopolymer, and may comprise a polymer of molecular weight of 1,000,000 or more. Examples of commercially available crospovidone include Cross-linked povidone, Kollidon CL, Polyplasdone XL, Polyplasdone XL-10, INF-10 (manufactured by ISP, Inc.), polyvinylpolypyrrolidone, PVPP and 1-vinyl-2-pyrrolidinone homopolymer. The disintegrants are optionally incorporated in a proportion of about 1-15 parts by weight, or about 1-10 parts by weight, or about 3-7 parts by weight, based on 100 parts by weight of the solid formulation.

Solid or liquid buccal or sublingual formulations are useful to administer a formula 1 compound to a subject (e.g., mammal or human) to achieve a prolonged plasma concentration of the compound. This is accomplished comprising the steps of (1) preparing a solution of the compound dissolved in an aqueous carrier solution; (2) disposing the solution within the subject's sublingual or buccal area in a quantity to deliver a dosage of about 0.01 to about 2.0 or 4.0 mg/kg of body weight or about 0.1-1 mg/kg, e.g., a dose of about 0.1 to about 100 mg or about 1-50 mg; and (3) contacting the formulation with the buccal or sublingual mucosa, which creates or maintains prolonged detectable plasma concentrations of the formula 1 compound or a metabolite thereof, e.g., for at least about 2, 4, 8, 24, 48 or 72 hours or more.

In other embodiments, buccal or sublingual delivery of a formula 1 compound is accomplished using formulations present as tablets or lozenges, which comprise a candy carrier or a hard candy matrix and sufficient compound, e.g., about 1-100 mg. The candy may be present as a sucker or lollipop.

Some embodiments include a solid buccal or sublingual formulation containing a formula 1 compound where unit doses of the formulation substantially or completely disintegrates or erodes within about 20-120 seconds in water at 37° C. or on insertion of the unit dose into the buccal area or upon placement under the tongue. Such formulations may comprise a swellable hydrophilic excipient, a water-soluble or a water-dispersible excipient, e.g., one or more of partially hydrolyzed gelatin, hydrolyzed dextran, dextrin, mannitol, alginates, polyvinyl alcohol, polyvinyl pyrrolidine, water soluble cellulose derivatives, methylcellulose, ethyl cellulose, carboxymethyl cellulose, hydroxymethylcellulose, hydroxypropyl methylcellulose, microcrystalline cellulose, alginates, gelatin, guar gum, gum tragacanth, gum acacia, polyacrylic acid, polymethacrylic acid, polysilicic acid, polylactic acid, polymaleic acid, polyvinyl alcohol, polyethylene glycol, polyvinyl pyrrolidone, nonionic blocked polymers, carbomers, polycarbophils, a water soluble starch, dicalcium phosphate, calcium carbonate, silica or polyethyleneglycol, e.g., PEG2000, PEG8000 or PEG20000, or a polyethylene oxide ("PEO"), PEO100000 or PEO5000000.

Buccal and sublingual formulations comprising a formula 1 compound are suitable for delivery of the compound to subjects using continuous or intermittent dosing protocols, e.g., any protocol described herein. Excipients disclosed for buccal or sublingual formulations may also be used in formulations suitable for administration by other routes disclosed herein, e.g., oral or parenteral. Other suitable excipients or formulations that may be modified to comprise a formula 1 compound or methods to make, use or characterize them have been described, see, e.g., U.S. Pat. Nos. 4,727,064, 4,877,774, 4,764,378, 5,135,752, 5,624,677, 5,763,476, 5,958,453, 6,284,262, 6,284,263, 6,264,974, 6,248,357, 6,200,593 and 6,103,257.

Other embodiments include the product obtained by storing invention compositions or formulations, e.g., unit dosage forms, any of embodiments (1)-(14) above, or compositions used to make formulations, at about 4-40° C. for at least about 3 days, e.g., storage at ambient temperature for about 1-24 months. Invention formulations will typically be stored in hermetically or induction sealed containers for these time periods. Compositions and formulations that comprise a formula 1 compound will typically be held in closed or sealed containers, particularly when the composition is a formulation for pharmaceutical or veterinary use. The specification and claims disclose exemplary suitable formulations and unit dosage forms for these embodiments.

Immune modulation. As noted elsewhere, the formula 1 compounds, or the biologically active substances produced from these compounds by hydrolysis or metabolism in vivo, have a number of clinical and non-clinical applications. The compounds are generally useful to correct immune dysregulation, e.g., imbalanced immune responses to disease conditions, pathogens or the like, suppression of an innate or acquired immune response(s) and inflammation conditions in vertebrate or mammalian subjects, e.g., as disclosed herein. Thus, while the compounds will generally enhance a deficient immune response in a given clinical condition, they will generally reduce the same immune response when it is too active in a different clinical condition. For example, they can enhance insufficient or suboptimal Th1 immune responses, reduce excess or undesirable Th2 immune responses, reduce excess or undesirable Th1 immune responses or enhance insufficient or suboptimal Th2 immune responses or they can reduce excess or undesirable inflammation or one or more of its symptoms. The compounds will generally also modulate dysregulated Tc1 and Tc2 immune responses (associated with $CD8^+$ T cells) in a similar manner, e.g., excessive Tc1 or Tc2 responses will be detectably decreased and deficient or suboptimal Tc1 or Tc2 responses will generally be detectably enhanced.

In modulating one or more activities of Th1, Th2, Tc1 or Tc2 cells or their function(s), the formula 1 compounds will typically detectably modulate one, two, three or more factors, e.g., immune cell subsets or populations, cytokines, interleukins, surface antigens such as a CD molecule(s) and/or their receptors that affect the development, migration, numbers or biological function(s) of such cells. When a Th1 or Tc1 cell or population is affected, the formula 1 compounds will typically increase or decrease the synthesis or level of one, two or more of an associated effector factor, e.g., IFNγ, IL-2, IL-12, IL-18, T-bet, PPARα and PPARγ or a cell surface molecule, e.g., as disclosed herein or in the cited references, that is associated with or needed for normal, optimal or enhanced Th1 or Tc1 cells or cell function. Such molecules are generally associated with development or enhancement of Th1 or Tc1 cells or their biological function(s). When a Th2 or Tc2 cell or population is affected, the formula 1 compounds will typically increase or decrease the synthesis or level of one, two or more of an associated effector factor, e.g., IL-4, IL-5, IL-6, IL-8, IL-10, IL-13, GATA-3, COX-2 or a cell surface molecule, e.g., as disclosed herein or in the cited references, that is associated with or needed for normal, optimal or enhanced Th2 or Tc2 cells or cell function(s). Such molecules are generally associated with development or enhancement of Th2 or Tc2 cells or their biological function(s).

Similarly, when a subject has or is subject to developing an unwanted or excessive inflammation, the formula 1 compounds will generally detectably modulate one or more relevant effector factors for inflammation, e.g., a decrease of one, two, three or more of IL-1α, IL-1β, TNFα, MIP-1α, γIFN, IL-6, IL-8, IL-10 and COX-2, or an increase of one or more suppressor factors or antagonists of inflammation. Such modulation can comprise increases or decreases of at least about 2%, 5%, 10%, 15%, 20%, 25%, 30%, 40%, 50%, 60%, 70%, 75%, 80%, 85%, 90%, 95%, 98%, 100%, 200%, 300%, 500%, 1000%, 5000% or within a range between any two of these values, e.g., between about 5-95%, about 10-90%, about 5-60% or about 40-95%. In general, such changes leads to a detectable amelioration of an inflammation-associated disease, condition, symptom or to the detectable slowing of the progression thereof or to a detectably reduced incidence or severity of or susceptibility to developing an unwanted inflammatory response.

In conditions where an unwanted or excessive Th1, Tc1, Th2 or Tc2 response is associated with or causes a disease(s), disease(s) progression, disease(s) state maintenance, condition(s) or symptom(s), the formula 1 compounds will generally decrease the level or one or more biological activity of one, two or more of their respective associated effector molecules. In conditions where a deficient or suboptimal Th1, Tc1, Th2 or Tc2 response is associated with or causes a disease(s), disease(s) progression, disease(s) state maintenance, condition(s) or symptom(s), the formula 1 compounds will generally increase the level or one or more biological activity of one, two, three or more of their respective associated effector molecules. Such changes in the level or biological activity(ies) the associated effector molecules is generally detectable using standard methods and is typically an increase (when a response is insufficient) or a decrease (when a response is in excess) of at least about 2%, 5%, 10%, 15%, 20%, 25%, 30%, 40%, 50%, 60%, 70%, 75%, 80%, 85%, 90%, 95%, 98% or within a range between any two of these values, e.g., between about 5-95%, about 10-90%, about 5-60% or about 40-95%. In general, such changes leads to a detectable amelioration of a disease, condition, symptom or to the detectable slowing of the progression thereof or to a detectably reduced incidence or severity of or susceptibility to developing a disease(s) or the occurrence of a symptom(s) for a at least a portion of subjects that are treated with a formula 1 compound, e.g., at least about 5%, 10%, 20%, 40%, 60% or 80% of treated subjects. The formula 1 compounds may facilitate the clinical cure of a disease(s), prolong remission of a disease(s) or eliminate or ameliorate a clinically detectable symptom(s).

The formula 1 compound will generally also affect the function of other immune cell subsets in a similar manner. Thus, when an insufficient macrophage, dendritic cell or neutrophil response is associated with the establishment, maintenance or progression of a disease, symptom or a condition, the formula 1 compounds will generally enhance of the level or a biological activity(ies) of one or more effector molecule associated with or needed for an optimal or more normal response or immune function that is mediated by the macrophages, dendritic cells or neutrophils. Similarly, when the subject suffers from a excessive or pathological activity associated with macrophages, dendritic cells or neutrophils, which is associated with the establishment, maintenance or progression of a disease, symptom or a condition, the formula 1 compounds will generally detectably reduce the level or a biological activity(ies) of one or more effector molecule associated with or needed for an optimal or more normal response or immune function that is mediated by the macrophages, dendritic cells or neutrophils. Such effector molecules are as described herein or in the cited references.

As used herein, reference to Th1 or Th2 immune responses means such responses as observed in mammals generally and not as observed in the murine system, from which the Th1 and Th2 terminology originated. Thus, in humans, Th1 cells are CD4+T lymphocytes and they usually preferentially display chemokine receptors CXCR3 and CCR5, while Th2 cells are CD4+T lymphocytes and usually preferentially express the CCR4, CCR8 and/or CXCR4 chemokine receptor molecule(s) and generally a smaller amount of CCR3, see, e.g., U. Syrbe et al., *Springer Semin. Immunopathol.* 1999 21:263-285, S. Sebastiani et al., *J. Immunol.* 2001 166:996-1002. Tc1 and Tc2 immune responses are mediated by $CD8^+$ lymphocytes and means to identify these cells and their associated lymphokines, cell specific antigens and biological activities have been described, see, e.g., M. B. Faries et al., *Blood* 2001 98:2489-2497, W. L. Chan et al., *J. Immunol.* 2001 167:1238-1244, C. Prezzi et al., *Eur. J. Immunol.* 2001 31:894-906, H. Ochi et al., *J. Neuroimmunol.* 2001 119:297-305, D. H. Fowler and R. E. Gress, *Leukemia and Lymphoma* 2000 38:221-234.

The formula 1 compounds are useful in reestablishing normal immune function in various immune dysregulation or immune suppression conditions. For example, they are useful to treat, slow progression of or to ameliorate one or more symptoms associated with one or more of an autoimmune condition(s), a inflammation condition(s), an infection(s), a cancer(s), a precancer(s), a chemotherapy(ies), radiation therapy, a burn(s), a trauma(s), a surgery(ies), a pulmonary condition, a cardiovascular disease(s) and a neurological or neurodegenerative disease(s). Without being limited to any theory, the formula 1 compounds are believed to act through several mechanisms, including by directly or indirectly modulating steroid receptor activity or by affecting or modulating other biological targets such as transcription factors, steroid binding proteins or enzymes in at least some of the diseases, conditions or symptoms disclosed herein.

The formula 1 compounds are useful to modulate delayed-type hypersensitivity ("DTH") responses and anergic conditions in subjects having to subject to developing abnormal DHT responses or anergy. Means to measure such responses and conditions are known and can be used to characterize the effects of the formula 1 compounds on these responses and conditions. See, e.g., A. E. Brown, et al., *J. Med. Assoc. Thailand* 83:633-639 2000, R. A. Smith et al., *J. Adolesc. Health* 27:384-390 2000, N. M. Ampel, *Med. Mycology* 37:245-250 1999. The compounds will generally detectably enhance or restore DTH in immune suppression conditions. They will also generally detectably reduce or eliminate anergy in subjects having significantly reduced or no immune response to, e.g., specific antigens or pathogens.

The invention provides a method to detectably enhance an antigen specific immune response, cell mediated immune response or a delayed-type hypersensitivity immune response in a subject having impaired or negligible antigen specific immune response, cell mediated immune response or delayed-type hypersensitivity immune response, comprising administering to the subject, or delivering to the subject's tissues, an effective amount of a formula 1 compound. The antigen specific immune response, cell-mediated immune response or delayed-type hypersensitivity immune response can be enhanced at least about 25%, at least about 40%, at least about 50%, at least about 60%, at least about 75% or at least about 90%. Some of the subjects may have an antigen specific immune response, cell mediated immune response or a delayed-type hypersensitivity immune response that is impaired or negligible, e.g., about 50% or less or about 30% or less or about 10% or less of the response that an otherwise normal subject would be expected to have. Such subjects may not detectably respond to at least 1 antigen out of 2, 3, 4 or 5 antigens that a normal subject would respond to. In some embodiments, the subject is an HIV-infected human having a CD4+T cell count of about 0-150 $cells/mm^3$ or about 2-100 $cells/mm^3$ and/or wherein the antigen specific immune response, cell mediated immune response or delayed-type hypersensitivity immune response is an enhanced response to a viral, bacterial, parasite or fungal antigen such as an HIV, HCV, HBV or CMV antigen such as a viral or HIV core antigen or HIV p24 antigen or a viral or HIV envelope antigen, a *Candida* antigen, a viral, bacterial, parasite or fungal antigen essentially as described herein or to phytohemagglutinin. The responses to treatment with a formula 1 compound may be quantitated by, e.g., mixed lymphocyte reaction, ELIspot analysis or flow cytometric analysis of, e.g., circulating blood cells such as $CD4^+$ or $CD8^+$ T cells or for levels of cytokines (e.g., IL-2, TNFα or IFNγ) in such cells. Such analyses have been described, e.g., V. P. Badovinac and J. T. Hardy, *J. Immunol. Methods* 2000, 238:107-117, N. Favre et al., *J. Immunol. Methods* 1997, 204:57-66, E. Hagiwara et al., *Cytokine* 1995, 7:815-822, N. W. Lukacs et al., *Blood* 1993, 82:3668-3674, M. Umemoto et al., *Clin. Exp. Immunol.* 1998, 112:459-463, A. Fietta et al., *Gerontology* 1994, 40:237-245, C. H. Orteu et al., *J. Immunol.* 1998, 161:1619-1629.

Clinical indications that have an association with or have a symptom(s) that is consistent or associated with an excessive or unwanted Th2 immune response include, e.g., fatigue, pain, fever or an increased incidence of infection, schizophrenia, acute myelitis, tumor progression, progressive systemic sclerosis, Omenn's syndrome, atopic disease, atopy, allergen hypersensitivity, atopic asthma, atopic dermatitis, burns, trauma (e.g., bone fracture, hemorrhage, surgery), immune responses to xenotransplantation, chronic periodontitis, SLE (systemic lupus erythematosus), discoid lupus erythematosus, osteoporosis, myasthenia gravis, Graves disease, mite-associated ulcerative dermatitis, rheumatoid arthritis and osteoarthritis. Excessive Th2 immune responses are also associated with an unwanted symptom or pathology, e.g., fatigue, pain, fever or an increased incidence of infection, that is associated with aging, allergy and inflammation conditions such as allergic bronchopulmonary aspergillosis in cystic fibrosis patients, allergic respiratory disease, allergic rhinitis, atopic dermatitis, subepithelial fibrosis in airway hyperresponsiveness, chronic sinusitis, perennial allergic rhinitis, fibrosing alveolitis (lung fibrosis). This common underlying immune component is at least part of the pathology or symptoms of all of these conditions. This allows a formula 1 compound to be effectively used to prevent or treat the condition or to treat or ameliorate one or more symptoms that are associated with these conditions. Thus, in some embodiments, an unwanted or excessive Th2 response is present and amelioration of one or more symptoms associated with this condition is accomplished by administering an effective amount of a formula 1 compound according to the methods described herein, e.g., formula 1 compound is administered using a formulation and a route of administration essentially as described herein on an intermittent or a daily basis.

Typically, unwanted Th2 immune responses are associated with, or caused by, increased expression of one or more cytokines or interleukins such as one, two, three or more of cortisol, IL-4, IL-5, IL-6, IL-10 and IL-13. Administration of a formula 1 compound will generally reduce the expression of one or more of the Th2-associated cytokines or interleukins. At the same time, the compounds generally enhance the expression of one or more cytokines or interleukins associated with Th1 immune responses. Because of their capacity to modulate or to balance Th1 and Th2 immune responses, the compounds are useful for a variety of clinical conditions, e.g., infection, immunosuppression or cancer, where an enhanced Th1 immune response is desired. Effects of the formula 1 compounds in treating, preventing or slowing the progression of the clinical conditions described herein can include one or more of (1) enhancing the Th1 character of a subject's immune response or immune status, (2) increasing the intensity of a Th1 or a Th2 immune response or both and (3) decreasing inflammation or a symptom thereof.

Exemplary conditions where an immune imbalance or an excessive Th1 immune response is involved include autoimmune diseases such as multiple sclerosis, Crohn's disease (regional enteritis), ulcerative colitis, inflammatory bowel disease, rheumatoid arthritis, reactive arthritis, acute allograft rejection, sarcoidosis, type 1 diabetes mellitus, *Helicobacter pylori* associated peptic ulcer, graft versus host disease and Hashimotos' thyroiditis. Because these conditions are associated with a similar type immune dysfunction, a formula 1 compound can be effectively used to prevent or treat these conditions or to treat or ameliorate one or more symptoms associated therewith. Thus, in some embodiments, an unwanted or excessive Th1 response is present and amelioration of one or more symptoms associated with this condition is accomplished by administering an effective amount of a formula 1 compound according to the methods described herein, e.g., formula 1 compound is administered using a formulation and a route of administration essentially as described herein on an intermittent or a daily basis. In other embodiments, a deficient Th1 response is enhanced, which is optionally observed as a detectable increase in one or more of IFNγ, IL-2, IL-12 or IL-18 in Th1 cells or in accessory cells such as a dendritic cell or macrophage. In all of the conditions where an insufficient or excess Th1, Th2, Tc1 or Tc2 response is present, amelioration of one or more symptoms associated with the condition is accomplished by administering an effective amount of a formula 1 compound according to the methods described herein.

Aspects of the invention include the use or administration of compositions or formulations that comprise a carrier and an amount of at least one formula 1 compound effective to detectably modulate an immune parameter. For example, to enhance the relative proportion of a desired immune cell subset, e.g., $CD4^+$ T cells, $CD8^+$ T cells, NK cells, LAK cells, neutrophils, granulocytes, basophils, eosinophils or dendritic cells, or to modulate (detectably increase or decrease) one or more functions of immune cell subsets. The formula 1 compounds can modulate the expression of CD molecules or alter the proportion of cell subsets, e.g., $CD4^+$ or $CD8^+$ T cells, or their relative numbers in a subject's blood or tissues. CD and related molecules participate in the function of various immune cell subsets and can be useful as markers for immune function in vivo. In some aspects, the formula 1 compounds activate immune cells which generally alters (increases or decreases) expression of, or changes the numbers of cells that express one or more of, CD4, CD6, CD8, CD25, CD27, CD28, CD30, CD36, CD38, CD39, CD43, CD45RA, CD45RO, CD62L, CD69, CD71, CD90 or HLA-DR molecules. Often, the numbers of cells that express these molecules are increased, e.g., CD25, CD16 or CD69. Typically, such increases are observed as an increased proportion of circulating white blood cells that express one or more of these molecules or white blood cells CXCR3, CCR5, CCR4, CCR8 and/or CXCR4. In some cases the number of such molecules per cell is detectably altered.

Expression of one or more adhesion molecules CD2, CD5, CD8, CD11a, CD11b, CD11c, CD18, CD29, CD31, CD36, CD44, CD49a, CD49b, CD49c, CD49d, CD49e, CD49f, CD50, CD54, CD58, CD103 or CD104 are also detectably modulated after administration of the formula 1 compounds to a subject. Often, the numbers of cells that express these molecules are increased, e.g., CD5 or CD56. The adhesion molecules function in various aspects of immune responses, such as binding to class I MHC molecules, transducing signals between cells or binding to molecules in the extracellular matrix associated with endothelial or other cell types. Administration of the formula 1 compounds to a subject also affects the numbers of certain immune cell subsets, e.g., NK cells (e.g., $CD8^-$, $CD56^+$ or $CD8^+$, $CD56^+$) or lymphokine activated killer cells (LAK). Increased circulating NK or LAK cells are typically observed, which is reflected in increased numbers of cells that express one or more of CD16, CD38, CD56, CD57 or CD94. Also, increased numbers of circulating dendritic cell precursors are observed, as shown by increases in cells that express one or more of CD11c, CD80, CD83, CD106 or CD123. Although one can observe an increased proportion of circulating white blood cells that express one or more of these molecules, in some instances the number of such molecules per cell is detectably altered. Both the cell numbers and the density of CD molecule per cell can also be detectably modulated. Modulation of immune cell subsets typically occurs on intermittent dosing of a formula 1 compound, but will arise from any suitable dosing regimen, e.g., as described herein.

Expression of one or more homing or other receptors or receptor subunits such as CD62L, CLA-1, LFA1, CD44, ICAM, VCAM or ECAM may also be detectably affected after administration of the formula 1 compounds to a subject. The numbers of cells that express these molecules, or the relative amounts per cell of, e.g., CD44 or CD62L, may be increased where a desired immune response is desired, e.g., migration of T cells to mucosal tissues or exposure of naïve T cells to antigen in lymph nodes. Alternatively, numbers of cells that express these molecules, or the relative amounts per cell of, e.g., CLA-1, may be decreased where inhibition of an undesired immune response, such as an inflammatory response is desired. The subject's response to such enhanced expression includes migration of cells such as movement of naïve T cells to peripheral lymph nodes in response to modulation of CD62L or other homing receptor expression. Thus, the formula 1 compounds can also facilitate migration of various immune cell types, e.g., dendritic cells, NK cells, LAK cells, macrophages or lymphocytes, from one location to another within a subject. For example, the compounds can enhance dendritic cell or lymphocyte migration from areas such as the skin tissues to the gut associated lymphoid tissue ("GALT"), lymph nodes or spleen. Such migration may facilitate the function of those cell types by increasing their transit to tissues where their effector functions, e.g., antigen presentation by dendritic cells, normally occur. The migration period is often relatively transient (e.g., observable over about 1-7 days) or occasionally longer (e.g., occurring for about 8-40 days), depending on the dosing regimen and other factors. This migration can be observed by standard methods, e.g., by cell staining, by PCR analyses or by determining the presence of a given cell type in circulation or determining a decrease in the number circulating cells. A decrease would generally reflect sequestration of an immune cell population(s) in a tissue(s) where the immune cell normally exercises its effector functions.

Thus, in some embodiments, the migration of one or more immune cell subsets such as $CD11C^+$ cells from tissue such as skin or lung through the blood to immune tissue such as lymph nodes or GALT is seen as a transient increase in the level of circulating $CD11C^+$ cells in response to exposure of the subject's tissues to a suitable amount of a formula 1 compound. Thus, the level of $CD11C^+$ cells in the blood will generally detectably increase, e.g., a statistically significant increase, plateau and then decrease as migration of the cells to immune tissue subsides. In these embodiments, the proportion of the cells of the affected immune cell subset is typically relatively low in most physiological immune states, e.g., normal or abnormal immune conditions, compared to the total white blood cell population in circulation. In other embodiments, the migration of one or more immune cell subsets such as $CD123^+$ cells from the circulation to immune tissue such as lymph nodes or GALT results in a decrease. In these embodiments, the decrease in the numbers of circulating immune cells reflects the migration of the immune cells from the blood to immune tissue such as lymph nodes or GALT. Such a decrease may be transient and followed by recovery of the affected immune cell subset(s) over about 2 to 24 weeks. In conducting these embodiments, administration of the formula 1 compound to the subject is accomplished using the formulations or the methods as described herein.

Thus, an aspect of the invention is a method to enhance the migration of one or more immune cell types in a subject from one location (e.g., bone marrow, circulating blood or a tissue such as the skin, liver, central nervous system or lung) to another (e.g., to the blood or to a lymphoid tissue such as a lymph node, spleen or a mucosal tissue such as GALT) by administration to a subject as described herein of an effective amount of a formula 1 compound essentially as described by any of the methods disclosed herein. A related aspect is the monitoring, e.g., by suitable blood counts or tissue biopsy, of the subject's response to determine the timing and extent of such immune cell migration.

Other CD molecules that are modulated by the presence of the formula 1 compounds in a subject include cytokine receptor molecules such as one or more of CD115, CDW116, CD117, CD118, CDW119, CD120a, CD120b, CD121a, CD121b, CD122, CD123, CD124, CD125 CD126, CDW127, CDW128 or CDW130. Often, the numbers of receptor molecules per cell will be modulated. For example, receptors for cytokines that mediate or facilitate Th1 immune responses or innate immune responses (e.g., one or more of IL-1α, IL-1β, IL-2, IL-4, IL-12, γIFN or α-interferon) will typically increase in or on cells that mediate Th1 or innate immune responses. Modulation of these molecules may be by direct interactions with a receptor(s) in the cell that expresses the cytokine receptor or indirectly by modulation of cytokine synthesis in the affected cells or in other cells, typically immune cells that may interact with the cells whose receptor synthesis is being modulated. Thus, autocrine or paracrine mechanisms may underlie some of the effects associated with administration of a formula 1 compound(s) such as altered cytokine profiles in immune cells or altered immune cell populations. Endocrine cytokine mechanisms may also contribute to desired immune responses.

Treatment of a subject with a formula 1 compound can result in a change of at least about 20-80% or about 25-50% above or below (e.g., at least 30% or at least 40% above or below) the control or basal level of affected immune cell subsets. For example, increases of more than about 30% in the total numbers of activated $CD8^+$ T cells, e.g., $CD8^+$, $CD69^+$, $CD25^+$ T cells, $CD8^+$, $CD69^+$, $CD25^-$ T cells or CD8+, $CD69^-$, $CD25^+$ T cells, can occur by 7 days after a single dose of a formula 1 compound to a subject. Such increases may be greater than 50%, 60% or 100% in the total numbers of activated $CD8^+$ T cells or subsets of activated $CD8^+$ T cells in individual subjects. Typically such increases are about in the total numbers of activated $CD8^+$ T cells or subsets of activated $CD8^+$ T cells averages about 30-40%, with individual subjects experiencing increases over 100% in the numbers of activated $CD8^+$ T cells per unit blood volume compared to the basal level.

Administration of the formula 1 compounds can affect other immune cell subsets. For example, the concentration of circulating $CD4^+$, $CD69^+$, $CD25^-$ (Th1 helper cells) and $CD8^+$, $CD16^+$, $CD38^+$ LAK cells or $CD8^-$, $CD16^+$, $CD38^+$ LAK cells typically increases during or after the course of dosing a subject with a formula 1 compound. Also, $CD8^-$, $CD16^+$, $CD38^+$ and $CD8^+$, $CD16^+$, $CD38^+$ (ADCC effector cells) and low side scatter $Lin^-$, $DR^+$, $CD123^+$ (dendritic precursors) or low side scatter $Lin^-$, $DR^+$, $CD11c^+$ (dendritic cells or precursors) may show modest to significant increases.

In subjects that are immunosuppressed, e.g., from certain infections (e.g., viral (HIV, HCV), bacterial infection or parasite infection) or from chemotherapy (e.g., an antiviral therapy, a cancer chemotherapy or a radiation therapy), administration of the formula 1 compounds to the subject results in a favorable shift in the balance of Th1 or Th2 responses the subject can mount in the face of immunosuppression. When Th1 responses are suboptimal or insufficient, treatment with a formula 1 compound results in enhancement of Th1 responses or a reduction in Th2 responses. Conversely, when Th2 responses are suboptimal or insufficient, treatment with a formula 1 compound results in enhancement of Th2 responses, which may occur with a concomitant modulation (increase or decrease) in Th1 responses. The formula 1 compounds can thus be used to shift the nature of a subject's immune response to result in a more balanced immune response from immunosuppression. Alternatively, the compounds can selectively suppress inappropriate or unwanted immune responses. Enhanced Th1 responses appears to be at least partly due to one or more of (i) a reduction in biological restraints, e.g., high levels of IL-4 or IL-10, on Th1 functions by preexisting primed Th1 effector cells, (ii) enhanced differentiation of Th0 cells to Th1 cells or enhanced responses mediated by Th1 cells, (iii) enhanced function of accessory cell function, e.g., antigen presentation by dendritic cells, dendritic precursor or progenitor cells or by macrophages or their precursors or progenitors, (iv) enhanced proliferation and differentiation of Th1 precursor or progenitor cells, (v) enhanced IL-12 expression in dendritic cells or their precursors, which results in enhanced differentiation of Th1 cells from Th0 precursors, (vi) enhanced expression or activity of factors associated with Th1 functions, e.g., IL-2, gamma interferon (γIFN or IFNγ), IL-18 or lymphotoxin.

An aspect of the invention methods is an alteration in the expression of IL-4 or IL-10 that occurs after administration of a formula 1 compound, e.g., BrEA, to a subject. A consistent observation is that extracellular IL-4 or IL-10 levels rapidly decrease to levels that are undetectable by ELISA. Intracellular IL-10 levels are reduced to levels that are near or below the limits of detection by flow cytometry. The administration of a formula 1 compound to a subject thus provides a means to inhibit either or both of these interleukins. Such inhibition may be associated with enhancement of Th1 immune responses relative to Th2 or Th0 responses, e.g., in subjects where Th1 responses are suppressed (e.g., from viral, bacterial or parasite infection (HIV, HCV, etc) or chemotherapy) or are otherwise suboptimal. In many subjects, levels of either IL-4 or IL-10, usually IL-10, before dosing with a formula 1 compound is low or undetectable. In these subjects, dosing with the formula 1 compound results in a rapid drop in the interleukin that is detectable, usually IL-4.

Clinical conditions are described in more detail below where the formula 1 compounds are useful for treating, preventing, slowing the progression of, or ameliorating one or more symptoms associated with the described conditions. In any these conditions, any formula 1 compound disclosed herein can be used according to one or more of the dosing methods that are disclosed herein. For these conditions, dosages for the formula 1 compounds, formulations and routes of administration are as described herein. Additional information regarding these and other clinical conditions or symptoms that can be treated, prevented or ameliorated with the formula 1 compounds are found at e.g., *The Merck Manual,* $17^{th}$ edition, M. H. Beers and R. Berkow editors, 1999, Merck Research Laboratories, Whitehouse Station, N.J., ISBN 0911910-10-7, or in other references cited herein.

Responses to treatment of a subject having a condition disclosed herein with a formula 1 compound is optionally monitored by observing changes in one or more immune or other appropriate clinical parameters, e.g., as described herein or in D. S. Jacobs et al., editors, *Laboratory Test Handbook,* $4^{th}$ edition, pages 11-686, Lexi-Comp Inc., Hudson, Ohio, ISBN 0-916589-36-6, or in any of the references cited herein, or by monitoring the progression or severity of the underlying condition according to known methods, e.g., J. B. Peter, editor, *Use and Interpretation of Laboratory Tests in Infectious Disease,* $5^{th}$ Edition, pages 1-309, 1998, Specialty Laboratories, Santa Monica, Calif., ISBN 1-889342-13-0.

Infection treatments. In some embodiments, the formula 1 compound(s) is administered to a subject who has a pathogen infection, such as a viral, bacterial, fungal, yeast, intracellular parasite or extracellular parasite infection. The formula 1 compounds can be considered for use in a broad scope of infections (see, e.g., J. B. Peter, editor, *Use and Interpretation of Laboratory Tests in Infectious Disease,* $5^{th}$ edition, Specialty Laboratories, Santa Monica, Calif. 90404, 1998, pages 1-271), since the compounds generally enhance Th1 immune responses and/or reduce Th2 immune responses and/or reduce inflammation or its symptoms. Difficulty in treating many infections, e.g., progressive toxoplasmic encephalitis, malaria, tuberculosis, Leishmaniasis and schistosomiasis, often appear to be associated with one or more of an unwanted Th2 immune responses, a suboptimal Th1 response or the development of resistance of the infectious agent to antimicrobial agents. For example, in disseminated or diffuse tuberculosis, a reduced Th2 response would be desirable to allow a patient to slow progression of the disease or to clear infected cells more efficiently. In treating chloroquine resistant or sensitive malaria, the formula 1 compounds have essentially the same activity.

Exemplary viral infections that the formula 1 compounds can be used to treat, prevent or ameliorate include infections by one or more DNA or RNA viruses, or a symptom(s) associated with such infection(s), such as a genogroup, Glade, serotype, serotype subtypes, isolate, strain, subtype or so forth of influenza viruses (e.g., a human influenza A virus, a human influenza B virus, an avian (e.g., chicken, duck, goose) influenza virus, a swine influenza virus or a recombinant avian-swine influenza virus), respiratory syncytial viruses, Rotaviruses, Hantaviruses, animal or human Papillomaviruses (e.g., HPV-16, HPV-18), Poxviruses, Poliovirus, rabies viruses, human and animal Retroviruses (e.g., HIV-1, HIV-2, LAV, human T-cell leukemia virus I ("HTLV I"), HTLV II, HTLV III, SIV, SHIV, FIV, FeLV), Togaviruses and Flaviviruses (e.g., West Nile Virus, Yellow Fever Virus, Dengue viruses), Herpesviruses (e.g., CMV, EBV, Varicella Zoster Virus, Herpes simplex virus 1 ("HSV-1"), Herpes simplex virus 2 ("HSV-2"), human Herpesvirus 6 ("HHV-6"), human Herpesvirus 8 ("HHV-8")), measles viruses, mumps viruses, rubella virus, Hepadnaviruses or hepatitis viruses, Adenoviruses, Retroviruses, Togaviruses, Alphaviruses, Arboviruses, Coronaviruses, Flaviviruses, Filoviruses, Rhinoviruses, Picornaviruses, Papovaviruses, Bunyaviruses, Picornaviruses, Poxviruses and/or Pestiviruses.

Specific viruses, including their genogroups, clades, isolates, serotypes, serotype subtypes, strains and so forth, that may establish a virus infection susceptible to the treatment methods disclosed herein include one or more of human hepatitis C virus ("HCV"), human hepatitis B virus ("HBV"), human hepatitis A virus ("HAV"), human hepatitis delta virus, human hepatitis E virus, duck hepatitis virus, woodchuck hepatitis virus, one or more of human herpesviruses 1, 2, 3, 4, 5, 6A, 6B, 7 or 8, one or more of human papilloma viruses 1-60, e.g., HPV 6, HPV 11, HPV 16, HPV 18, HPV 31, HPV 45, animal papilloma viruses, poliovirus 1, poliovirus 2, poliovirus 3, one or more of Dengue virus types 1, 2, 3 or 4, one or more of foot-and-mouth disease virus 1-7, including serotypes 0, A, C, SAT 1, SAT 2, SAT 3 and ASIA 1, one or more of coxsackievirus A1-A22, A24, and B1-B6, one or more of human echovirus 1-9, 11-27 and 29-34, one or more of human enterovirus 68-71, one or more of adenovirus 1-49, one or more of Parainfluenza viruses 1, 2, 3 or 4, Human respiratory coronaviruses 229E and OC43, one or more of Human rotaviruses, BK virus, Bunyamwera virus, California Encephalitis Virus, Central European Encephalitis Virus, encephalomyocarditis virus, Colorado tick fever virus, Cowpox virus, Eastern equine encephalitis virus, Venezuelan equine encephalitis virus, Argentine hemorrhagic fever virus, Bolivian hemorrhagic fever virus, Lacrosse virus, Hantaan virus, JC virus, Lassa virus, Lymphocytic choriomeningitis virus, Kyasanur forest virus, Marburg virus, Measles virus, Mokola virus, Monkeypox virus, Molluscum contagiosum virus, Mumps virus, Murray Valley encephalitis virus, Norwalk virus, O'nyong-nyong virus, Omsk hemmorhagic virus, Orf virus, Rabies virus, RA-1 virus, Western equine encephalitis virus, Japanese encephalitis virus, Yellow Fever Virus, West Nile virus, Variola (smallpox) virus, cowpox virus, Vaccinia virus, Ebola virus, Respiratory syncytial virus, human cytomegalovirus, Rhinoviruses 1-113, Rift Valley fever virus, Ros river virus, Rubella virus, Russian spring-summer encephalitis virus, Sandfly fever viruses, St. Louis encephalitis virus, SV40 virus, vaccinia virus, Varicella-zoster virus, Vesicular stomatitis viruses and Bovine Viral Diarrhea Virus. Exemplary viruses have been described. See, for example B. N. Fields, et al., editors, *Fundamental Virology,* $3^{rd}$ edition, 1996, Lippencott-Raven Publishers, see chapter 2 at pages 23-57, including table 4 at pages 26-27, table 5 at pages 28-29, chapter 17 at pages 523-539, chapters 26-27 at pages 763-916, chapter 32 at pages 1043-1108 and chapter 35 at pages 1199-1233.

In an exemplary embodiment, human patients infected with HCV are dosed with an aqueous isotonic α-cyclodextrin or β-cyclodextrin, e.g., hydroxypropyl-β-cyclodextrin, formulation containing about 20 mg/mL BrEA. The formulation is delivered intravenously in a single daily dose or two subdoses per day. The patients are dosed with 1 to 10 mg/kg/day for 4 to 10 days, followed by no dosing for 5 to 30 days, followed by dosing again with the cyclodextrin formulation for 4 to 10 days. The dosing regimen is repeated one, two or more times. Clinical markers for HCV infection are followed during treatment, e.g., viral nucleic acid in the blood or plasma, liver enzyme levels in the blood or plasma (e.g., AST/SGOT, ALT/SGPT, alkaline phosphatase). For these patients, an anti-HCV treatment(s), e.g., γIFN, αIFN, a retroviral protease inhibitor, a nucleoside analog, and/or ribavirin, is optionally started or continued according to the recommendations of the patient's doctor and with the patient's informed approval. In some of these embodiments, a formula 1 compound(s) is administered daily continuously as a component in an oral or parenteral composition or formulation, e.g., for a formula 1 compound(s) that is a new compound per se. BrEA is optionally also administered systemically using, e.g., a parenteral formulation to deliver 0.1-5 mg/kg/day either daily or every other day for about 1 to 4 months, or an oral formulation to deliver about 0.5-40 mg/kg/day either daily or every other day for about 1 to 4 months.

In related embodiments, the formula 1 compounds are used to treat, prevent or ameliorate Arbovirus infections, Arenavirus infections, Hantavirus infections and hemorrhagic fever virus infections, or a symptom(s) or complication(s) thereof, in subjects such as humans. In treating such infections, the formula 1 compound is administered at a dosage disclosed herein, e.g., about 0.5-4 mg/kg/day by buccal delivery or by a parenteral route such as subcutaneous or intramuscular injection, for about 5-14 consecutive days. An oral dosage would be about 10-25 mg/kg/day of a formula 1 compound for about 5-14 consecutive days. Typically dosing with the formula 1 compound will begin at the time that (or shortly thereafter, e.g., within about 1-12 hours) the infection is suspected or is diagnosed. The patient is optionally monitored and the amelioration of one or more symptoms or a slowed disease progression is observed. For example, arbovirus encephalitis, which is typically a serious brain infection, can be treated, prevented or ameliorated. Several types of viral encephalitis are transmitted by insect bites, e.g., western equine encephalitis, eastern equine encephalitis, St. Louis encephalitis, and California encephalitis. In these infections the formula 1 compounds can treat, prevent or ameliorate one or more symptoms including fever, headache, drowsiness, vomiting, stiff neck, mental confusion, muscle trembling, convulsions, and coma. Hemorrhagic fevers in humans are associated with infection by Hantaviruses and Filoviruses such as Ebola and Marburg viruses, which can cause infections that include Korean, Bolivian and Argentinean hemorrhagic fevers, Congo fever and Lassa fever. The formula 1 compounds can be used to treat, prevent or ameliorate one or more symptoms of these infections, e.g., a hemorrhagic fever virus infection, in a subject such as a human. Ebola virus and Marburg virus infections can be accompanied by mucous membrane bleeding, fever, diarrhea, bleeding, myalgia, lymphadenopathy, pain, e.g., chest pain, coughing, vomiting, stupor, coma or loss of consciousness and failure of multiple organs. In these embodiments, the formula 1 compounds can function by one or more mechanisms, including enhancing innate immune responses, modulating, e.g., detectably increase or decrease, the level or activity of one or more of IL-1α, IL-1β, TNFα, IL-6, IL-8, IL-10, gro-α, IFN-γ, MCP-1, MIP-1α, MIP-1β, IP-10, GM-CSF, RANTES or their isotypes or homologs or cortisol. The compounds can also detectably increase the synthesis or level of IFN-α, IFN-β, IgG1 and/or IgG3 in these conditions.

Treatment of a subject such as a human who is anticipated to potentially come in contact with Arbovirus, Arenavirus, Hantavirus or a hemorrhagic fever virus is accomplished by administering a formula 1 compound to the subject by, e.g., daily or intermittent dosing, beginning at about 1-14 days before an anticipated potential exposure. The daily doses and routes of administration are essentially as described herein, e.g., for an adult human, about 0.5-4 mg/kg/day by buccal delivery or by a parenteral route such as subcutaneous or intramuscular injection for 1, 2, 3, 4, 5, 6, 7 or 8 consecutive days or on alternate days over a 4, 6, 8, 10, 12 or 14 day period in advance of a potential exposure.

Hantavirus infection is a viral disease that rodents can transmit to humans and the infection is associated with serious lung or kidney infection. Symptoms of Hantavirus infection of the lungs include one or more of fever, muscle pain, myalgia, headache, abdominal pain, conjunctival bleeding, diarrhea, vomiting, coughing, shortness of breath or low blood pressure (shock). Hantavirus kidney infection may be mild or severe and is associated with fever, headache, backache, abdominal pain, small bruise-like patches on the whites of the eyes, abdominal rash, impaired kidney function, nausea, loss of appetite, fatigue and intracranial bleeding.

The formula 1 compounds can also be used to treat, prevent or ameliorate infections caused by members of the Poxyiridae family, e.g., members of the Orthopoxvirus genus in subjects such as mammals or humans. The compounds can be used to treat, ameliorate or prevent one or more symptoms associated with Orthopoxvirus infections. For example, the variola or smallpox virus causes a serious infection with symptoms that include fever, chills, backache, headache, skin lesions and death. In treating Orthopoxvirus infections, the formula 1 compound is administered at a dosage disclosed herein, e.g., about 0.5-4 mg/kg/day by buccal delivery or by a parenteral route such as subcutaneous or intramuscular injection, for about 5-14 consecutive days. Typically dosing with the formula 1 compound will begin at the time that (or shortly thereafter, e.g., within about 1-12 hours) the infection is suspected or is diagnosed. In treating Orthopoxvirus infections such as a variola infection, the formula 1 compounds can result in enhanced efficacy of host factors such as CC cytokines or interferons such as IFN-α or IFN-γ. The subject may also be optionally treated with another agent such as IFN-γ, a nucleoside analog or a nucleotide analog such as one described herein or in the cited references.

Treatment of a subject such as a human who is anticipated to potentially come in contact with an Orthopoxvirus such as the variola virus or the vaccinia virus is accomplished by administering a formula 1 compound to the subject by, e.g., daily or intermittent dosing, beginning at about 1-14 days before an anticipated potential exposure. The daily doses and routes of administration are essentially as described herein, e.g., for an adult human, about 0.1-10 mg/kg/day by buccal delivery or by a parenteral route such as subcutaneous or intramuscular injection for 1, 2, 3, 4, 5, 6, 7 or 8 consecutive days or on alternate days over a 4, 6, 8, 10, 12 or 14 day period in advance of a potential exposure.

In other embodiments, formula 1 compound(s) are administered to a subject or delivered to the tissues of a subject who has a pathogen infection (or is susceptible to an infection) such as one caused by or associated with a parasite, bacterium, fungus or yeast, to slow the progression of infection, interfere with replication or development of the infectious agent or to ameliorate one or more of the associated symptoms, e.g., weight loss, anemia, fever, pain, fatigue, inflammation, immune dysfunction, secondary infections, skin lesions or ulcers or mood changes such as depression. Parasites include malaria parasites, sleeping sickness parasites and parasites associated with gastrointestinal infections.

Exemplary parasite, fungi, yeast and bacterial infections that can be treated, prevented or ameliorated in subjects such as mammals or humans, include ones caused by or associated with species, groups, genotypes, serotypes, strains or isolates of gastrointestinal helminths, microsporidia, *isospora*, cryptococci, cryptosporidia (*Cryptosporidium parvum*), *Trypanosoma* sp. (e.g., *T. brucei, T. gambiense, T. cruzi, T. evansi*), *Leishmania* sp. (e.g., *L. donovani, L. major, L. braziliensis*), *Plasmodium* sp. (e.g., *P. falciparum, P. knowlesi, P. vivax, P. berghei, P. yoelli*), *Ehrlichia* sp. (e.g., *E. canis, E. chaffeensis, E. phagocytophila, E. equi, E. sennetsu*), *Entamoeba* sp., *Babesia microti, Bacillus anthracis, Brucella* sp. (e.g., *B. militensis, B. abortus*), *Bartonella* sp. (*B. henselae*), *Bordetella* sp. (e.g., *B. bronchiseptica, B. pertussis*), *Enterococcus* sp. (e.g., *E. faecalis, E. faecium*), *Enterobacter* sp., *Erysipelothrix rhusiopathiae, Escherichia* sp. (*E. coli*), *Haemophilus* sp. (e.g., *H. somnus, H. influenzae, H. parainfluenzae*), *Klebsiella* sp. *Legionella pneumonia, Listeria* (e.g., *L. monocytogenes, L. ivanovii*), *Morganella* sp. (e.g., *M. morganii*), *Mycobacterium* sp. (e.g., *M. avium*, M. bovis, M. leprae, M. tuberculosis, M. *pneumoniae. M. penetrans*), *Mycoplasma* sp. (e.g., *M. fermentans, M. penetrans, M. pneumoniae*), *Neisseria* (e.g., *N. gonorrhoeae, N. meningitidis*), *Nocardia asteroides, Proteus* sp. (e.g., *P. mirabilis, P. vulgaris, P. myxofaciens*), *Providencia* sp. (e.g., *P. rettgeri, P. stuartii*), *Pseudomonas* sp. (*P. aeruginosa*), *Salmonella* sp. (e.g., *S. typhimurium, S. tyhpi, S. paratyhpi, S. dublin, S. enteritidis, S. schottmuelleri, S. hirschfeldii*), *Serratia* sp., *Shigella* sp. (e.g., *S. flexneri, S. sonnei, S. dysenteriae*), *Streptococcus* sp. (e.g., *S. pneumoniae, S. pyogenes, S. faecalis, S. faecium, S. agalactiae, S. mutans, S. sanguis*), *Staphylococcus* sp. (e.g., *S. aureus*), *Rickettsia* sp. (e.g., *R. rickettsii*), *Treponema* sp. (e.g., *T. pallidum*), *Vibrio* sp. (e.g., *V. cholerae*), *Yersinia* sp. (e.g., *Y. enterocolitica, Y. pestis*), *Pneumocystis* sp. (e.g., *P. carinii*), *Aspergillis* sp. (e.g., *A. fumigatus, A. terreus, A. flavus*), *Candida* sp. (e.g., *C. albicans, C. krusei, C. tropicalis*), *Chlamidya* sp., *Schistosoma* sp. (e.g., *S. mansoni, S. japonicum, S. haematobium*), *Strongyloides stercoralis, Trichomonas* sp., (e.g., *T. vaginalis*) and *Tinea* sp., (e.g., *T. pedis*). For any of these infections, a subject who has the infection, or is susceptible of developing the infection, e.g., by suspected exposure to an infectious agent, is treated by administering an effective amount of a formula 1 compound to the subject. In these embodiments, the formula 1 compounds can function by one or more mechanisms, including enhancing innate immune responses, modulating, e.g., detectably increase or decrease, the level or activity of one or more of the transcription factors, enzymes or other biomolecules described herein, e.g., IL-1α, IL-1β, TNFα, IL-6, IL-8, IL-10, gro-α, IFN-γ, MCP-1, MIP-1α, MIP-1β, IP-10, GM-CSF, RANTES or their isotypes or homologs or cortisol. For example, molecules such as IL1α, TNFα, MIP-1α or MCP-1 are generally decreased in infections where there is an overexpression of one or more of these molecules. Generally a decrease of one or more of these molecules occurs.

Fungal infections that can be treated, prevented or ameliorated thus include invasive aspergilliosis, allergic bronchopulmonary aspergillosis, aspergilloma and chronic necrotizing aspergillosis. Bacterial infections that can be treated, prevented or ameliorated thus include infections by intracellular or extracellular gram positive bacteria, gram-negative bacteria, acid fast bacteria or by Mycoplasma. Other pathogens that are amenable to treatments according to the present invention are as described. See, e.g., J. B. Peter, editor, *Use and Interpretation of Laboratory Tests in Infectious Disease*, 5$^{th}$ Edition, pages 1-309, 1998, Specialty Laboratories, Santa Monica, Calif., ISBN 1-889342-13-0.

In an exemplary embodiment, a subject such as a human that is known or suspected of having been exposed to *B. anthracis* spores or cells is treated with a formula 1 compound. The subject may have overt symptoms of either cutaneous or pulmonary infection. The formula 1 compound is administered at a dosage disclosed herein, e.g., about 0.05-10 mg/kg/day or about 0.1-5 mg/kg/day by buccal delivery or by a parenteral route such as subcutaneous, intramuscular or intravenous injection, for about 5-14 consecutive days. An oral dosage would be about 10-25 mg/kg/day of a formula 1 compound for about 5-14 consecutive days. Dosing with the formula 1 compound will typically begin at about the time that the infection is suspected or is diagnosed, or shortly thereafter, e.g., within about 1-12 hours.

During or after treatment, the patient is optionally monitored and the amelioration of one or more symptoms or a slowed disease progression is observed. Such symptoms can include one or more of a red-brown bump with swelling at the edges, blisters, formation of a black scab or eschar at the site of skin infection, edema, respiratory difficulty and swelling of regional or local lymph nodes. Other symptoms of cutaneous anthrax that can be ameliorated include fever, headache, muscle ache, nausea, and vomiting. In treating *B. anthracis* infections, the formula 1 compounds will typically enhance innate immune responses, enhance humoral immune responses, reduce TNFα, IL-1α or IL-1β levels or activity and/or enhance killing or phagocytosis of pathogen in the infected subject or the subject's immune cells, e.g., monocytes, neutrophils or macrophages.

Treatment of a subject such as a human who is anticipated to potentially come in contact with a pathogen described herein, e.g., spores or vegetative *B. anthracis* cells, is accomplished by administering a formula 1 compound to the subject by, e.g., daily or intermittent dosing, beginning at about 1-14 days before an anticipated potential exposure. The daily doses and routes of administration are essentially as described herein, e.g., for an adult human, about 0.05-5 mg/kg/day by buccal delivery or by a parenteral route such as subcutaneous, intramuscular or intravenous injection for 1, 2, 3, 4, 5, 6, 7 or 8 consecutive days or on alternate days over a 4, 6, 8, 10, 12 or 14 day period in advance of a potential exposure.

For a pulmonary anthrax infection, amelioration of one or more of fever, bleeding and necrosis of lymph nodes near the lung, local chest infection, shock, coma or death can occur. Infection of the brain and meningoencephalitis may occur and is treated in a similar manner, although an increased dosage can be utilized, e.g., about 20-50 mg/kg/day of the formula 1 compound is administered by a parenteral, e.g., intravenous, sublingual or buccal route. In any of these skin, pulmonary or gastrointestinal infections, the subject is also optionally treated using one or more standard antibiotics and routes of administration, e.g., (1) 600,000 U i.m. bid for about 7-10 days of procaine penicillin G, optionally combined with about 500 mg/day of streptomycin, optionally administered q 8 h i.m., (2) 2 g/day of tetracycline for 5-10 days for an adult human, (3) oral erythromycin administered at about 250 to 1000 mg/day in subdoses administered at 12 or 8 hour intervals, (4) intravenous or oral ciprofloxacin for about 5-30 days with daily doses optionally subdivided for administration 2 or 3 times per day, e.g., about 250-500 mg of ciprofloxacin administered twice per day orally for a human adult, (5) doxycycline administered, e.g., at an induction dose of 100 mg twice on the first day and a maintenance dose of 50 mg twice per day for about 7-20 days for a human adult, (6) a fluoroquinoline antibiotic such as levofloxacin, norfloxacin or oxofloxacin is administered according to standard dosing and administration protocols or (7) a corticosteroid for local or systemic inflammation, e.g., of the lung, for a pulmonary anthrax infection, which permits the corticosteroid to exert an antiinflammatory activity while avoiding at least some of the immune suppression generally associated with corticosteroids.

The use of the formula 1 compounds will generally ameliorate the inflammation, sepsis or shock that can occur when antibiotics are administered to subjects having a systemic or pulmonary B. anthracis infection. A potential adverse effect of antibiotic use to treat a systemic or pulmonary B. anthracis infection is serious or potentially lethal inflammation, sepsis and/or shock that results from release of anthrax lethal toxin or factor or other inflammatory molecules on lysis of the bacteria. Release of bacterial lethal factor from lysed bacterial cells is associated with an intense inflammation, which is at least partially mediated by one or more inflammatory factors such as TNFα, IL-1β, IL-1α, IL-6, IL-8 or COX-2. The formula 1 compounds detectably reduce the level and/or biological effects of such inflammatory factors and can also detectably maintain or facilitate macrophage viability or one or more desired macrophage function(s) at the same time, e.g., phagocytosis, killing of phagocytosed bacterial cells or debris or limiting of reactive oxygen species generation by the macrophages. Similar considerations apply for the use of antibiotics to kill other types of bacteria, e.g., bacteria disclosed herein, that can release pro-inflammatory molecules such as lipopolysaccharide, when an antibiotic kills or lyses bacterial cells.

Similarly, the formula 1 compounds can be used to treat, prevent or ameliorate an infection by one or more gram-negative enteric bacteria. Such bacteria are commonly members of the Bartonella, Brucella, Campylobacter, Enterobacter, Escherichia, Francisella, Klebsiella, Morganella, Proteus, Providencia, Pseudomonas, Salmonella, Serratia, Vibrio or Yersinia genera. For these infections, the formula 1 compound is administered to a subject such as a human at a dosage disclosed herein, e.g., about 0.5-4 mg/kg/day by buccal delivery or by a parenteral route such as subcutaneous, intramuscular or intravenous injection, for about 5-14 consecutive days. An oral dosage would be about 10-25 mg/kg/day of a formula 1 compound for about 5-14 consecutive days. Typically dosing with the formula 1 compound will begin at the time that (or shortly thereafter, e.g., within about 1-12 hours) the infection is suspected or is diagnosed. The patient is optionally monitored and the amelioration of one or more symptoms or a slowed disease progression is observed. The compounds can reduce the adverse effects of bacterial lipopolysaccharide or endotoxin that is associated with these organisms. For example, the compounds are therapeutically useful for infection by Yersinia pestis, which causes plague. Several forms of plague can exist, i.e., bubonic, pneumonic, septicemic, or pestis minor. The compounds ameliorate one or more of the symptoms associated with these infections. For example, in a bubonic plague infection, symptoms typically arise several days after exposure to Y. pestis, and can include a fever of up to 106° F., chills, rapid weak heartbeat, low blood pressure, lymph node swelling accompanied by tenderness, restlessness, confusion, uncoordinated movements, liver and spleen swelling. Symptoms associated with pneumonic plague include high fever, chills, rapid heartbeat, severe headache, coughing, blood-tinged sputum and rapid and labored breathing.

Treatment of a subject such as a human who is anticipated to potentially come in contact with cells of a gram negative enteric bacterium is accomplished by administering a formula 1 compound to the subject by, e.g., daily or intermittent dosing, beginning at about 1-14 days before an anticipated potential exposure. The daily doses and routes of administration are essentially as described herein, e.g., for an adult human, about 0.5-4 mg/kg/day by buccal delivery or by a parenteral route such as subcutaneous or intramuscular injection for 1, 2, 3, 4, 5, 6, 7 or 8 consecutive days or on alternate days over a 4, 6, 8, 10, 12 or 14 day period in advance of a potential exposure.

In Y. pestis infections, the subject is optionally treated using one or more standard antibiotics and routes of administration, e.g., one or more of (1) for septicemic or pneumonic infection, streptomycin at 30 mg/kg/day is administered IM in 4 divided doses for about 7-10 days for an adult human, (2) tetracycline at 30 mg/kg/day is administered IV in 4 divided doses for about 7-10 days for an adult human or (3) gentamycin or chloramphenicol according to standard doses and dosing routes.

In a subject having a V. cholerae infection, symptoms typically arise several days after exposure to the pathogen, and can include a fever, chills, diarrhea, which can be serious or fatal if untreated, oliguria, muscle cramps and hypovolemia. In V. cholerae infections, the subject is treated with a formula 1 compound and optionally with one or more standard therapies, e.g., one or more of (1) intravenous and/or oral replacement of water, glucose and electrolytes, (2) tetracycline for about 3-4 days at 500-1000 mg/day in 2, 3 or 4 optionally subdivided doses for adult humans, (3) doxycycline at 300 mg/day for several days, (4) erythromycin, furazolidone norfloxacin, trimethoprim and/or sulfamethoxazole, according to standard dosages and routes of administration, e.g., oral or parenteral.

In any of these bacterial infections, the subject is optionally treated with a suitable or appropriate antibacterial agent(s). Such agents include one, two or more antibacterial agents selected from an aminoglycoside, an amphenicol, an ansamycin, a β-lactam, a lincosamide, a macrolide, a peptide, a tetracycline, a 2,4-diaminopyrimidine, a nitrofuran, a quinolone, a sulfonamide, a sulfone, cycloserine, mupirocin and tuberin, wherein the aminoglycoside optionally is dihdrostreptomycin, fortimicin(s), gentamicin, kanamycin, neomycin, neomycin undecylenate, spectinomycin, streptomycin, streptonicozid or tobramycin; the amphenicol optionally is azidamfenicol, chloramphenicol, chloramphenicol palmitate, chloramphenicol pantothenate, florfenicol or thiamphenicol; the ansamycin optionally is rifamide, rifampin or rifamycin; the β-lactam optionally is imipenem, cefactor, cefadroxil, cefamandole, cefatrizine, cefazedone, cefazolin, cefixime, ceftibuten, ceftizoxime, ceftriaxone, cefuroxime, cefuzonam, cephacetrile sodium, cephalexin, cephaloglycin, cephaloridie, cephalosporin, cephalothin, cephapirin sodium, amidinocillin, amdinocillin pivoxil, amoxicillin, apalcillin, carbenicillin, carfecillin sodium, carindacillin, floxicillin, a penicillin G, penicillin G potassium, penicillin G procaine, penicillin N, penicillin O, penicillin V or pivapicillin; the lincosamide optionally is clindamycin or lincomycin; the macrolide optionally is azithromycin, clarithromycin or erythromycin; the polypeptide optionally is amphomycin, bacitracin, a gramicidin, gramicidin S, mikamycin, polymyxin, polymyxin B-methanesulfonic acid, or zinc bacitracin; the tetracycline optionally is clomocycline, demeclocycline, doxycycline, oxytetracycline, or tetracycline; the 2,4-diaminopyrimidine optionally is brodimoprim, tetroxoprim or trimethoprim; the nitrofuran optionally is furaltadone, nifuradene, nifuratel, or nifurpirinol; the quinolone optionally is amifloxacin, cinoxacin, ciprofloxacin, difloxacin, enoxacin, fleroxacin, flumequine, nomefloxacin, miloxacin, nalidixic acid, norfloxacin, ofloxacin, oxolinic acid, pefloxacin, pipemidic acid, piromidic acid, rosoxacin, temafloxacin or tosufloxacin; the sulfonamide is optionally selected from acetyl sulfamethoxypyrazine, azosulfamide, benzylsulfamide, chloramine-T, p-nitrosulfathiazole, succinylsulfathiazole or sulfathiazole; and the sulfone optionally is acedapsone, acetosulfone sodium, dapsone, solasulfone, succisulfone, sulfanilic acid, sulfoxone sodium or thiazolsulfone.

The formula 1 compounds are useful to detectably reduce the incidence, severity or progression of one or more symptoms or conditions associated with a viral, bacterial, fungal, yeast or parasite infection. Exemplary symptoms and conditions associated with infections such as one or more of those described above include one or more of sepsis, septicemia, fever, e.g., moderate to high fever, inflammation, pain, e.g., chest pain, muscle pain, joint pain, back pain or headache, chills, itching, rash, skin lesions, erythema, e.g., peripheral erythema, lymphadenopathy, e.g., local, regional or systemic lymphadenopathy, nausea, vomiting, cyanosis, shock, coma, necrosis, hemorrhage, encephalitis, meningoencephalitis, cramping, mild to severe diarrhea, cough, weakness, splenomegaly, anorexia and weight loss. Specific symptoms that are associated with infections are known. See, e.g., *The Merck Manual*, 17$^{th}$ edition, M. H. Beers and R. Berkow editors, 1999, Merck Research Laboratories, Whitehouse Station, N.J., ISBN 0911910-10-7, J. B. Peter, editor, *Use and Interpretation of Laboratory Tests in Infectious Disease*, 5$^{th}$ Edition, pages 1-309, 1998, Specialty Laboratories, Santa Monica, Calif., ISBN 1-889342-13-0. In treating any of these infections, the formula 1 compound will act through one or more mechanism, e.g., by decreasing TNF-α, IL-1α or IL-1β where, e.g., inflammation is a symptom, or by enhancing the activity of cell mediated immune responses in clearing infected cells or extracellular infectious agents.

In any of the embodiments or treatment methods disclosed herein, one can optionally administer an additional therapeutic treatment in conjunction with, i.e., before, during or after, administration of a formula 1 compound(s) to a subject(s). For example, in subjects who have a viral or parasite infection and are in the course of administration of a formula 1 compound, other treatments can also be administered to the subject, e.g., nucleoside analogs for viral infections or an antimalarial(s) agent such as one or more of artemisinin, dihydroartemisinin, a artemisinin analog (e.g., as disclosed in J. Han et al., *J. Nat. Products* 64:2101-1205 2001 or G. A. Balint *Pharmacol. Ther.* 90:261-265 2001), dapsone, sulfadoxin, pyrimethamine, chloroquine, mefloquine, halofantrine, proguanil, proguanil hydrochloride, cycloguanil, chlorocycloguanil, atovaquone, quinine, berberine, and/or primaquine for subjects having or subject to developing a malaria infection. Subjects suffering from or subject to developing a fungal infection can optionally be treated with a formula 1 compound and an antifungal agent, e.g., an azole or a polyene such as ketoconazole, fluconazole, anidalfungin, amphotericin B or a liposomal formulation that comprises an azole or polyene such as amphotericin B. Subjects suffering from another condition such as an inflammation condition, an autoimmune condition or a cancer are optionally treated using one or more additional treatments. Such additional treatments will typically include standard therapies for the subject's pathological condition(s), but they can also include experimental or other treatments. For example, one can coadminister vitamins (e.g., multivitamins, individual vitamins), antioxidants or other agents (e.g., vitamin E, allopurinol, folinic acid, carnitine, a C2-8 alkanoyl carnitine such as acetyl or propionyl L-carnitine), nutritional supplements (e.g., liquid protein or carbohydrate preparations) or other therapies as the patient's medical condition warrants or as the patient's doctor recommends. Any of these additional treatments can be coupled with the administration of any of the formula 1 compounds, e.g., BrEA, an ester, carbamate, carbonate or amino acid or peptide conjugate thereof, in any of the embodiments described herein.

Such additional therapeutic agents or therapeutic treatments are apparent to the skilled artisan. Such treatments are selected based on the condition(s) to be treated, cross-reactivities of ingredients and pharmaco-properties of the combination. For example, when treating a viral infection(s), e.g., a retroviral infection, in a human or other subject, the formula 1 compounds are combined with one or more reverse transcriptase inhibitors, protease inhibitors, antibiotics or analgesics. Suitable formula 1 compounds that are combined with such therapeutic agents include those described, e.g., in the compound groups, embodiments or claims disclosed herein.

In some embodiments, the dosages and administration of an additional therapeutic agent or treatment will be used with a formula 1 compound treatment in essentially the same manner as usual for the agent or treatment. In other embodiments, the use of the formula 1 compound is coupled with an altered dosage or dosing protocol, either of which may be appreciably increased or decreased. For example, in subjects such as adult humans that are infected with malaria parasites, the use of a formula 1 compound such as BrEA is optionally preceded by administration of about 25-500 mg/day, e.g., about 50 mg/day, about 100 mg/day or about 200 mg/day, of the antimalarial agent artemisinin for 1, 2, 3, 4, 5, 6, 7 or more consecutive days followed one day after artemisinin or dihydroartemisinin dosing by administration of about 25-200 mg/day of BrEA for 1, 2, 3, 4, 5, 6, 7 or more consecutive days. In related embodiments, the formula 1 compound and artemisinin are administered at partly or completely overlapping times or the formula 1 compound is administered before artemisinin or dihydroartemisinin is administered to the infected subject. The daily dosage or the total dosage for a course of therapy with other therapeutic agents such as cancer chemotherapy agents or antimicrobial agents (e.g., antiviral, antiparasite, antibacterial or antifungal agents as disclosed herein or in a cited reference) may be increased or decreased by at least about 5%, 10%, 20%, 30%, 40%, 50%, 60%, 70%, 80%, 90% or more compared to standard dosages for such additional agents. The use of the formula 1 compounds with other therapeutic agents can reduce the toxicity of other therapeutic agents and/or enhance their potency or their therapeutic index (or selectivity), thereby allowing effective increased or decreased dosages of the other therapeutic agent.

Exemplary antiviral agents suitable for use in the method include reverse transcriptase or polymerase inhibitors such as AZT (zidovudine or 3'-azido-3'-deoxythymidine), 3TC, D4T, ddI, ddC, 2',3'-dideoxynucleosides such as 2',3'-didoxycytidine, 2',3'-dideoxyadenosine, 2',3'-didoxyinosine, 2',3'-didehydrothymidine, carbovir and acyclic nucleosides, e.g., acyclovir, ganciclovir. Exemplary protease inhibitors, fusion inhibitors or other antiviral or antiretroviral agents that may be used in a combination therapy with a formula 1 compound include lamivudine, indinavir, nelfinavir, amprenavir, ritonavir, crixivan, sequanavir, nevirapine, stavudine, a HIV fusion inhibitor, efavirenz, co-trimoxazole, N-(tert-butyl-dechydro-2)-2(R)-hydroxy-4-phenyl-3(S)-{N-2-quinolylcarbonyl)-L-asparginyl!butyl}-(4a,S,8a,S)-isoquinoline-3 (S)-carboxamide (Ro 31-8959), oxathiolan nucleoside analogues such as cis-1-(2-hydroxymethyl)-1,3-oxathiolan-5-yl)-cytosine or cis-1-(2-(hydroxymethyl)-1,3-oxathiolan- 3-yl)-5-fluoro-cytosine, 3'-deoxy-3'-fluoro-thymidine, 2'3'-dideoxy-5-ethynyl-3'-fluorouridine, 5-chloro-2',3'-dideoxy-3'-fluorouridine, ribavirin, 9->4-hydroxy-2-(hydroxymethyl) but-1-yl-guanine (H2G), adefovir dipivoxil, 9-[2-(R)-[[bis [[(isopropoxy-carbonyl)oxy]-methoxy]phosphinoyl] methoxy]propyl]adenine, (R)-9-[2-(phosphonomethoxy)-propyl]adenine, tenofivir disoproxil and its salts (including the fumarate salt) and adefovir, TAT inhibitors such as 7-chloro-5-(2-pyrryl)-3H-1,4-benzodiazepin-2(H)-one ($R^{o5}$-3335), or 7-chloro-1,3-dihydro-5-(1H-pyrrol-2-yl)-3H-1,4-benzodiazepin-2-amine (Ro24-7429), renal excretion inhibitors such as probenecid, nucleoside transport inhibitors such as dipyridamole; pentoxifylline, N-acetylcysteins, procysteine, α-trichosanthin, phosphonoformic acid, as well as immunodulators or related agents such as interleukin II, granulocyte macrophage colony stimulating factors, erythropoetin, soluble CD4, tucaresol, 4-(2-formyl-3-hydroxy-phenoxymethyl)benzoic acid and oligonucleotides or nucleic acids that comprise one or more unmethylated CpG sequences essentially as disclosed in, e.g., U.S. Pat. No. 6,194,388.

When treating other viral infections of the respiratory system, liver, blood, skin or other systems, e.g., human hepatitis C virus ("HCV"), human hepatitis B virus ("HBV"), HIV-1, HIV-2, an Orthopoxvirus infection, a filovirus infection, a picornavirus infection or an influenza virus infection (e.g., human influenza A or B), a formula 1 compound are optionally is used in conjunction with antivirals or treatments for such viruses. Examples of such therapeutic agents or treatments which are useful in these methods include carbovir, oxathiolan nucleoside analogs such as cis-1-(2-hydroxymethyl)-1,3-oxathiolan-5-yl)-cytosine or cis-1-(2-hydroxymethyl)-1,3-oxathiolan-5-yl-5-fluoro-cytosine, 2',3'-didoxy-5-ethynyl-3'-fluorouridine, 5-chloro-2',3'-didoxy-3'-fluorouridine, 1-(6-D-arabinofuranosy)-5-propynyluracil, tenofovir, tenofovir disoproxil, tenofovir disoproxil fumarate, bis(POC)-PMEA, bis(POM)-PMEA, bis(POC)-PMPA, bis(POM)-PMPA, acyclovir, HPMPC, amantadine, rimantadine, ribavirin, oseltamivir or compounds disclosed in U.S. Pat. No. 5,763,483 (especially compounds recited in claims 1 and 2), U.S. Pat. Nos. 5,866,601 and 6,043,230, mucolytics, expectorants, bronchodilators, antibiotics, antipyretics, analgesics or cytokines or interleukins that can augment one or more aspects of a desired immune response, e.g., IL-1, IL-2, IL-3, IL-6, α-interferon, β-interferon, γ-interferon, G-CSF, GM-CSF, M-CSF or thrombopoietin. Such cytokines or interleukins can be used for any viral infection essentially according to known dosing methods and dosages, e.g., as disclosed herein or in the cited references.

In these treatment methods the infectious agent in the infected subject (or one susceptible to infection) may be sensitive or resistant to one or more antimicrobial agents. For example, bacteria causing an infection can be sensitive or resistant to antibiotics such as a penicillin (e.g., ampicillin, amoxicillin, ampicillan, carbenicillin, cloxacillin, cyclacillin, dicloxacillin, floxicillin, penicillin G, penicillin G calcium or penicillin N), a cephalosporin (e.g., cefadroxil, cefamandole, or cefatrizine), a sulfa drug, a tetracycline, oxytetracycline, doxycycline, vancomycin, chloramphenicol, trimethoprim, erythromycin, rifampin, tobramycin, gentamycin, amikacin, a fluoroquinolone (e.g., ciprofloxacin, norfloxacin, ofloxacin, levofloxacin) or a quinoline. Infecting parasites can similarly be sensitive or resistant to antimicrobials, e.g., chloroquine resistant or sensitive *Plasmodium* parasites. Thus, in some embodiments, the subject's therapeutic regimen will optionally include treatment of resistant or sensitive infectious agents with one or more known antimicrobial agents. The antimicorbial can be administered orally, by intravenous injection or drip or as otherwise indicated by the subject's condition. Exemplary antimicrobial agents are as described, e.g., herein or in G. J. Galasso et al., editors, *Antiviral Agents and Human Viral Diseases*, $4^{th}$ edition, pages 1-833, 1997, Lippincott-Raven, Philadelphia, Pa., ISBN 0-397-51709-2, U.S. Pat. No. 4,753,925, or in any reference cited herein. Invention embodiments include treating a subject who has a bacterial or parasite infection as described with a formula 1 compound as described herein and a an antibacterial agent(s) or an antiparasitic agent(s) as described herein or in the cited references.

The antiviral or antimicrobial agents or treatments in combination therapies with a formula 1 compound will be or are used essentially according to new or to known dosing and administration methods for those agents or treatments. Their use may precede, overlap or be coincident in time with or follow a treatment protocol with a formula 1 compound. In some embodiments, the other therapeutic agents or treatments will overlap and will thus be administered on one or more of the same days on which a formula 1 compound is administered to a subject having a viral infection, or subject to a viral infection. In other embodiments, the other therapeutic agents or treatments will be administered to such a subject within about 1 day to about 180 days before or after a treatment protocol or a dosing period with a formula 1 compound begins or ends. In exemplary embodiments, the other suitable treatment or agent is administered within 1 day, 2 days, 3 days, 4 days, about 7 days, about 14 days, about 28 days or about 60 days before or after a treatment protocol or a dosing period with a formula 1 compound begins or ends.

Although the forgoing combination therapies have been described in the context of viral or other infections, the protocols and methods that employ a formula 1 compound can be used in conjunction with any suitable new or known therapeutic agent(s) or treatment protocol(s) for other any other clinical condition described herein. Exemplary conditions include one or more of a non-viral pathogen infection(s), a cancer(s), a precancer(s), an inflammation condition(s), an autoimmune condition(s), an immunosuppression condition(s), a neurological disorder(s), a cardiovascular disorder(s), a neurological disorder(s), diabetes, obesity, wasting, anorexia, anorexia nervosa, a cancer chemotherapy(ies) side-effect(s), a side-effect(s) of a chemotherapy(ies) or a radiation therapy(ies) of any other clinical condition disclosed herein or in the cited references, or the like. Thus, invention embodiments include the use of a formula 1 compound before, during or after a treatment that uses another suitable therapeutic agent(s) or therapeutic treatment(s) for any of the diseases or conditions disclosed herein, any of which diseases or conditions may be acute, chronic, severe, mild, moderate, stable or progressing.

Examples of such agents or treatments include the use of one or more adrenergic agents, adrenocortical suppressants, aldosterone antagonists, anabolics, analeptics, analgesics, anesthesia, anthelmintics, antiacne agents, anti-adrenergics, anti-allergics, anti-amebics, anti-androgens, antianginals, anti-anxiety agents, anti-arthritics, anti-asthmatic agents, anti-atherosclerotic agents, antibacterials, anticholinergics, anticoagulants, anticonvulsants, antidepressants, antidiabetics, antidiarrheals, antidiuretics, anti-emetics, anti-epileptics, anti-estrogens, antifibrinolytics, antifungals, antihistamines, antihyperlipidemia agents, antihyperlipoproteinemic agents, antihypertensive agents, antihypotensives, anti-infectives, anti-inflammatory agents such as entanercept (a dimeric fusion comprising a portion of the human TNF receptor linked to the Fc portion of human IgG1 containing the $C_H2$ and $C_H3$ domain and hinge regions of IgG1) or a COX-2 inhibitor such as celexicob (4-5[-(4-methylphenyl)-3-(trifluoromethyl)-1H-pyrazole-1-yl]benzenesulfonamide) or rofecoxib (4-[4-methylsulfonyl)phenyl]-3-phenyl-2(5H)-furanone), antimalarial agents, antimicrobials, antimigraine agents, antimycotic agents, antinausea agents, antineoplastic agents, antiparasitics, antiparkinsonian agents, antiproliferatives, antiprostatic hypertrophy agents, antiprotozoals, antipruritics, antipsychotics, antirheumatics, antischistosomals (e.g., praziquantel, artemisinin), blood glucose regulators, bone resorption inhibitors, bronchodilators, cardiac depressants, cardioprotectants, choleretics, depressants, diuretics, dopaminergic agents, enzyme inhibitors, free oxygen radical scavengers, glucocorticoids, peptide hormones, steroid hormones, hypocholesterolemics, hypoglycemics, hypolipidemics, hypotensives, immunomodulators, liver disorder treatments, mucosal protective agents, nasal decongestants, neuromuscular blocking agents, plasminogen activators, platelet activating factor antagonists, platelet aggregation inhibitors, post-stroke and post-head trauma treatments, progestins, psychotropics, radioactive agents, relaxants, sclerosing agents, sedatives, sedative-hypnotics, selective adenosine A1 antagonists, serotonin antagonists, serotonin inhibitors, serotonin receptor antagonists, thyroid inhibitors, thyromimetics, tranquilizers, vasoconstrictors, vasodilators, wound healing agents, xanthine oxidase inhibitors or a treatment(s) or therapeutic agent(s) for amyotrophic lateral sclerosis, ischemia, e.g., cereberal ischemia, cardiac ischemia or cardiovascular ischemia, or unstable angina. The selection and use of these agents for a particular subject will typically use dosing methods, dosages and routes of administration essentially according to known methods, dosages and routes of administration. Such methods, dosages and routes of administration are described in detail at, e.g., *Textbook of Autoimmune Diseases*, R. G. Lahita, editor, Lippincott Williams & Wikins, Philadelphia, Pa., 2000, ISBN 0-7817-1505-9, pages 81-851, *Holland•Frei Cancer Medicine* $^{e}$·5, $5^{th}$ edition, R. C. Bast et al., editors, 2000, ISBN 1-55009-113-1, pages 168-2453, B. C. Becker Inc. Hamilton, Ontario, Canada, *Hematology, Basic Principles and Practice*, $3^{rd}$ edition, R. Hoffman, et al., editors, 2000, ISBN 0-443-77954-4, pages 115-2519, Churchill Livingstone, Philadelphia, Pa., *Rheumatology*, $2^{nd}$ edition, J. H. Klippel et al., editors, 1998, ISBN 0-7234-2405-5, volume 1, sections 1-5 and volume 2, sections 6-8, Mosby International, London, UK, *Alzheimer's Disease and Related Disorders: Etiology, Pathogenesis and Therapeutics*, K. Iqbal, et al., editors, 1999, ISBN 0-471986386, John Wiley & Son Ltd, and Cardiovascular Medicine, E. J. Topol, editor, Lippincott Williams & Wikins, Philadelphia, Pa., 1998, ISBN 0781716810.

In some infections, the formula 1 compound(s) effects an improvement of one or more of the symptoms associated with the infection or a symptom thereof. For example, treatment of subjects who are immune suppressed, e.g., from a retrovirus infection, cancer chemotherapy or other cause, generally show improvement of one or more associated symptoms, such as weight loss, fever, anemia, pain, fatigue or reduced infection symptoms that are associated with a secondary infection(s), e.g., HSV-1, HSV-2, papilloma, human cytomegalovirus ("CMV"), *Pneumocystis* (e.g., *P. carinii*) or *Candida* (*C. albicans, C. krusei, C. tropicalis*) infections.

In some embodiments, the formula 1 compound(s) is administered as a nonaqueous liquid formulation as described herein or the formula 1 compound(s) is administered according to any of the intermittent dosing protocols described herein using a solid or liquid formulation(s). In the case of a subject who has a retroviral infection, e.g., a human with an HIV infection, with symptoms that include one or more of, a relatively low CD4 count (e.g., about 10-200, or about 20-100 or about 20-50), one or more additional pathogen infections (HSV-1, HSV-2, HHV-6, HHV-8, CMV, HCV, a HPV, *P. carinii* or *Candida* infection) and one or more of anemia, fatigue, Kaposi's sarcoma, fever or involuntary weight loss (at least about 5% of body weight), administration of about 0.1 to about 10 mg/kg/day (usually about 0.4 to about 5 mg/kg/day) of a formula 1 compound(s) to the subject typically results in noticeable improvement of one or more of the symptoms within about 1-4 weeks. In other embodiments, the formula 1 compound(s) is administered to a subject who has a condition that appears to be associated with a viral infection, e.g., pneumonia or retinitis associated with CMV, nasopharyngeal carcinoma or oral hairy leukoplakia associated with Epstein-Barr virus, progressive pancephalitis or diabetes associated with Rubella virus or aplastic crisis in hemolytic anemia associated with Parvovirus 19.

One or more intermittent dosing protocols disclosed herein or one or more of the liquid non-aqueous formulations described herein can be applied by routine experimentation to any of the uses or applications described herein. For a formula 1 compound(s) that is a new compound per se, the compound(s) can be administered to a subject according to an invention intermittent dosing protocol(s) or by other protocols, e.g., continuous daily dosing of a single dose or two or more subdoses per day. In addition any of the formula 1 compounds, e.g., one or more formula 1 compounds that are new per se, can be present in any solid or liquid formulation described herein. These formulations and dosing protocols can be applied by routine methods to any of the uses or applications described herein.

Antibodies, vaccines and vaccine adjuvants. The formula 1 compounds disclosed herein may also be used as vaccine adjuvants with immunogens or components of immunogenic compositions to prepare antibodies capable of binding specifically to the formula 1 compounds, their metabolic products which retain immunologically recognized epitopes (sites of antibody binding) or prepare antibodies that bind to antigens that can be used for vaccination against, e.g., infectious agents or malignant cells. The immunogenic compositions therefore are useful as intermediates in the preparation of antibodies that bind to formula 1 compounds for use, e.g., in diagnostic, quality control, or the like, methods or in assays for the compounds or their novel metabolic products. In addition, the compounds are useful for raising antibodies against otherwise non-immunogenic polypeptides, in that the compounds may serve as haptenic sites stimulating an immune response against the polypeptide.

The hydrolysis products or metabolites of formula 1 compounds include products of the hydrolysis of the protected acidic, basic or other reactive groups that variable groups, e.g., $R^1$-$R^9$, optionally comprise. In some embodiments, acidic or basic amides comprising immunogenic polypeptides such as albumin (e.g., human or mammalian), keyhole limpet hemocyamin and any other peptide described herein are used as immunogens. The metabolites of formula 1 compounds may retain a substantial degree of immunological cross reactivity with the unmetabolized parent compounds. Thus, in some embodiments, the antibodies will be capable of binding to the metabolites of the parent formula 1 compound without binding to the parent compound itself. In other embodiments, the antibodies, will be capable of binding to the parent compounds only, while in other cases the antibodies will be capable of binding to either of these. Some of the antibodies will not substantially cross-react with naturally occurring materials or epitopes that are present in the subject.

Substantial cross-reactivity is reactivity under specific assay conditions for specific analytes sufficient to interfere with the assay results.

The immunogens of this invention may comprise a formula 1 compound that has 1 or more epitopes in association with another immunogenic substance. Within the context of the invention such association means covalent bonding to form an immunogenic conjugate (when applicable) or a mixture of non-covalently bonded materials, or a combination of the above. Immunogenic substances include adjuvants such as Freund's adjuvant, immunogenic proteins such as viral, bacterial, yeast, plant and animal polypeptides, including keyhole limpet hemocyanin, serum albumin, bovine thyroglobulin or soybean trypsin inhibitor, and immunogenic polysaccharides. Typically, the formula 1 compound having one, two or more epitopes is covalently conjugated to an immunogenic polypeptide or polysaccharide by the use of a polyfunctional (ordinarily bifunctional) cross-linking agent. Methods for the manufacture of immunogens that comprise one or more haptens are conventional per se. Any suitable known method for conjugating haptens to immunogenic polypeptides or the like are used here, taking into account the functional groups on the precursors or hydrolytic products which are available for cross-linking and the likelihood of producing antibodies specific to the epitope in question as opposed to the immunogenic substance.

Typically a polypeptide, polysaccharide or other suitable immunogenic moiety is conjugated to a site on a formula 1 compound in a location that is distant from the epitope on the formula 1 compound to be recognized.

The conjugates are prepared in conventional fashion. For example, the cross-linking agents N-hydroxysuccinimide, succinic anhydride or $C_{2-8}$ alkyl-N=C=N—$C_{2-8}$ alkyl are useful in preparing the conjugates. The conjugates comprise a formula 1 compound that is attached by a bond or a linking group of 1-100, typically, 1-25, more typically about 1-10 carbon atoms to the immunogenic substance. The conjugates are separated from starting materials and by-products using chromatography or the like, and then are optionally sterile filtered, or otherwise sterilized, or are optionally vialed for storage. Synthetic methods to prepare hapten-carrier immunogens have been described, see e.g., G. T. Hermanson, Bioconjugate *Techniques* Academic Press, 1996, pages 419-493.

The formula 1 compounds are cross-linked for example through any one or more of the following groups: a hydroxyl group, a thiol group, a carboxyl group, a carbon atom, or an amine group. Included within such compounds are amides of polypeptides where the polypeptide serves as an above-described protecting group.

Animals or mammals are typically immunized once, twice or more times against the immunogenic conjugates that comprise a formula 1 compound or their derivatives and polyclonal antisera or monoclonal antibodies prepared in conventional fashion. In some embodiments, about 0.0001 mg/kg to about 1 mg/kg, e.g., about 0.001 or about 0.01 or about 0.1 mg/kg, of immunogenic conjugate or derivative is used on one, two, three or more occasions to immunize the subject as described herein. The immunogenic conjugates are administered, orally, topically or parenterally as described herein, e.g., by i.m. or s.c. injection. Methods to prepare antibodies, including methods to obtain antibodies that bind to steroids have been described, see, e.g., R. O, Neri et al., *Endocrinology* 74:593-598 1964, M. Ferin et al., *Endocrinology* 85:1070-1078 1969, J. Vaitukaitis et al., *J. Clin. Endocr. Metab.* 33:988-991 1971 and M. Ferin et al., *Endocrinology* 94:765-775 1974. Such methods can be used essentially as described to prepare antibodies or monoclonal antibodies that bind to a formula 1 compound. Invention embodiments include serum or other preparations that comprise any polyclonal or monoclonal antibodies that bind to a formula 1 compound(s), methods to make them and compounds or compositions that are used in conducting these methods.

In other embodiments the formula 1 compounds are used as adjuvants to enhance a subject's immune response to antigens such as proteins, peptides, polysaccharides, glycoproteins or killed or attenuated viruses or cell preparations. In these methods, an effective amount of the formula 1 compound is administered at about the same time that the antigen is delivered to the subject, e.g., within about 1, 2, 3, 4, 5, 6, or 7 days of when the antigen is administered to the subject. In some embodiments, the formula 1 compound is administered 1, 2, 3, 4 or more times (usually once or twice per day) at 1, 2, 3 or 4 days before or after the antigen is administered to the subject. In other embodiments, the formula 1 compound is administered on the same day that the antigen is administered to the subject, e.g., within about 1-4 hours. Such immunization methods may be repeated once, twice or more as needed. The formula 1 compound can be administered to the subject using any of the formulations or delivery methods described herein or in the references cited herein. Subjects suitable for these vaccinations include young and elderly mammals, including humans, e.g., humans about 3-36 months of age or older and humans about 60, 65, 70, 75 years of age or older. The amount of antigen used can be about 0.01 µg/kg to about 20 mg/kg, typically about 1-100 µg/kg. Dosages of the formula 1 compound used in these vaccinations is essentially as described herein, e.g., about 10 mg to about 1000 mg of a formula 1 compound is used per day on days when it is administered as part of the vaccination method.

Related embodiments include compositions or formulations that comprise a formula 1 compound, an antigen(s) or antigen(s) preparation and optionally one or more excipients. The antigen is essentially as disclosed herein or in a cited reference. Antigen preparations may comprise one or more of (1) lethally or sublethally radiated cells or pathogens, (2) disrupted cells or viruses or such as attenuated viruses, (3) a nucleic acid or DNA vaccine, (4) an antigenic protein, glycoprotein, polysaccharide or a fragment or derivative of any of these molecules, (5) chemically treated cells or pathogens, e.g., formalin or detergent treated cells, viruses or cell or virus extracts and (6) genetically engineered viral or bacterial vectors that express one or more antigens or antigen fragments, e.g., canarypox virus containing HIV or other pathogen sequences or other animal viruses carrying HIV or other pathogen sequences. Pathogens include prions or the etiologic agents of, e.g., Creutzfelt-Jacob disease, bovine spongiform encephalopathy and scrapie in sheep, goats or mice. Where cells or disrupted are present in an antigen preparation, they may by genetically modified, e.g., to express one or more antigens or epitopes against which an immune response is desired. Such cells may also be genetically modified to optionally express one or more factors, e.g., an interleukin or a cytokine, such as one described herein, to enhance the desired immune response. As used here, an antigen means a moiety that can be used to elicit an immune response when it is administered to a subject. In some embodiments, the antigen is foreign to the subject. For foreign antigens, the subject to be vaccinated may not encode or express the antigen, while the antigen is usually part of or expressed by a pathogen or by a subject or mammal of a different species. In other embodiments, antigens are endogenous or non-foreign to the subject, e.g., they are usually encoded or expressed by the subject or another subject of the same species. Endogenous antigens are suitable for use in, e.g., tumor vaccination methods.

Exemplary tumors from which a suitable antigen(s) may be obtained are as described herein or in the cited references. A DNA vaccine as used here typically comprises a nucleic acid, usually DNA, that encodes one or more antigens or epitopes that a pathogen, e.g., a parasite, fungus, virus or bacterium, or a tumor encodes or can express. Tumor antigens that are suitable for use in vaccination methods that employ a formula 1 compound include tumor-associated antigens and tumor-specific antigens. These molecules typically comprise one or more protein, glycoprotein, carbohydrate or glycolipid. Vaccinations that employ a tumor antigen(s) may comprise autologous tumor cells or allogenic tumor cells, which are optionally disrupted and optionally used with a non-formula 1 adjuvant, such as *bacillus* Calmette-Guerin (BCG), purified protein derivative, Freund's complete adjuvant, *Corynebacterium parvum, Mycobacterium vaccae*, oligonucleotides that consist of or comprise an unmethylated CpG dimer or an alum precipitate. In some embodiments, tumor cells treated with neuraminidase comprise all or part of the tumor antigen source. The non-formula 1 adjuvants are also optionally used in any of the vaccination methods disclosed herein. As used here, tumor associated antigens, e.g., the carcinoembryonic antigen, α-fetoprotein or the prostate specific antigen, are molecules that are often associated with or detectably expressed by premalignant or malignant cells or cell populations and also with some normal tissues during at least part of the subject's life cycle.

Tumor-specific antigens, e.g., the R24c mutation of the cyclin dependent kinase-4 protein or certain sialylated glycoconjugates such as protein containing N-glycolyl neuraminic acid that is found in some human tumors (e.g., colon cancers, liver cancer, lymphoma), are molecules whose expression is restricted to pretumors or tumors and they are not expressed in normal adult or fetal tissue of a subject or a species to a significant extent. Vaccination with one or more tumor antigens and a formula 1 compound may be administered to a subject who has a cancer or a precancer, or to a subject who is considered potentially susceptible to developing such a condition. The tumor antigens are optionally combined with protein or other non-formula 1 adjuvants, e.g., keyhole-limpet hemocyanin or an immunoglobulin from a different species, which may be covalently bonded to the tumor antigen(s).

Suitable natural and synthetic nucleic acid sequences, cells, attenuated pathogens or infectious agents such as attenuated viruses, and protein, glycoprotein, polysaccharide, oligosaccharide or peptide antigens derived various infectious agents and tumors have been described, e.g., U.S. Pat. Nos. 4,053,585, 4,081,334, 4,115,543, 4,503,036, 4,466,917, 4,508,708, 4,601,903, 4,632,830, 4,683,200, 4,727,136, 4,735,799, 4,784,850, 4,784,941, 4,803,164, 4,831,121, 4,831,126, 4,853,333, 4,863,200, 4,857,452, 4,916,055, 4,939,240, 4,960,716, 4,963,484, 5,013,661, 5,032,397, 5,075,218, 5,077,220, 5,093,118, 5,011,920, 5,110,588, 5,112,749, 5,126,264, 5,134,075, 5,162,226, 5,185,432, 5,198,535, 5,231,168, 5,225,193, 5,283,321, 5,302,386, 5,328,835, 5,378,814, 5,393,532, 5,395,614, 5,456,911, 5,474,900, 5,478,556, 5,348,887, 5,455,332, 5,489,525, 5,527,891, 5,541,292, 5,582,831, 5,591,596, 5,609,872, 5,614,194, 5,639,621, 5,639,863, 5,641,492, 5,643,567, 5,654,136, 5,679,342, 5,688,657, 5,688,658, 5,705,341, 5,712,118, 5,723,130, 5,747,028, 5,756,101, 5,780,591, 5,798,445, 5,814,617, 5,824,316, 5,824,777, 5,837,830, 5,843,451, 5,844,075, 5,849,306, 5,849,476, 5,858,685, 5,866,679, 5,871,936, 5,874,060, 5,895,285, 5,895,651, 5,916,571, 5,916,754, 5,916,879, 5,932,412, 5,935,818, 5,942,235, 5,948,410, 5,948,412, 5,961,985, 5,968,514, 5,985,571, 5,993,813, 5,993,828, 5,994,523, 6,013,765, 6,013,779, 6,017,527, 6,020,478, 6,024,961, 6,025,191, 6,025,474, 6,030,624, 6,030,797, 6,045,802, 6,056,963, 6,060,280, 6,083,703, 6,083,683, 6,087,441, 6,093,540, 6,096,320, 6,100,049, 6,100,088, 6,100,241, 6,100,444, 6,110,468, 6,110,724, 6,110,898, 6,120,770, 6,113,917, 6,120,770, 6,127,116, 6,127,333, 6,130,082, 6,207,170, PCT publication Nos. WO 0025820, WO 0050645, WO 0050897, WO 0050900, WO 0052165, WO 0057904, WO 0057906, WO 0097907, WO 00/58438 and R. C. Bast et al., editors, *Holland•Frei Cancer Medicine* $^{e\cdot}$5, 5$^{th}$ edition, 2000, pages 800-814, B. C. Becker Inc. Hamilton, Ontario. Antigens suitable for use with the formula 1 compounds include the molecules disclosed in any of these references or antigenic fragments thereof. Such antigenic fragments will typically retain at least about 20% of the antigenicity of the unmodified antigen. Thus, these fragments will retain at least about 20% of the native antigen's capacity to generate an antibody response or to generate a T cell response against the unmodified antigen or the like.

Other suitable antigens include STn, sialyl Tn-KLH, carbohydrate conjugates, carcinogenic embryonic antigen, MAGE-1, MUC-1, HER-2/neu, prostate specific antigen, p53, T/Tn, bacterial flagella antigens or capsular polysaccharide antigens (e.g., *Staphylococcus aureus* capsular polysaccharide antigens) and antigenic fragments or antigenic synthetic derivatives of any of these molecules. See, e.g., L. A. Holmberg et al., *Bone Marrow Transplant*. 2000 25:1233-1241, J. W. Hadden, *Int. J. Immunopharmacology* 1999 21:79-101, G. Ragupathi et al., *Glycoconj. J.* 1998 15:217-221, A. I. Fattom et al., *Infect. Immun*. 1998 66:4588-4592, U.S. Pat. Nos. 5,770,208, 5,866,140 and 6,194,161 and citations elsewhere herein, including the preceding paragraph.

An antigenic protein, peptide or glycoprotein can be identified by standard methods, e.g., protein or nucleic acid sequencing, for any of the infectious agents or tumors that are described herein or in the cited references. Thus, in some embodiments, an effective amount of a formula 1 compound and an antigen are administered to a subject, or delivered to the subject's tissues, to stimulate an immune response against the antigen. The antigen may comprise one, two or more antigenic epitopes, which may come from one, two or more genes. In some embodiments, the subject is optionally monitored to follow or determine the immune, dendritic cell, B cell, T cell, antibody or cytokine response, such as one disclosed herein, e.g., modulation or increase in γIFN, IL-2 or IL-12 levels or measurement of the production of one or more immunoglobulin types or subtypes. The subject may also be monitored by in vitro cell assays, e.g., for activation of T cells or subsets of T cells or other relevant white blood cell types. Such assays include measuring T cell activation using chromium release assays, or mixed lymphocyte assays. The subject is optionally treated with one or more additional booster vaccinations, when this is called for under the circumstances.

Nucleic acid or DNA vaccines as used here will typically comprise a nucleic acid comprising an expressible region that encodes one, two or more suitable antigens or epitopes, e.g., all or an antigenic portion of a viral, bacterial, fungal or parasite protein or glycoprotein. The expressible region will usually comprise a transcription promoter and optionally other control sequences that are operatively linked to the antigen coding region where the promoter and control sequences are transcriptionally active in the intended subject or tissue. Suitable control sequences include enhancers, recognition sequences for transcription factors and termination sequences. Such expression vectors may optionally comprise one, two or more expressible genes or gene fragments, which may each comprise their attendant operatively linked expression sequences. Suitable methods and expression vectors to deliver nucleic acids for vaccine purposes have been described, e.g., U.S. Pat. Nos. 5,223,263, 5,580,859, 5,703,055, 5,846,946 and 5,910,488.

Thus, in some embodiments, an effective amount of a formula 1 compound and an antigen are administered to a subject to stimulate an immune response against the antigen, wherein the antigen is encoded by a suitable expression construct. Exemplary antigens that are suitable in these methods are, e.g., essentially as described in any reference cited herein or as is apparent to the skilled artisan. In some embodiments, the antigen is encoded by a parasite such as a *Plasmodium* or a *Trypanosome* species such as one described herein. The formula 1 compound can be administered before, essentially simultaneously with or after administration of the antigen, as noted above. The dosages of the formula 1 compound are essentially as described for the other conditions described herein.

Vaccinations that utilize a formula 1 compound and an antigen(s) are generally suitable for eliciting or enhancing desired immune responses in conjunction with exposure of a subject to an antigen(s), compared to vaccination without the compound. Antigen specific humoral antibody responses or antigen specific T cell responses may be enhanced or elicited. Typically vaccination using a formula 1 compound and a suitable antigen is conducted to prevent a potential infection or to reduce the severity of a future infection. However, in some cases the vaccination is conducted in a subject that has an infection such as a chronic or a latent infection such as a parasite or a retrovirus or herpesvirus infection, which may be latent or in relapse. In other cases the subject may have a cancer or precancer. Thus, the subject may be exposed to, or contain, one or more of the antigens that are used in one of these vaccination procedures. Such vaccinations are included within the scope of the invention.

In related embodiments, the formula 1 compounds are useful to facilitate preparation of hybridoma clones that express monoclonal antibodies. In these methods, a suitable amount of a formula 1 compound, e.g., about 100 µg to about 2 mg for a small mammal, is administered to a subject, e.g., a mouse, to enhance the immune response to the desired antigen, which is also administered to the subject. After antigen challenge, suitable cells are recovered from the subject, e.g., anti-antigen immunoglobulin expressing HPRT$^+$ spleen cells from a mouse. These cells are then fused with suitable immortal cells (e.g., mouse melanoma cells) using, e.g., PEG or Sendai virus, and selected in suitable selection growth medium, e.g., tissue culture medium that contains hypoxanthine, aminopterin and thymidine, to obtain a group or panel of hybridomas that express anti-antigen monoclonal antibodies. The hybridoma panel is used to generate individual clones, which are optionally screened to determine the antibody specificity and antigen binding properties. About one, 100, 1000, 10,000, 100,000 or more individual clones are screened by standard methods. The monoclonal antibodies may be from any suitable source, e.g., murine, human, human-murine hybrid or the like. Methods to obtain human, human-murine hybrid or related monoclonal antibodies have been described, e.g., U.S. Pat. Nos. 5,562,903, 5,461,760, 5,705,154, 5,854,400, 5,858,728, 5,874,082, 5,874,540, 5,877,293, 5,882,644, 5,886,152, 5,889,157, 5,891,996, 5,916,771, 5,939,598, 5,985,615, 5,998,209, 6,013,256, 6,075,181, 6,901,001, 6,114,143, 6,114,598, 6,117,980. The formula 1 compounds can be used in any of the methods disclosed in these references to facilitate generation or recovery of hybridoma panels and clones that express monoclonal antibodies.

An aspect of these methods comprise a product, i.e., a hybridoma panel or a hybridoma clone, that is obtained by the process of contacting a subject (such as a mouse) with (1) a suitable amount of a formula 1 compound and (2) a suitable amount of an antigen, allowing sufficient time to generate an immune response in the subject against the antigen and then fusing suitable anti-antigen immunoglobulin producing cells from the subject, e.g., the subject's spleen cells, with a suitable immortal cell line (e.g., a HPRT$^+$ mouse myeloma). The antigen or immunogen is as described above, e.g., a suitable protein, protein fragment or glycoprotein such as an interleukin, cytokine or antigen from an infectious agent. In these methods, a mouse is typically the subject, but other mammals, e.g., humans or other rodents, are also suitable according to known methods.

The amount of antigen for immunization used in preparing monoclonal antibodies in a small mammal will typically be about 1 µg to about 100 µg, e.g., about 2 µg, 5 µg, 10 µg or 50 µg of antigen. The antigens are essentially as described in the vaccination methods described above, e.g., disrupted cell, a protein or glycoprotein, which is optionally combined with a suitable amount of an adjuvant such as Freund's complete adjuvant, alum precipitate, a bacterial lipopolysaccharide or BCG. The formula 1 compound is typically parenterally administered, e.g., subcutaneous or intraperitoneal, within about 2-4 days (e.g., about 1, 2, 3, 4, 5 or 6 days before or after antigen challenge) of the time that the subject is challenged with antigen. In some cases, the antigen and the formula 1 compound is administered at the same time or at about the same time, e.g., within about 5 minutes to about 1 hour. The formula 1 compound may be administered on one, two, three or more occasions in the process, e.g., a formula 1 compound is administered once per day on one or more of the four days before antigen challenge and then it is optionally administered again on the same day as antigen challenge and then optionally administered daily at one, two, three or more days after antigen challenge.

Related embodiments include a method comprising administering to a subject (e.g., a mammal such as a human or a primate), or delivering to the subject's tissues, an effective amount of a formula 1 compound and a specific antigen. Immune responses that are enhanced include a mucosal immune response to an antigen such as a protein, peptide, polysaccharide, microorganism, tumor cell extract or lethally radiated tumor or pathogen cells (e.g., antigens or cells from melanoma, renal cell carcinoma, breast cancer, prostate cancer, benign prostatic hyperplasia, virus or bacteria, or other tumor or pathogen as disclosed herein). Aspects of these embodiments include enhancement of the subject's immune response when an antigen or immunogen is administered intranasally or orally. In these aspects, the formula 1 compound is administered about simultaneously with the antigen or within about 3 hours to about 6 days of antigen administration. The use of immune modulating agents to enhance immune responses to a vaccine has been described, e.g., U.S. Pat. No. 5,518,725.

Other uses for the formula 1 compound(s) include administering the compound(s) to a subject who suffers from a pathological condition(s). The treatment may treat or ameliorate the source of the condition(s) and/or symptoms associated with the pathological condition(s) such as infection with a pathogen(s) (viruses, bacteria, fungi), a malignancy, unwanted immune response, i.e., an immune response that causes pathology and/or symptoms, e.g., autoimmune conditions or allergy or conditions such as hypoproliferation conditions, e.g., normal or impaired tissue growth, or wound healing or burn healing, or in immunosuppression conditions, e.g., conditions characterized by an absence of a desired response and/or an inadequate degree of a desired response.

As noted in the foregoing applications where a formula 1 compound and an antigen are administered to a subject to enhance the subject's immune response, the antigen may be obtained from any suitable source. The antigen will generally be capable of eliciting an immune response against the original pathogen or cell. Desirable immune responses obtained from vaccination of a subject with an antigen and a formula 1 compound include one or more of an enhanced antibody response, an enhanced antigen specific CD4$^+$ T cell response or an enhanced cytotoxic T cell response to pathogen infected cells, extracellular pathogen or to tumor cells.

Enhanced antibody responses include detectable enhancement of antibody titer or a shift in the antibody response from a Th2 biased response to an increased Th1 biased component of the response. In such antibody shifts, the Th1 and Th2 character of the response is determined by known methods. For example, a relatively low ratio of IgG1 (or the analogous antibody subclass in humans and other subjects) to IgG2a (or the analogous antibody subclass in humans and other subjects), e.g., about 6:1 to about 12:1, that is generated after exposure of a subject (a mouse for the IgG1 and IgG2a subclasses) to an antigen indicates a Th1 biased antibody response. Conversely a higher ratio, e.g., about 20:1 to about 30:1 indicates a Th1 biased antibody response. Generation of antigen-specific IgG1 generation involves T-helper type 2 (Th2) cells, and for IgG2a, T-helper type 1 (Th1) cells. The formula 1 compounds can detectably increase the Th1 character of an antibody response to an antigen or they can increase the magnitude of both the Th1 and Th2 response.

Exemplary antigen sources include pathogens, cells or their individual proteins, peptides, glycoproteins or polysaccharides or antigenic fragments of any of these molecules. The antigenic material is recovered from suitably treated pathogens or cells and administered to a subject, or it can be recovered using recombinant means to obtain a purified or partially purified antigen source.

Exemplary pathogens or cells that are suitable sources for antigens or a gene(s) that encode suitable antigens include influenza viruses (e.g., influenza A, influenza B), respiratory syncytial viruses, Rotaviruses, Hantaviruses, human Papilloma viruses (e.g., HPV-16, HPV-18), Poxviruses, Polioivirus, rabies viruses, Retroviruses (e.g., HIV-1, HIV-2), hepatitis viruses (e.g., human HAV, HBV or HCV), Togaviruses and Flaviviruses (e.g., West Nile Virus, Yellow Fever Virus, Dengue viruses), Herpesviruses (e.g., CMV, EBV, Varicella Zoster Virus, HSV-1, HSV-2, HHV-6, HHV-8), measles viruses, mumps viruses, rubella virus, pneumococci such as *Klebsiella pneumonia* cells or capsule material, enteric bacterial cells (e.g., *E. coli*, or *Shigella* or *Salmonella* species), gram positive bacterial pathogens (e.g., *Staphylococcus, Streptococcus*), gram negative bacterial pathogens, diphtheria pathogens, or human or animal cells obtained from a melanoma or skin cancer, breast cancer, prostate cancer, colon cancer, liver cancer, bone cancer, nervous tissue cancer (e.g., neuroblastoma, glioma), lymphoma, leukemia cells, kidney or renal cell cancer, ovarian cancer or lung cancer (e.g., small cell carcinoma, non-small cell carcinoma). Exemplary parasites or antigen sources include *Plasmodium, Leishmania* and *Cryptosporidium*. The antigen(s) that is used may comprise a pathogen coat protein(s), pathogen cell wall or other structural proteins. Antigen(s) from tumor cells or parasites may comprise cell membrane associated structures or intracellular molecules that are characteristic of, or unique to, the tumor or parasite. Other suitable antigen or pathogen sources are as described herein or in the cited references.

Cancer and hyperproliferation conditions. Many cancers, precancers, malignancies or hyperproliferation conditions are associated with an unwanted Th2 immune response, a deficient Th1 response or unwanted inflammation. An insufficient Th1 immune response may play a role in the capacity of malignant or premalignant cells to escape immune surveillance. The formula 1 compounds, including those in the compound groups and embodiments disclosed herein, may thus be used to treat, prevent or slow the progression of one or more cancers, precancers or cell hyperproliferation conditions or they may be used to ameliorate one or more symptoms thereof. In these conditions, the formula 1 compounds are useful to enhance the subject's Th1 responses or to reestablish a more normal Th1-Th2 balance in the subject's immune responses. The formula 1 compounds may function at least in part by decreasing inflammation or inflammation associated markers such as IL-6 and/or by enhancing hemopoiesis in many of these conditions.

These conditions include cancers or precancers comprising carcinomas, sarcomas, adenomas, blastoma, disseminated tumors and solid tumors such as one associated with or arising from prostate, lung, breast, ovary, skin, stomach, intestine, pancreas, neck, larynx, esophagus, throat, tongue, lip, oral cavity, oral mucosa, salivary gland, testes, liver, parotid, biliary tract, colon, rectum, cervix, uterus, vagina, pelvis, endometrium, kidney, bladder, central nervous system, glial cell, astrocyte, squamous cell, blood, bone marrow, muscle or thyroid cells or tissue. The formula 1 compounds are thus useful to treat, prevent, slow the progression of, or ameliorate one or more symptoms of a precancer, cancer or related hyperproliferation condition such as myelodysplastic syndrome, actinic keratoses, endometriosis, Barrett's esophagus, leiomyoma, fibromyoma, benign or precancerous intestinal or bowel polyps or benign prostatic hyperplasia. The compounds can also be used to treat, prevent, slow the progression of, slow the replication or growth of, or to ameliorate one or more symptoms of a primary tumor, a metastasis, an advanced malignancy, a blood born malignancy, a leukemia or a lymphoma.

The formula 1 compounds can be used to treat paraneoplastic syndromes or conditions such as ones associated with lung or breast cancers that secrete calcitonin or that enhance osteoclast activity. Such conditions include hypercalcemia, Cushing's syndrome, acromegaly and non-islet cell tumor hypoglycemia. The compounds are used to decrease osteoclast activity or other symptoms associated with such conditions.

Hyperproliferation conditions that can be treated include melanoma, Kaposi's sarcoma, leiomyosarcoma, non-small cell lung cancer, small cell lung cancer, bronchogenic carcinoma, renal cell cancer or carcinoma, glioma, glioblastoma, pancreatic or gastric adenocarcinoma, gastrointestinal adenocarcinoma, human papillomavirus associated cervical intraepithelial neoplasia, cervical carcinoma, hepatoma, hepatocellular carcinoma, hepatocellular adenoma, cutaneous T-cell lymphoma (mycosis fungoides, Sezary syndrome), colorectal cancer, chronic lymphocytic leukemia, chronic myelogenous leukemia, ALL or follicular lymphoma, multiple myeloma, carcinomas with p53 mutations, colon cancer, cardiac tumors, adrenal tumors, pancreatic cancer, retinoblastoma, a small cell lung cancer, a non-small cell lung cancer, intestinal cancer, testicular cancer, stomach cancer, neuroblastoma, neuroma, myxoma, myoma, endothelioma, osteoblastoma, osteoclastoma, osteosarcoma, chondrosarcoma, adenoma, breast cancer, prostate cancer, Kaposi's sarcoma, ovarian cancer, squamous cell carcinoma of the gastrointestinal tract. Treating a subject with a formula 1 compound can ameliorate one or more side effects of chemotherapy or cancer symptoms such as alopecia, pain, fever, malaise, chronic fatigue and cachexia or weight loss. Other cancers, precancers or their symptoms that can be treated, prevented or ameliorated are described in, e.g., Holland•Frei Cancer Medicine$^{e \cdot}$5, 5$^{th}$ edition, R. C. Bast et al., editors, 2000, ISBN 1-55009-113-1, pages 168-2453, B. C. Becker Inc. Hamilton, Ontario, Canada or The Merck Manual, 17$^{th}$ edition, M. H. Beers and R. Berkow editors, 1999, Merck Research Laboratories, Whitehouse Station, N.J., ISBN 0911910-10-7.

In some of these embodiments, the subject's hyperproliferation or malignant condition may be associated with or caused by one or more pathogens. Such conditions include hepatocellular carcinoma associated with HCV or HBV, Kaposi's sarcoma associated with HIV-1 or HIV-2, T cell leukemia associated with HTLV I, Burkitt's lymphoma associated with Epstein-Barr virus or papillomas or carcinoma associated with papilloma viruses (e.g., human HPV 6, HPV 11, HPV 16, HPV 18, HPV 31, HPV 45) or gastric adenocarcinoma, gastric MALT lymphoma or gastric inflammation associated with Helicobacter pylori, lactobacillus, enterobacter, staphylococcus or propionibacteria infection.

In some of these embodiments, the formula 1 compounds may be used to treat, prevent or slow the progression of or ameliorate one or more conditions in a subject having or subject to developing a hyperproliferation condition where angiogenesis contributes to the pathology. Abnormal or unwanted angiogenesis or neovascularization contributes to the development or progression of solid tumor growth and metastases, as well as to arthritis, some types of eye diseases such as diabetic retinopathy, retinopathy of prematurity, macular degeneration, corneal graft rejection, neovascular glaucoma, rubeosis, retinoblastoma, uvietis and pterygia or abnormal blood vessel growth of the eye, and psoriasis. See, e.g., Moses et al., Biotech. 9:630-634 1991, Folkman et al., N. Engl. J. Med., 333:1757-1763 1995, and Auerbach et al., J. Microvasc. Res. 29:401-411 1985.

Dosages of the formula 1 compound, routes of administration and the use of combination therapies with other standard therapeutic agents or treatments could be applied essentially as described above for cancer or hyperproliferation conditions or other conditions as disclosed herein. This, in some embodiments, the use of the formula 1 compound is optionally combined with one or more additional therapies for a cancer or precancer(s), e.g., one or more of surgery and treatment with an antiandrogen or an antiestrogen as described herein or in the cited references, an antineoplastic agent such as an alkylating agent, a nitrogen mustard, a nitrosourea, an antimetabolite or cytotoxic agent, or an analgesic such as propoxyphene napsylate, acetaminophen or codeine. Exemplary anticancer and adjunct agents include methotrexate, thioguanine, mercaptopurine, adriamycin, chlorambucil, cyclophosphamide, cisplatin, procarbazine, hydroxyurea, allopurinol, erythropoietin, G-CSF, bicalutamide, anastrozole, fludarabine phosphate and doxorubicin. Such therapies would be used essentially according to standard protocols and they would precede, be essentially concurrent with and/or follow treatment with a formula 1 compound. In some embodiments, such additional therapies will be administered at the same time that a formula 1 compound is being used or within about 1 day to about 16 weeks before or after at least one round of treatment with the formula 1 compound is completed. Other exemplary therapeutic agents and their use have been described in detail, see, e.g., Physicians Desk Reference 54$^{th}$ edition, 2000, pages 303-3250, ISBN 1-56363-330-2, Medical Economics Co., Inc., Montvale, N.J. One or more of these exemplary agents can be used in combination with a formula 1 compound to ameliorate, slow the establishment or progression of, prevent or treat any of the appropriate cancers, precancers or related conditions described herein, or any of their symptoms.

In treating cancers or hyperproliferation conditions, the formula 1 compounds may detectably modulate, e.g., decrease or increase, the expression or level or activity of one or more biomolecules associated with the prevention, establishment, maintenance or progression of the cancer or hyperproliferation condition. Such biomolecules include one or more of carcinoembryonic antigen, prostate specific antigen, her2/neu, Bcl-XL, bcl-2, p53, IL-1a, IL-1β, IL-6, or TNFα, GATA-3, COX-2, NFκB, IkB, an IkB kinase, e.g., IkB kinase-α, IkB kinase-β or IkB kinase-γ, NFAT, calcineurin, calmodulin, a ras protein such as H-ras or K-ras, cyclin D, cyclin E, xanthine oxidase, or their isoforms, homologs or mutant forms, which may have either reduced or enhanced biological activity(ies), and which may be detectably decreased. Biomolecules or their activity(ies) that can be detectably increased include IL-2, IFNγ, IL-12, T-bet, O6-methylguanine-DNA-methyltransferase, calcineurin, calmodulin, a superoxide dismutase (e.g., Mn, Zn or Cu), a tumor suppressor protein such as the retinoblastoma protein (Rb) or CDKN2A (p16), BRCA1, BRCA2, MeCP2, MBD2, PTEN, NBR1, NBR2 or the isoforms, homologs or mutant forms, which may have either attenuated or enhanced biological activity(ies), of any of these molecules. One or more of these biomolecules may be modulated in any the cancers or conditions described herein.

The formula 1 compounds can modulate the synthesis or a biological activity of one or more other gene products such as transcription factors, enzymes or steroid or other receptors that are associated with the establishment, progression or maintenance of a cancer or precancer or associated symptom. The compounds can inhibit AIB-1 coactivator or HER2/neu synthesis or activity in breast cancer cells or breast cancer conditions. They can enhance the synthesis or an activity of an estrogen receptor such as ERα, ERβ1 or ERβ2 or progesterone receptor in breast cancer or colon cancer cells or conditions. These effects can include modulation of the expression or one or more biological activities of proteins or enzymes that contribute to disease establishment or progression. Thus, the compounds can decrease IL-4, IL-6 or IL-13 expression by stromal cells or immune cells that are in proximity to or adjacent to solid or diffuse tumor cells in a subject such as a human or another mammal. In the cancers or precancers described herein, the compounds can thus directly or indirectly modulate (e.g., decrease) the activity or expression of relevant enzymes such as STAT-6, neutral endopeptidase, a hydroxysteroid dehydrogenase, such as a 17β-hydroxysteroid dehydrogenase or a 3β-hydroxysteroid dehydrogenase.

In an exemplary embodiment, human patients suffering from melanoma or melanoma precursor lesions are treated with a topical cream formulation containing 2-20% BrEA (w/w). The cream is applied to primary nevi (dysplastic nevi or common acquired nevi), primary cutaneous melanomas, secondary cutaneous melanomas and the skin surrounding the nevi or melanomas. The areas to be treated are washed with soap or swabbed with an alcohol (e.g., ethanol or isopropanol) prior to administering the cream, when this is practical. About 0.1-0.4 g of cream, depending on the size of the treated area, is applied once or twice per day per treated region or lesion for about 10-20 days. The cream is left undisturbed at the administration site for about 15-30 minutes before the patient resumes normal activity. Progression of the nevi and melanomas is retarded in the majority of patients and significant regression is observed for some lesions. Following initial treatment, the formulation is administered every other day for at least 1 to 4 months using the same dosing described for the initial round of treatment. For these patients, standard therapy to treat precursor lesion or melanoma, e.g., dimethyl triazeno imidazole carboxamide or nitrosoureas (e.g., BCNU, CCNU), is optionally started or continued according to the recommendations of the patient's doctor and with the patient's informed approval. In cases where a tumor or precursor lesion is surgically removed and the site has sufficiently healed, the patient optionally continues using the topical formulation at the site and the adjacent surrounding area every other day for at least 1 to 4 months. In some of these embodiments, a formula 1 compound(s) is administered daily continuously as an oral composition or formulation, e.g., for a formula 1 compound(s) that is a new compound per se. BrEA is optionally also administered systemically using, e.g., a formulation described in the examples below to deliver 0.1-5 mg/kg/day every other day for about 1 week to about to 4 months, e.g., in the case of malignant melanoma.

Cardiovascular applications. The formula 1 compounds, including those in the compound groups and embodiments disclosed herein, may be used to treat, prevent or slow the progression of one or more of congenital heart defects, cardiovascular diseases, disorders, abnormalities and/or conditions, or to ameliorate one or more symptoms thereof in a subject. These include peripheral artery disease, arterio-arterial fistula, arteriovenous fistula, cerebral arteriovenous malformations, aortic coarctation, cor triatum, coronary vessel anomalies, patent ductus arteriosus, Ebstein's anomaly, hypoplastic left heart syndrome, levocardia, transposition of great vessels, double outlet right ventricle, tricuspid atresia, persistent truncus arteriosus, and heart septal defects, such as aortopulmonary septal defect, endocardial cushion defects, Lutembacher's Syndrome, ventricular heart septal defects, cardiac tamponade, endocarditis (including bacterial), heart aneurysm, cardiac arrest, congestive heart failure, congestive cardiomyopathy, paroxysmal dyspnea, cardiac edema, postinfarction heart rupture, ventricular septal rupture, heart valve diseases, myocardial diseases, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, cardiovascular syphilis, cardiovascular tuberculosis, arrhythmias such as sinus arrhythmia, atrial fibrillation, atrial flutter, bradycardia, extrasystole, Adams-Stokes Syndrome, bundle-branch block, sinoatrial block, long QT syndrome, parasystole, sick sinus syndrome, ventricular fibrillations, tachycardias such as paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia and heart valve diseases such as aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

The formula 1 compounds can be used to treat, prevent or ameliorate one or more symptoms of myocardial diseases or pathological myocardial or vascular conditions such as alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, myocardial fibrosis, endomyocardial fibrosis, Kearns Syndrome, myocardial reperfusion injury, myocarditis, cardiovascular or vascular diseases such as dissecting aneurysms, false aneurysms, infected aneurysms, ruptured aneurysms, aortic aneurysms, cerebral aneurysms, coronary aneurysms, heart aneurysms, and iliac aneurysms, angiodysplasia, angiomatosis, bacillary angiomatosis, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, thrombosis, erythromelalgia, hemorrhoids, hepatic veno-occlusive disease, hypertension, hypotension, idiopathic pulmonary fibrosis, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, venous insufficiency and arterial occlusive diseases such as arteriosclerosis, intermittent claudication, carotid stenosis, fibromuscular dysplasias, mesenteric vascular occlusion, Moyamoya disease retinal artery occlusion, thromboangiitis obliterans or atherosclerosis, any of which may be at an early stage or at a more advanced or late stage.

The formula 1 compounds can also be used to treat, prevent or ameliorate one or more symptoms of cerebrovascular diseases, thrombosis, and/or conditions such as carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subarachnoid hemorrhage, cerebral infarction, cerebral ischemia (including transient), subclavian steal syndrome, periventricular leukomalacia, vascular headache, cluster headache, migraine, vertebrobasilar insufficiency, air embolisms, embolisms such as cholesterol embolisms, fat embolisms, pulmonary embolisms or amniotic fluid embolism, thromboembolisms, thrombosis such as coronary thrombosis, hepatic vein thrombosis, retinal vein occlusion, carotid artery thrombosis, sinus thrombosis, Wallenberg's syndrome, and thrombophlebitis.

The formula 1 compounds can also be used to treat, prevent or ameliorate one or more symptoms of vascular ischemia or myocardial ischemias, vasculitis and coronary diseases, including angina pectoris, coronary aneurysm, coronary arteriosclerosis, coronary thrombosis, coronary vasospasm, myocardial infarction and myocardial stunning, cerebral ischemia, ischemic colitis, compartment syndromes, anterior compartment syndrome, myocardial ischemia, reperfusion injuries, peripheral limb ischemia, aortitis, arteritis, Behcet's Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Exemplary symptoms that the use of the formula 1 compounds can ameliorate include one or more of pain such as arm, jaw or chest pain, edema or swelling, high blood pressure, shortness of breath or dyspnea, e.g., on exertion or while prone, fatigue or malaise and low cardiac injection fraction. In treating a cardiovascular condition in a subject or in improving one or more symptoms thereof, the formula 1 compounds may accomplish one or more of increasing cardiac ejection volume or fraction, decreasing levels of IL-6, decreasing levels of C reactive protein, fibrinogen, cardiac creatinine kinase, increasing fatty acid metabolism or utlization by cardiac tissue, increasing carnityl palmitoyl fatty acid transferase or other cardiac metabolic enzymes, activating potassium dependent calcium channels, vasodilating or enhancing oxygen delivery to ischemic tissues or decreasing levels of scarring or plaque formation that occurs, e.g., after vascular damage. Symptoms associated with a cardiovascular condition such as ischemia that can be ameliorated also include acidosis, expression of one or more immediate early genes in, e.g., glial cells, vascular smooth muscle cells or endothelial cells, neuronal membrane depolarization and increased neuronal extracellular calcium and glutamate concentration. Other biological effects associated with treatment using a formula 1 compound may also be monitored, e.g., and increase or decrease of a cell surface antigen, a cytokine or an interleukin as disclosed herein.

Useful biological effects of the formula 1 compounds in cardiovascular indications such as myocardial ischemias also include preventing or reducing heart or vascular cell death and subsequent fibrosis. These effects are associated with a decreased oxidative capacity of heart cells or myocytes, which is associated with a decreased capacity of the cells to metabolize fatty acids efficiently. The compounds enhance fatty acid metabolism and ameliorate the deleterious effects of a limited oxidative capacity.

The formula 1 compounds also can limit inflammation or cell injury that is associated with ischemia or oxygen reperfusion after ischemia. Ischemia, which is a detrimental decrease in oxygenated blood delivery to affected cells or tissues, may arise from a cardiovascular condition or event such as an infarction, or from thermal injury or burns. Ischemia may also arise from accidental or surgical trauma. Reperfusion after cells have become hypoxic for a sufficient period of time can lead to tissue or cell injury that varies from slight to lethal. The compounds can reduce cell or tissue injury or death associated with ischemia and reperfusion, by, e.g., reducing inflammation or the level of a molecule associated with inflammation. Thus, levels of a proinflammatory cytokine or molecule such as leukotriene B4, platelet activating factor or levels of extracellular P-selectin may result from administration of a formula 1 compound to a subject who may experience reperfusion injury. Thus, the compounds can reduce injury or death of, e.g., neuron, cardiac, vascular endothelium, myocardial, pulmonary, hepatic or renal cells or tissues. Without wishing to be bound by any theory, the compounds may act in part by reducing one or more of neutrophil activation, platelet activation, platelet aggregation, endothelial cell activation and neutrophil adherence or adhesion to endothelial cells in these conditions.

The use of any formula 1 compound or species in any genus of formula 1 compounds disclosed herein to treat, prevent or ameliorate any of these cardiovascular conditions or symptoms will generally use one or more of the routes of administration, dosages and dosing protocols as disclosed herein. Thus, in exemplary embodiments, about 0.5 to about 100 mg/kg or about 1 to about 25 mg/kg, of the formula 1 compound will be administered per day by an oral, buccal, sublingual or parenteral route. Such administration can be, e.g., daily for about 5 to about 60 days in acute conditions or it can be intermittent for about 3 months to about 2 years or more for chronic conditions. Alternatively, intermittent dosing can be used essentially as described herein for acute cardiovascular conditions. In conditions such as ischemia, administration of the formula 1 compound should generally occur before or as soon after the ischemic event as possible, e.g., within about 6 hours of an ischemic event or about 12-24 hours before an anticipated ischemic event.

In related embodiments, the use of the formula 1 compound is optionally combined with one or more additional therapies for cardiovascular disorders, e.g., vascular surgery, cardiac surgery, angioplasty, or treatment with andrenergic blockers, coronary vasodilators, calcium channel blockers, nitrates, angiotensin converting enzyme inhibitors, anti-hypertensives, anti-inflammatory agents, diuretics, anti-arrhythmia agents, thrombolytic agents, enzyme inhibitors such as hydroxymethylglutaryl CoA reductase inhibitors or xanthine oxidase inhibitors. Exemplary hydroxymethylglutaryl CoA reductase inhibitors include statins such as mevastatin, lovastatin, pravastatin, simvastatin or compounds described in U.S. Pat. Nos. 4,346,227, 4,448,979, 4,739,073, 5,169,857, 5,006,530 or 5,401,746. Other additional therapies include treatment with one or more of digoxin, nitroglycerin, doxazosin mesylate, nifedipine, enalapril maleate, indomethicin, tissue plasminogin activator, urokinase, acetylsalicylic acid, allopurinol or the like. Any of such additional therapies would be used essentially according to standard protocols and such therapies would precede, be concurrent with or follow treatment with a formula 1 compound. In some embodiments, such additional therapies will be administered at the same time that a formula 1 compound is being used or within about 1 day to about 16 weeks before or after at least one round of treatment with the formula 1 compound is completed. Other exemplary therapeutic agents and their use have been described in detail, see, e.g., *Physicians Desk Reference* $54^{th}$ edition, 2000, pages 303-3251, ISBN 1-56363-330-2, Medical Economics Co., Inc., Montvale, N.J. One or more of these exemplary agents can be used in combination with a formula 1 compound to treat any of the appropriate cardiovascular disorders described herein.

Applications in autoimmunity, allergy, inflammation and related conditions. As mentioned above, the formula 1 compounds, including those in the compound groups and embodiments disclosed herein, may be used to treat, prevent or slow the progression of one or more autoimmune allergic or inflammatory diseases, disorders, or conditions, or to ameliorate one or more symptoms thereof in a subject. These diseases and conditions include Addison's Disease, autoimmune hemolytic anemia, antiphospholipid syndrome, acute or chronic rheumatoid arthritis and other synovial disorders, an osteoarthritis including post-traumatic osteoarthritis and hypertrophic pulmonary osteoarthropathy, psoriatic arthritis, polyarthritis, epichondylitis, type I diabetes, type II diabetes, rheumatic carditis, bursitis, ankylosing spondylitis, multiple sclerosis, a dermatitis such as contact dermatitis, atopic dermatitis, exfoliative dermatitis or seborrheic dermatitis, mycosis fungoides, allergic encephalomyelitis, autoimmune glomerulonephritis, Goodpasture's Syndrome, Graves'Disease, Hashimoto's Thyroiditis, multiple sclerosis, myasthenia gravis, neuritis, bullous pemphigoid, pemphigus, polyendocrinopathies, purpura, Reiter's Disease, autoimmune thyroiditis, systemic lupus erythematosus, scleroderma, fibromyalgia, chronic fatigue syndrome, autoimmune pulmonary inflammation, Guillain-Barre Syndrome, type 1 or insulin dependent diabetes mellitus, autoimmune inflammatory eye disease, hepatitis C virus associated autoimmunity, postinfectious autoimmunity associated with, e.g., virus or bacterial infection such as a parvovirus such as human parvovirus B19 or with rubella virus, autoimmune skin and muscle conditions such as pemphigus vulgaris, pemphigus foliaceus, systemic dermatomyositis or polymyositis or another inflammatory myopathy, myocarditis, asthma such as allergic asthma, allergic encephalomyelitis, allergic rhinitis, a vasculitis condition such as polyarteritis nodosa, giant cell arteritis or systemic necrotizing vasculitis, chronic and an acute or chronic inflammation condition such as chronic prostatitis, granulomatous prostatitis and malacoplakia, ischemia-reperfusion injury, endotoxin exposure, complement-mediated hyperacute rejection, nephritis, cytokine or chemokine induced lung injury, cachexia, sarcoidosis, inflammatory bowel disease, regional enteritis, ulcerative colitis, Crohn's disease, inflammatory bowel disease or inflammation associated with an infection, e.g., septic shock, sepsis, or systemic inflammatory response syndrome. Any of these diseases or conditions or their symptoms may be acute, chronic, mild, moderate, severe, stable or progressing before, during or after the time administration of the formula 1 compound to a subject such as a human, is initiated. In general, a detectable improvement is observed in the subject within a period of about 3 days to about 12 months after initiation of a dosing protocol, e.g., the severity of the disease or condition will detectably decrease, the rate of progression will detectably slow or the severity of a symptom(s) will detectably decrease.

As used herein, acute inflammation conditions are characterized as an inflammation that typically has a fairly rapid onset, quickly becomes moderate or severe and usually lasts for only a few days or for a few weeks. Chronic inflammation conditions as used herein are characterized as an inflammation that may begin with a relatively rapid onset or in a slow, or even unnoticed manner, tends to persist for at least several weeks, e.g., about 3-6 weeks, months, or years and may have a vague or indefinite termination. Chronic inflammation may result when the injuring agent (or products resulting from its presence) persists in the lesion, and the subject's tissues respond in a manner (or to a degree) that is not sufficient to overcome completely the continuing effects of the injuring agent. Other exemplary conditions are described in, e.g., *Textbook of Autoimmune Diseases*, R. G. Lahita, editor, Lippincott Williams & Wikins, Philadelphia, Pa., 2000, ISBN 0-7817-1505-9, pages 175-851 and *Rheumatology*, $2^{nd}$ edition, J. H. Klippel et al., editors, 1998, ISBN 0-7234-2405-5, volume 1, sections 1-5 and volume 2, sections 6-8, Mosby International, London, UK.

A formula 1 compound can be used to inhibit or ameliorate one or more inappropriate immune responses or their symptoms in autoimmunity, inflammation, allergy or related conditions. The effects of the formula 1 compounds include detectably ameliorating one or more of (1) the proliferation, differentiation or chemotaxis of T cells, (2) reducing unwanted cytotoxic T cell responses, (3) reducing unwanted autoantibody or other antibody synthesis, e.g., an unwanted IgA, IgE, IgG or IgM, in allergy, asthma or another autoimmune or inflammation condition, (4) inhibiting the development, proliferation or unwanted activity of autoreactive T or B cells, (5) altering the expression of one or more cytokines, interleukins or cell surface antigens, e.g., a cytokine, interleukin or cell surface antigen described herein (decreasing IL-8 in an autoimmune condition, decreasing the level of acute phase proteins such as C reactive protein or fibrinogen in inflammation conditions, (6) decreasing eosinophilia in allergy conditions, (7) detectably decreasing the level or activity of one or more of ICAM-1, IL-1$\alpha$, IL-1$\beta$, TNF$\alpha$ or IL-6 in, e.g., inflammation conditions or in autoimmune conditions such as an arthritis or a myocarditis condition such as osteoarthritis, rheumatoid arthritis, toxic myocarditis, indurative myocarditis or idiopathic myocarditis, (8) decreasing the level or biological activity of one or more of anti-islet antibody, TNF, IFN-$\gamma$, IL-1, an arthritis symptom(s), nephritis, skin rash, photosensitivity, headache frequency or pain, migraine frequency or pain, abdominal pain, nausea or anti-DNA antibodies in, e.g., insulin dependent diabetes mellitus or an autoimmune or inflammation condition such as systemic lupus erythematosus, rheumatoid arthritis or Crohn's disease, (9) reducing induction of arachidonic acid metabolism or reducing eicosanoid metabolites such as thromboxanes or prostaglandins in, e.g., inflammation, asthma or allergy, (10) reducing IL-4, IL-8 or IL-10 synthesis, levels or activity in, e.g., allergy or inflammation such as idiopathic pulmonary fibrosis or allergic asthma or (11) reducing or interfering with neutrophil chemotaxis by, e.g., reducing thioredoxin release from affected cells in conditions such as cancer, infections, inflammation or autoimmunity.

Exemplary symptoms that the use of the formula 1 compounds can ameliorate in these autoimmune, inflammatory and allergy conditions include one or more of pain such as shoulder, hip, joint, abdominal or spine pain, joint stiffness or gelling, bursitis, tendonitis, edema or swelling, fatigue or malaise, headache, dyspnea, skin rash, fever, night sweats, anorexia, weight loss, skin or intestine ulceration, muscle weakness, pericarditis, coronary occlusion, neuropathy and diarrhea. In treating one of these conditions in a subject or in improving one or more symptoms thereof, the formula 1 compounds may accomplish one or more of decreasing levels of one or more of IL-1, IL-4, IL-6 or TNF$\alpha$, decreasing levels of C reactive protein, fibrinogen or creatinine kinase. Other biological effects associated with treatment using a formula 1 compound may also be monitored or observed, e.g., an increase or decrease of a cell surface antigen, a cytokine or an interleukin as disclosed herein.

In treating inflammation or any condition described herein where inflammation contributes to the condition, the formula 1 compounds may detectably modulate, e.g., decrease or increase, the expression or level or activity of one or more biomolecules associated with the prevention, establishment, maintenance or progression of the inflammation condition. Such biomolecules include one or more of carcinoembryonic antigen, prostate specific antigen, her2/neu, Bcl-XL, bcl-2, p53, IL-1$\alpha$, IL-1$\beta$, IL-6, or TNF$\alpha$, GATA-3, COX-2, NF$\kappa$B, I$\kappa$B, an I$\kappa$B kinase, e.g., I$\kappa$B kinase-$\alpha$, I$\kappa$B kinase-$\beta$ or I$\kappa$B kinase-$\gamma$, NFAT, a ras protein such as H-ras or K-ras, cyclin D, cyclin E xanthine oxidase, or their isoforms, homologs or mutant forms, which may have either reduced or enhanced biological activity(ies), and which may be detectably decreased. Biomolecules that can be detectably increased include IL-2, IFN$\gamma$, IL-12, T-bet, O6-methylguanine-DNA-methyltransferase, calcineurin, calmodulin, a superoxide dismutase (e.g., Mn, Zn or Cu), a tumor suppressor protein such as the retinoblastoma protein (Rb) or CDKN2A (p16), BRCA1, BRCA2, MeCP2, MBD2, PTEN, NBR1, NBR2 or the isoforms, homologs or mutant forms, which may have either attenuated or enhanced biological activity(ies), of any of these molecules. One or more of these biomolecules may be modulated in any inflammation condition described herein.

The use of any formula 1 compound or species in any genus of formula 1 compounds disclosed herein to treat, prevent or ameliorate any of these autoimmune, inflammatory or allergy conditions or symptoms will generally use one or more of the routes of administration, dosages and dosing protocols as disclosed herein. Thus, in exemplary embodiments, about 0.5 to about 100 mg/kg or about 1 mg/kg to about 15 mg/kg, of the formula 1 compound will be administered per day by, e.g., an oral, buccal, sublingual, topical or parenteral route. Such administration can be, e.g., daily for about 5 to about 60 days in acute conditions or it can be intermittent for about 3 months to about 2 years or more for chronic conditions. Alternatively, intermittent dosing can be used essentially as described herein for acute autoimmune, inflammatory and allergy conditions.

In related embodiments, the use of the formula 1 compound is optionally combined with one or more additional therapies for an autoimmune, inflammatory or allergy disorder(s), e.g., one or more of surgery and treatment with a corticosteroid or glucocorticoid such as hydrocortisone, hydrocortisone acetate, prednisone, prednisolone, prednisolone acetate, methylprednisolone, dexamethasone, dexamethasone acetate or triamcinolone acetonide, leflunomide, an antibody, e.g., a human or humanized monoclonal antibody, that decreases the activity or level of C5 complement, TNFα or TNFα receptor, an antirheumatic drug such as methorexate, D-penicillamine, sodium aurothiomalate, sulfasalazine or hydroxychloroquine, immunosuppressive agents such as 6-thioguanylic acid, chlorambucil, cyclophosphamide or cyclosporin, a non-steroidal antiinflammatory agent such as celecoxib, ibuprofin, piroxicam or naproxin, an antihistamine such as loratidine or promethazine hydrochloride or an analgesic such as propoxyphene napsylate, acetaminophen or codeine. Such therapies would be used essentially according to standard protocols and such they would precede, be concurrent with or follow treatment with a formula 1 compound. In some embodiments, such additional therapies will be administered at the same time that a formula 1 compound is being used or within about 1 day to about 16 weeks before or after at least one round of treatment with the formula 1 compound is completed. Other exemplary therapeutic agents and their use have been described in detail, see, e.g., *Physicians Desk Reference* 54$^{th}$ edition, 2000, pages 303-3267, ISBN 1-56363-330-2, Medical Economics Co., Inc., Montvale, N.J. One or more of these exemplary agents can be used in combination with a formula 1 compound to ameliorate, prevent or treat any of the appropriate autoimmune, inflammatory or allergy conditions or disorders described herein or any of their symptoms.

Regeneration and wound healing. The formula 1 compounds can be used to facilitate cell differentiation or proliferation where regeneration of tissues is desired. The regeneration of tissues could be used to repair, replace, protect or limit the effects of tissue damaged by congenital defects, trauma (wounds, burns, incisions, or ulcers), age, disease (e.g. osteoporosis, osteoarthritis, periodontal disease, liver failure), surgery, including cosmetic plastic surgery, fibrosis, reperfusion injury, or systemic cytokine damage. Tissues for which regeneration may be enhanced include organs (e.g., pancreas, liver, intestine, kidney, skin, endothelium, oral mucosa, gut mucosa), muscle (e.g., smooth, skeletal or cardiac), vasculature (including vascular and lymphatics), nervous tissue, hematopoietic tissue, and skeletal tissue (e.g., bone, cartilage, tendon, and ligament). These effects may be accompanied by decreased scarring or an increased rate of healing.

The formula 1 compounds are thus useful to enhance healing or tissue repair in a subject having a bone fracture(s), e.g., a simple or compound skull, spine, hip, arm or leg bone fracture. Similarly, nerve or brain tissue treatment using a formula 1 compound allows treating, slowing the progression of, ameliorating or preventing diseases such as central and peripheral nervous system diseases, neuropathies, or mechanical and traumatic diseases, disorders, and/or conditions (e.g., spinal cord disorders, head trauma, cerebrovascular disease, and stoke). The compounds are useful to treat diseases associated with peripheral nerve injuries, peripheral neuropathy (e.g., resulting from chemotherapy or other medical therapies), localized neuropathies, and central nervous system diseases such as Alzheimer's disease, Parkinson's disease, Huntington's disease and amyotrophic lateral sclerosis. The subjects undergoing treatment in these conditions may be elderly, e.g., a human at least 55, 60, 65 or 70 years of age. Where the condition is acute, e.g., a bone fracture or a burn, the treatment may comprise administration of a formula 1 compound to the subject on a daily or intermittent basis for about 3 days to about 12 months, e.g., administration for about 2-12 weeks beginning after the subject sustains an injury.

Dosages of the formula 1 compound, routes of administration and the use of combination therapies with other standard therapeutic agents or treatments could be applied essentially as described herein, e.g., for cardiovascular conditions or other conditions as disclosed herein.

Neurological conditions. Nervous system diseases, disorders, or conditions, which can be ameliorated, treated or prevented with any of the formula 1 compounds disclosed herein include, but are not limited to, nervous system trauma or injury, and diseases or conditions which result in either a disconnection of axons, a diminution of neuron function or degeneration of neurons, demyelination or pain.

Nervous system lesions which may be treated, prevented, or ameliorated in a subject include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia, (2) traumatic lesions, including lesions caused by physical injury or associated with surgery, for example, lesions which sever a portion of the nervous system, or compression injuries, (3) malignant lesions, in which a portion of the nervous system is destroyed or injured by malignant tissue which is either a nervous system associated malignancy or a malignancy derived from non-nervous system tissue, (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis, (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS), (6) lesions associated with nutritional diseases, disorders, and/or conditions, in which a portion of the nervous system is destroyed or injured by a nutritional disorder or disorder of metabolism including but not limited to, vitamin B 12 deficiency, folic acid deficiency, Wernicke disease, tobacco-alcohol amblyopia, Marchiafava-Bignami disease (primary degeneration of the corpus callosum), and alcoholic cerebellar degeneration, (7) neurological lesions associated with systemic diseases including, but not limited to, diabetes (diabetic neuropathy, Bell's palsy), systemic lupus erythematosus, carcinoma, or sarcoidosis, (8) lesions caused by toxic substances including alcohol, lead, or particular neurotoxins, (9) demyelinated lesions in which a portion of the nervous system is destroyed or injured by a demyelinating disease including, but not limited to, multiple sclerosis, human immunodeficiency virus-associated myelopathy, progressive multifocal leukoencephalopathy, and central pontine myelinolysis or a myelopathy, e.g., diabetic meylopathy or a transverse myelopathy, (10) neurological conditions such as insomnia, epilepsy, schizophrenia, depression, addiction to a drug, substance such as tobacco, nicotine, caffeine, alcohol, a barbiturate, a tranquilizer, a narcotic such as hydromorphone HCl, propoxyphene napsylate, meperidine HCl, codeine, cocaine, morphine, heroin or methadone and (11) cognitive dysfunction conditions or diseases such as one or more of impaired long-term or short-term memory, impaired concentration impaired attention or impaired learning, where the cognitive dysfunction condition or disease is optionally associated with chemotherapy, radiation therapy or exposure, aging, trauma, e.g., CNS trauma, or neurodegeneration.

The formula 1 compounds are useful to ameliorate, treat or prevent the onset, severity or length of other neurological diseases or conditions such as headache or a migraine condition or symptom such as classic migraine, cluster headache, abdominal migraine, common migraine, hemiplegic migraine, ocular migraine, fulminating migraine, complicated migraine or a symptom of any of these such as head pain, vertigo, nausea, vomiting or potophobia.

In some embodiments, the formula 1 compound is used to protect neural cells from the damaging effects of cerebral hypoxia, cerebral ischemia or neural cell injury associated with cerebral infarction, heart attack, stroke or elevated levels of glucocorticoids such as cortisol. The compounds are also useful for treating or preventing a nervous system disorder may be selected, e.g., by assaying their biological activity in promoting the survival or differentiation of neurons. For example, and not by way of limitation, compositions of the invention which elicit any of the following effects are useful: (1) increased survival time of neurons in culture, (2) increased sprouting of neurons in culture or in vivo, (3) increased production of a neuron-associated molecule in culture or in vivo, e.g., dopamine or choline acetyltransferase or acetylcholinesterase with respect to motor neurons or (4) decreased symptoms of neuron dysfunction in vivo. Such effects may be measured by any method known in the art. Increased survival of neurons may be measured using known methods, such as, for example, the method set forth in Arakawa et al. (*J. Neurosci.* 10:3507-3515 1990); increased sprouting of neurons may be detected by methods known in the art, such as the methods set forth in Pestronk et al. (*Exp. Neurol.* 70:65-82 1980) or Brown et al. (*Ann. Rev. Neurosci.* 4:17-42 1981). Increased production of neuron-associated molecules may be measured by, e.g., bioassay, enzymatic assay, antibody binding or Northern blot assay, using techniques known in the art and depending on the molecule to be measured. Motor neuron dysfunction may be measured by assessing the physical manifestation of motor neuron disorder, e.g., weakness, motor neuron conduction velocity, or functional disability. In other embodiments, motor neuron diseases, disorders, and/or conditions that may be treated, prevented, and/or ameliorated include diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, poliomyelitis and the post polio syndrome, and hereditary motorsensory neuropathy.

In some conditions such as mood changes, depression anxiety, memory loss or motor function impairment, the formula 1 compounds can modulate one or more biological activities of a transcription factor or a steroid receptor such as ERα in tissue such as the hypothalamus or amygdala or ERβ in tissue such as the hippocampus, thalamus or entorhinal cortex.

For any of these diseases, conditions or their associated symptoms, the presence of the disease, condition or symptom may be determined by suitable objective or subjective means, e.g., assays to detect tissue damage, levels of diagnostic markers, or an etiological agent, patient questionaires or behavior performance tests, measurement of a diagnostic marker(s), e.g., an enzyme, hormone, cytokine or drug substance in blood or tissue, electroencephalography, imaging methods such as X-ray, MRI scan or CAT scan, observation and diagnosis of clinical features or symptoms or biopsy of affected tissue or cells, e.g., aspiration biopsy, needle biopsy, incision biopsy or punch biopsy of tissue or cells. Neurological conditions, diseases and symptoms, which the formula 1 compounds can be used to treat or ameliorate and methods to diagnose and characterize such conditions or diseases have been described. See, e.g., Ph. Demaerel, A. L. Baert et al., eds. *Recent Advances in Diagnostic Neuroradiology (Medical Radiology: Diagnostic Imaging)* 2001 Springer Verlag, ISBN: 3504657231, W. G. Bradley et al., *Neurology in Clinical Practice: Principles of Diagnosis and Management* 1995, see, e.g., vol. 1 Ch. 1-55 and vol 2. Ch. 1-66, Butterworth-Heinemann Medical, ISBN 0750694777, H. J. M. Barnett et al., eds. *Stroke: Pathophysiology, Diagnosis and Management* $3^{rd}$ edition, 1998, see, e.g., pages 10-1450, Churchill Livingstone, ISBN 0443075514, P. J. Vinken et al., eds. *Neurodystrophies and Neurolipidoses* $2^{nd}$ ed. 1996, see, e.g., pages 8-780, Elsevier Science, ISBN 0444812857, P. L. Peterson and J. W. Phillis eds. *Novel Therapies for CNS Injuries: Rationales and Results* 1995, see, e.g., pages 8-380, CRC Press, ISBN 0849376521, D. Schiffer, *Brain Tumors: Pathology and Its Biological Correlates* $2^{nd}$ ed. 1997, see, e.g., pages 5-450, Springer Verlag, ISBN 3540616225 and E. Niedermeyer and F. Lopes Da Silva, eds. *Electroencephalography: Basic Principles, Clinical Applications and Related Fields* $4^{th}$ ed. 1999 see, e.g., pages 13-1238, Lippincott, Williams & Wilkins, ISBN 0683302841. The use of the formula 1 compounds in these conditions is optionally combined with one or more of the therapeutic treatments that are described in these references. The formula 1 compound may be administered before, during or after another treatment is employed to treat or ameliorate a given neurological disease, condition or symptom.

Dosages of the formula 1 compound, routes of administration and the use of combination therapies with other standard therapeutic agents or treatments could be applied essentially as described above for cardiovascular conditions or as disclosed elsewhere herein. Thus, the formula 1 compounds may be administered prophylactically or therapeutically in chronic conditions or they may be administered at the time of or relatively soon after an acute event such as an epileptic seizure, onset of a migraine or occurrence of trauma, accidental head or central nervous system injury or a cereberal stroke or infarction. For acute events, the formula 1 compounds may thus be administered concurrently, e.g., within about 15 minutes or about 30 minutes of the onset or occurrence of the acute event, or at a later time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours after the onset or occurrence of the acute event. The formula 1 compounds may thus be administered at about 6-120 hours, or about 8-48 hours, about 10-24 hours or about 12-16 hours after an acute event starts or occurs.

Skin treatments. The affect of the formula 1 compounds on immune function permits their use to improve the function of organs or organ systems that rely on the optimal functioning of one or more immune responses. Thus, the formula 1 compounds can be administered to a subject to prevent, treat, ameliorate, slow the progression of or enhance the healing of certain skin conditions such as skin inflammation, lesions, atrophy or rash. As used here, skin includes external skin and internal skin or surfaces such as oral, intestinal and rectal mucosa. These conditions include lesions, rashes or inflammation associated with, e.g., burns, infections and the thinning or general degradation of the dermis often characterized by a decrease in collagen or elastin as well as decreased number, size and doubling potential of fibroblast cells. Such skin conditions include keratoses such as actinic keratosis, psoriasis, eczema, warts such as papillomavirus-induced warts, ulcers or lesions such as herpesvirus-induced ulcers or lesions or diabetes associated ulcers or lesions, discoid lupus erythematosus, erythema nodosum, erythema multiform, cutaneous T cell lymphoma, atopic dermatitis, inflammatory vasculitis, relapsing polychondritis, exfoliative dermatitis, sarcoidosis, burns, melanoma, rash or irritation from poison oak, poison ivy or poison Sumac, blemished or hyperpigmented skin, hyperkeratotic skin, dry skin, dandruff, acne, inflammatory dermatoses, scarring such as from a chemical or thermal burn and age-related skin changes. In these embodiments, treatment with the formula 1 compounds is optionally combined with other appropriate treatments or therapies essentially as described herein, e.g., one or more of a corticosteroid such as hydrocortisone or cortisol, prednisone, or prednisolone, an α-hydroxybenzoic acid or an α-hydroxycarboxylic acid(s) is coadministered with a formula 1 compound to treat, prevent or ameliorate a skin condition such as atrophy or a lesion. α-Hydroxybenzoic acids and α-hydroxycarboxylic acids suitable for use in these embodiments are described in, e.g., U.S. Pat. Nos. 5,262,407, 5,254,343, 4,246,261, 4,234,599 and 3,984,566. The formula 1 compound can be used to minimize cutaneous atrophy caused by corticosteroids, a side-effect of their application to the skin.

In these embodiments that address skin conditions, dosages, routes of administration and dosing protocols for the formula 1 compounds are essentially as described herein. In some embodiments, the formula 1 compound is administered to the subject in the form of a topical cream, ointment, spray, foam or gel. These topical formulations will optionally comprise about 0.1% w/w to about 20% w/w, or about 0.2% w/w to about 10% w/w of a formula 1 compound in a composition that comprises one or more excipients that are suitable for such topical formulations, including, e.g., one or more agents that enhance penetration or delivery of the formula 1 compound into the skin. Such topical formulations can be administered, e.g., once, twice or three times per day using about 0.1 g to about 8 g or about 0.2 g to about 5 g of the topical formulation on each occasion. Administration may be daily for about 1 to about 28 days, or it may be intermittent and used as needed. The amount of a topical formulation that can be administered may be higher, e.g., about 15 g or about 20 g, if the size of the area to be treated is relatively large, e.g., at least about 30 cm$^2$ to about 100 cm$^2$ or more. Alternatively, systemic administration of the formula 1 compound such as oral, parenteral, sublingual or buccal delivery may be used, particularly when the area of the skin to be treated is relatively large. In some cases, both topical and systemic administration of a formula 1 compound can be used. Excipients that topical or other formulations may contain include those described herein, or agents that enhance permeation or solubilization of the formula 1 compound, e.g., DMSO or an alkylalkanol, such as a 2-alkylalkanol or a 3-alkyloctanol that comprises about 8-36 carbon atoms (e.g., 8, 9, 10, 11, 12, 13, 14, 15, 16, 17, 18, 19 or 20 carbon atoms) such as 2-ethyloctanol, 2-propyloctanol, 2-octyldodecanol, 2-butyloctanol, 2-hexyldecanol, 2-pentylnonanol, 3-ethyloctanol, 3-propyloctanol, 3-octyldodecanol, 3-butyloctanol, 3-hexyldecanol, 3-pentylnonanol, isostearyl alcohol, isocetyl alcohol, or mixtures thereof. Such alkylalkanol moieties include those having the structure HO—CH$_2$—(CH$_2$)$_{0-4}$—CH(C1-10 alkyl)-(CH$_2$)$_{0-6}$—CH$_3$, any of which are optionally substituted at the alkanol or the alkyl moiety with one, two, three or more independently selected substituents as described herein, e.g., with one, two, three or more independently selected —O—, —F, —OH, —CN or —CH═CH— moieties. Such formulations can be used in therapeutic applications described herein or in cosmetic applications.

Enhancement of hematopoiesis. The invention includes methods to treat or prevent various blood cell deficiencies such as TP or NP. Without being bound to any theory, the treatment methods may at least in part result in enhanced hematopoiesis (or hemopoiesis) or the treatment methods may reduce the loss of cells such as platelets or neutrophils. Increased platelet or neutrophil production or reduced loss is typically observed as increased circulating blood cell counts. Thus, invention aspects comprise methods to treat or prevent neutropenia in a subject in need thereof, comprising administering to a subject in need, or delivering to the subject's tissues, an effective amount of a formula 1 compound.

Normal ranges of various white blood cells or blood components in adult (about 18-49 years of age) human blood are as follows. Total adult white blood cell counts average about 7500/mm$^3$, with an approximate normal range of about 4.5-11.0×10$^3$/mm$^3$. The normal basophil level is about 35 mm$^{-3}$, with a normal range of about 10-100/mm$^3$. The normal adult neutrophil level is about 4400/mm$^3$, with a normal range of about 2000-7700/mm$^{-3}$. The normal eosinophil level is about 275 mm$^{-3}$, with a normal range of about 150-300/mm$^3$. The normal monocyte level is about 540 mm$^{-3}$, with a normal range of about 300-600/mm$^3$. The normal adult platelet level is about 2.5×10$^5$/mm$^3$, with a normal range of about 2.1×10$^5$-2.9×10$^5$/mm$^3$. The normal adult red cell mass corresponds to about 4.6×10$^{12}$ red cells/L in females and about 5.2×10$^{12}$ red cells/L in males.

Thus, a human patient in need of treatment will typically have, or be subject to, a cell count below these values. As used herein, neutropenia means generally a circulating neutrophil count of less than about 1800/mm$^3$, generally a count of about 1500/mm$^3$ or less. Thrmobocytopenia generally means a circulating platelet count of less than about 1.6×10$^5$/mm$^3$, less than about 1.5×10$^5$/mm$^3$, less than about 1.3×10$^5$/mm$^3$ or less than about 1.0×10$^5$/mm$^3$. Anemia generally means a red cell mass corresponding to less than about 4.0×10$^{12}$ red cells/L in adult females and less than about 4.5×10$^{12}$ red cells/L in adult males (a hemoglobin level of less than about 12.0 g/dL in adult females and less than about 13.5 g/dL in adult males).

In some cases, the diagnosis of a deficiency may cover a cell count that falls outside these ranges, due, e.g., to individual variations in a subject's age, sex, race, animal strain or normal blood cell status for the individual. Such variations are identified by known means such as by identification of a change from the subject's normal status or by multiple cell measurements over time that reveal a deficiency. See, e.g., *Hematology—Basic Principles and Practice*, 2$^{nd}$ edition, R. Hoffman, E. J. Benz Jr. et al., editors, Churchill Livingstone, New York, 1995. Subjects with an identified or identifiable deficiency outside these standard ranges are included in the definition of a blood cell deficiency or a subject in need of treatment, as used herein.

Specific conditions that are amenable to prophylaxis or treatment by the invention methods include the acquired blood cell deficiencies. Exemplary deficiencies or groups of deficiencies are neonatal alloimmune TP, immune TP, immune thrombocytopenic purpura, thrombotic thrombocytopenic purpura, post-transfusion purpura, radiation associated TP, chemotherapy associated TP (e.g., NSAID treatments such as with indomethicin, ibuprofen, naproxen, phenylbutazone, piroxicam or zompirac, or β-lactam antibiotic treatments such as with ampicillin, carbenicillin, penicillin G, ticarcillin, or cephalosporin treatments such as with cefazolin, cefoxitin or cephalothin, anticoagulant treatments such as heparin, hirudin, lepirudin or aspirin, treatment with plasma expanders or psychotropic drugs), amegakaryocitic TP, chemotherapy associated TP, radiation associated TP, TP associated with solid organ allograft or xenograft rejection or immune suppression therapy in solid organ or other tissue transplants (e.g., liver, lung, kidney, heart, bone marrow, hematopoietic stem cell or endothelial cell transplant, implant or transfusion), cardiopulmonary bypass surgery or chemotherapy associated TP (e.g., an anticancer, antiviral, antibacterial, antifungal or antiparasite therapy), cardiovascular disease or therapy associated TP (e.g., congenital cyanotic heart disease, valvular heart disease, pulmonary embolism, pulmonary hypertension disorders or diltiazem, nifedipine, nitroglycerin or nitroprusside therapy), TP associated with chronic or acute renal failure or treatment for these conditions (e.g., dialysis), TP associated with infection such as a virus or bacterial infection, postinfectious NP, drug-induced NP, autoimmune NP, chronic idiopathic NP, basophilic leukopenia, eosinophilic leukopenia, monocytic leukopenia, neutrophilic leukopenia, cyclic NP, periodic NP, chemotherapy associated NP, radiation associated NP, chemotherapy associated NP, radiation associated NP, NP associated with solid organ allograft or xenograft rejection or immune suppression therapy in solid organ or other tissue transplants (e.g., liver, lung, kidney, heart, bone marrow, hematopoietic stem cell or endothelial cell transplant, implant or transfusion), chemotherapy associated leukopenia, radiation associated leukopenia, leukopenia associated with solid organ allograft or xenograft rejection or immune suppression therapy in solid organ or other tissue transplants (e.g., liver, lung, kidney, heart, bone marrow, hematopoietic stem cell or endothelial cell transplant, implant or transfusion), immune hemolytic anemias, anemia associated with chronic or acute renal failure or treatment for these conditions (e.g., dialysis), anemia associated with chemotherapy (e.g., isoniazid, prednisone) or anemia associated with radiation therapy.

Some of the blood cell deficiencies are associated with, or caused by, other therapeutic treatments, e.g., cancer chemotherapy, anti-pathogen chemotherapy, radiation therapy and chemotherapy for suppression of autoimmunity or immune suppression therapy for organ or tissue transplantation or implantation. The formula 1 compounds are thus useful to facilitate or speed up immune system recovery in autologous bone marrow transplant or stem cell transplant situations. In many cases it would be medically sound to continue the treatment associated with causing or exacerbating the blood cell deficiency. Thus, one would generally conduct the invention methods with subjects who are undergoing another therapy at the same time or near the same time, e.g., within a few days to within about 1-6 months. Such subjects typically will have an identified blood cell deficiency such as a NP or a TP, e.g., as disclosed herein. However, the formula 1 compounds are generally suitable for preventing the onset of such deficiencies, and they can thus be used prophylactically in these indications. The invention includes all of these embodiments.

In some embodiments, the invention method is accomplished using an effective amount of one or more growth factors or cytokines as a means to further enhance the effect of the formula 1 compounds for their intended uses or to modulate their effects. Suitable growth factors and cytokines are as described herein or in the cited references. For example, when one administers the formula 1 compound to enhance generation of platelets in humans or other subjects, or their precursor cells such as CFU-GEMM, BFU-Mk, CFU-Mk, immature megakaryocytes or mature postmitotic megakaryocytes, one can also administer one or more of G-CSF, GM-CSF, SCF, Steel factor ("SF"), leukemia inhibitory factor ("LIF"), interkeukin-1α, ("IL-1α"), IL-3, IL-6, IL-11, TPO, EPO, their isoforms, their derivatives (e.g., linked to a PEG or fusions such as PIXY321) or their homologs for other species. Similarly, administration of the formula 1 compound to enhance the generation or function of myelomonocytic cells such as neutrophils, basophils or monocytes in humans or other subjects, one can also administer one or more of G-CSF, GM-CSF, M-CSF, LIF, TPO, SF, interleukin-1 ("IL-1"), IL-2, IL-3, IL-4, interleukin-5 ("IL-5"), IL-6, IL-11, interleukin-12 ("IL-12"), interleukin-13 ("IL-13"), FLT3 ligand, their isoforms, homologs or derivatives (e.g., linked to a PEG or fusions such as PIXY321) or their homologs for other species. To enhance generation of red cells or their precursor cells such as CFU-GEMM, BFU-E or CFU-E in humans being treated with a formula 1 compound, one can co-administer one or more of G-CSF, GM-CSF, IL-1, IL-3, IL-6, TPO, EPO, transforming growth factor-[3], their isoforms, their derivatives (e.g., linked to a PEG or fusions such as PIXY321) or their homologs for other species. See, e.g., *Hematology—Basic Principles and Practice*, $3^{rd}$ edition, R. Hoffman, E. J. Benz Jr. et al., editors, Churchill Livingstone, New York, 2000 (see, e.g., Chapters 14-17 at pages 154-260). The co-administration of such factors in these methods is intended to enhance the efficacy of the formula 1 compound treatment, which is optionally measured by taking suitable blood or tissue, e.g., bone marrow, samples at one or more times before and after the compounds have been administered. Such co-administration will generally be compatible with a subject's condition and other therapeutic treatments. Co-administration of such factors can precede, be simultaneous with, or follow the times of administration of the formula 1 compound(s) to the subject. Dosages of such growth factors would generally be similar to those previously described, e.g., typically an initial course of treatment comprises administering about 1.0 to about 20 μg/kg/d for about 1-10 days, or as described in, e.g., *Hematology—Basic Principles and Practice*, $3^{rd}$ edition, R. Hoffman, E. J. Benz Jr. et al., editors, Churchill Livingstone, New York, 2000 (see, e.g., Chapter 51 at pages 939-979 and the references cited therein).

In cases where a subject's blood cell deficiency is caused by, or associated with another therapy, the invention contemplates that the other therapy will continue, if this is reasonable under the circumstances. The timing of other therapies can precede, be simultaneous with, or follow the times of administration of the formula 1 compound(s) to the subject. For example, chemotherapy for some malignancies is accompanied by myelosuppression or a deficiency in one or more blood cell types, e.g., TP or NP. Continued treatment would be called for in some cases, and then the invention methods would be employed to deliver to the subject an effective amount of a formula 1 compound. Thus, alkylating agents, antimicrotubule agents, antimetabolites, topoisomerase I or II inhibitors, or platinum compounds such as one or more of mechlorethamine, vincristine, vinblastine, bleomycin, doxorubicin, epirubicin, tamoxifen, cyclophosphamide, etoposide, methotrexate, ifosfamide, melphalan, chlorambucil, busulfan, carmustine, lomustine, streptozocin, dacarbazine, vinorelbine, paclitaxel (taxol), docetaxel, cytosine arabinoside, hydroxyurea, fludarabine, 2'-chlorodeoxyadenosine, 2'-deoxycoformycin, 6-thioguanine, 6-mercaptopurine, 5-azacytidine, gemcitabine, arabinofuranosylguanine, daunorubicin, mitoxantrone, amsacrine, topotecan, irinotecan, cisplatin, carboplatin, pilcamycin, procarbazine, aspariginase, aminoglutethimide, actinomycin D, azathioprine and gallium nitrate may be administered in conjunction with administration of any formula 1 compound(s) that is disclosed herein. Treatments with other therapeutic agents such as heparin or nucleoside analogs such as 3-thiacytosine, azidothymidine or dideoxycytosine, or other antimicrobials such as cephalosporin, quinine, quinidine, gold salts (e.g., aurothioglucose), a fluoroquinolone (e.g., ciprofloxacin), clarithromycin, fluconazole, fusidic acid, gentamycin, nalidixic acid, penicillins, pentamidine, rifampicin, sulfa antibiotics, suramin or vancomycin may result in a blood cell deficiency(s) and they can thus be combined with administration of a formula 1 compound to treat the deficiency, or to ameliorate a symptom thereof. Similarly, anti-inflammatory drugs (e.g., salicylates, entanercept (a dimeric fusion comprising a portion of the human TNF receptor linked to the Fc portion of human IgG1 containing the $C_H2$ and $C_H3$ domain and hinge regions of IgG1) or a COX-2 inhibitor such as celexicob (4-5[-(4-methylphenyl)-3-(trifluoromethyl)-1H-pyrazole-1-yl]benzenesulfonamide) or rofecoxib (4-[4-methylsulfonyl)phenyl]-3-phenyl-2(5H)-furanone) or an IL-1 receptor antagonist such as anakinra), cardiac drugs (e.g., digitoxin), β-blockers or antihypertensive drugs (e.g., oxprenolol or captopril), diuretics (e.g., spironolactone), benzodiazepines, (e.g., diazepam) or antidepressants (e.g., amitriptyline, doxepin). Any of these methods also optionally include co-administration of one or more of the growth factors described above, e.g., IL-3, G-CSF, GM-CSF or TPO.

In some embodiments, the formula 1 compounds that are used to enhance hematopoiesis or to treat associated conditions such as a TP or a NP disease or condition as disclosed herein, are characterized by having a lack of appreciable androgenicity. In these embodiments, the formula 1 compounds are characterized by having about 30% or less, about 20% or less, about 10% or less or about 5% or less of the androgenicity of an androgen such as testosterone, testosterone proprionate, dihydrotestosterone or dihydrotestosterone proprionate as measured in a suitable assay using suitable positive and/or negative controls. Suitable assays for androgenicity of various compounds have been described, e.g., J. R. Brooks, et al., *Prostate* 1991, 18:215-227, M. Gerrity et al., *Int. J. Androl.* 1981 4:494-504, S. S. Rao et al., *Indian J. Exp. Biol.* 1969 7:20-22, O. Sunami et al., *J. Toxicol. Sci.* 2000 25:403-415, G. H. Deckers et al., *J. Steroid Biochem. Mol. Biol.* 2000 74:83-92. The androgenicity of the formula 1 compounds are optionally determined as described or essentially as described in one or more of these assays or any other assay. Thus, one such embodiment comprises a method to enhance hematopoiesis or to treat TP or NP comprising administering to a subject in need thereof an effective amount of a formula 1 compound, or delivering to the subject's tissues an effective amount of a formula 1 compound, wherein the formula 1 compound has about 30% or less, about 20% or less, about 10% or less or about 5% or less of the androgenicity of an androgen such as testosterone, testosterone proprionate, dihydrotestosterone or dihydrotestosterone proprionate as measured in a suitable assay, e.g., as described in the citations above. In conducting such methods, the subjects, e.g., rodents, humans or primates, are optionally monitored for e.g., amelioration, prevention or a reduced severity of a disease, condition or symptom. Such monitoring can optionally include measuring one or more of cytokines (e.g., TNFα, IL-1β), WBCs, platelets, granulocytes, neutrophils, RBCs, NK cells, macrophages or other immune cell types, e.g., as described herein or in the cited references, in circulation at suitable times, e.g., at baseline before treatment is started and at various times after treatment with a formula 1 compound such as at about 2-45 days after treatment with a formula 1 compound has ended.

In related embodiments, the activity or numbers of neutrophils or monocytes is enhanced by co-administering the formula 1 compound with an neutrophil or monocyte stimulator, which is an non-protein agent or molecule that can stimulate the activity or number of neutrophils or monocytes in a subject. This aspect of the present invention encompasses any technique to enhance neutrophil or monocyte counts or activity. Means to accomplish this include administering an effective amount of a formula 1 compound and an effective amount of one or more of lithium, e.g., in the form of a salt such as lithium carbonate or chloride, deuterium oxide, levamisole (an antihelminthic agent), lactoferrin, thyroxine, tri-iodothyroxine, anthrax toxin, ascorbic acid, I-palmitoyl-lysophosphatidic acid, a calcium ionophore, e.g., A23187, cytochalasin B, sodium butyrate, piracetamine, micronized L-arginine, hydroxyurea and a bacterial lipopolysaccharide.

The neutrophil or monocyte stimulator can be administered at various time relative to administration of the formula 1 compound, including about 2-4 hours to about 1 or 2 weeks before administering the formula 1 compound and including administration that is essentially simultaneous with administering the formula 1 compound. Typically a neutrophil or monocyte stimulator will be dosed according to known methods, including daily dosing of about 0.01 mg/kg/day to about 25 mg/kg/day. For example, about 1 g/day of ascorbic acid (e.g., about 0.5 to about 1.5 g/day) can be administered to humans. When deuterium oxide is used as a neutrophil or monocyte stimulator, liquid aqueous formulations may comprise a formula 1 compound and deuterium oxide in place of some or all of the water. Naturally occurring water contains approximately 1 part of deuterium oxide per 6500 parts water. Thus, the water present in a formulation may comprise, e.g., at least 1 part $D_2O$ in 6000 parts $H_2O$, or at least 1 part in 100 parts, or about 50 parts or more per 100 parts of water. These aqueous formulations may comprise one or more additional excipients such as a cyclodextrin such as hydroxypropyl-β-cyclodextrin. Formulations comprising cyclodextrin and deuterium oxide, or comprising cyclodextrin, deuterium oxide and water, may thus comprise deuterium oxide in an amount greater than 1 part per 6500 parts water, such as 1 part deuterium oxide per 1-100 parts water, e.g., 50 parts deuterium oxide per 100 parts water. The amount of cyclodextrin can be in the range of from about 2 to about 85 grams per liter of water and/or deuterium oxide, such as in the range of from about 5 to about 70 grams per liter of water and/or deuterium oxide, one example of a suitable amount being in the range of about 45 grams per liter of water and/or deuterium oxide.

In conducting any of these methods, one can monitor the subject's clinical condition at any relevant time before, during or after administration of the formula 1 compounds, which treatments are optionally combined with any of the other agents or treatments disclosed herein, such as cytokines, interleukins or an agent or molecule that can stimulate the activity or number of neutrophils or monocytes. The subject's blood can be drawn on one, two or more occasions in advance of treatment to, e.g., obtain a baseline or initial level of white or red blood cells, to verify a presumptive diagnosis of a blood cell deficiency or to determine a blood parameter such as circulating myelomonocyte counts, circulating neutrophil counts, circulating platelet counts or the myeloperoxidase index. Then, during the course of treatment or thereafter the subject's blood can be drawn on one, two or more occasions to follow the subject's response.

Invention embodiments include methods that comprise administering to a subject in need thereof an effective amount of a formula 1 compound and an effective amount of at least one form of interferon, such as γ-Interferon or a growth factor or interleukin such as G-CSF or IL-6. Interferons can enhance the biological activity of the white cells that arise from increased hemopoiesis. This can be particularly useful when the subject's circulating blood cell deficiency is associated with, e.g., an infection or a chemotherapy that suppresses hemopoiesis. Administration of an growth factor or an interleukin such as IL-6 can facilitate hemopoiesis by stimulating quiescent stem cells or other progenitors that give rise to deficient cell types. Related embodiments replace growth factor or interferon administration partially or completely by increasing endogenous production in the subject using conventional methods, e.g., administering double stranded RNA to stimulate γ-IFN.

For cases where γ-IFN is administered, the administration is usually relatively constant, e.g., daily. This is because in patients in whom γ-IFN is not generated endogenously in significant amounts, there is a tendency for levels of γ-IFN to drop relatively quickly, i.e., within one day. In other words, in a patient in whom initially, γ-IFN levels are close to zero, it should be administered in an amount which is effective to bring γ-IFN levels to within normal levels, e.g., up to 10 nanograms per milliliter, and a similar amount of γ-IFN should be administered each day thereafter.

Suitable forms of γ-IFN and their biological properties and methods to obtain them have been described, see, e.g., U.S. Pat. Nos. 4,289,690, 4,314,935, 4,382,027, 4,376,821; 4,376, 822, 4,460,685, 4,604,284 and 5,145,677, European patent publication nos. EP 063,482 EP 088 540, and EP 087 686, N. Fujii et al., *J. Immunol.*, 1983 130:1683-86. A. Zlotnick et al., *J. Immunol.* 1983 131:794-80, M. deLey et al., *Eur. J. Immunol.* 1980 10:877-83, F. Dianzani et al., *Infection and Immunity*, 1980 29:561-63, G. H. Reem et al., *Infection and Immunity* 1982 37:216-21 (1982), R. Devos et al., *Nucleic Acids Research* 1982 10(8):2487-501, G. Simons et al., *Gene* 1984 28:55-64, P. W. Gray et al., *Nature*, 1982 295:503-508, D. Novick et al., *EMBO Journal*, 1983 2:1527-30.

An aspect of the invention is method to enhance hemopoiesis in a subject in need thereof comprising administering to the subject, or delivering to the subject's tissues, an effective amount of a compound of formula 1. In some embodiments, the formula 1 compound is not 5-androstene-3β-ol-17-one, 5-androstene-3β,17β-diol, 5-androstene-3β,7β,17β-triol or a derivative of any of these three compounds that can convert to these compounds by hydrolysis. Exemplary formula 1 compounds in this method include compounds wherein (1) one or two $R^{10}$ at the 1, 4, 6, 8, 9, 12 and 14 positions is not —H, wherein the one or two $R^{10}$ at the 1, 4, 6, 8, 9, 12 and 14 positions are independently selected from —F, —Cl, —Br, —I, —OH, =O, —CH$_3$, —C$_2$H$_5$, an ether optionally selected from —OCH$_3$ and —OC$_2$H$_5$, and an ester optionally selected from —O—C(O)—CH$_3$ and —O—C(O)—C$_2$H$_5$, and/or (2) $R^1$, $R^2$, $R^3$ and $R^4$ are independently selected from —H, —OH, =O, an ester and an ether. In these embodiments, the subject may have thrombocytopenia or neutropenia or the subject's circulating platelets, red cells, mature myelomonocytic cells, or their precursor cells, in circulation or in tissue may be detectably increased. In some cases the subject has renal failure. These methods may further comprise the steps of obtaining blood from the subject before administration of the formula 1 compound and measuring the subject's white or red cell counts and optionally, on one, two, three or more occasions, measuring the subject's circulating white cell or red cell counts after administration of the formula 1 compound, e.g., within about 12 weeks after an initial administration of a formula 1 compound or during or within about 12 weeks after a course of treatment. Such a treatment course may as described herein.

In any of the methods disclosed herein, a treatment may be interrupted briefly or for extended periods of time. The reason for such interruption can be any of a wide variety, e.g., patient non-compliance, apparent improvement in a subject's condition or by design. Any such interruption would not take a regimen outside the scope of the present invention. For example, a patient might miss a day or several days of administration. Similarly, the regimen might call for administration of one or more compounds for one or more day, and then non-administration of the one or more compounds for one or more day, and then resumption of the administration of the one or more compounds. Furthermore, a regimen according to the present invention can be altered in view of a patient's current condition, and can continue for any length of time, including the entire subject's lifetime.

For administration of γ-IFN, a volume of about 1 mL of a solid or liquid sublingual formulation that comprises about 100 micrograms of γ-IFN may be used. An exemplary liquid formulation comprises a saline solution containing 45 weight % β-hydroxypropylcyclodextrin. It would be expected that such a dosage would provide in the range of 30 to 40 micrograms of γ-IFN to the patient's blood. Such sublingual formulations would be held under the patient's tongue for a period of time sufficient to allow some or all of the γ-IFN to be delivered to the patient while held under the patient's tongue. Such administration has not been previously known in the art, in which conventionally, it has been thought that administration of γ-IFN must be by injection, e.g., subcutaneous injection. Subcutaneous injection of γ-IFN is associated with unwanted side effects, including fatigue, headache, night sweats, fever, local pain at the injection site, nausea, vomiting, diarrhea and others. The above-described sublingual γ-IFN formulations of the present invention is an aspect of the present invention, which can be of use in accordance with other aspects of the present invention as described herein. In general, however, a wide variety of routes of administration could be employed for γ-IFN in accordance with the present invention, including those disclosed in U.S. Pat. No. 5,145, 677.

Modulation of transcription factors, receptors and gene expression. In treating any of the diseases, conditions or symptoms disclosed herein, the formula 1 compounds can modulate, i.e., detectably enhance or increase or detectably inhibit or decrease, the expression or a biological activity(ies) of one or more transcription factors or receptors. This can lead to detectable modulation of target gene activity or expression as part of the treatment or amelioration of the disease, condition or symptom. Such modulation can arise from changes in the capacity of a transcription factor or receptor to bind to or form a complex with other natural ligands such as a target DNA sequence(s), another transcription factor(s), a transcription cofactor, a receptor such as a steroid receptor or cell membrane receptor (e.g., a lipid, peptide, protein or glycoprotein receptor such as an interleukin receptor or a growth factor receptor), a receptor cofactor or an enzyme such as a polymerase, kinase, phosphatase or transferase. The effects of formula 1 compounds on these biomolecules can be exerted in immune cells or in non-immune tissue, e.g., cells or tissue adjacent to diseased tissue such as infected or malignant cells. The formula 1 compounds may directly or indirectly modulate the capacity of any of these molecules to transduce signals that are part of normal signal trandsuction processes.

In many of the clinical conditions described herein, e.g., in cancers, infections, acute inflammation, chronic inflammation or autoimmunity, the formula 1 compounds can modulate, e.g., detectably decrease or increase, a biological activity(ies), protein or molecule level or RNA level of 1, 2, 3, 4, 5, 6 or more biomolecules that are involved in establishment, maintenance or progression of a disease, condition or symptom. Such biomolecules include 1, 2, 3, 4, 5, 6 or more of AP-1, a cyclooxygenase such as cyclooxygenase-1 (COX-1) or cyclooxygenase-2 (COX-2), TNFα, TNFα receptor 1, TNFα receptor 2, TNF receptor-associated factor, TNFβ, TNFβ receptor, MIP-1α, monocyte chemoattractant-1 (MCP-1), interferon gamma (IFNγ or γIFN), IL-1α, IL-1β, IL-1α receptor, IL-1β receptor, IL-2, IL-3, IL-4, IL-4 receptor (IL-4R), IL-5, IL-6, IL-6 receptor (IL-6R), IL-8, IL-8 receptor (IL-8R), IL-10, IL-10 receptor (IL-10R), IL-12, an IL-12 receptor, (e.g., IL-12Rβ2), IL-13, IL-15, IL-17, IL-18, nuclear factor kappa B (NFκB), AP-1, c-maf, v-maf, mafB, NrI, mafK, mafG, the maf family protein p18, reactive oxygen species, e.g., hydrogen peroxide or superoxide ion (collectively ROS), a 17β-hydroxysteroid dehydrogenase (17β-HSD) or an 11β-hydroxysteroid dehydrogenase (11β-HSD), e.g., 11β-HSD type 1, 11β-HSD type 2, 17β-HSD type 1, 17β-HSD type 2 or 17β-HSD type 5, a steroid aromatase, e.g., cytochrome P450 aromatase, steroid 5α-reductase, serum or blood cortisol cytosolic phospholipase A2 (cPLA2), calcium-independent phospholipase A2 (iPLA2), a prostaglandin, e.g., prostaglandin E2 (PGE2) or prostaglandin D2 (PGD2), a leukotriene, e.g., leukotriene B4, inducible nitric oxide synthetase (iNOS), nitric oxide (NO), GM-CSF, RANTES (regulated on activation, normal T cells expressed and secreted), eotaxin, GATA-3, CCR1, CCR3, CCR4, CCR5, CXCR4, in, e.g., a subject's cell(s) or tissue(s) or in enzyme, tissue or cell-based assays. In these subjects, the levels of other biomolecules, their RNAs or the level of their activity can be detectably modulated include IFNα, INFα receptor, PPARα, PPARγ, PPARδ or a transcription factor such as T-bet is detectably increased. Other biomolecules or their polymorphs or homologs that the formula 1 compounds directly or indirectly modulate include one or more of, e.g., Janus kinase 1 (JAK1), Janus kinase 2 (JAK2), Janus kinase 3 (JAK3), signal transducer and activator of transcription 1 (STAT1), signal transducer and activator of transcription 2 (STAT2) and signal transducer and activator of transcription 3 (STAT3). The formula 1 compounds can modulate the other biologically active analogs of any these enzymes, chemokines, cytokines, their receptors or ligands, including their polymorphs or homologs. In some cells or tissues, one or more of these biomolecules may be detectably increased, while in other cells or tissues, the same biomolecule may be detectably decreased. Thus, the biomolecules that the formula 1 compounds can modulate, e.g., detectably increase or decrease, include the intracellular or extracellular level or biological activity of one or more enzyme, cytokine, cytokine receptor, chemokine and/or chemokine receptor.

Additional exemplary mammalian or human and other biomolecules, e.g., transcription factors or receptors, including orphan nuclear receptors, their homologs, isoforms and co-factors (e.g., co-repressors, co-activators, transcription factors, gene promoter regions or sequences) and related molecules that the formula 1 compounds can directly or indirectly from complexes with, or modulate (detectably increase or decrease) the synthesis, level or one or more biological activities of, include steroidogenic factor-1 (SF-1), steroidogenic acute regulatory protein (StAR), chicken ovalbumin upstream promoter-transcription factor (COUP-TFI) and its mammalian homologs, silencing mediator for retinoid and thyroid hormone receptor (SMRT) and its mammalian homologs, sterol regulatory element binding protein (SREBP) 1a (SREBP-1a), SREBP-1c, SREPB-2, NF-E3, FKHR-L1, COUP-TFII and its mammalian homologs, IκB, IκBα, AML-3, PEBP2αA1, Osf2, Cbfa1, RUNX2, activating transcription factor 2 (ATF2), c-Jun, c-Fos, a mitogen activated kinase (MAP) such as p38 or JNK or an isoform thereof, a mitogen activated kinase kinase (MKK) or an isoform thereof, steroid receptor coactivator-1 family (SRC-1, SRC-1/serum response factor), SRC-2, SRC-3, SET, nerve growth factor inducible protein B, StF-IT, NFAT, NFAT interacting protein 45 (NIP45), IkB, an IkB kinase, NFATp, NFAT4, an AP-1 family protein, p300, CREB, CREB-binding protein (CPB), p300/CBP, p300/CPB-associated factor, SWI/SNF and their human and other homologs, BRG-1, OCT-1/OAF, AP-1, AF-2, Ets, androgen receptor associated protein 54 (ARA54), androgen receptor associated protein 55 (ARA55), androgen receptor associated protein 70 (ARA70), androgen receptor-interacting protein 3 (ARIP3), ARIP3/PIASx α complex, PIASx α, Miz1, Miz1/PIASx β complex, PIASx β, PIAS1, PIAS3, GBP, GBP/PIAS1 complex, RAC3/ACTR complex, SRC-1α, receptor interacting protein-140 (RIP-140), transcription factor activator protein-1, activation function-2, glucocorticoid receptor-interacting protein-1 (GRIP-1), receptor interacting protein-160 (RIP-160), suppressor of gal4D lesions (SUG-1), transcription intermediary factor-1 (TIF-1), transcription intermediary factor-2 (TIF-2), SMRT, N—CoR, N—CoA-1, p/CIP, p65 (ReIA), the 120 KD rel-related transcription factor, heat shock proteins (HSP) such as HSP90, HSP70 and HSP72, heat shock factor-1, Vpr encoded by the human immunodeficiency virus and its isoforms and homologs thereof, testicular orphan receptor TR2, thyroid hormone α1 (TR α1), retinoid X receptor α, TR α1/RXR α heterodimer, direct repeat-4 thyroid hormone response element (DR4-TRE), an estrogen receptor (ER) such as ERα or ERβ, estrogen receptor related receptor α (ERRα), estrogen receptor related receptor β (ERRβ), estrogen receptor related receptor γ (ERRγ), steroid xenobiotic receptor (SXR), hepatocyte nuclear factor 4 (HNF-4), hepatocyte nuclear factor 3 (HNF-3), liver X receptors (LXRs), LXRα, LXRβ, estrogen receptor α (ERα), constitutive androstane receptor-β (CAR-β), RXR/CAR-β heterodimer, short heterodimer partner (SHP; NROB2), SHP/ERα heterodimer, estrogen receptor β, SHP/ERβ heterodimer, testicular orphan receptor TR4, TR2/TR4 heterodimer, pregnane X receptor (PXR) and isoforms, cytochrome P-450 monooxygenase 3A4, including its gene promoter region and isoforms thereof, HNF-4/cytochrome P-450 monooxygenase 3A4 gene promoter region and isoforms complex, HIV-1 long terminal repeat (LTR), HIV-2 LTR, TR2/HIV-1 LTR complex, TR4/HIV-1 LTR complex, TR4/HIV-1 LTR complex, TR α1/TR4/HIV-1 LTR complex, TR2 isoforms (TR2-5, TR7, TR9, TR11), DAX-1, DAX-1/steroidogenic acute regulatory protein gene promoter region, RevErb, Rev-erbA α, Rev-erb β, steroid receptor coactivator amplified in breast cancer (AIB 1), p300/CREB binding protein-interacting protein (p/CIP), thyroid hormone receptor (TR, T3R), thyroid hormone response elements (T3REs), retinoblastoma protien (Rb), tumor suppressor factor p53, transcription factor E2F, mammalian acute phase response factor (APRF), constitutive androstane receptor (CAR), *Xenopus* xSRC-3 and mammalian (human) homologs, TAK1, TAK1/peroxisome proliferator-activated receptor α (PPARα) complex, PPARα/RXRα complex, peroxisome proliferator-activated receptor β (PPARβ), peroxisome proliferator-activated receptor γ (PPARγ), peroxisome proliferator-activated receptor δ (PPARδ), farnesoid X receptor, retina X receptor, TAK-1/RIP-140 complex, retinoic acid receptor (RAR), RARβ, TR4/RXRE complex, SF-1/steroid hydroxylase gene promoter region, SF-1/oxytocin, including its gene promoter region, bile acid receptor (FXR), nuclear receptor corepressor (NcoR), liver receptor homologous protein-1 (LRH-1; NR5A2), SF-1/ACTH receptor gene promoter region, rat Ear-2 and mammalian homologs, human TR3 orphan receptor (TR3), RLD-1, OR-1, androgen receptor, glucocorticoid receptor, estrogen receptor, progesterone receptor, mineralcorticoid receptor, aldosterone receptor, E6-associated protein (E6-AP), OR1, OR1/RXRα complex, TIF-1, CBP/P300 complex, TRIP1/SUG-1 complex, RIP-140, steroid receptor coactivator 1 (SRC1), SRC1α/P160 complex and TIF-2/GRIP-1 complex, RAR/N—CoR/RIP13 complex, RAR/SMRT/TRAC-2 complex and protein X of hepatitis B virus. The homologs, orthologs and isoforms of these transcription factors, receptors and other molecules are included among the molecules that the formula 1 compounds can modulate the synthesis or one or more biological activities of. Such factors are biologically active or function in one or more of a number of cell types such as T cells, B cells, macrophages, dendritic cells, platelets, monocytes, neutrophils, neurons, epithelial cells, endothelial cells, cartilage cells, osteoblasts, osteoclasts, splenocytes, thymocytes and GALT associated cells. Methods to identify these molecules and their biological activities have been described, e.g., U.S. Pat. Nos. 6,248,781, 6,242,253, 6,180,681, 6,174,676, 6,090,561, 6,090,542, 6,074,850, 6,063,583, 6,051,373, 6,024,940, 5,989,810, 5,958,671, 5,925,657, 5,958,671, 5,844,082, 5,837,840, 5,770,581, 5,756,673, and PCT publication Nos. WO 00/24245, WO 0073453 and WO 97/39721.

In one aspect, the compounds are used to treat, prevent or to ameliorate conditions or symptoms that are associated with unwanted or expression or activity of one or more of these molecules in conditions such as, e.g., acute inflammation, chronic inflammation or their symptoms, acute allergy, chronic allergy or their symptoms, e.g., allergic rhinitis or acute or chronic asthma, psoriatic arthritis, osteoporosis, osteoarthritis, rheumatoid arthritis, neurological dysfunction or their symptoms, e.g., dementias such as Alzheimer's Disease, Parkinson's Disease, or memory loss conditions, in osteoporosis or in cancer such as breast cancer. The compounds can prevent NFκB from translocating from the cytoplasm into the nucleus and thus can increase the ratio of cytoplasmic NFκB to nuclear NFκB. The formula 1 compounds may inhibit activation of NFκB-mediated transcription while NFκB is bound to target DNA sequences in the nucleus. Alternatively, the formula 1 compounds can activate or enhance the expression of or one or more activity of a transcription factor such as T-bet in, e.g., a subject's cell(s) or tissue(s) or in enzyme or cell-based assays. In this aspect the compounds are used to treat, prevent or to ameliorate conditions or symptoms that are associated with deficient expression or activity of T-bet in conditions such as immune dysfunction in an immunosuppression condition, aging, an infection, a cancer or precancer as described herein or in the cited references.

Thus, in some embodiments, the level or a biological activity of 4, 5, 6, 7, 8, 9, 10, 11, 12, 13, 14, 15 or more of COX-2, IL-1β, TNFα, TNFα receptor 1, TNFα receptor 2, TNF receptor-associated factor, MIP-1α, MCP-1, IFNγ, IL-4, IL-4R, IL-6, IL-6R, IL-8, IL-8R, IL-10, IL-10R, NFκB, IkBα, AP-1, GATA-3, 11β-HSD1, cPLA2, iPLA2, cortisol, ROS, PGE2, PGD2, leukotriene A4, leukotriene B4, leukotriene C4, iNOS or GM-CSF are optionally measured and they are generally detectably reduced, e.g., RNA or protein levels are reduced by about 10-95% or about 20-95% or more compared to suitable untreated controls. In these embodiments, the level or a biological activity of 4, 5, 6 or more of IFNα, INFα receptor, IL-12, an IL-12 receptor, (e.g., IL-12Rβ2), PPARα, PPARγ, and T-bet are optionally measured and they are generally detectably increased. In a chronic infection condition, e.g., HIV in humans, autoimmunity, a chronic fungal or parasite infection or in a precancer or cancer condition, e.g., benign prostatic hyperplasia, the progression of the condition may be slowed over a period of 1, 2, 3, 4, 5 or more years. In these embodiments, the subject's condition becomes more manageable with a reduced incidence or severity of side effects, e.g., a detectable halt, slowing, reversal or decreased incidence of wasting, dementia, CD4 cell count decreases or viral load increases, which tend to occur over time in HIV infected humans or a halt, slowing or reversal of pathogen or precancer or cancer cell replication. The detectable halt, slowing, reversal of the condition or decreased incidence of side effects can be observed as a decrease of about 10% or more, e.g., about a 20%, 30%, 40%, 50%, 60%, 70%, 80%, 90%, 95% or more decline.

These effects are typically observed after administration of an effective amount of a formula 1 compound using, e.g., a method or dose essentially as disclosed herein. The simultaneous reduction of multiple biomolecules provides a method to modulate immune responses by modulating multiple pathways that lead to a common condition such as inflammation. This provides a method to treat or ameliorate, e.g., acute or chronic inflammation, a cancer, an infection or a symptom associated therewith, or to slow the progression of or reduce the severity of these conditions or their symptoms.

Previously described methods can be used to measure the amount, activity or cellular location of various biomolecules such as cytokines or transcription factors. See, e.g., U.S. Pat. Nos. 6,107,034, 5,925,657, 5,658,744, 4,016,043 and 3,850,752, S. Szabo et al., *Cell* 2000 100:655-669, Y. Nakamura et al., *J. Allergy Clin. Immunol.* 1999 103(2 pt. 1):215-222., R. V. Hoch et al., *Int. J. Cancer* 1999 84:122-128. These methods can be used to measure the effects of the formula 1 compounds on transcription factors or receptors in cells or tissues that have been exposed to the compounds.

Without wishing to be bound to any theory, the formula 1 compounds may modulate multiple biomolecules in a microenvironment sensitive manner or context. The effects of the compounds can provide a decrease in a particular molecule such as IFNγ and a decrease in inflammation associated with elevated IFNγ levels or activity without eliminating beneficial effects of the molecule. This effect arises from decreasing the level or activity of a biomolecule such as IFNγ in cells that are dysregulated, while allowing normal immune cells to produce sufficient amounts of the same molecule to perform normal immune functions. In locations where the biomolecule is needed for activity, e.g., in lymph nodes or spleen cells, sufficient amounts of the modulated molecule are present to elicit a desired response, while the level of the molecule in cells in circulation decreases. The compounds can increase IL-13, IL-15, IL-17 or IL-18 in conditions where a subject has a deficient Th1 immune response, e.g., in infection or cancer. Conversely, the compounds can decrease IL-13, IL-15 or IL-18 in conditions such as allergy or autoimmune conditions, e.g., multiple sclerosis, where an excess Th1 immune status may prevail.

In general, the formula 1 compounds will detectably decrease the synthesis or one or more biological activity of one or more of these molecules (or other transcription factors or receptors disclosed herein) when such synthesis or activities is associated with the establishment, maintenance, progression or enhanced severity of a clinical condition or symptom disclosed herein. Conversely, the formula 1 compounds will generally detectably increase the synthesis or one or more biological activities of one or more of these molecules (or other transcription factors or receptors disclosed herein) when such synthesis or activity is associated with the treatment, prevention, cure or amelioration of a clinical condition or symptom disclosed herein.

These decreases or increases compared to suitable controls can be relatively small, including changes near the lower limits of detectability for such molecules using known or new assays, e.g., a decrease or increase in the synthesis or biological activity of at least about 2%, about 5%, about 10% or about 20%. Such changes can be modest or relatively large, e.g., at least about a 50% change, at least about a 90% change, or at least about a 200% change, up to about a 5-fold, about a 10-fold, about a 100-fold or greater decrease or increase in the synthesis or biological activity of the affected molecule(s) compared to suitable controls. These changes are typically measured relative to controls that lack a formula 1 compound or that use known agonists or antagonists of one or more relevant molecules. Assays can be based on measuring decreases or increases in, e.g., one or more of protein levels, RNA or mRNA levels, a ligand binding activity, transcription of a target gene(s) and the like. Suitable assay protocols include any suitable polymerase chain reaction assay to measure an RNA or mRNA, any suitable blotting protocol for nucleic acid or for protein such as a Northern or Western blot method or any transcription assay, including DNA footprinting or a gene expression or gene function assay. Typically the formula 1 compounds will effect detectable changes in the synthesis or one or more biological activities in a concentration range of about $0.5 \times 10^{-9}$ M to about $3 \times 10^{-5}$ M. Exemplary compositions that comprise a formula 1 compound for use in, e.g., in vivo animal assays, in vitro cell or tissue culture assays or in cell free assays, will comprise one or more suitable solvents or vehicles including DMSO, ethanol, water and tissue culture medium, which optionally contains calf, horse or goat serum or another serum.

One or more of these transcription factors, receptors or complexes can be a component in methods when, e.g., they are used with a formula 1 compound in cell-free assays or in tissue culture assays. Formation of these complexes in cells or analysis of the effects of formula 1 compounds on one or more of their biological activities is facilitated by inserting into the cells a DNA construct(s) that expresses one or more of these proteins, e.g., mammalian or yeast cells containing a stable DNA construct or a construct used for transient transfection assays. Methods to perform assays or to induce biological responses in vitro or in vivo using the formula 1 compounds as agonists, antagonists or as reference standards are essentially as described, see, e.g., U.S. Pat. Nos. 5,080, 139, 5,696,133, 5,932,431, 5,932,555, 5,935,968, 5,945,279, 5,945,404, 5,945,410, 5,945,412, 5,945,448, 5,952,319, 5,952,371, 5,955,632, 5,958,710, 5,958,892 and 5,962,443; International Publication Numbers WO 96/19458, WO 99/41257 and WO 99/45930. The complexes or assay systems, that comprise a formula 1 compound and one or more of these molecules are embodiments of the invention, as are the use of these compositions when employed in the practice of any of the assay methods or in any of the clinical treatment methods disclosed herein or in the cited references.

In exemplary applications, invention embodiments include a method comprising contacting a formula 1 compound(s) with a cell(s), whereby the formula 1 compound(s) forms a complex with a steroid hormone receptor or results in the modulation of a biological activity of the steroid hormone receptor or a gene that it regulates. The steroid hormone receptor may be an orphan nuclear hormone receptor or a characterized receptor such as the glucocorticoid receptor, estrogen receptor or the androgen receptor that displays a moderate or high binding affinity for the formula 1 compound(s). In some embodiments, the steroid receptor is a known steroid receptor. Biological effects from interaction of a formula 1 compound and a receptor can lead to interference with the replication or development of a pathogen or the cell(s) itself. For example, expression of HIV transcripts in HIV-infected cells may be altered. The receptor-formula 1 compound complex may directly interfere with LTR-dependent transcription of HIV genes, leading to reduced viral replication. Alternatively, such effects can include the decreased synthesis or biological activity of a protein or gene product that is associated with the establishment, maintenance or progression of a disease condition described herein or in the cited references.

Invention embodiments include compositions comprising a partially purified or a purified complex comprising a formula 1 compound and a steroid receptor. Such a steroid receptor(s) may be an orphan steroid receptor or a characterized steroid receptor, where either type binds the formula 1 compound with a moderate or high binding affinity, e.g., less than about $0.5$-$10 \times 10^{-6}$ M, usually less than about $1 \times 10^{-7}$ M, or, for higher affinity interactions, less than about $0.01$-$10 \times 10^{-9}$ M. The formula 1 compound(s) may also enhance immune responses such that both immune responses and altered intracellular conditions simultaneously exist to ameliorate one or more of the pathological conditions described herein.

The formula 1 compounds may be used to identify receptors that modulate biological responses, e.g., receptors that participate in effecting enhanced Th1 cytokine synthesis. Invention embodiments include a method, "Method 1", which permits the determination of one or more effects of a test compound on a steroid receptor in various biological systems. Generally, the test compound is a formula 1 compound. Such systems include cells containing a DNA construct that constitutively or inducibly expresses a steroid receptor(s) of interest, e.g., SXR, CARβ, RXR, PXR, PPARα, PPARβ, PPARγ or mixtures or dimers thereof, e.g., SXR/RXR. In other biological systems, the steroid receptor can be under the transcriptional control of a regulatable promoter. Alternatively, the expression another gene such as a steroid-inducible gene, e.g., a steroid-inducible cytochrome P-450. For this method, a source of steroid receptors is generally combined with a means of monitoring them, e.g., by measuring the transcription of a gene regulated by the receptor. Cells that comprise the steroid receptor and optional monitoring means are sometimes referred to herein as the "biological system." Sources of steroid receptors include cell lines and cell populations that normally express the steroid receptor of interest and extracts obtained from such cells. Another source for a useful biological system for purposes of this method is tissues from experimental animals that express the receptor.

In one aspect, method 1 allows one to determine one or more effects of a formula 1 compound on a steroid receptor using a method that comprises (a) providing a biological system, e.g., a cell extract, cells or tissue, comprising cells having a plurality of steroid receptors that comprise monomers, homodimers or heterodimers that comprise a steroid receptor, e.g., SXR, CAR-β, RXR, PPARα, PPARβ, PPARγ, PXR or dimers that comprise one or more of these; (b) activating or inhibiting the plurality of monomers, homodimers or heterodimers that comprise the steroid receptor by contacting the cells with a steroid receptor (e.g., SXR, CAR-β, RXR, PPARα, PPARβ, PPARγ or PXR) agonist or antagonist; (c) removing substantially all of the steroid receptor agonist or antagonist from the cells; (d) determining an activity of the plurality of monomers, homodimers or heterodimers that comprise the steroid receptor while in an activated state in the absence of agonist or antagonist; (e) exposing the cells to the test compound; (f) determining at least one effect of the test compound on the activity of the plurality of monomers, homodimers or heterodimers that comprise one or more of the steroid receptors while they remain substantially free of agonist or antagonist; and (g) optionally classifying the test compound as an agonist or an antagonist of the steroid receptor, or a neutral compound having little or no detectable effect.

The effects that method 1 can measure includes determining or measuring an effect on a gene whose expression is affected by the steroid receptor. The gene could be a gene associated with a pathological condition such as an infectious agent, an immune disorder such as an inflammation condition or a hyperproliferation condition disclosed herein or in the cited references.

Thus, another aspect of method 1, "method 1A", is determining if a compound not previously known to be a modulator of protein biosynthesis can transcriptionally modulate the expression of a gene that encodes a protein associated with the maintenance or treatment of one or more symptoms of a pathological condition (the "target gene" or "target protein"). This method comprises: (a) contacting an assay system that comprises eucaryotic cells or a suitable lysate with a formula 1 compound, wherein the eucaryotic cells or suitable lysate comprises one, two or a plurality of steroid receptor proteins and optionally comprises one or more coactivator proteins and a DNA construct comprising operatively linked sequences that comprise (i) a modulatable transcriptional regulatory sequence(s) of the target gene, (ii) a promoter of the gene, and (iii) either the target gene's nucleic acid coding protein region or a coding region for a suitable reporter gene, either of which is capable of expressing the DNA construct's coding region, which is coupled to, and under the control of, the modulatable transcriptional regulatory sequence(s) and the promoter, under conditions such that the formula 1 compound, if capable of acting as a transcriptional modulator of the gene encoding the protein of interest, causes a measurable or detectable signal (e.g., an increased or decreased nucleic or protein expression level compared to a suitable control); (b) quantitatively or qualitatively determining the amount of the signal so produced; and (c) optionally comparing the amount of the signal so determined with the amount of signal detected in the presence of the formula 1 compound with a suitable control, e.g. in the absence of any compound being tested or upon contacting the sample with a known activator or inhibitor of expression of the target gene so as to identify the chemical as one that causes a change in the detectable signal produced by the polypeptide. The method thus permits one to determine if the formula 1 compound specifically transcriptionally modulates expression of the target gene or protein. Suitable steroid receptors and their coactivators are as described herein, e.g., androgen receptor, estrogen receptor, glucocorticoid receptor, mineralcorticoid receptor, aldosterone receptor, PPARα, PPARβ, PPARγ, PPARδ, RXR or CARβ. Information regarding these receptors has been described, see, e.g., relevant U.S. patents cited herein and PCT publication WO 0025800 and WO 0031286.

In method 1A the assay system may comprise a transformed cell line, primary cells or untransformed cells or a suitable lysate or extract of any of these. Exemplary cell lines include ones derived from human or other mammalian tumors or precancers. The source of such cells may be human or animal, e.g., a mammal such as a primate or a rodent. In some embodiments, the assay system comprises a rodent such as a mouse, transgenic mouse or other transgenic animal (see e.g., PCT publication WO 000602). Measurement of the formula 1 compound's effect on the assay system includes detecting increased or decreased expression of nucleic acid or polypeptide by the target gene in response to the formula 1 compound's presence. Exemplary conditions include conducting the method under conditions suitable for maintaining the cells in tissue culture or under conditions suitable for enzyme assays using cell extracts or lysates, e.g., tissue culture medium or a buffered aqueous solution that is, e.g., a nearly isotonic solution at about 32-38° C., a pH of about 6 to about 8, a formula 1 compound concentration of about $1 \times 10^{-11}$ M to about $1 \times 10^{-3}$ M (including any concentration in any single unit increment of, e.g., $1 \times 10^{-11}$ M, e.g., $1 \times 10^{-10}$ M, $1 \times 10^{-9}$ M, $1 \times 10^{-8}$ M, $1 \times 10^{-7}$ M, $1 \times 10^{-6}$ M, $1 \times 10^{-5}$ M or $1 \times 10^{-4}$ M) and contacting the formula 1 compound and the assay system for about 20 minutes to about 72 hours. Detection of a change in expression of the target gene or the reporter gene includes, e.g., detecting (1) changes in gene nucleic acid levels by qualitative or quantitative PCR methods and (2) changes in gene protein levels by enzyme or antibody-based assays such as measuring enzyme activity using a suitable substrate or measuring protein levels, e.g., by ELISA or western blotting.

In conducting method 1A, one typically contacts a sample that contains a predefined number of identical or essentially identical eucaryotic cells, e.g. about $5 \times 10^3$ to about $5 \times 10^6$ cells, with a predetermined concentration of a compound of formula 1. The eucaryotic cells comprise a DNA construct that is made using conventional molecular biology methods and protocols. The assay system is maintained under conditions such that the formula 1 compound, if capable of acting as a transcriptional modulator of the gene encoding the protein of interest, causes a measurable or detectable signal to be produced by the polypeptide expressed by the reporter gene. Once sufficient time for generation of a detectable response or signal has passed, one can determine the amount of the signal produced. Typically the response or signal is measured quantitatively, but a qualitative measurement can be useful for rapid screening purposes.

For method 1A, one can also optionally compare the detectable signal with the amount of produced signal that (i) one detects in the absence of any formula 1 compound or (ii) when contacting the sample with other chemicals, which identifies the formula 1 compound as a chemical that causes a change in the detectable signal the polypeptide produces. One then typically determines whether the formula 1 compound specifically transcriptionally modulates expression of the gene associated with the maintenance or treatment of one or more symptoms of the pathological condition.

Other aspects of the method 1 and 1A include a screening method comprising separately contacting each of a plurality of identical, essentially identical or different samples, each sample containing a predefined number of such cells with a with a predetermined concentration of each different formula 1 compound to be tested, e.g., wherein the plurality of samples comprises more than about $1 \times 10^3$ or more than about $1 \times 10^4$ samples or about $0.5 - 5 \times 10^5$ samples. In other aspects one determines the amount of RNA by quantitative polymerase chain reaction. In any of methods 1 or 1A, a formula 1 compound such as any one of those described or named herein may be utilized.

Aspects of the invention include another method, "method 2", which centers on identifying a gene whose expression is modulated by a candidate binding partner for infectious disease therapeutic agents. Typically the binding partner is a steroid receptor, e.g., a monomer, homodimer or heterodimer that comprises SXR, CAR-β, PXR, PPARα, PPARβ, PPARγ, PPARδ or RXR or a homolog or isoform thereof. The steroid receptor is typically present as a complex that comprises, e.g., the formula 1 compound and the regulated gene's DNARS, which the steroid receptor, or a complex that comprises the steroid receptor, recognizes and specifically binds to. Such complexes can also comprise a transcription factor that binds to the steroid receptor or to nucleic acid sequences adjacent to or near the DNARS. Exemplary transcription factors that may be present include one or more of ARA54, ARA55, ARA70, SRC-1, NF-κB, NFAT, AP1, Ets, p300, CBP, p300/CBP, p300/CPB-associated factor, SWI/SNF and human homologs of SWI/SNF, CBP, SF-1, RIP140, GRIP1 and Vpr. In general, one provides a first and a second group of cells in vitro or in vivo and contacts the first group of cells with the infectious disease therapeutic agent, but does not contact the second group of cells in vitro or in vivo with the infectious disease therapeutic agent. Recovering RNA from the cells, or generating cDNA derived from the RNA, is accomplished by conventional protocols. Analysis of the RNA, or cDNA derived from the RNA, from the first and the second group of cells identifies differences between them, which one can use to identify a gene whose regulation is modulated by the candidate binding partner for the infectious disease therapeutic agent or any DNARS associated with that gene.

An aspect of method 2 is determining the capacity of a formula 1 compound to modulate, or participate in the modulation of, the transcription of a gene associated with the maintenance or treatment of one or more symptoms of a pathological condition. It is expected that in general, the formula 1 compounds will cause an increase in the transcription of such genes. The pathological condition is typically one associated with an infectious agent, e.g., virus, parasite or bacterium, but can also include an immune condition, e.g., an autoimmune condition or an immune deficiency. The pathological condition may also be an insufficient immune response to an infection or an insufficient response to a hyperproliferation condition or malignancy. Other pathological conditions that one can apply the method to are inflammation conditions.

In some aspects, the formula 1 compounds used in method 2 will be labeled. Such compounds are prepared by conventional methods using standard labels, such as radiolabels, fluorescent labels or other labels as described herein and in the cited references.

An embodiment of method 2 involves analyzing the RNA, or cDNA derived from it, by subtraction hybridization. In this embodiment, the RNA or cDNA obtained from the first and second groups of cells is hybridized and the resulting duplexes are removed. This allows recovery of nucleic acids that encode genes whose transcription is modulated by the candidate binding partner, which is usually a steroid receptor. One can use conventional methods to amplify and obtain nucleic acid and protein sequence information from the nucleic acids recovered by this method. The nucleic acid sequences that are transcriptionally induced or repressed by the formula 1 compound are candidate binding partners.

A transcriptionally induced gene(s) will be enriched in the group 1 cells treated with the formula 1 compound, while any repressed gene(s) will be depleted or absent. In these embodiments, the RNA recovered after removal of duplexes is typically amplified by standard RT-PCR or PCR protocols. These protocols typically use specific sets of random primer pairs, followed by analysis of the amplified nucleic acids by gel electrophoresis. Nucleic acids that are induced by the formula 1 compound will appear as a band(s), usually duplex DNA, that is not present in the control or second set of cells. Nucleic acids that are transcriptionally repressed by the formula 1 compound's binding partner will be depleted or absent in the first group of cells. Once such gene candidates are identified, they can be cloned and expressed and the capacity of the DNARS associated with the gene to form a complex that comprises a candidate binding partner and an optionally labeled formula 1 compound is analyzed by conventional methods, e.g., equilibrium dialysis, affinity chromatography using, e.g., the DNARS immobilized on a column, or coprecipitation of complexes that comprise an optionally labeled DNARS and candidate binding partner using anti-binding partner antibodies. Nucleic acid sequence analysis is usually used to identify regions adjacent to the coding regions of the regulated gene to identify any DNARS associated with the gene. The identity of a DNARS can be established by the binding to the DNARS of complexes that comprise a candidate binding partner, e.g., a steroid receptor, and optionally also comprise a formula 1 compound. The location and identity of the DNARS can be accomplished by DNA footprinting or other methods for detecting binding interactions. The DNARS, the receptor or the formula 1 compound can be labeled in these variations of method 2.

In general, the second group of cells will be identical or essentially identical to the first group of cells. In embodiments (for both methods 1 and 2) where the cells are "essentially identical", the first or the second group of cells may differ from each other by the presence or absence of a DNA construct(s) that expresses (i) a steroid receptor and/or (ii) an easily detected protein, e.g., a β-galactosidase, a peroxidase, a phosphatase, a luciferase or a chloramphenicol acetyltransferase, whose transcriptional regulation is usually modulated by a steroid receptor. In these embodiments, the difference between the first and the second group of cells is used to facilitate the analysis of the biological effects of the formula 1 compound and the steroid receptor binding partner. Groups of cells are considered "identical" if they do not display known or obvious morphological or genetic differences.

Usually, the second group of cells will serve as a control, and they will thus not be exposed to any formula 1 compound before obtaining the RNA or cDNA. But, for some embodiments, one can expose the second group of cells to a known agonist or antagonist of the steroid receptor binding partner. This allows one to compare the potency of the formula 1 compound with the potency of the agonist or antagonist.

In other embodiments, one can modify method 2 by providing a third group of cells, which is optionally used as an untreated control when the second group of cells is treated with a steroid receptor agonist or antagonist. In these embodiments, one will typically compare the effect of the formula 1 compound and the agonist or the antagonist of the expression of a gene or DNA construct. The DNA construct would comprise a promoter or other regulatory sequences that are subject to transcriptional modulation, usually increase transcription, by the formula 1 compound in concert with its binding partner.

The formula 1 compounds can directly or indirectly modulate the activity or synthesis of one or more biological ligands to effect a detectable biological response or activity change. To facilitate the identification of candidate binding partners for the formula 1 compounds, one can use a radiolabeled formula 1 compound that is linked to a support, usually a solid support, as a means to recover the candidate binding partners. The formula 1 compound can be linked to the support through a variable group that is bonded to the formula 1 compound, e.g., at the 2-, 3-, 7-, 11-, 15-, 16- or 17-position of the steroid nucleus. Linking agents are known for such uses and include homobifunctional and heterobifunctional agents, many of which are commercially available. The linker one uses will typically comprise about 2-20 linked atoms. The linked atoms usually comprise mostly carbon, with one, two or three oxygen, sulfur or nitrogen atoms that optionally replace one or more carbon or hydrogen atoms. One can use a cDNA expression library that one has made from suitable cells or tissues as a source of candidate binding partners. The cells or tissues can be obtained from a mammalian or a vertebrate host, e.g., human, mouse, bird, primate, or from other sources, e.g., insects (e.g., *Drosophila*), other invertebrates (e.g., yeast, bacteria, *Mycoplasma* sp., *Plasmodium* sp., *Tetrahymena* sp., *C. elegans*) or other organism groups or species listed herein or in the cited references. Suitable tissues include skin, liver tissue or cells, including hepatocytes and Küpfer cells, fibrocytes, monocytes, dendritic cells, kidney cells and tissues, brain or other central nervous system cells or tissues, including neurons, astrocytes and glial cells, peripheral nervous system tissues, lung, intestine, placenta, breast, ovary, testes, muscle, including heart or myocyte tissue or cells, white blood cells, including T cells, B cells, bone marrow cells and tissues, lymph tissues or fluids and chondrocytes.

Typically a candidate binding partner that one isolates from a non-human source will have a human homolog that has similar binding properties for the formula 1 compound. Non-human candidate binding partners can thus be used to facilitate recovery of the human homologs, e.g., by preparing antiserum for precipitating the human homolog from a solution that comprises the human homolog or by comparing the sequence of the non-human candidate binding partner with known human gene sequences. Once a source of the candidate binding partner is obtained, it can be contacted with labeled formula 1 compound, usually radiolabeled with, e.g., $^{14}C$ or $^3H$, and complexes that comprise the labeled formula 1 compound and the candidate binding partner is recovered using, e.g., affinity chromatography or antibody precipitation methods. The recovery of the complex provides a source of at least partially purified candidate binding partner, i.e., the candidate binding partner is enriched, e.g., at least 10-fold enriched, or at least 100-fold enriched, or at least 500-fold enriched, compared to its abundance in the original candidate binding partner source material.

Embodiments of the invention include a composition comprising a partially purified (purified at least about 2-fold to about 10-fold relative to natural sources, e.g., cells or a cell lysate) complex or a purified (purified at least about 20-fold to about 5000-fold relative to natural sources, e.g., cells or a cell lysate) complex (where the partially purified or purified complex is optionally isolated) comprising a formula 1 compound and a steroid receptor, a serum steroid-binding protein (e.g., human serum albumin, a1-acid glycoprotein, sex hormone-binding globulin, testosterone-binding globulin, corticosteroid-binding globulin, androgen binding protein (rat)) or another binding partner, e.g., transcription factor or DNARS. An aspect of these compositions includes a product produced by the process of contacting the partially purified or the purified composition with one or more cells, one or more tissues, plasma or blood.

Other embodiments include a method to modulate a cellular response or to determine a biological activity of a formula 1 compound comprising: (a) contacting the formula 1 compound(s) with a cell or cell population; (b) measuring one or more of (i) a complex between a binding partner and the formula 1 compound, (ii) proliferation of the cell or cell population, (iii) differentiation of the cell or cell population (iv) an activity of a protein kinase C, (v) a level of phosphorylation of a protein kinase C substrate, (vi) transcription of one or more target genes, (vii) inhibition of unwanted cellular responses to certain steroids, e.g., inhibition of glucocorticoid-induced immune suppression or inhibition of glucocorticoid-induced bone loss, (viii) inhibition or modulation of steroid-induced transcription, e.g., increased or decreased expression induced by glucocorticoids or sex steroids or (ix) inhibition of HIV LTR-driven transcription; and (c) optionally comparing the result obtained in step (b) with an appropriate control. Aspects of this embodiment include (i) the method wherein the binding partner is a steroid receptor, a transcription factor or a DNARS, (ii) the method wherein the biological activity determined is a modulating activity of the formula 1 compound for replication or cytopathic effects associated with a retrovirus, a hepatitis virus or a protozoan parasite, (iii) the method wherein the biological activity determined is a modulating activity of the formula 1 compound for replication, cytopathic effects associated with the retrovirus, the hepatitis virus or the protozoan parasite or the biological activity determined is metabolism (assay by $^3H$-thymidine uptake or other assay as referenced or described herein) of a cell or cell population comprising NK cells, phagocytes, monocytes, macrophages, basophils, eosinophils, dendritic cells, synoviocytes, microglial cells, fibrocytes, transformed (neoplastic) cells, virus-infected cells, bacteria-infected cells or parasite-infected cells, and (iv) the method wherein the target gene is a virus gene, a bacterial gene, a parasite gene, a gene associated with cancer, e.g., wherein the virus gene is a DNA or an RNA polymerase gene, a reverse transcriptase gene, an envelope gene, a protease gene or a gene associated with viral nucleic acid replication or a viral structural gene.

Another embodiment is a method comprising contacting a complex that comprises a steroid receptor and a formula 1 compound with a transactivator protein, whereby a complex comprising the steroid receptor protein, the formula 1 compound and the transactivator protein forms, wherein the transactivator protein is in (1) a cell or tissue extract (e.g., nuclei, lysate containing nuclei or lysate without nuclei from a cell(s) or tissue(s)), (2) a partially purified or purified cell or tissue extract, (3) a cell(s) in tissue culture or (4) a cell(s) in a subject, where any of (1)-(4) optionally comprises a target gene (native gene or introduced by standard gene manipulation techniques) whose level of expression is optionally assayed after the complex forms. In some of these embodiments, the transactivator protein is partially purified or purified and is in the cell or tissue extract or the partially purified or purified cell or tissue extract. The transactivator protein may be TIF-1, CBP/P300, TRIP1/SUG-1, RIP-140, SRC1α/P160, or TIF-2/GRIP-1. In any of these embodiments the complex comprising the steroid receptor protein, the formula 1 compound and the transactivator protein may increase or decrease transcription of the target gene compared to a suitable control (e.g., control under same conditions, but lacking any added compound that corresponds to the formula 1 compound, or where another compound (e.g., a steroid that is known to bind to the steroid receptor) is used as a benchmark or reference standard against which altered target gene expression is measured). In these methods, the target gene may be a pathogen gene (e.g., virus, bacterium, parasite, fungus, yeast) or a gene associated with a pathological condition (autoimmunity, inflammation, hyperproliferation).

The formula 1 compounds are suitable for use in certain described methods that use steroids to modulate biological activities in cells or tissues. For example, a formula 1 compound(s) can be used to selectively interact with specific steroid receptors or steroid orphan receptor, or their subtypes, that are associated with a pathological condition(s) in a subject, essentially as described in U.S. Pat. No. 5,668,175. In these applications, the formula 1 compound may act as a ligand for the receptor to modulate abnormal expression of a gene product(s) that correlates with the pathological condition (a steroid hormone responsive disease state). Such genes are normally regulated by steroid hormones. In other applications, one can use the formula 1 compounds to screen for ligands that bind to or detectably affect a biological activity of a steroid receptor or steroid orphan receptor and one or more transcription factors (or cofactors) such as AP-1 and/or with a DNA sequence(s), essentially as described in U.S. Pat. No. 5,643,720. Similarly, the formula 1 compounds can be used essentially as described in U.S. Pat. Nos. 5,597,693, 5,639, 598, 5,780,220, 5,863,733 and 5,869,337 to detectably modulate a biological activity of one of these molecules. In some of these embodiments, the formula 1 compound(s) is labeled to facilitate its use. Suitable labels are known in the art and include radiolabels (e.g., $^3$H, $^{14}$C, $^{32}$P, $^{35}$S, $^{131}$I, $^{99}$Tc and other halogen isotopes), fluorescent moieties (e.g., fluorescein, resorufin, Texas Red, rhodamine, BODIPY, arylsulfonate cyanines), chemiluminescent moieties (e.g., acridinium esters), metal chelators, biotin, avadin, peptide tags (e.g., histidine hexamer, a peptide recognized by monoclonal or polyclonal antibodies), covalent crosslinking moieties. One prepares the labeled compounds according to known methods.

Methods suitable to measure the cellular response or biological effects caused by various compounds, e.g., activation, on immune system cells (e.g., NK cells, phagocytes, monocytes, macrophage, neutrophils, eosinophils, dendritic cells, synoviocytes, microglial cells, fibrocytes) have been described, e.g., Jakob et al., *J. Immunol.* 1998 161:3042-3049, Pierson et al., *Blood* 1996 87:180-189, Cash et al., *Clin. Exp. Immunol.* 1994 98:313-318, Monick et al., *J. Immunol.* 1999 162:3005-3012, Rosen et al., *Infect. Immun.* 1999 67:1180-1186, Grunfeld et al., *J. Lipid Res.* 1999 40:245-252, Singh et al., *Immunol. Cell Biol.* 1998 76:513-519, Chesney et al., *Proc. Natl. Acad. Sci. USA* 1997 94:6307-6312, Verhasselt et al., *J. Immunol.* 1999 162:2569-2574, Avice et al., *J. Immunol.* 1999 162:2748-2753, Cella et al., *J. Exp. Med.* 1999 189:821-829, Rutalt et al., *Free Radical Biol. Med.* 1999 26:232-238, Akbari et al., *J. Exp. Med.* 1999 189:169-178, Hryhorenko et al., *Immunopharmacology* 1998 40:231-240, Fernvik et al., *Inflamm. Res.* 1999 48:28-35, Cooper et al., *J. Infect. Dis.* 1999 179:738-742, Betsuyaku et al., *J. Clin. Invest.* 1999 103:825-832, Brown et al., *Toxicol. Sci.* 1998 46:308-316, Sibelius et al., *Infect. Immunol.* 1999 67:1125-1130. The use of formula 1 compounds in such methods are aspects of the invention and they permit, e.g., measurement of the biological effects of formula 1 compounds on, e.g., one or more of (1) the cell's biological activities, (2) genes whose expression is regulated by the formula 1 compound or (3) a steroid receptor. Exemplary biological effects that the formula 1 compounds may exert include one or more of (1) stimulation of ion flux or ion channel activity in one or more immune cell subsets such as one or more of those described herein, (2) binding to one or more ligands such as a steroid receptor and modulation of a biological activity of the receptor, (3) detectably enhanced transcription of one or more genes whose expression is affected by a steroid receptor(s) or other biomolecule whose activity is directly or indirectly affected by the formula 1 compound's presence and (4) detectably decreased transcription of one or more genes whose expression is affected by a steroid receptor(s) or other biomolecule whose activity is directly or indirectly affected by the formula 1 compound's presence.

Embodiments include any of the methods described above, e.g., method 1, wherein the cells or biological system comprises NK cells, phagocytes, monocytes, macrophage, neutrophils, eosinophils, dendritic cells, synoviocytes, microglial cells, glial cells, fibrocytes or hepatocytes, that optionally comprise a DNA construct that expresses one or two cloned steroid receptors. The method optionally analyzes the effect of a formula 1 compound on the cells compared to controls. Controls include the use of a known agonist or antagonist for the steroid receptor or the comparison of cells exposed to a formula 1 compound with control cells (usually the same cell type as the treated cells) that are not exposed to the formula 1 compound. A response, e.g., activation of the steroid receptor can be measured by known assays compared to controls.

The formula 1 compound will, in some cases modulate (increase or decrease) transcription of one or more genes in the cells. In other cases, the formula 1 compound will enhance lysosome movement in one or more of the subject's NK cells, phagocytes, monocytes, macrophages, neutrophils, eosinophils, dendritic cells synoviocytes, microglial cells or fibrocytes. Such effects will typically be mediated directly or indirectly through one or more transcription factors or steroid receptors that act to modulate gene transcription, e.g., cause enhanced protein kinase C (a PKC such as PKCα, PKCβ, PKCγ or PKCζ) activity in the cells used in the assay, or another effect as disclosed herein.

Other related embodiments are a composition comprising a partially purified or a purified complex comprising a formula 1 compound and a steroid receptor, a serum steroid-binding protein (e.g., human serum albumin, α1-acid glycoprotein, sex hormone-binding globulin, testosterone-binding globulin, corticosteroid-binding globulin, androgen binding protein (rat) or a homolog or isoform of any of these) or another binding partner, e.g., transcription factor or DNARS. An aspect of these compositions includes a product produced by the process of contacting the partially purified or the purified composition with one or more cells, one or more tissues, plasma or blood.

In a related embodiment, a formula 1 compound is used to exert a cytostatic effect on a subject's cells, e.g., mammalian cells, in vitro or in vivo. Typically such cells are lymphoid cells, e.g., T cell populations from, e.g., blood or organs that are rich in lymphoid cells (e.g., spleen, lymph tissue or nodes), or transformed T cell lines. Such activity provides an estimate of the potency of formula 1 compounds to mediate immunological effects, such as enhancing Th1 immune responses or suppressing expression of one or more Th2-associated cytokines. Thus, an invention method comprises (a) contacting a formula 1 compound and lymphoid cells in vitro, (b) determining the degree of cytostasis that the compound exerts to identify a cytostatic compound and (c) optionally administering the cytostatic compound to an immune suppressed subject to determine the effect of the compound on one or more of the subject's immune responses as described herein, e.g., enhanced Th1 cytokine or cell response or decreased Th2-associated cytokine expression. Typically, such methods are conducted using a range of formula 1 compound concentrations and suitable controls, such as a known cytostatic agent or a blank that contains solvent that lacks the formula 1 compound. Inhibition of cell proliferation is measured by standard methods. Methods to measure the cytostatic effects of the compounds includes measuring viable cell numbers in treated and untreated cultures or by measuring DNA synthesis using e.g., $^3$H-thymidine incorporation into DNA in treated and untreated cultures. Typical ranges of formula 1 concentrations in the cell growth medium are about 0.1 µM to about 100 µM, using about 4-6 different concentrations of compounds with a fixed number of cells (e.g., about $0.4 \times 10^5$ to about $5 \times 10^5$). The formula 1 compound is left in contact with the cells in tissue culture for a sufficient time to observe cytostasis, e.g., about 16 hours to about 6 days, typically about 24-72 hours. In these embodiments, one may optionally screen for modulation of a biological activity of a steroid receptor, e.g., activation of PPARα, which may be associated with the cytostasis the compound induced.

Other therapeutic and biological applications and activities. The formula 1 compounds are useful to treat autoimmune or metabolic conditions or disorders, or their symptoms, in subjects such as mammals or humans that relate to impaired insulin synthesis or use or that relate to abnormal or pathological lipid or cholesterol metabolism or levels. Such conditions and symptoms include Type 1 diabetes (including Immune-Mediated Diabetes Mellitus and Idiopathic Diabetes Mellitus), Type 2 diabetes (including forms with (1) predominant or profound insulin resistance, (2) predominant insulin deficiency and some insulin resistance and (3) forms intermediate between these), obesity, hyperglycemia, hyperlipidemia conditions such as hypertriglyceridemia and hypercholesterolemia. In diabetes, the compounds are useful to (1) enhance β-cell function in the islets of Langerhans (e.g., increase insulin secretion), (2) reduce the rate of islet cell damage, (3) increase insulin receptor levels or activity to increase cell sensitivity to insulin and/or (4) modulate glucocorticoid receptor activity to decrease insulin resistance in cells that are insulin resistant. The compounds are thus useful to treat, prevent, ameliorate or slow the progression of diabetes or hyperglycemia, or a related symptom or condition, in a subject such as a human or a mammal.

Beneficial effects that can the formula 1 compounds can exert on such related symptoms or conditions include improved glucose tolerance, improved glucose utilization, decreased vascular disease (e.g., decreased severity or progression of microvascular or macrovascular disease, including nephropathy, neuropathy, retinopathy, hypertension, cerebrovascular disease and coronary heart disease), decreased severity or progression of atherosclerosis, decreased severity or progression of an arteriosclerosis condition (e.g., coronary arteriosclerosis, hyperplastic arteriosclerosis, peripheral arteriosclerosis or hypertensive arteriosclerosis), decreased level or activity of inflammatory macrophages (foam cells) in atherosclerotic plaques, decreased severity or progression of diabetic osteoarthropathy, decreased severity or progression of skin lesions, decreased severity or progression of ketosis, decreased generation of autoantibodies against islet cells or decreased expression or levels of one or more of IL-1 (e.g., IL-1β), IL-6, TNF (e.g., TNFα), and IFN-γ. In these any of these diseases or conditions, the formula 1 compounds can also modulate, e.g., enhance CARβ, RXR, PPARα or PPARβ levels. As used herein, obesity includes a human with a body mass index of about 27, 28, 29, 30, 31, 32, 33, 34 or greater.

The formula 1 compounds are useful in treating insulin resistance and associated symptoms and conditions. Insulin resistance is typically observed as a diminished ability of insulin to exert its biological action across a broad range of concentrations. This leads to less than the expected biologic effect for a given level of insulin. Insulin resistant subjects or human have a diminished ability to properly metabolize glucose or fatty acids and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, impaired glucose tolerance, gestational diabetes, hypertension, obesity, atherosclerosis and a variety of other disorders. Insulin resistant individuals can progress to a diabetic state. The compounds can also be used in the treatment or amelioration of one or more condition associated with insulin resistance or glucose intolerance including an increase in plasma triglycerides and a decrease in high-density lipoprotein cholesterol, high blood pressure, hyperuricemia, smaller denser low-density lipoprotein particles, and higher circulating levels of plasminogen activator inhibitor-1. Such diseases and symptoms have been described, see, e.g., G. M. Reaven, *J. Basic Clin. Phys. Pharm.* 1998, 9: 387-406, G. M. Reaven, *Physiol. Rev.* 1995, 75: 473-486 and J. Flier, *J. Ann. Rev. Med.* 1983, 34:145-60.

The compounds can thus be used in diabetes, obesity, hyperlipidemia or hypercholesterolemia conditions to reduce body fat mass, increase muscle mass or to lower one or more of serum or blood low density lipoprotein, triglyceride, cholesterol, apolipoprotein B, free fatty acid or very low density lipoprotein compared to a subject that would otherwise be considered normal for one or more of these characteristics. These beneficial effects are typically obtained with little or no effect on serum or blood high density lipoprotein levels. The formula 1 compounds are useful to reduce or slow the rate of myocardial tissue or myocyte damage, e.g., fibrosis, or to enhance cardiac fatty acid metabolism in conditions, such as inflammation, where fatty acid metabolism is depressed or decreased. Elevated cholesterol levels are often associated with a number of other disease states, including coronary artery disease, angina pectoris, carotid artery disease, strokes, cerebral arteriosclerosis, and xanthoma, which the formula 1 compounds can ameliorate or slow the progression or severity of. Abnormal lipid and cholseterol conditions that can be treated include exogenous hypertriglyceridemia, familial hypercholesterolemia, polygenic hypercholesterolemia, biliary cirrhosis, familial combined hyperlipidemia, dysbetalipoproteinemia, endogenous hypertriglyceridemia, mixed hypertriglyceridemia and hyperlipidemia or hypertriglycidemia secondary to alcohol consumption, diabetic lipemia, nephrosis or drug treatments, e.g., corticosteroid, estrogen, colestipol, cholestyramine or retinoid treatments. Dosages, routes of administration and dosing protocols for the formula 1 compounds are essenitally as described herein. Where the condition is chronic, the formula 1 compounds will generally be administered to a subject such as a human for a relatively long time period, e.g., for about 3 months to about 10 years or more. Dosages, routes of administration and dosing protocols for the formula 1 compounds are essenitally as described herein. Dosing of the compound can be daily or intermittent using a dosing protocol using dosages as described herein, e.g., about 0.01 to about 20 mg/kg of a formula 1 compound administered to a subject once or twice per day daily or intermittently. The use of the formula 1 compounds can be combined with other suitable treatments, e.g., diet control or HMG-CoA reductase inhibitors such as Simvastatin™, Pravastatin™, Mevastatin™ or Lovastatin™.

The formula 1 compounds are also useful for preventing, slowing the progression of or treating certain chronic conditions in a subject such as a mammal or a human. Chronic conditions include diseases and conditions that arise or develop over a relatively long time period, e.g., over about 3 months to 10 years or more. Such conditions include chronic renal failure, which may result from polycystic kidney disease, from, e.g., an autoimmune condition such as acute or chronic glomerulonephritis, or from diabetes, interstitial nephritis, hypertension and other conditions discussed elsewhere herein. Chronic conditions include chronic pulmonary conditions such as chronic bronchitis, lung fibrosis, right ventricular hypertrophy, pulmonary hypertension, emphysema, asthma and chronic obstructive pulmonary disease, which may be treated with a formula 1 compound. These conditions or their symptoms may be mild, moderate or severe. The subject may be suffering from the disease or condition or may be subject to developing the condition, e.g., the subject may display early signs or a predisposition to develop a chronic condition. Such treatment will generally facilitate prevention of the disease, delay the onset or severity of the disease or condition, ameliorate one or more symptoms, e.g., reduce shortness of breath, coughing or dyspnea, or slow progression of the disease or condition. In these and other chronic conditions described herein, the formula 1 compounds will generally be administered to a subject such as a human for a relatively long time period, e.g., for at least about 3 months to about 10 years or more. Dosages, routes of administration and dosing protocols for the formula 1 compounds are essenitally as described herein. Dosing of the compound can be daily or intermittent using a dosing protocol using dosages as described herein, e.g., about 0.1 to about 20 mg/kg of a formula 1 compound administered to a subject once or twice per day daily or intermittently. The use of the formula 1 compounds can be combined with other treatments, e.g., β-agonists such as metaproterenol or albuterol, or corticosteroids, e.g., prednisone, for asthma or chronic obstructive pulmonary disease.

The formula 1 compounds can modulate the biological activity of cytokines or interleukins that are associated with various immune deficiency or dysregulation conditions, which may be transient or chronic. They can thus be used to ameliorate, treat or prevent naturally occurring age-related decline in immune function in a subject or immune deficiency or dysregulation resulting from trauma, stress, burns, surgery, autoimmunity or infections as described herein. Such immune deficiency dysregulation may be associated with, e.g., an age-related increase in production of one or more of IL-4, IL-5 and IL-6 or an age-related decrease in production of one or more of IL-2, IL-3, γ-IFN, GM-CSF or antibodies. In these embodiments, the formula 1 compound is administered to the subject to detectably decrease production or levels of one or more of IL-4, IL-5 and IL-6 or to detectably increase production or levels of one or more of IL-2, IL-3, IL-5, IL-12, GM-CSF and γ-IFN. These cytokine changes facilitate normalization of the subject's immune responses. Such normalization can be observed by various means. These means include monitoring appropriate cytokine RNA or protein level(s) in the subject or by measuring biological responses such as restoration or detectable improvement of contact hypersensitivity in a subject with depressed or suboptimal contact hypersensitivity response. The formula 1 compounds can thus be used to enhance or restore a deficient or suboptimal immune response such as contact hypersensitivity response in a subject with a chronic or transient state of immune deficiency or dysregulation. In these embodiments, the formula 1 compound is administered using the dosages, routes of administration and dosing protocols for the formula 1 compounds essenitally as described herein. Treatment with the formula 1 compounds is optionally combined with other appropriate treatments or therapies essentially as described herein, e.g., a antibacterial or antiviral agent(s) is coadministered with a formula 1 compound to treat, prevent or ameliorate an infection in an infected subject or a subject suffering from, e.g., a burn. Methods to measure changes in cytokine levels or contact hypersensitivity are known and can option-ally be applied in these embodiments, see, e.g., U.S. Pat. Nos. 5,919,465, 5,837,269, 5,827,841, 5,478,566.

The capacity of the formula 1 compounds to modulate immune functions permits their use for treating, preventing, slowing the progression of or alleviating the a symptom(s) of subjects with psychological disorders, metabolic disorders, chronic stress, sleep disorders, conditions associated with sexual senescence, aging, or premature aging. Metabolic disorders include parathyroidism, pseudoparathyroidism, hypoparathyroidism, hypercalcemia, hypocalcemia and detectable symptoms thereof such as fatigue, constipation, kidney stones and kidney malfunction. Chronic stress and related disorders include fibromyalgia, chronic fatigue syndrome and hypothalamic-pituitary axis dysregulation. In these embodiments, treatment of subjects with a formula 1 compound is optionally combined with other suitable agents such as triiodothyronine, tetraiodothyronine, an insulin-like growth factor or insulin-like growth factor binding protein-3.

Another aspect of the invention provides for the use of a formula 1 compound and a flavonoid, e.g., a naragin flavonoid, to enhance the bioavailability of the formula 1 compound. In these embodiments, the an effective amount of a flavonoid is administered to a subject who is receiving a formula 1 compound. Typically about 1-10 mg of flavonoid per kg of body weight is administered to the subject a flavonoid such as bavachinin A, didymin (isosakuranetin-7-rutinoside or neoponcirin), flavanomarein (isookanine-7-glucoside), flavanone azine, flavanone diacetylhydrazone, flavanone hydrazone, silybin, cirsiliol, silychristin, isosilybin or silandrin. The flavonoid compound is typically administered with the formula 1 compound or a few hours, e.g., about 1, 2 or 3 hours, before the formula 1 compound is administered to the subject.

As noted above, in some embodiments a treatment with a formula 1 compound is combined with a corticosteroid or glucocorticoid. Corticosteroids are used in a number of clinical situations to, e.g., decrease the intensity or frequency of flares or episodes of inflammation or autoimmune reactions in conditions such as acute or chronic rheumatoid arthritis, acute or chronic osteoarthritis, ulcerative colitis, acute or chronic asthma, bronchial asthma, psoriasis, systemic lupus erythematosus, hepatitis, pulmonary fibrosis, type I diabetes, type II diabetes or cachexia. However, many corticosteroids have significant side effects or toxicities that can limit their use or efficacy. The formula 1 compounds are useful to counteract such side effects or toxicities without negating all of the desired therapeutic capacity of the corticosteroid. This allows the continued use, or a modified dosage of the corticosteroid, e.g., an increased dosage, without an intensification of the side effects or toxicities or a decreased corticosteroid dosage. The side-effects or toxicities that can be treated, prevented, ameliorated or reduced include one or more of bone loss, reduced bone growth, enhanced bone resorption, osteoporosis, immunosuppression, increased susceptibility to infection, mood or personality changes, depression, headache, vertigo, high blood pressure or hypertension, muscle weakness, fatigue, nausea, malaise, peptic ulcers, pancreatitis, thin or fragile skin, growth suppression in children or preadult subjects, thromboembolism, cataracts, and edema. Dosages, routes of administration and dosing protocols for the formula 1 compound would be essentially as described herein. An exemplary dose of formula 1 compound of about 0.5 to about 20 mg/kg/day is administered during the period during which a corticosteroid is administered and optionally over a period of about 1 week to about 6 months or more after dosing with the corticosteroid has ended. The corticosteroids are administered essentially using known dosages, routes of administration and dosing protocols, see, e.g., *Physicians Desk Reference* 54th edition, 2000, pages 323-2781, ISBN 1-56363-330-2, Medical Economics Co., Inc., Montvale, N.J. However, the dosage of the corticosteroid may optionally be adjusted, e.g., increased about 10% to about 300% above the normal dosage, without a corresponding increase in all of the side effects or toxicities associated with the corticosteroid. Such increases would be made incrementally over a sufficient time period and as appropriate for the subject's clinical condition, e.g., daily corticosteroid dose increases of about 10% to about 20% to a maximum of about 300% over about 2 weeks to about 1 year.

Such corticosteroids include hydrocortisone (cortisol), corticosterone, aldosterone, ACTH, triamcinolone and derivatives such as triamcinolone diacetate, triamcinolone hexacetonide, and triamcinolone acetonide, betamethasone and derivatives such as betamethasone dipropionate, betamethasone benzoate, betamethasone sodium phosphate, betamethasone acetate, and betamethasone valerate, flunisolide, prednisone, fluocinolone and derivatives such as fluocinolone acetonide, diflorasone and derivatives such as diflorasone diacetate, halcinonide, dexamethasone and derivatives such as dexamethasone dipropionate and dexamethasone valerate, desoximetasone (desoxymethasone), diflucortolone and derivatives such as diflucortolone valerate), fluclorolone acetonide, fluocinonide, fluocortolone, fluprednidene, flurandrenolide, clobetasol, clobetasone and derivatives such as clobetasone butyrate, alclometasone, flumethasone, and fluocortolone.

In some applications, the formula 1 compound(s) may directly and/or indirectly interfere with replication, development or cell to cell transmission of a pathogen such as a virus or a parasite (malaria). Improvement in a subject's clinical condition may arise from a direct effect on an infectious agent or on a malignant cell. Interference with cellular replication can arise from inhibition of one or more enzymes that a parasite or an infected cell uses for normal replication or metabolism, e.g., glucose-6-phosphate dehydrogenase, which affects cellular generation of NADPH (see, e.g., Raineri et al., *Biochemistry* 1970 9: 2233-2243). This effect may contribute to cytostatic effects that some formula 1 compounds can have. Modulation of cellular enzymes expression or activity may also interfere with replication or development of a pathogen, e.g., HIV or malaria parasites or with replication or development of neoplastic cells, e.g., inhibition of angiogenesis. Clinical improvement will also generally result from an enhanced immune response such as an improved Th1 response.

Administration of a formula 1 compound can lead to a decrease in adenosine levels in a subject's tissue(s), e.g., lung or central nervous system tissue. This effect can be used to treat, prevent, ameliorate one or more symptoms of or slow the progression of a disease(s) or clinical condition(s) where a relatively high level of adenosine is a factor in or can contribute to the disease or condition, e.g., in asthma.

Adenosine is associated with the symptoms of bronchial asthma, where it can induce bronchoconstriction or contraction of airway smooth muscle in asthmatic subjects, see, e.g., J. Thorne and K. Broadley, *American Journal of Respiratory & Critical Care Medicine* 149(2 pt. 1):392-399 1994, S. Ali et al., *Agents & Actions* 37:165-167 1992, Bjorck et al., *American Review of Respiratory Disease* 145:1087-1091 1992. This effect is not observed in non-asthmatic subjects. In the central nervous system, adenosine can inhibit the release of neurotransmitters such as acetylcholine, noradrenaline, dopamine, serotonin, glutamate, and GABA. It can also depress neurotransmission, reduce neuronal firing to induce spinal analgesia and it possesses anxiolytic properties, see, e.g., A. Pelleg and R. Porter, *Pharmacotherapy* 10:157 1990. In the heart, adenosine suppresses pacemaker activity, slows AV conduction, possesses antiarrhythmic and arrhythmogenic effects, modulates autonomic control and triggers the synthesis and release of prostaglandins. In addition, adenosine has vasodilatory effects and can modulate vascular tone.

The unwanted effects of excess adenosine can be ameliorated or reduced by administering sufficient amounts of a formula 1 compound to a subject who is subject to developing or who has an unwanted level of adenosine in one or more tissues or organs. In typical embodiments, one will administer about 10 mg/kg/day to about 100 mg/kg/day of a formula 1 compound to a subject over a period of about 1 week to about 4 months to effect detectable changes in adenosine levels or amelioration in one or more symptoms associated with high adenosine in one or more of the subject's tissues. Such changes may be determined by comparing the subject's adenosine levels before treatment with the formula 1 compound is started. Alternatively, for subjects with symptoms that are consistent with high adenosine levels, the decrease can be inferred by comparing the normal level of adenosine in the target tissue(s) for subjects of the same species and similar age or sex with the level that is observed after treatment. Methods to measure adenosine levels in mammalian tissue are known and can optionally be used in these embodiments, e.g., U.S. Pat. No. 6,087,351.

In some clinical conditions, the formula 1 compounds can inhibit activated T lymphocytes in vivo, and they can inhibit the expression or biological activity of one or more of TNF-α, IFN-γ, IL-6, IL-8 or insulin like growth factor-1 receptor (IGF-1R) or IL-6 receptor. The compounds are thus useful to treat, prevent or ameliorate conditions where this is a component of pathology. Such conditions include inflammation conditions such as psoriasis, psoriatic arthritis, osteoarthritis, and rheumatoid arthritis. The compound can thus ameliorate the inflammation, e.g., by inhibiting expression of one or more of TNF-α, IFN-γ, IL-6, IL-8 or IGF-1R. Also, the compounds can inhibit unwanted T cell activity. They can thus ameliorate one or more psoriasis symptoms such as skin scaling, skin thickening, keratinocyte hyperproliferation, deficient filaggrin expression (B. Baker et al., *Br. J. Dermatol.* 1984, 111:702), deficient strateum corneum lipid deposition or they can improve a clinical assessment such as the Psoriasis Activity and Severity Index. The formula 1 compounds can be delivered to a subject with psoriasis using topical or systemic formulations as described herein. Topical formulations include gels, lotions and creams, e.g., as described herein. Daily or intermittent administration of the compound can be used essentially as described herein. The use of the formula 1 compounds is optionally combined with one more current psoriasis treatments, e.g., topical emollients or moisturizers, tars, anthralins, systemic or topical corticosteroids, vitamin D analogs such as calcitriol, methotrexate, etretinate, acitretin, cyclosporin, FK 506, sulfasalazine, ultraviolet B radiation optionally combined with one or more of a topical corticosteroid, tar, anthralin, emollient or moisturizer or ultraviolet A plus psoralen. Such additional treatments essentially would use known dosages and routes of administration, which are applied, e.g., within a month before, during or within a month after a treatment course with a formula 1 compound.

Other desirable modulation effects of the formula 1 compounds on cells or tissues include (1) inhibition of one or more of bone resorption or calcium release or gp80, gp130, tumor necrosis factor (TNF), osteoclast differentiation factor (RANKL/ODF), RANKL/ODF receptor, IL-6 or IL-6 receptor expression or biological activity in, e.g., bone loss or osteoporosis conditions or in osteoclasts, or in cancers such as prostate cancer, metastatic breast cancer or metastatic lung cancer (e.g., with bone metastases), (2) inhibition of osteoclastogenesis or osteoclast development from progenitor cells, (3) enhancement of NFκB inhibition that is mediated by steroid receptors, e.g., enhanced inhibition of estrogen receptor-α or estrogen receptor-β mediated inhibition of NFκB in inflammation, rheumatoid arthritis or osteoporosis, (4) enhancement of osteoblastogenesis, osteoblast, bone callus or bone development, e.g., from progenitor cells in bone fractures, depressed bone healing situations (e.g., in a burn patient or in a patient being treated with a glucocorticoid), bone growth or osteoporosis or other bone loss conditions, by, e.g., modulation or enhancement of osteoblast replication or development or modulation or enhancement of the synthesis or biological activity of a transcription factor such as Cbfa1, RUNX2 or AML-3 (5) normalization of hypothalamic-pituitary-adrenal axis function in conditions where there is dysregulation such as in chronic inflammatory diseases, chronic asthma or rheumatoid arthritis (increased cortisol to ACTH ratio), (6) modulation of ligand-gated ion channels in neurons in, e.g., depression, sleep or memory disorders, (8) modulation of G-protein coupled receptors in neurons in, e.g., depression, sleep or memory disorders, (9) modulation, e.g., induction, of the synthesis or biological activity of metabolic enzymes such as a cytochrome (e.g., a CYP enzyme such as CYP1A1, CYP2B1, CYP2b10, CYP4A, CYP7A, CYP7A1, CYP7B, CYP7B1, P450 3A4, P450c17, P450scc, P450c21 or an isozyme, homolog or mutant of any of these) in cells or tissues such as liver cells, neurons, neuron precursor cells, brain, breast, testes or colon, (10) enhancement of collagen synthesis or levels in, e.g., skin in aging or skin damage from, e.g., trauma, thermal injury or solar radiation, (11) inhibition of nitric oxide production in cells or tissue, e.g., in nervous system tissue or in microglial cells in dementias such as Alzheimer's disease, (12) enhancing glucose-stimulated insulin synthesis in hyperglycemia or diabetes conditions, (13) modulation of gamma-aminobutyric acid (GABA), dopamine or N-methyl-D-aspartate (NMDA) receptor activity or levels in, e.g., brain tissue or neurons, (e.g., decreased GABA-mediated chloride currents or potentiation of neuronal response to NMDA in the hippocampus) in, e.g., conditions such as a dementia (Alzheimer's Disease), depression, anxiety, schizophrenia or memory loss due to, e.g., aging or another condition described herein, (14) modulating (e.g., enhancing) the expression or activity of a transcription factor(s), or a homolog(s) or isoform(s), such as SET, nerve growth factor inducible protein B, StF-IT, SF-1 in cells or tissues such as nerve cells, neuronal precursor cells or liver cells, (15) inhibition of eosinophil infiltration or reduction IgE levels in allergic responses or in lung or other tissue, (16) modulation, e.g., a decrease, in serum or blood of leptin levels in, e.g., obese subjects such as humans with a body mass index of about 27, 28, 29, 30, 31, 32, 33, 34 or greater, (17) increased corticotropin releasing hormone synthesis or activity in, e.g., elderly subjects such as humans at least about 60 years of age or at least about 70 years of age, (18) enhancement of memory or reduction of memory loss or disorientation in aging or dementias such as Alzheimer's Disease, (20) enhancement of the synthesis or activity of one or more enzymes responsible for thermogenesis, e.g., liver glycerol-3-phosphate dehydrogenase or malic enzyme, in subjects such as obese or diabetic humans, (21) modulation, e.g., reduction, of the synthesis or biological activity of the CXCR4 receptor or the CXCL12 chemokine in hyperproliferation conditions such as breast cancers or precancers, (22) modulation of the synthesis or biological activity of one or more of holocytochrome c, cytochrome c, second mitochondria-derived activator of caspase, Apaf-1, Bax, procaspase-9, caspase-9, procaspase-3, caspase-3, caspase-6 and caspase-7, e.g., enhanced translocation of these molecules from mitochondria to cytosol or activation of these molecules in the cytosol in cancer precancer cells, cancer cells or cells that mediate autoimmunity, (23) modulation of the synthesis or biological activity of one or more of tumor necrosis factor-α, interleukin-1β converting enzyme, IL-6, IL-8, caspase-4 and caspase-5, e.g., decreased activation of these molecules in injured cells or cells subject to injury from, e.g., ischemia or infarction (e.g., vascular, cardiac or cerebral), reperfusion of hypoxic cells or tissue or an inflammation condition such as rheumatoid arthritis, ulcerative colitis, viral hepatitis, alcoholic hepatitis, or another inflammation condition disclosed herein, (24) decrease of the synthesis, biological activity or activation of one or more of phospholipase A2, caspase-1, caspase-3 and procaspase-3 in neurodegeneration disorders or dementias such as Alzheimer's disease, Huntington's disease, or another neurological condition disclosed herein. The formula 1 compounds can thus be used where one or more of these conditions or their symptoms is present. Methods to measure the synthesis or biological activity of these molecules has been described, see, e.g., U.S. Pat. Nos. 6,200,969, 6,187,767, 6,174,901, 6,110,691, 6,083,735, 6,024,940, 5,919,465 and 5,891,924.

The formula 1 compounds can facilitating release of myeloperoxidase from granulated neutrophils. The enzyme generates free hydrogen peroxide. Some of the formula 1 compounds, e.g., compounds with a halogen such as bromine or iodine at, e.g., the 16 position, can be metabolized to provide a source of halogen. In cases where the halogen is released, the released halogen can react with hydrogen peroxide ($H_2O_2$) to generate hypohalogenous acid such as hypobromous acid (HOBr). Exemplary compounds include a halogenated formula 1 compound such as 16-bromoepiandrosterone. Alternatively, a halogen salt, e.g., KBr, NaBr, KI or NaI, can be administered to the subject to provide a source of halogen. The halogen source can be administered to a subject as a component in a formulation that comprises a formula 1 compound or it can be administered separately. Hypohalogenous acid is a potent antimicrobial agent, which may be effective in reducing pathogens in the circulatory system of subjects with a blood cell deficiency who also have a pathogen infection. Hypohalogenous acid that is generated in vivo would provide benefits to such subject as shown by, e.g., a reduced quantitative circulating viral or bacterial culture measurement, without the toxicity that is normally associated with its direct administration to a subject. Biological activities of white blood peroxidase enzymes have been described, see, e.g., M. Saran et al., *Free Radical Biol. Med.* 1999 26:482-490, W. Wu et al., *J. Clin. Invest.* 2000 105:1455-1463 and Z. Shen et al., *Biochemistry* 2000 39:5474-5482.

Delayed radiation effects. Invention embodiments include a method to prevent, treat or ameliorate a symptom or condition associated with one or more delayed adverse effect, symptom or condition from radiation exposure in a subject in need thereof comprising administering to the subject, or delivering to the subject's tissues, an effective amount of a formula 1 compound. Radiation exposure may arise from a radiation therapy where exposure is intentional, or it may arise from an accidental exposure.

Radiation therapy ("RT") can generate a number of early or late delayed-onset conditions or symptoms. Delayed radiation effects are conditions or symptoms that generally arise or become detectable to the subject or to a health care provider at least about 1 month after exposure to radiation. Thus the conditions or symptoms may detectable at about 2 months, about 3 months, about 4 months, about 1 year, about 20 years or more after radiation exposure. For example, transient nervous system symptoms may develop early after RT, but progressive, permanent, often disabling nervous system damage may appear months or years later. The total radiation dose, size of the fractions, duration of RT, and volume of tissue irradiated influence the probability of the injury and its severity. Individual patient and tissue susceptibility to delayed injuries is variable, which factors into the selection of safe and effective radiation doses for RT. Total radiation doses that a subject may receive may comprise single doses or 2, 3, 4, or more doses within a range of about 1 to about 400 Gy, e.g., about 1, 1.4, 1.6, 1.8, 2, 2.5, 3, 5, 10, 20, 40, 50, 80, 100, 130, 150, 180, 200, 250, 300, 400 or more Gy. Such doses in a given course of treatment may be the same or different.

In some embodiments, the total radiation dose occurs on a single exposure that occurs in a relatively short time period, e.g., about 1-20 minutes to about 12 hours. In other embodiments, the total dose is delivered to the subject in multiple doses or over a longer time, e.g., over about 2 days to about 12 months or more in multiple doses in, e.g., 2, 3, 4, 6, 8, 10 or more individual doses. Ameliorating a side effect may comprise detectably slowing the progression of a symptom or condition or detectably reducing the ultimate expected severity of a symptom or condition. The affected condition or symptom may be detectably reduced as determined by the subject or the health care provider. Thus, after administration of a formula 1 compound, the target symptom or condition may be moderately reduced, slightly reduced, essentially nonexistent or subclinical, e.g., present at a low level that is not deemed significant by the subject or the health care provider. Amelioration of one or more conditions or symptoms that can be suitably quantified may be observed as a decrease of about 5% or more, e.g., at least about 10%, at least about 20%, at least about 30%, at least about 40%, at least about 50%, at least about 70%, at least about 80% or at least about 90% in the relative expected or potential severity or extent of the condition or symptom.

For example, in lung pneumonitis, administration of a formula 1 compound can lead to detectably increased oxygen saturation in the subject's blood by about 5% or by about 10% or more, e.g., oxygen saturation can rise from about 83% to about 88%, which would typically be detectable by the subject and the health care provider. Such decreased severity of a condition or symptom may be objectively measured in some instances, e.g., by determining the number or activity of circulating platelets or neutrophils or by evaluation of fever, severity or frequency of diarrhea or blood oxygen saturation levels. For other symptoms or conditions, prevention may be subjectively observed by a significant or detectable improvement in a relevant score, e.g., decreased fever or pain or a decreased need for treatment of fever, pain or inflammation.

Symptoms or conditions of radiation exposure that can be treated also include encephalopathy, myelopathy, nausea, diarrhea, acute inflammation, chronic inflammation, edema, pain, fever, headache, depression, malaise, weakness, hair loss, skin atrophy, skin ulceration, skin lesion, keratosis, telangiectasia, infection, e.g., bacterial, viral, fungal or yeast infection, hypoplasia, atrophy, marrow hypoplasia, hemorrhage, fibrosis, e.g., lung fibrosis, pneumonitis, bone marrow hypoplasia, hemorrhage or cytopenia, e.g., anemia, leukopenia or thrombocytopenia, edema, fibrosis or hemorrhage or the need for edema, fibrosis or hemorrhage treatment. Such symptoms or conditions may arise from one or more radiation-damaged tissues or cells, including lymphoid cells, bowel or intestinal epithelium or tissue, bone marrow, testicles, ovaries, brain tissue, spinal cord tissue or skin epithelium.

Exemplary symptoms or conditions associated with late effects of radiation exposure include (1) acute or chronic radiation-induced enteritis or diarrhea, e.g., in patients receiving pelvic radiotherapy, (2) pseudomembranous inflammation, (3) perivascular fibrosis, (4) endothelial cell damage or death, e.g., associated with vascular radiation therapy, (5) cardiac tissue inflammation or damage or pericardial disease, e.g., in pediatric or adult patients receiving radiation therapy for a leukemia, thoracic neoplasm or other malignancy, (6) pulmonary tissue inflammation or damage, (7) hematopoietic or marrow cell inflammation or damage, e.g., in wide field radiation therapy, (8) endocrine or thyroid dysfunction, e.g., in thalamic or hypothalamic tumors in pediatric or other patients, (9) decreased growth or decreased bone development or density, e.g., in pediatric patients receiving radiation therapy for a childhood leukemia or other malignancy, (10) central nervous system inflammation or damage, e.g., in pediatric or adult patients receiving radiation therapy for a leukemia (e.g., CNS acute lymphocytic leukemia) or other malignancy, (11) connective tissue damage after radiation therapy, (12) incidence or severity of a secondary leukemia such as acute myelogenous leukemia or myelodysplasia and (13) gastric ulceration, bleeding, small bowel obstruction or fistula formation in, e.g., patients receiving radiation therapy to the gastrointestinal tract. These symptoms or conditions are treated or ameliorated using the formula 1 compounds essentially as disclosed herein.

In treating such symptoms or conditions, slowing the progression of a symptom, condition or side effect will detectably reduce the rate at which the condition, symptom or side effect worsens or intensifies. In some embodiments, pronounced slowing of the rate of progression is, e.g., the time needed to progress to an expected or a measurable point, which may be increased by a period of about 1, 2, 3, 4, 5, 10, 20, 30 or more days to a period of about 1, 2, 3, 4, 6, 8, 10, 12, 18, 24, 36, 48, 72 or more months.

Radiation-associated brain damage can give rise to acute encephalopathy with symptoms such as headache, nausea, vomiting, somnolence, depression, disorientation, and worsening neurologic signs. The encephalopathy may arise from the first, second or a subsequent radiation fraction, e.g., when high intracranial pressure has not been treated with, e.g., corticosteroids. Late-delayed radiation damage to the brain or nervous system can arise at about 5, 6, 7, 8, 9, or 10 months to 1, 2, 3 or more years after leukemia prophylaxis in children or after brain tumor prophylaxis or treatment in adults. Symptoms often include pain or headache and progressive dementia without focal signs and adults typically also develop an unsteady gait. Cerebral atrophy appears on CT scans in some cases. Late-delayed damage can arise at about 1 week, about 2 weeks about 2 months or about 1-2 years after irradiation of extracranial tumors or high-dose irradiation of intracranial tumors, e.g., brachytherapy or radiosurgery, although the symptoms are generally more focal. The invention method would be used during the time period when such symptoms would be expected to arise, e.g., commencing at about 1-5 days or about 7-60 days after radiation exposure and ending at about 0.5, 1, 2, 3, 4, 5 or more years later. Exemplary brachytherapies and unsealed source therapies include prostate $^{125}$I seed implants in prostate conditions such as prostate cancer, $^{90}$Yt conjugated to monoclonal antibodies or in endovascular brachial radiotherapy.

Early-delayed radiation spinal cord myelopathy follows radiation therapy to the spinal cord, neck, upper thorax or lumbar region or and it is often characterized by Lhermitte's sign, i.e., an electric shock-like sensation radiating down the back and into the legs on neck flexion. Late-delayed radiation myelopathy can arise months or years after therapy for extraspinal tumors, e.g., Hodgkin's disease. Other symptoms can include progressive weakness and sensory loss, such as a Brown-Séquard type, i.e., a proprioceptive sensory loss and weakness on one side of the body and loss of temperature and pain sensation on the other side. Progression times vary, but many human patients suffering from late-delayed radiation spinal cord myelopathy become paraplegic. Late-delayed radiation neuropathy may produce brachial neuropathy, e.g., after treatment for breast or lung cancer. Radiation can also give rise to gliomas, meningiomas, or peripheral nerve sheath tumors at about 1, 2, 3, 4, 5 or more years after therapy. The formula 1 compounds will generally be administered at about the time period when these symptoms would be expected to arise, e.g., commencing at about 1-5 days, or about 7-60 days or about 6 or 12 months after radiation exposure and ending at about 3, 4, 6 months later or about 1, 2, 3, 4, 5, 6 or more years later. In some embodiments, the formula 1 compound is administered to the subject on the same day that a planned or accidental radiation exposure occurs and dosing is continued for about 1, 2, 3, 4, 8, 12 or more weeks to about 2, 3, 4, 5, 6 or more years, or for a time as disclosed elsewhere herein.

Early-delayed encephalopathy often arises or is detectable at about 2, 3 or 4 months after radiation therapy. This encephalopathy in adults, is distinguished from worsening or recurrent brain tumor by, e.g., computed tomography (CT) or magnetic resonance imaging (MRI). The condition in children can occur as a somnolence syndrome, e.g., after whole-brain irradiation for leukemia. The condition in children typically improves spontaneously over several days to weeks. Such encephalopathies can be prevented, delayed in onset, recede more rapidly and/or be less severe when a formula 1 compound is administered to the subject throughout the period when encephalopathy can arise, e.g., beginning about a week, two weeks or a month before the expected onset of a symptom or condition and ending about a week or month or two months after it would be expected to arise or to resolve.

In some embodiments, a radiation late effect is a symptom or condition that may arise months or years after radiation exposure, treatment with the formula 1 compound can commence shortly, e.g., about 0.5, 1, 2, 3, 4, 5, 10, 14, 21 or 28 days, after the radiation exposure or after initiation of a radiation treatment. In other embodiments, the invention treatment method can commence after radiation exposure has terminated, e.g., about 1-30 days or about 1-72 months or more after radiation exposure. In these embodiments, the treatment method can be administered over a period of months or years, e.g., about 0.5, 1, 2, 3, 4, 5, 6, 12, 18, 24, 36, 48, 72, 96 or more months. In some embodiments, dosing of the subject will occur for a period of about 2-12 months or for a period of about 4-6 months. Occasionally, treatment for radiation late effects will commence on the day of or before initiation of a planned radiation treatment, e.g., at about 1, 2, 3, 4, 5, 7, 14, 21, 28 or more days before a planned exposure to radiation of a sufficient dose to a subject that will potentially generate, or is likely to generate, one or more radiation late effects, symptoms or conditions in the subject, e.g., any radiation-associated symptom or condition disclosed herein. In any of these embodiments, dosing of the subject with the formula 1 compound can be on a daily dosing basis or on an intermittent basis, e.g., using a treatment protocol essentially as described herein or in the cited references.

The formula 1 compounds can be used to prevent, ameliorate, slow the progression and/or reduce the ultimate severity of marrow hypoplasia, hemorrhage, e.g., brainstem hemorrhage, cerebral hemorrhage or gastric hemorrhage or cytopenia, e.g., a blood cell count about 4-25% or more below the low end of a normal range for the subject, e.g., one or more of anemia (e.g., less than about $4.0 \times 10^{12}$ red cells/L for adult human females and less than about $4.5 \times 10^{12}$ red cells/L in adult human males or a hemoglobin level of less than about 12.0 g/dL in adult human females and less than about 13.5 g/dL in adult human males), late effect leukopenia (e.g., adult human white blood cell counts less than about 3,800, 4,000 or 4,300 $mm^{-3}$; adult human basophil counts less than about 10 or 15 $mm^{-3}$; adult human neutrophil counts less than about 1,600, 1,800 or 2,000 $mm^{-3}$; human eosinophil level less than about 100, 120 or 150 $mm^{-3}$; monocyte level less than about 260 or 300 $mm^{-3}$) or late effect thrombocytopenia (e.g., human platelet counts less than about 15,000, 18,000 or 20,000 $mm^{-3}$).

In some embodiments, an effective amount of a formula 1 compound is administered to a subject, or delivered to the subject's tissues, wherein the subject has received or has been exposed to a total radiation dose of at least about 0.5 Gy to about 100 Gy or more. The radiation dosage may comprise a single dose or two, three, four, five, six, 10 or more divided doses or subdoses. Thus, in exemplary embodiments, the subject may have received a total radiation dose in ranges of about 0.2-300 Gy, about 0.2-100 Gy, about 0.2-80 Gy 0.2-60 Gy, about 0.2-40 Gy, about 0.2-20 Gy, about 0.2-12 Gy, about 0.2-10 Gy, about 0.2-8 Gy, about 0.2-6 Gy or about 0.2-4 Gy. Subdivided doses may be administered on 1, 2, 3, 4, 5, 6, 7, 8, 9, 10 or more occasions and such doses may be, e.g., about 0.05, 0.1, 0.3., 0.5, 0.8, 1, 2, 3, 4, 5, 6 or more Gy per subdose. The subject may be exposed to radiation subdoses over a period of about one day or over several days, e.g., about 2, 3, 4, 5, 6, 8, 10, 20 or 25 days, or over a period of months, e.g., about 1, 2, 3, 4, 5, 6, 8, 10, 12, 15, 18, 24, 36, 48 or more months. When a subject is exposed to a full dose or a subdose of radiation, the exposure will occur over a period of about 1 minute to about 48 hours, typically about 2-120 minutes or about 4-60 minutes. Radiation doses or subdoses may be, e.g., about 0.01, 0.05, 0.1, 0.2, 0.5, 0.8, 1, 1.5, 2, 2.5, 3, 4, 5, 6 or 8 Gy per dose or subdose.

Administration of the formula 1 compound will typically commence at about 1 day to about 6 months after a subject has received a total radiation exposure, e.g., any dose or dose range disclosed herein. Typically, the formula 1 compound is used in the invention method commencing at about 2-30 days after radiation exposure or at about the time that radiation delayed effects become apparent to the subject or the subject's health care provider, e.g., within about 1-30 days after a condition or symptom is detected. Administration of the formula 1 compound may continue for a period of about 5 days to about 60 days for conditions or symptoms that tend to resolve over a relatively short time period. In other embodiments, the formula 1 compound is administered for a period of 2, 3, 4, 5, 6, 8, 10, 12, 15, 18, 24, 36, 48, 60 or more months for conditions or symptoms that tend to be chronic (e.g., neurological damage or inflammation), arise over a long time period (e.g., secondary cancers or neurological damage) or to progress over a relatively long time, e.g., about 1-5 years or more (e.g., cancers or neurological damage).

In any of the radiation exposure embodiments or dosing protocols disclosed herein, the formula 1 compound can be administered to the subject daily or on an intermittent basis, e.g., on about 1-5 days/week or about 2-10 days/month. In daily dosing embodiments, the formula 1 compound is administered to the subject daily for about 3 days to about 5 years or longer. Exemplary daily dosing embodiments include daily administration of a formula 1 compound for about 14, 30, 60, 90, 120, 180, 360 or more days. Daily doses may be administered in a single dose or as divided subdoses that are given, e.g., twice, three times, four times or more per day. In intermittent dosing embodiments, the formula 1 compound can be administered to the subject on 1, 2, 3, 4 or 5 days within a one week period, followed by a period of about 1, 2, 3, 4, 5, 6, 7, 8, 9, 10, 12, 16, 20, 24, 28 or 32 weeks without administration of the formula 1 compound, followed by administration of the formula 1 compound to the subject on 1, 2, 3, 4 or 5 days within a one week period. In other intermittent dosing embodiments, the formula 1 compound is administered to the subject every other day, every two days, every three days, every 4 days or every seven days.

For any radiation exposure situation where delayed radiation effects may arise, e.g., a radiation exposure as disclosed herein, daily administration may comprise administering about 0.01 mg/kg to about 500 mg/kg of the formula 1 compound to a subject per day. Exemplary dosages are about 0.1-100 mg/kg/day and about 0.2-30 mg/kg/day. Exemplary unit doses comprise about 1, 5, 10, 15, 20, 25, 30, 40, 50, 75, 100, 200, 300 or 500 mg of a formula 1 compound in a suitable formulation. Exemplary unit dosages for humans or other subjects disclosed herein comprise a formulation that comprises about 1-1000 mg of a formula 1 compound or about 5-400 mg or about 10-300 mg, e.g., about 5, 10, 20, 25, 30, 40, 50, 60 75, 100, 150, 200, 250, 300, 400 or 500 mg. Larger unit dosages, e.g., about 10-400 mg, will generally be used with larger subjects such as humans, while smaller subjects such as rodents or dogs will generally utilize lower unit dosages, e.g., about 0.5-25 mg.

In some embodiments, the formula 1 compound is present in a formulation that comprises micronized compound, e.g., compound that is milled, sieved, ground or the like. Micronized compound may be prepared using any suitable process for micronizing, a number of which are known in the art. The micronized particles may include a percentage of particles that are less than or equal to about 0.1-20 µm in diameter. Micronized preparations may comprise formula 1 compounds having an average particle size of about 0.02, 0.05, 0.1, 0.2, 0.4, 0.5, 1, 2, 5, 10 15, 20, 30 or 50 µm. Ranges of average particle sizes include formula 1 compounds of about 0.1-0.5 µm, about 0.1-0.4 µm, about 0.5-1 µm, about 1-20 µm or about 2-50 µm. An alternative to micronizing a compound is to solubilize the compound and incorporate it into liposomes of appropriate size. The manufacture of liposomes and the insertion of active ingredients into such liposomes are known.

Numbered embodiments. Several aspects of the invention and related subject matter includes the following numbered embodiments.

In some aspects, the invention relates to non-aqueous liquid formulations that comprise a formula 1 compound. Exemplary embodiments are as follows.

1. A composition comprising one or more compounds of formula 1 or formula 2 and one or more nonaqueous liquid excipients, wherein the composition comprises less than about 3% v/v water.

2. The composition of embodiment 1 wherein the one or more formula 1 compounds has the structure

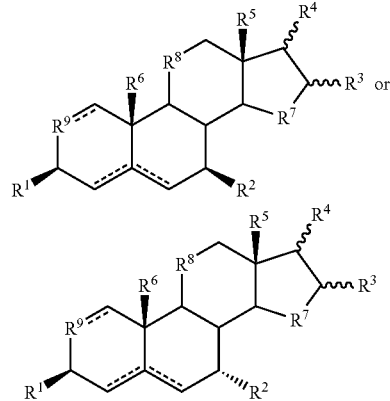

wherein $R^7$ and $R^9$ independently are —$CHR^{10}$—, —$CH_2$—, —CH=, —O—, —S— or —NH—, wherein $R^{10}$ is —OH, —SH, $C_{1-10}$ optionally substituted alkyl, $C_{1-10}$ optionally substituted alkoxy, $C_{1-10}$ optionally substituted alkenyl or $C_{1-10}$ optionally substituted alkynyl; and $R^8$ is —$CH_2$—, —O—, —S— or —NH—, wherein hydrogen atoms at the 5 (if present), 8, 9 and 14 positions respectively are α.α.α.α (i.e., 5α, 8α, 9α, 14α), α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β, typically α.α.β.α or β.α.β.α.

3. The composition of embodiment 2 wherein the one or more formula 1 compounds has the structure

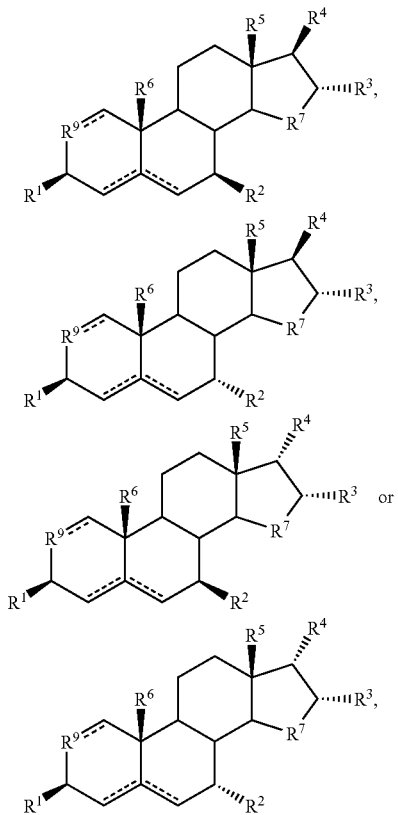

wherein hydrogen atoms at the 5 (if present), 8, 9 and 14 positions respectively are α.α.α.α, α.α.α.β, α.α.β.α, α,β,α,α, β,α,α,α, α,α,β,β, α,β,α,β, β,α,α,β, β,α,β,α, β,β,α,α, α,β,β,α, α,β,β,β, β,α,β,β, β,β,α,β, β,β,β,α or β,β,β,β, typically α,α,β,α or β,α,β,α.

4. The composition of embodiments 1, 2 or 3 wherein one, two, three or four formula 1 compounds are present.

5. The composition of embodiments 1, 2, 3 or 4 wherein the composition comprises less than about 0.3% v/v water.

6. The composition of embodiments 1, 2, 3, 4 or 5 wherein the one or more nonaqueous liquid excipients is one, two or more of an alcohol, a polyethylene glycol, propylene glycol or benzyl benzoate.

7. The composition of any of embodiments 1-6 (embodiment 1, 2, 3, 4, 5 or 6) wherein the formula 1 compound is 16α-bromo-3β-hydroxy-5α-androstan-17-one, 16α-bromo-3β,7β-dihydroxy-5-androstan-17-one, 16α-bromo-3β,7β,17β-trihydroxy-5α-androstene, 16α-bromo-3β,7α-dihydroxy-5α-androstan-17-one, 16α-bromo-3β,7α,17β-trihydroxy-5-androstene, 16α-bromo-3β,7β-dihydroxy-5α-androstane, 16α-bromo-3β,7β-dihydroxy-5-androstene, 16α-bromo-3β,7β,17β-trihydroxy-5α-androstane, 16β-bromo-3β,17β-dihydroxy-5α-androstane, 16β-bromo-3β,17β-dihydroxy-5-androstene, 16β-bromo-3β,7β,17β-trihydroxy-5α-androstane, 16β-bromo-3β-hydroxy-5α-androstane, 16β-bromo-3β-hydroxy-5α-androsten-17-one, 16β-bromo-3β,7β,-dihydroxy-5α-androstan-17-one, 16β-bromo-3β,7β,-dihydroxy-5α-androsten-17-one, 3β,7α,-dihydroxyepiandrosterone, 3β,7β,-dihydroxyepiandrosterone, 3β,-hydroxy-7-oxoepiandrosterone.

8. The composition of embodiment 7 wherein the formula 1 compound is 16α-bromo-3β-hydroxy-5α-androstan-17-one.

9. The composition of any of embodiments 1-8 wherein the composition comprises two, three, four or five nonaqueous liquid excipients.

10. The composition of embodiment 9 wherein the composition comprises three or more nonaqueous liquid excipients.

11. The composition of any of embodiments 1-10 wherein the formula 1 compound comprises about 0.0001-99% w/v of the composition.

12. The composition of any of embodiments 1-11 wherein the composition comprises a unit dose.

13. The composition of embodiment 12 wherein the unit dose comprises about 0.5-100 mg/mL of the formula 1 compound.

14. The composition of embodiment 10 wherein the composition comprises about 1.0-60 mg/mL of the formula 1 compound.

15. The composition of embodiment 14 wherein the formula 1 compound is 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstene, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one or 16β-bromo-3β,7β,-dihydroxy-5α-androsten-17-one.

16. The composition of embodiment 1 wherein the one or more nonaqueous liquid excipients comprise a polyethylene glycol, propylene glycol and benzyl benzoate.

17. The composition of embodiment 16 wherein the composition comprises less than about 0.3% v/v water.

18. The composition of embodiment 17 wherein the formula 1 compound is 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstene, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one or 16β-bromo-3β,7β,-dihydroxy-5α-androsten-17-one.

19. The composition of embodiment 18 wherein the formula 1 compound is 16α-bromo-3β-hydroxy-5α-androstan-17-one.

20. The composition of embodiment 16 that further comprises an alcohol.

21. The composition of embodiment 20 wherein the formula 1 compound is 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstene, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one or 16β-bromo-3β,7β,-dihydroxy-5α-androsten-17-one.

22. The composition of embodiment 1 wherein the one or more nonaqueous liquid excipients comprise benzyl benzoate, a polyethylene glycol, an alcohol and optionally an additional nonaqueous liquid excipient.

23. The composition of embodiment 22 wherein the composition comprises less than about 0.3% v/v water.

24. The composition of embodiment 22 or 23 wherein the formula 1 compound is 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstane, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one or 16β-bromo-3β,7β,-dihydroxy-5α-androsten-17-one.

25. The composition of embodiment 24 wherein the formula 1 compound is 16α-bromo-3β-hydroxy-5α-androstan-17-one.

26. The composition of embodiment 22, 23, 24 or 25 wherein the polyethylene glycol is polyethylene glycol 300 and/or polyethylene glycol 200.

27. The composition of embodiment 26 wherein the alcohol is polyethylene glycol is polyethylene glycol 300.

28. The composition of embodiments 22 or 23 that comprises about 2.5-25% v/v ethanol, about 1-10% v/v benzyl benzoate, about 10-35% v/v polyethylene glycol 300, about 40-65% v/v propylene glycol and about 2-60 mg/mL 16α-bromo-3β-hydroxy-5α-androstan-17-one.

28A. The composition of embodiments 22, 23, 24, 25 or 26 that comprises about 0.1-10% v/v benzyl benzoate, about 0.1-10% v/v benzyl alcohol, about 1-95% v/v polyethylene glycol 200, about 1-95% v/v propylene glycol and about 2-60 mg/mL 16α-bromo-3β-hydroxy-5α-androstan-17-one. The embodiment 28A composition may comprise about 2% v/v benzyl benzoate, about 2% v/v benzyl alcohol, about 40% v/v polyethylene glycol 200, about 51% v/v propylene glycol (qs) and about 50 mg/mL 16α-bromo-3β-hydroxy-5α-androstan-17-one.

29. The composition of embodiment 28 that comprises about 12.5% v/v ethanol, about 5% v/v benzyl benzoate, about 25% v/v polyethylene glycol 300, about 57.5% v/v propylene glycol and about 50 mg/mL 16α-bromo-3β-hydroxy-5α-androstan-17-one.

30. The composition of any of embodiments 1-29 that further comprises a local anesthetic.

31. The composition of embodiment 30 wherein the local anesthetic is procaine, benzocaine or lidocaine.

32. The composition of any of embodiments 1-31 wherein the composition comprises a solvate, a suspension, a colloid, a gel or a combination of any of the foregoing.

33. A product produced by the process of contacting a composition comprising one or more compounds of formula 1 and a first nonaqueous liquid excipient with a second nonaqueous liquid excipient wherein the product comprises less than about 3% water and the salts, analogs, configurational isomers and tautomers thereof.

34. The product of embodiment 33 wherein the product comprises less than about 0.3% water.

35. The product of embodiments 33 or 34 wherein the first nonaqueous liquid excipient is a polyethylene glycol (e.g., PEG300 or PEG 200) or propylene glycol.

36. The product of embodiments 33, 34 or 35 wherein the second nonaqueous liquid excipient is a polyethylene glycol (e.g., PEG300 or PEG 200) or propylene glycol.

38. A product produced by the process of contacting a composition comprising one or more compounds of formula 1 and two nonaqueous liquid excipients with a third nonaqueous liquid excipient wherein the product comprises less than about 3% water and the salts, analogs, configurational isomers and tautomers thereof.

39. The product of embodiment 38 wherein the product comprises less than about 0.3% water.

40. The product of embodiments 38 or 39 wherein the two nonaqueous liquid excipients are selected from a polyethylene glycol (e.g., PEG300 or PEG 200), propylene glycol, benzyl benzoate and an alcohol (e.g., ethanol).

41. The product of embodiments 38, 39 or 40 wherein the third nonaqueous liquid excipient is a polyethylene glycol (e.g., PEG300 or PEG 200), propylene glycol, benzyl benzoate or an alcohol (e.g., ethanol).

42. A product produced by the process of contacting a composition comprising one or more compounds of formula 1 and three nonaqueous liquid excipients with a fourth nonaqueous liquid excipient wherein the product comprises less than about 3% water and the salts, analogs, configurational isomers and tautomers thereof.

43. The product of embodiment 42 wherein the product comprises less than about 0.3% water.

44. The product of embodiments 42 or 43 wherein the three nonaqueous liquid excipients are selected from a polyethylene glycol (e.g., PEG300 or PEG 200), propylene glycol, benzyl benzoate and an alcohol (e.g., ethanol).

45. The product of embodiments 42, 43 or 44 wherein the fourth nonaqueous liquid excipient is a polyethylene glycol (e.g., PEG300 or PEG 200), propylene glycol, benzyl benzoate or an alcohol (e.g., ethanol).

46. The product of any of embodiments 33-45 wherein the product has been stored at reduced temperature (about 4° C. to about 8° C.) or at ambient temperature for about 30 minutes to about 2 years.

47. The product of any of embodiments 33-46 wherein the one or more compounds of formula 1 comprise 1, 2, 3 or 4 formula 1 compounds.

48. The product of any of embodiments 33-46 wherein the one or more compounds of formula 1 comprises one formula 1 compound.

49. The product of any of embodiments 33-48 wherein the one or more formula 1 compound is selected from 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstene, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one and 16β-bromo-3β,7β,-dihydroxy-5α-androsten-17-one.

50. The product of embodiment 49 wherein the formula 1 compound is 16α-bromo-3β-hydroxy-5α-androstan-17-one.

51. The product of embodiment 49 that comprises about 2.5-25% v/v ethanol, about 1-10% v/v benzyl benzoate, about 10-35% v/v polyethylene glycol 300, about 40-65% v/v propylene glycol and about 2-60 mg/mL 16α-bromo-3β-hydroxy-5α-androstan-17-one.

52. The product of embodiment 51 that comprises about 12.5% v/v ethanol, about 5% v/v benzyl benzoate, about 25% v/v polyethylene glycol 300, about 57.5% v/v propylene glycol and about 50 mg/mL 16α-bromo-3β-hydroxy-5α-androstan-17-one.

53. The product of any of embodiments 33-52 that further comprises a local anesthetic.

54. The composition of 52 wherein the local anesthetic is procaine, benzocaine or lidocaine.

55. A product produced by the process of contacting a composition comprising a compound of formula 1 with a nonaqueous liquid excipient wherein the product comprises less than about 3% v/v water and the salts, analogs, configurational isomers and tautomers thereof.

56. The product of embodiment 55 wherein the product comprises less than about 0.3% v/v water.

57. The product of embodiment 53 wherein the product has been stored at reduced temperature (about 0° C. to about 8° C.) or at ambient temperature for about 1 hour to about 2 years.

58. The product of embodiment 53 wherein the first nonaqueous liquid excipient is a polyethylene glycol, an alcohol, propylene glycol or benzyl benzoate.

59. The product of any of embodiments 33-58 wherein the formula 1 compound comprises about 0.01% to about 99% w/v of the product.

60. The product of any of embodiments 33-59 wherein the product is a unit dose.

61. The unit dose of embodiment 60 comprising a solution containing about 0.5-70 mg/mL of the one or more formula 1 compound.

62. The product of any of embodiments 55-61 wherein the one or more formula 1 compound is selected from 16α-bromo-3β-hydroxy-5α-androstan-17-one, 16α-bromo-3β, 7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstene, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one and 16β-bromo-3β,7β,-dihydroxy-5α-androsten-17-one.

63. The product of embodiment 62 wherein the formula 1 compound is 16α-bromo-3β-hydroxy-5α-androstan-17-one.

64. The product of any of embodiments 33-61 wherein the one or more formula 1 compound is selected from the compounds or one or more of the species of compounds within the genera named in compound groups 1 through 21-10-6.

65. A method comprising administering the composition or product of any of embodiments 1-64 to a subject suffering from a pathogen infection or a malignancy or an immune suppression or disregulation condition, e.g., a suppressed Th1 immune response or an unwanted Th2 immune response.

66. The method of embodiment 65 wherein the pathogen infection is a DNA virus infection or an RNA virus infection.

67. The method of embodiment 66 wherein the RNA virus infection is a retrovirus infection or a hepatitis virus infection.

68. The method of embodiment 67 wherein the retrovirus infection or hepatitis virus infection is an HIV, FIV, SIV, SHIV or hepatitis C virus infection.

69. The method of embodiment 65 wherein the pathogen infection is an intracellular parasite infection.

70. The method of embodiment 69 wherein the intracellular parasite infection is a malaria infection.

71. The method of embodiment 65 wherein the formula 1 compound has the structure

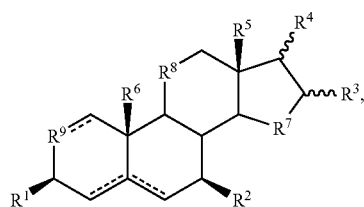

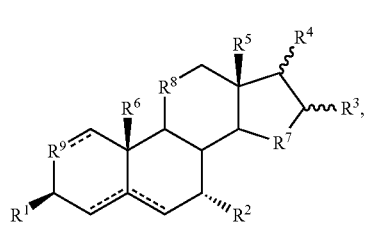

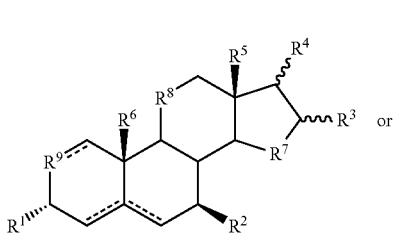

-continued

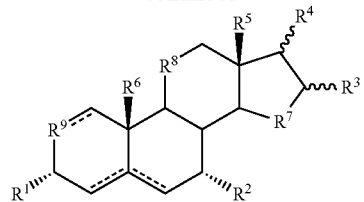

wherein one, two or three of $R^7$, $R^8$ and $R^9$ are —$CH_2$— or —CH= and wherein the configuration of hydrogen atoms at the 5 (if present), 8, 9 and 14 positions respectively are α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β, typically α.α.β.α or β.α.β.α.

72. The method of embodiment 71 wherein the formula 1 compound has the structure

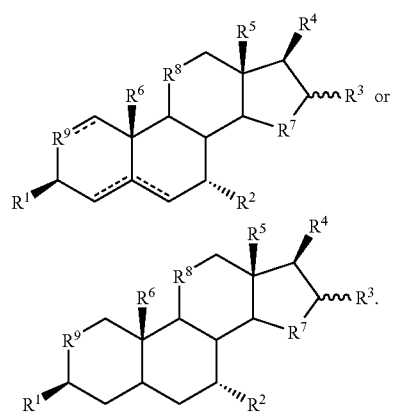

73. The method of embodiment 72 wherein $R^1$, $R^2$ and $R^4$ independently are —OH, aC2-C20 ester or C1-C20 alkoxy, $R^3$ is —H and two or three of $R^7$, $R^8$ and $R^9$ are —$CH_2$—.

74. The method of embodiment 72 or 73 wherein the formula 1 compound has the structure

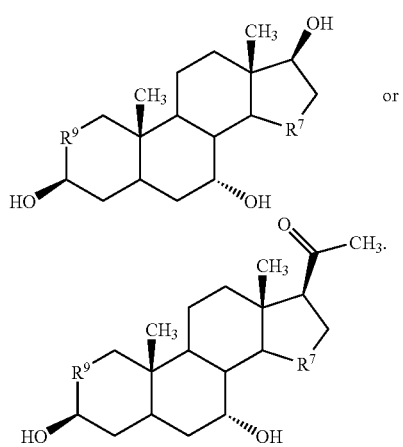

75. The method of any of embodiments 71-74 wherein the configuration of hydrogen atoms at the 5 (if present), 8, 9 and 14 positions respectively are α.α.β.α or β.α.β.α.

In other embodiments, the formula 1 compounds include new compounds, some of which are described in the following numbered embodiments.

1A. A compound of formula 1 having the structure

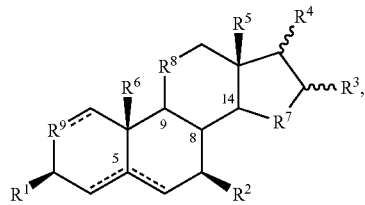

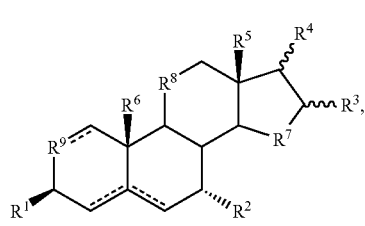

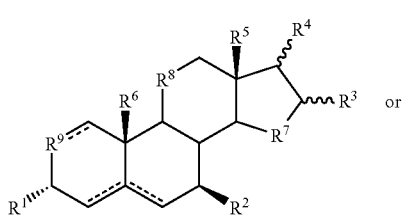

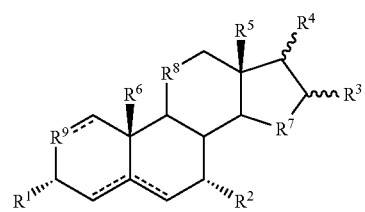

wherein $R^7$, $R^8$ and $R^9$ are independently selected and wherein one, two or three of $R^7$, $R^8$ and $R^9$ are not —CH$_2$— or —CH═ and wherein hydrogen atoms at the 5 (if present), 8, 9 and 14 positions respectively are in the α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.βconfigurations, typically α.α.β.α or β.α.β.α.

2A. The compound of embodiment 1A wherein $R^8$ is —CH$_2$—, —O—, —S— or —NH—.

3A. The compound of embodiment 1A or 2A wherein $R^7$ is —CH$_2$—CHR$^{10}$—, —O—CHR$^{10}$— or —O—C(O)—.

4A. The compound of embodiment 1A, 2A or 3A wherein $R^8$ or $R^9$ is absent.

5A. The compound of embodiment 1A or 2A wherein $R^7$ and $R^9$ independently are —CHR$^{10}$—, —CH$_2$—, —CH═, —O—, —S— or —NH—, wherein $R^{10}$ is —OH, —SH, a $C_{1-30}$ organic moiety, a $C_{1-30}$ ester, $C_{1-10}$ optionally substituted alkyl, $C_{1-10}$ optionally substituted alkoxy, $C_{1-10}$ optionally substituted alkenyl or $C_{1-10}$ optionally substituted alkynyl.

6A. The compound of embodiment 1A, 2A, 3A, 4A or 5A wherein the formula 1 compound has the structure

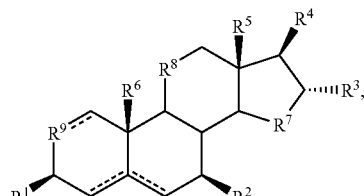

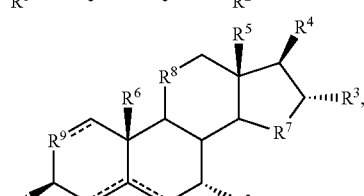

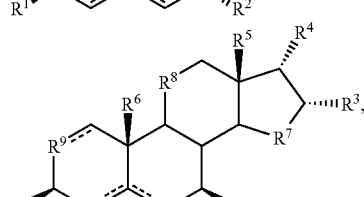

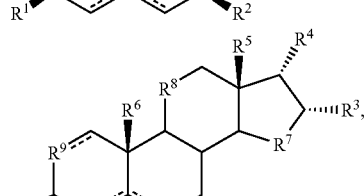

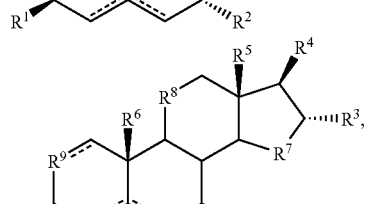

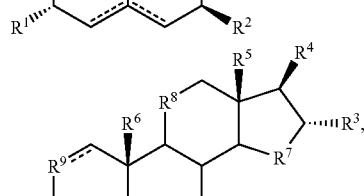

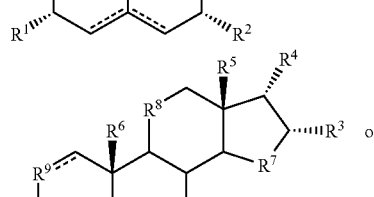

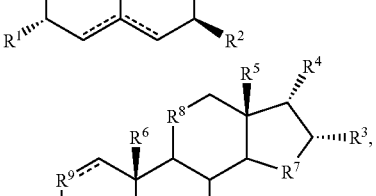

wherein hydrogen atoms at the 5 (if present), 8, 9 and 14 positions respectively are in the α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β configurations, typically α.α.β.α or β.α.β.α.

7A. The compound of embodiment 6A wherein $R^4$ is —OH, =O, —SH, a $C_{1-30}$ ester or $C_{1-30}$ alkoxy, wherein the ester or alkoxy moiety is optionally substituted with one, two or more independently selected substituents, which are optionally selected from —F, —Cl, —Br, —I, —O—, =O, —S—, —NH—, —OR$^{PR}$, —SR$^{PR}$ or —NHR$^{PR}$.

8A. The compound of embodiment 6A or 7A wherein $R^1$ is —OH, =O, —SH, a $C_{1-30}$ ester or $C_{1-30}$ alkoxy, wherein the ester or alkoxy moiety is optionally substituted with one, two or more independently selected substituents, which are optionally selected from —F, —Cl, —Br, —I, —O—, =O, —S—, —NH—, —OR$^{PR}$, —SR$^{PR}$ or —NHR$^{PR}$.

9A. The compound of embodiment 1A, 2A or 3A wherein the formula 1 compound has the structure

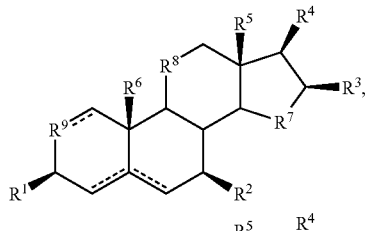

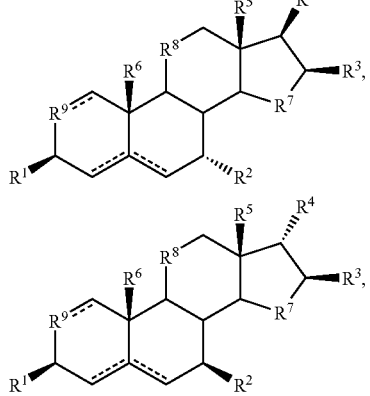

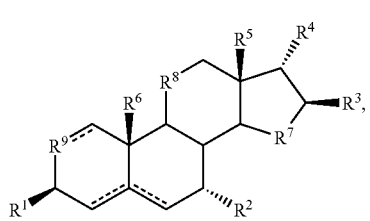

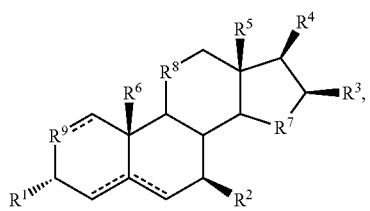

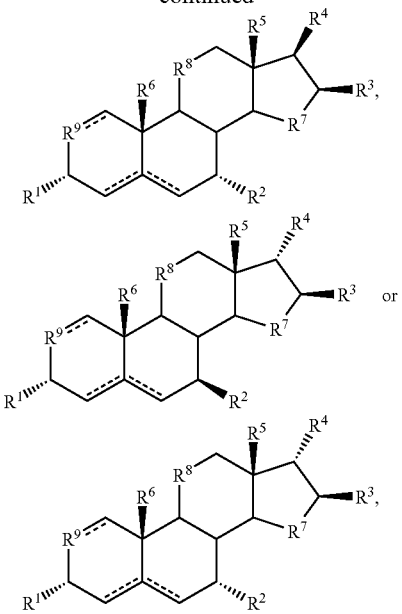

wherein hydrogen atoms at the 5 (if present), 8, 9 and 14 positions respectively are α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β, typically α.α.β.α or β.α.β.α.

10A. The compound of embodiment 9A wherein $R^4$ is —OH, =O, —SH, a $C_{1-30}$ ester or $C_{1-30}$ alkoxy, wherein the ester or alkoxy moiety is optionally substituted with one, two or more independently selected substituents, which are optionally selected from —F, —Cl, —Br, —I, —O—, =O, —S—, —NH—, —OR$^{PR}$, —SR$^{PR}$ or —NHR$^{PR}$.

11A. The compound of embodiment 9A or 10A wherein $R^1$ is —OH, =O, —SH, a $C_{1-30}$ ester or $C_{1-30}$ alkoxy, wherein the ester or alkoxy moiety is optionally substituted with one, two or more independently selected substituents, which are optionally selected from —F, —Cl, —Br, —I, —O—, =O, —S—, —NH—, —OR$^{PR}$, —SR$^{PR}$ or —NHR$^{PR}$.

12A. A composition comprising a compound of any of embodiments 1A-11A and an excipient suitable for human pharmaceutical use or for veterinary use, e.g., an excipient disclosed herein or in the cited references.

13A. A product produced by the process of contacting a compound of any of embodiments 1A-11A and an excipient suitable for human pharmaceutical use or for veterinary use, e.g., an excipient disclosed herein or in the cited references.

14A. The use of a compound, composition or product of any of embodiments 1A-13A to prepare a medicament for use to prevent or to treat, or to ameliorate one or more symptoms associated, with an infection, an immunosuppression condition, a malignancy, a pre-malignant condition or to modulate a mammal's immune response, such as enhancing a Th1 response or decreasing a Th2 response, e.g., an infection, malignancy or immune dysregulation as described herein or in the cited references.

15A. The use of embodiment 14A, wherein the infection is a viral infection (e.g., HIV, HCV, a Herpesvirus, a togavirus, a human papilloma virus infection or other virus described herein or in the cited references), a bacterial infection (e.g., *Borrelia* sp., *Legionella* sp. or other bacterium described herein or in the cited references), a fungal or a yeast infection (e.g., *Candida* sp., *Aspergillus* sp. or other yeast described herein or in the cited references) or a parasite infection (e.g., a malaria parasite, a gastrointestinal nematode, a helminth, *Leishmania* sp., *Cryptosporidium* sp., *Toxoplasma gondii*, *Pneumocystis Schistosoma* sp. (e.g., *S. mansoni, S. japonicum, S. haematobium*), *Strongyloides stercoralis* or other parasite described herein or in the cited references).

16A. The compound, composition, product or use of any of embodiments 1A-15A, wherein the formula 1 compound is a compound named in any of compound groups 1 through 54-53-52-51a6-50c27-49c27-48-47-46-45-44-43-42-41-40-39-38-37-36-35-34-33-32-31-30-29-28-27-39-38-37-36-35-34-33-32-31-30-29-28-27-26-25-23-21-17-10-8-6, or the formula 1 compound is a species in any genus described in any of compound groups 1 through 54-53-52-51a6-50c27-49c27-48-47-46-45-44-43-42-41-40-39-38-37-36-35-34-33-32-31-30-29-28-27-39-38-37-36-35-34-33-32-31-30-29-28-27-26-25-23-21-17-10-8-6.

In other aspects, the invention provides dosing methods suitable to treat the conditions described herein. The following embodiments describe some of these methods.

1B. A method comprising intermittently administering one or more compounds of formula 1 (or a composition comprising a formula 1 compound) to a subject or delivering to the subject's tissues a formula 1 compound(s) (or a composition comprising a formula 1 compound), e.g., any formula 1 compound named or described herein, or a metabolic precursor or a biologically active metabolite thereof, including the compounds described in embodiments 1-64 and 1A-11A above.

2B. The method of embodiment 1B wherein the subject has an infection, a hyperproliferation disorder, a hypoproliferation condition, an immunosuppression condition, an unwanted immune response or wherein the subject has recently experienced or will shortly experience trauma, surgery or a therapeutic treatment wherein the therapeutic treatment is one other than the method of embodiment 1B.

3B. The method of embodiment 2B wherein the immunosuppression condition or the unwanted immune response is associated with a viral infection, an intracellular bacterial infection, an extracellular bacterial infection, a fungal infection, a yeast infection, an extracellular parasite infection, an intracellular parasite infection, a protozoan parasite, a multicellular parasite, an autoimmune disease, a cancer, a precancer, a chemotherapy, a radiation therapy, an immunosuppressive therapy, an anti-infective agent therapy, a wound, a burn, the presence of an immunosuppressive molecule, gastrointestinal irritation or an inflammation condition optionally selected from or associated with irritable bowel disease, Crohn's disease or chronic diarrhea, or any combination of the foregoing.

4B. The method of embodiment 3B wherein the subject's immunosuppression condition is ameliorated or the unwanted immune response (e.g., a Th2 response) is reduced or wherein the subject's Th1 immune response is enhanced.

5B. The method of embodiment 3B wherein the subject's innate immunity, specific immunity or both is enhanced.

6B. The method of embodiment 5B wherein the subject's innate immunity is enhanced.

7B. The method of embodiment 6B wherein the subject's specific immunity is enhanced, e.g., wherein the subject's Th2 immune response is reduced or wherein the subject's Th1 immune response is enhanced.

8B. The method of embodiment 2B wherein the one or more compounds of formula 1 is or are administered according to the a dosing regimen comprising the steps, (a) administering the one or more compounds of formula 1 to the subject at least once per day for at least 2 days; (b) not administering the one or more formula 1 compounds to the subject for at least 1 day; (c) administering the one or more formula 1 compounds to the subject at least once per day for at least 2 days; and (d) optionally repeating steps (a), (b) and (c) at least once or variations of steps (a), (b) and (c) at least once.

9B. The method of embodiment 8B wherein step (c) comprises the same dosing regimen as step (a).

10B. The method of embodiment 9B wherein step (a) of the dosing regimen comprises administering the one or more formula 1 compounds once per day, twice per day, three times per day or four times per day.

11B. The method of embodiment 10B wherein step (a) of the dosing regimen comprises administering the one or more formula 1 compounds once per day or twice per day.

12B. The method of embodiment 10B wherein step (a) comprises administering the one or more formula 1 compounds for about 3 to about 24 days.

13B. The method of embodiment 12B wherein step (a) comprises administering the one or more formula 1 compounds for about 4 to about 12 days.

14B. The method of embodiment 13B wherein step (a) comprises administering the one or more formula 1 compounds for about 4 to about 8 days.

15B. The method of embodiment 14B wherein step (b) comprises not administering the one or more formula 1 compounds for about 3 to about 120 days.

16B. The method of embodiment 15B wherein step (b) comprises not administering the one or more formula 1 compounds for about 4 to about 60 days.

17B. The method of embodiment 16B wherein step (b) comprises not administering the one or more formula 1 compounds for about 5 to about 30 days.

18B. The method of embodiment 16B wherein step (b) comprises not administering the one or more formula 1 compounds for about 8 to about 60 days. 19B.

The method of embodiment 15B wherein steps (a), (b), and (c) are repeated at least about 4 times.

20B. The method of embodiment 15B wherein steps (a), (b), and (c) are repeated about 5 times to about 25 times.

21B. The method of embodiment 15B wherein steps (a), (b), and (c) and repetitions of steps (a), (b), and (c) occur over a time period of at least about 2 months.

22B. The method of embodiment 15B wherein steps (a), (b), and (c) and repetitions of steps (a), (b), and (c) occur over a time period of at least about 12 months.

23B. The method of embodiment 8B wherein step (b) comprises not administering the one or more formula 1 compounds for about 3 to about 120 days.

24B. The method of embodiment 23B wherein step (b) comprises not administering the one or more formula 1 compounds for about 4 to about 60 days.

25B. The method of embodiment 24B wherein step (b) comprises not administering the one or more formula 1 compounds for about 5 to about 30 days.

26B. The method of embodiment 23B wherein step (b) comprises not administering the one or more formula 1 compounds for about 8 to about 60 days.

27B. The method of embodiment 8B wherein step (d) comprises repeating steps (a), (b), and (c) at least once.

28B. The method of embodiment 27B wherein step (d) comprises repeating steps (a), (b), and (c) about 3 times to about 25 times.

29B. The method of embodiment 1B wherein steps (a), (b), and (c) and repetitions of steps (a), (b), and (c) occur over a time period of at least about 2 months.

30B. The method of embodiment 29B wherein steps (a), (b), and (c) and repetitions of steps (a), (b), and (c) occur over a time period of at least about 12 months.

31B. The method of any of embodiments 8B-30B wherein the immunosuppression condition or the unwanted immune response is associated with a viral infection, an intracellular bacterial infection, an extracellular bacterial infection, a fungal infection, a yeast infection, an extracellular parasite infection, an intracellular parasite infection, a protozoan parasite, a multicellular parasite, an autoimmune disease, a cancer, a precancer, a chemotherapy, a radiation therapy, an immunosuppressive therapy, an anti-infective agent therapy, a wound, a burn, the presence of an immunosuppressive molecule, gastrointestinal irritation or an inflammation condition optionally selected from or associated with irritable bowel disease, Crohn's disease or chronic diarrhea, or any combination of the foregoing.

32B. The method of embodiment 31B wherein the subject's immunosuppression condition is ameliorated or the unwanted immune response is reduced.

33B. The method of embodiment 32B wherein the subject's innate immunity, specific immunity or both is enhanced.

34B. The method of embodiment 33B wherein the subject's innate immunity is enhanced.

35B. The method of embodiment 34B wherein the subject's specific immunity is enhanced.

36B. The method of embodiment 8B wherein step (c) comprises the a shorter dosing regimen than step (a).

37B. The method of embodiment 36B wherein step (a) comprises administering the formula 1 compound for 7 to about 24 days.

38B. The method of embodiment 37B wherein step (c) comprises administering the formula 1 compound for 4 to about 12 days.

39B. The method of embodiment 38B wherein step (b) comprises not administering the formula 1 compound for about 3 to about 120 days.

40B. The method of embodiment 39B wherein step (b) comprises not administering the formula 1 compound for about 4 to about 60 days.

41B. The method of embodiment 40B wherein step (b) comprises not administering the formula 1 compound for about 5 to about 30 days.

42B. The method of embodiment 36B wherein step (d) comprises repeating steps (a), (b), and (c) at least once.

43B. The method of embodiment 42B wherein step (d) comprises repeating steps (a), (b), and (c) about 3 times to about 25 times.

44B. The method of embodiment 36B wherein steps (a), (b), and (c) and repetitions of steps (a), (b), and (c) occur over a time period of at least about 2 months.

45B. The method of embodiment 44B wherein steps (a), (b), and (c) and repetitions of steps (a), (b), and (c) occur over a time period of at least about 12 months.

46B. The method of any of embodiments 36B-45B wherein the immunosuppression condition or the unwanted immune response is associated with a viral infection, an intracellular bacterial infection, an extracellular bacterial infection, a fungal infection, a yeast infection, an extracellular parasite infection, an intracellular parasite infection, a protozoan parasite, a multicellular parasite, an autoimmune disease, a cancer, a precancer, a chemotherapy, a radiation therapy, an immunosuppressive therapy, an anti-infective agent therapy, a wound, a burn, the presence of an immunosuppressive molecule, gastrointestinal irritation or an inflammation condition optionally selected from or associated with irritable bowel, Crohn's disease, chronic diarrhea, or any combination of the foregoing.

47B. The method of embodiment 46B wherein the subject's immunosuppression condition is ameliorated or the unwanted immune response is reduced.

48B. The method of embodiment 47B wherein the subject's innate immunity, specific immunity or both is enhanced.

49B. The method of embodiment 48B wherein the subject's innate immunity is enhanced.

50B. The method of embodiment 48B wherein the subject's specific immunity is enhanced.

51B. The method of embodiment 8B wherein step (c) comprises a longer dosing period than step (a).

52B. The method of embodiment 51B wherein step (a) comprises administering the formula 1 compound for 7 to about 24 days.

53B. The method of embodiment 52B wherein step (c) comprises administering the formula 1 compound for 4 to about 12 days.

54B. The method of embodiment 53B wherein step (b) comprises not administering the formula 1 compound for about 3 to about 120 days.

55B. The method of embodiment 54B wherein step (b) comprises not administering the formula 1 compound for about 4 to about 60 days.

56B. The method of embodiment 55B wherein step (b) comprises not administering the formula 1 compound for about 5 to about 30 days.

57B. The method of embodiment 51B wherein step (d) comprises repeating steps (a), (b), and (c) at least once.

58B. The method of embodiment 57B wherein step (d) comprises repeating steps (a), (b), and (c) about 3 times to about 25 times.

59B. The method of embodiment 51B wherein steps (a), (b), and (c) and repetitions of steps (a), (b), and (c) occur over a time period of at least about 2 months.

60B. The method of embodiment 59B wherein steps (a), (b), and (c) and repetitions of steps (a), (b), and (c) occur over a time period of at least about 12 months.

61B. The method of any of embodiments 51B-60B wherein the immunosuppression condition or the unwanted immune response is associated with a viral infection, an intracellular bacterial infection, an extracellular bacterial infection, a fungal infection, a yeast infection, an extracellular parasite infection, an intracellular parasite infection, a protozoan parasite, a multicellular parasite, an autoimmune disease, a cancer, a precancer, a chemotherapy, a radiation therapy, an immunosuppressive therapy, an anti-infective agent therapy, a wound, a burn, the presence of an immunosuppressive molecule, gastrointestinal irritation or an inflammation condition optionally selected from or associated with irritable bowel disease, Crohn's disease or chronic diarrhea, or any combination of the foregoing.

62B. The method of embodiment 61B wherein the subject's immunosuppression condition is ameliorated or the unwanted immune response is reduced.

63B. The method of embodiment 62B wherein the subject's innate immunity, specific immunity or both is enhanced or wherein the subject's Th1 immune response is enhanced or the subject's Th2 immune response is decreased.

64B. The method of embodiment 8B wherein the variations of steps (a), (b) and (c) comprise conducting a first dosing regimen of steps (a), (b) and (c) once, twice or three times, followed by one or more second dosing regimens of steps (a'), (b') and (c') wherein one or more of the (a'), (b') and (c') steps in the second dosing regimen is longer than the corresponding step in the first dosing regimen.

65B. The method of embodiment 8B wherein the variations of steps (a), (b) and (c) comprise conducting a first dosing regimen of steps (a), (b) and (c) once, twice or three times, followed by one or more second dosing regimens of steps (a'), (b') and (c') wherein one or more of the (a'), (b') and (c') steps in the second dosing regimen is shorter than the corresponding step in the first dosing regimen.

66B. The method of any of embodiments 1B-67B wherein the one or more formula 1 compounds is or are administered orally, intramuscularly, intravenously, subcutaneously, topically, vaginally, rectally, intracranially, intrathecally, intradermally, as an aerosol or by a buccal route.

67B. The method of embodiment 66B wherein the one or more formula 1 compounds is or are present in a solid formulation predominantly as a solid or the one or more formula 1 compounds is or are present in a liquid formulation predominantly as a solvate, colloid or a suspension or the one or more formula 1 compounds is or are present in a gel, cream or paste.

68B. The method of any of embodiments 2B-67B wherein the subject's viral infection, intracellular bacterial infection, extracellular bacterial infection, fungal infection, yeast infection, extracellular parasite infection, intracellular parasite infection, protozoan parasite, multicellular parasite, autoimmune disease, cancer, precancer, chemotherapy, radiation therapy, immunosuppressive therapy, anti-infective agent therapy, a wound, a burn, or the presence of an immunosuppressive molecule, gastrointestinal irritation or an inflammation condition optionally selected from or associated with irritable bowel disease, Crohn's disease or chronic diarrhea, or any combination of the foregoing is (a) a DNA virus infection or an RNA virus infection (HSV, CMV, HBV, HCV, HIV, SHIV, SIV); (b) a *Mycoplasma* infection, a *Listeria* infection or a *Mycobacterium* infection; (c) extracellular bacteria infection; (d) fungal infection; (e) a yeast infection (*Candida, Cryptococcus*); (d) protozoa (malaria, *Leishmania, Cryptosporidium, Toxoplasmosis, Pneumocystis*); (e) a multicellular parasite; (f) autoimmune diseases (SLE, RA, diabetes); (g) cancers (solid cancers selected from, e.g., ovarian, breast, prostate, glioma; disseminated cancers selected from lymphoma, leukemia, colon cancer, sarcoma); (h) precancers; (i) chemotherapies (adriamycin, cisplatin, mitomycin C); (j) radiation therapies; (k) immunosuppressive therapies; (l) anti-infective agent therapies; (m) wounds (surgical or otherwise); (n) $1^{st}$ degree, $2^{nd}$ degree or $3^{rd}$ degree burns; (o) immunosuppressive molecules; (p) gastrointestinal irritation or an inflammation condition optionally selected from or associated with irritable bowel, Crohn's disease, chronic diarrhea; or (q) any combination of (a) through (p).

69B. The method of embodiment 68B wherein the RNA virus infection is a retroviral infection or a hepatitis virus infection.

70B. The method of embodiment 68B or 69B wherein the one or more formula 1 compounds is one formula 1 compound.

71B. The method of embodiment 70B wherein the one or more formula 1 compounds is or are in a composition that comprises, (a) one or more nonaqueous liquid excipients, wherein the composition comprises less than about 3% v/v water; (b) a solid that comprises a pharmaceutically acceptable excipient; or (c) one or more liquid excipients, wherein the composition comprises more than about 3% v/v water.

72B. The method of embodiment 68B or 71B wherein the formula 1 compound is 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstene, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one or 16β-bromo-3β,7β,-dihydroxy-5α-androsten-17-one.

73B. The method of embodiment 72B wherein the formula 1 compound is 16α-bromo-3β-hydroxy-5α-androstan-17-one.

74B. The method of embodiments 1B-73B wherein the formula 1 compound excludes one or more of any formula 1 compounds.

75B. A method to treat involuntary weight loss, oral lesions, skin lesions, opportunistic infections, diarrhea or fatigue in an subject comprising intermittently administering one or more compounds of formula 1 to the subject (e.g., involuntary weight loss from viral infection, gastrointestinal infection, chemotherapy, anorexia, gastrointestinal irritation or an inflammation condition optionally selected from or associated with irritable bowel, Crohn's disease, chronic diarrhea).

76B. The method of embodiment 75B wherein the subject has an immunosuppression condition.

77B. The method of embodiment 76B wherein the subject is a human.

78B. The method of embodiment 77B wherein the subject is a human 1 day to 18 years old (e.g., 1 month to 6 years old).

79B. The method of any of embodiments 75B-78B wherein the subject's specific immunity remains impaired compared to a typical comparable control subject who does not have the subject's pathological condition.

80B. The method of embodiment 79B wherein the subject's CD4 cell count does not increase significantly during one or more courses of dosing (e.g., dosing for 1 week to about 2 weeks or more).

81B. The method of clam 80B wherein the subject's CD4 cell count is about 20 to about 100 $CD4^+$ cells/$mm^3$ or about 20 to about 75 $CD4^+$ cells/$mm^3$.

82B. The method of any of embodiments 1B-81B wherein the subject has a pathogen(s) infection or a malignancy and the pathogen(s) or malignancy does not become resistant to the formula 1 compound over a time normally associated with the development of measurable resistance in at least about 50% of subjects who are treated with a therapeutic treatment(s) other than a formula 1 compound(s).

83B. The method of embodiment 82B wherein the pathogen infection is an HIV, SIV, SHIV or HCV infection.

84B. The method of embodiments 82B or 83B wherein the formula 1 compound is one or more of 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstene, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one, 16β-bromo-3β,7β,-dihydroxy-5α-androsten-17-one or a physiologically acceptable ester, carbonate, carbamate, amino acid conjugate or peptide conjugate thereof.

85B. The method of embodiment 84B wherein the formula 1 compound is 16α-bromo-3β-hydroxy-5α-androstan-17-one or a physiologically acceptable ester, carbonate, carbamate, amino acid conjugate or peptide conjugate thereof.

86B. The method of any of embodiments 1B-85B or 87B-90B wherein the formula 1 compound is a compound named in any of compound groups 1 through 54-53-52-51a6-50c27-49c27-48-47-46-45-44-43-42-41-40-39-38-37-36-35-34-33-32-31-30-29-28-27-39-38-37-36-35-34-33-32-31-30-29-28-27-26-25-23-21-17-10-8-6, or the formula 1 compound is a species in any genus described in any of compound groups 1 through 54-53-52-51a6-50c27-49c27-48-47-46-45-44-43-42-41-40-39-38-37-36-35-34-33-32-31-30-29-28-27-39-38-37-36-35-34-33-32-31-30-29-28-27-26-25-23-21-17-10-8-6.

87B. A method to treat, ameliorate, prevent or slow the progression of an unwanted condition or symptom associated with the presence of a natural or synthetic glucocorticosteroid ('GCS') in a subject comprising administering to the subject, or delivering to the subject's tissues, an effective amount of a formula 1 compound, whereby the condition or symptom is detectably treated, ameliorated, prevented or its progression is detectably slowed.

88B. The method of embodiment 87B wherein the unwanted condition or symptom associated with the presence of the natural or synthetic GCS is an immune suppression disease, condition or symptom.

89B. The method of embodiment 88B wherein the immune suppression disease, condition or symptom is associated with a pathogen infection, a cancer or precancer, aging, trauma (stress, burn, surgery, accidental tissue injury) or inflammation.

90B. The method of embodiment 89B wherein the chemotherapy comprises treatment of the subject with a GCS.

In other embodiments, the invention provides methods to modulate immune cells or immune responses in a subject. The following numbered embodiments describe some of these methods.

1C. A method to modulate a subject's innate immunity or to enhance a subject's Th1 immune response or to reduce a subject's Th2 immune responses comprising administering to the subject a compound(s) of formula 1, or a metabolic precursor or a biologically active metabolite thereof, including any formula 1 that is described or disclosed herein, including the compounds described in embodiments 1-64 and 1A-11A above.

2C. The method of embodiment 1C wherein the subject's innate immunity is enhanced.

3C. The method of embodiment 1C or 2C wherein the subject suffers from an innate immunity suppression condition, a suppressed Th1 immune response or an unwanted Th2 immune response.

4C. The method of embodiment 3C wherein the innate immunity suppression condition, the suppressed Th1 immune response or the unwanted Th2 response is associated with a viral infection, an intracellular bacterial infection, an extracellular bacterial infection, a fungal infection, a yeast infection, an extracellular parasite infection, an intracellular parasite infection, a protozoan parasite, a multicellular parasite, an autoimmune disease, a cancer, a precancer, a chemotherapy, a radiation therapy, an immunosuppressive therapy, an anti-infective agent therapy, a wound, a burn, the presence of an immunosuppressive molecule or any combination of the foregoing.

5C. The method of any of embodiments 1C-3C wherein the subject's Th1 immune response is enhanced.

6C. The method of embodiment 1C wherein the subject's Th2 immune response is reduced.

7C. The method of embodiment 6C wherein the subject has a condition comprising an unwanted immune response (e.g., autoimmune disease, SLE, diabetes).

9C. The method of embodiment 6C or 7C wherein the subject is a vertebrate, a mammal, a primate or a human.

10C. The method of embodiment 9 wherein the vertebrate's, the mammal's the primate's or the human's specific immunity modulation is (i) an enhanced CTL or Th1 response to a virus infection or to a malignant cell in vitro or in vivo, (ii) enhanced antigen presentation or biological activity by dendritic cells or dendritic cell precursors, or (iii) enhanced killing of virus-infected or of malignant cells.

11C. The method of 10C wherein the vertebrate is a human, the virus infection is an HIV infection and the CTL or Th1 response comprises an enhanced response to one or more of the HIV's gag protein or to the HIV's gp120.

12C. The method of embodiment 1C, 4C, 10C or 11C wherein the subject's Th1 cells, tumor-infiltrating lymphocytes (TIL cells), NK cells, peripheral blood lymphocytes, phagocytes, monocytes, macrophage, neutrophils, eosinophils, dendritic cells or fibrocytes are activated as measured by, e.g., enhanced $^3$H-thymidine uptake compared to untreated controls or by an increase in the number of the cell type in circulation or demonstrable movement of the cell type from one tissue or compartment (e.g., skin) to another tissue or compartment (e.g., blood, lymph node, spleen or thymus).

13C. The method of embodiment 1C, 4C, 10C, 11C or 12C, wherein the formula 1 compound(s) modulates transcription of one or more genes in the subject's NK cells, phagocytes, monocytes, macrophages, neutrophils, eosinophils, dendritic cells or fibrocytes are detectably activated (e.g., as measured by increased protein kinase C activity or by modulation of a biological activity of a steroid receptor or an orphan nuclear hormone receptor).

14C. The method of embodiment 1C wherein the formula 1 compound(s) enhances lysosome movement in one or more of the subject's NK cells, phagocytes, monocytes, macrophages, neutrophils, eosinophils, dendritic cells or fibrocytes.

15C. The method of embodiment 1C wherein the formula 1 compound(s) enhances protein kinase C activity in one or more of the subject's NK cells, phagocytes, monocytes, macrophages, neutrophils, eosinophils, dendritic cells or fibrocytes (e.g., PKCα, PKCβ, PKCγ and PKCζ).

16C. A composition comprising a partially purified or a purified complex comprising a formula 1 compound and a steroid receptor, a serum steroid-binding protein (e.g., human serum albumin, α1-acid glycoprotein, sex hormone-binding globulin, testosterone-binding globulin, corticosteroid-binding globulin, androgen binding protein (rat)) or a binding partner (e.g., complexing agent, liposome, antibody).

17C. A product produced by the process of contacting the partially purified or the purified composition of embodiment 16C with one or more sterile containers, one or more syringes, one or more pharmaceutically acceptable excipients (e.g., excipient as defined in draft spec above and including sugars, lactose, sucrose, fillers, lubricants, binders, or any excipient named in any reference cited herein), one or more cells, one or more tissues, plasma or blood.

18C. The method of any of embodiments 1C-17C wherein the subject has an infection, a hyperproliferation disorder, a hypoproliferation condition, an immunosuppression condition, an unwanted immune response or wherein the subject has recently experienced or will shortly experience trauma, surgery or a therapeutic treatment wherein the therapeutic treatment is one other than the method of embodiment 1C.

19C. The method of embodiment 18C wherein the immunosuppression condition or the unwanted immune response is associated with a viral infection, an intracellular bacterial infection, an extracellular bacterial infection, a fungal infection, a yeast infection, an extracellular parasite infection, an intracellular parasite infection, a protozoan parasite, a multicellular parasite, an autoimmune disease, a cancer, a precancer, a chemotherapy, a radiation therapy, an immunosuppressive therapy, an anti-infective agent therapy, a wound, a burn, the presence of an immunosuppressive molecule, gastrointestinal irritation or an inflammation condition optionally selected from or associated with irritable bowel disease, Crohn's disease or chronic diarrhea, or any combination of the foregoing.

20C. The method of embodiment 19C wherein the subject's immunosuppression condition is ameliorated or the unwanted immune response is reduced.

21C. The method of embodiment 19C wherein the subject's immunosuppression condition is associated with a viral infection.

22C. The method of embodiment 21C wherein the viral infection comprises a DNA virus or an RNA virus infection.

23C. The method of embodiment 22C wherein the RNA virus infection comprises a retroviral infection or a hepatitis virus infection.

24C. The method of any of embodiments 18C-23C wherein the subject suffers from one or more of chronic diarrhea, involuntary weight loss (usually at least about 5% or more), cachexia (usually at least about 5% or more), muscle wasting, one or more oral lesions (usually at least about 1 cm$^2$), one or more genital lesions (usually at least about 1 cm$^2$), skin lesions (usually at least about 1 cm$^2$) or an opportunistic infection associated with AIDS.

25C. A method (e.g., to determine a biological activity of a formula 1 compound or to modulate transcription of a gene in a cell or cell-free transcription system) comprising: (a) contacting the formula 1 compound(s) with a cell or cell population in vitro or in vivo; (b) measuring one or more of (i) a complex between a binding partner and the formula 1 compound, (ii) proliferation of the cell or cell population, (iii) differentiation of the cell or cell population (iv) an activity of a protein kinase C, (v) a level of phosphorylation of a protein kinase C substrate, (vi) transcription of one or more target genes, (vii) enhancement or inhibition of the cellular response to steroids, e.g., glucocorticoids, (viii) inhibition of steroid-induced transcription, e.g., glucocorticoids, sex steroids, (ix) inhibition of retrovirus (e.g., HIV, SIV, FIV or SHIV) LTR-driven transcription, or (x) modulation of the numbers of an immune cell population in circulation in vivo (e.g., circulating peripheral blood lymphocytes in a mammal such as a primate or a human); and (c) optionally comparing the result obtained in step (b) with an appropriate control.

26C. The method of embodiment 25C wherein the binding partner is a steroid receptor, a transcription factor or a steroid hormone superfamily orphan receptor.

27C. The method of embodiment 25C wherein the biological activity determined is a modulating activity of the formula 1 compound for replication or cytopathic effects associated with a retrovirus, a hepatitis virus or a protozoan parasite.

28C. The method of embodiment 25C wherein the biological activity determined is a modulating activity of the formula 1 compound for replication, cytopathic effects associated with the retrovirus, the hepatitis virus or the protozoan parasite or the biological activity determined is metabolism (assay by $^3$H-thymidine uptake) of a cell or cell population comprising NK cells, phagocytes, monocytes, macrophages, basophils, eosinophils, fibrocytes, transformed cells, virus-infected cells, bacteria-infected cells or parasite-infected cells.

29C. The method of embodiment 25C wherein the target gene is a virus gene, a bacterial gene, a parasite gene, a gene associated with cancer.

30C. The method of embodiment 29C wherein the virus gene is a polymerase gene, a reverse transcriptase gene, an envelope gene, a protease gene or a gene associated with viral nucleic acid replication or a viral structural gene.

31C. The method of embodiment 30C wherein the polymerase gene encodes a DNA polymerase or encodes an RNA polymerase.

32C. The method of embodiment 30C wherein the reverse transcriptase gene encodes a human, primate, avian or feline retrovirus reverse transcriptase.

33C. A method comprising administering a compound(s) of formula 1 to a human or primate who has a retroviral infection and a CD4 count of 550 or less.

34C. The method of embodiment 33C wherein the human has a CD4 count of about 20 to about 100 or about 20 to about 80.

35C. The method of embodiment 33C wherein the human has a CD4 count of about 30 to about 150.

36C. The method of embodiment 33C wherein the human has a CD4 count of about 500 or less, about 450 or less, about 400 or less, about 350 or less, about 300 or less, about 250 or less, about 200 or less, about 150 or less, about 100 or less, about 50 or less or about 25 or less or about 20 or less.

37C. The method of any of embodiments 33C-36C wherein the formula 1 compound(s) is present in a composition that comprises one or more nonaqueous liquid excipients and less than about 3% v/v water or any of the formulations as disclosed in the specification or any of the numbered embodiments above.

38C. The method of any of embodiments 33C-37C wherein the formula 1 compound(s) is administered according to an intermittent dosing protocol as disclosed in the specification or any of the numbered embodiments above.

39C. The method of any of embodiments 30C-45C wherein the human is coinfected with hepatitis C virus, hepatitis B virus, HSV-1, HSV-2, a malaria parasite, a *Pneumocystis* parasite, or a *Cryptosporidium* parasite.

40C. The method of embodiment 46C wherein level of the HCV is reduced in the human.

41C. A method comprising administering a formula 1 compound(s) to a subject, or to a nervous system cell(s) in tissue culture whereby the formula 1 compound(s) binds to a receptor associated with a cell(s) in the nervous system and (1) elicits a biological response in the cell(s) in the nervous system or in the cell(s) in tissue culture and/or (2) elicits a neuronal response that is transmitted to a distant site(s) or cell(s) where the method optionally is used to screen a formula 1 compound(s) for its biological activity, to treat a pathological condition (e.g., pathogen infection such as a virus (HIV), a malignancy or a neurological disorder, e.g., AIDS associated dementia, Alzheimer's, Parkinson's, Multiple Sclerosis) in the subject or to determine the bioavailability or metabolism of the formula 1 compound(s) to the subject or the cell(s) in the nervous system or in tissue culture, wherein metabolism is optionally determined by comparing the biological effect of a formula 1 compound(s) with a control compound, which can be a different formula 1 compound.

42C. The method of embodiment 41 wherein the receptor associated with the cell in the nervous system is a neurotransmitter receptor(s) (e.g., a γ-aminobutyric acid receptor such as type A, a NMDA receptor) and/or a steroid receptor (e.g., androgen receptor, estrogen receptor).

43C. The method of embodiment 41C or 42C wherein the cell(s) in the nervous system is a neuron(s), and astrocyte(s) and/or a glial cell(s).

44C. The method of embodiment 41C, 42C or 43C wherein the biological response in the cell(s) in the nervous system or in the cell(s) in tissue culture is increased or decreased transcription of a gene(s) (e.g., a neurotransmitter, vasopressin, a heat shock protein), increased or decreased secretion of a protein(s) (e.g., vasopressin), reduced damage from oxidative stress, enhanced nitric oxide release and/or enhanced neurite growth.

45C. The method of any of embodiments 1C-44C wherein the compound(s) of formula 1 is any one or more formula 1 compound selected from the compounds or one or more of the species of compounds within the genera named in compound groups 1 through 21-10-6.

46C. A method to (a) modulate (detectably increase or decrease) the expression of at least one immune cell antigen by an immune cell in a subject, wherein the immune cell antigen is selected from CD3, CD11c, CD14, CD16, CD19, CD25, CD38, CD56, CD62L, CD69, CD45RA, CD45RO, CD123, HLA-DR, IL-1, IL-2, IL-4, IL-6, IL-8, IL-10, IL-12, TNFα, IGF$_1$ and γIFN, or (b) activate CD8$^+$ T cells or CD8$^-$ T cells in a subject, wherein the activation comprises at least transiently enhanced expression of CD25 or CD69 by the T cells, or (c) increase the proportion of CD8$^+$ or CD8$^-$ lymphokine activated killer cells in a subject's CD16+ cells (e.g., CD8$^+$, CD16$^+$, CD38$^+$ or cells CD8$^-$, CD16$^+$, CD38$^+$), or (d) increase the proportion of (i) CD8$^-$, CD16$^+$ natural killer cells, (ii) CD8$^+$, CD16$^+$ natural killer cells or (iii) CD8$^-$, CD16$^+$ cells that mediate antibody-dependent cell-mediated cytotoxicity, or (iv) CD8$^+$, CD16$^+$ cells that mediate antibody-dependent cell-mediated cytotoxicity, or (e) increase the proportion of dendritic cell precursors in a subject's circulating white blood cells (e.g., Lin$^-$, HLA-DR$^+$, CD123$^+$ or Lin$^-$ HLA-DR$^+$, CD11c$^+$ cells) or (f) increase the proportion of CD45RA$^+$ T cells or CD45$^+$, RO$^+$ T cells in a subject's circulating white blood cells, or (g) change (increase or decrease) the proportion or relative numbers of CD62L$^+$ T cells in a subject's circulating white blood cells, or (h) increase the proportion of CD8$^+$ or CD4$^+$ T cells that express CD62L in a subject's circulating CD8$^+$ or CD4$^+$ T cells, or (i) decrease the proportion of CD8$^+$ or CD4$^+$ T cells that express CD62L in a subject's circulating CD8$^+$ or CD4$^+$ T cells, or (j) increase the proportion of HLA-DR$^+$, CD8$^+$, CD38$^+$ cells in a subject's circulating white blood cells, or (k) decrease the level of IL-4 or IL-10 that is expressed by or present in a subject's white blood cells or in a subject's plasma (or that is expressed after the subject's white cells are stimulated in vitro), (l) at least transiently increase the number of dendritic cell precursors or dendritic cells that are present in a subject's white blood cells or in a subject's plasma, or (m) enhance the capacity of an immune cell, e.g., macrophages, CD4$^+$ T cells, CD8$^+$ T cells to express IL-2, IL-12 or γIFN or to activate such cells, the method comprising administering to the subject an effective amount of a formula 1 compound, which is optionally present in a composition comprising a pharmaceutically acceptable excipient.

47C. The method of embodiment 46C wherein formula 1 has the structure

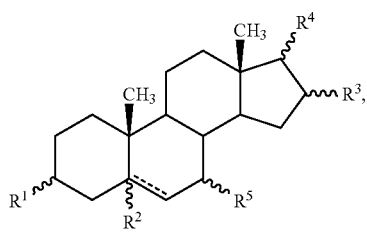

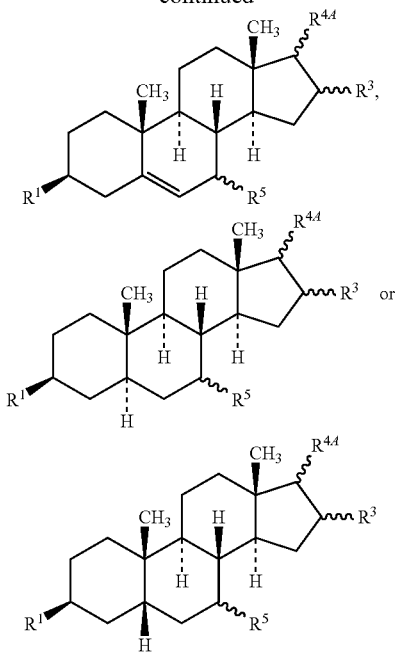

wherein R$^1$ is —OH or a group (e.g., a C1-30 ester) that can hydrolytically convert under physiological conditions to —OH, either of which may be in the α- or β-configuration; R$^2$ is hydrogen in the α- or β-configuration, or R$^2$ is absent when there is a double bond at the 5-6 position; R$^3$ is —H or —Br, either of which may be in the α- or β-configuration; R$^4$ is —OH or a group (e.g., a C1-30 ester) that can hydrolytically convert under physiological conditions to —OH, either of which may be in the α- or β-configuration, or R$^4$ is =O and the hydrogen atom bonded to the same carbon is absent; R$^{4,4}$ is R$^4$, —C(O)—CH$^3$ or —C(O)—(CH$_2$)$_{1-6}$—CH$^3$; R$^5$ is —H or —OH or a group (e.g., a C1-30 ester) that can hydrolytically convert under physiological conditions to —OH, either of which may be in the α- or β-configuration, or R$^5$ is =O and the hydrogen atom bonded to the same carbon is absent; and the dotted line at the 5-6 position is an optional double bond, or wherein the formula 1 compound has the structure shown in any formula 1 compound named or described herein, including the compounds described in embodiments 1-64 and 1A-11A above.

48C. The method of embodiment 46C or 47C wherein the formula 1 compound is administered to the subject daily over a period from one to about 15 days, e.g., for 1, 2, 3, 4, 5, 6, 7, 8, 9, 10, 11, 12, 13, 14, 15 or more days.

49C. The method of embodiment 48C wherein the expression of the immune cell antigen is detectably modulated for at least about 4-7 days after the last administration of the formula 1 compound to the subject, e.g., for at least 4, 5, 6, 7 or more days.

50C. The method of embodiment 48C or 49C wherein the expression of the immune cell antigen is detectable at least about 8-90 days after the last administration of the formula 1 compound, e.g., for at least about 8, 10, 12, 15, 20, 25, 28, 30, 35, 40, 42, 45, 49, 50, 55, 56, 60, 63, 65, 70, 75, 77, 80, 84, 85, 90, 91 95, 98, 100 or more days.

51C. The method of any of embodiments 46C-51C wherein the subject has an immunosuppression condition, a pathogen infection or a conditions associated with a deficient Th1 immune response or an excessive Th2 immune response.

52C. The method of embodiment 51C wherein the pathogen infection is a viral infection, a bacterial infection, a yeast infection, a fungal infection or a viroid infection, e.g., wherein the pathogen infection is a viral infection such as a DNA virus infection or an RNA virus infection (e.g., an infection caused by a Hepadnavirus, a Parvovirus, a Papovavirus, an Adenovirus, a Herpesvirus, Retrovirus, a Flavivirus, a Togavirus, a Rhabdovirus, a Picornavirus, a Bunyavirus, a Reovirus, an Orthomyxovirus or a Paramyxovirus, such as a HIV1, HIV2, SIV, SHIV or another virus described herein or in the cited references).

53C. The method of embodiment 52C wherein the subject has an immunosuppression condition that is associated with or caused by a pathogen infection.

54C. The method of any of embodiments 46C-53C wherein the subject is a mammal, a human, a primate or a rodent.

55C. The method of any of embodiments 46C-54C wherein about 0.05 mg/kg/day to about 20 mg/kg/day is administered parenterally (e.g., by intravenous, subcutaneous, intramuscular, or intramedullary injection), topically, orally, sublingually or bucally to the subject, e.g., about 0.1 mg/kg/day, about 0.2 mg/kg/day, about 0.5 mg/kg/day, about 1.0 mg/kg/day, about 1.5 mg/kg/day, about 2 mg/kg/day, about 2.5 mg/kg/day, about 3.0 mg/kg/day, about 4 mg/kg/day or about 6 mg/kg/day, i.e., about 0.1-10 mg/kg/day, typically about 0.2-7 mg/kg/day.

56C. The method of embodiment 55C wherein the subject is concurrently taking one or more second therapeutic agents to treat a pathogen infection, e.g., a viral infection, such as a HIV-1 infection, a HIV-2 infection, a HAV infection, a HBV infection, a HCV infection, an Epstein Barr virus infection, a HSV-1 infection, a HSV-2 infection, human herpesvirus 6 infection, human herpesvirus 7 infection, human herpesvirus 8 infection, or a bacterial infection or a parasite infection, such as a malaria infection, Leishmaniasis, Cryptosporidiosis, Toxoplasmosis, a *Mycoplasma* infection, a *Trichomonas* infection, a *Chlamidya* infection, a *Pneumocystis* infection, a *Salmonella* infection, a *Listeria* infection, an *Escherichia coli* infection, a *Yersinia* infection, a *Vibrio* infection, a *Pseudomonas* infection, a *Mycobacterium* infection, a *Haemophilus* infection, a *Neisseria* infection, a *Staphylococcus* infection or a *Streptococcus* infection.

57C. The method of embodiment 56C wherein the one or more second therapeutic agents is a protease inhibitor, a reverse transcriptase inhibitor, a viral, bacterial or parasite DNA or RNA polymerase inhibitor, an antibacterial antibiotic or an antifungal agent, such as AZT, ddI, ddC, D4T, 3TC, a viral (e.g., HIV) fusion inhibitor, hydroxyurea, nelfinavir, amprenavir, saquinavir, ritonavir, indinavir, chloroquine, a chloroquine analog, amphotericin B, fluconazole, clotrimazole, itraconazole, ketoconazole, isoniazid, dapsone, rifampin, cycloserine, erythromycin, a tetracycline antibiotic, vancomycin, ethambutol, pyrazinamide, a fluororoquinolone (e.g., ciprofloxacin, norfloxacin), a cephalosporin antibiotic, a β-lactam antibiotic or an aminoglycoside antoibiotic (e.g., streptomycin, kanamycin, tobramycin).

58C. The method of any of embodiments 46C-57C wherein the subject is a human, a primate, a canine, a feline or a rodent.

59C. A composition comprising an effective amount of an immune cell subset modulatory compound of formula 1 and a pharmaceutically acceptable carrier.

60C. The composition of embodiment 59C wherein the immune cell subset is (1) $CD8^+$ T cells, (2) $CD4^+$ T cells, (3) $CD8^+$ lymphokine activated killer cells, (4) $CD8^-$ lymphokine activated killer cells, (5) $CD8^-$, $CD16^+$ natural killer cells, (6) $CD8^+$, $CD16^+$ natural killer cells, (7) $CD8^-$, $CD16^+$ cells that mediate antibody-dependent cell-mediated cytotoxicity, (8) $CD8^+$, $CD16^+$ cells that mediate antibody-dependent cell-mediated cytotoxicity, (9) dendritic cells or dendritic cell precursors, (10) $CD45RA^+$ T cells, (11) $CD45RO^+$ T cells, (12) $CD45RA^+$, $CD45RO^+$ T cells, (13) $CD8^+$, $CD62L$ T cells, (11) $CD4^+$, $CD62L^+$ T cells or (14) $HLA-DR^+$, $CD8^+$, $CD38^+$ T cells.

61C. A method to detect a biological response associated with the administration of a compound of formula 1 to a subject comprising (1) obtaining a sample from the subject, (2) administering the compound of formula 1 to the subject to obtain a treated subject (3) obtaining a second sample from the treated subject, (4) within 24 hours of obtaining the sample, analyzing the sample to obtain control information for detecting the biological response, (5) within 24 hours of obtaining the second sample, analyzing the second sample for the presence or absence of a biological response to obtain experimental information and (6) optionally comparing the control information with the experimental information to detect the presence, absence, relative magnitude or absolute magnitude of the biological response 62C. The method of embodiment 61C wherein the compound of formula 1 further comprises a pharmaceutically acceptable carrier.

63C. The method of embodiment 61C or 62C wherein the biological response associated with the administration of the compound of formula 1 to the subject is modulation of the expression of a cell surface antigen, an increased absolute or relative number of cells in an immune cell subset, a decreased absolute or relative number of cells in an immune cell subset or an unchanged absolute or relative number of cells in an immune cell subset.

64C. The method of embodiment 63C wherein the immune cell subset is $CD8^+$ T cells, $CD4^+$ T cells, CD8+lymphokine activated killer cells, $CD8^-$, $CD16^+$ natural killer cells, circulating dendritic cell precursors, circulating dendritic cells, tissue dendritic cell precursors, tissue dendritic cells, $CD8^+$ lymphokine activated killer cells, $CD8^-$ lymphokine activated killer cells, $CD8^-$, $CD16^+$ natural killer cells, $CD8^+$, $CD16^+$ natural killer cells, $CD8^-$, $CD16^+$ cells that mediate antibody-dependent cell-mediated cytotoxicity, $CD8^+$, $CD16^+$ cells that mediate antibody-dependent cell-mediated cytotoxicity, $CD45RA^+$ T cells, $CD45RA^+$, $CD45RO^+$ T cells, $CD45RO^+$ T cells, $CD8^+$, $CD62L$ T cells, $CD4^+$, $CD62L^+$ T cells or $HLA-DR^+$, $CD8^+$, $CD38^+$ T cells, monocytes or macrophages.

65C. The method of embodiment 64C wherein the biological response is at least transient modulation of an immune cell antigen or an immune accessory cell antigen (e.g., an adhesion molecule at the surface of endothelial cells or a cytokine receptor at the surface of T cells or B cells).

66C. The method of embodiment 65C wherein the immune cell antigen is a protein, glycoprotein or cell surface antigen usually or only expressed by lymphoid cells (lymphocytes or white blood cells or their precursors, e.g., T cells, B cells, monocytes, macrophage, LAK cells, NK cells, dendritic cells).

67C. The method of embodiment 65C wherein the immune cell antigen is a CD molecule, an interleukin or a cytokine, optionally selected from CD16, CD25, CD38, CD62L, CD69, CD45RA, CD45RO, IL-1, IL-2, IL-4, IL-6, IL-8, IL-10, TNFα, $IGF_1$ and γIFN.

68C. The method of any of embodiments 61C-67C wherein the subject is a human, a primate, a canine, a feline or a rodent.

69C. A method to alter the Th1-Th2 balance in a subject comprising administering an effective amount a compound of formula 1 to a subject whereby the subject's expression or secretion of IL-4 or IL-10 is detectably modulated.

70C. The method of embodiment 30 wherein the subject's expression or secretion of IL-4 or IL-10 is decreased and the Th1-Th2 balance in the subject's Th1 immune responses to an infection or immunosuppression condition is detectably enhanced.

71C. The method of any of embodiments 1C-70C, wherein the formula 1 compound is a compound named in any of compound groups 1 through 54-53-52-51a6-50c27-49c27-48-47-46-45-44-43-42-41-40-39-38-37-36-35-34-33-32-31-30-29-28-27-39-38-37-36-35-34-33-32-31-30-29-28-27-26-25-23-21-17-10-8-6, or the formula 1 compound is a species in any genus described in any of compound groups 1 through 54-53-52-51a6-50c27-49c27-48-47-46-45-44-43-42-41-40-39-38-37-36-35-34-33-32-31-30-29-28-27-39-38-37-36-35-34-33-32-31-30-29-28-27-26-25-23-21-17-10-8-6.

72C. A method to prevent or treat an immune disregulation condition in a subject in need thereof comprising administering to the subject, or delivering to the subject's tissues, an effective amount of a compound of formula 1, including compounds where, 0, 1, 2 or 3 of $R^7$, $R^8$ and $R^9$ are not —$CH_2$— or —$CHR^{10}$— e.g., where $R^7$ is —O—, —S— or —NH—, or where $R^8$ is —O—, —S— or —NH—, or where $R^9$ is —O—, —S—, —NH— or =N— or where all of $R^7$, $R^8$ and $R^9$ are —$CH_2$— or —$CHR^{10}$—.

73C. The method of embodiment 72C where two of $R^7$, $R^8$ and $R^9$ are not —$CH_2$—, e.g., where $R^7$ is —O— and $R^8$ is —O—, $R^7$ is —O— and $R^9$ is —O—, $R^8$ is —O— and $R^9$ is —O—, $R^7$ is —O— and $R^8$ is —N—, $R^7$ is —O— and $R^9$ is —NH— or =N—, $R^8$ is —O— and $R^9$ is —NH— or =N—, $R^7$ is —O— and $R^8$ is —S—, $R^7$ is —O— and $R^9$ is —S—, $R^8$ is —O— and $R^9$ is —S—, $R^7$ is —NH— and $R^8$ is —NH—, $R^7$ is —NH— and $R^9$ is —NH— or =N—, $R^8$ is —NH— and $R^9$ is —NH— or =N—, $R^7$ is —NH— and $R^8$ is —O—, $R^7$ is —NH— and $R^9$ is —O—, $R^8$ is —NH— and $R^9$ is —O—, $R^7$ is —NH— and $R^8$ is —S—, $R^7$ is —NH— and $R^9$ is —S—, $R^8$ is —NH— and $R^9$ is —S—, $R^7$ is —S— and $R^8$ is —S—, $R^7$ is —S— and $R^9$ is —S—, $R^8$ is —S— and $R^9$ is —S—, $R^7$ is —S— and $R^8$ is —N—, $R^7$ is —S— and $R^9$ is —NH— or =N—, $R^8$ is —S— and $R^9$ is —NH— or =N—, $R^7$ is —S— and $R^8$ is —O—, $R^7$ is —S— and $R^9$ is —O— or $R^8$ is —S— and $R^9$ is —O—.

74C. The method of embodiment 72C wherein none of $R^7$, $R^8$ and $R^9$ are —$CH_2$—, e.g., wherein $R^7$ is —O—, $R^8$ is —O— and $R^9$ is —O—, $R^7$ is —O—, $R^8$ is —O— and $R^9$ is —NH— or =N—, $R^7$ is —O—, $R^8$ is —NH— and $R^9$ is —O—, $R^7$ is —NH—, $R^8$ is —NH— and $R^9$ is —O—, $R^7$ is —O—, $R^8$ is —O— and $R^9$ is —S—, $R^7$ is —O—, $R^8$ is —S— and $R^9$ is —O—, $R^7$ is —S—, $R^8$ is —S— and $R^9$ is —O—, $R^7$ is —NH—, $R^8$ is —NH— and $R^9$ is —NH— or =N—, $R^7$ is —O—, $R^8$ is —NH— and $R^9$ is —NH— or =N—, $R^7$ is —NH—, $R^8$ is —O— and $R^9$ is —NH— or =N—, $R^7$ is —O—, $R^8$ is —O— and $R^9$ is —NH— or =N—, $R^7$ is —S—, $R^8$ is —NH— and $R^9$ is —NH— or =N—, $R^7$ is —NH—, $R^8$ is —S— and $R^9$ is —NH— or =N—, $R^7$ is —S—, $R^8$ is —S— and $R^9$ is —NH— or =N—, $R^7$ is —S—, $R^8$ is —S— and $R^9$ is —S—, $R^7$ is —O—, $R^8$ is —S— and $R^9$ is —S—, $R^7$ is —S—, $R^8$ is —O— and $R^9$ is —S—, $R^7$ is —S—, $R^8$ is —S— and $R^9$ is —O—, $R^7$ is —NH—, $R^8$ is —S— and $R^9$ is —S—, $R^7$ is —S—, $R^8$ is —NH— and $R^9$ is —S—, $R^7$ is —NH—, $R^8$ is —S— and $R^9$ is —O—, $R^7$ is —S—, $R^8$ is —O— and $R^9$ is —NH— or =N—, $R^7$ is —O—, $R^8$ is —S— and $R^9$ is —NH— or =N—, $R^7$ is —NH—, $R^8$ is —O— and $R^9$ is —S—, or $R^7$ is —O—, $R^8$ is —NH— and $R^9$ is —S—.

75C. The method of any of embodiments 72C through 74C wherein the there are no double bonds in the formula 1 compound, $R^1$, $R^5$ and $R^6$ are in the βconfiguration, one $R^4$ is hydrogen and the immune disregulation condition is caused by or is associated with inflammation, an autoimmune condition, an organ or tissue transplant rejection, an infection or its treatment, a cancer or its treatment, a chemotherapy, a radiation therapy, trauma, surgery, an allergy condition or an insufficient Th1 immune response.

76C. The method of embodiment 75C, wherein the formula 1 compound is a compound named in any of compound groups 1 through 54, or the formula 1 compound is a species in any genus described in any of compound groups 1 through 54.

Invention embodiments include stimulation of hemopoiesis in a subject. The following embodiments exemplify various aspects if these embodiments 1D. A method to enhance hemopoiesis in a subject in need thereof comprising administering to the subject, or delivering to the subject's tissues, an effective amount of a compound of formula 1

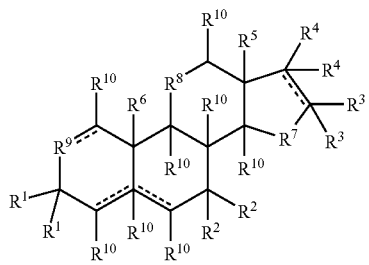

wherein, each $R^1$, $R^2$, $R^3$, $R^4$, $R^5$, $R^6$ and $R^{10}$ independently are —H, —$OR^{PR}$, —$SR^{PR}$, —$N(R^{PR})_2$, —O—Si—$(R^{13})_3$, —CHO, —CHS, —CH=NH, —CN, —SCN, —$NO_2$, —$OSO_3H$, —$OPO_3H$, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, an acetal, a thioacetal, a halogen, an optionally substituted alkyl group, an optionally substituted alkenyl group, an optionally substituted alkynyl group, an optionally substituted aryl moiety, an optionally substituted heteroaryl moiety, an optionally substituted heterocycle, an optionally substituted monosaccharide, an optionally substituted oligosaccharide, a nucleoside, a nucleotide, an oligonucleotide, a polymer, or, one more of $R^1$, $R^2$, $R^3$, $R^4$, $R^5$, $R^6$, $R^{10}$, $R^{15}$, $R^{17}$ and $R^{18}$ are =O, =S, =N—OH or =$CH_2$ and the hydrogen atom or the second variable group that is bonded to the same carbon atom is absent, or, all $R^3$ and $R^4$ together comprise a structure of formula 2

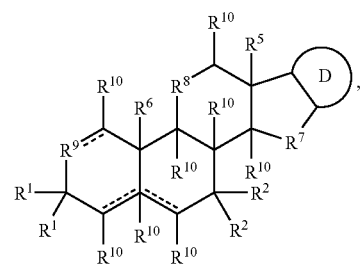

$R^7$ is —C(R$^{10}$)$_2$—, —C(R$^{10}$)$_2$—C(R$^{10}$)$_2$—, —C(R$^{10}$)$_2$—C(R$^{10}$)$_2$—C(R$^{10}$)$_2$—, —C(R$^{10}$)$_2$—O—C(R$^{10}$)$_2$—, —C(R$^{10}$)$_2$—S—C(R$^{10}$)$_2$—, —C(R$^{10}$)$_2$—NR$^{PR}$—C(R$^{10}$)$_2$—, —O—, —O—C(R$^{10}$)$_2$—, —S—, —S—C(R$^{10}$)$_2$—, —NR$^{PR}$— or —NR$^{PR}$—C(R$^{10}$)$_2$—, including —CHR$^{10}$—, —CHR$^{10}$—CHR$^{10}$—, —CHR$^{10}$—CHR$^{10}$—CHR$^{10}$—, —CHR$^{10}$—O—CHR$^{10}$—, —CHR$^{10}$—S—CHR$^{10}$—, —CHR$^{10}$—NR$^{PR}$—CHR$^{10}$—, —O—, —O—CHR$^{10}$, —S—, —S—CHR$^{10}$—, —NR$^{PR}$— or —NR$^{PR}$—CHR$^{10}$—

$R^8$ and $R^9$ independently are —C(R$^{10}$)$_2$—, —C(R$^{10}$)$_2$—C(R$^{10}$)$_2$—, —O—, —O—C(R$^{10}$)$_2$—, —S—, —S—C(R$^{10}$)$_2$—, —NR$^{PR}$— or —NR$^{PR}$—C(R$^{10}$)$_2$—, including —CHR$^{10}$—, —CHR$^{10}$—CHR$^{10}$—, —O—, —O—CHR$^{10}$—, —S—, —S—CHR$^{10}$—, —NR$^{PR}$— or —NR$^{PR}$—CHR$^{10}$—, or one or both of $R^8$ or $R^9$ independently are absent, leaving a 5-membered ring;

$R^{13}$ independently is $C_{1-6}$ alkyl;

$R^{16}$ independently are —CH$_2$—, —O—, —S— or —NH—;

D is a heterocycle or a 4-, 5-, 6- or 7-membered ring that comprises saturated carbon atoms, wherein 1, 2 or 3 ring carbon atoms of the 4-, 5-, 6- or 7-membered ring are optionally independently substituted with —O—, —S— or —NR$^{PR}$— or where 1, 2 or 3 hydrogen atoms of the heterocycle or where 1 or 2 hydrogen atoms of the 4-, 5-, 6- or 7-membered ring are substituted with —OR$^{PR}$, —SR$^{PR}$, —N(R$^{PR}$)$_2$, —O—Si—(R$^{13}$)$_3$, —CN, —NO$_2$, an ester, a thioester, a thionoester, a phosphoester, a phosphothioester, a sulfite ester, a sulfate ester, an amide, an amino acid, a peptide, an ether, a thioether, an acyl group, a thioacyl group, a carbonate, a carbamate, an acetal, a thioacetal, a halogen, an optionally substituted alkyl group, an optionally substituted alkenyl group, an optionally substituted alkynyl group, an optionally substituted aryl moiety, an optionally substituted heteroaryl moiety, an optionally substituted monosaccharide, an optionally substituted oligosaccharide, a nucleoside, a nucleotide, an oligonucleotide or a polymer, or, one more of the ring carbons are substituted with =O or =S, or D comprises two 5- or 6-membered rings, wherein the rings are fused or are linked by 1 or 2 bonds, or a metabolic precursor or a biologically active metabolite thereof, optionally provided that the compound is not 5-androstene-3β-ol-17-one, 5-androstene-3β,17β-diol, 5-androstene-3β,7β,17β-triol or a derivative of any of these three compounds that can convert to these compounds by hydrolysis 2D. The method of embodiment 1D wherein the subject's circulating platelets, red cells, mature myelomonocytic cells, or their precursor cells, in circulation or in tissue is detectably increased.

3D. The method of embodiment 2D wherein the subject's circulating platelets are detectably increased.

4D. The method of embodiment 3D wherein the method optionally further comprises administration of an effective amount of G-CSF, GM-CSF, IL-3, IL-6, IL-11, erythropoietin or thrombopoietin.

5D. The method of embodiment 2D wherein the subject's circulating myelomonocytic cells are detectably increased.

6D. The method of embodiment 2D wherein the circulating myelomonocytic cells are neutrophils.

7D. The method of embodiment 2D wherein the method further comprises administration of an effective amount of G-CSF, GM-CSF, M-CSF, IL-3, IL-5 or IL-6.

8D. The method of embodiment 2D wherein the myelomonocytic cells are basophils, neutrophils or eosinophils.

9D. The method of embodiment 2D wherein the subject's circulating red cells are detectably increased.

10D. The method of embodiment 9D wherein the subject is has renal failure.

11D. The method of embodiment 9D wherein the method further comprises administration of an effective amount of G-CSF, GM-CSF, IL-3, IL-6 or erythropoietin.

12D. The method of embodiment 2D wherein the formula 1 compound is present in a composition comprising an acceptable carrier and the method optionally further comprises administration of a neutrophil or monocyte stimulator.

13D. The method of embodiment 12D wherein neutrophil or monocyte stimulator is a TNF, a lithium salt, deuterium oxide, levamisole, lactoferrin, thyroxine, triiodothyromine, anthrax toxin, ascorbic acid, 1-palmitoyl-lysophosphatidic acid, a calcium ionophore, cytochalasin B, sodium butyrate, piracetamine, micronized L-arginine, hydroxyurea or a bacterial lipopolysaccharide.

14D. The method of embodiment 2D further comprising the steps of obtaining blood from the subject before administration of the formula 1 compound and measuring the subject's white or red cell counts and optionally, on one, two, three or more occasions, measuring the subject's circulating white cell counts after administration of the formula 1 compound.

15D. The method of embodiment 2D wherein the formula 1 compound is a compound named in any of the compound groups disclosed herein.

16D. The method of embodiment 1D wherein the subject has, or is subject to developing, thrombocytopenia or neutropenia.

17D. The method of embodiment 16D wherein the subject has thrombocytopenia or neutropenia.

18D. The method of embodiment 1D wherein about 0.05 mg to about 30 mg of the formula 1 compound is administered per kg of the subject's weight per day.

19D. The method of any of embodiments 1D-18D wherein the compound of formula 1 has formula 3

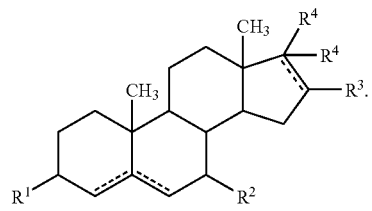

3

20D. The method of embodiment 19D wherein $R^1$ is —OH, alkoxy or an ester, $R^2$ is —OH, =O, alkoxy or an ester, $R^3$ is —H, —OH, alkoxy, an ester or a halogen, one $R^4$ is —H or it is absent and the other $R^4$ is —OH, =O, —SH, —C(O)—CH$_3$, alkoxy or an ester and wherein $R^1$, $R^2$ and $R^3$ are independently in the α or the β configuration when they are not =O.

21D. The method of embodiment 20D wherein there is no double bond present in the molecule.

22D. A method to enhance thrombopoiesis, myelopoiesis or erythropoiesis in a subject comprising administering to the subject, or delivering to the subject's tissues, an effective amount of the compound of embodiment 1.

23D. The method of embodiment 22D wherein the subject has or is subject to thrombocytopenia or neutropenia.

24D. The method of embodiment 23D wherein the subject has thrombocytopenia or neutropenia.

25D. The method of embodiment 22D wherein the subject is a human.

26D. The method of embodiment 22D wherein the formula 1 compound is a compound named in any of the compound groups disclosed herein.

27D. The method of embodiment 22D wherein about 0.05 mg to about 30 mg of the formula 1 compound is administered per kg of the subject's weight per day.

28D. The method of embodiment 27D wherein the formula 1 compound is present in a composition that comprises a pharmaceutically acceptable carrier.

29D. The method of embodiment 28D wherein the pharmaceutically acceptable carrier is deuterium oxide, which comprises at least about 20% v/v of the water in the composition.

30D. The method of embodiment 19D wherein the subject's myeloperoxidase index is enhanced.

31D. The method of embodiment 30D wherein the formula 1 compound is present in a composition that comprises one or more pharmaceutically acceptable carriers, which optionally include a halogen salt.

32D. A method to treat a blood cell deficiency in a subject comprising administering to the subject, or delivering to the subject's tissues, an effective amount of a compound of formula 1.

33D. The method of embodiment 32D wherein the formula 1 compound has the structure

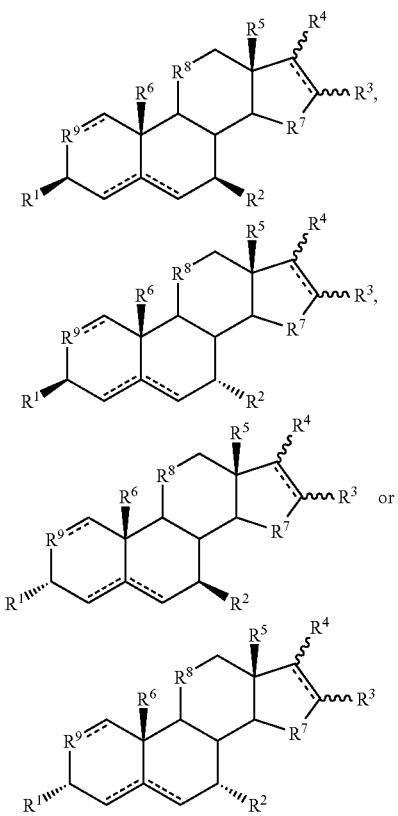

wherein one, two or three of $R^7$, $R^8$ and $R^9$ are —$CH_2$— or —CH= and wherein the configuration of hydrogen atoms at the 5 (if present), 8, 9 and 14 positions respectively are α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β, typically α.α.β.α or β.α.β.α.

34D. The method of embodiment 33D wherein the formula 1 compound has the structure

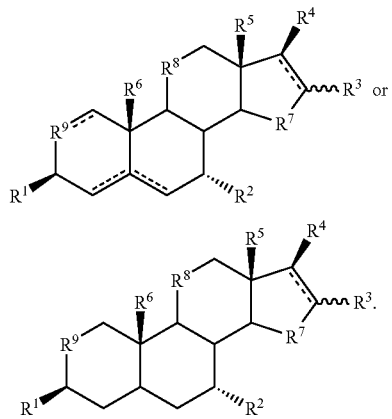

35D. The method of embodiment 34D wherein $R^1$, $R^2$ and $R^4$ independently are —OH, —SCN, a C2-C20 ester or C1-C20 alkoxy, $R^3$ is —H and two or three of $R^7$, $R^8$ and $R^9$ are —$CH_2$—.

36D. The method of embodiment 34D or 35D wherein the formula 1 compound has the structure

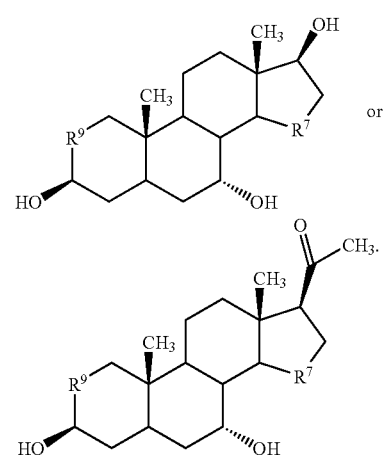

37D. The method of any of embodiments 33D-36D wherein the configuration of hydrogen atoms at the 5 (if present), 8, 9 and 14 positions respectively are α.α.β.α or β.α.β.α.

38D. The method of embodiment 32D wherein the formula 1 compound has the structure

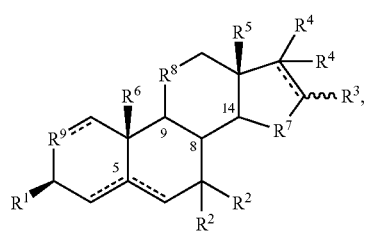

-continued

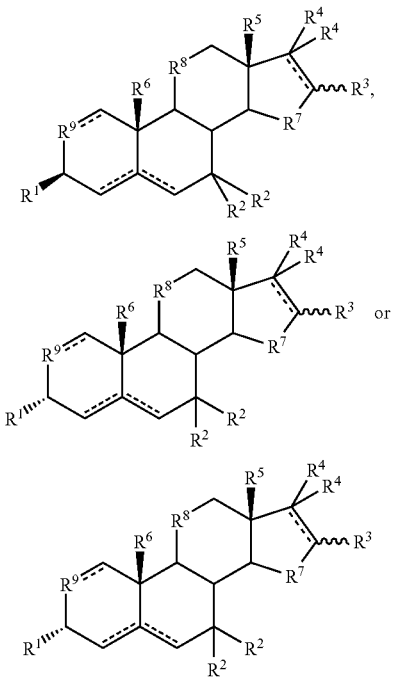

wherein one $R^4$ is absent when there is a double bond at the 16-17 position and wherein $R^7$, $R^8$ and $R^9$ are independently selected and wherein one, two or three of $R^7$, $R^8$ and $R^9$ are not —$CH_2$— or —CH= and wherein hydrogen atoms at the 5 (if present), 8, 9 and 14 positions respectively are in the α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β, configurations, typically α.α.β.α or β.α.β.α.

39D. The method of embodiment 38D wherein $R^8$ is —$CH_2$—, —O—, —S— or —NH—.

40D. The method of embodiment 38D or 39D wherein $R^7$ is —$CH_2$—$CHR^{10}$—, —$CH_2$—, —O—$CHR^{10}$— or —O—C(O)—.

41D. The method of embodiment 38D, 39D or 40D wherein $R^8$ or $R^9$ is absent.

42D. The method of embodiment 38D or 39D wherein $R^7$ and $R^9$ independently are —$CHR^{10}$—, —$CH_2$—, —CH=, —O—, —S— or —NH—, wherein $R^{10}$ is —OH, —SH, a $C_{1-30}$ organic moiety, a $C_{1-30}$ ester, $C_{1-10}$ optionally substituted alkyl, $C_{1-10}$ optionally substituted alkoxy, $C_{1-10}$ optionally substituted alkenyl or $C_{1-10}$ optionally substituted alkynyl.

43D. The method of embodiment 32D wherein the formula 1 method has the structure

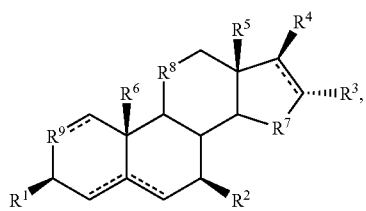

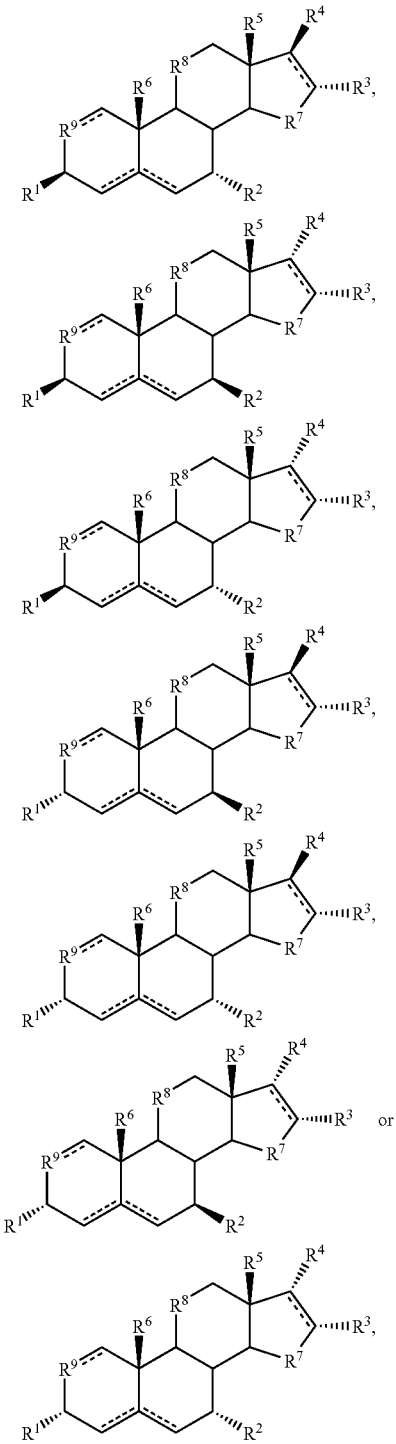

wherein hydrogen atoms at the 5 (if present), 8, 9 and 14 positions respectively are in the α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β configurations, typically α.α.β.α or β.α.β.α.

44D. The method of embodiment 43D wherein $R^4$ is —OH, =O, —SH, —SCN, a $C_{1-30}$ ester or $C_{1-30}$ alkoxy, wherein the ester or alkoxy moiety is optionally substituted with one, two or more independently selected substituents, which are optionally selected from —F, —Cl, —Br, —I, —O—, =O, —S—, —NH—, —$R^{PR}$, —$OR^{PR}$, —$SR^{PR}$ or —$NHR^{PR}$.

45D. The method of embodiment 43D or 44D wherein $R^1$ is —OH, =O, —SH, —SCN, a $C_{1-30}$ ester or $C_1$-$C_{30}$ alkoxy, wherein the ester or alkoxy moiety is optionally substituted with one, two or more independently selected substituents, which are optionally selected from —F, —Cl, —Br, —I, —O—, =O, —S—, —NH—, —$R^{PR}$, —$OR^{PR}$, —$SR^{PR}$ or —$NHR^{PR}$.

46D. The method of any of embodiments 32D-45D wherein a second $R^1$ is present and it is a moiety other than hydrogen, e.g., —OH, —SH, —SCN, a $C_{1-30}$ ester, $C_{1-30}$ alkoxy, $C_{1-30}$ alkynyl or a monosaccharide wherein the ester, alkoxy, alkynyl or monosaccharide is optionally substituted with one, two or more independently selected substituents, which are optionally selected from —F, —Cl, —Br, —I, —O—, =O, —S—, —NH—, —$R^{PR}$, —$OR^{PR}$, —$SR^{PR}$ or —$NHR^{PR}$.

47D. The method of any of embodiments 32D-46D wherein a second $R^2$ is present and it is a moiety other than hydrogen, e.g., —OH, —SH, —SCN, a $C_{1-30}$ ester or $C_{1-30}$ alkoxy, $C_{1-30}$ alkynyl or a monosaccharide wherein the ester, alkoxy, alkynyl or monosaccharide is optionally substituted with one, two or more independently selected substituents, which are optionally selected from —F, —Cl, —Br, —I, —O—, =O, —S—, —NH—, —$R^{PR}$, —$OR^{PR}$, —$SR^{PR}$ or —$NHR^{PR}$.

48D. The method of any of embodiments 32D-47D wherein a second $R^3$ is present and it is a moiety other than hydrogen, e.g., —OH, —SH, —SCN, a $C_{1-30}$ ester or $C_{1-30}$ alkoxy, $C_{1-30}$ alkynyl or a monosaccharide wherein the ester, alkoxy, alkynyl or monosaccharide is optionally substituted with one, two or more independently selected substituents, which are optionally selected from —F, —Cl, —Br, —I, —O—, =O, —S—, —NH—, —$R^{PR}$, —$OR^{PR}$, —$SR^{PR}$ or —$NHR^{PR}$.

49D. The method of any of embodiments 32D-48D wherein a second $R^4$ is present and it is a moiety other than hydrogen, e.g., —OH, —SH, —SCN, a $C_{1-30}$ ester or $C_{1-30}$ alkoxy, $C_{1-30}$ alkynyl or a monosaccharide wherein the ester, alkoxy, alkynyl or monosaccharide is optionally substituted with one, two or more independently selected substituents, which are optionally selected from —F, —Cl, —Br, —I, —O—, =O, —S—, —NH—, —$R^{PR}$, —$OR^{PR}$, —$SR^{PR}$ or —$NHR^{PR}$.

50D. The method of any of embodiments 32D-49D wherein there is a double bond at the 1-2 position.

51D. The method of any of embodiments 32D-49D wherein there is a double bond at the 4-5 position.

52D. The method of any of embodiments 32D-49D wherein there is a double bond at the 5-6 position.

53D. The method of any of embodiments 32D-49D wherein there is a double bond at the 16-17 position.

54D. The method of any of embodiments 32D-49D wherein there are double bonds at the 1-2 and 4-5 positions.

55D. The method of any of embodiments 32D-49D wherein there are double bonds at the 1-2 and 5-6 positions.

56D. The method of any of embodiments 32D-49D wherein there are double bonds at the 1-2 and 16-17 positions.

57D. The method of any of embodiments 32D-49D wherein there are double bonds at the 4-5 and 16-17 positions.

58D. The method of any of embodiments 32D-49D wherein there are double bonds at the 5-6 and 16-17 positions.

59D. The method of any of embodiments 32D-49D wherein there are double bonds at the 1-2, 4-5 and 16-17 positions.

60D. The method of any of embodiments 32D-49D wherein there are double bonds at the 1-2, 5-6 and 16-17 positions.

61D. A compound of formula 1, e.g., a compound in any compound group or embodiment disclosed herein.

62D. A composition comprising a compound of formula 1, e.g., a compound in any compound group or embodiment disclosed herein, and an excipient.

63D. Use of a compound of formula 1, e.g., a compound in any compound group or embodiment disclosed herein, to manufacture a medicament for the treatment of a blood cell deficiency, e.g., NP of TP, in a subject, e.g., a mammal or a human.

64D. A product produced by the process of contacting a formula 1 compound, e.g., a compound in any compound group or embodiment disclosed herein, and an excipient.

65D. A kit comprising a formulation that comprises a unit dosage or a multiple dosage comprising a formula 1 compound, e.g., a compound in any compound group or embodiment disclosed herein, and one or more excipients wherein the formulation is dispensed in a suitable container, wherein the kit further comprises a label that provides information about one or more of (1) the formula 1 compound's chemical structure, (2) any recommended dosing regimen, (3) any adverse effects of administering the formula 1 compound to a subject that are required to be disclosed and (4) the amount of the formula 1 compound that is present in each unit dose or in the entire container.

Embodiments related to BrEA hemihydrate include the following.

1E. 16α-Bromo-3β-hydroxy-5α-androstan-17-one hemihydrate substantially free of other forms of 16α-bromo-3β-hydroxy-5α-androstan-17-one.

2E. The 16α-bromo-3β-hydroxy-5α-androstan-17-one hemihydrate substantially free of other forms of 16α-bromo-3β-hydroxy-5α-androstan-17-one of embodiment 1E wherein 16α-bromo-3β-hydroxy-5α-androstan-17-one hemihydrate comprises at least about 55% w/w of the 16α-bromo-3β-hydroxy-5α-androstan-17-one that is present.

3E. The 16α-bromo-3β-hydroxy-5α-androstan-17-one hemihydrate substantially free of other forms of 16α-bromo-3β-hydroxy-5α-androstan-17-one of embodiment 1E wherein 16α-bromo-3β-hydroxy-5α-androstan-17-one hemihydrate comprises at least about 98% w/w of the 16α-bromo-3β-hydroxy-5α-androstan-17-one that is present.

4E. The 16α-bromo-3β-hydroxy-5α-androstan-17-one hemihydrate of embodiment 3E, characterized by one or more of (1) an absorption endotherm onset as measured by differential scanning calorimetry analysis of about 100° C., (2) two carbonyl absorption bands at about 1741 $cm^{-1}$ and 1750 $cm^{-1}$ as measured by Fourier transform infrared absorption spectroscopy, (3) a water content of about 2.4% w/w to about 2.6% w/w as measured by Karl Fisher titration and (4) 1, 2, 3, 4, 5, 6 or more of the X-ray powder diffraction peaks at 17.8, 23.8, 24.2, 26.9-27.2, 28.6, 30.1 or 32.2 Theta, obtained from an XRD spectrum of 16α-bromo-3β-hydroxy-5α-androstan-17-one hemihydrate using Cu—Kα radiation.

5E. The 16α-bromo-3β-hydroxy-5α-androstan-17-one of embodiment 1E, 2E or 3E in a composition comprising an excipient suitable for human pharmaceutical use or for veterinary use.

6E. A method to make 16α-bromo-3β-hydroxy-5α-androstan-17-one hemihydrate comprising contacting water, 16α-bromo-3β-hydroxy-5α-androstan-17-one and a C1C6 alcohol.

7E. The method of embodiment 6E wherein the C1-C6 alcohol is ethanol.

8E. The method of embodiment 6E wherein the solution comprises about 5-25% w/w water, about 30-45% w/w ethanol and about 30-45% w/w of a 16α-bromo-36-hydroxy-5α-androstan-17-one preparation.

9E. The method of embodiment 6E wherein the solution comprises about 18-22% w/w water, about 37-43% w/w ethanol and about 37-43% w/w of a 16α-bromo-36-hydroxy-5α-androstan-17-one preparation.

10E. The method of embodiment 9E wherein the solution is at a temperature of about −20° C. to about 45° C.

11E. The 16α-bromo-3β-hydroxy-5α-androstan-17-one hemihydrate of embodiment 1E substantially free of anhydrous 16α-bromo-3β-hydroxy-5α-androstan-17-one or substantially free of amorphous 16α-bromo-3β-hydroxy-5α-androstan-17-one.

12E. A product produced by the process of contacting a solution comprising water, 16α-bromo-3β-hydroxy-5α-androstan-17-one and a C1-C6 alcohol.

13E. The product of embodiment 12E that is 16α-bromo-3β-hydroxy-5α-androstan-17-one hemihydrate.

14E. The product of embodiment 12E wherein the solution comprises about 5-25% w/w water, about 30-45% w/w ethanol and about 30-45% w/w of a 16α-bromo-3β-hydroxy-5α-androstan-17-one preparation.

Embodiments related to buccal and sublingual formulations that comprise a formula 1 compound include the following.

1F. A solid buccal, sublingual or transmucosal oral mucosa formulation (or composition) having dimensions, e.g., as disclosed herein, which fit into the buccal cavity or under the tongue of a subject, comprising (1) a suitable amount of any formula 1 compound, e.g., about 0.1 to about 100 mg or about 0.5-50 mg, or about 20-30 mg disclosed herein, (2) about 20 to about 75 percent by weight of a PEG having a molecular weight of from about 100-4000, (3) about 2 to about 54 percent by weight of a PEG having a molecular weight of from about 6000-20,000, and (4) about 1 to about 40 percent by weight of polyethylene oxide having a molecular weight of from about 100,000 to about 5,000,000. The formulation may comprise about 10, 20, 25, 30 or 40 mg of the formula 1 compound.

2F. The formulation of embodiment 1 wherein comprising a formulation that substantially or completely erodes or disintegrates over a period of about 10-30 minutes while in water at about 37° C. or in a subject's oral cavity.

3F. The formulation of embodiments 1F or 2F wherein the formula 1 compound is homogeneously or nonhomogenously dispersed in a non-crystalline, solidified polymeric matrix which adheres to oral mucosa after being activated by or contacting sufficient water or saliva.

4F. The formulation of embodiments 1F-3F wherein the PEG of component (2) is a mixture of low molecular weight polyethylene glycols, which optionally comprises 1, 2 or more of PEG1000, PEG1450 and PEG3350.

5F. The formulation of embodiments 1F-4F wherein the PEG of component (2) is present in a proportion of from about 35% to about 65% by weight of the total composition.

6F. The formulation of embodiments 1F-5F wherein the PEG of component (3) comprises PEG8000.

7F. The formulation of embodiments 1F-6F wherein the PEG of component (3) comprises (i) PEG20000 or (ii) a mixture of PEGs, e.g., a mixture of PEG8000 and PEG20,000.

8F. The formulation of embodiments 1F-7F wherein the PEG of component (4) comprises polyethylene oxide having a molecular weight of about 100,000 (which is optionally present in an amount from about 2% to about 10% by weight) or a molecular weight of about 5,000,000.

9F. The formulation of embodiments 1F-8F wherein the formulation further comprises a plasticizer, e.g., propylene glycol, which is optionally present in a proportion of about 3 percent by weight.

10F. A method to prevent, treat, ameliorate or slow the progression or development of a condition or symptom disclosed herein in a subject comprising administering to the subject an effective amount of the formulation of embodiments 1F-9F, e.g., using a dosing protocol essentially as described herein, e.g., by continuous daily dosing or by intermittent administration. Related embodiments provide the use of the formulation of embodiments 1F-9F to prepare a medicament to prevent, treat, ameliorate or slow the progression of a condition or symptom disclosed herein, e.g., by continuous daily dosing or by intermittent administration. Suitable subjects include mammals, humans or subjects disclosed herein.

11F. The method of embodiment 10F wherein the formula 1 compound is a compound disclosed in any of the compound groups contained herein, e.g., compound groups 1-54, or any formula 1 structure disclosed herein.

12F. A method for administering a formula 1 compound to a subject in need of treatment comprising contacting the mucosa of the subject an effective amount of a composition comprising a formula 1 compound and a cyclodextrin. The composition may comprise a formulation that comprises about 0.1 to about 100 mg, e.g., about 10, 20, 25, 30 or 40 mg of the formula 1 compound per unit dosage. Suitable subjects include mammals, humans or subjects disclosed herein. The subject may have or be subject to developing a condition or symptom disclosed herein and the method is used to prevent, treat, ameliorate or slow the progression or development of the condition or symptom. The formulation optionally comprises a cyclodextrin-formula 1 compound complex.

13F. The method of embodiment 12F wherein the cyclodextrin is γ-cyclodextrin, β-cyclodextrin or hydroxypropyl-β-cyclodextrin, any of which are crystalline, amorphous or a mixture thereof.

14F. The method of embodiments 12F and 13F wherein the formulation further comprises propylene oxide or epichlorohydrin, which are optionally prepared as condensation products with the cyclodextrin.

15F. The method of embodiments 12F-14F wherein the formula 1 compound is a compound disclosed in any of the compound groups contained herein, e.g., compound groups 1-54, or any formula 1 structure disclosed herein.

16F. A method for administering a formula 1 compound to a subject in need of treatment comprising contacting the mucosa of the subject with an effective amount of a composition comprising a formula 1 compound and about 70-90% w/w (e.g., about 80-85%) of a low molecular weight PEG (a mol. weight of about 200 to about 2000, e.g., PEG1000), about 0-4% w/w (e.g., about 0.5%) of a higher molecular weight PEG (a mol. weight of about 3000 to about 20000, e.g., PEG3350 or PEG 8000), about 0-4% w/w (e.g., about 0.5%) of a long chain saturated or unsaturated carboxylic acid (e.g., a 010-24 carboxylic acid or C12-18 such as myristic acid), about 0.1-4% w/w of polyethylene oxide (e.g., about 0.5%) (mol. weight about 100,000-5,000,000) and about 10-20% w/w colloidal silica (e.g., about 12-18% or about 16%). The composition may comprise a formulation that comprises about 0.1 to about 100 mg, e.g., about 10, 20, 25, 30 or 40 mg of the formula 1 compound per unit dosage. Suitable subjects include mammals, humans or subjects disclosed herein. The subject may have or be subject to developing a condition or symptom disclosed herein and the method is used to prevent, treat, ameliorate or slow the progression or development of the condition or symptom.

17F. A method for administering a formula 1 compound to a subject in need of treatment comprising contacting the mucosa of the subject with an effective amount of a composition comprising a formula 1 compound, erythritol, a crystalline cellulose, a crospovidone and optionally mannitol. The composition may comprise a formulation that comprises about 0.1 to about 100 mg, e.g., about 10, 20, 25, 30 or 40 mg of the formula 1 compound per unit dosage. Suitable subjects include mammals, humans or subjects disclosed herein. The subject may have or be subject to developing a condition or symptom disclosed herein and the method is used to prevent, treat, ameliorate or slow the progression or development of the condition or symptom.

18F. The method of embodiment 17F wherein the composition comprises a solid formulation and the erythritol is comprises a proportion of 5-90 parts by weight, based on 100 parts by weight of the composition.

19F. The method of embodiments 17F or 18F wherein the crystalline cellulose comprises a proportion of 3-50 parts by weight, based on 100 parts by weight of the composition.

20F. The method of embodiments 17F-19F wherein the crospovidone comprises a proportion of 1-10 parts by weight of the composition.

21F. The method of embodiments 17F-20F wherein the formula 1 compound, the erythritol, the crystalline cellulose, the crospovidone and the optional mannitol, are uniformly mixed.

22F. The method of embodiments 17F-20F wherein the composition comprises a tablet or lozenge.

23F. The method of embodiments 17F-20F wherein the composition comprises about 0.3-50 parts by weight of the formula 1 compound, about 50-80 parts by weight of erythritol, about 5-20 parts by weight of crystalline cellulose and about 3-7 parts by weight of crospovidone. Embodiments related to treatment of the delayed effects of radiation include the following.

1G. A method to treat a symptom or condition associated with one or more delayed adverse or unwanted effects of radiation exposure in a subject in need thereof comprising administering to the subject, or delivering to the subject's tissues, an effective amount of a compound of formula 1, wherein the formula 1 compound is administered or delivered to the subject's tissues beginning at least 1 day (e.g., at 2, 4, 6, 7, 14, 30 or more days) after the subject has been exposed to a dose of radiation that will cause or could potentially cause the one or more delayed adverse or unwanted effects of the radiation exposure, or wherein the formula 1 compound is administered or delivered to the subject's tissues beginning at least 1 day (e.g., at 2, 4, 6, 7, 14, 30 or more days) after the subject has been exposed to at least one subdose of a planned course of radiation exposures that will cause or could potentially cause the one or more delayed adverse effects or unwanted effects of the radiation exposure.

2G. The method of embodiment 1G wherein the subject has received a total radiation dose of at least about 0.5 Gy to about 300 Gy, wherein the subject received the radiation dose in a single dose or in two or more divided doses.

3G. The method of embodiment 1G or 2G wherein the subject has received a total radiation dose of at least about Gy 1 to about 200 Gy.

4G. The method of embodiment 1G, 2G or 3G wherein the subject has received a total radiation dose of at least about Gy 2 to about 150 Gy.

5G. The method of embodiment 1G, 2G, 3G, or 4G wherein the symptom or condition associated with one or more delayed adverse effect of radiation is one or more of encephalopathy, myelopathy, nausea, vomiting, diarrhea, acute inflammation, chronic inflammation, edema, pain, headache, depression, fever, malaise, weakness, hair loss, skin atrophy, skin ulceration, skin lesion, keratosis, telangiectasia, infection, hypoplasia, atrophy, fibrosis, pneumonitis, bone marrow hypoplasia, hemorrhage or cytopenia.

6G. The method of embodiment 5G wherein the infection is a bacterial, viral, fungal, parasite or yeast infection, or wherein the fibrosis is lung fibrosis or wherein the cytopenia is anemia, leukopenia or thrombocytopenia.

7G. The method of embodiment 1G, 2G, 3G, or 4G wherein the symptom or condition associated with one or more delayed adverse or unwanted effect of the radiation exposure is caused by or associated with radiation damage to one or more of bone marrow cells, bowel epithelium, bone marrow, testicles, ovaries, brain nerves or tissue, peripheral nerves, spinal cord nerves or tissue or skin epithelium.

8G. The method of embodiment 1G to 7G wherein the subject has received or will receive a total radiation dose of at least about 0.5 Gy, at least about 2 Gy, at least about 4 Gy, at least about 6 Gy or at least about 10 Gy.

9G. The method of embodiment 1G to 7G wherein the subject has received or is anticipated to receive a total radiation dose of at least about 10 Gy, e.g., about 10, 20, 30, 40, 50, 100, 150, 200 or 300 Gy.

10G. The method of embodiment 1G to 9G wherein the formula 1 compound is administered to the subject or delivered to the subject's tissues by daily administration of the formula 1 compound or the formula 1 compound is administered to the subject or delivered to the subject's tissues using an intermittent dosing protocol or method and wherein the administration to the subject or the delivery to the subject's tissues is conducted for a period of at least about 2 days to at least about 2 years.

11G. The method of embodiment 1G to 10G wherein about 0.05 mg/kg/day to about 500 mg/kg/day of the formula 1 compound is administered to the subject or delivered to the subject's tissues.

12G. The method of embodiment 11G wherein about 0.1 mg/kg/day to about 50 mg/kg/day of the formula 1 compound is administered to the subject or delivered to the subject's tissues.

13G. The method of embodiment 12G wherein about 0.4 mg/kg/day to about 25 mg/kg/day of the formula 1 compound is administered to the subject or delivered to the subject's tissues.

14G. The method of any of embodiments 1G to 13G wherein the all or some of the formula 1 compound is administered to the subject or delivered to the subject's tissues by one or more of an oral, parenteral, topical, aerosol, nasal, rectal, vaginal, buccal or sublingual route.

15G. The method of any of embodiments 1G to 14G wherein the formula 1 compound has the formula 20

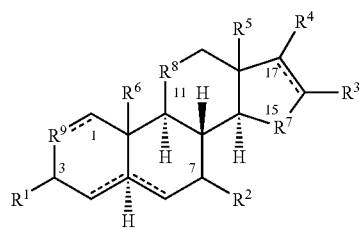

wherein $R^1$ is —H, —OH, =O, —SH, =S, —OCH$_3$, —OC$_2$H$_5$, —O—S(O)(O)—O—Na$^+$, —O—S(O)(O)—OC$_2$H$_5$, —CH$_3$, —C$_2$H$_5$, —OC(O)C(CH$_3$)$_3$, —OC(O)CH$_3$, an optionally substituted monosaccharide, an optionally substituted oligosacccharide comprising two, three or more covalently linked optionally substituted monosaccharides, or an amino acid;

$R^2$ is —H, —OH, =O, —CH$_3$, —CF$_3$, —OCH$_3$, —OC$_2$H$_5$, —C$_2$H$_5$, —OCH$_2$CH$_2$CH$_3$, —OCH$_2$CH$_2$CH$_2$CH$_3$, —F, —Cl, —Br or —I;

$R^3$ is —H, —F, —Cl, —Br, —I, —OH, —SH, =O, =CH$_2$, —NH$_2$, —CH$_3$, —CF$_3$, —C$_2$H$_5$, —O—C(O)—CH$_3$, —O—C(O)—CH$_2$CH$_3$, —O—C(O)—CH$_2$CH$_2$CH$_3$, —C(O)—CH$_3$, —C(O)—CH$_2$CH$_3$, —C(O)—CH$_2$CH$_2$CH$_3$;

$R^4$ is —H, —F, —Cl, —Br, —I, —OH, =O, =CH$_2$, —CCH, —SH—O—C(O)—CH$_3$, —O—C(O)—CH$_2$CH$_3$, —O—C(O)—CH$_2$CH$_2$CH$_3$, —C(O)—CH$_3$, —C(O)—CH$_2$CH$_3$, —C(O)—CH$_2$CH$_2$CH$_3$, —CHOH—CH$_3$, —CHOH—CH$_2$CH$_3$, —CHOH—CH$_2$CH$_2$CH$_3$, —CHOH—C$_6$H$_{13}$, an optionally substituted monosaccharide, an optionally substituted oligosacccharide comprising two, three or more covalently linked optionally substituted monosaccharides or an amino acid;

$R^5$ and $R^6$ are independently —H, —CH$_3$, —CH$_2$OH, —CHO, —CH$_2$F, —CH$_2$Cl, —CH$_2$Br, —CH$_2$I;

$R^7$ is —CH$_2$—, —CHF—, —CHCl—, —CHBr—, —CHI—, —C(CH$_2$)— or —CH(C$_{1-8}$ alkyl, e.g., —CH(CH$_3$)—, —CH(C$_2$H$_5$)— or —CH(C$_3$H$_7$)—);

$R^8$ is —CH$_2$—, —CHF—, —CHCl—, —CHBr—, —CHI—, —C(CH$_2$)—, —CH(CH$_3$)—, —CH(C$_2$H$_5$)— or —CH(C$_3$H$_7$)—;

$R^9$ is —CH$_2$—, —CHOH—, —CHF—, —CHCl—, —CHBr—, —CHI—, —C(CH$_2$)—, —CH(CH$_3$)—, —CH(C$_2$H$_5$)—, —CH(C$_3$H$_7$)—, —CH(OCH$_3$)—, —CH(OC$_2$H$_5$)— or —CH(OC$_3$H$_7$)—; and the hydrogen atom at the 5-position, if present, is in the α- or β-configuration.

16G. The method of embodiment 15G wherein $R^1$, if monovalent, is in the β-configuration.

17G. The method of embodiment 15G wherein $R^1$, if monovalent, is in the α-configuration.

18G. The method of embodiment 15G, 16G or 17G wherein $R^2$, if monovalent, is in the β-configuration.

19G. The method of embodiment 15G, 16G or 17G wherein $R^2$, if monovalent, is in the α-configuration.

20G. The method of embodiment 15G, 16G, 17G 18G or 19G wherein $R^3$, if monovalent, is in the α-configuration.

21G. The method of embodiment 15G, 16G, 17G 18G or 19G wherein $R^3$, if monovalent, is in the β-configuration.

22G. The method of embodiment 15G, 16G, 17G, 18G, 19G, 20G or 21G wherein $R^4$, if monovalent, is in the 6-configuration.

23G. The method of embodiment 15G, 16G, 17G, 18G, 19G, 20G or 21G wherein $R^4$, if monovalent, is in the α-configuration.

24G. The method of any of embodiments 15G, 16G, 17G, 18G, 19G, 20G, 21G, 22G or 23G wherein $R^5$ and $R^6$ are both in the β-configuration.

25G. The method of any of embodiments 1G to 24G wherein $R^7$, $R^8$ and $R^9$ independently are —CH$_2$—, —CHF—, —CHCl—, —CHBr—, —CHI—, —CH(C$_{1-8}$ alkyl)- or —CHOH—.

26G. The method of any of embodiments 1G to 25G wherein $R^5$ and $R^6$ independently are —CH$_3$—CH$_2$F, —CH$_2$Cl, —CH$_2$Br, —CH$_2$I, or —CH$_2$OH or wherein $R^5$ and $R^6$ are both —CH$_3$.

27G. The method of any of embodiments 15G-26G wherein the formula 1 compound comprises 0, 1 or 2 double bonds, wherein the double bonds are optionally at the 1-2, 4-5 or 5-6 positions, or wherein the double bonds are optionally at the 4-5, 5-6 or 16-17 positions, or wherein the double bonds are optionally at the 1-2, 4-5 or 16-17 positions, or wherein the double bonds are optionally at the 1-2, 5-6 or 16-17 positions.

28G. The method of embodiment 27G wherein the formula 1 compound is 16α-bromoepiandrosterone, 16α-bromoepiandrosterone hemihydrate, 3β,7β,17β-trihydroxyandrost-5-ene, 3β,17β-dihydroxyandrost-5-ene, 3β-hydroxyandrost-5-ene-7,17-dione or 16α-fluoroandrost-5-ene-17-one.

In other embodiments, the formula 1 compounds have the structures shown in embodiment 43D wherein hydrogen atoms at the 5 (if present), 8, 9 and 14 positions respectively are in the α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β configurations, typically α.α.β.α or β.α.β.α., $R^1$, $R^2$ and $R^3$ independently are a moiety as defined herein such as —H, —OH, =O, an ester, an ether, a lipid moiety or —O—S(O)(O)—N(R$^{35}$)$_2$, where each $R^{35}$ independently is —H, optionally substituted alkyl (e.g., C1-8 alkyl, methyl, ethyl, propyl, butyl or hexyl optionally substituted with one or more —OH, =O or —O—), optionally substituted alkenyl, a heterocycle, phenyl or benzyl, $R^4$ is a moiety as defined herein such as —H, —OH, =O, an ester, an ether, —C(O)—CH$_2$OH, —C(O)—CH$_2$—COOH, —C(O)—CH(O), —C(O)—CH$_3$, —C(O)—CH$_2$(halogen), —C(O)—CH$_2$F, —C(O)—CHF$_2$, —C(O)—CF$_3$, —C(O)—CH$_2$Cl, —C(O)—CHCl$_2$, —C(O)—CCl$_3$, —C(O)—CH$_2$CH$_2$OH, —C(O)—CH$_2$CH$_3$, —C(O)—CH$_2$CH$_2$F, —C(O)—CH$_2$CHF$_2$, —C(O)—CH$_2$CF$_3$, —C(O) —CH$_2$CH$_2$Cl, —C(O)—CH$_2$CHCl$_2$, —C(O)—CH$_2$CCl$_3$, —C(O)—O—CH$_2$OH, —C(O)—O—CH$_3$, —C(O)—O—CH$_2$(halogen), —C(O)—O—CH$_2$F, —C(O)—O—CHF$_2$, —C(O)—O—CF$_3$, —C(O)—O—CH$_2$Cl, —C(O)—CHCl$_2$, —C(O)—O—CCl$_3$, —C(O)—O—CH$_2$CH$_2$OH, —C(O)—O—CH$_2$CH$_3$, —C(O)—O—CH$_2$CH$_2$F, —C(O)—O—CH$_2$CHF$_2$, —C(O)—O—CH$_2$CF$_3$, —C(O)—O—CH$_2$CH$_2$Cl, —C(O)—O—CH$_2$CHCl$_2$, —C(O)—O—CH$_2$CCl$_3$, —CH(OH)—CH$_2$OH, —CH(OH)—CH(O), —CH(OH)—CH$_3$, —CH(OH)—CH$_2$(halogen), —CH(OH)—CH$_2$F, —CH(OH)—CHF$_2$, —CH(OH)—CF$_3$, —CH(OH)—CH$_2$Cl, —CH(OH)—CHCl$_2$, —CH(OH)—CCl$_3$, —CH(OH)—CH$_2$CH$_2$OH, —CH(OH)—CH$_2$CH$_3$, —CH(OH)—CH$_2$CH$_2$F, —CH(OH)—CH$_2$CHF$_2$, —CH(OH)—CH$_2$CF$_3$, —CH(OH)—CH$_2$CH$_2$Cl, —C(O)—CH$_2$CHCl$_2$, —CH(OH)—CH$_2$CCl$_3$, —CH(OH)—O—CH$_2$OH, —CH(OH)—O—CH$_3$, —CH(OH)—O—CH$_2$(halogen), —CH(OH)—O—CH$_2$F, —CH(OH)—O—CHF$_2$, —CH(OH)—O—CF$_3$, —CH(OH)—O—CH$_2$Cl, —CH(OH)—CHCl$_2$, —CH(OH)—O—CCl$_3$, —CH(OH)—O—CH$_2$CH$_2$OH, —CH(OH)—O—CH$_2$CH$_3$, —CH(OH)—O—CH$_2$CH$_2$F, —CH(OH)—O—CH$_2$CHF$_2$, —CH(OH)—O—CH$_2$CF$_3$, —CH(OH)—O—CH$_2$CH$_2$Cl, —C(O)—O—CH$_2$CHCl$_2$, —CH(OH)—O—CH$_2$CCl$_3$ or —CH(CH$_3$)CH$_2$CH$_2$CH(C$_2$H$_5$)—CH(CH$_3$)$_3$, $R^7$ and $R^9$ independently are a moiety as defined herein such as —CH$_2$—, —O—, —CHOH— with the —OH moiety in the α or β configuration or —C(O)—O and $R^8$ is a moiety as defined herein such as —CH$_2$—, —O—, —CHOH— with the —OH moiety in the α or β configuration, —C(O)—O, —CH(hydroxyl ester, e.g., a C1-8 ester)-, —CH(alkyl, e.g., a C1-8 alkyl)-, —CH(alkenyl, e.g., C1-8)-, —CH(ether, e.g., C1-8) or —C(OH)$_2$—. Related formula 1 compounds are optionally substituted at the 3, 7 or 17 positions with a second $R^1$, $R^2$ or $R^4$ that is not hydrogen, e.g., —CCH, halogen, —OH, alkyl such as methyl, ethyl or butyl or alkynyl such as ethynyl, 1-propynyl or 1-butynyl. For these compounds, double bonds may be absent, or they may be present at, e.g., the 1-2 and 4-5 positions or at a single position such as the 4-5 or the 5-6 positions. For some of these compounds, $R^5$ and $R^6$ independently are —H, —CH$_3$, —CH$_2$OH, —CH(O) or —C$_2$H$_5$. Also, 1, 2 or 3 of $R^{10}$ at the 1, 4 or 6 positions may independently be a moiety other than hydrogen, e.g., alkyl such as methyl, a halogen =CH$_2$, —CN, —OH or an ester. All of these formula 1 compounds are suitable for the uses and compositions disclosed herein.

In some embodiments, 1, 2 or more of, e.g., $R^1$, $R^2$, $R^3$, $R^4$ and $R^{10}$ can comprise a lipid moiety such as a fatty acid, a monoacylglyceride, a diacylglyceride, a phospholipid, a glycolipid, a sphingolipid or a glycerophospholipid that is esterified, linked through an ether (—O—) or acyl moiety or otherwise bonded to the formula 1 compound. Exemplary fatty acid esters include —C(O)—(CH$_2$)$_m$—H where m is 4, 5, 6, 7, 8, 9, 10, 11, 12, 13, 15, 17, 19 or 21 and —C(O)—(CH$_2$), —CH=CH—(CH$_2$)$_n$—H where each n independently is 1, 2, 3, 4, 5, 6, 7 or 8. Other lipid moieties that can be bonded to the steroid include phosphatidic acid, phosphatidylethanolamine, phosphatidylcholine, phosphatidylserine and phosphatidylglycerol. The lipid moiety may be bonded to the steroid through a hydroxyl or oxygen, phosphate, sulfate or amine at $R^1$, $R^2$, $R^3$, $R^4$ or $R^{10}$. Such lipid moieties may be bonded to any of the formula 1 compounds or genera of formula 1 compounds disclosed herein.

Variations and modifications of these embodiments, the claims and the remaining portions of this disclosure will be apparent to the skilled artisan after a reading thereof. Such variations and modifications are within the scope and spirit of this invention. All citations herein are incorporated herein by reference in their entirety. All citations herein are incorporated herein by reference with specificity.

EXAMPLES

The following examples further illustrate the invention and they are not intended to limit it in any way.

Example 1

16α-bromoepiandrosterone (BrEA) formulation. Two lots of a non-aqueous BrEA formulation were made at a BrEA concentration of 50 mg/mL in 25% polyethylene glycol 300, 12.5% dehydrated ethyl alcohol, 5% benzyl benzoate, and 57.5% propylene glycol as follows. BrEA was obtained from Procyte, Inc. The remaining excipients are shown below.

| Excipient | Specification | Supplier Lot No. | Final Product Concentration |
|---|---|---|---|
| Propylene glycol | USP | Arco Chemical HOC-61220-01104 | 57.5% (v:v) |
| Polyethylene glycol 300 | NF | Union Carbide 695752 | 25% (v:v) |
| Dehydrated alcohol | USP | McCormick Distilling 97K10 | 12.5% (v:v) |
| Benzyl benzoate | USP | Spectrum Pharmaceuticals MG025 | 5% (v:v) |

The formulation was prepared by suspending BrEA in polyethylene glycol 300, and sequentially adding propylene glycol, benzyl benzoate, and dehydrated ethyl alcohol to form a solution, which was diluted to the final desired volume with additional propylene glycol. The procedure is described below.

The calculated amount of polyethylene glycol 300 was added to a compounding vessel. Then, while mixing, the calculated amount of BrEA was added to the vessel, and mixed for at least 5 minutes to form a smooth, creamy liquid propylene glycol was added to the vessel, and mixed for a minimum of 5 minutes to form a uniform suspension. The calculated amount of benzyl benzoate is added to the vessel, and mixed for approximately 5 minutes to form a translucent liquid suspension. Dehydrated alcohol was added to the vessel, and mixed for approximately 5 minutes to form a clear, colorless solution. Propylene glycol was then added to achieve the desired final formulation, and mixed for approximately 5 minutes. The drug solution was transferred to a volume dispensing device set to deliver 1.2 mL per vial. Under nitrogen pressure, the solution was filtered through two 0.2 μm polyvinylidene fluoride filters in series into 2 cc amber glass vials. The vials were capped with Teflon-coated, butyl-rubber stoppers and crimp sealed. Materials used in the product vials are listed below.

| Material | Source | Product Code | Description |
|---|---|---|---|
| Vial | Wheaton | 2702-B51BA | Tubing vial, 2 mL/13 mm, glass, type 1 amber |
| Stopper | Omniflex | V9239 FM257/2 | 13 mm, Teflon coated, butyl rubber stopper |
| Seal | West | 4107 | Flip seal, 13 mm, mist gray bridge |

Product specifications were examined by one or more of the following assays.

| Test | Specification | Method |
|---|---|---|
| Physical Examination | Clear colorless solution with slight alcoholic odor | |
| Volume recovery | NLT* 1.0 mL | USP23<1> |
| Specific gravity | TBD | USP23<841> |
| Assay for active component | 90-110% of label | HPLC |
| Sterility | sterile | USP23<71> |
| Endotoxin | <0.1 EU/mg | USP23<85> |
| Particulate matter | ≧10 μm NMT** 6000/cnt ≧25 μm NMT 600/cnt | USP23<788> |

*NLT—no less than
**NMT—no more than

| | Lot Analysis | | |
|---|---|---|---|
| Test | Specification | Lot 1 | Lot 2 |
| Physical Examination | Clear colorless solution with slight alcoholic odor | Positive | Positive |
| Volume recovery | NLT 1.0 mL | 1.15 mL | — |
| Specific gravity | TBD | 1.0411 | — |
| Assay for active component | 90-110% of label | 103.10% | 104.25% |
| Sterility | sterile | sterile | — |
| Endotoxin | <0.1 EU/mg | 0.024 EU/mg | — |
| Particulate matter | ≧10 μm NMT 6000/cnt ≧25 μm NMT 600/cnt | 26 15 | — |

Example 2

BrEA drug substance and BrEA formulation stability. An accelerated stability study of 6 months duration is conducted using BrEA and the formulations from example 1. Samples are taken at 1, 2, 3, 4, 5, and 6 month time points and compared with the specifications listed in example 1. Real time stability (25° C., 60% relative humidity) is conducted using BrEA formulation Lots 1 and 2, with sampling time points at 3, 6, 9, 12, 18, 24, and 36 months. After 3 months of storage at 40° C. and 75% relative humidity, the assay potency of BrEA is at least 95% of the label value. The results from the stability testing indicate that BrEA is stable for at least 3 months at elevated temperature and humidity in the Lot 1 and 2 formulations.

Example 3

Primate intermittent dosing protocol. Pig-tail Macaque monkeys infected with the $SHIV_{229}$ retrovirus were treated with a BrEA formulation as described in example 1. $SHIV_{229}$ is a recombinant retrovirus containing HIV and SIV sequences. J. Thompson et al., abstract #75, 16$^{th}$ Annual Symposium on Nonhuman Primate Models for AIDS, Oct. 7-10, 1998, Atlanta, Ga., M. Agy et al., abstract #67, 16$^{th}$ Annual Symposium on Nonhuman Primate Models for AIDS, Oct. 7-10, 1998, Atlanta, Ga. In monkeys, it establishes an aggressive infection that leads to severe symptoms of end-stage disease in infected untreated animals at about 180-210 days after infection. Four pig-tail macaques (2/group) received subcutaneous injections of the formulation at 1 or 2 mg/kg body weight for 10 consecutive days (Protocol 1). On week 8, 3 of the 4 monkeys were retreated and 2 treatment naïve monkeys were treated with 5 mg/kg of the formulation on an every other day basis for a period of 20 days (Protocol 2). On week 19, all primates receiving treatment began a 3 course treatment regimen with 3 mg/kg of the BrEA formulation once daily for 10 consecutive days, repeated every four weeks for a total of 3 treatment courses (Protocol 3).

The animals were infected with 1-100 $TCID_{50}$ units administered intravenously or intrarectally. Viral titers in the first group of animals ranged from $10^6$ to $10^8$ before dosing began. All animals demonstrated an initial rise in plasma viral SHIV RNA. After a period of 2 to 3 weeks, titers began to decline and 3 of the 4 animals showed a response to therapy with average viral titers of 0.76 log below baseline at weeks 4 to 5 after initiation of treatment. By week 8, titers in all animals had returned to baseline values. Blood glucose levels dropped significantly, alkaline phosphatase levels were elevated and SGOT/GGT values trended towards the high end of normal. No other significant changes were observed in any of the parameters monitored. The CD4 levels in all monkeys remained less than 100 cells/mm$^3$ at the end of the first protocol.

Three of the five monkeys on the second regimen (Protocol 2) responded to the BrEA therapy with a greater depth and duration of response than observed at the lower dose levels. In the responding animals, the average decline below baseline was 1.47 log. The non-responding animal from Protocol 1 responded when administered the BrEA formulation in Protocol 2. Two animals did not respond, one each from the treatment experienced and treatment naïve groups.

The monkeys on this study were salvaged from an infectivity study and the first cohort of four monkeys on study (Protocol 1) were expected to live only a few weeks past the initiation of these experiments as they were beginning to deteriorate due to disease related causes. One animal died at day 356 from a toxic reaction to the anesthetic used during acquisition of a blood sample for analysis. Survival was greater than 380 days from the time of infection. Treatment by intermittent dosing of the BrEA formulation was used. Three control monkeys were infected with 1-10,000 $SHIV_{229}$ $TCID_{50}$ units and did not receive treatment. These animals are considered the no treatment arm of a survival study. The mean time to death for pig-tailed macaques infected with $SHIV_{229}$ was 193 days. Monkeys receiving therapy remained in good clinical health for over 350 days with CD4 levels less than 20 cells/mm$^3$ and without opportunistic infections or disease-related symptoms, other than a mild anemia in one animal.

These results show completely unexpected therapeutic responses by the primates infected with the SHIV retrovirus, which is quite virulent. The results show that the majority of subjects in these treatment protocols not only had significantly prolonged survival compared to untreated controls, but also the clinical symptoms associated with retroviral infection improved dramatically, despite the fact that CD4 counts remained low, i.e., less than about 100 CD4 cells/mm$^3$ initially and less than about 20 CD4 cells/mm$^3$ later in the treatment protocols. To date, results such as this, i.e., (1) good clinical health in a majority of subjects having low CD4 levels (less than about 150 cells/mm$^3$, especially less than about 75 cells/mm$^3$) and (2) no clinical sign of viral resistance to treatment despite intermittent dosing over a prolonged time period, are unprecedented in primates, humans or any other animal. The $SHIV_{229}$ model is extremely pathogenic in pig-tailed macaques. Events that occur in this model over several weeks would typically take several years in humans infected with HIV. Treatment of monkeys infected with this virus and treated with commonly used antiretrovirals, e.g., AZT, 3TC or a protease inhibitor, are not expected to significantly affect the course of disease progression. The clinical condition of the animals continues to improve, e.g., weight gain is about 8-15% per animal. These results show that the treatment using the intermittent dosing protocol is highly effective despite the apparent impairment of the subject's specific immunity, as shown by the low CD4 counts. Increased CD4 counts may be attained using immune stimulators such as IL2 or they may increase spontaneously in some subjects such as humans, depending on the treatment protocol, the duration of dosing or the subject's initial medical condition. The antiviral effects shown here appear to function at least in part by enhancing the subject's immune responses, e.g., enhanced immune response by phagocytic cells (NK cells, monocytes and/or macrophages), and/or enhancing any residual specific immune responses, if any, that the subject may be able to muster.

Example 4

Human treatment protocol. A dose escalation clinical trial is performed using a nonaqueous formulation containing BrEA or another formula 1 compound(s) that is prepared essentially as described in example 1. The patients are treatment naïve or treatment experienced and about 3-10 patients are examined at each dose level. The initial dose is 25 mg of BrEA or another formula 1 compound(s) that is administered parenterally, e.g., s.c. or i.m. The dose is administered once or once or twice per day for 1-12 days, followed by no dosing for at least 7 days (e.g., 7 to 90 days). Subsequent doses are administered once or once per day for 1-12 days, followed by no dosing for at least 7 days (e.g., 7 to 90 days). Other dose levels tested are 20 mg, 50 mg, 75 mg, 100 mg, 150 mg, 200 mg, 250 mg and 300 mg with each dose administered once per day as a single dose or as two, three or more subdivided doses.

An efficacy dosing trial is performed using the same dosing protocol as the dose escalation trial or it may alternatively comprise dosing once or twice every other day for 3-17 days, followed by no dosing for 7-90 days and then repeating the dosing once or twice every other day for 3-17 days. This protocol is repeated indefinitely (e.g., at least about 3-18 months) using the optimal dose(s) obtained from the dose escalation trial, e.g., about 10-200 mg/day of a formula 1 compound.

Example 5

Animal pharmacological studies. Nonclinical studies were conducted using an oral and a subcutaneous formulation of BrEA. Rats were orally administered $^{14}$C BrEA solubilized in different excipients to determine the levels of drug in blood and various tissues. The results of these preliminary pharmacokinetics studies indicated that the absorption of BrEA by oral administration is about 0.1 to 15%, with at least about 80% excreted in the feces.

The nonaqueous BrEA formulation of example 1 was administered as a single subcutaneous dose to rabbits. More than 90% of the drug left the injection site within 24 hours of administration, and reached a maximum concentration in the plasma of about 1.2% of the injected dose at eight to twelve hours post administration. The circulating half-life of the drug in the plasma was about twelve hours. The drug did not accumulate to a significant extent in any major organ and was primarily excreted in the urine.

BrEA was administered subcutaneously to rats using the formulation of example 1. Approximately 90% of the drug left the injection site within 24 hours of administration, and reached a maximum concentration in the plasma of about 0.2% of the injected dose at one hour post administration. Elimination from the plasma was biphasic, with half-lives of about 12 and 72 hours respectively. BrEA did not accumulate to a significant extent in any major organ, and was excreted primarily in the feces. A study is also performed in Rhesus Monkeys with the example 1 formulation to determine plasma pharmacokinetics.

A pharmacokinetic analysis of $^{14}$C BrEA in plasma was conducted in two female Rhesus Monkeys. Trace labeled compound (16α-bromo-3-beta-hydroxy-5α-[4-$^{14}$C]-androstan-17-one [50 mCi/mmole]) was used at a dose of 1 mg/kg as a subcutaneous injection in the scapular region using an injection volume of 1 mL/kg. The BrEA was formulated in 25% polyethylene glycol 300, 12.5% absolute ethanol, 5% benzyl benzoate, and qs with propylene glycol. 40 μCi were injected per animal. Blood samples were taken at 0, 0.5, 1, 2, 4, 8, and 24 hours for determination of $^{14}$C activity. The radioactivity in the plasma rose to near peak concentration in 8 hours and remained at approximately the same level through the end of the study at 24 hours.

A pharmacokinetic analysis of $^{14}$C BrEA was conducted in New Zealand White rabbits. Twenty μCi of $^{14}$C 16α-bromo-3-beta-hydroxy-5α-[4-$^{14}$C]-androstan-17-one (50 mCi/mmole) plus 1 mg/kg unlabeled BrEA was administered to each of three New Zealand White rabbits as a subcutaneous injection in the scapular region using an injection volume of 1 mL/kg. The drug was formulated in 25% polyethylene glycol 300, 12.5% absolute ethanol, 5% benzyl benzoate, and qs with propylene glycol. Blood samples were taken at 0.5, 1, 2, 4, 8, 12, 24 hours for all three animals, and at 48 hours for two of the animals. Twenty-four hour and 48 hours after administration, one and two animals respectively, were sacrificed, and the following organs/tissues were collected: brain, heart, kidneys, liver, lungs, skeletal muscle, spleen, and injection site muscle and skin. In addition to the organs and tissues, urine and feces were collected as well as the cage wash. BrEA did not accumulate to a significant degree in any of the organs listed above. Of the organs, the greatest mass of drug was observed in the liver, containing approximately 0.8% and 0.12% of the injected dose at 24 and 48 hours, respectively (average 0.13%).

| Percentage of Drug in Organs (Rabbits) | | | |
|---|---|---|---|
| Organ or Tissue | Animal 201 24 hours | Animal 301 48 hours | Animal 302 48 hours |
| Brain | 0.005 | 0.002 | 0 |
| Heart | 0.008 | 0.003 | 0.002 |
| Kidneys | 0.155 | 0.055 | 0.050 |
| Liver | 0.76 | 0.145 | 0.125 |
| Lungs | 0.029 | 0.019 | 0.011 |
| Spleen | 0.002 | 0 | 0 |
| Skeletal muscle | 0.002 | 0 | 0 |
| (sample wt. in grams) | (3.8 g) | (6 g) | (5 g) |
| Skin | 0.008 | 0.002 | 0.004 |
| (sample wt. in grams) | (8 g) | (6 g) | (9 g) |

The average percentages of the administered dose in whole blood was calculated by multiplying the concentration of drug in whole blood by the assumed volume of blood in the animals, 200 mL. The amount of drug in the blood reaches a maximum at around 8 hours, and a small amount was still evident at 48 hours. The amount of BrEA in whole blood was consistently lower than in plasma, suggesting the drug is not taken up to an appreciable extent by red blood cells.

In vivo experiments were conducted to determine the bioavailability of BrEA via oral administration using different formulations. BrEA was (1) solubilized in soya oil, vitamin E oil, a mixture of vitamin E and cremophore or (2) BrEA was micronized and combined with or without a surfactant. These formulations are described below. The formulations were administered orally to rats and BrEA levels were determined in the blood, liver, spleen, kidney, and the lymph nodes. In the studies using micronized BrEA, the brain was evaluated for drug uptake. Twenty-four hour urine and feces were collected when BrEA was solubilized in vitamin E and soya oils and vitamin E mixed with Cremophore. The data from these studies indicate that BrEA enters into the lymphatics but is eliminated rapidly from the other tissues. The amount of $^{14}$C radioactivity recovered in the feces 24 hours after administration was 78 to 83%. A brief summary of each experiment is provided below and the results are provided in Table 6.

BrEA (5 mg in 1.0 mL of soya oil or vitamin E oil) supplemented with $^{14}$C-labelled BrEA was administered intragastrically to rats. Solubilization of BrEA in the vitamin E or soya oil was facilitated with 50 μL ethanol. Animals (3/time point) were assayed at 1.5, 3, 5.5, and 24 hours after administration and the $^{14}$C-radioactivity was measured in the blood, liver, spleen, kidney, lymph nodes and 24 hour feces and urine. The results indicate that, on the basis of $^{14}$C-radioactivity, some of the BrEA is taken into the lymphatic system. The uptake is greater with soya oil than vitamin E oil in the blood, liver, and lymph nodes.

BrEA (5 mg in 1.0 mL of a vitamin E and cremophore) supplemented with $^{14}$C-labelled BrEA was administered intragastrically to rats. Solubilization of BrEA in the vitamin E-cremophore mixture was facilitated by the adding 60 μL ethanol. Animals (4/time point) were sacrificed at 2, 3, 5.5, and 24 hours and $^{14}$C-radioactivity was measured in the blood, liver, spleen, kidney, lymph nodes and 24 hour feces and urine. The results indicate that a small portion of the drug is taken up by the lymphatic system. Judging from the values in plasma, liver and lymph nodes, it appears that drug uptake is slower compared with soy oil or vitamin E and its presence in the tissues is more persistent.

Rats, in groups of three males, were orally administered 1.0 mL of 0.9% NaCl containing 10 or 32 mg BrEA micronized with a surfactant, Synperonic PE/F 127 (2.5% wt/wt). Rats were examined at 1.5, 5 and 24 hours after administration. Blood, liver, spleen, kidney, lymph nodes, and brain were assayed for $^{14}$C radioactivity. The levels of BrEA in the blood, in comparison to the experiments with BrEA in Vitamin E oil and soya, were higher, 0.3% at 1.5 hours, and increased after 5 hours to 0.8% and 0.9% of the 10 and 32 mg dose, respectively. Additionally, the values in the lymph nodes were similar to those measured at 1.5 hours and the levels were sustained at 5 hours (5.3 and 5.0%) and 24 hours (3.7 and 3.1%) for the 10 and 32 mg dose, respectively (refer to Table 6).

In a repeated dose experiment, rats were intragastrically administered 1.0 mL 0.9% NaCl containing 2 mg BrEA micronized with Synperonic PE/F 127 (2.5% wt/wt) every 6 to 16 hours. Rats (3/time point) were sacrificed at 40, 72, 84, 90 and 96 hours after the first administration. Blood, liver, spleen, kidney and lymph nodes were assayed for $^{14}$C radioactivity. Higher levels in the blood, liver, kidneys and lymph nodes were noted in this experiment over previous studies.

Rats, in groups of three males, were orally administered 1.0 mL of 0.9% NaCl containing 2, 4 or 10 mg BrEA micronized without a surfactant. Rats were sacrificed at 1.5, 5 and 24 hours after administration and blood, liver, spleen, kidney, lymph nodes and brain were assayed for $^{14}$C radioactivity. The concentration of BrEA micronized without a surfactant in the observed tissues was lower than BrEA plus a surfactant.

Example 6

Inhibition of parasites in vitro. For in vitro antimalarial testing, micro-titer plates were used. The concentration of drugs were prepared as pMol/well according to WHO standard procedures (WHO, 1990). The test compound was dissolved in 15% DMSO in sterile RPMI-1640. Both chloroquine sensitive (e.g., WS/97) and resistant (e.g., MN/97) isolates of *Plasmodium* species are used.

A schizont inhibition assay was performed as follows. The micro-titer plates were predosed with various concentrations of the test compound. 50 μL of parasitised erythrocyte suspension in RPMI-1640 (0.2 mL erythrocyte+0.3 mL serum+ 4-5 ml RPMI-1640) were dispensed in microtiter wells that contained various concentrations of drug. Triplicate readings were made for each concentration.

A $^3$H-hypoxanthine incorporation assay was performed as follows. The testing was carried out according to the procedure of Desjardins et al. 1979. After 30 hr culture at 37 degrees C., the same microtiter plates from schizont inhibition assays with another triplicate wells were pulsed with $^3$H-hypoxanthine for overnight. The cell suspensions were washed twice on Millipore glass fiber filter with Millipore filter apparatus. The filter discs were counted for DPM by a Beckman LS6000 β-scintillation counter. The activity of the drug was measured by plotting DPM against concentration of drug.

Activity of Compounds Against Chloroquine Sensitive T996/86 *P. falciparum* in vitro

| Concentration (μM) | DHEA* | BrEA* | Etienic Acid Methyl Ester* | Etianic Acid Methyl Ester* |
|---|---|---|---|---|
| 30 | 65.6 | 98 | 60 | 61.5 |
| 15 | 44 | 60.1 | 45.7 | 47.4 |
| 7.5 | 38.3 | 50 | 40.9 | 45.3 |
| 3.25 | 37.2 | 43.7 | 46 | 41.4 |
| 1.875 | 23.2 | 40.9 | 41 | 43.4 |
| 0.938 | 37.2 | 31.8 | 43.3 | 47.1 |
| IC$_{50}$ | 19.0 μM | 7.5 μM | 19.5 μM | 17.5 μM |

*% inhibition

| Concentration (nM) Chloroquine | % Inhibition Chloroquine |
|---|---|
| 200 | 95.9 |
| 100 | 94.6 |
| 50 | 97.3 |
| 25 | 94.5 |
| 12.5 | 86.8 |
| 6.25 | 27.2 |
| IC$_{50}$ | 9.0 nM |

The activity of 16α-chloroepiandrosterone and 16α-bromodehydro-epiandrosterone against chloroquine sensitive T996.86 and chloroquine resistant KI *P. falciparum* in vitro is shown below.

| | | T996.86 | KI |
|---|---|---|---|
| 16-chloroepiandrosterone | IC$_{50}$ | ~9.25 pg/mL | ~9.25 μg/mL |
| DHEA-Br | IC$_{50}$ | ~25.0 pg/mL | ~25.0 μg/mL |

Other formula 1 compounds, e.g., any compound in compound group 1 through 25-6 are used in a similar manner to inhibit *Plasmodium* parasites.

Example 7

Four-day in vivo protocol for inhibition of *Plasmodium berghei*. The 4-day suppressive test has been widely used and it can be performed within a 1 week period. The test consists of the inoculation of parasitised erythrocytes on the first day of the experiment (D$_0$), followed by an injection of the test compound, which is also administered on the 2$^{nd}$, 3$^{rd}$ and 4$^{th}$ days of the protocol. On the 5$^{th}$ day, blood films are taken and antimalarial activity is assessed either by calculating parasitemia, or by scoring parasite numbers on a predetermined scale (i.e., 1-5). Peters (*Ann. Trop. Med. Parasitol.* 64: 25-40, 1970) described a basic procedure using this 4-day test.

The protocol is summarized as follows. Five female TO mice were used per test group. *P. berghei* HP15 ANKA parasites were collected by cardiac puncture using a heparinised syringe from a donor mouse having a 30+% parasitaemia. The blood was diluted with diluting agent (50% HIFCS+50% sterile PBS) to a final concentration of 1% parasitaemia or $1 \times 10^7$ infected erythrocytes per 0.2 mL of the infecting suspension. Each mouse was inoculated intravenously, which produced a more uniform infection rate than intraperitoneal administration of 0.2 mL of the infecting suspension. Test compounds were prepared at doses of 100 mg/kg in (16.7% DMSO+83.3% Celacol). The steroid formulations were administered intraperitoneally 2 hours after parasite inoculation. The compounds were administered once a day starting on $D_0$, and continued on the following three days. Blood films were made from tail blood on the day after the last dosing of compound and the blood was fixed with 100% methanol and stained with 10% Giemsa. Parasitaemias were scored on a scale of 0-5, where 5 is equal to the control.

An inoculum of 1% parasitaemia $1 \times 10^7$ erythrocytes/mL, 0.2 mL per mouse (female strain TO mice), was delivered by intravenous injection. Drug administration commenced 2 hours after inoculation on Day 1 and continued for 3 days. The results are shown below from blood films from all 20 mice on Day 5 when parasitaemias were assessed.

| Compound | Treatment | Parasitaemia Score (0-5) |
|---|---|---|
| BrEA | 100 mg/kg × 4 days i.p.* | 1 |
| Etienic Acid | 100 mg/kg × 4 days i.p. | 2 |
| DHEA | 100 mg/kg × 4 days i.p. | 1 |
| Chloroquine | 3 mg/kg × 4 days i.p. | 1 |
| control | N/A | 5 |

*i.p. = intraperitoneal injection

In a similar protocol, mice are inoculated with a solution containing $1 \times 10^7$ erythrocytes/mL by I.V. injection. Two hours later give drug is delivered by I.V. injection. BrEA or another formula 1 compound is given (0.2 mL I.V. or S.C.) once a day for 4 days. Tail snips are used to obtain blood after the study. Mice infected with *P. berghei* were used to obtain infected cells. Parasites are harvested from cardiac mouse blood, and uninfected mice are infected using 0.2 ml of blood with 14% parasitaemia per mouse I.V. Two hours later, the first dose of BrEA (100 mg/kg I.V. or S.C.) is delivered to the infected animals. The BrEA formulation was a sterile solution containing 15 mg/mL of BrEA in 45% hydroxypropyl-β-cyclodextrin and 0.9% saline. At 1, 2, 3 and 4 days after the infection of the animals, BrEA (100 mg/kg I.V. or S.C.) is delivered to the infected animals. No deaths occurred in the group receiving I.V. BrEA at day 30, but all control animals were dead by day 10. All animals treated with BrEA by S.C. delivery were dead by Day 11.

Example 8

Rat in vitro and in vivo study. In the in vitro protocol the parasite (*Plasmodium falciparum*, chloroquine sensitive strain WT and chloroquine resistant strain Dd2) level is adjusted to 1% and the hemocrit is adjusted to 7% with medium. Using a 96 well plate, 50 µL of parasite and 100 µL of drug mixed with media are added to each well and the procedure is done in triplicate. The plate is placed in a chamber containing a physiological gas mixture and incubated at 37° C. The media/drug mixture is changed at 24, 48 and 72 hours. On day 5 (96 hours) slides of each well are made, stained with Gemsia and 500 red blood cells are counted for each slide. The triplicates are averaged and data are reported in percent inhibition.

In the in vivo protocol, Lewis rats weighing 80-85 grams were given a standardized IP injection of parasite (*Plasmodium berghei*). Rats were then intravenously injected 2 hours later with one of the treatments described in the table below, returned to their housing, fed standard lab chow and allowed free access to water. Animals were weighed and treated again 24, 48, and 72 hours after the first treatment and again returned to their housing and they were allowed free access to food and water. The animals were weighed again and then bled using a 26-gauge needle on day 5, 11 and 28 post inoculation. Hemocrits were measured and blood smears are prepared for each rat. The blood smears were then stained using Gemsia and the level of parasitemia (defined as the percent of red cells with parasites) were determined. Animals were again returned to their housing and observed twice daily for evidence of progressive disease, defined as listlessness and or adverse drug reaction, which is defined as a loss of 20% of original body weight, for a total of 28 days. If either progressive disease or drug reaction is noted, the animals are euthanized.

The BrEA formulation was a sterile solution containing 15 mg/mL of BrEA in 45% hydroxypropyl-β-cyclodextrin and 0.9% saline.

| Group 1 | Group 2 | Group 3 | Group 4 |
|---|---|---|---|
| Control 0.9% saline | Chloroquine Control 40 mg/kg | BrEA Low Dose 30 mg/kg | BrEA High Dose 60 mg/kg |

The intravenous injections were given on days 0, 1, 2 and 3 and the results are shown below. The results showed that treatment in vivo with a formulation comprising BrEA reduced parasitemia to a level comparable to that seen with the chloroquine ("Clq") control. The results are summarized in the table below.

| | % RBC parasitemia |
|---|---|
| Day 4 | |
| saline control | 16% |
| chloroquine control | 10% |
| low dose BrEA | 9% |
| high dose BrEA | 7% |
| Day 11 | |
| saline control | 36% |
| chloroquine control | 16% |
| low dose BrEA | 12% |
| high dose BrEA | 11% |

Example 9

Human clinical study—parasite infection. Response to drug treatment was graded as per World Health Organization criteria (WHO 1973) in infected patients. Evaluation of therapeutic response was determined using the parasitic and fever clearance times. Parasite clearance was expressed as three indices; the time for the parasite count to fall by 50% of the pre-treatment (baseline) value ($PC_{50}$), (ii) the time for the parasite count to fall by 90% of the baseline value ($PC_{90}$) and (iii) the time for the parasite count to fall below the level of microscopic detection (parasite clearance time PCT) (N. J. White and S. Krishna *Trans. R. Soc. Trop. Med. Hyg.* 83: 767-777, 1989; White et al., *J. Infect. Dis.* 165: 599-600, 1992; White et al., *J. Infect. Dis.* 166: 1195-1196, 1992). The fever clearance time was defined as the time from drug administration till the oral or rectal temperature fell to or below 37.2° C. and remained so for at least 48 h.

Venous blood (5 mL) was obtained from two patients before treatment and at 4, 6, 8, 12, 18, 20, 24, 30 and 36 h after treatment or at 4 or 6-hourly intervals after treatment until there was complete clearance of peripheral parasitemia. Blood was collected aseptically and transferred to 10 mL syringes containing 2 mL of acid citrate dextrose (ACD) for in vitro culture. Prior to incubation, the plasma was separated from the red blood cells and the red blood cells were washed twice. Parasites were cultured by modification of standard in vitro culture techniques (W. Trager and J. B. Jensen, *Science* 193:673-675, 1976; A. M. Oduola et al., *J. Protozool.* 39: 605-608, 1992). Samples were dispensed into sterile centrifuge cubes within 10 min of collection and spun down. The supernatant plasma was stored while the packed cells were washed twice with culture medium (washing medium, RPMI-1640 medium, containing 25 mM HEPES buffer and 25 mmol/L NaOH). The buffy coat was removed by vacuum aspiration. A 1:10 fold dilution was done for each blood sample with complete washing medium [CMP (washing medium supplemented with 10% human plasma)]. One milliliter each of the sample was transferred into 2 wells of a 24 well micro culture plate. Cultures were incubated at 37 degrees C. in an atmosphere of 5% $CO_2$, 5% $O_2$ and 90% $N_2$ premixed gas. The culture medium was changed daily and thin blood smears were prepared for microscopy at 24 and 48 h after the culture has been set up. The culture samples were diluted with unparasitized washed type A Rh-positive red blood cells if the proportion of parasitized red blood cells was more than 2%.

Microscopy. During the in vivo study, thin and thick blood films were fixed with dehydrated methanol (100%) and heat, respectively, were stained with 10% Giemsa for 20 min. Parasitemia was quantified in thin films by counting 2000 red blood cells in clear contiguous fields and finding the proportion that was parasitized. In thick films, parasitemia was quantified by counting parasites against leukocytes. A film was declared negative if no parasites were found after examination of 200 microscope fields of a thick smear. During in vitro and ex vivo study, pretreatment thin and thick smears were, graded for ring stages by the method of Jiang as modified by Li et al. (J. B. Jiang et al, *Lancet* 2(8293): 285-288, 1982; K. Silamut and N. J. White *Trans. R. Soc. Trop. Med. Hyg.* 87: 436-443, 1993; X. L. Li et al, *Chi. J. Parasitol. Dis.* 12: 296, 1994). Approximately 5000 erythrocytes were counted in clear contiguous fields 24 and 48 h after incubation of blood obtained at each time point and graded for maturity into tiny rings, small rings, large rings, pigmented trophozoites and schizonts. Functional viability was estimated as the percentage of asexual ring forms capable of maturing to pigmented trophozoites or schizonts after 24-48 h of in vitro culture (W. M. Watkins et al., *Trans. R. Soc. Trop. Med. Hyg.* 87: 75-78, 1993).

Calculation of parameters. The patients presented with acute symptomatic severe non-cerebral pure *P. falciparum* malaria. They had oral fluid intolerance, body temperatures greater than 39° C., greater than 5000 parasites per micro liter of blood, asexual parasitemia and they had a negative urine test for antimalarial drugs. They were administered 25 mL intravenously every four hours with BrEA suspended in sterile 45% β-cyclodextrin in saline at a concentration of 25 mg/mL. This regimen was continued for four days. Parasitemia quantification and clinical examination were done once every 6 hours for the first 72 hours, followed by daily assessment of the parameters up to day 7 (168 hrs) and thereafter on day 14.

Blood films were Giemsa-stained and parasitemia quantification was done in thick films by counting 2000 parasites against leukocytes, and the thin films by finding the proportion of infected red blood cells. Response to drug treatment was graded according to WHO criteria. Evaluation of therapeutic response was done using the parasitic and fever clearance times. Parasite clearance was expressed as three indices: The time for the parasite count to fall by 50% of the pretreatment (baseline) value ($PC_{60}$); to fall by 90% of the baseline value ($PC_{90}$); and to fall below the level of microscopic detection (parasite clearance time) PCT.

The fever clearance time was defined as the time from drug administration until the oral/rectal temperature fell to below 37.2 degrees C. and remained so for greater than 48 hours. The parasite clearance rate at day 14 was 100%. The clinical response thus included an effect on parasitemia in both patients and amelioration of one or more symptoms of infection.

| Intravenous BrEA Malaria Patient Trial | | |
|---|---|---|
| | Patient A | Patient B |
| Fever clearance time | 12 hrs | 18 hrs |
| Parasite clearance times | | |
| Time to 50% clearance | 18 hrs | 24 hrs |
| Time to 90% clearance | 24 hrs | 48 hrs |
| Time to 100% clearance | 48 hrs | 64 hrs |

Example 10

Cellular studies in vitro. The effect of BrEA on pentose-phosphate shunt (PPS) activity in normal human RBC was examined using whole cells. Since glucose-6-phosphate dehydrogenase ("G6PD") is the limiting enzyme of the PPS, PPS flux measurement is considered to better reflect G6PD activity in the whole cell compared to G6PD activity measurement in a cell lysate. G6PD activity measured in a cell lysate is typically about 1100-fold higher than the PPS flux in whole resting unstimulated RBC (G6PD activity in cell lysate: 165; PPS flux 0.142 micromoles/hour/ml RBC). PPS flux and G6PD activity in the whole RBC depends on a number of factors (the concentration of NADPH, NAD, and ATP, and intracellular pH), which are kept constant if the measurement is performed in the lysate and may vary in the whole RBC. Levels of G6PD activity in cells is considerably above normal basal needs and inhibition of overall G6PD activity might have no or minor consequence on PPS flux in the whole cell. For example, RBC with the Mediterranean G6PD mutant with about 1-3 percent residual activity compared with normal individuals have no impairment in basal PPS flux, but show impaired flux when flux through PPS is stimulated by methylene blue addition. A series of experiments were performed using varying amounts of BrEA and PPS flux was measured in unstimulated basal RBC and in methylene-blue (MB)-stimulated RBC.

The data below shows PPS flux (micromoles/hour/ml RBC) in basal unstimulated, and MB-stimulated normal RBC. Different concentrations of BrEA (0.3, 3.5 and 7 micromolar, final) were supplemented to suspensions of washed RBC suspended in RPMI, pH 7.4 at 10% hematocrit, whereby PPS flux was immediately measured without further incubation and without further washings. A minor inhibition of MB-stimulated PPS flux was observed with BrEA at 7 μM.

|  | PPS flux |
|---|---|
| control, unstimulated RBC | 230 |
| DMSO control, unstimulated RBC | 270 |
| DMSO control, MB stimulated RBC | 5090 |
| 0.3 μM BrEA, unstimulated | 250 |
| 0.3 μM BrEA, MB stimulated | 5000 |
| 3.5 μM BrEA, unstimulated | 270 |
| 3.5 μM BrEA, MB stimulated | 4950 |
| 7 μM BrEA, unstimulated | 295 |
| 7 μM BrEA, MB stimulated | 4660 |

The data below shows average values of 3 experiments, where basal, unstimulated, and MB-stimulated PPS flux (micromoles/hour/ml RBC) was measured in normal RBC. In these experiments, different concentrations of BrEA ~0.8, 8 and 80 micromolar, final) were supplemented to suspensions of washed RBC suspended in RPMI, pH 7.4 at 10% hematocrit. After a 90-min incubation at 37° C. with and without BrEA, PPS flux was measured. The results showed a dose-dependent inhibition of MB-stimulated PPS flux. Inhibition was 10% at 8 micromolar (p=0.006 vs control+DMSO) and 25% at 80 micromolar (p=0.002 vs control+DMSO).

|  | PPS flux |
|---|---|
| control, unstimulated RBC | 430 |
| control, MB stimulated RBC | 5410 |
| DMSO control, unstimulated RBC | 480 |
| DMSO control, MB stimulated RBC | 4890 |
| 0.8 μM BrEA, unstimulated | 410 |
| 0.8 μM BrEA, MB stimulated | 4930 |
| 8 μM BrEA, unstimulated | 450 |
| 8 μM BrEA, MB stimulated | 4430 |
| 80 μM BrEA, unstimulated | 450 |
| 80 μM BrEA, MB stimulated | 3660 |

Example 11

Inhibition of parasite growth. The effect of Epi (16α-bromoepiandrosterone) on parasite (*Plasmodium falciparum*) growth was shown. Epi was active at a concentration of 1 μM.

| | Parasitemia after treatment | | | |
|---|---|---|---|---|
| | Time 0 | 24 hrs | 48 hrs | 72 hrs |
| control + DMSO | 5% | 5.40% | 3.10% | 5.20% |
| Epi 1 μM | 5% | 5.70% | 5.50% | 160% |
| Epi 10 μM | 5% | 5.60% | 0.90% | 0 |
| Epi 100 μM | 5% | 0 | 0 | 0 |
| Epi 500 μM | 5% | 0 | 0 | 0 |
| control + DMSO | 2% | 8.80% | 11% | 8% |
| Epi 50 nM | 2% | 9.90% | 9.20% | 8.30% |
| Epi 1 μM | 2% | 5.80% | 6.10% | 2.10% |
| Epi 2.5 μM | 2% | 7.30% | 5.80% | 3.20% |
| Epi 5 μM | 2% | 5.40% | 6% | 1.80% |
| Epi 10 μM | 2% | 4.20% | 3% | 0 |
| Epi 50 μM | 2% | 0 | 0 | 0 |

Parasitemias were determined by standard methods (microscopic inspection of at least 500 cells, stained with Diff-Quick™ (Baxter). Parasites were cultured under standard conditions in RPMI-1640 supplemented with Hepes/Glucose (10 mM), glutamine (0.3 g/liter) and 10% human plasma. The hematocrit was 1%.

Example 12

Stimulation of phagocytosis. The capacity of BrEA to influence phagocytosis of *Plasmodium* parasite-infected RBC is examined using adherent human monocytes. The parasitemia level is about 8-10% and human monocytes are obtained from buffy coats from blood as follows. Peripheral blood mononuclear cells are separated from freshly collected platelet-poor buffy coats discarded from blood samples of healthy adult donors of both sexes. Separated cells are washed once with luke-warm PBS supplemented with 10 mM glucose (PBS-G) and resuspended at $5 \times 10^6$ cells/mL in ice-cold RPMI 1640 medium supplemented with 23 mM NaHCO$_3$ and 25 mM Hepes, pH 7.4 (RMBH). Dynabeads M450 Pan B and Pan T (Dynal) are added to cells in a 4:1 ratio for 20 min at 4° C. B-lymphocytes and T-lymphocytes are removed as specified by the manufacturer. The remaining monocytes are washed 2 times in RMBH, resuspended in AIM V cell culture medium (Gibco) at $1 \times 10^6$ cell/mL. The monocyte layer is collected, washed with PBS-G at 37° C. and resuspended in AIM V medium at $1 \times 10^6$ cells/mL. Purified cells are >90% monocytes as assessed by CD14 expression.

Phagocytosis of opsonized parasitized RBC (PE) is determined as follows. Phagocytosis of fresh-serum opsonized PE is initiated by mixing 10 PE/monocyte. Suspensions are briefly centrifuged (150×g for 5 sec at room temperature) to improve contact between PE and monocytes. To avoid attachment of monocytes after centrifugation and during the whole incubation period, cells are kept in suspension at $5 \times 10^6$ cells/5 mL AIM V medium in 6 cm diameter teflon bottom dishes (Heraeus) in a humidified incubator (95% air, 5% CO$_2$) at 37° C. On average, at least 90% of the monocytes phagocytose PE, as assessed by microscopic inspection. Control cells are kept under similar conditions without phagocytosis. Quantitative assessment of phagocytosis is performed by a previously described bioluminescence method (E. Schwarzer, et al., *Br. J. Haematol.* 1994 88: 740-745).

Erythrocyte treatments and parasite cultures are as follows. Fresh blood (Rh+) is used to isolate erythrocytes (RBC). Washed RBC are infected with schizont/trophozoite parasite stages (Palo Alto strain, mycoplasma-free). Stage specific parasites are isolated by the Percoll-mannitol method. Briefly, normal schizont-stage parasitized RBC(SPE) separated on Percoll-mannitol gradient (parasitemia>95% SPE) are mixed with RBC suspended in growth medium (RPMI 1640 medium containing 25 mmol/L Hepes, 20 mmol/L glucose, 2 mmol/L glutamine, 24 mmol/L NaHCO$_3$, 32 mg/L gentamicin and 10% AB or A human serum, pH 7.30) to start synchronous cultures at selected hematocrit values. The inoculum parasitemia is adjusted to 20% normal SPE for isolation of ring parasitized RBC (RPE) and to 5% normal SPE for isolation of trophozoite-stage parasitized RBC (TPE). At 14-18 hours after inoculum parasites are at ring-stage in the first cycle; at 34-33 hours, parasites are at trophozoite-stage in the first cycle; and at 40-44 hours after inoculum parasites are at schizont-stage in the first cycle. RPE, TPE and SPE are separated on Percoll-mannitol gradients. The parasitemia is usually 8-10% RPE, and >95% TPE. Nonparasitized and parasitized RBC are counted electronically. To assess total parasitemia and relative contribution of RPE, TPE and SPE, slides are prepared from cultures at indicated times, stained with Diff-Quik™ parasite stain and about 400-1000 cells are examined microscopically.

The effect of a formula 1 compound such as BrEA in parasitized RBC is examined using various concentrations of the compound, e.g., BrEA, e.g., 0.5 µM, 1 µM, 10 µM, 25 µM and 50 µM. Trophozoite-parasitized RBC, schizont-parasitized RBC or ring-parasitized RBC are examined as described.

Example 13

Human malaria clinical trial. The clinical trial protocol that incorporates about 15-20 patients is established. For a phase I, I/II or II trial, the patients are mildly infected with one or more *Plasmodium* parasites and they are mildly symptomatic (less than about 8-10% parasitemia of RBC). Before treatment, the patients are optionally tested for infection with HIV, HCV, TB, and *Cryptosporidium*. Patients with one or more co-infections are given standard care for the coinfection. The patients are hospitalized for treatment for one week. Two or more dose groups, e.g., 25, 50 or 100 mg/day of BrEA administered parenterally, e.g., by intramuscular, subcutaneous or intravenous injection, on 3, 4 or 5 days of the week when patients are dosed. Dosing is on consecutive days or on an intermittent schedule, e.g., 2, 3 or 4 doses with one dose administered every other day.

The formulation containing BrEA is as described herein, e.g., the formulation of example 1 or a formulation that comprises 100 mg/mL BrEA, PEG300-30% v/v, propylene glycol 30% v/v, benzyl benzoate 30% v/v and benzyl alcohol 2% v/v. At day 5-7, if less than about 50% reduction in parasitemia is observed, the patients are given standard care for malaria (mefloquine). During the week of treatment and for 1, 2 3, or more weeks there after, blood samples are taken periodically for evaluation of parasitemia, pharmacokinetics, plasma cytokines (e.g., IL-2, IL-4, IL-10, IGF1, γIFN, GM-CSF), and intracellular cytokines (e.g., IL-2, IL-4, IL-10, IGF1, γIFN, GM-CSF). The patients are optionally treated again at about 2 to 12 weeks after the initial dosing, using the same or a similar protocol as that used in the initial dosing protocol.

An exemplary open-label study of a BrEA formulation administered intramuscularly to semi-immune patients with uncomplicated malaria is conducted. The formulation comprises 100 mg/mL BrEA, PEG300 ~30% v/v, propylene glycol 30% v/v, benzyl benzoate 30% v/v and benzyl alcohol 2%. Patients will remain at the hospital as in-patients for the first 7 days of the study. Patients will receive one daily intramuscular administration of 50 mg or 100 mg of BrEA for 5 consecutive days. Daily evaluation for the first 7 days, and up to study day 14, may include parasitemia evaluation (twice daily), chemistry, hematology and drug levels (pharmacokinetic evaluation). If, after study day 7, the parasitemia levels decrease from the screening value and the patient is clinically stable, the patient may be followed on a daily basis for parasitemia (twice daily) for up to an additional 7 days as hospital in-patients. If a patient becomes clinically unstable at any time during the study, the patient will be discontinued and may be offered the standard treatment for malaria. Patients deficient in glucose-6-phosphate dehydrogenase enzyme may be excluded, since BrEA inhibits the enzyme. Other considerations that may lead to exclusion of patients from the trial include patients diagnosed with any of the following: severe anemia (hematocrit <21% or hemoglobin <7 g/dL); renal or liver failure by history and/or laboratory results respiratory distress as evidenced by dyspnea or respiratory rate ≧30 per minute; hypotension (systolic blood pressure <90 mm Hg); tachycardia (heart rate >130 beats/minute); pregnant or breast-feeding women; significant active co-morbid illness (acute medical diagnosis requiring specific therapy; patients with parasitemia >10% on peripheral smear.

Blood samples may be collected from each patient for future clinical evaluation such as the determination of activation markers or immunological analyses (e.g., assay for intracellular or extracellular interleukins IL-1β, IL-2, IL-4, IL-6, IL-10 and IL-12, γIFN and TNFα).

Example 14

Liposome formulation. Liposomes suitable for parenteral administration are prepared as follows. 400 mg of phosphatidyl choline and 80 mg of BrEA are dissolved in chloroform and methanol (2:1 v/v) and the solution is dried by rotary evaporation under reduced pressure. The resulting film is rehydrated by adding 8.0 mL of a 0.9% w/v NaCl solution and agitating the solution. The sizes of the liposomes are optionally measured, e.g., by photon correlation spectroscopy (Malvern Zetasizer 3000 or equivalent). The liposomes are optionally sized by, e.g., sonication to reduce the average size below 400 nm, or by filtration using suitable filters. Similar procedures are used to prepare liposome preparations that contain a formula 1 compound at about 15-100 mg/mL. The formulation is used to deliver the compound orally or parenterally (I.M., S.C., I.V.).

Example 15

Cyclodextrin formulation. A cyclodextrin formulation containing BrEA is prepared as follows. 450 g of hydroxypropyl-β-cyclodextrin is added to about 1 L of ethanol and the mixture is stirred for about 4-24 hours, until a clear solution is obtained. Non-micronized or micronized BrEA is added to give a concentration of 20 mg/mL and the mixture is stirred until a clear solution is obtained. The solution is dried, e.g., by rotary evaporation under reduced pressure. The dried material is added to 1 L of physiological saline and stirred until a clear solution is obtained. The solution is sterilized by filtration using a 0.2 µm pore size filter and dispensed into sterile containers. Similar procedures are used to prepare cyclodextrin formulations that contain a formula 1 compound at about 10-100 mg/mL. The formulation is used to deliver the compound orally, parenterally (I.M., S.C., I.V.) or by a buccal or sublingual route.

Example 16

Suppository formulation. A suppository formulation containing a formula 1 compound such as BrEA is prepared as follows. Sufficient non-micronized BrEA is measured to obtain a desired number of units that comprise 500 mg each of BrEA. The BrEA is blended with a suppository base, e.g., triglyceride from edible vegetable oil, to provide desired characteristics, e.g., a free fatty acid content of about 0.1% w/w, a saponification value of about 242, an iodine value of about 3, moisture at about 0.1% w/w and a closed capillary melting point of about 35° C.

Example 17

Human HCV clinical trial. A female patient infected with HIV and HCV was dosed I.V. with BrEA for 3 consecutive days using a formulation that contained 20 mg/mL BrEA in 45% w/v hydroxypropyl-β-cyclodextrin and saline. Four mL of the formulation (80 mg BrEA) was administered to the patient every 4 hours during the 3 day treatment period. The patient's predosing HCV level was 6.5 $Log_{10}$) as measured by PCR and the HCV level was 6.2 $Log_{10}$) on the first day of dosing, 5.5 $Log_{10}$) on the $3^{rd}$ day of dosing and 4.9 $Log_{10}$)

three days after the last dose was administered. HIV RNA levels as measured by PCR was 5.2 $Log_{10}$) (predosing), 5.8 $Log_{10}$) (first day), 5.9 $Log_{10}$) (third day) and 5.4 $Log_{10}$) (day 6). The NK cell counts (cells/mm$^3$) were 28, 41 and 38 at predosing, day 0 and day 3.

Example 18

A formulation comprising 100 mg/mL BrEA, ~30% v/v PEG300, 30% v/v propylene glycol, 30% v/v benzyl benzoate and 2% v/v benzyl alcohol was prepared by suspending BrEA in polyethylene glycol 300, and sequentially adding propylene glycol and benzyl benzoate, to form a solution, which was diluted to the final desired volume with additional propylene glycol. The procedure is described below.

The calculated amount of polyethylene glycol 300 was added to a compounding vessel. Then, while mixing, the calculated amount of BrEA was added to the vessel, and mixed for at least 5 minutes to form a smooth, creamy liquid propylene glycol was added to the vessel, and mixed for a minimum of 5 minutes to form a uniform suspension. The calculated amount of benzyl benzoate is added to the vessel, and mixed for approximately 5 minutes to form a translucent liquid suspension. Propylene glycol was then added to achieve the desired final formulation, and mixed for approximately 5 minutes. The drug solution was transferred to a volume dispensing device set to deliver 1.2 mL per vial. Under nitrogen pressure, the solution was filtered through two 0.2 μm polyvinylidene fluoride filters in series into 2 cc amber glass vials. The vials were capped with Teflon-coated, butyl-rubber stoppers and crimp sealed.

Example 19

Opportunistic infection clinical protocol. A double blind, randomized, placebo controlled study of 100 mg of BrEA administered intramuscularly to late stage HIV-infected patients at risk for opportunistic infections (Ols). HIV-1 seropositive patients with a CD4 cell count ≦100 cells/mm$^3$, HIV RNA at 1×10$^6$ copies/mL and a Karnofsky score of at least 60 are identified for potential inclusion into the protocol. Patients in all clinical protocols must understand and sign a written informed consent form prior to screening evaluations.

BrEA in the formulation of example 16 is used. Administration of drug or vehicle will be for 3 to 5 consecutive days followed by about 35-90 days of observation, e.g., 37 days of observation. An exemplary treatment regimen comprises 5 days of treatment followed by 37 days of observation, which is repeated for a total of 7 courses over 42 weeks. The incidence rate of Ols as well as the time to resolution or control of the Ols will be monitored and compared to a placebo control group. The patients may be monitored monthly for 2 or 3 months after completion of the study for follow-up. The incidence of Ols or conditions associated with AIDS are monitored, e.g., as tuberculosis (TB), candadiasis, *Pneumocystis* pneumonia (PCP), diarrhea, or Kaposi's sarcoma, may be evaluated as protocol endpoints. If a patient is diagnosed with one or more of the protocol specified opportunistic infections, the protocol regimen a treatment for the OI will be initiated, e.g., Fluconazole for Candidiasis or for PCP, trimethoprim and sulfamethoxazole or Dapsone. A similar protocol is used with other formula 1 compounds.

Example 20

Human HIV clinical protocol. Patients infected with HIV are dosed with an i.m. injection of 25-200 mg of BrEA using a formulation containing 100 mg/mL BrEA, PEG300 ~30% v/v, propylene glycol 30% v/v, benzyl benzoate 30% v/v and benzyl alcohol 2% v/v. The pateints are dosed once per day for 5 consecutive days followed by a period of about 28 days or longer with no BrEA treatment. The patients were them provided with one more course of 5 consecutive days of dosing with BrEA, followed by a non-dosing period of at least about 28 days. Up to 8 rounds of 5-day treatments, followed by at least 28 days of no dosing were provided. Immunological responses were then assayed using blood or plasma samples from the patients by flow cytometry and other known analytical methods. Immune cell subsets or other measured markers were assayed within 24 hours of obtaining the sample from each patient. Labeled antibodies, e.g., anti-CD antigen antibodies conjugated with fluorescent dyes (FITC, phycoerythrin, allophycocyanin or PerCP), were prepared and used essentially according to standard protocols using commercially available reagents, see, e.g., PharMingen, 1998 Research Products Catalog, technical protocols at pages 732-774, human cell surface molecules at pages 182-295 and mouse, rat and hamster cell surface molecules at pages 2-173 and cytokine and chemokine reagents at pages 344-489.

Otherwise untreated patients with CD4 counts of ≧200/4 and HIV-1 viral RNA between 5,000 and 1,000,000 copies/mL (branched-DNA, version 3.0, Bayer, Tarrytown, N.Y.) provided informed consent and were enrolled into a Phase I/II dose-escalation study of the safety and efficacy of intramuscular injections of BrEA. The protocol was conducted in South Africa. In the first cohort, four patients received an initial injection of 1 mL (50 mg), followed by a safety and pharmacokinetic study for seven days, and then received five daily injections of 1 mL (50 mg). The second cohort of 8 patients was randomized in a 1:2 ratio to receive either 50 mg (1 mL) or 100 mg (2 mL) on the same schedule. Patients were allowed at the discretion of the investigators to receive up to three additional courses each, repeated after 28 days of observation. The protocol was amended to introduce an improved formulation, and to extend the initial pharmacokinetic and safety period to 14 days, the observation period following the five daily doses to 35 days, and to allow up to 7 treatment courses. A third cohort of 24 patients was randomized in a 1:2:4 ratio to receive either 50 mg (0.5 mL), 100 mg (1 mL), or 200 mg (2 mL) of BrEA. The patients were all male, since initial safety studies are not permitted in females in South Africa. Within the group of 39 patients randomized, the ethnic demographic included was 18 Caucasian, 17 African, and 4 other. The average age was 34 (range 20-63), the average initial CD4/4 was 434 (range 176-1210), and the average viral load was 13,772 copies/mL (range 3,020-158,489). Patients underwent physical examinations and provided samples for chemistry, hematology, virology and immunology testing approximately every two weeks.

The clinical protocol is a phase I/II, open-label, randomized study of 3 dose levels of BrEA administered intramuscularly to HIV-infected patients who are treatment naïve. There will be 3 treatment groups and each group will consist of 2 parts (Parts A and B). Patients will receive the same dosage of BrEA throughout Parts A and B of the study. If a patient experiences an antiviral response (an HIV RNA titer at least 0.5 log below the average of the screening and baseline values) or benefits (any decrease in HIV RNA titers below the average of the screening and baseline values) from the treatment received during Parts A and B of the study, the patient may continue receiving 5-day treatment courses of the BrEA formulation of example 2 at the dose initially received. This treatment course may be repeated up to 30 times or more.

All patients may be monitored for levels of HIV RNA (Chiron Quantiplex™ branched chain DNA assay), T-cell subsets [CD4/CD8], proviral HIV DNA (PBMC), interleukins [IL-2, 4, 6, 8, 10, and 12] (serum), γIFN (serum), insulin-like growth factor [IGF-1] (serum) and tumor necrosis factor [TNF] (serum) throughout the study. PBMC quantitative co-culture (cells) may be conducted on a subset of patient samples. Assays for additional activation markers may be conducted. Analysis of chemistry and hematology panels and urinalysis is planned. Additionally, patients co-infected with hepatitis B and/or C viruses, malaria or tuberculosis may be monitored regularly for viral titers or microbiological cultures. Serial blood and urine samples will be collected from a subset of patients for pharmacokinetic determination after the first dose on Part A and the last dose on Part B.

Treatment may consist of more than one intramuscular injection. Intramuscular injections may be administered in different locations (i.e., left or right upper arms or thighs or buttocks) and a single 100 mg or 200 mg dose of BrEA may be delivered to patients in two or more subdoses of less than 100 mg (e.g., 50 mg).

There are two segments of this study, Segment 1 and 2. Both segments consist of two parts, Part A and Part B. The first 12 patients enrolled on the study will be assigned to the design described in Segment 1. The remaining 24 patients will be assigned to Segment 2 of the study. The design of each segment is provided below.

Part A will consist of a single intramuscular injection of a BrEA formulation. The day the patient receives the injection will be study day 1. Patients participating in the pharmacokinetic subgroup will have serial blood and urine samples collected, beginning on study day 1. Part B of the study begins on study day 8 (Segment 1) or study day 15 (Segment 2).

Segment 1 Part B consists of 5 consecutive daily intramuscular injections of the formulation of example 1 at the same dose as received in Part A of the study. The day the patient receives the first dose will be on about study day 8-12. The 5-day treatment course is followed by an approximate 28-day observation period (or approximately 32 days from a first dose on day 8 to the initiation of a second treatment course on day 40). During the observation period, patients will be asked to return to the clinic on a weekly basis for various tests. Patients participating in the pharmacokinetic subgroup will have serial blood and urine samples collected, beginning approximately on study day 12-17.

Segment 2 Part B consists of 5 consecutive daily intramuscular injections of the formulation of example 2 at the same dose the patient received during Part A of the study. The day the patient receives the first dose will be about at study day 15. The 5-day treatment course is followed by an approximate 45 day observation period (or approximately 49 days from the first dose on study day 15 to the initiation of the next treatment course on study day 64). During the observation period, patients will be asked to return to the clinic on a weekly basis for various tests. Patients participating in the pharmacokinetic subgroup will have serial blood and urine samples collected, beginning approximately on study day 19.

Randomization in this dose escalation study is as follows. When 4 of the 12 patients per treatment group have completed 5 days of daily dosing on Part B and have not experienced a serious drug-related adverse event, enrollment into the next higher dose level will occur, after consultation between the sponsor and investigators.

The first four patients enrolled will be assigned to the 50 mg dose group. If no serious drug-related adverse events are experienced, the next 8 subjects will be randomized to either the 50 mg or 100 mg dose level in a 1:1 fashion. If no serious drug-related adverse events occur in patients receiving 100 mg, then the next 24 patients will be randomized to either the 50, 100, or 200 mg dose group in a 1:2:3 fashion.

If 4 of the 12 patients in a dose group experiences a serious drug-related event (Grade III or IV), 2 additional patients will be enrolled at the same dose level. Additionally, patient enrollment on to the next dose level, if enrolling, will be temporarily on hold until safety is assessed. If one of the 2 additional patients experiences a serious drug-related event, dosing in this dose level will discontinue. Upon consultation with the sponsor and investigators, additional patients may be enrolled at a dose between the dose-limiting group and the next lower dose group to determine the maximum tolerated dose (MTD). Enrollment of additional patients at a specific dose level will be determined in a protocol amendment.

The results indicated that a single 50 mg or 100 mg dose of BrEA increased the numbers of activated CD8$^+$ and CD4$^+$ T cells (e.g., CD8$^+$, CD69$^+$, CD25$^-$ cells) that were circulating in the patient's blood. Also, the circulating numbers of dendritic precursor cells, NK cells, LAK cells and cells that mediate ADCC (antibody-dependent cell-mediated cytotoxicity mediated by the CD8$^+$, CD16$^-$ immune cell subset) functions were increased. Further increases were usually observed on dosing for 5 consecutive days.

Some of the results are summarized below. Course 1, 2 and 3 refer to each 5 consecutive day treatment regimen of one daily injection with BrEA (50 or 100 mg BrEA per injection). The formulation contained 100 mg/mL BrEA, PEG300~30% v/v, propylene glycol 30% v/v, benzyl benzoate 30% v/v and benzyl alcohol 2% v/v. The data shown below was obtained from patient blood samples at baseline (on the day dosing was initiated) and at various times after the patients received at least one dose of BrEA. The results showed significant increases in immune cell populations and cytokine expression profiles associated with Th1 responses. The patients in this protocol initially had CD4 counts of at least 200 per mm$^3$ and a serum HIV RNA load of 5,000 to 1×10$^6$ RNA copies/mL. After dosing with one course of BrEA (5 consecutive daily i.m. injections), all patients showed increases in levels of immune cells including activated CD8 T cells (e.g., CD8$^+$, CD69$^+$, CD25$^-$), LAK cells (e.g., CD8$^+$, CD16$^+$, CD38$^+$), NK cells (e.g., CD8$^-$, CD16$^+$), ADCC cells (e.g., CD8$^-$, CD16$^+$) and dendritic cells (Lin$^-$, HLA-DR$^+$, CD11c$^+$ or Lin$^-$, HLA-DR$^+$, CD123$^+$). Average CD4 IL-10 production dropped from a median of 66% to 4% of the cells, while CD4 IFNγ went from a median of 8% to 63%, leading to a Th2 to a Th1 shift in cytokine production.

In the tables below, baseline data is indicated by "BL" or by "pre".

| Increased immunophenotypes after BrEA therapy | | | | |
|---|---|---|---|---|
| Phenotype | Baseline$^a$ | Course 1 | Course 2 | Course 3 |
| CD8 + CD69 + CD25 − | 18 | 54 | 56 | 75 |
| n = | (13) | (13) | (9) | (4) |
| $^b$p = | | <0.001 | <0.001 | 0.04 |
| CD8 + CD16 + CD38 + | 8 | 27 | 28 | 25 |
| n = | (10) | (10) | (4) | (4) |
| p = | | <0.001 | 0.047 | 0.02 |
| CD8 − CD16 + | 53 | 253 | 288 | 249 |
| n = | (12) | (12) | (4) | (2) |
| p = | | <0.001 | 0.02 | 0.04 |

-continued

Increased immunophenotypes after BrEA therapy

| Phenotype | Baseline[a] | Course 1 | Course 2 | Course 3 |
|---|---|---|---|---|
| Lin − HLA − DR + CD11C + /CD123 + | 3.2 | 17.7 | 11.4[c] | 14.7[c] |
| n = | (10) | (10) | (5) | (4) |
| p = | | <0.001 | 0.02 | 0.04 |

[a]Median values of cells/µL

[b]paired value t test

[c]Test not available at baseline for patients receiving second and third courses, baseline value from initiation of 2nd course = 6.4

[d]% of CD4

[e]Baseline values from day 8 (preceding the first five-day treatment)

Median activated T cells ($CD8^+$ $CD69^+$ $CD25^−$ cells), LAK cells ($CD8^+$ $CD16^+CD38^+$), NK (ADCC responders) cells ($CD8^−$ $CD16^+$), dendritic cells ($Lin^−HLA-DR^+CD123^+/CD11^+$), and cells that mediate Th1 immune responses ($IFN\gamma^+$ white blood cells) compared to baseline cell counts for 3 16α-bromoepiandrosterone treatments or treatment courses in the HIV-infected patients gave the following results. The results shown below for the treated patients were obtained about 1 week after the last dose of 16α-bromoepiandrosterone was administered.

Activated T cells ($CD8^+$ $CD69^+$ $CD25^−$)

cells/µL

| Treatment 1 | |
|---|---|
| baseline | 19 |
| treated | 54 (n = 13, p < 0.001) |
| Treatment 2 | |
| baseline | 19 |
| treated | 56 (n = 9, p < 0.001) |
| Treatment 3 | |
| baseline | 18 |
| treated | 74 (n = 4, p = 0.04) |

LAK cells ($CD8^+$ $CD16^+$ $CD38^+$)

cells/µL

| Treatment 1 | |
|---|---|
| baseline | 8 |
| treated | 27 (n = 10, p < 0.001) |
| Treatment 2 | |
| baseline | 12 |
| treated | 28 (n = 4, p = 0.04) |
| Treatment 3 | |
| baseline | 12 |
| treated | 25 (n = 4, p = 0.02) |

NK (ADCC responders) cells ($CD8^−$ $CD16^+$)

cells/µL

| Treatment 1 | |
|---|---|
| baseline | 54 |
| treated | 253 (n = 12, p < 0.001) |
| Treatment 2 | |
| baseline | 58 |
| treated | 285 (n = 4, p = 0.02) |
| Treatment 3 | |
| baseline | 56 |
| treated | 250 (n = 2, p = 0.04) |

Dendritic cells ($Lin^−$ $HLA-DR^+$ $CD123^+/CD11^+$)

cells/µL

| Treatment 1 | |
|---|---|
| baseline | 3.5 |
| treated | 18 (n = 10, p = 0.001) |
| Treatment 2 | |
| baseline | 6.5 |
| treated | 11.5 (n = 5, p = 0.02) |
| Treatment 3 | |
| baseline | 6 |
| treated | 55 (n = 4, p = 0.04) |

These results show that the compound enhances the proportion of circulating cells that mediate cytotoxic immune responses and Th1 immune responses.

Treatment of HIV infected patients normalized their IL-10 producing $CD4^+$ T cells. In the same patients, 16α-bromoepiandrosterone was shown to enhance the proportion of $CD4^+$ T cells that express detectable IFNγ. $CD4^+$ $IL-10^−$ $IFN\gamma^+$ T cells mediate Th1 responses. These results show that the compound reduced the Th2 component of the immune system and enhanced the Th1 component.

The results given above are a preliminary analysis based on data obtained from 13 patients. Additional data was obtained for the patients as follows.

CD4 counts were assessed using a FACScount (BDIS), and viral loads were measured using the bDNA assay (Bayer). Quality assurance procedures were adhered to and internal and external controls were used to validate each batch of samples. On some occasions plasma viral loads were performed on batched samples between cycles of dosing.

Whole blood was labeled with a cocktail of four monoclonal antibodies (Becton Dickinson Immunocytometry Systems, BDIS, San Jose, Calif.) per cell subset using allophycocyanin, phycoerytherin, PerCP and FITC conjugates to measure surface phenotypes using a FACSCalibur (BDIS). In addition, four-color immunofluorescent analysis of blood cells was performed on the same schedule. The four color panels consisted of APC, PerCP, FITC, and PE reagents respectively in the following combinations: memory/naïve T cells (CD3/CD8/CD45RA/CD62L, CD3/CD4/CD45RA/CD62L), T cell activation (CD3/CD8/CD69/CD25, CD3/CD4/CD69/CD25, CD3/CD8/HLA-DR/CD38, CD3/CD4/HLA-DR, CD38), B cell, LAK and NK (CD19/CD8/CD16/CD38) and dendritic cells (CD11c/HLA-DR/lineage markers CD3, CD16, CD14, CD19, CD56/CD123). Listmode data (25,000 to 50,000 events) were analyzed using FCS Express (De Novo Software, Thornhill, Ontario, Canada). CD3$^+$ cell subsets were identified by serial gating of (1) nucleated cells, (2) lymphocyte/lymphoblastoid cells, and (3) CD3+ cells, followed by the gating of the subset of interest. For example, the absolute frequency per μL of any CD4+ cell subset (S) was estimated by the equation: S=(proportion of CD4+ cells)×(CD4+ cell frequency per μL).

The CD4$^+$ cell frequency was determined using the FACSCount test. The absolute frequency of a CD8$^+$ cell subset was calculated in a similar fashion. The absolute white blood cell (WBC) count was determined using an automated cell counter (Advia 120, Bayer, Tarrytown, N.Y.). The nucleated cell region was defined using a forward versus orthogonal scatter plot. The absolute frequency per μL of CD3$^-$ Natural Killer or Dendritic Cell subsets (F) was estimated by the equation: F=(proportion of nucleated cells)×(absolute WBC count per μL).

Statistical analysis of changes in surface phenotypes, hematological, and viral parameters were performed by calculating the area under the curve (AUC) of the percentage difference from baselines (phenotype), percentage difference from the mean of screen and baseline values (hematology), or $\log_{10}$ change from the mean of screen and baseline values (plasma viral RNA) for individual patients. AUC were calculated using the actual number of days between analysis visits for each patient. Because patients were on study for varying periods of time, this value was normalized to the time-averaged AUC by dividing by the number of days of observation. The Student's t-test was then used to analyze the difference from zero for the AUCs from all patients with data available for each parameter. A significant increase in the AUC for the entire 5-month period was interpreted as a nonrandom change in the given parameter.

Changes occurred soon after the intermittent dosing for a number of the measurements, and patients showed variability in the kinetics of immunologic, hematologic and virologic responses. For these reasons, the time-averaged AUC values for the 5-month period underestimate the magnitude of the individual responses. Maximal individual patient responses were calculated as the mean of the maximal percentage changes from baselines for individual patients at any analysis visit after dosing.

To investigate the kinetics of the responses for the entire population related to the time after dosing, the maximum analysis visit responses were calculated as the average of the maxima of the mean percentage changes from baselines for each analysis visit. Due to the altered BrEA administration interval for cohort 3, the analysis visits were aligned relative to the last dosing visit.

BrEA treatment of the HIV infected patients caused changes in T cell and dendritic cell phenotypes that persisted for weeks after intermittent dosing was discontinued. Increases were observed after dosing in both the total activated and early activated stage CD8$^+$ T cells as well as in circulating total dendritic cells consisting of both the CD11c$^+$ and the CD123$^+$ phenotypes. The significant increases observed in the AUC analyses over the entire 5-month intermittent dosing period indicate that these changes are not random fluctuations. Although activation of CD8$^+$ cells is linked with disease progression, intact dendritic cell function and activation of CD8$^+$ T cells is also requisite for stimulation of CTL, both for specific anti-HIV-1 responses, as well as for anti-opportunistic infection responses. In HIV infection there is a progressive decrease in circulating CD4$^+$ T cells, an increase in circulating CD8$^+$ T cells, and a decrease in the CD4/CD8 ratio. In this study, the decreases in both circulating CD4$^+$ and CD8$^+$ T cells with no change in the CD4:CD8 ratio may indicate that activated T cells are trafficking to sites of infection in the lymph nodes and mucosal tissue.

In this study, there was no overall decrease in viral load after three 5-day courses of intermittent dosing over a period of 153 days. It is possible that a CTL-driven elimination of HIV-1 infected cells with long-term effects on viral levels may result from continued dosing or from adjustments in the route of administration or the dose-schedule.

Treatment with BrEA resulted in significant changes in hematology parameters in the patients including increased circulating platelets (an average 20% increase over baseline on study day 126), monocytes (an average 49% increase over baseline on study day 50) and neutrophils (an average 51% increase over baseline on study day 81). These changes may due to stimulation of hematopoiesis or redistribution of the hematopoietic elements from the tissues to the circulation. The duration of the increases in neutrophils and platelets that have in vivo half-lifes of approximately 10 and 107 hours respectively suggest that at least part of the observed responses is due to enhanced hemopoiesis in these patients.

Some of the data that was obtained is summarized below.

| Timing of BrEA Dosing and Analyses | | |
|---|---|---|
| Dosing Visit Days$^A$ | Analysis Visit Days$^B$ | Median Days After Last Dose to Analysis Visit (Range)$^C$ |
| 1 | 7 | 7 (7-11) |
| 15-19 | 22 | 3 (2-10) |
|  | 36 | 17 (13-24) |
|  | 50 | 31 (26-36) |
| 60-64 | 67 | 3 (0-5) |
|  | 81 | 17 (13-19) |
|  | 95 | 31 (25-33) |
| 118-122 | 126 | 3 (0-5) |
|  | 139 | 17 (12-23) |
|  | 153 | 31 (26-33) |

$^A$Aligned study days on which patients received injections of BrEA.

$^B$Aligned study days on which analysis samples were taken.

$^C$The median number and range of days after patients received the last dose of BrEA prior to the analysis visit.

For the following table, the symbols in the table have the meanings given here. $^A$Number of patients with data for phenotype, dendritic cell analysis was not initiated at start of study. $^B$Mean increase in the time-averaged individual AUC differences from baseline values for all patients. $^C$p value for Student's t-Test for individual AUC percentage increases from baseline. $^D$Maximal individual patient responses were calculated as the mean of the maximal percentage changes from baselines for individual patients at any analysis visit after dosing. The range of responses is indicated in parentheses. $^E$Maximum analysis visit responses were calculated as the average of the maxima of the mean percentage changes from baselines for each analysis visit. The day of maximal response is indicated in parentheses. $^F$CD3$^+$ CD8$^+$ and CD69$^+$ or CD25$^+$. $^G$CD3$^+$ CD8$^+$ CD69$^+$ D25$^-$. $^H$CD8$^-$ CD16$^+$. $^I$CD8$^+$ CD16$^+$. $^J$Lineage$^-$ HLA-DR$^+$ CD11c$^+$. $^K$Lineage$^-$ HLA-DR$^+$ CD123$^+$.

| Immune Phenotype Changes after BrEA Intramuscular Administration ||||||
| Phenotype | n[A] | Time-averaged AUC Increase Mean ± SEM[B] | t-Test p-value[C] | Maximum Individual Patient Responses Mean (range)[D] | Maximum Analysis Visit Responses Mean (analysis visit day)[E] |
| --- | --- | --- | --- | --- | --- |
| Activated CD8+ T cells[F] | 36 | 15 ± 5% | 0.005 | 70% (−10 to 340%) | 25% (22) |
| Early Activation-Stage CD8+ T cells[G] | 36 | 67 ± 33% | 0.049 | 210% (0 to 3.090%) | 162% (153) |
| NK[H] | 36 | 29 ± 22% | 0.20 | 140% (−40 to 1.220%) | 41% (36) |
| LAK[I] | 36 | 13 ± 9% | 0.19 | 90% (−90 to 630%) | 34% (67) |
| Total Dendritic Cells | 31 | 38 ± 14% | 0.010 | 100% (−20 to 600%) | 38% (139) |
| DC1 (CD11c+) Dendritic Cells[J] | 31 | 50 ± 18% | 0.010 | 130% (−20 to 870%) | 58% (22) |
| DC2 (CD123+) Dendritic Cells[K] | 31 | 32 ± 13% | 0.021 | 100% (−30 to 480%) | 44% (80) |
| DC1 to DC2 Ratio | 31 | 44 ± 13% | 0.003 | | |

| Increase In Circulating Hematologic Elements After Intramuscular BrEA Administration ||||||
| Hematologic Elements | n[A] | Time-averaged AUC Increase Mean ± SEM[B] | t-Test p-value[C] | Maximum Individual Patient Responses Mean (range)[D] | Maximum Analysis Visit Responses Mean (analysis visit day)[E] |
| --- | --- | --- | --- | --- | --- |
| WBC | 37 | 4.4 ± 3% | 0.132 | 36% (−1 to 159%) | 23% (81) |
| Neutrophils | 37 | 11 ± 4% | 0.009 | 67% (−25 to 297%) | 51% (81) |
| Eosinophils | 33 | 20 ± 11% | 0.086 | 110% (−37 to 656%) | 129% (22) |
| Basophils | 37 | 42 ± 12% | 0.001 | 182% (−20 to 1.100%) | 113% (126) |
| Monocytes | 37 | 10 ± 5% | 0.029 | 60% (−14 to 189%) | 49% (50) |
| Platelets | 37 | 7 ± 2% | <0.001 | 31% (0 to 122%) | 20% (126) |

[A]Number of patients with data for hematologic element.
[B]Mean increase in the time-averaged individual AUC differences from baseline values for all patients.
[C]p value for Student's t-Test for individual AUC percentage increases from baseline.
[D]Maximal individual patient responses were calculated as the mean of the maximal percentage changes from baselines for individual patients at any analysis visit after dosing. The range of responses is indicated in parentheses.
[E]Maximum analysis visit responses were calculated as the average of the maxima of the mean percentage changes from baselines for each analysis visit. The day of maximal response is indicated in parentheses.

In a separate clinical trial using 100 mg of BrEA delivered to patients once per day for 5 consecutive days by intramuscular injection, several patients were evaluated for changes in the ratio of CD4+ memory T cell 1 cells (intracellular IFN$\gamma^+$ CD45RA$^-$ CD62L$^-$ CD11a$^{bright}$) or MT1 cells to memory T cell 2 cells (intracellular IL-4+ CD45RA$^-$ CD62L+ CD11a$^{dim}$) or MT2 cells. MT1 cells mediate or facilitate Th1 immune responses and MT2 cells mediate or facilitate Th2 immune responses. An increase in the MT1:MT2 ratio indicates an enhanced Th1 immune response or immune status. See, e.g., D. K. Mitra et al., *International Immunology* 1999 11:1801-1810. The tested patients (7/7) showed a transient increase in the MT1:MT2 ratio after a 5 day course of dosing with BrEA. The maximum observed increase was about 700% in one patient at 10 days after the last dose of BrEA was administered. The increase usually persisted for more than 10 days after the last dose of BrEA was administered. These results showed that BrEA was capable of enhancing the numbers of circulating immune cell subsets that mediate Th1 type responses.

Example 21

Treatment of symptoms of HIV infection. Two HIV infected patients with chronic diarrhea were dosed with BrEA as follows. A BrEA formulation (40 mg/mL BrEA in 25% v/v PEG 300, 12.5% v/v ethanol, 5% v/v benzyl benzoate, ~57.5% v/v propylene glycol) was delivered subcutaneously. The patients received 60 mg of BrEA in 1.5 mL daily for 10 days. During the period of dosing, the diarrhea ceased. After the 10-day dosing period ended, diarrhea resumed. In other patients receiving oral BrEA, diarrhea also went into remission.

Example 22

Subcutaneous formulation. A BrEA formulation was prepared essentially as described herein. The formulation contained 50 mg/mL BrEA, 40% v/v PEG 200, 2% v/v benzyl alcohol, 2% v/v benzyl benzoate and ~66% v/v propylene glycol (qs). The formulation is particularly suitable for subcutaneous administration of the compound.

Example 23

Preparation of BrEA hemihydrate-procedure 1. Crude BrEA was prepared by bromination of epiandrosterone, followed by crystallization from methanol. The hemihydrate was prepared by dissolving 25 g of crude BrEA in 75 mL of refluxing ethanol with moderate agitation. To the BrEA solution 12.5 mL of water was slowly added while maintaining the solution at reflux with agitation. Agitation of the solution was maintained and the solution was then allowed to cool to about 20-25° C. and kept at about 20-25° C. for about 15 minutes to obtain a suspension of BrEA hemihydrate crystals. The crystals were recovered by filtration, washed with a solution of 25 mL of water:ethanol (5:1 v/v) at about 20-25° C.

and then vacuum dried for about 13 hours at 50-60° C. until the product weight was constant. The crystals were primarily rod and needle shaped, with smaller amounts of other shapes such as tablets.

The procedure gave 22.5 g of BrEA hemihydrate (yield 90%) with a water content of 2.6% w/w by KF analysis, a purity of 100% by HPLC area analysis, an FTIR spectrum with carbonyl peaks at 1741 cm$^{-1}$ and 1752 cm$^{-1}$. The FTIR scan of anhydrous BrEA shows a single carbonyl peak at 1749 cm$^{-1}$. The DSC scan showed three endotherms. One had a broad shallow peak with an onset at about 109-110° C. and ending at about 150° C. This broad DSC peak is consistent with the loss of water from the hemihydrate crystals as the temperature of the sample increased. The second endotherm at about 83-100° C. is consistent with the loss of the small amount of residual ethanol from the sample. A DSC scan of anhydrous BrEA does not have the broad endotherm that is observed with the hemihydrate. Also consistent with the loss of water from the hemihydrate over the 100-150° C. range is a sharp third endotherm peak in the hemihydrate DSC scan at about 163-164° C., which is the melting point of anhydrous BrEA. The FTIR was obtained using USP method <197>, where the BrEA hemihydrate sample was prepared in KBr. The DSC thermogram was obtained by scanning from 25° C. to 250° C. with a heating rate of 10° C./minute.

Example 24

Preparation of BrEA hemihydrate—procedure 2. The hemihydrate was prepared by dissolving 10 g of crude BrEA in 40 mL of refluxing acetone with moderate agitation. To the BrEA solution 4.0 mL of water was slowly added while maintaining the solution at reflux with agitation. Agitation of the solution was maintained and the solution was then allowed to cool to about 20-25° C. and kept at about 20-25° C. for about 15 minutes to obtain a suspension of BrEA hemihydrate crystals. The crystals were recovered by filtration, washed with a solution of 6.0 mL of water:acetone (10:1 v/v) at about 20-25° C. and then vacuum dried overnight (about 13-15 hours) at 50-60° C. until the product weight was constant. The procedure gave 7.0 g of BrEA hemihydrate (yield 70%) with a water content of 2.6% w/w by KF analysis and an FTIR spectrum with carbonyl peaks at 1741 cm$^{-1}$ and 1752 cm$^{-1}$.

Example 25

Analysis of BrEA hemihydrate particle size. BrEA hemihydrate crystals were prepared essentially as described herein and sized using a particle sizing apparatus (Malvern Instruments). The analysis model used was for a polydisperse sample and a volume distribution type. The analysis showed a range of crystal diameter sizes from about 0.5 μm to about 880 μm. About 90% of the crystals had a diameter of about 20 μm to about 220 μm and the majority of the crystals had a diameter of about 30-200 μm. The mean crystal diameter was about 93 μm. The specific surface area of the crystals was about 0.25 m$^2$/g.

Example 26

Formulations containing BrEA hemihydrate were prepared. Similar formulations using other formula 1 compounds are prepared using the same or similar excipients, e.g., a different preservative can be used in the suspension formulation instead of methylparaben.

A formulation containing BrEA hemihydrate in aqueous suspension was prepared. The BrEA hemihydrate had an average particle size of less than 20 μm and it was mixed with polysorbate 80 before addition to the liquid components. The final aqueous composition contained 100 mg/mL BrEA, 2% w/v polysorbate 80, 0.1% w/v carboxymethylcellulose sodium, 0.82% w/v sodium chloride, 0.023% w/v dibasic sodium phosphate, 0.101% w/v monobasic sodium phosphate, 0.5% v/v ethanol and 0.1% w/v methylparaben, pH 6.5+/−0.4. The formulation was prepared using sterile technique. This formulation is suitable for subcutaneous, intramuscular or intraperitoneal delivery of BrEA, which can be delivered in a bolus or depot in the skin, muscle, peritoneal cavity or other suitable site in a subject. The formulation is not generally used for intravenous delivery, particularly in humans, due to the presence of the drug particles.

A caplet (capsule shaped tablet) containing BrEA hemihydrate was prepared using compressible sucrose. The caplets each contained 25 mg BrEA hemihydrate, 6.25 mg povidone (1-ethenyl-2-pyrrolidinone polymer), 0.62 mg magnesium stearate, 45 mg mannitol and 48.12 mg of compressible sucrose. Sterile BrEA and excipients were used to prepare the caplets. The formulation is suitable for buccal or sublingual, delivery of BrEA (or another formula 1 compound) to a subject.

Example 27

Inhibition of inflammation. The capacity of formula 1 compounds to limit or inhibit inflammation or symptoms of inflammation was shown using animal models for inflammatory bowel disease.

Groups of 3 male Wistar rats (180±20 grams) fasted for 24 hours before 2,4-dinitrobenzene sulfonic acid (DNBS) or saline challenge were used. Distal colitis was induced by intra-colonic instillation of 0.5 mL of an ethanolic solution of DNBS (30 mg in 0.5 mL of a 30% ethanol in saline solution) after which 2 mL of air was injected through the cannula to ensure that the solution remained in the colon. The volume used was 0.1 mL per injection of 2 and 20 mg/mL of 7-oxodehydroepiandrosterone in a liquid formulation, was administered by subcutaneous injection once a day for 6 days. The formulation contained 100 mg/mL of 7-oxodehydroepiandrosterone in a non-aqueous suspension that contained 2% benzyl alcohol w/v, 0.1% Brij 96 w/v and equal volumes of PEG 300 and propylene glycol. Concentrations of 2 mg/mL and 20 mg/mL were obtained by diluting the 20 mg/mL formulation with vehicle that lacked the active substance.

The first dose was given 30 minutes after DNBS challenge. Sulfasalazine (30 mg/mL in 2% Tween 80 in distilled water) was administered orally (PO) once a day (10 mL/kg/day) for 7 days, the first two doses beginning 24 hours and 2 hours before DNBS challenge. The presence of diarrhea was recorded daily by examining the anal area. Animals were fasted for 24 hours prior to being sacrificed. Animals were sacrificed on day 7 or day 8 and their colons were removed and weighed. Before removal of the colon, signs of adhesion between the colon and other organs were recorded. Also, the presence of ulcerations was noted after weighing of each colon. The "net" change of colon-to-body weight (BW) ratio was normalized relative to saline-challenged baseline group. A 30% decrease in "net" colon-to-body weight ratio was considered significant.

A total of five studies were conducted. Data from several studies are combined. The 7-oxodehydroepiandrosterone at 2 and 20 mg/mL, decreased the net colon-to-body weight ratio by 19 and by 14% relative to vehicle-treated group, respectively. Adhesions were absent in all three tested animals. Colonic ulceration was noted in ⅓ animals. All animals had diarrhea. Similarly, all animals treated with Sulfazalazine had diarrhea. Sulfasalazine exhibited significant protection from inflammation (−33% change in net colon-to-body weight (BW) ratio relative to EE-1 treated group) and no animals exhibited adhesions or colonic ulceration. The formula 1 compound 3β,7β,17β-trihydroxyandrost-5-ene (AET) was administered by subcutaneous injections of 0.2 and 2.0 mg/day for 5 or 6 days, with the first dose injected 30 minutes post-DNBS challenge. The AET formulation was the same as the 7-oxodehydroepiandrosterone formulation, except that AET replaced 7-oxodehydroepiandrosterone. AET decreased the net colon-to-body weight ratio by 15% and 21% relative to controls (see the table below). Animals treated with AET (2 mg) had no diarrhea. Adhesion was absent and fewer animals had colonic ulcerations (33% relative to untreated animals, N=9, pooled data from two studies). The same formulations containing BrEA (100 mg/mL) or dehydroepiandrosterone (20 mg/mL) decreased the net colon-to-body weight ratio by 21 and 3%, respectively relative to controls. In four subsequent studies, AET variably reduced the net colon-to-body weight ratio, ulcers and diarrhea.

Severe acute inflammation, measured 7 days after DNBS challenge, was observed in 3 of 10 immunosteroid vehicle control animals, while AET, dehydroepiandrosterone, sulfasalazine, and sulfasalazine vehicle (polysorbate 80) resulted in severe inflammation in 4, 10, 3, and 8 animals respectively. Moderate acute inflammation, measured 7 days after DNBS challenge, was observed in 5 of 10 immunosteroid vehicle control animals, while AET, dehydroepiandrosterone, sulfasalazine, and sulfasalazine vehicle (polysorbate 80) resulted in moderate inflammation in 6, 0, 6, and 2 animals respectively. Severe inflammation at day 7 was observed in 3, 4, 10 and 3 animals that were treated with vehicle, AET, dehydroepiandrosterone and sulfasalazine respectively. Severe chronic inflammation, measured 14 days after DNBS challenge, was observed in 8 of 10 immunosteroid vehicle control animals, while AET, dehydroepiandrosterone, sulfasalazine, and sulfasalazine vehicle (polysorbate 80) resulted in severe inflammation in 3, 3, 2, and 6 animals respectively.

At day 7 (acute inflammation) after DNBS challenge, 8 of 10 animals treated with vehicle control had severe ulceration, while 2 of 10 animals treated with AET had severe ulceration. Such ulceration was observed in 3 of 10 sulfasalazine control and in 10 of 10 animals treated with dehydroepiandrosterone. Delaying the initiation of AET treatment until 2 days after DNBS challenge resulted in increased chronic ulceration, with 5 of 10 animals showing ulcers 14 days after challenge, compared to only 1 animal with ulcers when treatment began the same day as challenge. This indicated that for acute inflammation in this model, AET is most effective early in the initiation of a flare of inflammatory cellular responses. At day 14 after DNBS challenge (chronic inflammation) 5 of 10 vehicle controls showed severe ulceration, 1 of 10 AET treated animals had severe ulceration, 0 of 10 animals treated with dehydroepiandrosterone had severe ulceration and 4 of 10 sulfasalazine treated animals (positive control) has severe ulceration. The results showed that the formula 1 compounds reduced inflammation or its symptoms compared to untreated control animals.

In another protocol formula 1 compounds were used in a similar animal model. Groups of 10 male Sprague Dawley rats (250-300 grams) were fasted for 24 hours before 2,4,6-trinitrobenzene sulfonic acid (TNBS) or saline challenge. This model presents a severe challenge to the animal's immune system. On Day 0, the rats were lightly anesthetized and a catheter inserted rectally into the colon such that the tip was 8 cm proximal to the anus. Distal colitis was induced by intra-colonic instillation of 0.5 mL of an ethanolic solution of TNBS (60 mg/mL ethanol 50% in water). The test substance, 7-oxodehydroepiandrosterone 20 mg/mL in vehicle or vehicle control was administered by subcutaneous injection (0.1 mL/injection) once a day for 6 days, the first dose being given 30 minutes after TNBS challenge. Sulfasalazine (30 mg/mL in 2% Tween 80 in distilled water) or vehicle control was administered orally (PO) once a day (10 mL/kg/day) for 7 days, the first two doses beginning 24 hours and 2 hours before DNBS challenge. Signs of diarrhea were recorded daily by examining the anal area. Animals were fasted for 24 hours prior to sacrifice on day 14 and the colon was removed and weighed. After gross observations of colonic tissues, 3 samples were taken from regions approximately 1, 3, and 8 cm proximal to the anus. If gross ulcers or inflammation were present, at least one sample was taken from the affected region. Before removal of the colon, signs of adhesion between the colon and other organs were recorded. Also, the presence of colonic ulcerations and intestinal adhesions was noted after weighing of each colon. Body weight, colon-to-body-weight ratio, and damage scores were assessed. Visible damage was scored on a 1-5 scale as follows: 0=No damage; 1=Localized hyperemia but no ulcers; 2=linear ulcers with no significant inflammation; 3=Linear ulcers with inflammation at one site; 4=Two or more sites of ulceration and/or inflammation; 5=Two or more major sites of ulceration and inflammation or one major site of ulceration and inflammation extending more than 1 cm along the length of the colon. Inflammation is defined as regions of hyperemia and bowel wall thickening.

Ulcerations were present more frequently at multiple colonic levels following 7-oxodehydroepiandrosterone treatment compared to controls. Moderate to severe ulcerative lesions associated with moderate to severe fibrosis of the mucosa and/or submucosa occurred in 8/9 (89%) of 7-oxodehydroepiandrosterone treated animals compared to 5/9 (56%) of controls. The severity and frequency of muscular, peritoneal and/or mesenteric inflammation appeared slightly more than in controls. These histopathological data suggests that 7-oxodehydroepiandrosterone exacerbated the inflammation. Moderate to severe ulcerative lesions occurred in 6/10 (60%) and 5/10 (50%) of sulfazalazine and vehicle treated animals, respectively. The severity and frequency of muscular, peritoneal and/or mesenteric inflammation appeared to be similar to that occurring in vehicle groups. The frequency of moderate to severe lesions and their severity based on their occurrence at multiple colonic levels appeared to be similar between the negative control (vehicle), reference control (sulfazalazine), BrEA and dehydroepiandrosterone, indicating that for these compounds the degree of inflammation was similar for the control compound and the tested compounds.

Example 28

Modulation of delayed type hypersensitivity. 3β,7β,17β-trihydroxyandrost-5-ene (AET) was examined for its capacity to modulate delayed type hypersensitivity (DTH). Groups of five female BALB/cByJ mice (20-25 grams) were anesthetized and 100 μL of a 3% solution of oxazolone was applied on day 0 to the shaved abdomen and dried. Seven days later, on day 7, the mice were challenged by applying 5 μL of oxazolone topically to each side of the right ear. The compound AET (40 mg/mL) in vehicle was administered by subcutaneous injection (2 mg/day, 50 µL/injection) one time on day 6, 24 hours before the oxazolone challenge. The vehicle as a non-aqueous suspension of AET in 2% benzyl alcohol w/v, 0.1% Brij 96 w/v and equal volumes of PEG 300 and propylene glycol.

Dexamethasone in saline (0.2 mg/mL) was administered daily for 9 days (day −1 to 7), first dose 24 hours before sensitization, last dose at challenge by subcutaneous injection (0.01 mg/dose, 50 µL/injection). On Day 8, 24 hours following the oxazolone challenge, both the right and left ear thicknesses were measured using a micrometer caliper and the differences determined. The differential ear thickness is measured as an indicator of the DTH response to topical oxazolone challenge. The DTH response was expressed as the difference in the thickness (mm) between the right and the left ears for each animal.

The differential ear thickness in animals receiving vehicle alone was 0.225 mm and treatment with dexamethasone (high dose) or cyclophosphamide reduced the DTH response (0.144 mm and 0.092 mm, respectively). AET administered subcutaneously had only a slight effect on the DTH response to oxazolone. When administered 24 hours before challenge or at challenge (2 mg/day), the effect was a 22-24% reduction in the response. When administered daily for 8 days (2 mg/day), first dose 24 hours before sensitization and last dose 24 hours prior to challenge, the effect was an enhancement of the response (23%). This result shows that if the compound was delivered to the animals during sensitization, the DTH response increased. This is consistent with an enhanced Th1 immune response. If the compound was delivered to the animals after sensitization, the DTH response was decreased. This is consistent with a decreased inflammatory response.

Example 29

Reversal of immunosenescence. Healthy aged (20-month) or immunologically-mature (3-month) BALB/c mice were vaccinated with hepatitis B surface antigen (HBsAg) (2 µg; Recombivax-HB; Merck) and Alum (2.75 µg). The aged mice were vaccinated with the antigen and also received a single subcutaneous injection of either 0.3 mg or 3.0 mg of 3β,7β,17β-trihydroxyandrost-5-ene (AET), BrEA or 7-oxodehydroepiandrosterone, dehydroepiandrosterone or the vehicle (placebo control). The AET, BrEA hemihydrate or dehydroepiandrosterone was present in a formulation that contained 60 mg/mL of the compound suspended in 0.1% w/v carboxymethyl cellulose sodium in 0.9% saline. 7-Oxodehydroepiandrosterone was in a formulation that contained 60 mg/mL of the compound suspended in 0.1% w/v gum arabic in 0.9% saline.

A concentration of 6 mg/mL was obtained by diluting the 60 mg/mL formulation with vehicle that lacked the active substance.

Blood samples were collected 14, 21 and 34 days after treatment and the sera were analyzed by ELISA to determine the concentration of HBsAg-specific IgG (total IgG). In addition, samples obtained on day 21 were analyzed to determine the concentration of HBsAg-specific IgG1 and IgG2a subclasses. The results summarized below were average values obtained with blood samples collected 21 days after vaccination of groups of 8 mice. Subcutaneous injection was performed after shaving the hair from the thighs of each mouse. The injected volume was 50 µL for compound (3.0 mg or 0.3 mg) or placebo, and for vaccine preparation. The vehicle control consisted of carboxymethylcellulose (0.5%) in saline (0.9%). Antibody titers were determined by ELISA.

Treatment of aged, vaccinated animals with the formula 1 compounds, resulted in higher anti-HBsAg IgG titers than aged animals receiving the vaccination only. Higher antibody titers were achieved in aged mice that received the compounds at the same time as vaccination, in the majority of cases. For all tested compounds, except for BrEA at the low dose (0.3 mg), the IgG titer increase was significant compared to aged controls. This result shows that the formula 1 compounds result in an enhanced immune response to antigen challenge in the immune senescent animals.

The serum samples were also analyzed for the titers of HBsAg-specific, IgG1 or IgG2a immunoglobulin subclasses. A bias to IgG1 is seen in aged mice and this is considered symptomatic of immune senescence or a suboptimal immune response associated with immune senescence. The IgG1/IgG2a ratio is an indicator of immune status. Th2 cells predominantly assist in the generation of humoral immunity, while Th1 cells enhance, e.g., cellular immunity. Humoral immunity (Th2) becomes predominant with age, while the decreasing cellular (Th1) immunity leads to increased susceptibility to, e.g., infectious diseases.

The ratio of IgG1 to IgG2a of about 8:1 was measured in the young mice and 27:1 in aged mice. Generation of antigen-specific IgG1 generation involves T-helper type 2 (Th2) cells, and for IgG2a, T-helper type 1 (Th1) cells. Treatment of aged animals with the formula 1 compounds shifted the IgG1/IgG2a ratios toward the ratio seen in young, vaccinated animals. The ratios observed from the animals treated with AET, BrEA, 7-oxodehydroepiandrosterone or dehydroepiandrosterone ranged from about 4 to about 13. The shift was statistically significant. The tested compounds all enhanced the proportion of IgG2a, and thus the associated Th1 response to the antigen.

Secondary antibody response. Later, 42 days after the initial exposure to HBsAg, serum samples were taken from the mice described in the previous section and these were tested for anti-HBsAg IgG. At this time-point, vaccine-specific IgG titers were either low or undetectable. Three days later (45 days after first vaccination), the mice were injected again with HBsAg in Alum, but this time, none of the mice received immunosteroid (secondary vaccination). Serum samples collected 7 days and 14 days after the second exposure to HBsAg vaccine were assayed for anti-HBsAg antibody. In the young mice, a marked increase in specific antibody was seen in response to the second vaccination. In contrast, in aged mice that had received no immunosteroid with the first HBsAg injection, low levels of anti-HBsAg were detectable, and only in 4 of the 8 mice in this group was antibody detectable. Increases in anti-HBsAg titers were seen following secondary vaccination in aged animals that had been treated with immunosteroid in conjunction with the first HBsAg exposure. The anti-HBsAg antibody titer in serum increased following secondary vaccination in all 8 mice in the groups of aged mice that were treated at primary vaccination with the higher dose (3 mg/mouse) of AET, BrEA or 7-oxodehydroepiandrosterone, or with dehydroepiandrosterone (0.3 mg/mouse). In those aged mice that had received the lower dose (0.3 mg/mouse) of AET, BrEA or 7-oxodehydroepiandrosterone at vaccination, an intermediate response was seen, with 6 of the 8 mice producing detectable anti-HBsAg in response to secondary vaccination. These results show that the tested compounds resulted in an enhanced secondary antibody response in the aged animals. The compounds delivered by a transmucosal route (e.g., buccal or sublingual) can also provide an unexpectedly superior effect to the compounds when they are delivered by other routes such as subcutaneous or oral.

Example 30

DNA Vaccine Adjuvant

Formula 1 compounds such as 3β,7β,17β-Trihydroxyandrost-5-ene (AET) and BrEA are used to modulate the immune response to an antigen(s) such as malaria antigens encoded by DNA expression vectors. Antigens such as a *Plasmodium*, e.g., *P. yoelii, P. falciparum, P. vivax* or *P. berghei*, circumsporozoite or merozoite protein are used to immunize a subject. AET or BrEA is administered on the same day or a day or two before antigen challenge. Suitable antigens, expression vectors and their delivery to a subject have been described. See, e.g., S. L. Hoffman et al., *Vaccine* 1994 12:1529-1533, R. Weiss et al., *Infect. Immunity* 2000 68:5914-5919, J. C. Rayner et al., *Proc. Nat'l. Acad. Sci. U.S.A.* 2000 97:9648-9653, S. Scheiblhofer et al., *Eur. J. Immunol.* 2001 31:692-298. The capacity of the compounds to enhance immune responses to the antigens by, e.g., measuring cytotoxic T lymphocytes or antibody titer after delivery of the formula 1 compound and immunization with an antigen(s). Typically the immune response is measured at about 10 days to about 21 days after a primary immunization. Methods to measure immune responses are essentially as described herein or in appropriate cited references. DNAs that encode an antigen(s) that is associated with, e.g., an infectious agent or a tumor described herein may be used in these assays. The capacity of the formula 1 compound to modulate the immune response(s) to antigen challenge is optionally compared to the response generated by AET or BrEA.

Example 31

Modulation of monocyte or macrophage activation or survival. The capacity of the formula 1 compounds to activate monocytes and/or increase monocyte or macrophage activity or survival is determined using methods known in the art. The formula 1 compounds are assayed using, e.g., the assays described below. For these assays, peripheral blood mononuclear cells (PBMC) are purified from a subject, e.g., a human leukopack (American Red Cross, Baltimore, Md.) by centrifugation through a histopaque gradient (Sigma). Monocytes are isolated from PBMC by counterflow centrifugal elutriation. In each of the assays, the activity of a given formula 1 compound is optionally compared to the response associated with AET or BrEA.

Modulation of monocyte survival is determined essentially as follows. Human peripheral blood monocytes progressively lose viability when cultured in absence of serum or other stimuli. Their death results from internally regulated process such as apoptosis. Addition to the culture of activating factors, such as TNF-α improves cell survival. Propidium iodide (PI) staining is used to measure apoptosis as follows. Monocytes are cultured for 48 hours in polypropylene tubes in serum-free medium (positive control), in the presence of about 100 ng/mL of TNF-α (negative control), and in the presence of varying concentrations of the formula 1 compound. Cells are suspended at a concentration of $2 \times 10^6$/mL in PBS containing PI at a final 5 concentration of about 5 μg/mL, and then incubated at room temperature for 5 minutes before FACScan analysis. PI uptake has been demonstrated to correlate with DNA fragmentation in this experimental paradigm. The activity of formula 1 compounds such as AET or BrEA can be used as a comparison standard for other formula 1 compounds.

The effect of formula 1 compounds on monocyte or macrophage cytokine release is determined essentially as follows. An important function of monocytes and macrophages is their regulatory activity on other cellular populations of the immune system through the cytokines release after stimulation. An ELISA to measure cytokine release is performed using, e.g., human, monocytes, which are incubated at a density of about $5 \times 10^5$ cells/mL. A range of formula 1 compound concentrations is used, e.g., 1 nm, 10 nm, 100 nm, 1 μm, 10 μm and 50 μm. To determine IL-12 production, the cells are primed overnight with IFN (100 U/mL) in presence of a formula 1 compound. LPS (10 ng/mL) is then added. Conditioned media are collected after 24 h and kept frozen until use. Measurement of TNF-alpha, IL-10, MCP-I and IL-8 is then performed using a commercially available ELISA kit (e.g., R & D Systems (Minneapolis, Minn.)) and applying the standard protocols provided with the kit.

Activation of monocytes or macrophages by formula 1 compound is measured by assaying the oxidative burst after stimulation of the cells. Purified monocytes are plated in 96-well plate at about $2 \times 10^5$ cells/well. A range of formula 1 compound concentrations, e.g., 1 nm, 10 nm, 100 nm, 1 μm, 10 μm and 50 μm, are added to the wells in a total volume of 0.2 mL culture medium (RPMI 1640+10% FCS, glutamine and antibiotics). After 3 days incubation, the plates are centrifuged and the medium is removed from the wells. To the macrophage monolayers, 0.2 mL per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 pL 1N NaOH per well. The absorbance is read at 610 nm. To calculate the amount of $H_2O_2$ produced by the macrophages, a standard curve of a $H_2O_2$ solution of known molarity is performed for each experiment.

Example 32

Modulation of central nervous system cell growth, differentiation or activity. The formula 1 compounds are used to modulate astrocyte or neuron survival, neurite outgrowth, phenotypic differentiation of cortical neuronal cells or for inducing the proliferation of glial fibrillary acidic protein immunopositive cells (astrocytes). A thymidine incorporation assay, for example, can be used to measure cell proliferation or survival. The biological effects of FGF-2 (basic FGF) on cortical or hippocampal neurons in vitro included increases in both neuron survival and neurite outgrowth (Walicke et al., *Proc. Natl. Acad. Sci. U.S.A.* 1986 83:3012-3016. Using primary cortical neuronal culture, the effect of a formula 1 compound to induce neurite outgrowth can be compared to the response achieved with FGF-2 using, for example, a thymidine incorporation assay.

The formula 1 compounds are used in a model for Parkinson disease essentially as follows. The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine (MPP) and released. Subsequently, MPP is actively accumulated in dopaminergic neurons by the high-affinity reuptake transporter for dopamine. MPP is then concentrated in mitochondria by the electrochemical gradient, which selectively inhibits nicotidamide adenine disphosphate; ubiquinone oxidoreductionase (complex 1), thereby interfering with electron transport and eventually generating oxygen radicals. It has been demonstrated in tissue culture and in vivo that FGF-2 (basic FGF) has trophic activity for nigral dopaminergic neurons. FGF-2 in gel foam implants in the striatum results in the near complete protection of nigral dopaminergic neurons from the toxicity associated with MPTP exposure. The formula 1 compounds are administered with or without FGF-2 to measure their capacity to enhance survival of dopaminergic neurons in vitro, or they are delivered in vivo to enhance protection of dopaminergic neurons in the striatum from the damage associated with MPTP treatment.

In vitro dopaminergic neuronal cell cultures are prepared by dissecting the midbrain floor plate from gestation day 14 Wistar rat embryos. The tissue is dissociated with trypsin and seeded at a density of about $2\times10^5$ cells/cm$^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days and are processed for tyrosine hydroxylase, a specific marker for dopminergic neurons, immunohistochemical staining. Dissociated cell cultures are prepared from embryonic rats. The culture medium is changed every third day and the factors are also added at that time. Since the dopaminergic neurons are isolated from animals at gestation day 14, a developmental time which is past the stage when the dopaminergic precursor cells are proliferating, an increase in the number of tyrosine hydroxylase immunopositive neurons represents an increase in the number of dopaminergic neurons surviving in vitro.

Example 33

Supression of TNF-α induced adhesion molecule expression. The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-α), is a proinflammatory cytokine and stimulates all three CAMs on endothelial cells. It may be involved in a wide variety of inflammatory responses, often resulting in a pathological outcome. The capacity of a formula 1 compound to mediate a suppression of TNF-α induced CAM expression can be examined. A modified ELISA assay which uses ECs as a solid phase absorbent is employed to measure the amount of CAM expression on TNF-α treated ECs when co-stimulated with a member of the FGF family of proteins. To perform the experiment, human umbilical vein endothelial cell (HUVEC) cultures are obtained from pooled cord harvests and maintained in growth medium (EGM-2, Clonetics, San Diego, Calif.) supplemented with 10% FCS and 1% penicillin/streptomycin in a 37° C. humidified incubator containing 5% $CO_2$. HUVECs are seeded in 96-well plates at concentrations of about $1\times10^4$ cells/well in EGM medium at 37° C. for 18-24 hrs or until confluent. The monolayers are subsequently washed 3 times with a serum-free solution of RPMI-1640 optionally supplemented with 100 U/mL penicillin and 100 mg/mL streptomycin, and treated with a given cytokine and/or growth factor(s) for 24 h at 37° C. Following incubation, the cells are then evaluated for CAM expression.

HUVECs are grown in a standard 96 well plate to confluence. Growth medium is removed from the cells and replaced with 90 µL of 199 Medium (10% FBS). Samples for testing and positive or negative controls are added to the plate in triplicate (in 10 µL volumes). Plates are incubated at 37° C. for either 5 h (selectin and integrin expression) or 24 h (integrin expression). Plates are aspirated to remove medium and 100 µL of 0.1% paraformaldehyde-PBS (with $Ca^{++}$ and $Mg^{++}$) is added to each well. Plates are held at 4° C. for 30 min. Fixative is then removed from the wells and wells are washed 1× with PBS(+Ca,Mg)+0.5% BSA and drained. Do not allow the wells to dry. 10 µL of diluted primary antibody is added to the test and control wells. Anti-ICAM-1-Biotin, Anti-VCAM1-Biotin and Anti-E-selectin-Biotin are used at a concentration of 10 pg/ml (1:10 dilution of 0.1 mg/ml stock antibody). Cells are incubated at 37° C. for 30 min. in a humidified environment. Wells are washed ×3 with PBS (with Ca, Mg) and 0.5% BSA. Then add 20 µL of diluted ExtrAvidin-Alkaline Phosphotase (1:5,000 dilution) to each well and incubate at 37° C. for 30 min. Wells are washed ×3 with PBS (with Ca, Mg) and 0.5% BSA. 1 tablet of p-Nitrophenol Phosphate pNPP is dissolved in 5 mL of glycine buffer (pH 10.4). 100 µl of pNPP substrate in glycine buffer is added to each test well. Standard wells in triplicate are prepared from the working dilution of the ExtrAvidin-Alkaline Phosphotase in glycine buffer: 5 µL of each dilution is added to triplicate wells and the resulting AP content in each well is 5.50 ng, 1.74 ng, 0.55 ng, 0.18 ng. 100 µl of pNNP reagent is then be added to each of the standard wells. The plate is incubated at 37° C. for 4 h. A volume of 50 µL of 3M NaOH is added to all wells. The results are quantified on a plate reader at 405 nm. The background subtraction option is used on blank wells filled with glycine buffer only. The template is set up to indicate the concentration of AP-conjugate in each standard well. Results are indicated as amount of bound APconjugate in each sample.

Example 34

Inhibition of a mixed lymphocyte reaction. This assay can be used to evaluate inhibition of a Mixed Lymphocyte Reaction (MLR) by formula 1 compounds. Inhibition of a MLR may be due to a direct effect on cell proliferation and viability, modulation of costimulatory molecules on interacting cells, modulation of adhesiveness between lymphocytes and accessory cells, or modulation of cytokine production by accessory cells. Multiple cells may be targeted by the compounds since the peripheral blood mononuclear fraction used in this assay includes T, B and natural killer lymphocytes, as well as monocytes and dendritic cells. Compounds that inhibit the MLR are useful in treating, preventing or ameliorating diseases associated with lymphocyte and monocyte activation or proliferation. These include, e.g., inflammatory or autoimmune conditions such as asthma, arthritis, diabetes, inflammatory skin conditions, psoriasis, eczema, systemic lupus erythematosus, multiple sclerosis, glomerulonephritis, inflammatory bowel disease, Crohn's disease, ulcerative colitis, arteriosclerosis, cirrhosis, graft vs. host disease, host vs. graft disease and hepatitis.

To perform the assay, PBMCs from, e.g., human, donors are purified by density gradient centrifugation using Lymphocyte Separation Medium (LSM™, density 1.0770 g/mL, Organon Teknika Corporation, West Chester, Pa.). PBMCs from two donors are adjusted to 2×10$^6$ cells/mL in RPMI-1640 (Life Technologies, Grand Island, N.Y.) supplemented with 10% FCS and 2 mM glutamine. PBMCs from a third donor is adjusted to 2×10$^5$ cells/ml. Fifty μL of PBMCs from each donor is added to wells of a 96-well round bottom microtiter plate. Several concentrations of the formula 1 compound in the wells is used in triplicate, e.g., 1 nm, 10 nm, 100 nm, 1 μm and 10 μm. Recombinant human IL-2 (R&D Systems, Minneapolis, Minn., catalog number 202-IL) is added to a final concentration of about 0.1 to 1 μg/mL and anti-CD4 monoclonal antibody (e.g., R&D Systems, clone 34930.11, catalog number MAB379) is added to a final concentration of about 1 to 10 μg/mL. Cells are cultured for 7-8 days at 37° C. in 5% CO$_2$, and 1 μCi of [$^3$H] thymidine is added to wells for the last 16 hrs of culture. Cells are harvested and thynudine incorporation determined using a suitable scintillation counter, e.g., a Packard TopCount. Data is expressed as the mean and standard deviation of triplicate determinations. Samples of the protein of interest are screened in separate experiments and compared to the negative control treatment, anti-CD4 mAb, which inhibits proliferation of lymphocytes and the positive control treatment, IL-2 (either as recombinant material or supernatant), which enhances proliferation of lymphocytes.

Previously described MLR protocols, sources of cells for use in the MLR and assay parameters can be used to evaluate the effects of the formula 1 compounds. See, e.g., K. V. Bromelow et al., *J. Immunol. Methods* 2001 247:1-8, Z. Amir-ghofran et al., *J. Ethnopharmacology* 2000 721:167-172, T. Itoh et al., *J. Antibiot (Tokyo)* 1993 46:1575-1581, P. Van Vlasselaer et al., *Cell. Immunol.* 1991 138:326-340, and A. Shaked et al., *Transplantation* 1991 52:1068-1072.

Example 35

Effects on the CNS. The effects of the formula 1 compounds on memory, learning, motor function or the status of a neurological condition or neurodegeneration condition are assayed using standard methods. For example, aged, two year old mice are tested in the Morris water maze procedure by training the mice to locate a pedestal in less than 15 seconds in three consecutive trials. Immediately upon completion of training one group of mice is treated with a formula 1 compound (5-30 mg/kg) and a second group is treated with a placebo. The treatment comprises one, two or three intraperitoneal, subcutaneous, intramuscular or intravenous injections of the formula 1 compound and the vehicle placebo. The injections are given once per day. Two weeks after treatment, the time to rescue is timed in the Morris water maze procedure and the control result is compared to the placebo control. The use of Morris water maze and other procedures to measure the effect of various conditions or compounds on learning, memory or neurological conditions have been described, see e.g., R. Gerlai *Trends Neurosci.* 1996, 19:177-181, J. L. W. Lau et al., *Proc. Nat'l. Acad. Sci.* 2001, 98:4716-4721, U.S. Pat. Nos. 6,348,489, 6,251,942 and 6,277,886.

Scopolamine induced amnesia is examined essentially as follows. Groups of 13 to 16 C57BL76 mice (about 35 gm) are trained in the Morris water maze procedure to locate a pedestal in less than 15 seconds in three consecutive trials. Immediately upon completion of training the mice in each of three groups are treated with scopolamine (1 mg/kg), scopolamine plus a formula 1 compound at one or more dosages (e.g., about 5-50 mg/kg), and scopolamine plus a placebo. The treatment comprises one, two or three intraperitoneal, subcutaneous, intramuscular or intravenous injections of the formula 1 compound and the vehicle placebo. The injections are given once per day. Six days after treatment the average time (sec) to rescue is timed using the Morris water maze procedure and the results from each group are compared. Results for a formula 1 compound such as 16α-fluoroandrost-5-ene-17-one or 7-hydroxy-16α-fluoroandrost-5-ene-17-one are optionally compared to the results that are obtained in these protocols using another control compound, e.g., (S)—(−)—N-propargyl-1-aminoindan or nefiracetam, or another formula 1 compound such as BrEA or AET to determine the relative potency of the formula 1 compounds with respect to each other.

Example 36

The capacity of formula 1 compounds to limit injury associated with ischemia and reperfusion is determined in an animal model essentially as follows. Male Sprague-Dawley rats weighing 130-170 g are randomly assigned to no pre-treatment, vehicle pre-treatment or formula 1 compound pre-treatment using one or more dosages, e.g., about 1-10 mg/kg. Animals are treated with vehicle or DHEA the day before and the day of surgery. Anesthesia is induced with intraperitoneal pentobarbital (60-70 mg/kg). The rats are placed on a heating pad, and body temperature is maintained at about 36° C. Detection of the cremaster muscle on its neurovascular pedicle is performed essentially according to conventional techniques, e.g., Anderson, G. L. et al., *Microvascular Res.* 1988 36:56-63, Siemionow, M. et al., *Microcirc. Endoth. Lymphatics* 1991 7:183-197, Siemionow, M. et al., *J. Hand Surgery* 1993 18A:963-971.

Briefly, a skin incision is made from the anterior iliac spine to the tip of the scrotum. The testis with cremaster muscle intact is then dissected away from the scrotum. An opening of 1 cm is made on the ventral surface of the cremaster, and the testis and spermatic cord are removed. Under a microscope, the neurovascular pedicle, consisting of the pubic-epigastric arteries, vein, and genitofemoral nerve, is then completely isolated by dissecting to the origin of the vessels from the external iliac artery and vein. The front wall of the cremaster muscle sac is opened and the island cremaster muscle flap is prepared for intravital videomicroscopy. The rat is secured on a tissue bath, and the cremaster muscle flap is spread over the coverglass in the opening at the bottom of the bath and fixed with 5-0 silk sutures. It is then transilluminated from below, using a fiber optic tungsten lamp. The muscle is kept moist and covered with impermeable plastic film. The tissue bath, designed specifically for temperature control, is filled with 0.9% saline and the temperature maintained at between 35-36° C. The microscope is equipped with a color video camera. The video image of the microcirculation is displayed on a 19" monitor, where the final magnification is 1800×. Measurement of microvascular activity is recorded after isolation of the muscle to establish the pre-ischemia baseline. After proper positioning of clamps to completely shut down blood flow to the muscle flap, the duration of the ischemic period is six hours. Following removal of clamps to induce reperfusion injury, activity in the microvasculature is measured at e.g., 30, 60 and 90 minutes post-reperfusion. In all experimental subjects, ischemia is followed by reflow and then by an initial period of flow of blood through the microcirculation. This burst of circulatory activity is followed by marked reperfusion injury that induces loss of flow.

One or more of the following parameters are used to evaluate the state of the cremaster muscle microvasculatory system prior to ischemia and after reperfusion. The density of perfused capillaries in each of three flap regions is measured by counting the number of flowing capillaries in proximity to the preselected post-capillary venule. Nine visual fields of capillaries are counted at each postcapillary venule site, for a total of 27 fields per cremaster muscle flap.

A leukocyte count in postcapillary venules is taken using video scans of three pre-selected post-capillary venules in proximal, middle and distal flap regions. For each venule, the number of leukocytes rolling through the lumen, the number adhering to the endothelium and the number migrating across the endothelium over a two-minute period are recorded. Results are optionally obtained for rollers, strikers and diapedesis.

Red blood cell velocities in first order and second order arterioles are measured. Red blood cell velocities are recorded in the main arterioles of the cremaster flap using an optical Doppler velocimeter. Results are obtained for velocity of venous and arterial blood.

In an exemplary protocol, six rats are untreated and six rats are pre-treated with vehicle. Under conditions of six hours of ischemia and 90 minutes of reperfusion, the absolute number of rolling, sticking and transmigrated leukocytes is determined within 60 minutes of reperfusion and at 90 minutes. Rats are pre-treated with a formula 1 compound by subcutaneous injection the day before and the day of surgery to measure any protective effect of the therapy. One or more of the three parameters are determined and are compared to normal values. The endothelial-adherent properties compared to baseline values are optionally determined, using numbers of rolling, sticking and transmigrating leukocytes. Red cell velocities in second order arterioles are compared to normal rates of flow at, e.g., 90 minutes post-reperfusion.

Example 37

Pulmonary vasoconstriction. The capacity of formula 1 compounds to limit hypoxia induced pulmonary vasoconstriction is demonstrated using an animal model essentially as follows. Isolated perfused ferret lungs are an established animal model to study secondary pulmonary hypertension. In brief, male ferrets are anesthetized with intraperitoneal pentobarbital sodium and the chest is opened. Stainless steel cannulae are secured in the left atrium and pulmonary artery, and the pulmonary artery and the aorta are ligated. The lungs are perfused with a mixture of autologous blood and Krebs-Henseleit buffer in a circulating manner at a constant rate of about 85 mL/min. The perfusion circuit includes a perfusate reservoir, a roller perfusion pump, filter, and a heat exchanger. The perfusion system is made of, e.g., tygon tubing, which is used for connections and for passage through the perfusion pump. The temperature of the perfusate is kept about 37-38° C. and the pH is maintained at 7.35 to 7.40 by adding sodium bicarbonate to the reservoir as needed. The venous reservoir is placed below the lowermost portion of the lung.

The lungs are ventilated with a hypoxic gas mixture of 5% $CO_2$, 4% $O_2$, and 91% $N_2$ by a tracheotomy with a Harvard animal respirator for 30 minutes. The animals are ventilated with a tidal volume of 30 mL, at a rate of 18 breaths/min. and with 2 cm of $H_2O$ positive end-expiatory pressure. For measurements, pulmonary arterial, left atrial and tracheal pressures are monitored using Gould Statha P231 D pressure transducers or an equivalent connected to the inflow circulation and recorded on, e.g., a Grass polygraph. After 30 minutes of ventilation with hypoxic gas mixture, a formula 1 compound in a dose between about 5-25 mg/kg body weight is added to the reservoir, and perfusate is allowed to perfuse the ferret lungs for 1.5 hours. Pulmonary artery pressure is measured until the end of the experiment, i.e., a total of two hours. Pressure that remains at or near basal level indicates the vasodilatory effect of the formula 1 compound in pulmonary circulation that is otherwise constricted in response to hypoxia. The effects of the formula 1 compounds can be compared to the effects and duration of nitric oxide, a therapeutic agent that is optionally used in this model as a control.

Example 38

Hemopoiesis modulaton. Enhanced hemopoiesis is observed in mammals with immune injury from, e.g., radiation exposure or from an immunosuppressive chemotherapy. In an example, animals are used to demonstrate the effect of formula 1 compounds on hemopoiesis after immune system injury due to radiation. Hemopoiesis in the murine immune system after radiation is optionally used because of the similar responses of murine and human hemopoiesis to drugs and toxic insults (see, e.g., J. H. Hendry and B. I. Lord, editors, *Radiation toxicology: Bone marrow and leukaemia* 1995 Taylor & Francis Inc., London).

In an exemplary protocol, B6D2F1/J female mice (Jackson Laboratory, Bar Harbor, Me.), 18-24 weeks of age, 22-30 g body weight, are obtained and held in quarantine for two weeks. Up to 10 mice are housed in sanitized 46×24×15 cm polycarbonate boxes with filter covers (MicroIsolator; Lab Products, Inc, Maywood, N.J.) on autoclaved hardwood chip bedding. Mice are given feed and acidified (pH 2.5) water freely. The animal holding room is maintained with conditioned fresh air at approximately 21° C. and 50° (±10%) relative humidity and with a 12-h light/dark full spectrum lighting cycle.

Mice are placed in ventilated Plexiglas containers and exposed bilaterally to gamma-radiation from a $^{60}Co$ source. Exposure time is adjusted so that each animal received a midline tissue-absorbed dose of 1-12 Gy at a nominal dose rate of 0.4 Gy/min at ambient temperature. Using a standardized technique, the midline dose rate is measured by placing a 0.5 cc tissue-equivalent ionization chamber at the center of a 2.5-cm diameter cylindrical acrylic mouse phantom. The tissue-air ratio, defined as the ratio of the dose rate measured in the phantom to the dose rate in free air, for this array is about 0.96. Variation within the exposure field is less than about 4%. Dosimetric measurements are made in accordance with the American Association of Physicists in Medicine protocol for the determination of absorbed dose from highenergy photon and electron beams (*Med. Phys.* 1983 10:741-771). Sham-irradiated mice are treated in the same way as the irradiated animals, except that the animals are not irridiated.

Various formula 1 compounds e.g., compounds such as those in the compound groups described herein are formulated with a suitable vehicle (e.g., PEG-400) or sterile 0.9% NaCl (saline) optionally containing other excipients such as a cyclodextrin. The compounds are injected subcutaneously in a volume of about 0.1 mL or they are delivered orally or they are administered by another route. Doses typically range from about 1 mg/kg to about 350 mg/kg, e.g., about 1, 10, 20, 40, 80, 160 or 320 mg/kg.

Blood (0.6-1.0 mL) is obtained from halothane-anesthetized mice by cardiac puncture using a heparinized syringe attached to a 21-gauge needle. Blood is collected in EDTA-containing sample tubes. Mice are euthanized by cervical dislocation after blood collection. White blood cell (WBC), red blood cell (RBC) and platelet (PLT) counts are performed using, e.g., a Hematology System 9000 (Biochem Immunosystems). Wright-stained blood smears from the same samples are made for differential counts of neutrophils and lymphocytes by light microscopy.

Hemopoietic progenitor cells committed to granulocyte-macrophage differentiation (GM-CFC) are assayed by a single-layer modification of a double-layer semisolid agar technique essentially as described (Patchen et al. *Adv. Space Res.* 1992 12:223-248). For example, femoral marrow is extracted and cell suspensions are prepared by flushing with 3 mL of McCoy's 5A medium containing 10% heat-inactivated fetal bovine serum (HIFBS; Hyclone, Logan, Utah). Each cell suspension represented a pool of marrow from four femurs, i.e., both femurs from each of two mice. The total number of nucleated cells in each suspension is determined with, e.g., a Coulter counter. The agar-medium mixture consisted of equal volumes of 0.66% agar and double-strength supplemented CMRL 1066 medium (Gibco, Grand Island, N.Y.). The medium is supplemented with final concentrations of 10% HIFBS, 5% tryptic soy broth, 5% heat-inactivated horse serum, antibiotics, and L-serine. One milliliter of the agar-medium mixture is added to each 35-mm plastic Petri dish (two dishes per suspension) and mixed with 50 µL of 0.1 ng/µL recombinant mouse GM-CSF (Genzyme, Cambridge, Mass.). Cell suspensions are then mixed into the agar-medium mixture to a final concentration of $0.5 \times 10^5$ cells/mL for unirradiated animals, and $1.0 \times 10^5$ or $1.5 \times 10^5$ cells/mL for irradiated animals to ensure sufficient colonies per plate for quantitation. Control experiments are done to confirm linearity of colonies at cell concentrations of $0.5-1.5 \times 10^5$ cells/mL. Colonies (>50 cells) are counted after seven days incubation in a 37° C. humidified environment containing 5% $CO_2$. The average of the counts for the two dishes is taken as the value for each pool. About six animals are used per group in each of two experiments.

For histological examination of myeloid hyperplasia in bone marrow after administration of the formula 1 compound, mice are euthanized with halothane, tissues are immersed in formalin, bones are decalcified and routine H&E-stained 6-µm paraffin sections are prepared.

For induced-infection studies, a clinical isolate of *K. pneumoniae*, capsule type 5 (strain AFRRI 7), that is kept frozen at 70° C. in skim milk, is grown overnight at 35° C. on Trypticase Soy Agar (Becton-Dickinson, Sparks, Md.). Five typical colonies are inoculated into 8 mL of brain heart infusion broth (Becton-Dickinson) and incubated overnight at 35° C. Two milliliters of this overnight suspension is inoculated into 95 mL of prewarmed brain heart infusion broth. The culture is incubated at 35° C. with shaking for approximately 2.5 h. The optical density of bacterial growth is monitored with a spectrophotometer at a wavelength of 550 nm. Late log-phase cells are ished and suspended in cold saline to yield $10^9$ viable bacteria per mL. Appropriate dilutions for inoculations are made in cold saline.

To induce a bacterial infection, all mice are injected sc with *K. pneumoniae* four days after sham-irradiation or irradiation when circulating leukocytes are depressed. Mice are inoculated sc rather than iv or ip, to establish infection leading to sepsis, but not rapid septic shock. After sc inoculations of *K. pneumoniae* in the mice, the infection remains largely localized to the injection site. *K. pneumoniae* are not detectable in blood of inoculated mice until a few hours before death.

Different doses of the bacteria are inoculated for each of three radiation dose levels (0, 1 or 3 Gy) to approximate the $LD_{95/30}$, because the effects of radiation on hemopoiesis and susceptibility to infection are dependent on the dose of radiation. The $LD_{95/30}$ for bacteria at each radiation dose is calculated from probit analysis. The actual doses are estimated by dilution plating of inocula onto Trypticase Soy Agar and incubating overnight at 35° C. Since different bacterial doses are expected to be needed for different radiation doses, the $LD_{95/30}$ is estimated for each group and different mortality rates are observed in the vehicle-injected control groups. Bacterial doses for induced-infection experiments are prepared and calculated in the same manner.

Animals are checked frequently, e.g., once or twice daily, six or seven days per week, to monitor survival and to euthanize mice that are in a moribund state. To verify that mortality in the induced-infection experiments is associated with *K. pneumoniae* injection, heart blood from recently deceased animals (or moribund animals euthanized by cervical dislocation) is cultured overnight at 35° C. on Columbia sheep blood agar plates (Becton-Dickinson, Sparks, Md.). Colonies are identified as *K. pneumoniae* by a suitable means, e.g., Biolog analysis.

For histological analysis of bone marrow, coded slides are scored blind using a five-level semiquantitative scale and the results analyzed with a randomization t-test to obtain exact P-values. Thirty-day survival values are compared using the generalized Savage (Mantel-Cox) procedure (BMDP Statistical Software, Inc, Los Angeles, Calif.). To calculate dose reduction factors (DRFs), probit analysis is performed on mortality data.

To test the ability of formula 1 compounds to ameliorate radiation-induced defects in hemopoiesis, mice are exposed to bilateral whole-body gamma-radiation and receive a dose of 3 Gy (or are sham-irradiated). One hour after irradiation or sham-irradiation, mice are injected with 320 mg/kg 3β, 17β-dihydroxyandrost-5-ene ("AED") or PEG-400 vehicle. Between-group differences in blood cell elements, e.g., neutrophils, GM-CFC and platelets are generally determined. Irradiation results in a decrease in neutrophils at about four days after radiation compared to sham-irradiated animals.

Example 39

BrEA was administered to relatively late stage HIV-infected patients (CD4 counts of $\leq 100$ cells/mm$^3$, HIV RNA at screening of $\leq 1 \times 10^6$ copies/mL) at least 18 years old who were at risk of developing opportunistic infections, but who had adequate hematological and renal function, e.g., WBC counts of $\geq 1.0 \times 10^9$ cells/L, absolute neutrophil counts of $\leq 0.75 \times 10^9$ cells/L, hemoglobin of $\leq 7$ g/dL and serum creatinine of 132 µmol/L. BrEA and vehicle placebo was administered by intramuscular injections of 50 or 100 mg per dose in a 1 or 2 mL volume. The treatment protocol is ongoing.

The incidence rate, time to resolution and time to recurrence of opportunistic infections is determined for patients receiving BrEA and for control patients receiving placebo during treatment and optionally every month for 3 or 4 months following the last treatment course. A treatment course consisted of intramuscular injections given daily for 5 consecutive days and repeated every 6 weeks. Treatment course one injections started on day 0. Treatments are optionally carried out for a total of 7 courses over 42 weeks.

In patients examined at day 4, 43, 46 and 56 after 1 course of treatment, the level of RNA for several inflammation associated genes was analyzed. The RNA was obtained from circulating white blood cells from the patients and the uninfected volunteers. Peripheral blood was collected into a CPT-Vacutainer (Becton Dickinson) and PBMC isolation was performed according to the manufacturer's protocol. The PBMC were maintained in 1 mL of RPMI 1640 with 10% FCS at 37° C. for 3 hours and then lysed in lysis buffer (300 µL MagnaPure™). RNA levels from PBMC lysates were measured by preparation of cDNA using commercial AMV reverse transcriptase and PCR kits and protocols (First Strand cDNA Synthesis™, Roche Diagnostics; LightCycler FastStart DNA Sybr Green I™ Kit, Roche Diagnostics; LightCycler Primer sets, Search-LC, Heidelberg). The results generally showed a detectable decrease compared to baseline levels of about 40-98%, generally about 50-90% for RNA encoding IL-1β, TNFα, IL-6, IL-8, IL-10, COX-2 and MCP-1. The level of GM-CSF was increased at 43 days and decreased at all of the other time points. In the HIV-infected patients before treatment with BrEA, compared to healthy uninfected, i.e., not HIV infected, volunteers, there was a statistically significant (Mann-Whitney analysis) increase in RNA encoding IL-1β, TNFα, MIP-1α, IL-6, IL-8, COX-2, M-CSF, GM-CSF, MCP-1 and IFNγ. BrEA treatment for 5 days thus resulted in a decrease in multiple inflammation-associated markers.

Other details of similar clinical protocols may include at least some of the following procedures. Prior to randomization, patients are optionally screened for acute, active HIV related infections or opportunistic infections. Screening may include vital sign measurements (temperature, heart rate, sitting blood pressure, and oxygen saturation by pulse oximetry), a chest X-ray, a complete physical examination including ophthalmic exam with funduscopy and pelvic examination including a PAP smear, and a complete blood laboratory examination. Additionally, patients may provide sputum samples to identify active TB infection and stool samples for culture and sensitivity for ova and parasites. Patients who require acute treatment, hospitalization, or chemotherapy for active infections are optionally excluded from participation.

The patients are optionally monitored for safety throughout the study and, e.g., every month for 3 months following the last treatment course. Patients who discontinue due to an clinically significant opportunistic infection are optionally followed for resolution and outcome. Patients may be evaluated for opportunistic infections (OIs) at the time of dosing. Suspected opportunistic infections are usually diagnosed by appropriate diagnostic methods. Opportunistic infections are generally documented and their course followed throughout the study. The opportunistic infections may be evaluated as protocol endpoints and may include one or more of tuberculosis, candidiasis, PCP, diarrhea, or any opportunistic infections such as Cryptosporidiosis (e.g., with >1 month diarrhea), Isosporiasis (e.g., with >1 month diarrhea), Microsporidiosis (e.g., with >1 week diarrhea or other manifestations), *Pneumocystis carinii* (pneumonia or extrapulmonary infection), Toxoplasmosis, Kaposi's sarcoma, invasive cervical cancer, cervical dysplasia, Candidiasis (oropharyngeal, vaginal, esophageal or pulmonary), Coccidiomycosis (disseminated or extrapulmonary), Aspergillosis (invasive or disseminated), CMV infection, an active Herpes simplex infection (bronchitis, pneumonitis, or esophagitis), progressive multifocal leukoencephalopathy, systemic *Mycobacterium avium* complex infection or a non-typhoidal *Salmonella septicemia*.

Microsporidiosis (with >1 month diarrhea or other manifestations) requiring premature study discontinuation. Patients may be prematurely discontinued from the study if they experience a serious opportunistic infection that requires more than ten days of hospitalization, or if the opportunistic infection does not respond to a specific treatment after two weeks of acute primary and/or secondary treatment. Patients who discontinue the study due to a serious opportunistic infection should complete the premature discontinuation visit, if possible. Whenever a patient is diagnosed with one or more opportunistic infections, an appropriate treatment is typically started based on the normal standard of care and/or the caregiver's judgment. Eligible patients are optionally provided prophylaxis treatment at the baseline visit for PCP. In addition, patients are optionally provided with a nutritional supplement of multivitamins with minerals.

All patients are optionally monitored for one or more of HIV RNA levels (e.g., by Chiron Quantiplex™ branched chain DNA assay), T-cell subsets (CD4/CD8), plasma dehydroepiandrosterone sulfate, plasma cortisol. Immunological analysis may include cytoplasmic or serum cytokines or interleukins (e.g., IL-2, 4, 6, 8, 10, and 12), gamma interferon, insulin-like growth factor (IGF-1) and tumor necrosis factor (TNFα), RANTES and expression of the protein or messenger RNA products for these or other genes.

Assessment of the patient's immune status by performing delayed hypersensitivity (DTH) skin testing may be done and read at 48 and/or 72 hours after application but prior to administering BrEA. The skin test is optionally done at the baseline visit, usually within two weeks of the initial dosing of BrEA. Skin test antigens for DTH may be repeated at later times, e.g., at weeks 6, 10, 18, 30, 42 and 57.

At clinic visits various examinations, including a thorough pulmonary exam may be done. This includes but is not limited to measuring body weight, Karnofsky Performance status, determining oxygen saturation and vital signs. Patients may be queried at visits with the caregiver for adverse events, symptoms of a suspected or existing opportunistic infection as well as any new opportunistic infection, HIV related events and changes in drug therapy.

Patients are dosed at the following times for the 5-day course of intramuscular injections: Week 1 (days 0-4); week 7 (days 42-46); week 13 (days 84-88); week 19 (days 126-130); week 25 (days 168-172); week 31 (days 210-214) and week 37 (days 252-256) for a total of seven treatment courses. BrEA or placebo is supplied as a liquid formulation in aliquots in 2 mL amber glass vials. Each vial with BrEA contains 50 mg of BrEA per mL in a vehicle formulation consisting of 40% polyethylene glycol 200, 2% benzyl benzoate, 2% benzyl alcohol and qs propylene glycol. BrEA should be injected slowly into the muscle. Pregnant females are optionally excluded from treatment. The use of some other compounds are optionally prohibited during the study (e.g., cancer chemotherapy, Moducare, testosterone, DHEA, decadurabolin or oxandrolone within, e.g., 4 weeks of study initiation, or hydroxyurea, methotrexate, antiretroviral agent treatments).

Example 40

BrEA was administered to treatment naïve HIV-infected patients. These patients had a total of 2 weeks or less of any prior antiretroviral treatment. The patients had CD4 counts of ≧200 cells/mm$^3$, HIV RNA at screening between 5,000 and 1×10$^6$ copies/mL. They were at least 18 years old and had adequate hematological and renal function, e.g., WBC counts of ≧1.0×10$^9$ cells/L, absolute neutrophil counts of ≧0.75× 10$^9$ cells/L, hemoglobin of ≧7 g/dL and serum creatinine of <132 µmol/L. BrEA was administered by subcutaneous injection of 50 or 100 mg per dose using the formulation described in the pervious example. The treatment protocol is ongoing.

After or during one treatment course of 100 mg of BrEA for 5 consecutive days, the HIV infected patients were examined at days 2-35. Day 1 was the first treatment day. The level of RNA for several inflammation associated genes was analyzed. At day 5, the results showed statistically significant decrease compared to baseline levels of RNA encoding IL-1β, TNFα, GM-CSF, MIP-1α and COX-2, and a statistically significant increase in PPARγ. The RNA was obtained from circulating white blood cells from the patients and the uninfected volunteers essentially as described in the preceeding example. In the HIV-infected patients before treatment with BrEA, compared to healthy uninfected, i.e., not HIV infected, volunteers, there was a statistically significant (Mann-Whitney analysis) increase in RNA encoding IL-1β, TNFα, MIP-1α, IL-6, IL-8, IL-10, COX-2, M-CSF, RANTES, GM-CSF, MCP-1 and IFNγ. At days 2-35 a statistically significant decrease (p<0.001 for all markers) in IL-1β, IL-6, TNFα, GM-CSF, MIP-1α, MCP-1 and COX-2 transcripts was observed and an increase in PPARγ (p=0.034) was observed. Increases in PPARα and t-Bet was also observed in the treated patients.

BrEA treatment for 2-5 days thus resulted in a modulation of multiple inflammation-associated markers, i.e., decreased proinflammatory cytokines and increased antiinflammatory markers.

Other details of similar clinical protocols may include at least some of the following procedures. The incidence rate, time to resolution and time to recurrence of toxicities or opportunistic infections is determined for patients receiving BrEA during the treatment and optionally every month for 3 or 4 months following the last treatment course. BrEA and the placebo vehicle are administered as a 1 mL subcutaneous injection. A treatment course consists of subcutaneous injections given daily for 5 consecutive days and repeated every 4, 5 or 6 weeks for a total of 3 or 4 courses over about 12-24 weeks. Treatment course one injections start on day 0. About 24 patients are randomized to different treatment groups: BrEA 50 mg or placebo equivalent or BrEA 100 mg or placebo equivalent. In each treatment group, patients are optionally randomized in a 2:1 or a 3:1 ratio to either active drug, 50 or 100 mg BrEA, or the placebo.

The day each patient receives a first of five once daily doses is day 1. In one treatment protocol, the 5-day treatment course is followed by a 5 week observation period and the patients receive a total of 3 treatment courses consisting of 5 consecutive days of once daily dosing of BrEA or placebo equivalent followed by a 5 week observation period. Patients receive 4 treatment courses over a 24-week period. In this protocol Approximately 24 patients will be randomized to one of two treatment groups. Within each treatment group, patients are randomized in a 3:1 ratio to BrEA or placebo equivalent (9 patients randomized to BrEA and 3 patients randomized to placebo equivalent).

Pregnant females are optionally excluded from treatment. The use of some other compounds are optionally prohibited during the study (e.g., cancer chemotherapy, Moducare, testosterone, DHEA, deca-durabolin or oxandrolone within, e.g., 4 weeks of study initiation, or hydroxyurea, methotrexate, antiretroviral agent treatments).

All patients are optionally monitored for levels of HIV RNA (Chiron Quantiplex™ branched chain DNA assay) and T-cell subsets (CD4/CD8). Activation markers/immunological analysis may include, but are not limited to, cytoplasmic cytokines, serum cytokines, gene expression, interleukins (IL-2, 4, 6, 8, 10 and 12), gamma interferon, insulin-like growth factor and tumor necrosis factor alpha. Additional research testing may be conducted on samples collected at each visit. Chemistry and hematology panels and urinalysis will be performed as indicated in the schedule of evaluations. Additionally, patients co-infected with hepatitis B and/or C viruses, malaria or tuberculosis are optionally monitored regularly for viral titers or microbiological cultures.

Example 41

BrEA was administered by transmucosal (buccal) administrations of BrEA to HIV-infected patients who were treatment-naïve (no previous treatment or less than 2 weeks of previous treatment with antiretroviral agents) and who had a viral load greater than 500 HIV copies/mL and a CD4 cell count ≧200 cells/mm$^3$. The treatment protocol is ongoing. BrEA or a placebo equivalent is administered by transmucosal delivery route according to the following 3 dosing groups.

For Group 1, a single treatment course is 50 mg of HE2000 or placebo administered for five consecutive days over one week followed by a five-week observation period. Each treatment course is six (6) weeks in duration and each patient receives three consecutive treatment courses over a total of 18 weeks. For Group 2, a single treatment course is 50 mg of BrEA or placebo given three times a week over four weeks followed by a two-week observation period. Each treatment course is six (6) weeks in duration and each patient receives three consecutive treatment courses over a total of 18 weeks. For Group 3, a single treatment course consists of 50 mg of BrEA or placebo given once a week over six weeks. Each treatment course is six weeks in duration and each patient receives three consecutive treatment courses over a total of 18 weeks. About 36 patients are enrolled (e.g., 12 patients per dosing Group). The dosing is summarized below.

| DOSING GROUP | NO. OF PATIENTS | BREA DOSE |
|---|---|---|
| 1 | 9 | 50 MG |
| 1 | 3 | PLACEBO (0 MG) |
| 2 | 9 | 50 MG |
| 2 | 3 | PLACEBO |
| 3 | 9 | 50 MG |
| 3 | 3 | PLACEBO |

The day the patient receives the first dose is day 1. A six-week period encompasses one treatment course. The patients are optionally followed by monthly follow-up visits for 1, 2 or 3 consecutive months after dosing.

A preliminary analysis of group 1 patients at day 5 indicated a general decrease in one or more inflammation-associated markers, e.g., IL-1p, TNFα, MIP-1α, COX-2 and GATA-3. In these HIV-infected patients before treatment with BrEA, compared to healthy uninfected, i.e., not HIV infected, volunteers, there were statistically significant (Mann-Whitney analysis, p<0.001) increases in RNA encoding IL-1p, TNFα, MIP-1a, IL-6, IL-8, IL-10, COX-2, M-CSF, RANTES, GM-CSF, MCP-1 and IFNγ. BrEA treatment in these patients was consistent with modulation of significant immune markers.

BrEA is provided as transmucosal or buccal tablets. Each tablet contained 25 mg of BrEA and sucrose, lactose, and Tween 80 excipients. Placebo transmucosal tablets containing the excipients, but lacking the BrEA are provided. Patients are instructed to drink water before placing two buccal tablets (50 mg dose) between the upper gingival surfaces of the jaw and buccal mucosa of the cheek pouch. The tablets are to be held in the mouth without disturbance for about 10 minutes. During this time, patients are observed to ensure that the tablets are not chewed or swallowed.

Other details of similar clinical protocols may include at least some of the following procedures. All patients are optionally monitored for levels of HIV RNA (Chiron Quantiplex™ branched chain DNA assay) and T-cell subsets (CD4/CD8). Immunological analyses may be conducted in a subset of patient samples and may include cytoplasmic cytokines, serum cytokines, gene expression, interleukins (IL-2, 4, 6, 8, 10 and 12), gamma interferon, insulin-like growth factor and tumor necrosis factor. Additional research testing may be conducted on samples collected at each visit. Safety laboratories, including chemistry, hematology and urinalysis are optionally performed. Patients co-infected with hepatitis B virus, C virus and/or tuberculosis, are optionally allowed on study and are optionally monitored for viral loads and/or microbiological cultures.

Example 42

A buccal formulation containing BrEA was prepared and contained 1.000 kg BrEA, 3.25 Kg Fast Flo Lactose (Foremost), 0.250 kg Polyplasdone XL 10™ (crospovidone NF), 0.100 kg Syloid 244FP (colloidal silicon dioxide), 0.250 Kg mannitol (USP) 0.050 kg Cab-O-Sil™ (amorphous silica) and 0.100 Kg magnesium stearate. Tablets containing 25 mg each of BrEA were prepared from the mixture. Similar formulations containing other formula 1 compounds, e.g., AED, AET or 7-oxodehydroepiandrosterone may contain one or more of these excipients or other excipients disclosed herein. Other formulations may utilize micronized compounds or analogous excipients, e.g., micronized BrEA hemihydrate.

Example 43

Formulations comprising formula 1 compounds were prepared and comprised the excipients described below. Formulations containing BrEA are generally stored in the dark and/or are dispensed into opaque or amber glass containers.

A liquid formulation for parenteral delivery, e.g., subcutaneous or intramuscular injection, was prepared that comprised 100 mg/mL BrEA, 2% benzyl alcohol, 30% benzyl benzoate, 30% polyethylene glycol 300 and 30% propylene glycol.

A liquid formulation for parenteral delivery, e.g., subcutaneous or intramuscular injection, was prepared that comprised 100 mg/mL BrEA, 2% benzyl alcohol, 2.5% ethanol, 50% PEG200 and qs propyleme glycol. Solubilization of the BrEA was facilitated by sonication and heating at 40° C. for 5 minutes.

A liquid formulation for parenteral delivery, e.g., subcutaneous or intramuscular injection, was prepared that comprised 50 mg/mL AET, 40% PEG200, 2% benzyl alcohol, 2% benzyl benzoate and qs propylene glycol.

A liquid formulation for parenteral delivery, e.g., subcutaneous or intramuscular injection, was prepared that comprised 15 mg/mL BrEA, 45% 2-hydroxypropyl-β-cyclodextrin and 0.9% saline.

A 125 mg tablet for oral or transmucosal delivery, e.g., buccal or sublingual administration, was prepared that comprised per tablet 20% w/w BrEA, 55% w/w lactose, 15% w/w mannitol, 5% w/w crospovidone, 2% w/w magnesium stearate, 3% w/w silica.

A sterile liquid suspension formulation for intravenous delivery of a formula 1 compound is prepared that comprises about 5-60 mg/mL of a formula 1 compound such as BrEA having an average particle size of about 100 to about 400 nm in saline and optionally comprising dextrose and/or a preservative such as EDTA, BHA or BHT, e.g., at about 0.1-2% w/w.

A liquid suspension formulation for transmucosal delivery, e.g., buccal or sublingual administration, was prepared that comprised 100 mg/mL of BrEA and equal volumes of PEG300 and propylene glycol.

Example 44

A clinical trial is conducted using human patients having an acute infection or suspected of having been exposed to an acute infectious pathogen. The patients are dosed with about 1 mg/kg, about 2 mg/kg, about 5 mg/kg or about 20 mg/kg of a formula 1 compound such as BrEA, 3β,17β-dihydroxyandrost-5-ene or 3β,7β,17β-trihydroxyandrost-5-ene orally, by a parenteral route, e.g., by subcutaneous or intramuscular injection, or by a transmucosal route such as by buccal, sublingual or rectal delivery. Dosages are single unit doses or subdivided and comprise about 25 mg, about 50 mg, about 100 mg, about 200 mg or about 500 mg for adults. For pediatric patients, the dosages are about 10 mg, about 20 mg, about 50 mg, about 100 mg or about 250 mg. Dosing is initiated, e.g., at the time the patient is diagnosed as having the infection or as having been potentially exposed to the pathogen. The dosages are administered daily or on an intermittent basis, e.g., daily for about 1, 2, 3, 4, 5, 6, 7 or 8 weeks, or 2 or 3 times per week every other day or every three days, for about 1, 2, 3, 4, 5, 6, 7 or 8 weeks, or essentially as disclosed elsewhere herein. The known or suspected pathogen can be cells, spores or virions of *Bacillus anthracis, Coccidoides immitis,* Ebola virus, Lassa virus, an *Aspergillus* sp. fungus or a *Mucor* sp. fungus, an Orthopoxvirus such as the variola virus (smallpox virus) or a gram negative bacterium such as *Pseudomonas aureginosa, Escherichia coli, Yersinia pestis, Vibrio cholerae* or *Salmonella typhi.*

The patients are also generally treated with one or more antiviral, antifungal or antibacterial agents, such as one or more of those disclosed herein, according to normal clinical practice. Such agents are administered before, during and/or after treatment with the formula 1 compound and they are administered essentially using standard doses and routes of administration. Such agents can optionally include one, two or more of amphotericin B, fluconazole, clotrimazole, itraconazole, ketoconazole, isoniazid, a fluororquinolone, e.g., ciprofloxacin, a penicillin, e.g., penicillin G, streptomycin, trimethoprim, tetracycline, doxycycline and erythromycin. Responses of the patients are optionally monitored, e.g., detectable amelioration of one or more symptoms, detectable reduction in the progression of the infection or a detectable change in an immune marker, such as one described herein, e.g., enhanced levels of molecules or cells associated with Th1 immune responses, a reduced level of a molecule(s) associated with inflammation such as TNFα, IL-1β, or IL-6, or enhanced humoral or innate immune reactions. Results obtained with patients in different groups are compared to determine the efficacy of a formula 1 compound under the clinical protocol. For example, patients who received standard therapy and a suitable placebo are compared with results from patients who received a standard therapy and a formula 1 compound.

Example 45

Enhancement of pathogen sensitivity to antimicrobial agents using formula 1 compounds. The capacity of the formula 1 compounds to increase the sensitivity of a bacterial, viral, fungal or yeast pathogen to a known or candidate antimicrobial agent is examined using standard antimicrobial susceptibility assays. The assays are performed using known or candidate antimicrobials alone, a formula 1 compound alone, a known or candidate antimicrobial with a formula 1 compound and a suitable untreated control(s). The antimicrobials and the formula 1 compounds are used over a range of concentrations, e.g., about 0.001 μg/mL to about 400 μg/mL and IC50, TC50 and/or MIC (the minimum concentration that completely inhibits detectable growth of the pathogen or detectable cytopathic effects of the pathogen on infected cells in the assay) values can be obtained for the antimicrobial agent using inhibition curves. The assays are performed using in vitro assays or in vivo assays, such as animal assays with, e.g., a rodent or canine. Exemplary antimicrobial and formula 1 compound concentrations include 0.1 µg/mL, 0.2 µg/mL, 0.5 µg/mL, 1 µg/mL, 2 µg/mL, 5 µg/mL, 10 µg/mL, 20 µg/mL, 50 µg/mL and 100 µg/mL. The capacity of the formula 1 compounds to enhance the susceptibility of pathogens that are sensitive or resistant to standard or experimental therapies is examined by comparing the efficacy of a known or candidate antimicrobial agent against the target pathogen in the presence and absence of a formula 1 compound and enhanced sensitivity of the pathogen in the presence of both indicates a beneficial or potentially synergistic effect. The effects of the formula 1 compounds on the IC50 (concentration of antimicrobial agent causing a 50% reduction in pathogen replication or cytopathic effects in a given assay), IC90 (concentration of antimicrobial agent causing a 90% reduction in pathogen replication or cytopathic effects in a given assay), TC50 (concentration of antimicrobial agent causing a 50% reduction in cell growth or killing of 50% of cells in the absence of the pathogen in a given assay), TC90, LD50 (pathogen inoculum size that causes death of 50% of host subjects), LD90 therapeutic index (e.g., the TC50 divided by the IC50) and/or the MIC of the antimicrobial agent are then determined, e.g., a decrease in the antimicrobial's IC50 or the MIC by at least about 10%, at least about 20%, at least about 30%, at least about 40% or at least about 50%.

In an exemplary protocol, the capacity of a formula 1 compound to potentiate the effect of an antibacterial agent or antibiotic is conducted using a whole cell growth inhibition assay. The assay is run in the presence of both the formula 1 compound and the antibacterial agent, with the antibacterial agent at a concentration of about 1/5 the MIC of the antibiotic alone. When testing for a combination that can be used against methicillin resistant *Staphylococcus aureus* ("MRSA") having a MIC for methicillin of >100 µg/mL, the MRSA cells are grown in the presence of 1-50 µg/mL of a formula 1 compound and 20 µg/mL of methicillin as follows.

A fresh inoculum of MRSA cells is grown at 35° C. in Mueller-Hinton Broth (MHB) overnight and is then diluted about 1/50 in the same medium. After regrowth at 35° C. to an $OD_{600}$ of 0.2-0.4 (about 1-2 hrs.), the cells are diluted 1/100 in MHB. In a microtiter plate, 50 µL of this diluted culture is combined with 50 µL MHB containing 10 µg/mL of the formula 1 compound and 40 µg/mL methicillin to give starting growth conditions of $5 \times 10^5$ cfu/ml in MHB, with 5 µg/mL formula 1 compound and 20 µg/mL methicillin. The plate is placed in a humidified 35° C. incubator for 5-24 hours, and cell growth or inhibition is read as turbidity ($OD_{600}$). Two positive and one negative controls for growth are cells grown in MHB alone, cells grown in MHB plus 20 µg/mL methicillin alone, and uninoculated MHB respectively. The capacity of the formula 1 compound to detectably inhibit growth, e.g., inhibition of at least about 20%, at least about 30%, at least about 40%, at least about 50% or at least about 60% of the growth of the positive control with methicillin, is determined in this assay. These results are compared to growth of the MRSA in MHB alone and in MHB with 5 µg/mL formula 1 compound to determine if the formula 1 compound alone appreciably inhibits growth of MRSA.

Further evaluation of the effect of the formula 1 compound on the MIC of an antibiotic such as methicillin is optionally evaluated in a microdilution assessment of the MIC with methicillin for MRSA, e.g., Lorian ed., *Antibiotics in Laboratory Medicine*, 3rd ed., pp. 72-75 1991. Also, a time-kill method, e.g., Eliopolous & Moellering, Ch. 13, *Antibiotics in Laboratory Medicine*, 3rd ed., Lorian ed., pp. 441-444 1991, is optionally used to characterize whether the formula 1 compound and antibiotic drug combination is bacteriostatic or bactericidal. As controls, normal growth of the pathogen (without antibiotic or formula 1 compound) and the effects of the antibiotic alone and the formula 1 compound alone are assessed using the same inoculum culture as is used in the combination time-kill test. Either bacteriostatic or bactericidal effect can be determined. Additional assays for other antimicrobial agents and pathogens, e.g., antivirals, antifungals, antibacterials, viruses, fungi or bacteria, are optionally performed using antimicrobial compounds disclosed herein or in cited references and using methods described herein and in cited references that are modified to incorporate the use of the formula 1 compounds and/or a variety of suitable antimicrobial agents, e.g., U.S. Pat. Nos. 6,306,880, 6,303,797, 6,297,401, 6,180,679 and 5,883,074, *Methods for Antimicrobial Susceptibility Testing/M*11-A2, 1990, NCCLS, ISBN 1562380990 or *Performance Standards for Antimicrobial Susceptibility Testing: Eighth International Supplement* (1998), 1998, NCCLS, ISBN 156238337X, D. F. Smee et al., *Antiviral Res.* 2001 52(3):251-259, R. T. Sarisky et al., *J. Clin. Virol.* 2002 23(3):191-200, Y. C. Huang et al., *Am. J. Perinatol.* 2001 18(3):141-146, J. Meletiadis et al., *J. Clin. Microbiol.* 2001 39(9):3402-3408, A. L. Barry et al., *Eur. J. Clin. Microbiol. Infect. Dis.* 1999 18(4):305-309. Such assays may comprise one or more of a radial diffusion assay, a plaque assay, a flow cytometry assay or an animal infection assay, e.g., for animal survival or amelioration of infection, a tissue culture assay, e.g., for viral reverse transcriptase levels, cytopathic effects or for levels of the pathogen or its protein(s), or another suitable assay described in the cited references.

Example 46

Domestic animals, e.g., cows, sheep, swine or goats, are dosed once or twice with about 1 mg/kg, about 5 mg/kg, about 20 mg/kg or with about 50 mg/kg of a formula 1 compound such as BrEA, 3β,17β-dihydroxyandrost-5-ene or 3β,7β,17β-trihydroxyandrost-5-ene by a parenteral route, e.g., by subcutaneous or intramuscular injection, at 1, 2, 3, 4, 5, 6, 7 or 14 days before the animals are to be transported by, e.g., truck or train, from one location to another. The one or two doses are administered on the same day or on different days within the two weeks before the animals are to be shipped and, for animals dosed two times, each dose is the same, e.g., two doses of doses 5 mg/kg or doses 20 mg/kg, or different, e.g., the first dose is doses 20 mg/kg or doses 50 mg/kg and the second dose is doses 1 mg/kg, doses 5 mg/kg or doses 20 mg/kg. Each dose is administered at 1, 2, 3 or more sites. The incidence and severity of stress, shipping fever, weight loss and infection associated with transport is monitored. The capacity of the formula 1 compound to detectably reduce the incidence, severity or rate of progression of an unwanted condition is monitored and is optionally compared to the effects of known agents for the same or similar uses.

In a related example, domestic animals are dosed with 5 mg/kg, 20 mg/kg, 50 mg/kg or 100 mg/kg of a formula 1 compound orally, e.g., in feed, or parenterally at intervals of about 4 weeks, about 8 weeks, about 12 weeks or about 16 weeks. Dosing optionally occurs over selected time periods, e.g., during the animals' entire lifespan, in the first 3-12 months of the animals' life or about 1-6 months before the animal is to be transported or otherwise expected to experience significant stress. The formula 1 compound is also optionally administered prophylactically to prevent or detectably reduce the rate of spread, the severity or the incidence of an anticipated or potential infection, e.g., a viral infection such as a foot-and-mouth disease virus infection, a bacterial infection or a prion infection. During dosing periods with the formula 1 compound, the amount of antibiotic that the animals receive in their feed is optionally decreased, e.g., by about 10%, about 20%, about 30%, about 40%, about 50% or more during and after, e.g., about 1-16 weeks after, the period of dosing has ended.

In another related example, animals are vaccinated against pathogen infection using a formula 1 compound and an antigen(s). The formula 1 compound is administered at 2, 3 or 4 different dosages over a range of dosages, e.g., between about 0.2 mg/kg and about 100 mg/kg. A suitable pathogen or portion of pathogen is used, e.g., fungal, bacterial or viral cells (live, killed or attenuated) or particles may be used. Alternatively, the antigen may comprise protein(s), glycoprotein(s) or an antigenic fragment(s) thereof, and optionally an adjuvant with the antigen. The adjuvant may comprise an immune stimulatory complex, lipopolysaccharide, Freund's complete adjuvant, Freund's incomplete adjuvant, aluminum hydroxide or Montanide ISA 206. A dosage of a formula 1 compound is administered as described above or elsewhere herein to the animal at about the same time or within about 1, 2 or 3 days before or after the antigen(s) is administered. The formula 1 compound is administered to the animal on 1, 2, 3 or more occasions, typically once or twice within 48 hours of vaccination or once on the same day the animals are vaccinated. The effect of the formula 1 compound on the animal's cellular and/or humoral immune response is optionally monitored. Viral antigens or viral expression vectors and immune response monitoring methods for foot-and-mouth disease virus vaccination are optionally used in this embodiment.

The response of the vaccinated animals to a subsequent challenge with infectious foot-and-mouth disease virus is generally determined. The animals are vaccinated on a single occasion or on two or more occasions, with the latter vaccinations optionally tested for a boost in the immune response after an initial vaccination. The animals' antibody, cytokine and/or immune cell response to vaccination is generally monitored at about 1-21 days after vaccination. One or more parameters may be monitored, e.g., the development of a specific cytotoxic T cell clone(s), modulation of macrophage activity, circulating levels of IgM or an IgG such as IgG1, IgG2 or IgG3 that binds to the vaccination pathogen or antigen(s), or resistance to a subsequent infectious challenge with the pathogen. Results obtained with animals vaccinated with and without the formula 1 compound are compared. Suitable controls such as formulation lacking the formula 1 compound or adjuvant lacking the antigen are optionally used.

A foot-and-mouth disease virus, viral antigen(s) or an immunogenic fragment(s) thereof is optionally used in the vaccination. See, e.g., J. Bayry et al., *Microbiol. Immunol.* 1999 43:765-771, J. Chinsangaram et al., *J. Virol.* 1999 73:9891-9898, G. A. Mayr, et al., *Vaccine* 2001 19:2152-2162, M. J. Grubman et al., *Vaccine* 1993 11:825-829, P. W. Mason et al., *Virology* 1997 227:96-102, M. Amadori et al., *Arch. Virol.* 1992 122:293-306 and C. C. Brown et al., *J. Virol.* 1996 70:5638-5641, A. Rodriguez et al., *J. Gen. Virol.* 1996 77(Pt. 9):2089-2096. Antigens and other pathogens that may be used in an animal vacination embodiment with a formula 1 compound include Aleutian mink disease virus, sheep border disease virus, equine borna disease virus, canine distemper virus, rabies virus, pseudorabies virus, Shope papilloma virus, canine parvovirus and hog cholera virus.

When a formulation that is suitable for parenteral delivery of the formula 1 compound to the animals is used, it optionally comprises a local anaesthetic such as procaine or lidocaine, e.g., a formulation comprising a formula 1 compound, 1, 2 or more excipients and about 0.01% w/w to about 2.5% w/w of the local anaesthetic.

Example 47

Human HIV-infected patients with impaired or negligible antigen specific immune responses, cell mediated immune responses or delayed-type hypersensitivity immune responses are treated with 16α-bromoepiandrosterone essentially as described herein. White blood cells from the patients are obtained before the compound is administered and at times after an initial treatment and a $2^{nd}$ treatment, e.g., dosing of about 50-200 mg at day 1 and at day 19, with assays at about 6-40 days after treatment, e.g., at day 8, 15, 22, 29 and 36. The patients' response to antigens such as HIV p24 and *Candida* antigen or to phytohemagglutinin is measured. Effects on the patients' antigen specific immune responses or markers of cell mediated immunity is measured. The capacity of other formula 1 compounds to restore antigen specific or cell mediated immune responses in immune suppressed subjects is characterized in a similar manner.

Example 48

Antiglucocorticoid effects of formula 1 compounds. Effects of formula 1 compounds and Hydrocortisone on Proliferation in the Absence of a Mitogen. A series of tests is run in triplicate using BALB/c mouse spleen cells to demonstrate the effect of the formula 1 compounds and hydrocortisone ("Hycort") on cellular proliferation in the absence of a mitogen. Cultures of spleen cells are prepared and steroids are added at, e.g., 0.1, 0.5, 1, 5 µM. Suitable controls are used. Twenty four hours after setup, about 50 µCi [$^3$H]-thymidine is added to each cell. Four to six hours later, the cells are harvested and counted on a scintillation counter.

Spleen cells are obtained from normal BALB/c mice and prepared as a single cell suspension at a concentration of about $1\times10^7$ cells/ml in RPMI 1640 supplemented with 2 mM L-glutamine, $5\times10^{-5}$ M 2-mercaptoethanol, 20 µg/ml gentamycin-sulfate, and 1% Nutridona-NS (Boehringer-Mannheim). Individual aliquots of cells are then pulsed for 30 minutes at 37° C. with selected concentrations of formula 1 compounds. After pulsing, the cells are washed several times in balanced salt solution, resuspended in fresh medium, and then dispensed into 24-well culture plates with a stimulatory concentration of anti-CD3 (e.g., Leo et al. Proc. Natl. Acad. Sci. U.S.A., 84:1374 (1987)). After a 24-hour incubation period, culture supernatants are harvested for assessment of proliferation or cytokine production, e.g., IL-2, IL-3 or IL-4 using, e.g., the method of Mossman (J. Immunol. Meth. 65:55 (1983)). 100% control titers of IL-3, IL-2 or IL-4 from normal stimulated splenocytes are obtained, exemplary values may be about 640 units/mL or IL-2 and 160 units/mL for IL-4.

Effects of formula 1 compounds and Hydrocortisone on Proliferation in the Presence of a Mitogen. A series of spleen cell cultures is run using a formula 1 compound and/or hydrocortisone with cell cultures to which concanavalin A is added. Preliminary tests on cultures to which concanavalin A is added at concentrations of 10.0, 5.0, 2.5 and 1.0 ng/mL. All tests on the effects of invention compounds on cultures stimulated with concanavalin A are performed with concanavalin A at, e.g., about 2.5 ng/mL. A mitogen such as ConA generally increases cell proliferation and the GCS can decrease proliferation. Detectable partial or complete reversal of the inhibitor effects of hydrocortisone indicate an anti-glucorticoid effect by the formula 1 compounds.

Effect of formula 1 compounds on IL-3 production. Exemplary formula 1 compounds are tested to determine whether their effect on the level of the cytokine IL-3 expression by spleen cells in tissue culture and for their capacity to reverse the effects of a GCS in IL-3 expression. The spleen cell cultures are prepared in accordance with the general method above. After 30 hours the level of IL-3 in the supernatants of the cultures was measured using the IL-3 ELISA kit manufactured by EndoGen Inc., Boston, Mass. A GCS such as hydrocortisone will generally suppress the production of IL-3 and the invention compounds are examined for their capacity to modify this effect. The IL-3 expressed by cells in culture may be recovered from the media containing IL-3 by known methods such as single or sequential reverse-phase HPLC steps on a preparative HPLC column. (See Urdal, et al., J. Chromatog. 296:171 (1984) and U.S. Pat. No. 5,128,450).

Example 49

Activity of formula 1 compounds in the treatment of symptoms or progression of a skin condition. Conditions such as psoriasis are examined using formula 1 compounds in a suitable animal model or in human patients. The compounds are administered to the subject by topical administration or by systemic administration, e.g., oral, buccal or subcutaneous injection. In one animal model of psoriasis, varying numbers of naïve and memory CD4$^+$ T cells from minor histocompatibility mismatched mice are used to reconstitute scid/scid mice. Skin lesions with characteristics of human psoriasis arises when no memory T cells are coinjected, and coinjection of memory T cells diminishes the symptoms (M. P. Schon et al., Nature Medicine 1999 3:183-188). Varying amounts of formula 1 compounds, e.g., 0 to 100 mg/kg/day, are used in the absence of memory T cells and with various numbers of memory T cells to characterize their effects on both types of T cells to cause disease or to reduce it.

Groups of the mice (e.g., about 4-15 animals per group) are injected subcutaneously with one or more dosage of about 1, 2.5, 5, 10 or 20 mg/kg of a formula 1 compound such as 16α-fluoroandrost-5-ene-17-one, 7β-hydroxy-16α-fluoroandrost-5-ene-17-one, 7α-hydroxy-16α-fluoroandrost-5-ene-17-one, 17α-hydroxy-16α-fluoroandrost-5-ene or 17β-hydroxy-16α-fluoroandrost-5-ene. The compound is administered once daily or once every 2, 3 or 4 days for 1, 2, 3, 4, 5 or 6 weeks beginning either before or at about the time when untreated control animals have developed symptoms or skin lesions characteristic of the disease. The formula 1 compounds can be used with other animal models and markers of psoriasis would be measured essentially as described. See, e.g., B. J. Nickoloff, J. Invest. Dermatol. Symp. Proc. 2000 5:67-73, M. P. Schon J. Invest. Dermatol. 1999 112:405-410, B. J. Nickoloff et al., Arch. Dermatol. 1999 135:546-552 and M. P. Schon et al., Nature Medicine 1997 3:183-188.

In a clinical dose ranging protocol, human patients suffering from psoriasis are treated topically or systemically with a formula 1 compound. Topical formulations would comprise about 1-20% w/w of a formula 1 compound in a suitable cream, gel or other topical formulation, e.g., as disclosed herein. Treatment is initiated at the onset of symptoms or is administered to patients with preexisting psoriatic lesions. The compound is administered twice per day, once per day or it is administered once or twice per day every other day, every third day, every fourth day or every seventh day for about 2-24 weeks, e.g., about 4, 8 or 12 weeks. The clinical response to treatment is monitored on one, two or more occasions during dosing and optionally again once or twice at 1 day to 6 weeks after dosing is completed. Treatment is optionally combined with another treatment(s), e.g., corticosteroid, calcipotriol or salicylic acid. Patient response is measured using standard assessment methods, e.g., the Psoriasis Scalp Severity Index for psoriasis of the scalp, the Psoriasis Disability Index or by assessment of erythema, scaling, induration or size of psoriatic lesions at various times before, during and/or after treatment.

The response of animals or humans is optionally examined by histopathological observation or other analysis, e.g., detectably reduced inflammation or epidermal thickening, erythema, induration or for a detectable modulation or reduction of inflammatory or pathology-associated cells, cytokines or markers, e.g., CD94$^+$ T cells, CD69$^+$T cells, CD45RO$^+$ T cells, CD25$^+$ T cells, IgE, IL-1α, IL-6, IL-8, IL-13, keratinocyte growth factor or transforming growth factor-α in skin or skin lesions from treated animals as compared to suitable control animals. Modulation, e.g., reduction, of one or more markers or cell types associated with the severity or progression of disease is monitored.

Example 50

Treatment of neurodegenerative conditions. Experimental allergic encephalomyelitis (EAE), is demyelinating disease of the central nervous system with many pathological and clinical similarities with multiple sclerosis (MS). EAE is thus a recognized animal model for human autoimmune conditions such as MS. Formula 1 compounds 16α-fluoroandrost-5-ene-17-one, 3β,7β,17β,-trihydroxyandrost-5-ene and 16α-bromoepiandrosterone were tested for their capacity to delay the onset of EAE or to reduce its symptoms. Female SJL mice (5 animals per group) were immunized with 150 to 200 μg of PLP-139-151 peptide/CFA to induce EAE. Starting 7 days before injection of the peptide, the animals were given daily injections (s.c.) of the compounds (3.0 mg) in 0.1 mL vehicle, or vehicle alone for 33 days. The vehicle consisted of a suspension of the formula 1 compound in saline and carboxymethylcellulose. 16α-Fluoroandrost-5-ene-17-one and 3β,7β,17β,-trihydroxyandrost-5-ene significantly delayed the onset, reduced peak clinical score (from 5.2±0.6 to 2.8±1.8) and cumulative disease index (>60%) of EAE, and prevented or significantly attenuated relapses. A lower dose (0.3 mg/mouse) or other routes (p.o.) of administration had less effect. The effect of 16α-bromoepiandrosterone was not significant under these assay conditions. T cells from mice treated with 16α-fluoroandrost-5-ene-17-one and 3β,7β, 17β,-trihydroxyandrost-5-ene had significantly reduced PLP-139-151 specific T cell proliferation responses and reduced numbers of TNF-α producing cells in the CNS. These compounds limited the production of autoimmune Th-1 associated cytokines, which is consistent with restoration of a more normal Th-1/Th-2 immune balance and/or with reduction of inflammation in this model.

The efficacy of the formula 1 compounds to treat other autoimmune conditions can be determined by incorporating their use with suitable animal models or assay methods, e.g., collagen-induced arthritis as a model for human autoimmune polyarthritis (e.g., L. K. Myers et al., Clin. Immunol. 2002, 102:185-191, A. Matejuk et al., Endocrinology 2002, 143: 313-319, S. Thornton et al., J. Immunol. 165:1557-1563). The effect of the compounds on markers of inflammation such as TNFα, MIP-1β, IL-13, IL-15, IL-17 or IL-18, e.g., reduced expression or activity, is optionally observed in any autoimmune or inflammatory condition.

Example 51

Human clinical use of the formula 1 compounds to treat delayed effects of radiation exposure is exemplified as follows. Patients scheduled to receive a radiation therapy for a malignancy or a related condition, e.g., breast cancer, prostate cancer or benign hyperstatic hyperplasia, begin the planned therapy. For patients scheduled to receive a total radiation dose of about 2-200 Gy (e.g., about 130-150 Gy, about 144 Gy or about 180 Gy) in one dose or in two or more divided subdoses, at 24 hours after initiation of the radiation therapy, about 1-8 mg/kg/day (about 50 mg, 100 mg, 200 mg or 400 mg per day) of a formula 1 compound is administered to the patient using a daily or an intermittent dosing protocol. The compound is administered by an intramuscular, subcutaneous, buccal or sublingual route. The intermittent dosing protocol provides dosing the formula 1 compound once per day for 5 consecutive days, followed by no dosing for 3 weeks and then again dosing the formula 1 compound once per day for 5 consecutive days, followed by no dosing for another 3 weeks. This treatment regimen is maintained until 4-6 months after the planned radiation therapy has ended.

In related treatment protocols, the patient is dosed with about 1-8 mg/kg/day of the formula 1 compound once every other per day over 5 days, until 3 doses are administered to the patient, followed by no dosing for 6 weeks and then again dosing the formula 1 compound once every other per day over 5 days, until 3 doses are administered to the patient, followed by no dosing for another 6 weeks. This treatment regimen is maintained until 6-24 months after the planned radiation therapy has ended.

In other related protocols, a dosing protocol as described in the two paragraphs above is used, except that initiation of dosing is delayed until 1 week or until 1 or 2 months after completion of the planned radiation protocol and the treatment regimen is maintained until 6-48 months after the planned radiation therapy has ended.

In any of these treatment protocols, the patient is optionally monitored for the time of appearance of a radiation late effect, its severity. The patient is also optionally treated with other therapeutic agents, e.g., analgesics (e.g., aspirin, ibuprofin, codeine or morphine), corticosteroids (e.g., prednisone or dexamethasome), antibiotics, antifungal agents, growth factors (e.g., erythropoietin, thrombopoietin, γ-interferon or IL-2), blood transfusion or surgery, as the clinical situation dictates.

Example 52

A buccal formulation containing 16α-fluoroandrost-5-ene-17-one for human or veterinary applications was prepared as follows. Micronized 16α-fluoroandrost-5-ene-17-one, PEG 3350, Cab-O-Sil™, Polyplasdone XL 10™, Pearlitol™, and sodium lauryl sulfate were dispensed into a double cone blender (Gemco) and blended for approximately 15 minutes. Three 0.15 gram samples were collected from top, middle and bottom regions of the blend and assayed by HPLC for uniform drug content. Results from the HPLC assay for uniform drug content were obtained prior to continuing the manufacture process. Blending was continued, if needed, until the blend contained 19% to 21% of 16α-fluoroandrost-5-ene-17-one by weight in selected samples. Magnesium stearate, sieved through a #40 screen, was then added to the mixture and blended for 5 minutes.

The uniform blend or mixture was then transferred to a double polyethylene bag and loaded into a tablet press hopper. Ten tablets (pillow shaped) were sampled at 15-minute intervals during the tabletting process to monitor thickness, weight and hardness of each tablet. Samples of 35 tablets were taken at the beginning, middle, and end of the tablet compression run for testing. The tablets were collected from the press in polyethylene bags and visually inspected prior to packaging in 100 cc high density polyethylene (HDPE) round bottles (38-400 finish) at 500 tablets per bottle. The tablets were stored at controlled room temperature (20°-25° C.).

Excipients used in the formulation were mannitol, (Pearlitol™, 200 µm diameter granules, Roquette), which provided a matrix for separation of drug particles in the tablet and a compression aid to promote free flowing of the drug blend into the tablet die. Crospovidone (Polyplasdone XL 10™, ISP Pharmaceutical), NF, was used as a dispersing agent and to facilitate tablet disintegration. PEG 3350 (Spectrum Quality Products, Gardena, Calif.), NF, was used as a wetting and dispersion agent. Sodium lauryl sulfate, NF, was used as a dispersion agent. Magnesium stearate (Spectrum Quality Products, Gardena, Calif.), NF, was used as a lubricant to facilitate ejection of tablets from the die. Amorphous silica dioxide (Cab-O-Sil, >98%, Cabot Corp.) was used as a glidant (flow enhancer) to promote free flowing of the drug blend into the tablet die. Average tablet weight was 125 mg, with 90% of the tablets varying by less than 15% in weight and no tablets varying by more than 25% in weight. The final composition of the tablets is shown below.

| Component | % w/w | mg/tablet | Total weight (g) |
| --- | --- | --- | --- |
| 16α-fluoroandrost-5-ene-17-one | 16 | 20 | 700 |
| Mannitol | 72 | 90 | 3150 |
| Crospovidone | 7 | 8.75 | 306.2 |
| Magnesium stearate | 2 | 2.5 | 87.5 |
| PEG 3350 | 1 | 1.25 | 43.8 |
| Sodium lauryl sulfate | 1 | 1.25 | 43.8 |
| Cab-O-Sil ™ | 1 | 1.25 | 43.8 |
| Total | 100% | 125 mg | 4375.1 |

Example 53

Synthesis of compounds is exemplified in the following examples. Melting points were determined in open capillaries in an electrically heated and stirred Thiel-type bath and are uncorrected. Solvents were removed on a rotary evaporator under water pump vacuum at 30° C. or less. Nuclear magnetic resonance (NMR) spectra were taken on Bruker WP-200SY and AM-300 MHz spectrometers. Spectra were measured in deuterated chloroform ($CDCl_3$) using tetramethylsilane (60) as reference for $^1H$ NMR spectra and the $CDCl_3$ triplet (δ77.0) for $^{13}C$ spectra. Abbreviations are s (singlet), d (doublet), t (triplet), q (quartet), m (multiplet). A Kratos MS-80RFA mass spectrometer was employed to determine the high resolution mass spectra (HRMS) of the compounds, and a Hewlett-Packard LC-MS, 1100 series was employed to determine the liquid chromatograph/mass spectra (LCMS) of the compounds. Spectral data were included for some known compounds where such data were not previously reported. Reagents and solvents used were purchased from Aldrich Chemical Co., Milwaukee, Wis. For column chromatography, Aldrich brand silica gel of 70-230 and 200-400 mesh size was used.

The glucuronides of 7-oxygenated androgens were synthesized by reacting the appropriately protected 7-oxygenated derivative with bromo glucuronates followed by selective hydrolysis to remove acetate protection on the glucose hydroxyls. Good yields were obtained when acetylated glucuronides of steroids were prepared first, acetates were hydrolyzed selectively and the resulting Δ-5 steroid glucuronates were oxygenated at the allylic 7-position.

Synthesis of β-pyranoside forms of steroid glucuronides (as their tri-O-acetyl methyl esters) was carried out by condensation of a specific, open hydroxyl group of the steroid, with 2, 3, 4,-tri-O-acetyl-1-bromo-1-deoxy-αD-glucopyranuronate utilizing the well known Loenigs-Knorr reaction. Acid acceptors such as silver carbonate or cadmium carbonate in anhydrous benzene were used to promote the reaction and freshly pulverized dry calcium sulfate was included as internal desiccant. Reactions were run in the dark (when silver carbonate was used), at room temperature for 23 to 48 hours, during which time ~40-60% conversion took place (identified by the $^1$H-NMR spectrum of the reaction mixture). The acetylated glucuronide methyl esters were isolated either by crystallization or by column chromatography on silica gel. Fractional crystallization was the major technique employed for isolating the Koenigs-Knorr product from the reaction mixture and it was found to be quite satisfactory in providing high purity glucuronides. In cases where isomeric ortho ester or other side products were formed in larger quantities, the desired products were purified by column chromatography on silica gel.

The structures of acetylated glucuronide methyl esters were confirmed by $^1$H-NMR, $^{13}$C-NMR, and mass spectrometry. The anomeric proton signal (1H) of the glucose moiety appeared as a doublet at 4.58-4.69 ppm (J=8-8.4 Hz) indicating 1β-glucuronoside linkage. The position of the olefinic 6-H of the 7-keto steroids, usually occurred at 5.65-5.70 ppm and showed a down field shift of 0.35-0.4 ppm from 6-H of non 7-keto steroids; this was another significant point in the characterization of 7-keto glucuronides. β-Anomers of these steroid glucuronopyranosides were generally obtained in good to excellent yield when corrected for recovered unreacted steroids.

Deacetylation of acetylated glucuronide methyl esters, with or without a 7-keto group was performed with freshly prepared sodium methoxide in anhydrous methanol at ambient temperature yielding methyl esters of steroid glucuronides as the major product in generally good to excellent yield. $^1$H-NMR spectra of deacetylated steroid glucuronides exhibited the anomeric proton as a doublet at 4.4-4.48 ppm (J=7.4-8.3 Hz) thereby confirming β-linkage. High resolution mass spectra (EI-MS) of steroid glucuronides helped confirm the structure of the products, but the expected molecular ion was absent. The molecular ion was obtained as a sodium adduct base peak in the FAB-MS spectra of the steroid glucuronides. Finally, allylic oxidation at the 7 position of Δ5-steroid glucuronides 8 and 12 was performed utilizing the aerobic oxidation procedure of described in Marwah and Lardy, U.S. Pat. No. 5,869,709 (1999), herein incorporated by reference in its entirety, in the presence of N-hydroxy phthalimide and a radical initiator to afford the corresponding 7-oxo derivatives of steroid glucuronides 9 and 13.

Molecules with small and long chain alkyl ethers were also synthesized. The methyl ether (20) of 7-oxo DHEA (2) was prepared in 67% yield by allylic oxidation of 3β-methoxy-DHEA (19) which was obtained by heating 3β-tosyl-DHEA to reflux in anhydrous methanol in 94% yield. Further reduction of the product 20 with sodium borohydride in methanol-dichloromethane (usually 90:10) at 0-5° C. in presence of cerium (III) chloride heptahydrate afforded 3β-methoxyandrost-5-en-7β,17β-diol (24). The 17-keto group of 3β-methoxy DHEA (19) was protected as ethylene ketal, and subsequent oxidation of the ketal derivative afforded the 7-oxo compound (21). The 7-oxo group of product 21 was further subjected to reduction with sodium borohydride in methanol at room temperature and a mixture of isomeric 7α- and 7β-hydroxy derivatives (22, 23) were formed, and were separated easily by column chromatography. Reduction of 3β-Methoxy DHEA (19) at position 17, at 0-5° C. afforded 3β-methoxy-17β-hydroxyandrost-5-ene (27) in 86% yield, which in turn was oxidized at the 7 position using N-hydroxy phthalimide, oxygen and a radical initiator in refluxing acetone to afford product 28 (53% yield).

3β-t-Butyl ether of 7-oxoDHEA (31) was prepared in 87% yield by oxidizing 3β-t-butyl-DHEA (30) using pyridinium dichromate and N-hydroxyphthalimide, a new, simple and high yielding procedure. 3β-t-ButylDHEA was synthesized in 67% yield by the procedure of Armstrong et al. (Armstrong et al., *Tet. Lett.*, 29:2483-2486 (1988), incorporated herein by reference in its entirety,) using DHEA and t-butyl trichloroacetimidate in a mixture of dichloromethane and cyclohexane.

According to the methods of the present invention, a mixture of diastereomeric 7-methoxy ethers (26) was prepared in a simple, short procedure, which unexpectedly resulted in very good yields (73%) by stirring 7α-bromo-DHEA (25) in methanol and silica gel at room temperature for 2 hours. No attempt was made to synthesize these derivatives in pure α and β forms.

A long, straight chain alkyl ether (39) was prepared in 83% yield from 3β-dodecanoxyDHEA by allylic oxidation of 3β-dodecanosyl-DHEA (38) using pyridinium dichromate and N-hydroxyphthalimide as mentioned above. 3β-Dodecanoxy DHEA (38) was synthesized using a standard procedure of refluxing 1-bromododecane and DHEA solution in tetrahydrofuran in presence of sodium hydride.

Etherification of DHEA utilizing ethyl vinyl ether in dichloromethane and in presence of p-toluene sulfonic acid, at room temperature for 6 hours afforded 3β-ethoxy ethyl ether of DHEA (40) in 84% yield based on 55% conversion. The product 40 was subjected to aerobic oxidation in presence of N-hydroxyphthalimide and a radical initiator in refluxing acetone to obtain 3β-(1'-ethoxy)ethoxyandrost-5-en-7,17-dione (41).

3β-tetrahydropyranyl ether of 7-oxo-DHEA (37) was made to test the effect of a saturated pyran ring having two stereogenic centers thus generated, on the induction of thermogenic enzymes. This compound was easily formed utilizing dihydropyran and pyridinium p-toluene sulfonate in anhydrous dichloromethane and was stable to most non-acidic reagents.

Silyl protected ethers especially t-butyldimethylsilyl (TB-DMS) ether, (32, 33, 35 and 36) substituted at hydroxyls 3, 3 and 17, 7, and 7 and 17 positions of the steroid molecule were also synthesized. TBDMS ethers are quite stable to a variety of organic reactions and have good stability toward base. Their synthesis involved use of t-butyl dimethylsilyl chloride and imidazole in dimethyl formamide. Dichloromethane was not appropriate for the synthesis of these specific 7-substituted derivatives because its acidic character caused the formation of dienes.

In another embodiment of the present invention, carbonate substitution on hydroxyls at 3 and 17 position of the corresponding sterols with 7-position oxygenated (keto or hydroxyl) in the steroid molecule was performed and its effect investigated. Various alkyl carbonates such as methyl (42), ethyl (44), allyl (43), isobutyl (45), and octyl (47) as well as tricyclic fluorenyl carbonates of the enzyme activator were made by standard procedures which involved a slow addition of respective chloroformates to the ice cold solution of steroid substrates in pyridine. Conversion was total in most of the cases and product yields were generally high. Carbonates 42 and 43 were isolated by column chromatography on silica gel. Some of the carbonate derivatives of the steroids (42, 44, 47) were subjected to borohydride reduction in methanol-dichloromethane with cerium (III) chloride heptahydrate at 0-5° C. and 7β- and 17β-hydroxy carbonate derivatives (49-51) were isolated in good yields.

The determination of the structure of the 7-oxygenated alkyl ethers as well as carbonates and sterochemical assignments were made on the basis of their $^1$H NMR and $^{13}$C NMR spectroscopic data, high resolution mass spectroscopy and LC-MS studies. Reaction products, as well as some precursors, when known, were also characterized by comparison of spectroscopic data with those available from the literature. Proton NMR of 6-olefinic hydrogen of all 7-oxo derivatives showed a characteristic absorption at δ 5.7-5.75 with a corresponding $^{13}$C absorption at about 200-202 ppm. On the other hand, 7-hydroxyl derivative showed different chemical shift values for 6-olefinic protons. In case of 7β-hydroxy compound the olefinic 6α-proton appeared high field and around 5.3 ppm, whereas 7α-hydroxy compound showed a doublet for 6β-olefinic proton downfield and around 5.6 ppm.

Assays of compounds for their ability to induce liver mitochondrial glycerophosphate dehydrogenase and cytosolic malic enzyme when fed to rats have been described. Lardy et al., *Steroids*, 63:158-165 (1998); Su and Lardy, *J Biochem*, 110:207-213 (1991), which are incorporated herein by reference in their entirety. In addition to the control rats that received no steroid supplement, each experiment included a group that received DHEA or 7-oxo-DHEA-acetate (usually at 0.04%-0.06% of the diet). Because of variation in enzyme activity of both control and treated groups from one experiment to another the activities are reported relative to the enzyme activities of the control group. Compounds are considered active in this assay if they enhance the activity of these thermogenic enzymes to greater than about 150% of that in livers of control rats.

Example 1

General Synthetic Procedure

Preparation of β-Pyranoside Forms of Steroid Glucopyranosides (as tri-acetylated methyl esters, 7, 10, 11, 14, 15, 17) Steroid (10.0 mmol), methyl-2,3,4-tri-O-acetyl-1-bromo-1-deoxy-α-D-glucopyranuronate (10.0 mmol) and freshly pulverized dry calcium sulfate (2.0 g) were taken up in dry benzene (150 mL). Dry silver carbonate (freshly prepared, 20.0 mmol) was added to the reaction mixture which was subsequently stirred at room temperature in the dark. Additional quantities of glucuronate (5 mmol) and silver carbonate (10 mmol) were added after 12 and 24 h. The reaction mixture was stirred for 48 to 72 h depending upon the nature of the steroid, and then worked up. The reaction mixture was filtered on a bed of celite and the clear filtrate was evaporated to dryness. The product was isolated from the crude solid either by crystallization or by chromatography on alumina or silica gel. These synthetic procedures have been described in P. Marwah et al., *Steroids* 2001 66:581-595.

Example 2

Methyl 2,3,4-tri-O-acetyl-1-O-(17-oxoandrost-5-ene-3β-yl)-β-D-glucopyranosiduronate (7)

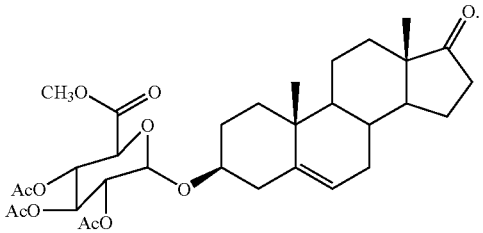

A mixture of DHEA (1) and methyl-2,3,4-tri-O-acetyl-1-bromo-1-deoxy-α,D-glucopyranosiduronate, dry calcium sulfate and silver carbonate in benzene was stirred for 48 h at room temperature. The NMR of the reaction mixture showed 60% conversion of the starting material to the product. After the usual work-up and subsequent crystallization of the crude product, twice, from acetone-hexane, product 7 was obtained as a pure white solid (61%, based on 60% conversion), m.p. 191-92° C. $^1$H NMR (CDCl$_3$ 200 MHz): δ 5.39 (1H, d, J=5.2 Hz, 6-H), 5.24 (2H, m, 3,4-H (glu)), 4.98 (1H, dd, J=8.0, 10.0 Hz, 2-H (glu)), 4.66 (1H, d, J=8.0 Hz, 1-H (glu)), 4.02 (1H, d, J=10 Hz, 5-H (glu)), 3.75 (3H, s, OCH$_3$), 3.52 (1H, m, 3α-H), 2.10, 2.05 (9H, 2s, OCOCH$_3$), 1.02 (3H, s, 19-CH$_3$), 0.89 (3H, s, 18-CH$_3$).

$^{13}$C NMR (CDCl$_3$, 300 MHz): δ 220.7 (C-17), 170.0, 169.2, 169.0, 167.5 (C=O, acetate, ester), 140.3 (C-5), 121.1 (C-6), 99.2 (C-1 (glu)), 79.6 (C-3), 72.9, 72.0, 70.15, 69.3 (C-2-5 (glu)), 52.8, 51.5, 50.0, 47.4, 38.4, 37.2, 37.0, 35.6, 31.6, 31.1, 29.6, 22.2 (C-1,2,4,7-16 and OCH$_3$), 21.0, 20.9, 20.8, 19.5, 14.4 (3×OCOCH$_3$, C-18, C-19).

Example 3

Methyl 2,3,4-tri-O-acetyl-1-O-(7,17-dioxoandrost-5-ene-3β-yl)-β-D-glucopyranosiduronate (10)

The product 10 was prepared by the glucuronidation of 3β-hydroxyandrost-5-ene-7,17-dione (2) and the reaction mixture was stirred at room temperature in the dark for 72 h. The crude product was purified by chromatography on alumina and eluted with ethyl acetate-hexane (15:85, v/v). The first fraction eluted from the column was crystallized from methanol and identified as androsta-3,5-diene-7-17-dione (15%, based on 69% conversion), m.p. 167-68° C. $^1$H NMR (ODCl$_3$, 200 MHz): δ 6.19 (2H, m, 3,4-H), 5.65 (1H, s, 6-H), 1.15 (3H, s, 19-CH$_3$), 0.90 (3H, s, 18-CH$_3$). Further elution from a 30:70 mixture of ethyl acetate-hexane afforded a thick syrupy material which was triturated with diethyl ether and cooled in the refrigerator for 2 h, to afford white crystalline compound 10, m.p. 206-8° C. (25%, based on 69% conversion).

$^1$H NMR (CDCl$_3$, 200 MHz): δ 5.75 (1H, s, 6-H), 5.24 (2H, m, 3,4-H (glu)), 4.98 (1H, t, J=8.3 Hz, 2-H (glu)), 4.65 (1H, d, J=8.3 Hz, 1-H (glu)), 4.03 (1H, d, J=9.9 Hz, 5-H (glu)), 3.75 (3H, s, OCH$_3$), 3.65 (1H, m, 3α-H), 2.04, 2.0 (9H, 2s, OCOCH$_3$), 1.20 (3H, s, 19-CH$_3$), 0.91 (3H, s, 18-CH$_3$).

$^{13}$C NMR (CDCl$_3$, 300 MHz): δ 220.4 (C-17), 201.1 (C-7), 170, 169.4, 169.2, 167.1 (C-acetate, ester), 165.1 (C-5), 126.2 (C-6), 100.0 (C-1 (glu)), 78.4 (C-3), 72.9, 72.1, 71.4, 69.4 (C-2-5 (glu)), 21.0, 17.6, 14.1 (3×OCOCH$_3$), 53.2, 48.2, 45.8, 44.6, 39.6, 39.0, 39.2, 36.2, 35.6, 31.0, 29.0, 24.3 (C-1, 2, 4, 8-16, OCH$_3$).

FAB m/z: 641.1 (M+23, 100%), 499 (M+1, −60, −60, 1%), 285 (M+1, −334, 4%). A final fraction eluted from the same composition of the eluent afforded the starting 3β-hydroxyandrost-5-ene-7,17-dione (2, 31%).

Example 4

Methyl 2,3,4-tri-O-acetyl-1-O-(3β-acetoxyandrost-5-ene-17β-yl)-β-D-glucopyranosiduronate (11)

After 48 hours of stirring, 3β-acetoxyandrost-5-ene-17β-ol (3) with acetobromoglucuronate methyl ester as described above, the $^1$H NMR spectrum of the reaction mixture showed the presence of equal amounts of 3 and the product steroid glucopyranoside 11. Prolonged stirring beyond 48 h did not alter the product ratio. The reaction mixture was processed and the resultant thick mass was heated to dissolve in a mixture of acetone-hexane. The solution was allowed to stand at room temperature for 4 h and the white crystalline compound 11 was collected and dried. $^1$H NMR spectrum of the crystalline solid confirmed the purity and structure of product 11, yield 94.8% (based on 50% conversion of starting steroid), m.p. 187-9° C.

$^1$H NMR (CDCl$_3$, 200 MHz): δ 5.36 (1H, d, J=5.2 Hz, 6-H), 5.23 (2H, m, 3,4-H (glu)), 5.02 (1H, t, J=8.4 Hz, 2-H (glu)), 4.60 (1H, d, J=8.4 Hz, 1-H (glu)), 4.60 (1H, m, 3α-H), 3.99 (1H, d, J=10 Hz, 5-H (glu)), 3.75 (3H, s, OCH$_3$), 3.59 (1H, t, J=8.7 Hz, 17α-H), 2.07, 2.05, 2.04, 2.03 (12H, 4s, OCOCH$_3$), 1.03 (3H, s, 19-CH$_3$), 0.74 (3H, s, 18-CH$_3$).

$^{13}$C NMR (CDCl$_3$, 300 MHz): δ 170.53, 170.23, 169.35, 169.07, 167.26 (C=O acetate and ester), 139, 67 (C-5), 122.24 (C-6), 101.43 (C-1 (glu)), 90.03 (C-3), 73.82, 72.54, 72.15, 71.42, 69.52 (C-17 and C-2, 3, 4, 5 (glu)), 52.83, 50.95, 50.05, 42.81, 38.07, 37.35, 37.0, 36.61, 31.6, 31.37, 28.56, 27.72, 23.35 (C-1, 2, 4, 7-16, and OCH$_3$), 21.41, 20.72, 20.63, 20.50, 19.32, 11.45 (acetate-CH$_3$, C-18, C-19).

Example 5

Methyl-2,3,4-tri-O-acetyl-1-O-(3β-acetoxyandrost-5-ene-7-oxo-17β-yl)-β-D-glucopyranosiduronate (14)

Glucuronidation of 3β-acetoxy-17β-hydroxyandrost-5-ene-7-one (4) was performed similarly and the reaction mixture was worked up after stirring for 48 h. $^1$H NMR analysis of the filtrate showed 60% of the starting material and 40% of the product. The crude mixture was treated with hexane and crystallization at room temperature afforded a white solid that was filtered and air dried. The crystalline white solid was found by $^1$H NMR to be pure compound 14. M.P. 122-25° C., yield 78.5% (based on 40% conversion).

$^1$H NMR (CDCl$_3$, 200 MHz): δ 5.71 (1H, d, 6-H), 5.23 (2H, M, 3,4-H (glu)), 5.02 (1H, t, J=8.0 Hz, 2-H (glu)), 4.72 (1H, m, 3α-H), 4.58 (1H, d, J=8.0 Hz, 1-H (glu)), 4.0 (1H, d, J=10.0 Hz, 5-H (glu)), 3.76 (3H, s, OCH$_3$), 3.6 (1H, t, J=8.0 Hz, 17α-H), 2.06, 2.046, 2.025, 2.02 (12H, 4s, OCOCH$_3$), 1.22 (3H, s, 19-CH$_3$), 0.74 (3H, s, 18-CH$_3$).

FAB m/z: 685.1 (M+23, 100%), 625.1 (M+23, −60, 6%), 269.2 (M, −334, −60, 8%).

Example 6

Methyl-2,3,4-tri-O-acetyl-1-O-(3β,17β-diacetoxyandrost-5-ene-7,3-yl)-β-D-glucopyranosiduronate (15)

The reaction mixture containing 3β,17β-diacetoxyandrost-5-ene-7β-ol (5), acetobromoglucuronate methyl ester, freshly dried calcium sulfate and silver carbonate in anhydrous benzene was stirred for 48 h at room temperature during which time 60% conversion of the starting steroid was detected on the basis of the NMR of the reaction mixture. The mixture was filtered over a small bed of celite and clear filtrate was evaporated to dryness under vacuum at 30° C. The resulting solid was chromatographed on a silica gel column using ethyl acetate-hexane (30:70, v/v) as an eluent to afford first the starting steroid followed by the product 15. Crystallization of steroid glucopyranoside 15 from methanol afforded a white crystalline compound m.p. 230-31° C., yield 54.5% (based on 61% conversion).

$^1$H NMR (CDCl$_3$, 200 MHz): δ 5.55 (1H, m, 6-H), 5.22 (2H, m, 3,4-H (glu)), 5.02 (1H, dd, J=8.0 Hz, 9.8 Hz, 2-H (glu)), 4.69 (1H, d, J=8.0 Hz, 1-H (glu)), 4.6 (1H, t, J=8.3 Hz, 17α-H and 1H, m, merged, 3α-H), 3.99 (1H, d, J=9.8 Hz, 5-H (glu)), 3.9 (1H, dm, J=8.0 Hz, 7α-H), 3.76 (3H, s, OCH$_3$), 2.04, 2.02, 2.00 (15H, 3 s, OCOCH$_3$), 1.05 (3H, s, 19-CH$_3$) 0.76 (3H, s, 18-CH$_3$).

FAB m/z: 729.1 (M+23, 100%), 669.1 (M+23, −60, 5%), 313.2 (M+1, −334, −60, 15%) 253.2 (M+1, −334, −60, −60, 7%).

Example 7

Methyl-2,3,4-tri-O-acetyl-1-O-(3β-acetoxy-17-oxoandrost-5-ene-7α-yl)-β-D-glucopyranosiduronate (17)

The reaction mixture comprised of 3β-acetoxy-7α-hydroxyandrost-5-ene-17-one (6), acetobromoglucuronate methyl ester, freshly dried calcium sulfate, silver carbonate and a catalytic amount (0.5 mole %) of silver triflate in anhydrous benzene was stirred for 48 h at room temperature in the dark. A total of 60% conversion of the starting steroid was detected on the basis of the NMR of the reaction mixture. The mixture was filtered over a small bed of celite and clear filtrate was evaporated to dryness. The product steroid glucopyranoside 17 was obtained in 34.8% yield (based on 60% conversion) by crystallization from acetone-hexane, m.p. 240-42° C.

$^1$H NMR (CDCl$_3$, 200 MHz): δ 5.64 (1H, d, J=5.37 Hz, 6-H), 5.24 (2H, m, 3,4-H (glu)), 4.96 (1H, t, J=7.81 Hz, 2-H (glu)), 4.68 (1H, d, J=7.81 Hz, 1-H (glu)), 4.58 (1H, m, 3α-H), 4.02 (1H, d, J=9.77 Hz, 5-H (glu)), 4.02 (1H, m, 7(3-H), 3.74 (3H, s, OCH$_3$), 2.047 (3H, s, OCOCH$_3$), 2.034 (3H, s, OCOCH$_3$), 2.03 (3H, s, OCOCH$_3$), 2.02 (3H, s, OCOCH$_3$), 1.03 (3H, s, 19-CH$_3$) 0.84 (3H, s, 18-CH$_3$).

FAB m/z: 685.1 (M+23, 50%), 329 (M+1, −334, 16%), 269 (M+1, −60, −334, 6.9%).

Alkaline hydrolysis of steroid acetylated glucuronide methyl esters.

Example 8

Methyl 1-O-(17-oxoandrost-5-ene-3β-yl-β-D-glucopyranosiduronate (8)

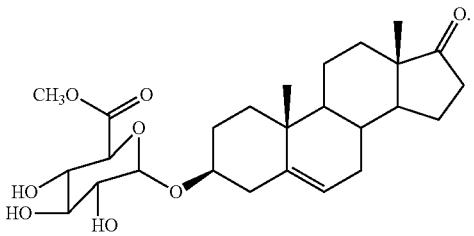

Methyl 2,3,4-tri-O-acetyl-1-O-(17-oxoandrost-5-ene-3β-yl)-β-D-glucopyranosid-uronate (7) (0.5 g, 0.83 mmol) was placed in a flame-dried flask with 50.0 mL of freshly dried and distilled methanol. A freshly prepared solution (0.65 mL) of sodium methoxide (prepared by dissolving 0.14 g sodium in 5 mL of methanol) was added to the solution and the mixture was stirred at room temperature for 3 h. Solvent was evaporated and the residue was taken up in distilled water (25 mL). The excess of base was neutralized with solid carbon dioxide or dilute acetic acid and the aqueous layer was saturated with sodium chloride. A white precipitated solid, thus formed, was extracted with ethyl acetate and the organic layer washed with brine, dried over magnesium sulfate and filtered. Solvent was removed and the residue, after trituration with ether, afforded a white solid which was filtered and dried. Recrystallization from acetone-hexane yielded 0.23 g (75.8%), m.p. 208-10° C.

$^1$H NMR (CDCl$_3$, 200 MHz): δ 5.41 (1H, d, J=4.6 Hz, 6-H), 4.45 (1H, d, J=8.3 Hz, 1-H (glu)), 3.92-3.24 (5H, m, 2-5H (glu) and 3-αH), 3.83 (3H, s, OCH$_3$, 1.04 (3H, s, 19-CH$_3$), 0.89 (3H, s, 18-CH$_3$).

$^{13}$C NMR (CDCl$_3$, 300 MHz): δ 221.2 (C-17), 170.0 (ester C=O), 140.9 (C-5), 121.8 (C-6), 101.4 (C-1 (glu)), 79.4 (C-3), 77.6, 74.3, 72.3, 71.8 (C-2-5 (glu)), 53.1, 52.2, 50.7, 48.1, 39.2, 37.4, 37.0, 36.2, 31.6, 31.2, 29.6, 22.2, 20.5 (C-1, 2, 4, 7-16 and OCH$_3$), 19.4, 14.6 (C-18, 19).

Example 9

Methyl 1-O-(3β-acetoxyandrost-5-ene-17β-yl)-β-D-glucopyranosiduronate (12)

To a solution of compound 11 (2.0 g. 3.08 mmol) in anhydrous methanol (100 mL), 1.3 mL of a freshly prepared standard solution of sodium methoxide (prepared as above), was added under argon. After 1 h stirring at room temperature, the methanol was distilled off at 25-30° C., the residue was taken up in cold water and neutralized with either solid carbon dioxide or dilute acetic acid. The aqueous layer was saturated with sodium chloride and the solid was extracted with dichloromethane. The organic layer was filtered, washed with saturated bicarbonate, dried over magnesium sulfate, and filtered. On trituration with ether the product 12 was obtained as pure white crystals (1.4 g, 87%), m.p. 192-5° C.

$^1$H NMR (CDCl$_3$, 200 MHz): δ 5.37 (1H, d, J=5.5 Hz, 6-H), 4.6 (1H, m, 3α-H), 4.41 (1H, d, J=8.2 Hz, 1-H (glu)), 3.83 (3H, s, OCH$_3$, 3.88-3.38 (5H, m, 17α-H, 2, 3, 4, 5-H (glu)), 2.038 (3H, s, OCOCH$_3$), 1.03 (3H, s, C-19), 0.82 (3H, s, C-18).

$^{13}$C NMR (DMSO, 300 MHz): δ 170.0, 169.8 (C=O, ester, acetate), 140.5 (C-5), 122.3 (C-6), 104.3 (C-1 (glu)), 89.1 (C-3), 76.8, 76.2, 74.4, 74.2, 71.1 (C-17, C-2, 3, 4, 5 (glu)), 21.0 19.2, 11.2 (C-18, C-19, acetate-CH$_3$).

FAB m/z: 559.2 (M+23, 100%), 499.2 (M+23, −60, 12%), 329 (M+1, −208, 30%), 269 (M+1, −208, −60, 5%).

Example 10

Methyl 1-O-(3β,17β-diacetoxyandrost-5-ene-7β-yl)-β-D-glucopyranosiduronate (16)

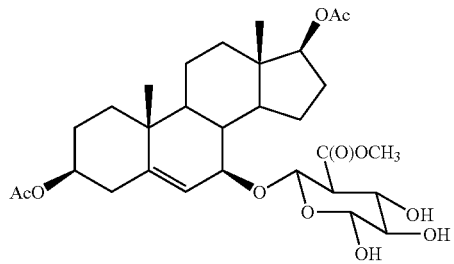

To a solution of compound 15 (0.19 g, 0.27 mmol) in dry methanol (10.0 mL) was added 0.2 mL of a solution of sodium methoxide prepared as described above. The solution was stirred at room temperature for 1 h. Methanol was removed at 25° C. and the resultant mass was taken up in 10 mL of cold distilled water. Dilute acetic acid was added to neutralize the excess base. The aqueous layer was extracted with ethyl acetate, washed with water and brine, and dried over magnesium sulfate. Ethyl acetate was completely evaporated under vacuum at 25° C. and the residue, on trituration with ether, afforded a white solid which was filtered, dried and identified as methyl 1-O-(3β,17β-diacetoxyandrost-5-ene-7β-yl)-β-D-glucopyranosiduronate (16) (0.1 g, 64%), m.p. 140-42° C.

$^1$H NMR (CDCl$_3$, 200 MHz): δ 5.59 (1H, s, 6-H), 4.68-4.50 (1H, t, J=8.5 Hz, 17α-H and 1H, m, 3α-H), 4.48 (1H, d, J=7.4 Hz, 1-H (glu)), 4.00-3.3 (5H, m, 2, 3, 4, 5-H (glu)+7α-H), 3.82 (3H, s, OC$_3$), 2.046 (6H, s, OCOCH$_3$), 1.06 (3H, s, 19-CH$_3$), 0.80 (3H, s, 18-CH$_3$).

$^{13}$C NMR (CDCl$_3$, 300 MHz): δ 172.2, 171.2, 170.0 (C=0 acetate, ester), 144.8 (C-5), 124.4 (C-6), 101.88 (C-1 (glu)), 82.94, 82.60 (C-3, 17), 75.61, 74.14, 73.31, 71.23 (C-7, and 2, 3, 4, 5 (glu)), 52.68 (C-ester), 50.64, 48.61, 37.9 (C-8, 9, 14), 42.93, 36.19 (C-10, 13), 37.83, 36.62, 27.66, 26.0, 20.9 (C-1, 2, 4, 11, 12, 15, 16), 21.38, 21.19 (CH$_3$-acetate) 18.83, 11.84 (C-18, 19).

HRMS m/z: 372.2274 for C$_{23}$H$_{32}$O$_4$ requires 372.2300 (M$^+$, −208, 4%), 330.2213 for C$_{21}$H$_{30}$O$_3$ requires 330.2195 (M$^+$, −191, −59, 100%), 312.2132 for C$_{21}$H$_{28}$O$_2$ requires 312.2089 (M$^+$, −208, −60, 20%), 271 (M$^+$, −191, −59, −59, 8%), 253.1972 for C$_{19}$H$_{25}$ requires 253.1956 (M$^+$, −208, −60, −60, 16%).

FAB m/z: 729.1 (M+23, 100%), 669.1 (M+23, −60, 5%), 609 (M+23, −60, −60, 20%), 313 (M, −333, −60, 18%), 253 (M, −60, −60, −333, 8%).

Example 11

General Procedure for Allylic Oxidation of Steroid Glucuronides

A solution of N-hydroxyphthalimide (5.0 mmol) and dibenzoyl peroxide (0.01 g) in acetone-ethyl acetate (1:0.5, 75.0 mL) was brought to reflux, and then a filtered hot solution of steroid methyl glucuronate (2.5 mmol) in acetone (20.0 mL) and dibenzoyl peroxide (0.01 g) were added. A slow stream of compressed air was passed into the solution and the mixture was heated to reflux for 12-16 h (checked with TLC). Solvent was removed completely and the resultant mass was taken up in toluene and the precipitated N-hydroxy phthalimide was filtered off. The organic layer was washed thoroughly with saturated sodium bicarbonate solution followed by water and brine and then dried over magnesium sulfate. The solvent was evaporated and the residue was chromatographed on silica gel using acetone-hexane (1:1, v/v) and crystallized from acetone-hexane.

Example 12

Methyl 1-O-(7,17-dioxoandrost-5-ene-3β-yl)-β-D-glucopyranosiduronate (9)

From compound 8, compound 9 was obtained, using the above general procedure, as white crystals, m.p. 203-5° C. (decomp.), yield 29%.

$^1$H NMR (CDCl$_3$, 200 MHz): δ 5.76 (1H, s, 6-H), 4.47 (1H, d, J=7.9 Hz, 1-H (glu)), 3.83 (3H, s, OCH$_3$), 3.95-3.35 (5H, m, 2-5H (glu) and 3α-H), 1.22 (3H, s, 19-CH$_3$), 0.90 (3H, s, 18-(CH$_3$).

$^{13}$C NMR (DMSO, 300 MHz): δ 219.12 (C-17) 200.48 (C-7), 169.54 (ester C=0), 166.3 (C-5), 125.23 (C-6), 101.3 (C-1 (glu)), 76.38, 75.79, 75, 31, 73.0, 71.7 (C-2-5 (glu) and C-3), 16.93, 13.43 (C-18, 19), 51.83, 49.30, 47.23, 44.98, 43.69, 38.64, 38.14, 35.80, 35.0, 29.2, 24.0, 20.02 (C-1, 2, 4, 8-16, and OCH$_3$).

FAB m/z: 515.2 (M+23, 4%), 455.3.2 (M+23, −60, 9%), 413.2 (M, −60, −18, −1, 100%), 241.8 (M, −208, −28, −15, 2%).

Example 13

Methyl 1-O-(3β-acetoxy-7-oxoandrost-5-ene-17β-yl)-β-D-glucopyranosiduronate (13)

White solid 13 was prepared from 12, using the above general procedure; yield 38%, m.p. 118-20° C.

$^1$H NMR (CDCl$_3$, 200 MHz): δ 5.71 (1H, s, 6-H), 4.72 (1H, m, 3α-H), 4.39 (1H, d, J=8.2 Hz, 1-H (glu)), 3.84 (3H, s, OCH$_3$), 3.88-3.27 (5H, m, 17α-H, and 2, 3, 4, 5-H (glu)), 2.06 (3H, s, OCOCH$_3$), 1.23 (3H, s, 19-CH$_3$), 0.83 (3H, s, 18-CH$_3$).

$^{13}$C NMR (DMSO, 300 MHz): δ 200.5 (C-7), 169.0, 169.2 (C=O acetate, ester): 165.0 (C-5), 125.8 (C-6), 104.1 (C-1 (glu)), 87.5 (C-3), 76.0, 75.37, 73.6, 71.54 (C-17 and C-2, 3, 4, 5 (glu)), 21.0, 16.79, 11.30 (C-18, 19, acetate CH$_3$), 51.8, 48.8, 45.0, 44.6, 43.3, 38.0, 37.5, 35.5, 28.7, 27.0, 25.3, 20.0 (C-1, 2, 4, 8-16 and OCH$_3$).

Ether derivatives.

Example 14

3β-Methoxyandrost-5-ene-7,17-dione (20)

A solution of 3β-tosyloxyandrost-5-ene-17-one (18) (4.0 g. 9.05 mmol) in anhydrous methanol (120 mL) was refluxed for 2 h. The reaction mixture was concentrated under vacuum. On cooling, a white solid 3β-methoxyandrost-5-ene-17-one (19) was obtained. Recrystallization from methanol afforded shining crystals (2.57 g. 94%), m.p. 133-5° C. (lit m.p. 118-120° C. aq. MeOH).

$^1$H NMR (CDCl$_3$, 200 MHz): δ 5.39 (1H, d, J=5.3 Hz, 6-H), 3.37 (3H, s, OCH$_3$), 3.09 (1 h, M. 3α-H), 1.04 (3H, s, 19-CH$_3$), 0.90 (3H, s, 18-CH$_3$).

Air was passed through a refluxing solution of 19 (2.0 g; 6.62 mmol) and N-hydroxyphthalimide (1.5 g, 9.2 mmol) in a mixture of acetone-ethyl acetate (1:1, 50 mL). 1,1'-azobis (cyclohexanecarbonitrile) (0.08 g) was added to the reaction mixture (Foricher et al., U.S. Pat. No. 5,030,739 (1991), incorporated herein by reference in its entirety) and the reaction continued for 10-12 h. After the usual work up as described in the general oxidation procedure, the crude product was dissolved in pyridine (5.0 mL) and stirred with acetic anhydride (3.0 mL) at room temperature for 3-4 h. The reaction mixture was poured into water and stirred for 2-3 h. The steroid was extracted with toluene and the organic layer washed with saturated bicarbonate solution and water. Toluene was distilled off and the residue was chromatographed on silica gel (ethyl acetate-hexane, 25:75, v/v) and crystallized from methanol. 3β-methoxyandrost-5-ene-7,17-dione (20) was obtained in 67% yield (1.4 g), m.p. 227-29° C.

$^1$H NMR (CDCl$_3$, 200 MHz): δ 5.76 (1H, d, J=1.8 Hz, 6-H), 3.39 (3H, s, OCH$_3$), 3.2 (1H, m, 3a–H), 1.22 (3H, s, 19-CH$_3$), 0.90 (3H, s, 18-CH$_3$.

$^{13}$C NMR (CDCl$_3$, 300 MHz): δ 220.27 (C-17), 200.99 (C-7), 166.22 (C-5), 125.85 (C-6), 78.79, 55.91, 50.05, 45.69, 44.26 (C-3, 8, 9, 14, OCH$_3$), 47.80, 38.72 (C-10, 13), 38.65, 36.13, 35.58, 30.67, 27.51, 24.12, 20.52 (C-1, 2, 4, 11, 12, 15, 16), 17.36, 13.71 (C-18, 19).

Example 15

3β-Methoxy-17,17-ethylenedioxyandrost-5-ene-7β- and 7α-ol (22 and 23)

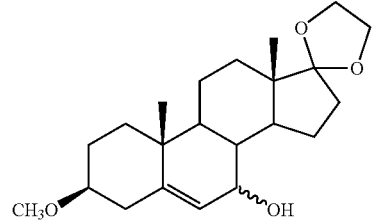

3β-Methoxyandrost-5-ene-17-one (19) was ketalized using ethylene glycol and p-toluene sulfonic acid in toluene, heated to reflux for 7 h; yield 95%, m.p. 138-40° C.

$^1$H NMR (CDCl$_3$, 200 MHz): δ 5.35 (1H, d, J=4.88 Hz, 6-H), 3.9 (5H, m, O—CH$_2$—CH$_2$—O and 7α-H), 3.36 (3H, s, OCH$_3$), 3.05 (1H, m, 3α-H), 1.0 (3H, s, 19-CH$_3$), 0.86 (3H, s, 18-CH$_3$).

The ketalized produce was oxidized at the allylic 7 position, using sodium periodate and t-butylhydroperoxide with sodium bicarbonate (Marwah and Lardy, U.S. Pat. No. 5,869, 709 (1999), incorporated herein by reference in its entirety,) to produce 3β-methoxy-17,17-ethylenedioxyandrost-5-ene-7-one (21) in 62% yield; m.p. 190-192° C.

¹H NMR (CDCl₃, 200 MHz): δ 5.7 (1H, d, J=1.96 Hz, 6-H), 3.89 (4H, m, —O—CH₂—CH₂—O—), 3.38 (3H, s, OCH₃), 3.2 (1H, m, 3α-H), 1.19 (3H, s, 19-CH₃), 0.87 (3H, s, 18-CH₃).

Subsequent reduction of the carbonyl group at position 7 of product 21 with sodium borohydride in a mixture of methylene chloride-methanol (1:9) at room temperature afforded 7-hydroxy derivatives. ¹H NMR spectrum of the product showed 7α- and 7β-forms in 2:8 ratio. The diastereomers were separated by column chromatography on silica gel (eluent, ethyl acetate:hexane, 3:7). 3β-Methoxy-17,17-ethylenedioxyandrost-5-ene-7β-ol (22) melted at 173-75° C.

¹H NMR (CDCl₃, 200 MHz): δ 5.29 (1H, t, J=1.95, 6-H), 3.89 (5H, m, O—CH₂—CH₂—O and 7α-H), 3.36 (3H, s, OCH₃), 3.14 (1H, m, 3α-H), 1.05 (3H, s, 19-CH₃), 0.88 (3H, s, 18-CH₃).

HRMS m/z: 362.2505 for C₂₂H₃₄O₄ requires 362.2457 (M⁺, 8.7%), 344.2338 for C₂₂H₃₂O₃ requires 344.2351 (M⁺, —H₂O, 2.4%), 329.2170 for C₂₁H₂₉O₃ requires 329.2117 (M⁺, H₂O, —CH₃, 7.2%), 261.1886 for C₁₇H₂₅O₂ requires 261.1854 (M⁺, -101, 100%), 229.1628 for C₁₆H₂₁O requires 229.1592 (M⁺, -101, CH₃OH, 8.3%), 211 for C₁₆H₁₉ (M⁺, -101, CH₃OH, —H₂O, 2%).

3β-Methoxy-17,17-ethylenedioxyandrost-5-ene-7α-ol (23) melted at 183-84° C.

¹H NMR (CDCl₃, 200 MHz): δ 5.62 (1H, dd, J=1.96, 5.62 Hz, 6-H), 3.89 (4H, m, O—CH₂—Ch₂-O), 3.89 (1H, 7β-H, merged in the ketal protons), 3.36 (3H, s, OCH₃), 3.14 (1H, m, 3α-H), 0.99 (3H, s, 19-CH₃), 0.87 (3H, s, 18-CH₃).

HRMS m/z: 362.2447 for C₂₂H₃₄O₄ requires 362.2457 (M⁺, 7%), 344.2347 for C₂₂H₃₂O₃ requires 344.2351 (M⁺, —H₂O, 3.5%), 330.2228 for C₂₁H₃₀O₃ requires 330.2195 (M⁺, —CH₃OH, 1.6%), 329.2149 for C₂₁H₂₉O₃ requires 329.2117 (M⁺, —H₂O, —CH₃, 4.2%), 261.1838 for C₁₇H₂₅O₂ requires 261.1854 (M⁺, -101, 100%), 229.1594 for C₁₆H₂₁O requires 229.1592 (M⁺, -101, CH₃OH, 10%), 211 for C₁₆H₁₉ (M⁺, -101, CH₃OH, —H₂O, 2%).

Example 16

3β-Methoxyandrost-5-ene-7β,17β-diol (24)

24 was prepared by reduction of 3β-methoxyandrost-5-ene-7,17-dione 20, with sodium borohydride in a mixture of methylene dichloride-methanol at room temperature. The product was purified by column chromatography.

¹H NMR (CDCl₃, 200 MHz): δ 5.29 (1H, t, J=1.95, 6-H), 3.84 (1H, dt, J=8.3 Hz, 7α-H), 3.65 (1H, t, J=8.3 Hz, 17α-H), 3.36 (3H, s, OCH₃), 3.09 (1H, m, 3α-H), 1.06 (3H, s, 19-CH₃), 0.78 (3H, s, 18-CH₃).

Example 17

3β-Acetoxy-7-methoxyandrost-5-ene-17-one (26)

A mixture of N-bromosuccimimide (2.15 g, 0.012 mol) and azobisisobutyronitrile (50 mg), a radical initiator, was added in one lot to refluxing solution of 3β-acetoxyandrost-5-ene-17-one (3.3 g, 0.01 mol) and azobisisobutyronitrile (50 mg) in carbon tetrachloride (70 mL). The mixture was refluxed for 20 min, cooled and solid succinimide was removed by filtration. The clear filtrate was concentrated at 20° C. and triturated with petroleum ether, cooled at 0° C. to obtain the white crystalline 7α-bromo derivative 25; yield 2.8 g (68.6%).

¹H NMR (CDCl₃, 200 MHz): δ 5.78 (1H, d, J=5.13 Hz, 6-H), 4.76 (1H, m. 7β-H), 4.68 (1H, m, 3α-H), 2.07 (3H, S, OCOCH₃), 1.07 (3H, s, 19-CH₃), 0.91 (3H, s. 18-CH₃).

To a clear solution of 3β-acetoxy-7α-bromoandrost-5-ene-17-one, 25, (0.5 g) in methanol (20 mL) was added silica gel (2.0 g, 70-230 mesh) and the mixture was stirred for 2 h at room temperature. The methanolic solution was cooled, neutralized with saturated sodium bicarbonate solution, and filtered on a thin bed of celite. The clear filtrate was cooled at 0° C. to obtain the white crystalline 7-methoxy derivative 26. Yield 0.32 g (72.7%), m.p. 175-78° C. The NMR spectrum of the white solid showed 55% 7β-methoxy- and 45% 7α-methoxy-compound. Spectral data described below were deduced from the spectrum of the mixture. The biological activity was assayed as the mixture (Table I).

7α-methoxy-derivative: ¹H NMR (CDCl₃, 200 MHz): δ 5.79 (1H, d, J=5.13 Hz, 6-H), 4.65 (1H, m, 3α-H), 3.49 (1H, m, 7(3-H), 3.37 (3H, s,)CH₃), 2.05 (3H, s, OCOCH₃), 1.03 (3H, s, 19-CH₃), 0.87 (3H, s, 18-CH₃).

¹³C NMR (CDCl₃, 300 MHz): δ 223.5 (C-17), 171 (C═O acetate), 146.5 (C-5), 121.0 (C-6), 81.3 (C-3), 72.29 (C-7), 56.5 (OCH₃), 44.43, 42.86, 37.03 (C-methines), 38.14, 36.62, 35.71, 30.93, 27.44, 21.83, 20.09 (C-methylenes), 21.32 (OCOCH₃), 18.17 (C-19), 13.06 (C-18).

7α-methoxy-derivative: ¹H NMR (CDCl₃, 200 MHz): δ 5.53 (1H, s, 6-H), 4.65 (1H, m, 3α-H), 3.5 (1H, m, 7α-H), 3.34 (3H, s, OCH₃), 2.05 (3H, s, OCOCH₃), 1.08 (3H, s, 19-CH₃), 0.89 (3H, s, 18-CH₃).

¹³C NMR (CDCl₃, 300 MHz): δ 223.5 (C-17), 171 (C═O acetate), 143.0 (C-5), 121.8 (C-6), 81.3 (C-3), 73.24 (C-7), 55.0 (OCH₃), 51.33, 48.18, 37.03 (C-methines), 37.83, 36.37, 35.92, 31.19, 27.6, 23.66, 20.39 (C-methylenes), 21.32 (OCOCH₃), 18.95 (C-19), 13.55 (C-18).

LCMS (APES, positive): m/z 383.3 (M+Na, 100%), 359.2 (M, -1, 2.5%), 299.3 (M, -60, 47%), 269.2 (M, -60, -32, 4%).

Example 17

3β-Methoxy-17β-hydroxyandrost-5-ene-7-one (28)

3β-methoxyandrost-5-ene-17-one (19, 0.7 g, 2.3 mmol) was dissolved in dry tetrahydrofuran (20 mL) and the solution was cooled to 0° C. Lithium tri-t-butoxyaluminum hydride (1.2 g) was added to the cooled solution and the mixture was stirred at the same temperature for 2.5 h. Excess base was neutralized with dilute acetic acid and the produce was extracted with methylene chloride. 3β-methoxyandrost-5-ene-17β-ol (27) was crystallized from methanol; yield 0.6 g (86%), m.p. 145-47° C.

¹H NMR (CDCl₃, 200 MHz): δ 5.35 (1H, d, J=5.3 Hz, 6-H), 3.65 (1H, t, J=7.5 Hz, 17α-H), 3.36 (3H, s, OCH₃), 3.07 (1H, m, 3α-H), 1.02 (3H, s, 19-CH₃), 0.76 (3H, s, 18-CH₃).

3β-methoxyandrost-5-ene-17β-ol (27) was subjected to air oxidation in the presence of N-hydroxyphthalimide and the producT 3β-methoxy-17β-hydroxyandrost-5-ene-7-one (28) was obtained in 53% yield. An analytical sample was obtained by recrystallization from acetone-hexane, m.p. 202-4° C.

¹H NMR (CDCl₃, 200 MHz): δ 5.7 (1H, d, J=1.47, 6-H), 3.36 (1H, t, J=7.8, 17α-H), 3.38 (3H, s, OCH₃), 3.2 (1H, m, 3α-H), 1.21 (3H, s, 19-CH₃), 0.77 (3H, s, 18-CH₃).

¹³C NMR (CDCl₃, 300 MHz): δ 202 (C-7), 165.9 (C-5), 125.8 (C-6), 80.8, 78.9 (C-3, 17), 55.9, 50.03, 45.22, 44.9, 43.32, 38.72, 38.58, 36.22, 35.63, 30.46, 27.56, 25.78, 20.85, 17.3, 11.1 (C-1, 2, 4, 8-16, 18, 19, OCH₃).

Example 18

3β-Methoxy-17β-acetoxyandrost-5-ene-7-one (29)

3β-methoxy-17β-hydroxyandrost-5-ene-7-one (28) was acetylated in pyridine-acetic anhydride mixture at room temperature to obtain product 29, m.p. 168-70° C.

$^1$H NMR (CDCl$_3$, 200 MHz): δ 5.71 (1H, d, J=1.73 Hz, 6-H), 4.63 (1H, t, J=7.1 Hz, 17α-H), 3.41 (3H, s, OCH$_3$), 3.21 (1H, m. 3α-H), 2.08 (3H, s, OCOCH$_3$), 1.2 (3H, s, 19-CH$_3$), 0.81 (3H, s, 18-CH$_3$).

$^{13}$C NMR (CDCl$_3$, 300 MHz): δ 201.3 (C-7), 171 (C=O acetate), 165.7 (C-5), 125.8 (C-6), 81.9, 78.9 (C-3, 17), 55.9, 49.9, 44.9, 44.6 (C-8, 9, 14 and OCH$_3$), 38.6, 36.2, 35.8, 30.46, 27.5, 25.8, 20.7 (C-1, 2, 4, 11, 12, 15, 16), 21.1, 17.3, 12.0 (C-18, 19, OCOCH$_3$).

HRMS m/z: 360.2311 for C$_{22}$H$_{32}$O$_4$ requires 360.23 (M$^+$, 100%), 329.2152 for C$_{21}$H$_{29}$O$_3$ requires 329.2117 (M$^+$-CH$_3$, 42%), 328.2101 for C$_{21}$H$_{28}$O$_3$ requires 328.2038 (M$^+$-CHOH, 9.5%), 300.2061 for C2$_{20}$H2$_{28}$O$_2$ requires 300.2089 (M$^+$-CH$_3$COOH, 12%), 268.1840 for C$_{19}$H$_{24}$O requires 268.1827 (M$^+$-CH$_3$OH, —CH$_3$COOH, 6%), 253.1640 for C$_{18}$H$_{21}$O requires 253.1592 (M$^+$-CH$_3$OH, —CH$_3$COOH, —CH$_3$, 20%).

Example 19

3β-t-Butoxyandrost-5-ene-17-one (30)

The product was prepared by the procedure of Armstrong et al. (*Tet. Lett.*, 29:2483-2486 (1988), incorporated herein by reference in its entirety), utilizing t-butyl trichloroacetimidate and borontrifluoro etherate in a solution of dichloromethane and cyclohexane, in 67.2% yield; m.p. 185-87° C.

$^1$H NMR (CDCl$_3$, 200 MHz): δ 5.34 (1H, d, J=4.89 Hz, 6-H), 3.32 (1H, m, 3α-H), 1.2 (9H, s, t-Bu), 1.02 (3H, s, 19-CH$_3$), 0.89 (3H, s, 18-CH$_3$).

Example 20

3β-t-Butoxyandrost-5-ene-7,17-dione (31)

3β-t-butoxyandrost-5-ene-17-one (30) was oxidized at the 7 position to obtain 3β-t-butoxyandrost-5-ene-7,17-dione (31) in 87% yield m.p. 189-91° C.

$^1$H NMR (CDCl$_3$, 200 MHz): δ 5.71 (1H, s, 6-H), 3.48 (1H, m, 3α-H), 1.2 (9H, s, t-Bu), 1.2 (3H, s, 19-CH$_3$), 0.89 (3H, s, 18-CH$_3$).

HRMS m/z: 358.2502 for C$_{23}$H$_{34}$O$_3$ requires 358.2508 (M$^+$, 2.4%), 302.1866 for C$_{19}$H$_{26}$O$_3$ requires 302.1882 (M$^+$-(CH$_3$)$_2$C=CH$_2$, 52%), 284.1798 for C$_{19}$H$_{24}$O$_2$ requires 284.1776 (M$^+$-(CH$_3$)$_2$C=CH$_2$, —H$_2$O, 17%), 274.1965 for C$_{18}$H$_{26}$O$_2$ requires 274.1933 (M$^+$-CO, —(CH$_3$)$_2$C=CH$_2$, 21%), 256.1843 for C$_{18}$H$_{24}$O requires 256.1827 (M+-H$_2$O, —CO, —(CH$_3$)$_2$C=CH$_2$, 25%), 246.1563 for C$_{16}$H$_{22}$O$_2$ requires 246.1620 (M$^+$-CO, —CH$_2$=CH$_2$, —(CH$_3$)$_2$C=CH$_2$, 100%), 231.1379 for C$_{15}$H$_{19}$O$_2$ requires 231.1385 (M$^+$-CO, —CH$_3$, —CH$_2$=CH$_2$, —(CH$_3$)$_2$C=CH$_2$, 9%), 228.1551 for C$_{16}$H$_{20}$O requires 228.1514 (M$^+$-CO, —CH$_2$=CH$_2$, —H$_2$O, —(CH$_3$)$_2$C=CH$_2$, 43%), 213.1383 for C$_{15}$H$_{17}$O requires 231.1446 (M$^+$-CO, —H$_2$O, —CH$_2$=CH$_2$, —CH$_3$, —(CH$_3$)$_2$C=CH$_2$, 8%).

Example 21

3β-t-Butyldimethylsilyloxyandrost-5-ene-7,17-dione (32)

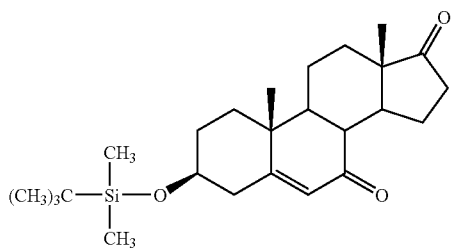

3β-hydroxyandrost-5-ene-7,17-dione (2) (0.3 g, 0.99 mmol) was dissolved in anhydrous dimethylformamide (10.0 mL). Imidazol (0.6 g, 8.82 mmol) and to-butyldimethysilyl chloride (0.3 g, 1.99 mmol) were added in sequence and the mixture was stirred at room temperature under argon for 3 h. The mixture was poured into cold water and the product was extracted with ether and washed with dilute acetic acid, saturated bicarbonate solution, then by water and brine. The solution was dried over MgSO$_4$ and the solvent was removed. The crude compound was crystallized from aqueous methanol to afford white crystals of 3β-t-butyldimethylsilyloxyandrost-5-ene-7,17-dione (32) in 92.6% yield (0.37 g), m.p. 135-6° C.

$^1$H NMR (CDCl$_3$, 200 MHz): δ 5.73 (1H, s, 6-H), 3.61 (1H, m, 3α-H), 1.22 (3H, s, 19-CH$_3$), 0.89 (12H, s, 18-CH$_3$ and C(CH$_3$)$_3$), 0.07 (6H, s, Si(CH$_3$)$_2$).

$^{13}$C NMR (CDCl$_3$, 300 MHz): δ 220.5 (C-17), 201 (C-7), 166.8 (C-5), 125.6 (C-6), 71.1 (C-3), 50.15, 46.0, 44.33 (C-8, 9, 14), 48.0, 38.5, 18.2 (C-18,19,0-Me$_3$); 42.62, 36.35, 35.63, 31.67, 30.73, 24.17, 20.57 (C-1, 2, 4, 11, 12, 15, 16), 25.82 ((CH$_3$)$_3$), 17.41, 13.74, (C-18, 19), −4.0 (Si(CH$_3$)$_2$.

LCMS (AP, positive ion mode): λmax 240, m/z 417.3 ((M+1)$^+$, 71%), 285.2 (M+1, -TBDMSiOH, 100%), 267.2 (M+1, -TBDMSiOH, —H$_2$O, 14%), 249.3 (M+1, -TBDMSiOH, -2(H$_2$O), 1%), 243.2 (M+1, —CH$_2$=C=O, 6%).

Example 22

3β,17β-di(t-butyldimethylsilyloxy)androst-5-ene-7-one (33)

The product was prepared from 3β-17β-dihydroxyandrost-5-ene-7-one as described for compound 32. M.P. 99-101° C.

$^1$H NMR (CDCl$_3$, 200 MHz): δ 5.65 (1H, s, 6-H), 3.60 (2H, m. 3α- and 17α-H), 1.18 (3H, s, 19-CH$_3$), 0.74 (3H, s, 18-CH$_3$), 0.87 (18H, s, Si-t-butyl), 0.04 (12H, s, Si-Me$_2$).

Example 23

3β-Acetoxyandrost-5-ene-7β,17β-di(t-butyldimethylsilyl)ether (35)

Prepared from 3β-acetoxyandrost-5-ene-7β,17β-diol (34) and t-butyldimethylsilyl chloride in dichloromethane. M.p. 85-87° C.

LCMS (APCl, positive ion mode): m/z 575.25 (M−1)$^+$, 515.35 (M−1, —CH$_3$COOH, 40%), 385.25 (M+1, —CH₃COOH, -TBDMSiOH, 11%), 253.15 (M+1, —CH₃COOH, -2(TBDMSiOH), 29%), 238.15 (M+1, —CH₃COOH, -2(TBDMSiOH), —CH₃, 7%).

Example 24

3β-Acetoxy-17β-t-butyldimethylsilyloxyandrost-5-ene-7-one (36)

Prepared from 3β-acetoxy-17β-hydroxyandrost-5-ene-7-one (4). M.p. 202-4° C.
¹H NMR (CDCl₃, 200 MHz): δ 5.7 (1H, d, J=1.3 Hz, 6-H), 4.72 (1H, m, 3α-H), 3.56 (1H, dd, J=1.7 Hz, 17α-H), 2.07 (3H, s, OCOCH₃), 1.22 (3H, s, 19-CH₃), 0.88 (9H, s, Si-t-butyl), 0.72 (3H, s, 18-CH₃), 0.009 (6H, s. SiMe₂).
¹³C NMR (CDCl₃, 300 MHz): δ 201.5 (C-7), 170 (O COCH₃), 164.1 (C-5), 126.5 (C-6), 80.9 (C-17), 72.1 (C-3), 50.1, 45.3, 44.5 (C-methines), 37.8, 36.0, 35.9, 30.9, 27.3, 26.2, 20.87 (C-methylenes), 25.9, 25.82, 21.2, 17.3, 11.3, –4.5, –4.9 (C-Methyls).

Example 25

3β-(2-tetrahydropyranoxy)androst-5-ene-7,17-dione (37)

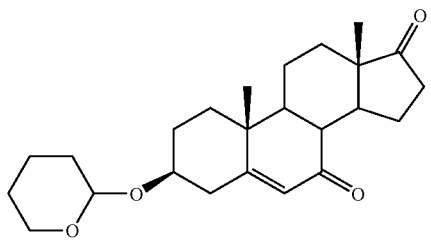

3β-hydroxyandrost-5-ene-7,17-dione (2) (0.5 g, 1.65 mmol) was placed in a dried, argon-flushed flask where it was dissolved in dry dichloromethane (20.0 mL). Pyridinium toluene-p-sulfonate (0.043 g. 0.17 mmol) was added followed by 3,4-dihydro-2H-pyran (0.23 mL, 2.5 mmol) and the solution was stirred at room temperature, under an atmosphere of argon, for 2-3 h. The reaction was quenched by adding water and the product was extracted thrice with ether (3×20 mL). The combined ether extracts were washed with dilute acetic acid, water and bicarbonate solution and dried (MgSO₄). Solvent was removed and the crude product was purified using chromatography on silica gel (ethyl acetate-hexane, 15:85, v/v). The compound first eluted was identified as androsta-3,5-diene-7,17-dione (0.150 g), m.p. 167-8° C.

Further elution with the same solvent gave 3β-(2-tetrahydropyranoxy)androst-5-ene-7,17-dione (37) as a white solid, which was crystallized from methanol (0.43 g, 68%), m.p. 137-39° C.

¹H NMR (CDCl₃, 200 MHz): δ 5.76, 5.73* (1H, dd, J=2 Hz, 6-H), 4.7 (1H, m, 2-H Pyran), 3.91 (1H, m, 6-H pyran), 3.67 (1H, m, 3α-H), 3.51 (1H, m, 6-H pyran), 1.23 (3H, s, 19-CH₃), 0.90 (3H, s, 18-CH₃).
¹³C NMR (CDCl₃, 300 MHz): δ 221 (C-17), 201 (C-7), 167, 166.4* (C-5), 125.8 (C-6), 97.4, 97.1*, 74.7, 74.53* (C-3, C-2 (Pyran)), 62.86 (C-6 (Pyran)), 50.05, 45.69, 44.26 (C-8, 9, 14), 47.82, 38.62 (C-10, 13), 40.10, 38.80, 36.41, 36.15, 35.59, 31.07, 30.68, 29.31, 27.64, 25.35, 24.14, 20.52, 19.83 (C-1, 2, 4, 11, 12, 15, 16, C-3, 4, 5 (Pyran))*, 17.35, 13.71 (C-18, 19).

LCMS (APES, positive): λmax 238; m/z 795.5 (2M+Na, 100%), 409.1 (M+Na, 85%), 285.1 (M, –101, 14%).
* Extra peaks are due to the diastereomers.

Example 26

3β-dodecanoxyandrost-5-ene-7,17-dione (39)

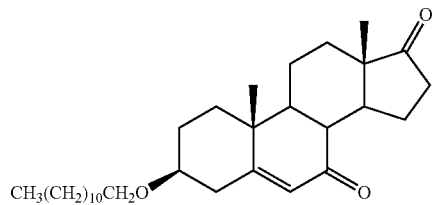

A solution of DHEA (1) (2.88 g. 0.01 mol) in anhydrous tetrahydrofuran (20 mL) was added to a mixture of sodium hydride (0.5 g, 60% in oil, washed twice with pentane) in anhydrous tetrahydrofuran (10 mL). The mixture was refluxed for 2 h, cooled to room temperature, and a solution of 1-bromododecane (2.74 g, 0.11 mol) was added slowly (10 min). The solution was refluxed for 4 h, cooled and poured into ice water and the product was extracted with ether-ethyl acetate mixture (1:1). 3β-Dodecanoxyandrost-5-ene-17-one (38) was purified by column chromatography on silica gel (eluent ethyl acetate-petroleum ether, 1:9), yield 0.6 g (43%, based on 30.5% conversion). Further elution with the same solvents at (4:6) afforded unreacted DHEA (2.0 g, 69.5%).
¹H NMR (CDCl₃, 200 MHz): δ 5.38 (1H, d, J=5.12 Hz, 6-H), 3.45 (2H, t, J=6.6, 6.83 Hz, —CH₂—O), 3.14 (1H, m. 3α-H), 1.03 (3H, s, 19-CH₃), 0.89 (3H, s, 18-CH₃).

3β-dodecanoxyandrost-5-ene-17-one (38) was subjected to oxidation by a procedure to be published and the product, 3β-dodecanoxyandrost-5-ene-7,17-dione (39) was obtained in 82.8% yield, m.p. 70° C.
¹H NMR (CDCl₃, 200 MHz): δ 5.74 (1H, d, J=1.71 Hz, 6-H), 3.47 (2H, t, J=6.35, 6.83 Hz, —CH₂—O), 3.27 (1H, m, 3α-H), 1.22 (3H, s, 19-CH₃), 0.9 (3H, s, 18-CH₃).
¹³C NMR (CDCl₃, 300 MHz): δ 220 (C-17), 200 (C-7), 166.0 (C-5), 125.8 (C-6), 77.45 (C-3), 68.58 (—CH₂—O), 50.14, 45.75, 44.3 (C-methines), 39.19, 36.31, 35.58, 31.9, 30.7, 30.1, 29.59, 29.46, 29.34, 28.07, 26.16, 24.15, 22.66, 20.55 (C-methylenes), 17.35, 14.07, 13.7 (C-methyls).
HRMS m/z: 470.3758 for C₃₁H₅₀O₃ requires 470.3760 (M⁺, 23%), 301.1783 for C₁₉H₂₅O₃ requires 301.1804 (M⁺-C₁₂H₂₅, 10%), 285.1870 for C₁₉H₂₅O₂ requires 285.1854 (M⁺—C₁₂H₁₅O, 12%), 284.1610 for C₁₉H₂₄O₂ requires 284.1776 (M⁺-C₁₂H₁₅OH, 5.6%).

Example 27

3β-(1'-ethoxy)ethoxyandrost-5-ene-7,17-dione (41)

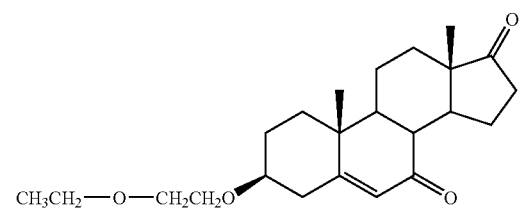

To a solution of DHEA (1) (1.5 g, 0.005 mol) and p-toluene sulfonic acid (35 mg) in methylene dichloride (20 mL), a solution of ethyl vinyl ether (1.17 g, 0.016 mol) in methylene dichloride was added slowly during 2 h at room temperature. The solution was stirred for an additional 6 h and poured into cold water. The organic layer was separated and the product was subject to column chromatography on silica gel (eluent, ethyl acetate-petroleum ether, 1:9) to afford 3β-(1'-ethoxy)ethoxyandrost-5-ene-17-one (40) as a viscous mass (0.92 g, 84% based on 55% conversion).

$^1$H NMR (CDCl$_3$, 200 MHz): δ 5.37 (1H, s, 6-H), 4.78 (1H, q, J=5.37 Hz, O—CH—O), 3.68 (2H, m, —CH$_2$—O), 3.5 (1H, m, 3α-H), 1.31 (3H, d, J=5.13, CH$_3$), 1.2 (3H, m, CH$_3$), 1.03 (3H, s, 19-CH$_3$), 0.89 (3H, s, 18-CH$_3$).

3β-(1'-ethoxy)ethoxyandrost-5-ene-17-one was oxidized at the allylic 7 position of the steroid using air and N-hydroxy phthalimide as described before to obtain 3β-(1'-ethoxy)ethoxyandrost-5-ene-7,17-dione (41) in 50% yield.

$^1$H NMR (CDCl$_3$, 200 MHz): δ 5.74 (1H, s, 6-H), 4.79 (1H, m, O—CH—O), 3.58 (3H, m, —CH$_2$—O and 3α-H), 1.34 (3H, d, J=5.13 Hz, CH$_3$), 1.22 (3H, m, CH$_3$), 1.22 (3H, s, 19-CH$_3$), 0.9 (3H, s, 18-CH$_3$).

$^{13}$C NMR (CDCl$_3$, 300 MHz): δ 220 (C-17), 200 (C-7), 166.0 (C-5), 125.77 (C-6), 98.42 (O—CH—O), 73.89 (C-3), 60.19 (O—CH$_2$), 50.06, 45.69, 44.27 (C-methines), 41.88, 40.03, 35.58, 30.67, 29.1, 24.1, 20.5 (C-methylenes), 20.7, 17.34, 15.28, 13.71 (C-methyls).

Carbonate Derivatives.

Example 28

3β-Carbomethoxyandrost-5-ene-7,17-dione (42)

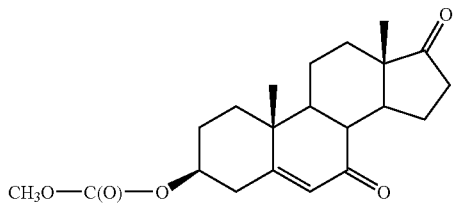

3β-Hydroxyandrost-5-ene-7,17-dione (2) (0.5 g, 0.0016 mol) was dissolved in dry pyridine (6 mL) and the solution was cooled to 0-5° C. Methyl chlorofmate (0.19 g, 0.002 mol) was added dropwise during 15 min and the mixture was stirred at the same temperature for 3 h. The reaction mixture was quenched with water and the product was extracted with methylene dichloride. The organic layer was washed, dried and solvent was removed. The crude product was purified by column chromatography on silica gel (eluent: acetone-hexane, 2:8) to afford 0.42 g (89%, conversion 80%) of white solid which was crystallized from methanol, m.p. 168-70° C.

$^1$H NMR (CDCL$_3$), 200 MHz): δ 5.77 (1H, d, J=0.7 Hz, 6-H), 3.78 (3H, s, OCH$_3$), 4.62 (1H, m, 3α-H), 1.24 (3H, s, 19-CH$_3$), 0.9 (3H, s, 18-CH$_3$).

$^{13}$C NMR (CDCl$_3$, 300 MHz): δ 220.1 (C-17), 200.2 (C-7), 164 (C-5), 155 (O—C—O), 126.7 (C-6), 75.7 (C-3), 54.8 (OCH$_3$), 49.9, 45.7, 44.3, (CH—, 8, 9 and 14), 37.7, 35.8, 35.6, 30.7, 27.2, 24.1, 20.6 (CH$_2$—, 1, 2, 4, 11, 12, 15 and 16), 17.4, 13.7 (CH$_3$-18, and 19).

HRMS m/z: 360.1929 for C$_{21}$H$_{28}$O$_5$ requires 360.1937 (M$^+$, 1.7%), 284.1789 for C$_{19}$H$_{24}$O$_2$ requires 284.1776 CH$_3$OH, —CO$_2$, 100%), 269.1521 for C$_{18}$H$_{21}$O$_2$ requires 269.1541 (M$^+$-CH$_3$OH, —CO$_2$, —CH$_3$, 54.%), 256.1856 for C$_{18}$H$_{24}$O requires 256.1827 (M$^+$-CH$_3$OH, —CO$_2$, —CO, 25.6%), 241.1623 for C$_{17}$H$_{21}$O requires 241.1592 (M$^+$-CH$_3$OH, —CO$_2$, —CH$_3$, —CO, 11%), 277.1461 for C$_{16}$H$_{19}$O requires 227.1463 (M$^+$-CH$_3$OH, —CO$_2$, —CH$_3$,—CO, —CH$_2$, 5.6%).

Example 29

3β-Carboallyloxyandrost-5-ene-7,17-dione (43)

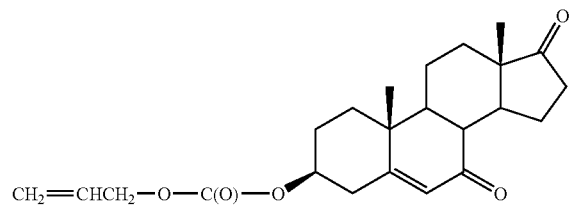

Compound 43 was prepared from 7-oxo-DHEA (2) (1.0 mmol) and allylchloroformate (4.0 mmol) in tetrahydrofuran-pyridine mixture at 0-5° C. After stirring 6 hours only 30% conversion had occurred; from the mixture the product was isolated in 78% yield (based on 30% conversion) by column chromatography. M.p. 159-61° C.

$^1$H NMR (CDCl$_3$, 200 MHz): δ 5.92 (1H, m, =CH$_2$—), 5.74 (1H, d, J=1.7 Hz, 6-H), 5.38 (q), 5.29 (m), 5.23 (m) (2H, J=18.5, 11.6, 1.47 Hz, —CH$_2$=), 4.62 (2H, dt, J=5.86, 1.22, 1.47 Hz, —CH$_2$—O—), 4.62 (1H, m, 3α-H) 1.21 (3H, s, 19-CH$_3$), 0.87 (3H, s, 18-CH$_3$).

$^{13}$C NMR (DCCl$_3$, 300 MHz): δ 219.2 (C-17), 200 (c-7), 164 (c-5), 154 (O—C—O), 131.5 (=O—), 126.5 (C-6), 118.7 (—CH$_2$=), 75.7 (C-3), 68.24 (O—CH$_2$), 50, 45.8, 44.3, (CH—, 8, 9 and 14), 47.64, 38.33 (c-, 10, 13), 37.7, 35.8, 35.4, 30.7, 27.2, 24.02, 20.53, (CH$_2$—, 1, 2, 4, 11, 12, 15, and 16), 17.3, 13.7 (CH$_3$-18, and 19).

LCMS (APES, positive): Amax 234 nm; λmax 409.1 (M+Na, 100%), 307.1 (M, -102, +Na, 80%), 285 (M, -101, 52%), 256 (M, -102, -28).

Example 30

3β-Carboethoxyandrost-5-ene-7,17-dione (44)

Prepared from (2) and ethylchloroformate in pyridine at 0-5° C. Yield 90%, m.p. 187-8° C.

$^1$H NMR (CDCl$_3$, 300 MHz): δ 5.77 (1H, d, J=1.65 Hz, 6-H), 4.6 (1H, m, 3α-H), 4.2 (2H, q, J=7.2 Hz, —CH$_2$—O), 1.32 (3H, t, J=7.2 Hz, CH$_3$), 1.23 (3H, s, 19-CH$_3$), 0.9 (3H, s, 18-CH$_3$).

$^{13}$C NMR (CDCl$_3$, 300 MHz): δ 220.2 (C-17), 200.7 (C-7), 164.4 (C-5), 154.3 (O—C—O), 126.7 (C-6), 75.4 (C-3), 64.1 (O—CH$_2$), 49.9, 45.7, 44.3, (CH—, 8, 9 and 14), 47.8, 38.4 (C—, 10, 13), 37.7, 35.8, 35.6, 30.7, 27.2, 24.1, 20.5 (CH$_2$—, 1, 2, 4, 11, 12, 15, and 16), 14.4, 14.2, 13.8 (CH$_3$, CH$_3$-18, 19).

Example 31

3β-Carboisobutoxyandrost-5-ene-7,17-dione (45)

Prepared from (2) and isobutylchloroformate in pyridine at 0-5° C. Yield 78%, m.p. 132-3° C.

$^1$H NMR (CDCl$_3$, 300 MHz): δ 5.77 (1H, d, J=1.66 Hz, 6-H), 4.6 (1H, m, 3α-H), 3.92 (2H, d, J=6.8 Hz, —CH$_2$—O), 1.24 (3H, s, 19-CH$_3$), 0.96 (6H, d, J=6.6 Hz, (CH$_3$)$_2$), 0.9 (3H, s, 18-CH$_3$).

$^{13}$C NMR (CDCl$_3$, 300 MHz): δ 220.2 (C-17), 200.7 (C-7), 164.4 (C-5), 154.5 (O—C—O), 126.6 (C-6), 75.5 (C-3), 74.14 (O—CH$_2$), 49.9, 45.7, 44.3, (CH—, 8, 9, and 14), 27.7 (—CH<), 37.8, 35.8, 35.6, 30.7, 27.2, 24.1, 20.6 (CH$_2$—, 1, 2, 4, 11, 12, 15, and 16), 18.91 (CH$_3$), 18.87 (CH$_3$), 17.35 (19-CH$_3$), 13.7 (18-CH$_3$).

Example 32

3β,17β-dicarbomethoxyandrost-5-ene-7-one (46)

Prepared from 3β,17β-dihydroxyandrost-5-ene-7-one and methylchloroformate in pyridine at 0-5° C. Yield 81%, m.p. 167-9° C.

$^1$H NMR (CDCl$_3$, 300 MHz): δ 5.73 (1H, d, J=1.66 Hz, 6-H), 4.57 (2H, m, 3α-H, 17α-H), 3.79 (3H, s, CH$_3$O), 3.77 (3H, s, CH$_3$O), 1.2 (3H, s, 19-CH$_3$), 0.84 (3H, s, 18-CH$_3$).
$^{13}$C NMR (CDCl$_3$, 300 MHz): δ 200.97 (C-7), 163.89 (c-5), 155.7, 154.88 (O—C—O), 126.6 (C-6), 85.65 (C-17), 75.8 (C-3), 54.72, 54.58)OCH$_3$), 49.65, 44.91, 44.55, (CH—, 8, 9 and 14), 43.03, 38.32 (C—, 10, 13), 37.7, 35.82, 35.65, 27.43, 27.21, 25.68, 20.67 (CH$_2$—, 1, 2, 4, 11, 12, 15, and 16), 11.94 (CH$_3$-18, and 19).

Example 33

3β-Carbooctyloxyandrost-5-ene-7,17-dione (47)

Prepared from (2) and octylchloroformate in pyridine at 0-5° C. The product was purified by column chromatography on silica gel. Yield 65%, m.p. 72-3° C.

$^1$H NMR (CDCl$_3$, 300 MHz): δ 5.77 (1H, d, J=1.66 Hz), 4.6 (1H, m, 3α-H), 4.13 (2H, t, J=6.6 Hz, —CH$_2$—O), 1.23 (3H, s, 19-CH$_3$), 0.88 (3H, s, 18-CH$_3$).
$^{13}$C NMR (CDCl$_3$, 300 MHz): δ 219.76 (C-17), 200.4 (C-7), 164.28 (C-5), 154.28 (O—C—O), 126.53 (C-6), 75.34 (C-3), 68.08 (O—CH$_2$), 49.81, 45.6, 44.2, (CH—, 8, 9 and 14), 47.69 (c-13), 38.31 (c-10), 37.67, 35.74, 35.46, 31.65, 30.61, 29.06, 29.04, 28.54, 27.15, 25.6, 24.05, 22.52, 20.47 (methylenes), 14.02, (CH$_3$), 17.25 (19-CH$_3$), 13.65 (18-CH$_3$).
LCMS (APES, positive): m/z 459.2 (M+1, 8%), 285.1 (M, −174, 100%).

Example 34

3β-Carbo(9-fluorenyl)methoxyandrost-5-ene-7,17-dione (48)

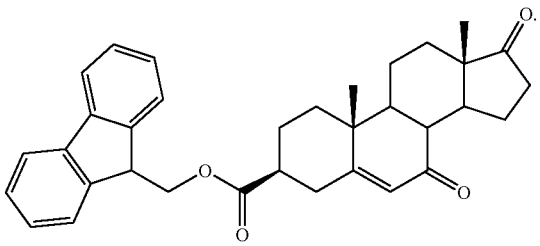

A mixture of 7-oxoDHEA (2) (0.3 g, mmol) and 9-fluorenylmethylchloroformate (0.285 g, 1.1 mmol) in pyridine (4.0 mL) was stirred at room temperature for 1 hour. The product was purified by column chromatography on silica gel, to yield 57% (0.3 g), m.p. 98-103° C., λ$_{max}$ 260 nm.

$^1$H NMR (CDCl$_3$, 200 MHz): δ 7.77 (2H, d, J=7.11 Hz, Ar—H), 7.62 (2H, d, J=6.83 Hz, Ar—H), 7.37 (4H, m, Ar—H), 5.77 (1H, d, J=1.46 Hz, 6-H), 4.61 (1H, m, 3-H), 4.43 (2H, d, J=6.96 Hz, AB system, OCH$_2$), 4.26 (1H, t, J=7.08 Hz, AB system, Ar—H), 1.25 (3H, s, 19-CH$_3$), 0.90 (3H, s, 18-CH$_3$).
LC-MS (API-ES) m/z: 547 (M+23, 100%), 285 (M+1, −240, 3%).

Example 35

3β-Carbomethoxyandrost-5-ene-7,17β-diol (49)

3β-Carbomethoxyandrost-5-ene-7,17-dione (42) (0.5 g, 0.0014 mol) was dissolved in a mixture of dichloromethane (5 mL) and methanol (10 mL). The mixture was stirred at room temperature and finely powdered sodium borohydride (0.16 g, 0.004 mol) was added slowly. After 15 min the reaction mixture was quenched with water and the product was extracted with methylene dichloride. The organic layer was washed, dried and solvent removed. The product was crystallized from acetone-petroleum ether to afford 0.35 g (70%) of 3β-carbomethoxyandrost-5-ene-7,17β-diol (49) as a white crystalline solid, m.p. 150-52° C. LC-MS and $^1$H NMR analysis of the product showed a 8:2 ratio of isomeric 7β-hydroxy and 7α-hydroxy compound.

$^1$H NMR for 7β-hydroxy isomer (CDCl$_3$, 200 MHz): δ 5.33 (1H, s, 6-H), 4.49 (1H, m, 3α-H), 3.77 (3H, s, OCH$_3$), 3.84 (1H, d, J=7.08 Hz, 7α-H), 3.64 (1H, s, 6-H), 4.49 (1H, m, 3α-H), 3.77 (3H, s, OCH$_3$), 3.84 (1H, d, J=7.08 Hz, 7α-H), 3.64 (1H, t, J=8.05 Hz, 17α-H), 1.07 (3H, s, 19-CH$_3$), 0.77 (3H, s, 18-CH$_3$).

7α-hydroxy isomer showed different chemical shifts for 6 and 19 protons, deduced from the spectrum of the mixture (1H, d, J=4.89 Hz, 6-H), 1.02 (3H, s, 19-CH$_3$).
LC-MS (API-ES) m/z: 387 (M+23 100%), 311 (M+23, −76, 25%), 271 (M+1, −76, −18, 5%), 253 (M+1, −76, −18, −18, 3%).

Example 36

3β-Carboethoxyandrost-5-ene-7β,17β-diol (50)

3β-Carbomethoxyandrost-5-ene-7,17-dione (44) (0.3 g, 0.8 mmol) in 5 mL dichloromethane and 10 mL methanol was treated with cerium (III) chloride heptahydrate (0.3 g, 0.8 mmol). To this cold solution, finely powdered sodium borohydride (0.09 g, 2.4 mmol) was added slowly. After 15 minutes the solvent was evaporated to complete dryness, the solid crude was taken up in dichloromethane, stirred for 30 minutes and filtered on a small bed of celite. The organic layer was washed once with water, dried and the solvent was removed. The product was crystallized from acetone-petroleum ether to afford 0.22 g (73%) of 3β-carboethoxyandrost-5-ene-7β, 17β-diol (50) as a white solid, m.p. 170-71° C.

$^1$H NMR (CDCl$_3$, 200 MHz): δ 5.33 (1H, s, 6-H), 4.48 (1H, m, 3α-H), 4.23 (2H, q, J=7.08, OCH$_2$), 3.84 (1H, d, J=7.57 Hz, 7α-H), 3.64 (1H, t, J=8.3 Hz, 17α-H), 1.31 (3H, t, J=7.08, CH$_3$), 1.07 (3H, s, 19-CH$_3$), 0.77 (3H, s, 18-CH$_3$).
LC-MS (API-ES) m/z: 401 (M+23, 100%), 311 (M+23, −90, 15%), 271 (M+1, −90, −18, 3%), 253 (M+1, −90, 18, −18, 5%).

Example 37

3β-Carbooctyloxyandrost-5-ene-7β,17β-diol (51)

3β-Carbooctyloxyandrost-5-ene-7,17-dione (47) (0.3 g, 0.65 mmol) was converted to 51 as described for compound 49. The product was crystallized from petroleum ether to afford 0.23 g (77%) of 3β-carbooctyloxyandrost-5-ene-7β,17β-diol (51) as a white solid, m.p. 86-87° C.

$^1$H NMR (CDCl$_3$, 200 MHz): δ 5.33 (1H, s, 6-H), 4.48 (1H, m, 3α-H), 4.12 (2H, t, J=6.6, OCH$_2$), 3.89 (1H, d, J=7.54 Hz, 7α-H), 3.65 (1H, t, J=8.3 Hx, 17α-H), 0.88 (3H, t, CH$_3$), 1.07 (3H, s, 19-CH$_3$), 0.77 (3H, s, 18-CH$_{33}$).

LC-MS (API-ES) m/z: 485 (M+23, 100%), 311 (M+23, −174, 3%), 293 (M+23, −174, −18, 2%).

Induction of the Synthesis of Mitochondrial Glycerophosphate Dehydrogenase and Cytosolic Malic Enzymes in Rat Livers

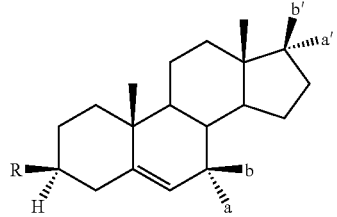

| # | R | b/a | b'/a' | Conc. & in diet | Enzymes GDPH % of control | Malic |
|---|---|---|---|---|---|---|
| * | AcO | O | O | 0.040 | 336 | 338 |
| 9 | Glu-ester | O | O | 0.085 | 166 | 306 |
| 10 | Glu-triAc-ester | O | O | 0.107 | 164 | 234 |
| 12 | AcO | H/H | Glu-ester | 0.083 | 128 | 229 |
| 13 | AcO | O | Glu-ester | 0.093 | 204 | 363 |
| 16 | AcO | Glu-ester/H | AcO | 0.071 | 241 | 367 |
| 17 | AcO | H/Glu-triAc-ester | O | 0.046 | 81 | 93 |
| 18 | OTs | H/H | O | | | |
| 19 | MeO | H/H | O | 0.085 | 241 | 312 |
| 20 | MeO | O | O | 0.055 | 323 | 424 |
| 21 | MeO | O | O—CH$_2$—CH$_2$—O | 0.042 | 194 | 311 |
| 22 | MeO | OH/H | O—CH$_2$—CH$_2$—O | 0.063 | 395 | 595 |
| 23 | MeO | H/OH | O—CH$_2$—CH$_2$—O | 0.063 | 262 | 324 |
| 24 | MeO | OH/H | OH/H | 0.055 | 403 | 444 |
| 25 | AcO | H/Br | O | | | |
| 26 | AcO | MeO•H** | O | 0.064 | 328 | 459 |
| 27 | MeO | H/H | OH/H | | | |
| 28 | MeO | O | OH/H | 0.055 | 322 | 307 |
| 29 | MeO | O | AcO/H | 0.06 | 188 | 166 |
| 30 | tert-BuO | H/H | O | | | |
| 31 | tert-BuO | O | O | 0.04 | 93 | 116 |
| 32 | TBDMSO | O | O | 0.036 | 241 | 313 |
| 33 | TBDMSO | O | TBDMSO/H | 0.085 | 168 | 380 |
| 34 | AcO | OH/H | OH/H | 0.046 | 497 | 508 |
| 35 | AcO | TBDMSO/H | TBDMSO/H | 0.082 | 123 | 100 |
| 36 | AcO | O | TBDMSO/H | 0.07 | 375 | 382 |
| 37 | Tetrahydropyran | O | O | 0.064 | 280 | 357 |
| 38 | Dodecanoxy | H/H | O | | | |
| 39 | Dodecanoxy | O | O | 0.068 | 156 | 189 |
| 40 | (Ethoxy)ethyl | H/H | O | | | |
| 41 | (Ethoxy)ethyl | O | O | 0.05 | 168 | 275 |
| 42 | Carbomethoxy | O | O | 0.1 | 500 | 786 |
| 43 | Carboallyloxy | O | O | 0.067 | 440 | 384 |
| 44 | Carboethoxy | O | O | 0.045 | 265 | 373 |
| 45 | Carbo, iso-butyloxy | O | O | 0.048 | 253 | 515 |
| 46 | Carbomethoxy | O | Carbomethoxy/H | 0.051 | 295 | 292 |
| 47 | Carbooctyloxy | O | O | 0.055 | 256 | 312 |
| 48 | Carbo(9-fluorene)methoxy | O | O | 0.09 | 218 | 310 |
| 49 | Carbomethoxy | OH, H** | OH/H | 0.042 | 377 | 359 |
| 50 | Carboethoxy | OH/H | OH/H | 0.044 | 277 | 321 |
| 51 | Carbooctyloxy | OH/H | OH/H | 0.054 | 343 | 260 |

Each compound was tested in a group of two or three rats. Enzyme activity in the livers of rats fed the stock diet without supplementation is termed 100%. The abbreviation TBDMSO = tert-butyldimethylsilyl oxy.
* Mean values from ten experiments (20 rats) in which 7-oxo-DHEA was the comparative standard.
**Products tested as diestereomeric mixture (% ratio of β and α , 26, 55:45, 49, 80:20)

The following compounds did not induce the liver enzymes: 17-oxoA-3β-glucopyranoside Me ester (8), 3β-acetoxy-17-oxoA-7-glucopyranoside Me ester (17), 3β-tert-butoxyandrost-5-ene-17-one (30), 3β-acetoxyandrost-5-ene-7β,17β-di-tert-butyldimethylsilyl ether (35); A = androst-5-ene.

It will be appreciated that the methods and compositions of the instant invention can be incorporated in the form of a variety of embodiments, some of which are disclosed herein. It will be apparent to the artisan that other embodiments exist and do not depart from the scope of the invention. Thus, the described embodiments are illustrative and should not be construed as restrictive.

For any of the uses of formula 1 compounds described herein, e.g., in any of the examples above, the results or biological effects that are obtained using individual formula 1 compounds are optionally compared to the results or biological effects that are obtained using a reference formula 1 compound such as AET, AED, BrEA, positive controls or negative controls or to other known modulators of the biological activity, symptom or clinical condition of interest. Such comparisons provide guidance for using the formula 1 compounds in the different methods or clinical conditions. Such comparison information allows, e.g., tailoring of dosages and dosing schedules, routes of administration or the like for individual applications for the formula 1 compounds.

To the extent not already indicated, it will be understood by those of ordinary skill in the art that any of the various specific embodiments, compounds or compositions described herein may be modified to incorporate other appropriate features, e.g., as shown in any other of the specific embodiments disclosed herein or in the cited references.

What is claimed is:

1. A compound having the structure

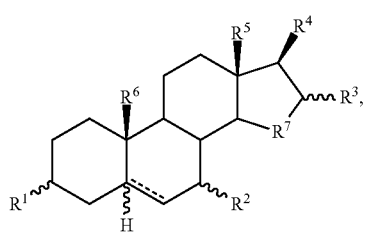

wherein the dotted line is an optional double bond;
wherein when $\Delta^5$ double bond is present, —H at position-5 is absent or when $\Delta^5$ double are bond is absent, —H at position-5 is in the α- or β-configuration.
$R^1$, $R^2$ and $R^4$ independently are —OH, an ester or an ether;
$R^3$ is —H, —OH, an ester, an ether or halogen;
$R^5$ is —CH$_3$ or —CH$_2$OH;
$R^6$ is —CH$_3$;
and $R^7$ is —O—.

2. The compound of claim 1 wherein $R^1$, $R^2$ and $R^4$ are —OH or an ester and $R^3$ is —OH, an ester or —Br.

3. The compound of claim 2 wherein $R^5$ is —CH$_3$.

4. The compound of claim 1 wherein the compound has the formula

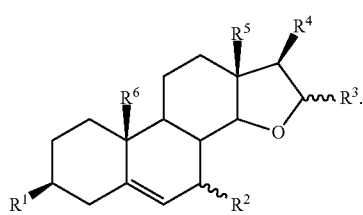

5. The compound of claim 4 wherein $R^1$, $R^2$ and $R^4$ are —OH or an ester and $R^3$ is —OH, an ester or —Br.

6. The compound of claim 5 wherein $R^5$ is —CH$_3$.

7. The compound of claim 4 wherein the compound has the structure

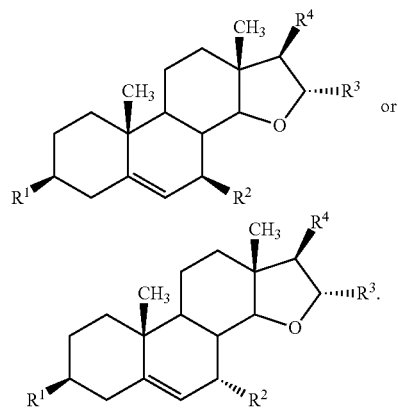

8. The compound of claim 7 wherein $R^1$, $R^2$ and $R^4$ are —OH and $R^3$ is —OH or —Br.

9. The compound of claim 1 wherein the compound has the formula

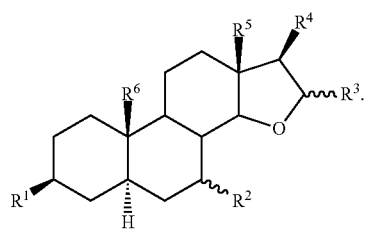

10. The compound of claim 9 wherein $R^1$, $R^2$ and $R^4$ are —OH or an ester and $R^3$ is —OH, an ester or —Br.

11. The compound of claim 10 wherein $R^5$ is —CH$_3$.

12. The compound of claim 9 wherein the compound has the structure

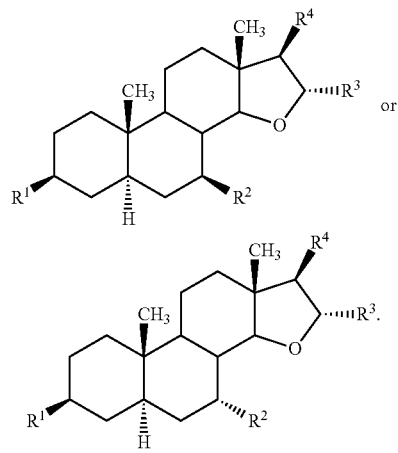

13. The compound of claim 12 wherein $R^1$, $R^2$ and $R^4$ are —OH and $R^3$ is —OH or —Br.

14. The compound of claim 4 wherein the compound has the structure
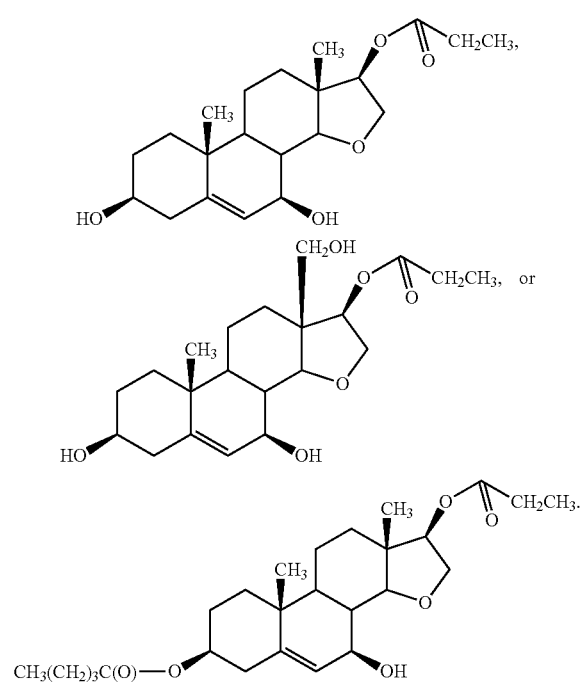
15. The compound of claim 9 wherein the compound has the structure
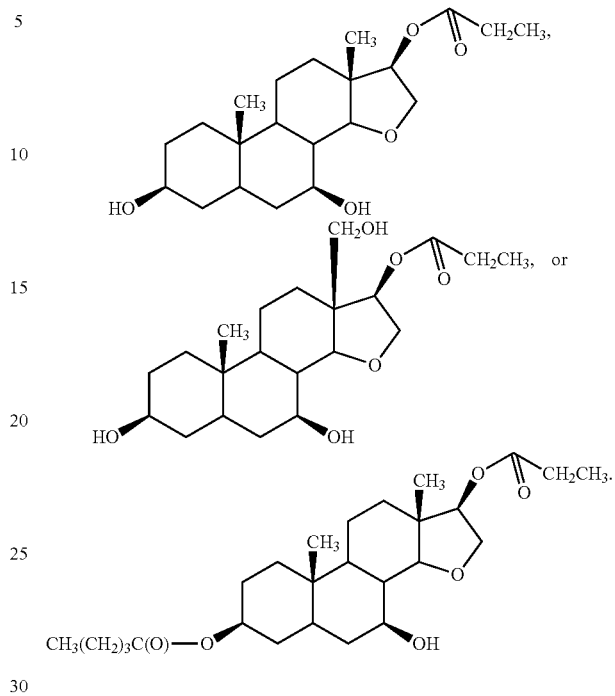
* * * * *